United States Patent
Meyerson et al.

(10) Patent No.: US 11,873,486 B2
(45) Date of Patent: Jan. 16, 2024

(54) MODULATING DSRNA EDITING, SENSING, AND METABOLISM TO INCREASE TUMOR IMMUNITY AND IMPROVE THE EFFICACY OF CANCER IMMUNOTHERAPY AND/OR MODULATORS OF INTRATUMORAL INTERFERON

(71) Applicant: Dana-Farber Cancer Institute, Inc., Boston, MA (US)

(72) Inventors: Matthew Meyerson, Concord, MA (US); William N. Haining, Newton, MA (US); Jeffrey Ishizuka, Boston, MA (US); Robert Manguso, Boston, MA (US); Hugh Gannon, Groton, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 514 days.

(21) Appl. No.: 16/497,294

(22) PCT Filed: Apr. 2, 2018

(86) PCT No.: PCT/US2018/025673
§ 371 (c)(1),
(2) Date: Sep. 24, 2019

(87) PCT Pub. No.: WO2018/184003
PCT Pub. Date: Oct. 4, 2018

(65) Prior Publication Data
US 2020/0377879 A1    Dec. 3, 2020

Related U.S. Application Data

(60) Provisional application No. 62/596,344, filed on Dec. 8, 2017, provisional application No. 62/588,657, filed on Nov. 20, 2017, provisional application No. 62/532,597, filed on Jul. 14, 2017, provisional application No. 62/480,228, filed on Mar. 31, 2017.

(51) Int. Cl.
*A61K 31/00* (2006.01)
*C12N 15/11* (2006.01)
*A61K 31/712* (2006.01)
*C12Q 1/6886* (2018.01)

(52) U.S. Cl.
CPC .......... *C12N 15/111* (2013.01); *A61K 31/712* (2013.01); *C12Q 1/6886* (2013.01); *C12N 2310/14* (2013.01); *C12N 2310/531* (2013.01); *C12Q 2600/106* (2013.01); *C12Q 2600/156* (2013.01); *C12Q 2600/158* (2013.01)

(58) Field of Classification Search
CPC .............. C12N 15/111; C12N 2310/14; C12N 2310/531; A61K 31/712; C12Q 1/6886; C12Q 2600/106; C12Q 2600/156; C12Q 2600/158
See application file for complete search history.

(56) References Cited

U.S. PATENT DOCUMENTS

| 2014/0302059 A1 | 10/2014 | Jamieson et al. |
| 2020/0377879 A1 | 12/2020 | Meyerson et al. |

FOREIGN PATENT DOCUMENTS

| WO | WO-2016/100261 A2 | 6/2016 | |
| WO | WO-2017182783 A2 * | 10/2017 | ............. A61K 31/00 |

OTHER PUBLICATIONS

Ishizuka et al. (Nature (2019) 565(7737):43-48). (Year: 2019).*
International Preliminary Report on Patentability for International Application No. PCT/US2018/025673 dated Oct. 1, 2019.
International Search Report and Written Opinion for International Application No. PCT/US2018/025673 dated Jul. 24, 2018.
Peacock et al., "Minor-Groove-Modulating Adenosine Replacements Control Protein Binding and RNAi Activity in siRNAs," ACS Chemical Biology, 5(12): 1115-1124 (2010).

* cited by examiner

*Primary Examiner* — J. E. Angell
(74) *Attorney, Agent, or Firm* — Foley Hoag LLP

(57) ABSTRACT

The present invention relates, in part, to methods of treating a subject afflicted with a cancer comprising administering to the subject a therapeutically effective amount of an agent that inhibits or promotes the copy number, the expression level, and/or the activity of one or more biomarkers listed in Table 1 or a fragment thereof. Also provided herein are methods of detecting ADAR1 or ISG15 dependency in a high proliferation cell (e.g., a cancer cell). Also provided are methods of detected increased interferon signaling pathway activity in a high proliferation cell (e.g., a cancer cell). Included herein are methods of treating cancer with inhibitors of ADAR1 or ISG15. Methods of screening for such inhibitors are also provided herein. Methods of identifying the likelihood of a cancer to be responsive to an ADAR1 inhibitor are also provided.

18 Claims, 91 Drawing Sheets
Specification includes a Sequence Listing.

Figure 1
A
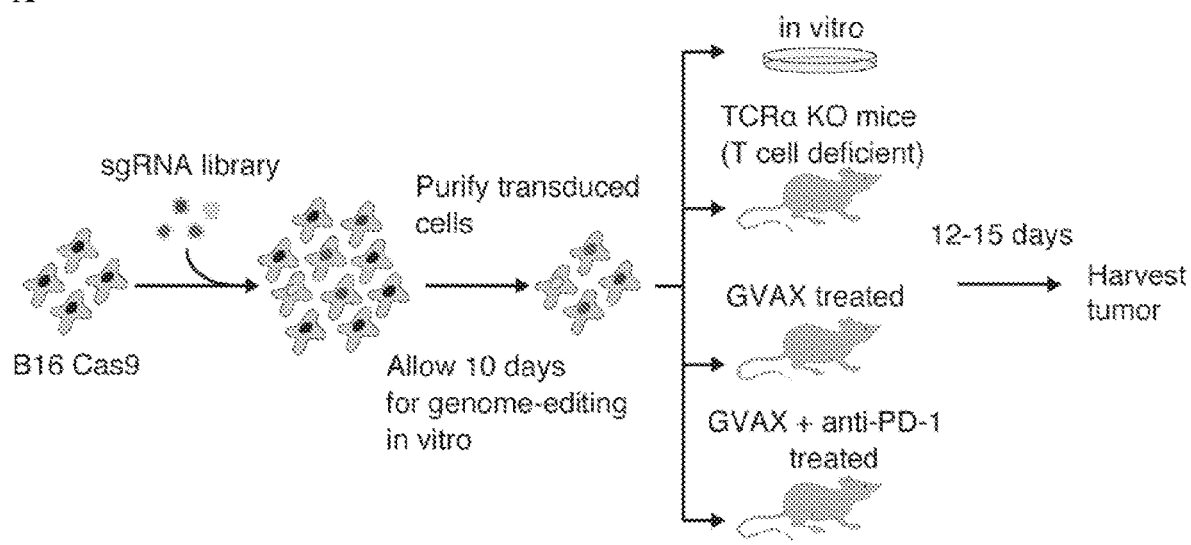
B
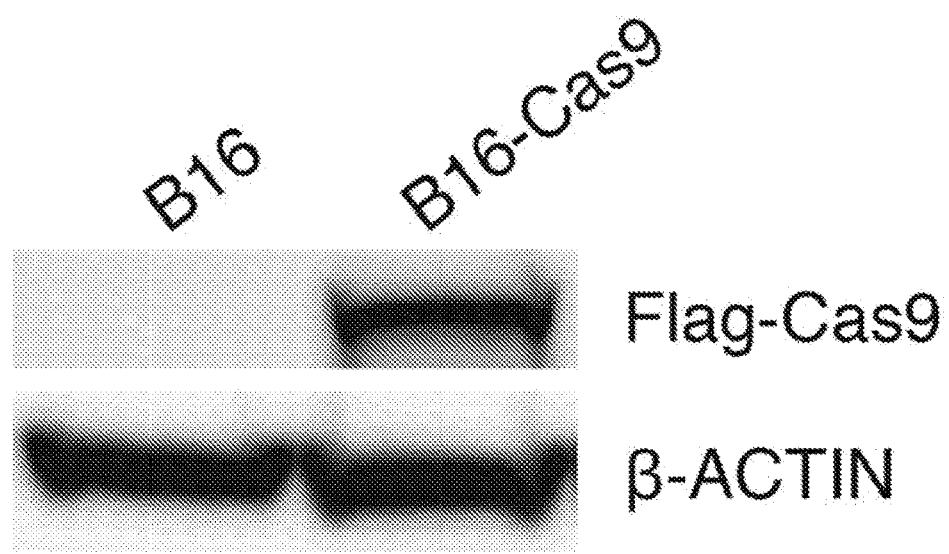

Figure 1 (cont.)
C
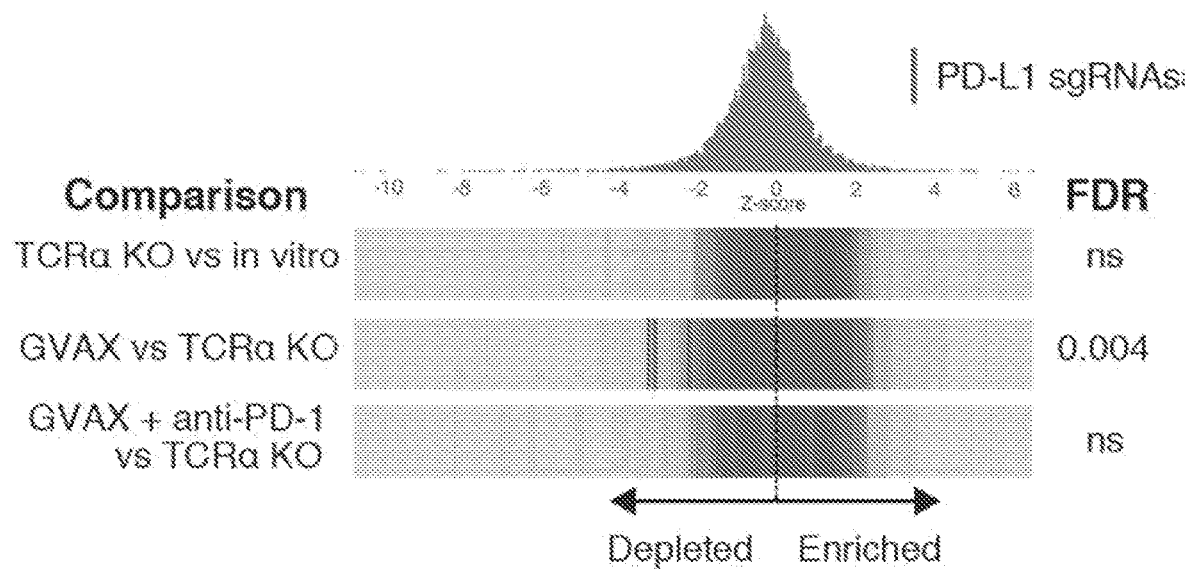
D
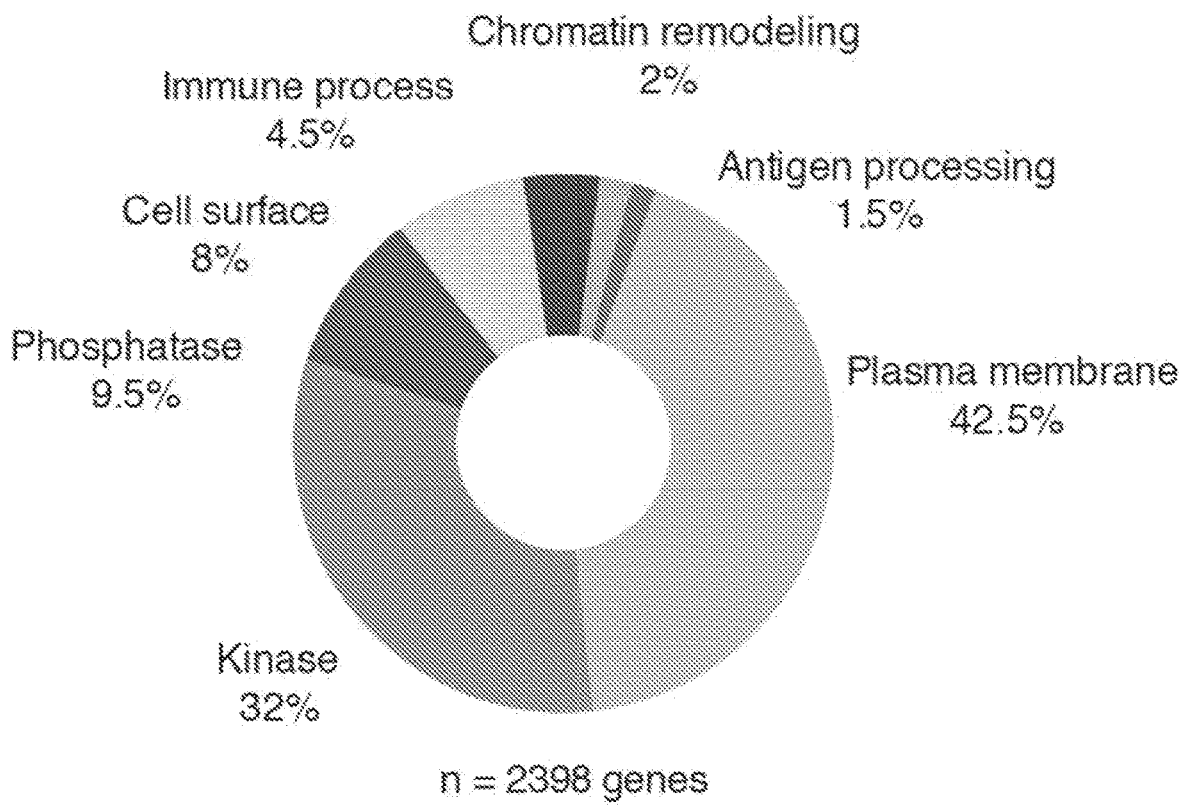

F

Figure 1(cont.)
G
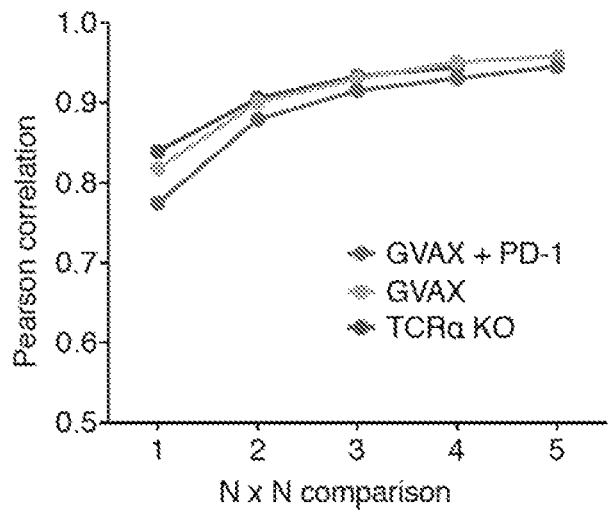
H
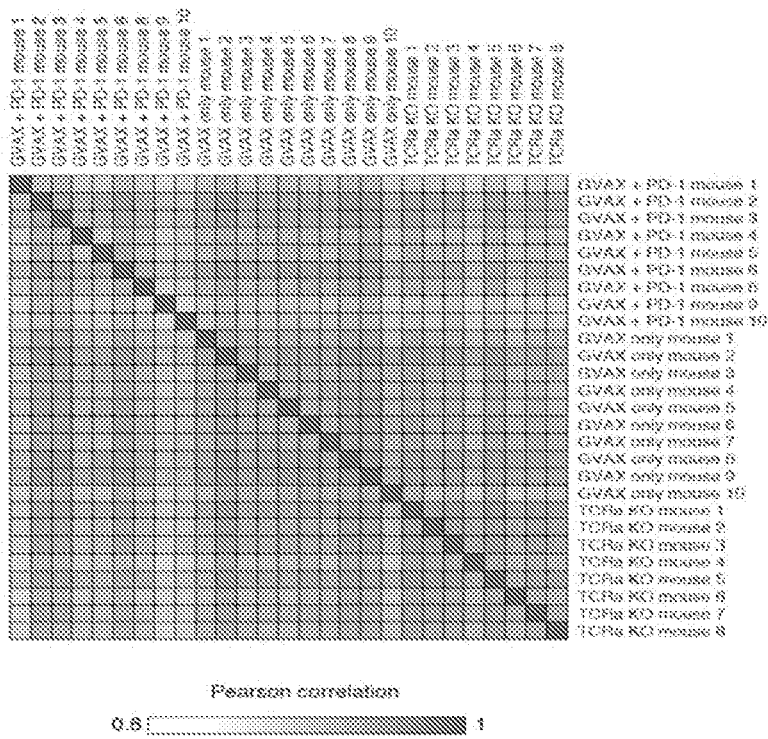

I

Figure 1 (cont.)
J
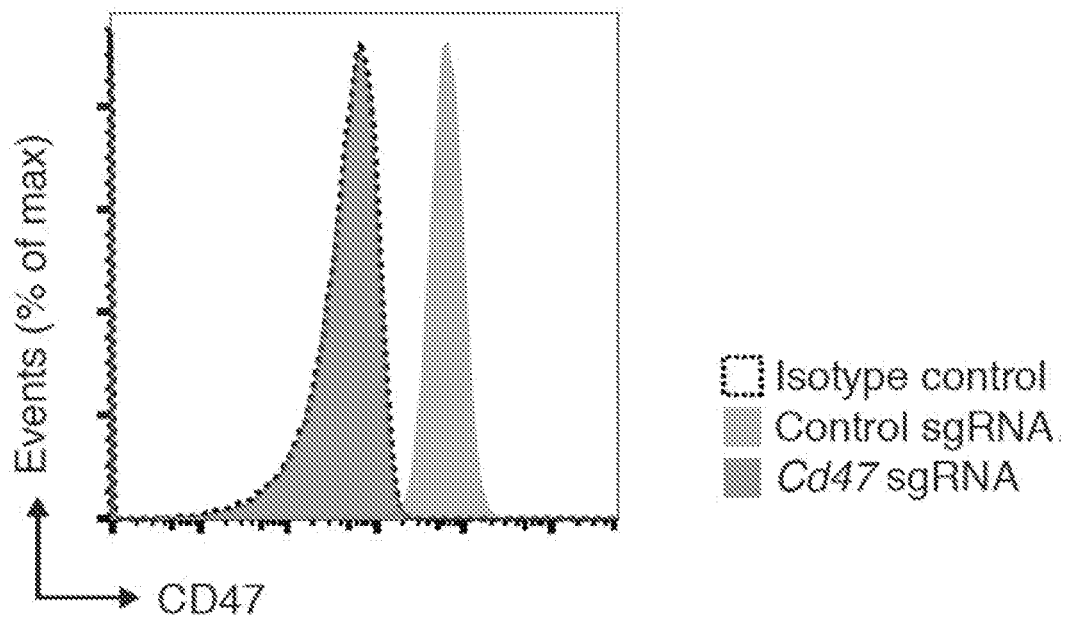
K
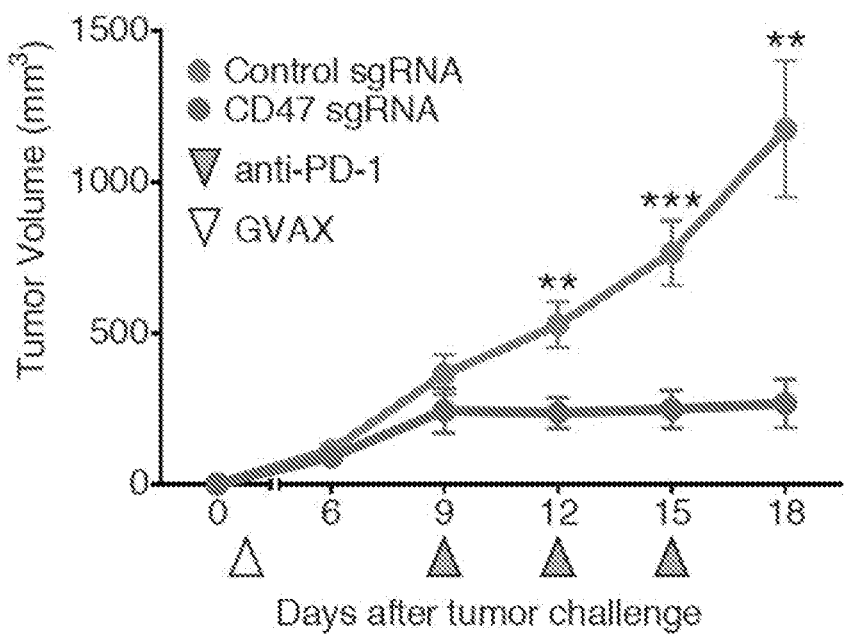

Figure 4
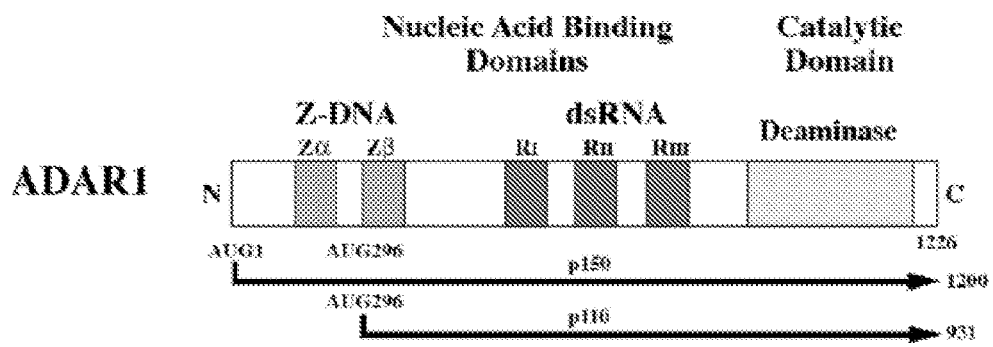
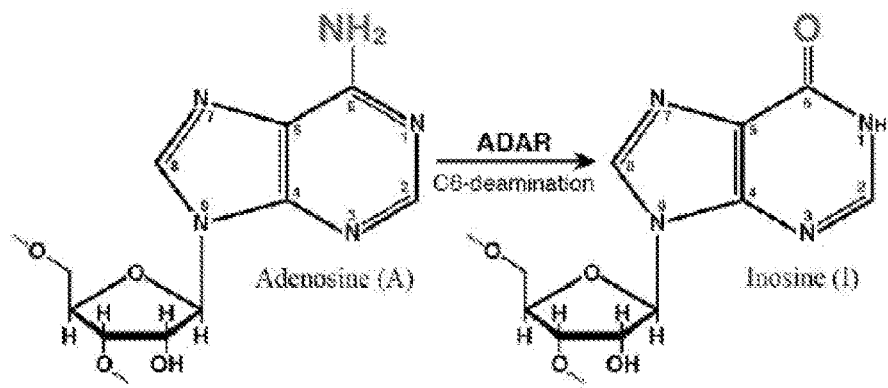
Figure 5
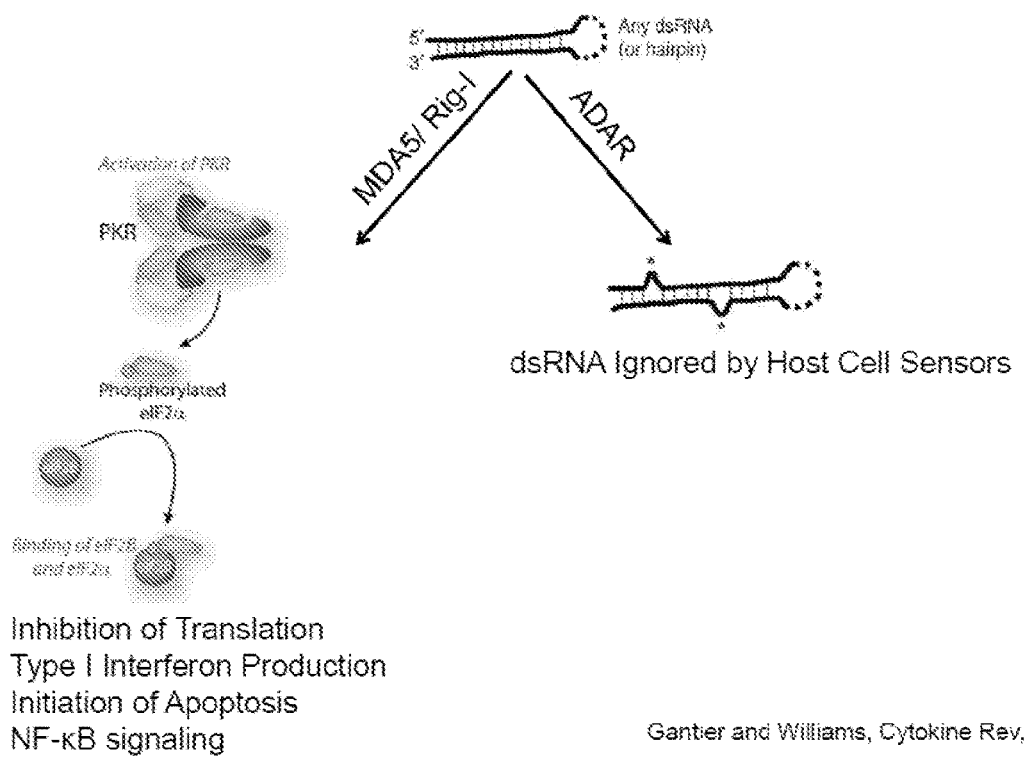
Inhibition of Translation
Type I Interferon Production
Initiation of Apoptosis
NF-κB signaling
Gantier and Williams, Cytokine Rev, 2007

Figure 8
A
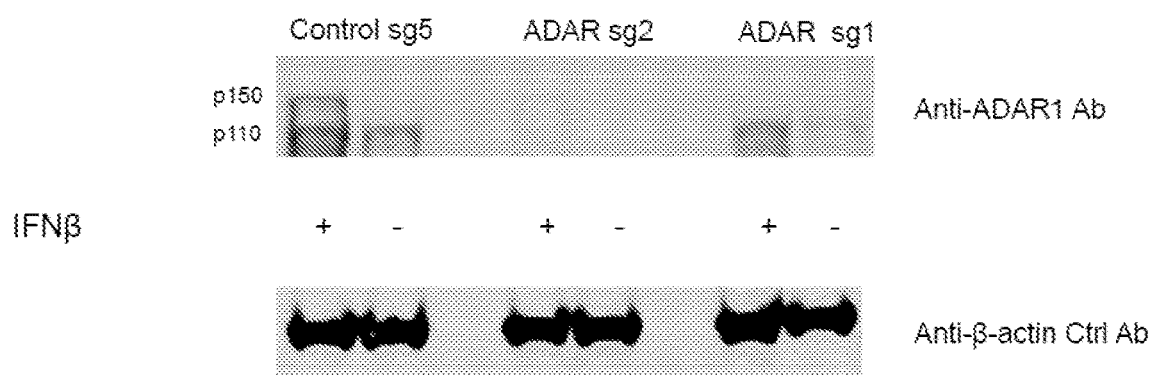
B
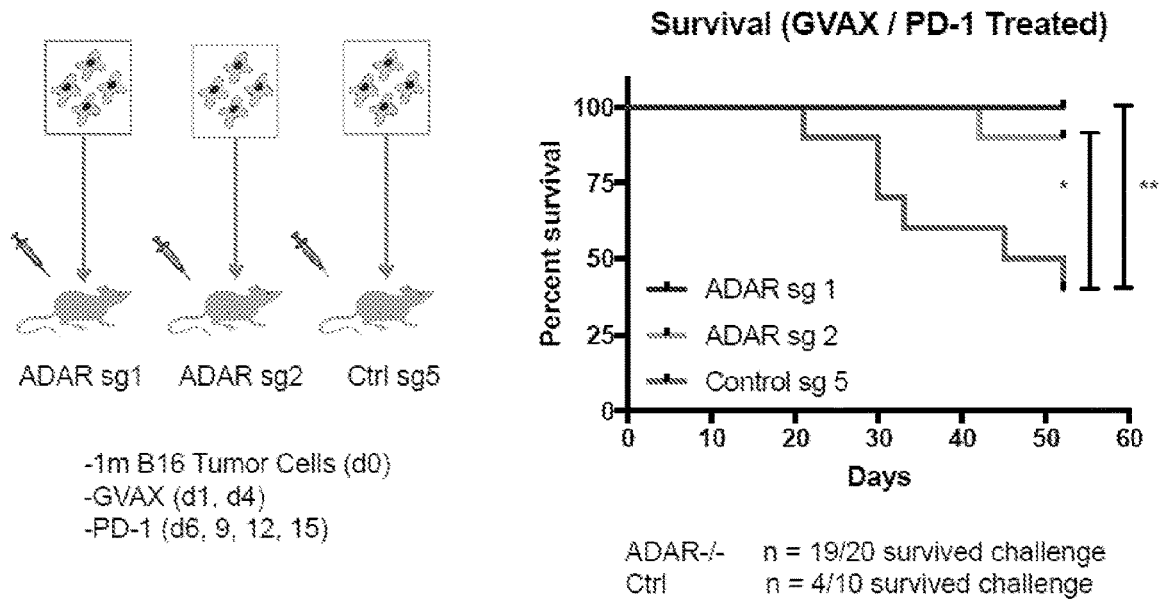

C

E

A

B

Viability after 3 days

Figure 35

| NCI-H1650 | HCC-366 | |
|---|---|---|
| Significant GO Category | Significant GO Category | Genes |
| keratinization | defense response to virus | PKR |
| type I interferon signaling pathway | defense response | ISG15 |
| defense response to virus | response to virus | MX1 |
| negative regulation of viral genome replication | response to external biotic stimulus | USP18 |
| response to virus | negative regulation of viral genome replication | OASL |
| regulation of viral process | response to biotic stimulus | HELZ2 |
| epidermis development | response to other organism | IFIT2 |
| regulation of viral genome replication | negative regulation of viral process | IFIT3 |
| wound healing | cytokine-mediated signaling pathway | |
| regulation of viral life cycle | regulation of viral process | |
| negative regulation of viral process | regulation of viral life cycle | |

Figure 36

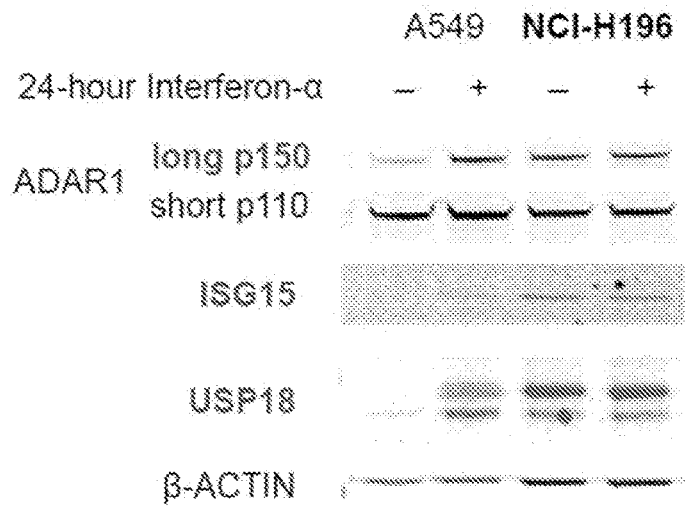

Interferon-inducible

Figure 39
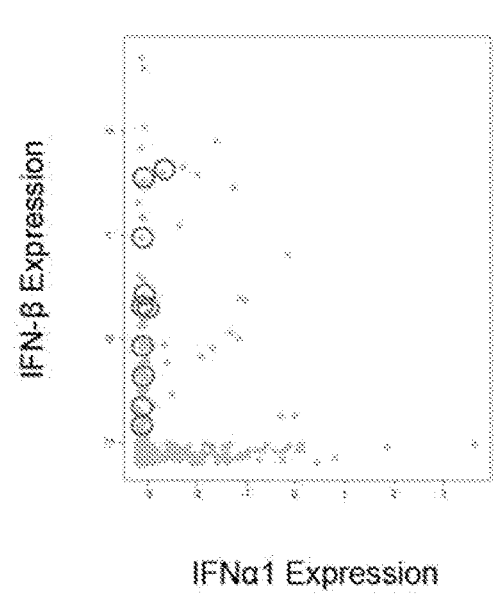
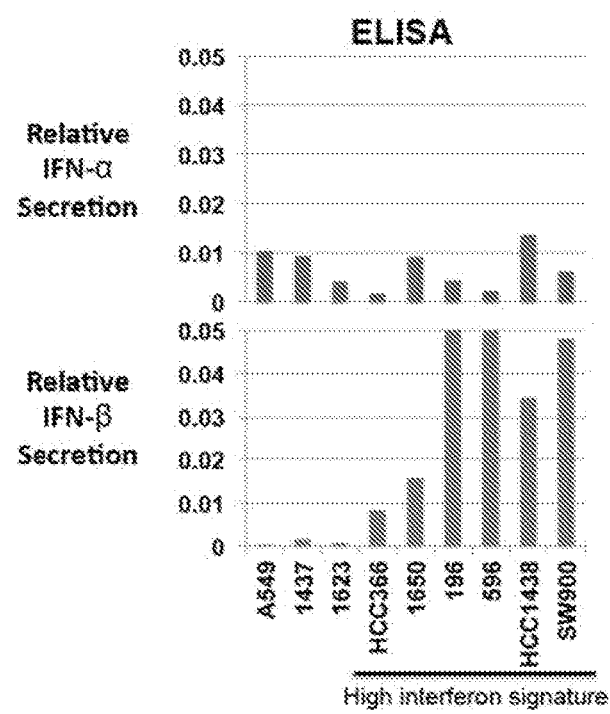
Figure 40
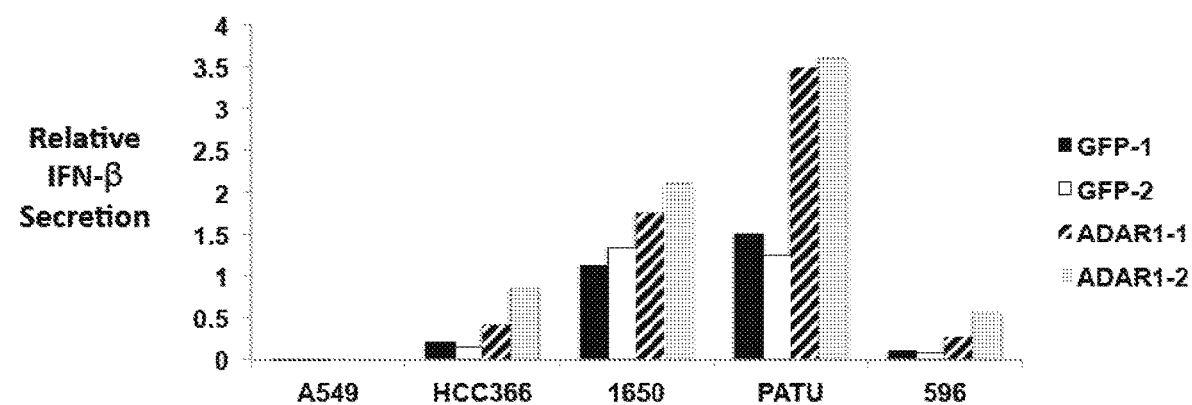

Interferon-inducible

Interferon-inducible

Figure 60
A
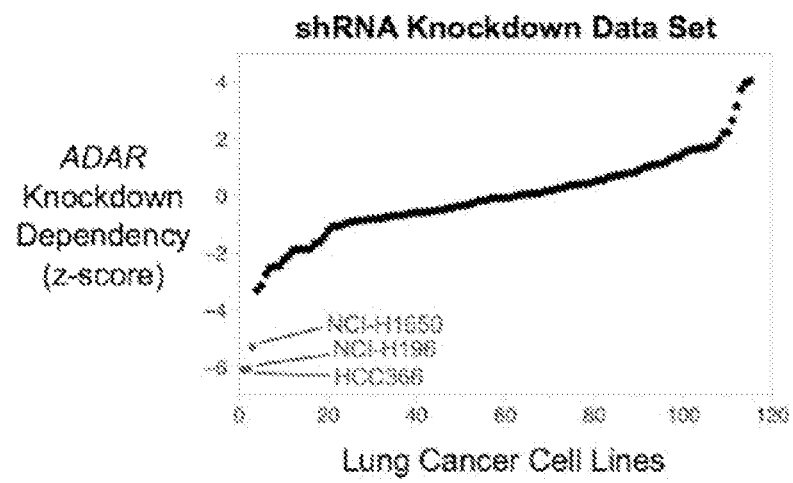
B
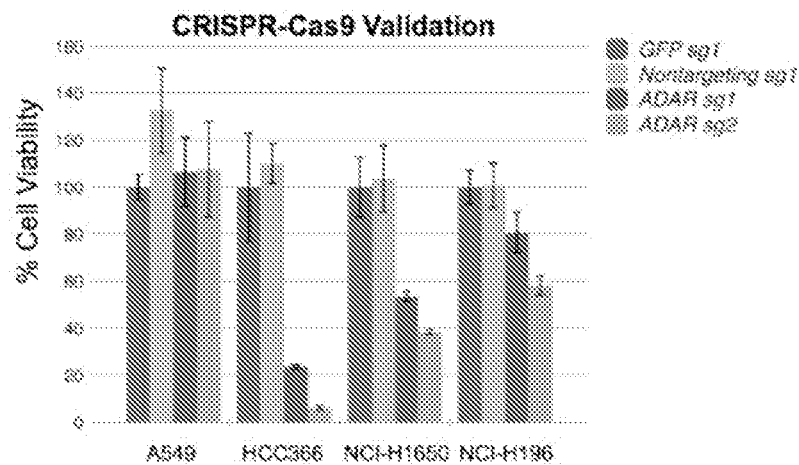
C
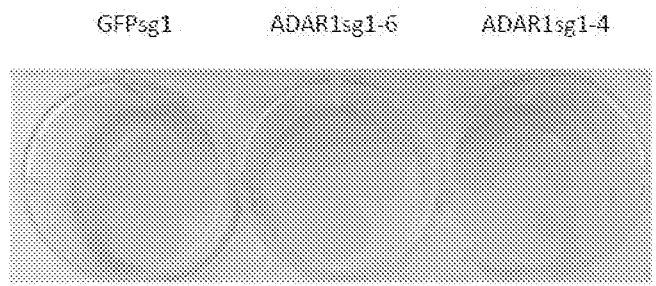

Figure 60 (cont.)
D
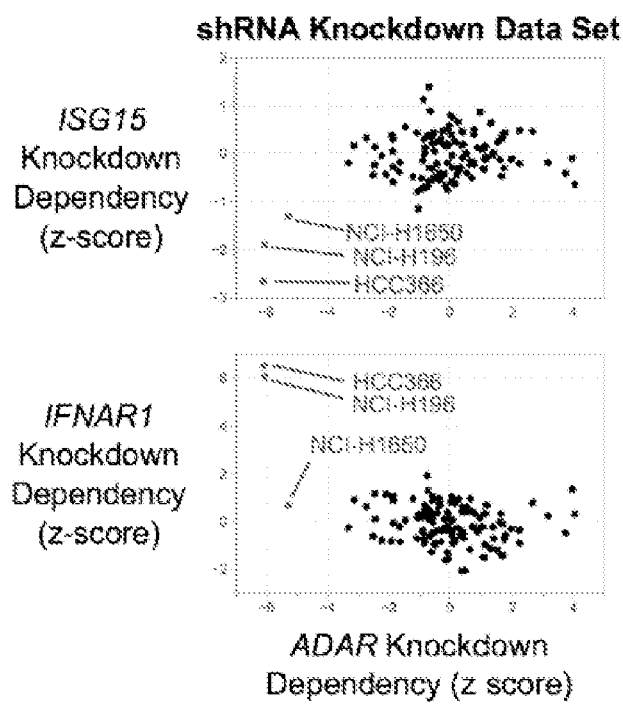
E
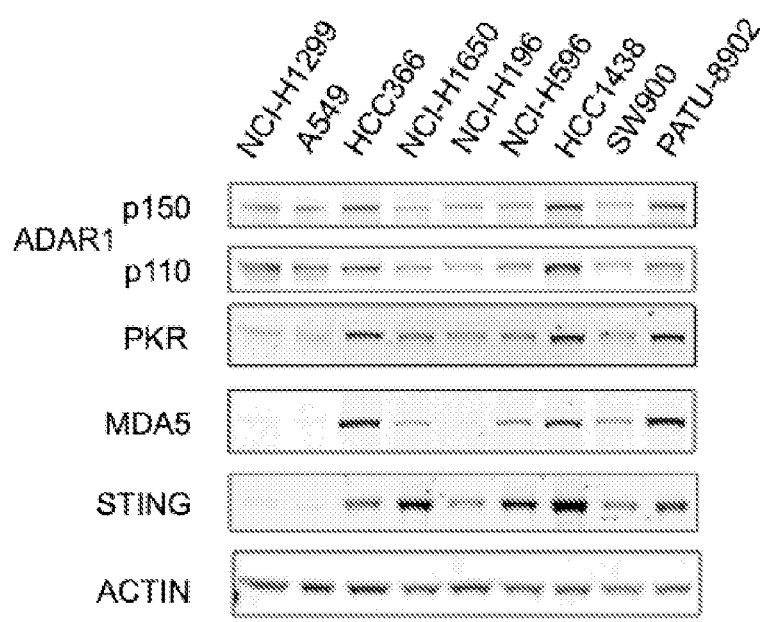

Figure 60
F
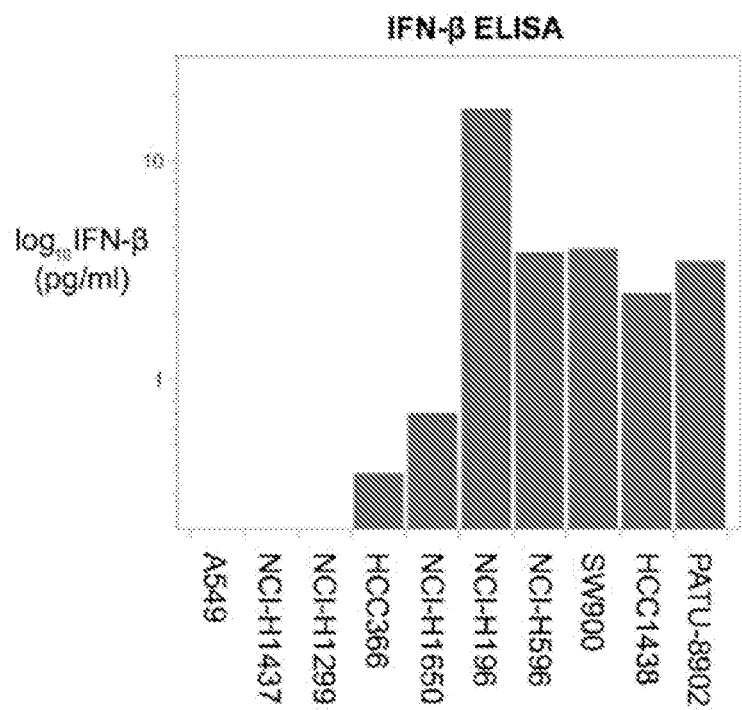
G
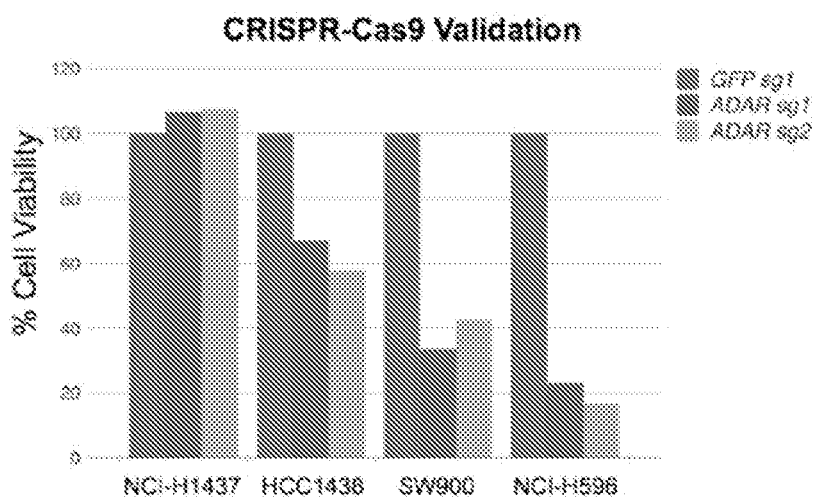

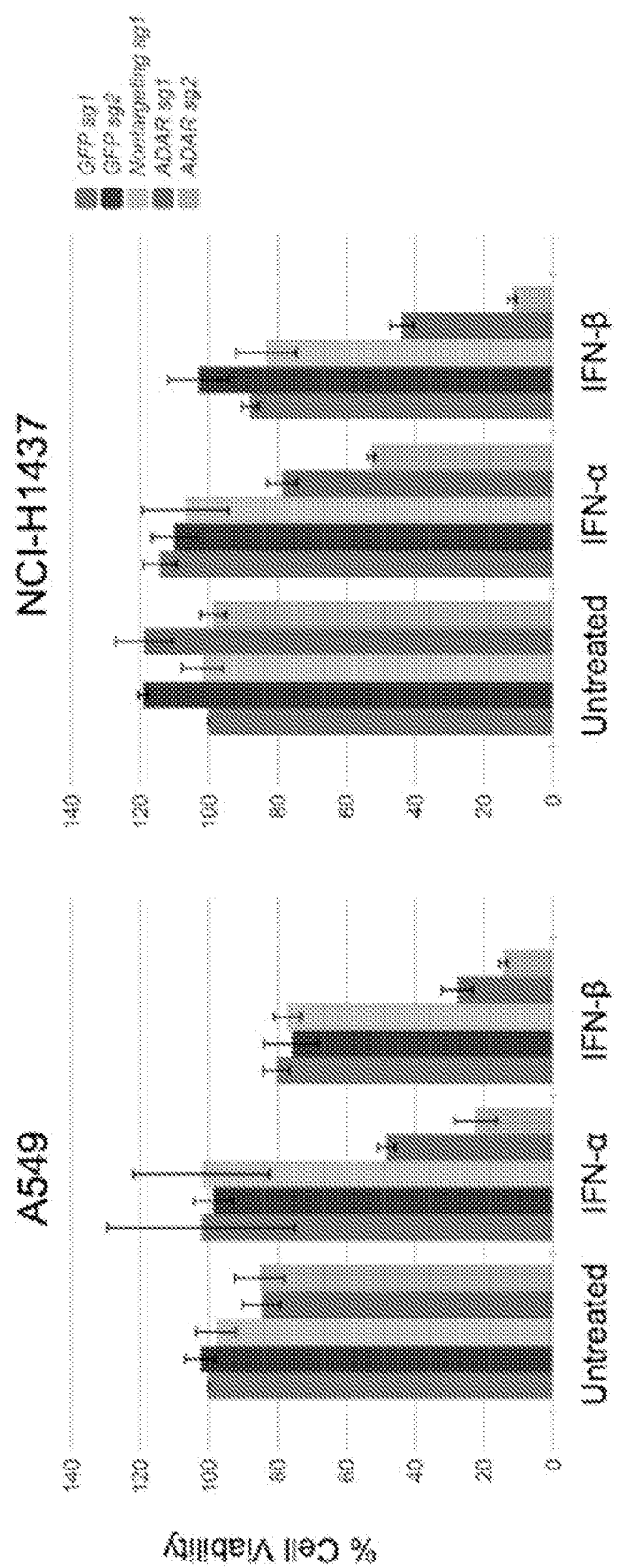
Figure 60 (cont.) H

I

A

Figure 61
B
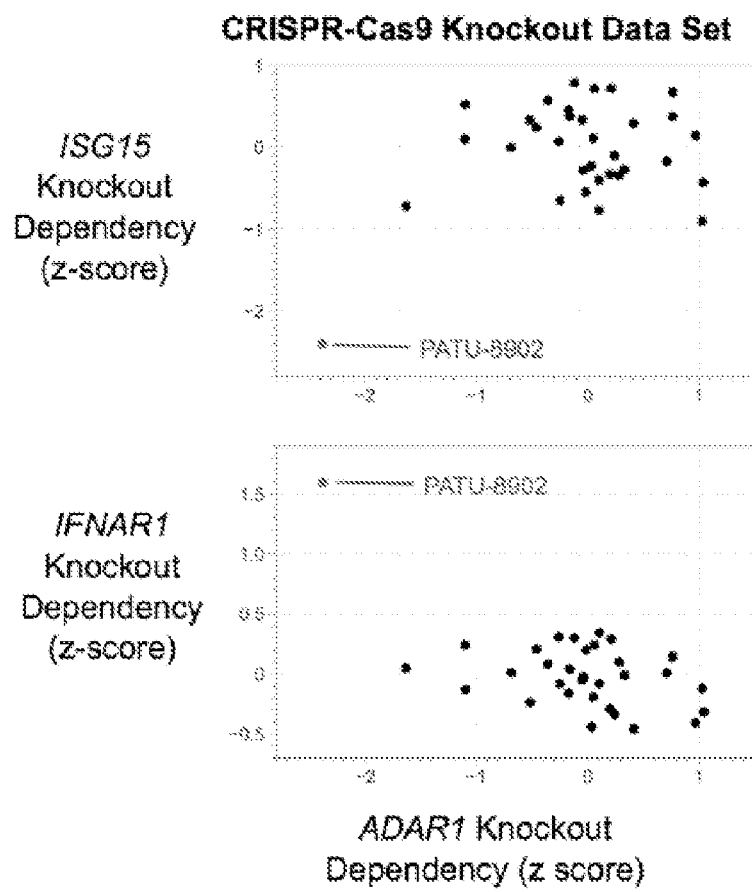
C
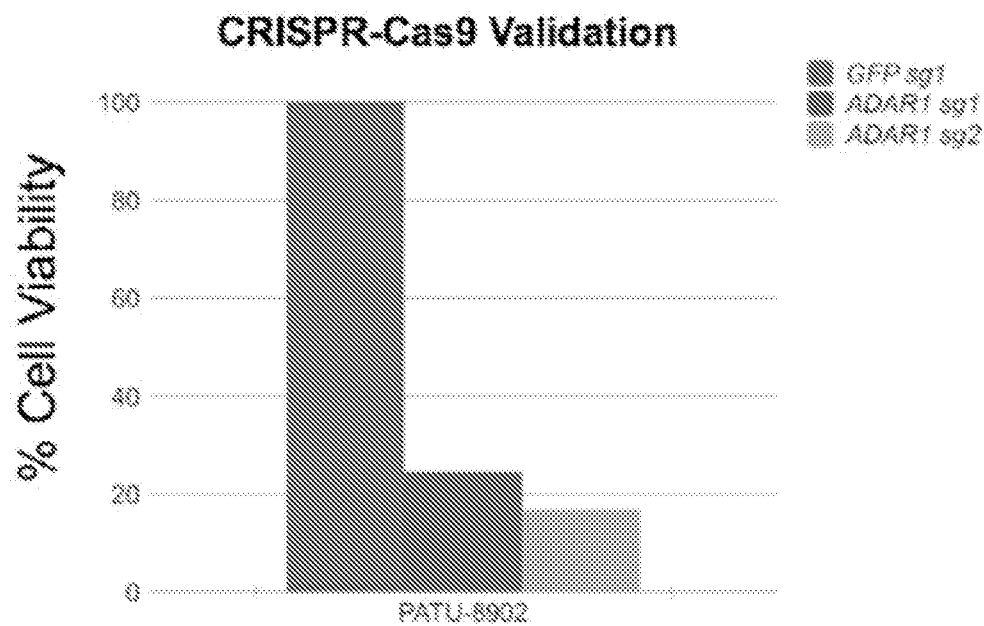

Figure 61
D (cont.)
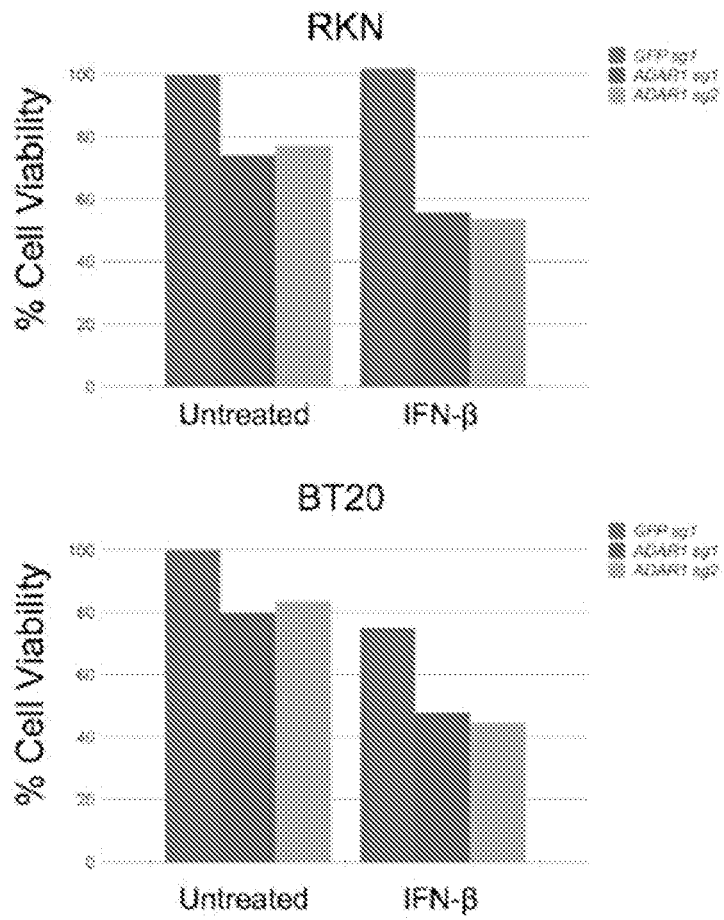
E
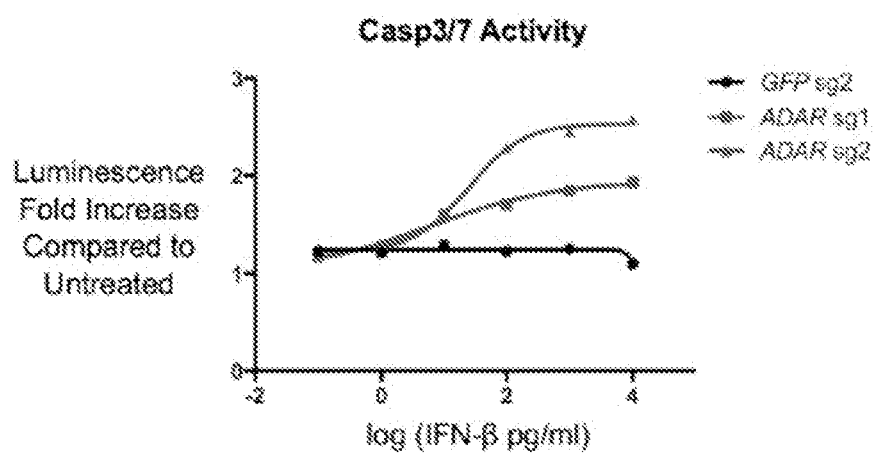

Figure 62
A
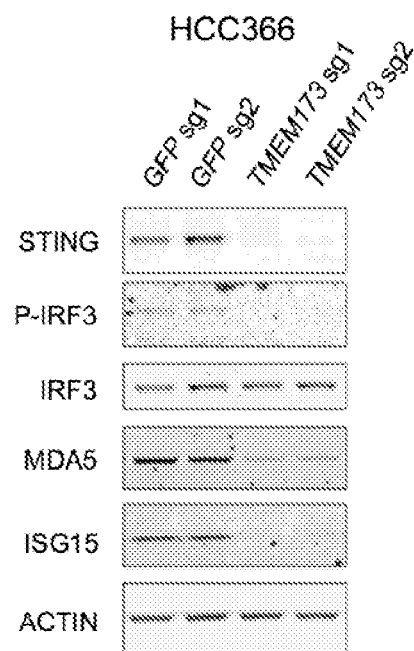
B
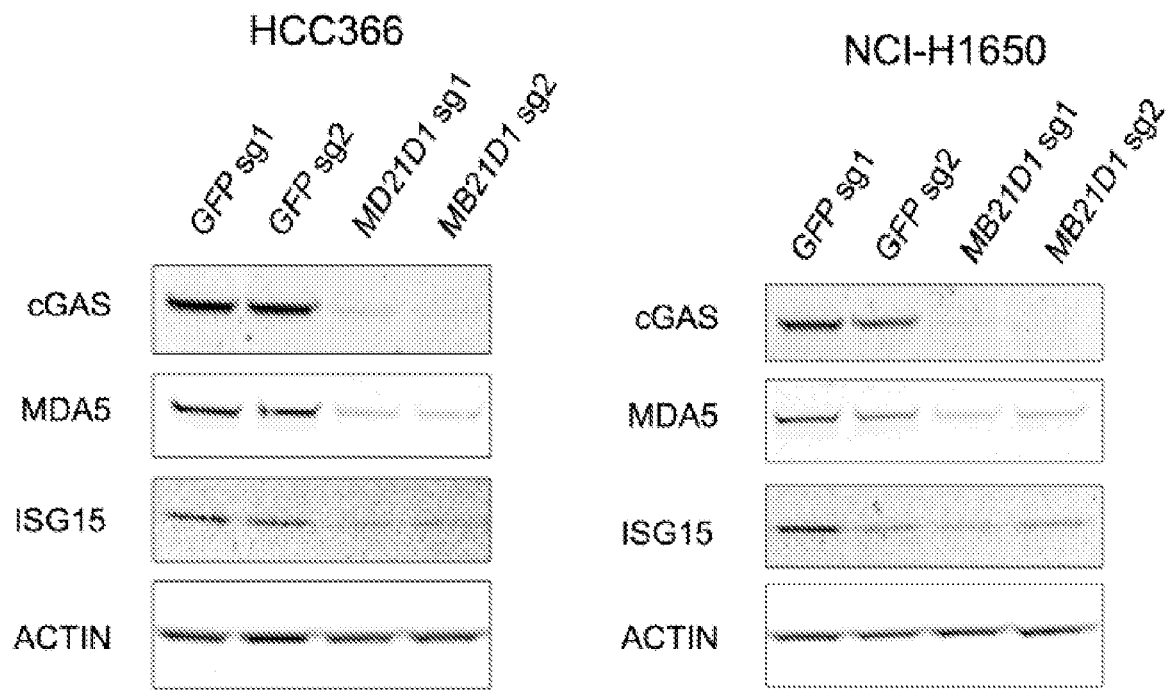

**Figure 62
B (cont.)**
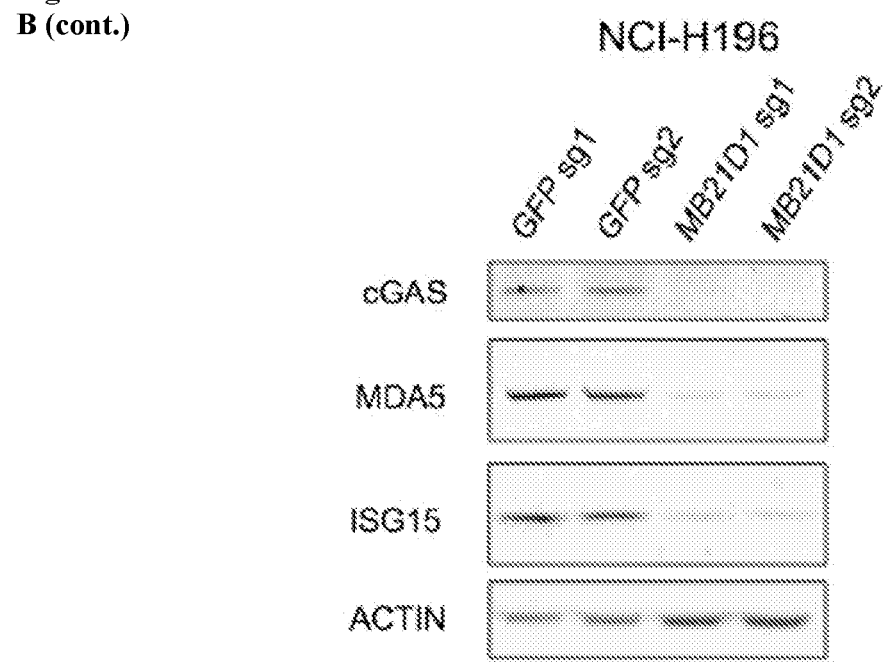
C
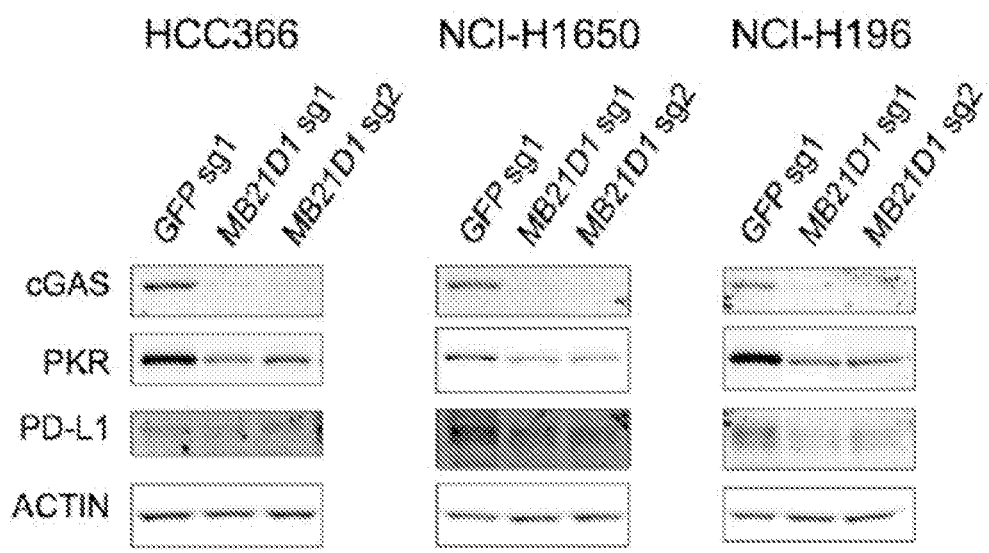

E

Figure 62 (cont.)
E
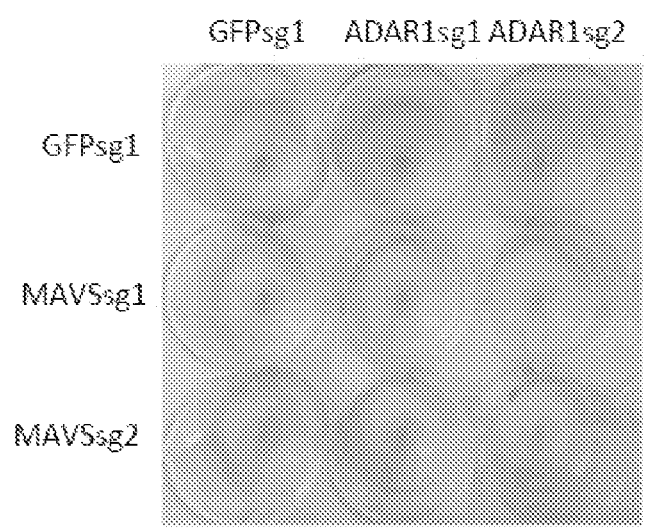
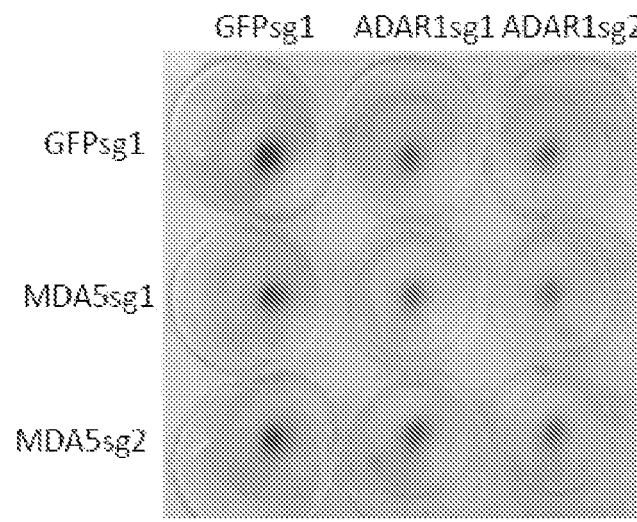

Figure 62 (cont.)
E
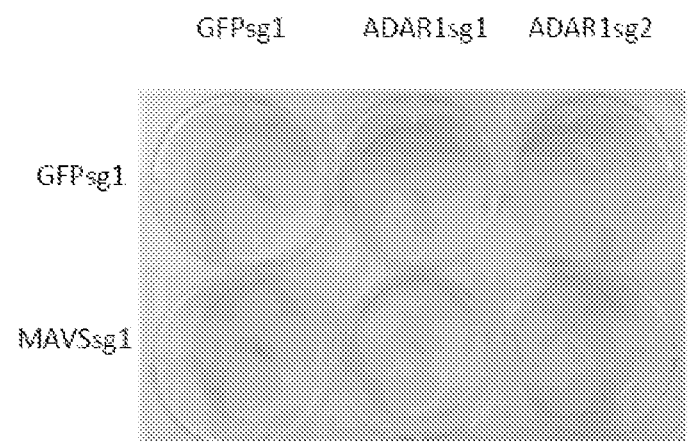
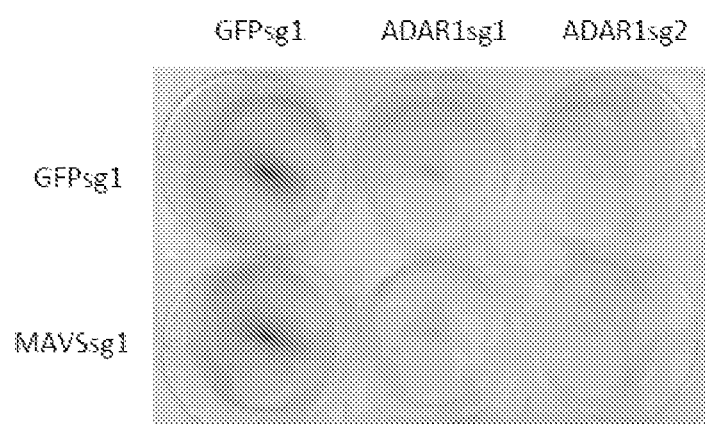

Figure 62 (cont.)
E
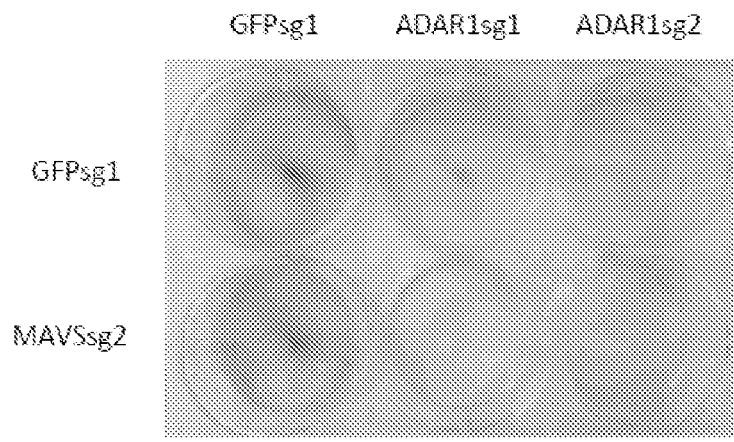
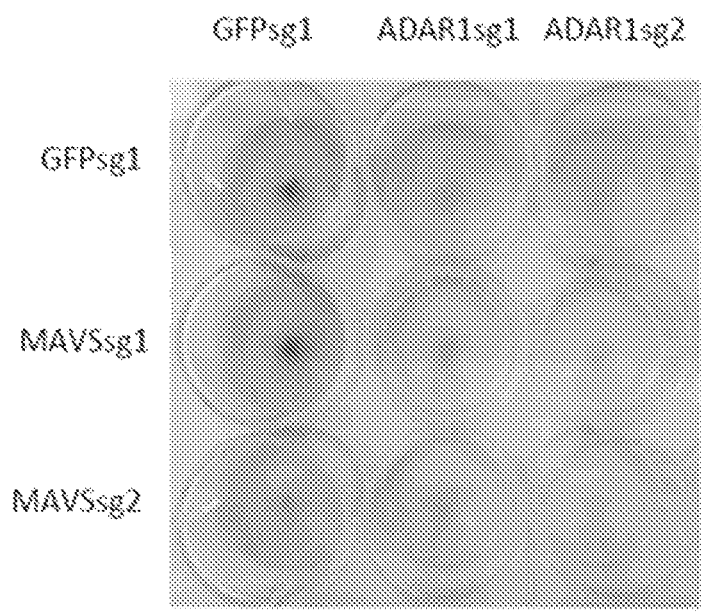

E

Figure 63 A
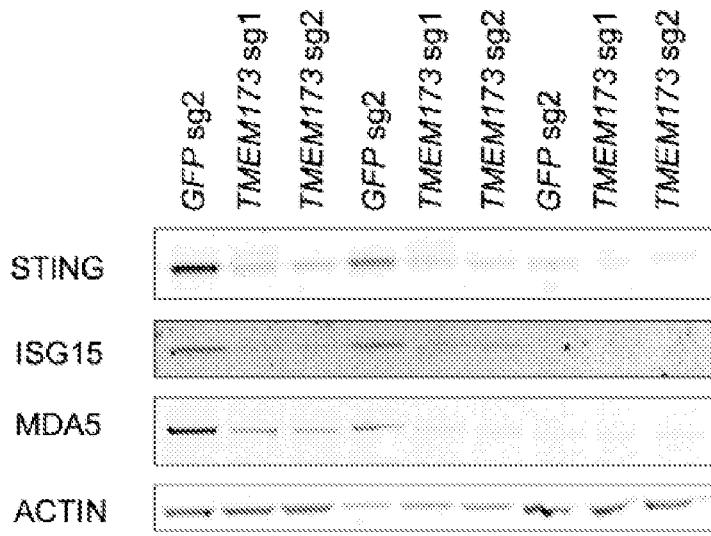
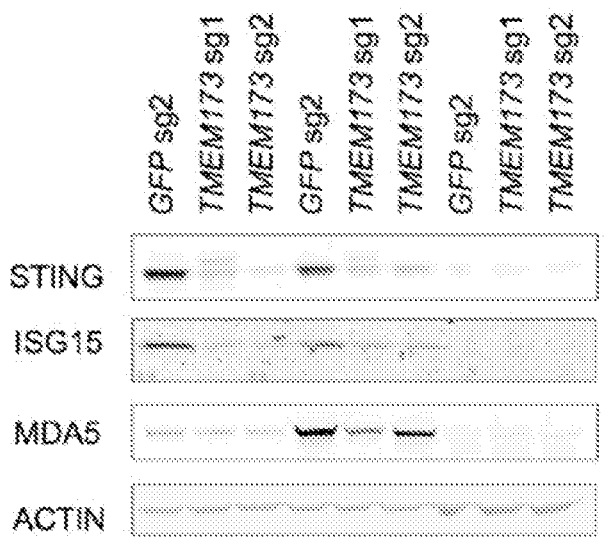
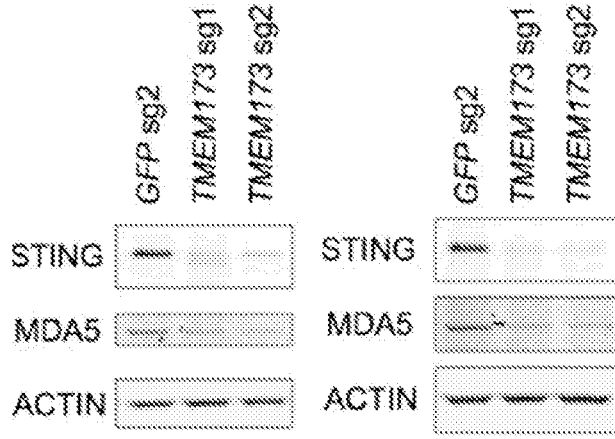

B

C

Figure 64
A
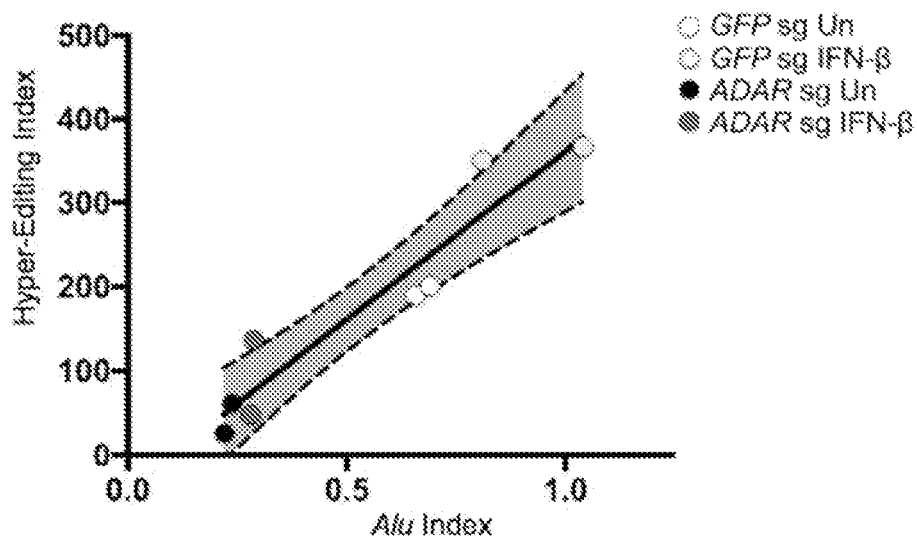
B
RNA-seq: *Alu* editing and hyper-editing
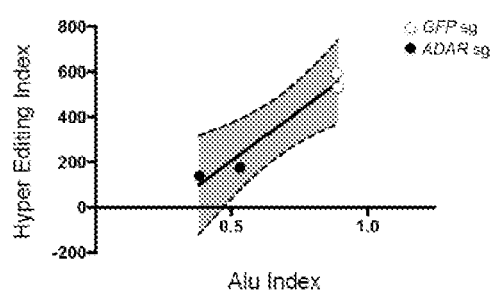
NCI-H1650 GFPsg1 and 2 and ADAR1sg1 and 2

Figure 64 (cont.)
C
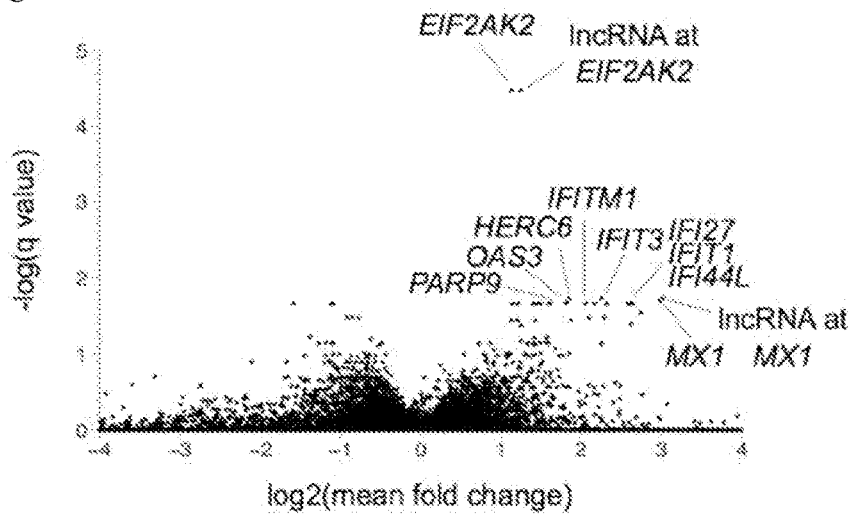
D
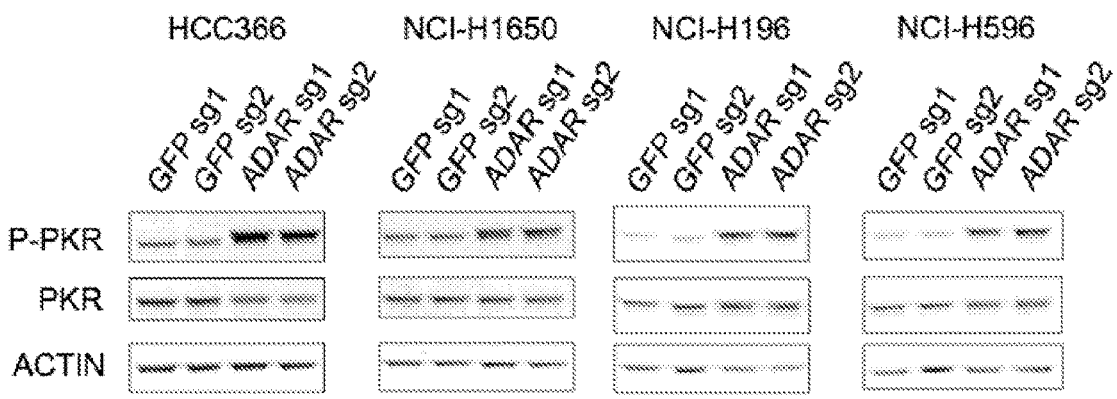
E
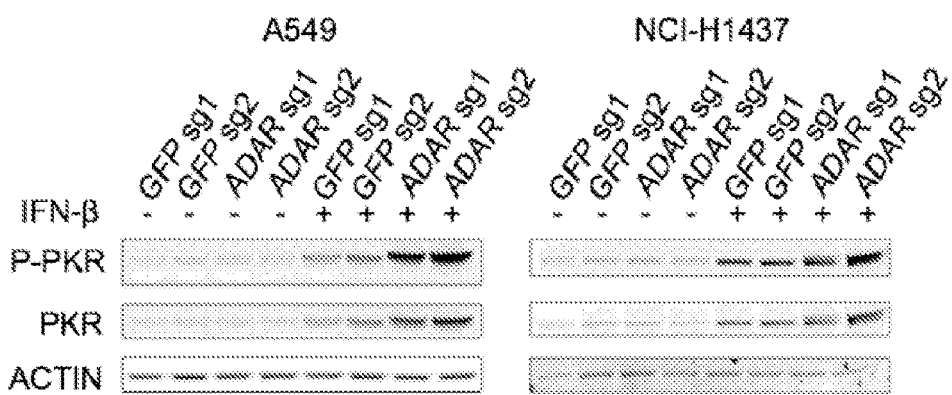

Figure 64 (cont.)
F
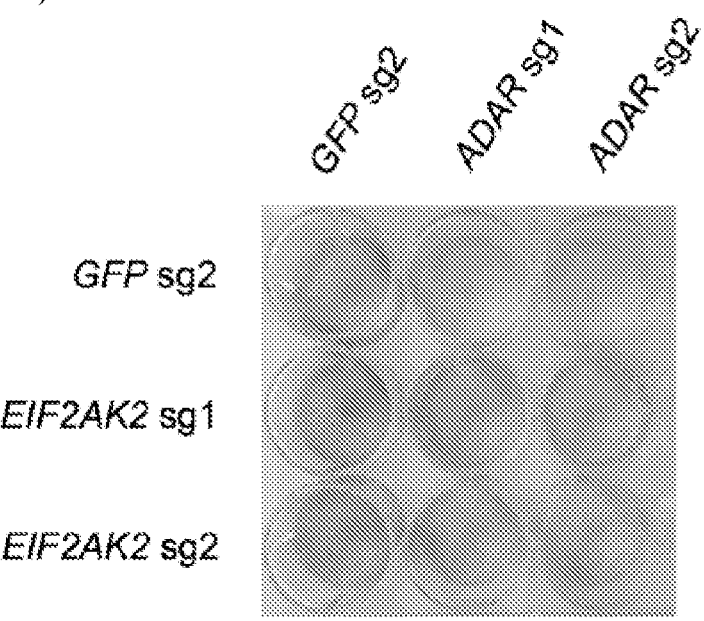
G
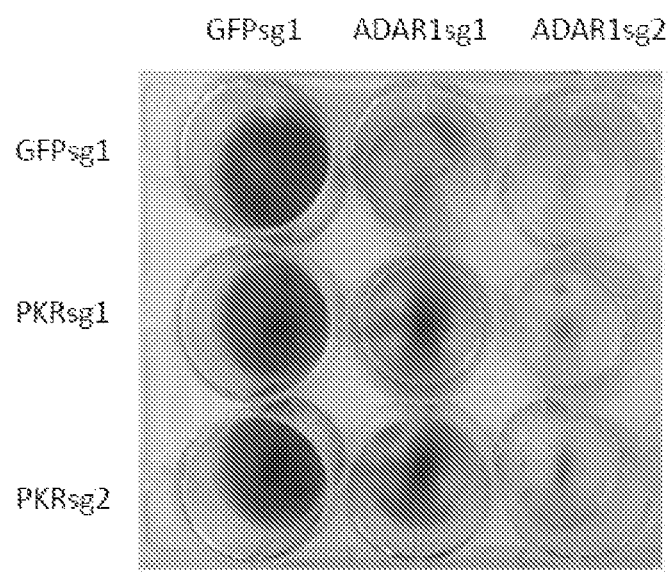

Figure 64
H
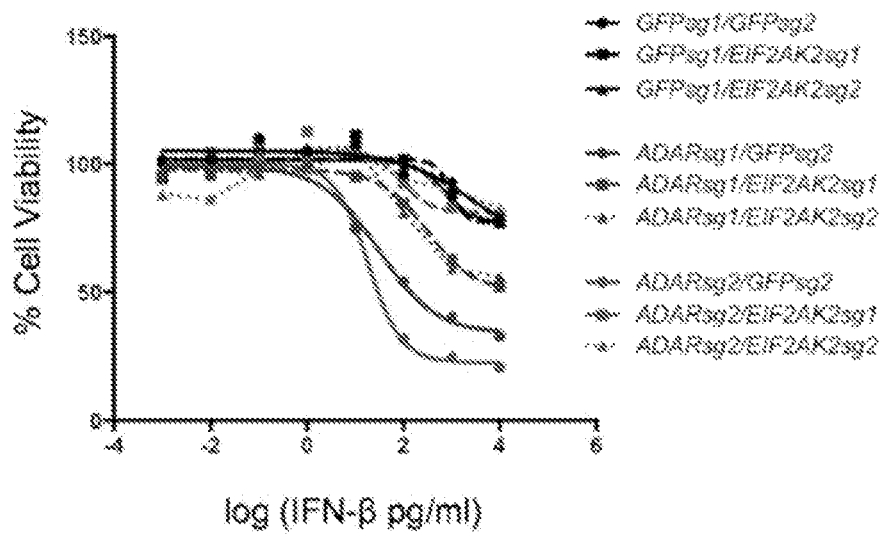
I
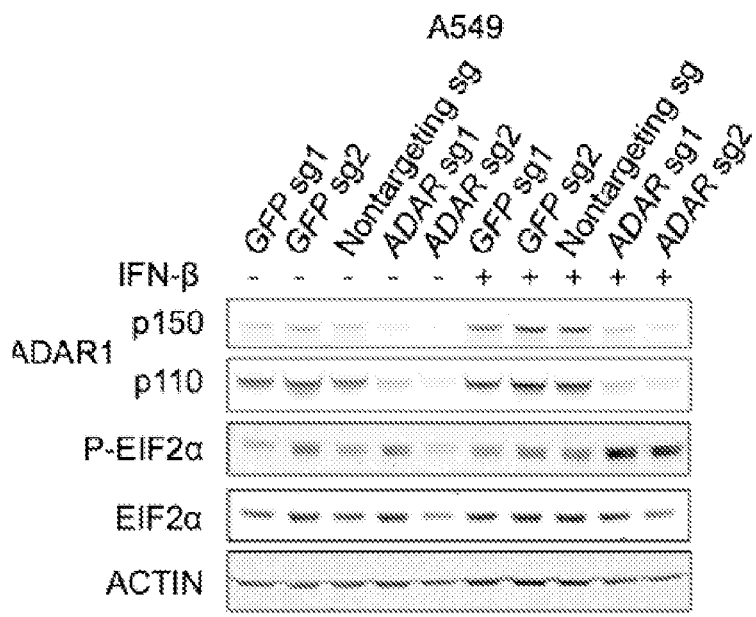

Figure 65
A
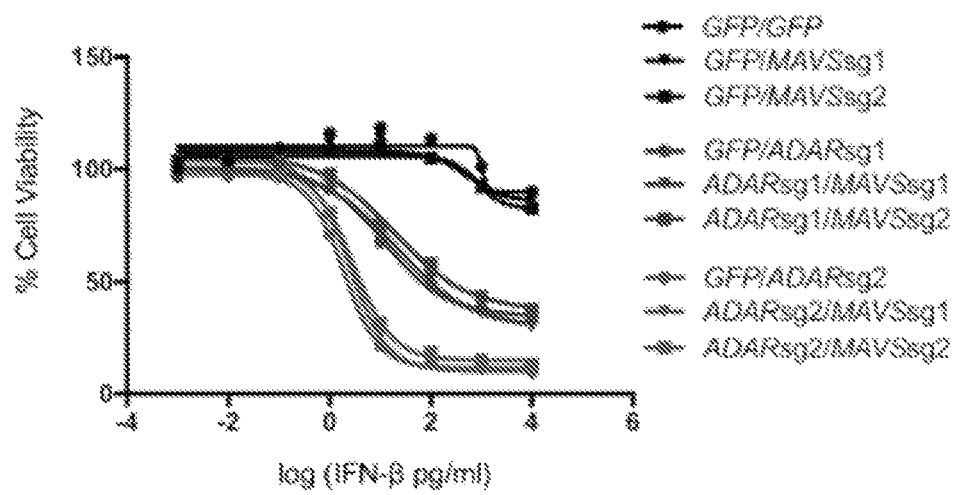
B
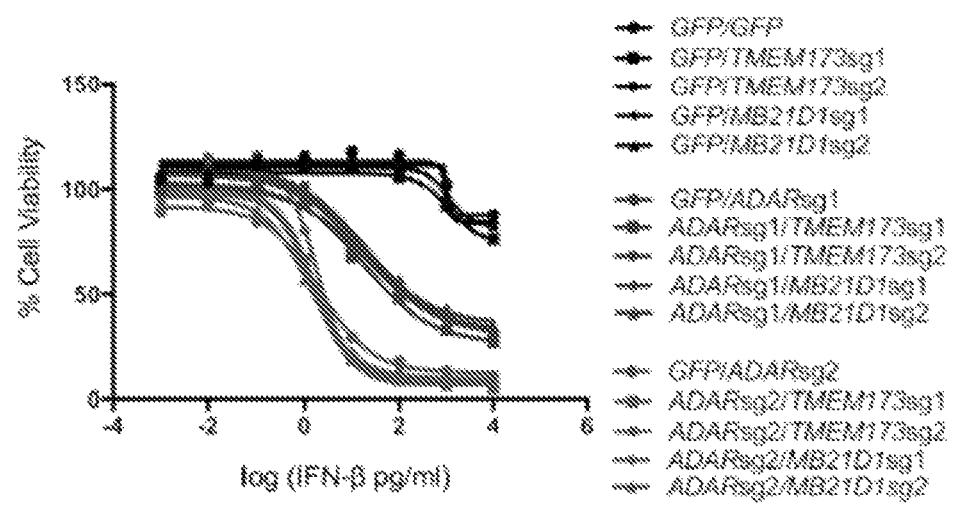

Figure 66
A
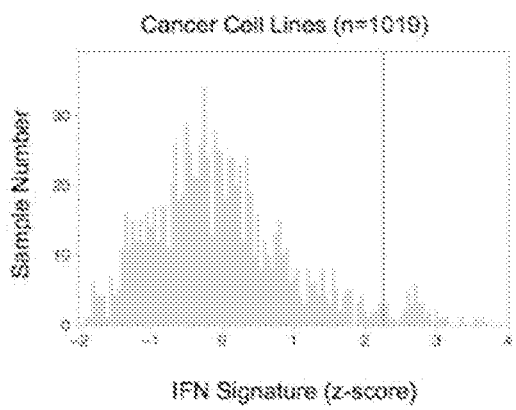
B
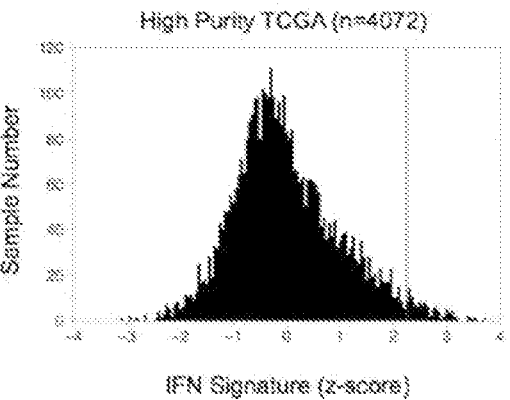
C
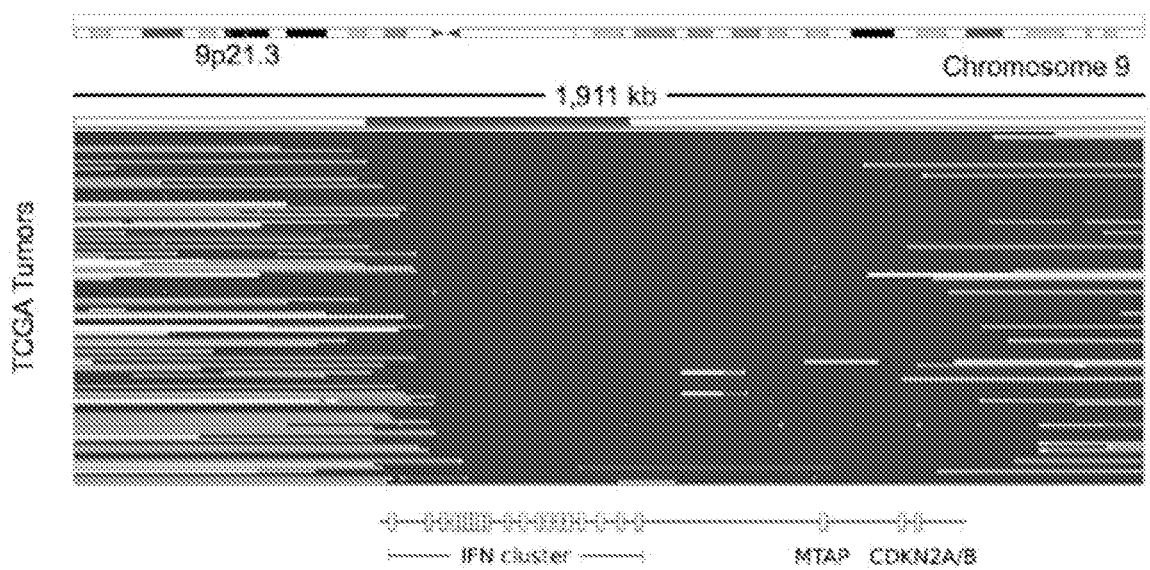
D
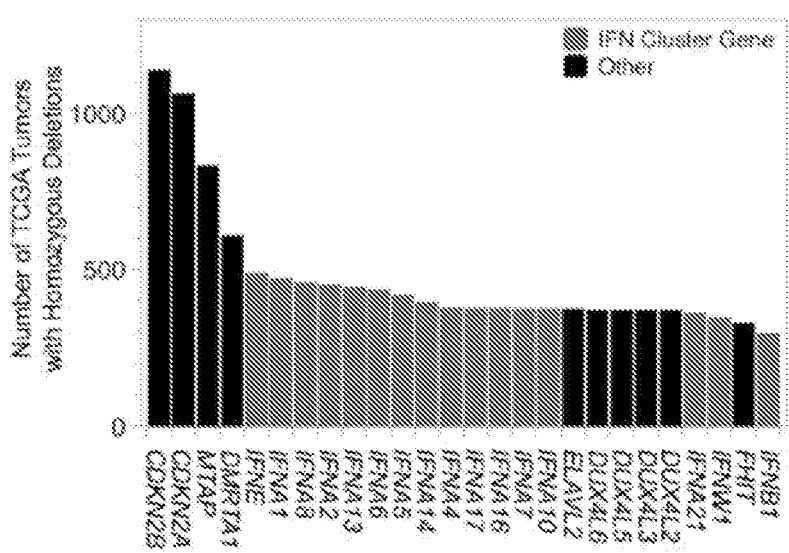

Figure 68
A
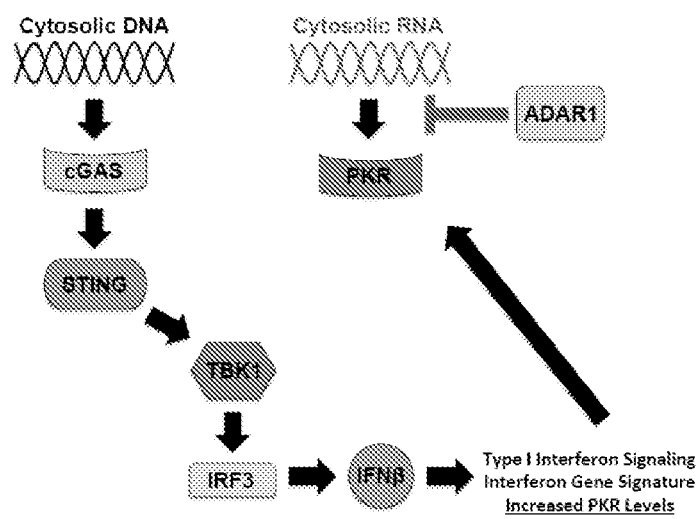
B
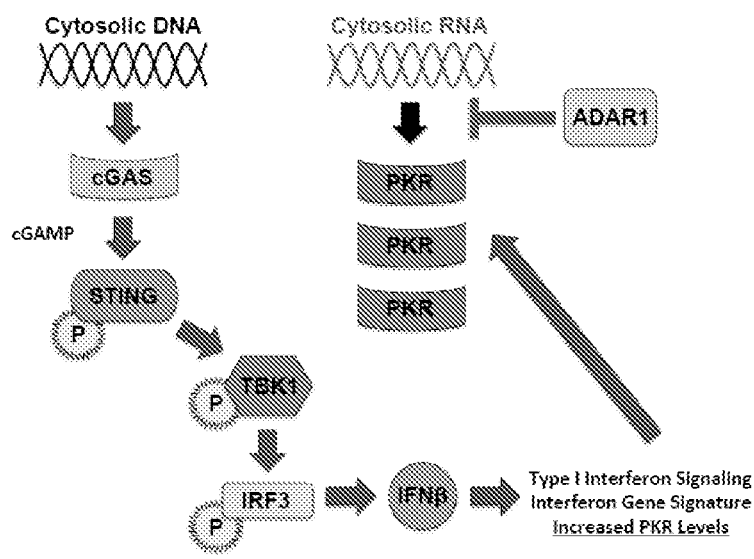

Figure 68 (cont.)
C
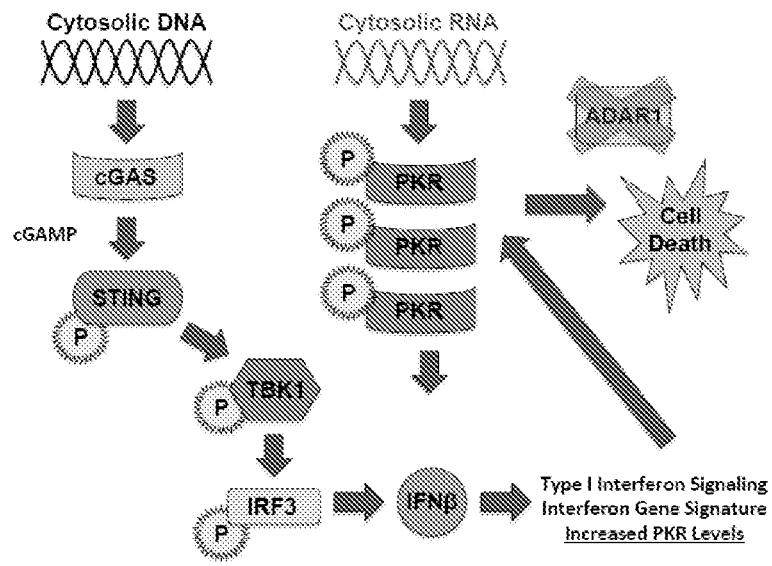
D
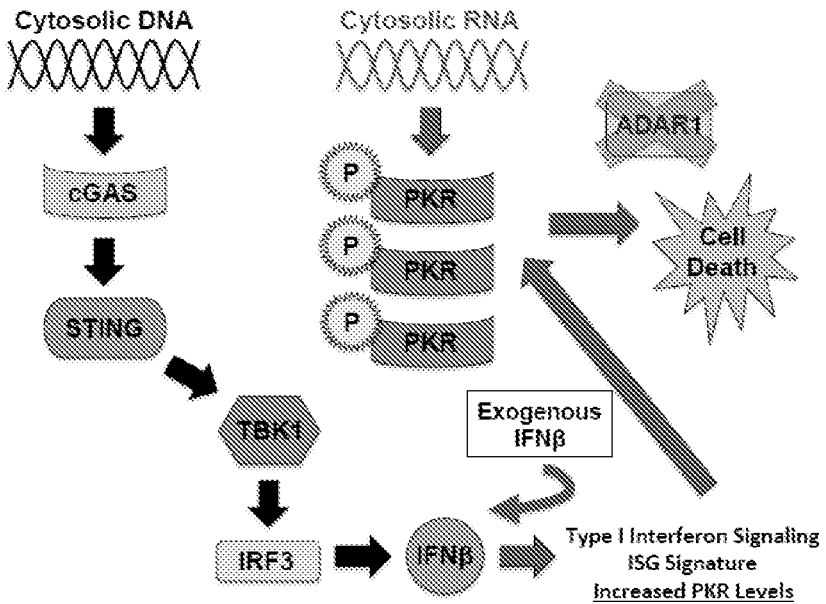

MODULATING DSRNA EDITING, SENSING, AND METABOLISM TO INCREASE TUMOR IMMUNITY AND IMPROVE THE EFFICACY OF CANCER IMMUNOTHERAPY AND/OR MODULATORS OF INTRATUMORAL INTERFERON

RELATED APPLICATIONS

This application claims the benefit of priority to U.S. Provisional Patent Application Ser. No. 62/532,597, filed Jul. 14, 2017, U.S. Provisional Patent Application Ser. No. 62/588,657, filed on Nov. 20, 2017, U.S. Provisional Patent Application Ser. No. 62/480,228, filed on Mar. 31, 2017, and U.S. Provisional Patent Application Ser. No. 62/596,344, filed on Dec. 8, 2017, each of which application is herein incorporated by reference in its entirety.

STATEMENT REGARDING FEDERALLY SPONSORED RESEARCH OR DEVELOPMENT

This invention was made with government support under grant numbers F32CA196141, P01CA154303, and R35CA197568 awarded by the National Institutes of Health. The government has certain rights in the invention.

BACKGROUND OF THE INVENTION

The striking clinical success of cancer immunotherapy with checkpoint blockade suggests it is likely to form the foundation of curative therapy for many malignancies (Reck et al. (2016) N. Engl. J. Med. 375:1823-1833; Hodi et al. (2010) N. Engl. J. Med. 363:711-723; Postow et al. (2015) N. Engl. J. Med. 372:2006-2017; Wolchok et al. (2013) N. Engl. J. Med. 369:122-133; Ferris et al. (2016) N. Engl. J. Med. 375:1856-1867; Brahmer et al. (2012) N. Engl. J. Med. 366:2455-2465; Nghiem et al. (2016) N. Engl. J. Med. 374:2542-2552; Topalian et al. (2012) N. Engl. J. Med. 366:2443-2454); Motzer et al. (2015) N. Engl. J. Med. 373:1803-1813). However, despite these successes, checkpoint blockade does not achieve sustained clinical response in most patients (Tumeh et al. (2014) Nature 515:568-571; Kelderman et al. (2014) Mol. Oncol. 8:1132-1139; Zaretsky et al. (2016) N. Engl. J. Med. 375:819-829). Additional therapeutic strategies are therefore needed to increase the clinical efficacy of immunotherapy. Moreover, the optimal strategy for combining emerging cancer immunotherapies with checkpoint blockade remains uncertain.

A relatively small number of genes, such as PD-L1, that enable tumors to evade the immune system have been discovered and most of these are already the focus of intense efforts to develop new immunotherapies (Freeman et al. (2000) J. Exp. Med. 192:1027-1034; Hirano et al. (2005) Cancer Res. 65:1089-1096; Dong et al. (2002) Nat. Med. 8:793-800; Balachandran et al. (2011) Nat. Med. 17:1094-1100; Spranger et al. (2013) Sci Transl Med. 5:200ra116; Holmgaard et al. (2013) J. Exp. Med. 210:1389-1402; Sockolosky et al. (2016) Proc. Natl. Acad. Sci. U.S.A. 113:E2646-654; Liu et al. (2015) Nat. Med. 21:1209-1215; Weiskopf et al. (2016) J. Clin. Invest. 126:2610-2620; Tseng et al. (2013) Proc. Natl. Acad. Sci. U.S.A. 110: 11103-11108; Sica et al. (2003) Immunity 18:849-861; Zang et al. (2007) Proc. Natl. Acad. Sci. U.S.A. 104, 19458-19463). Although cancer cells could, in theory, express many more genes that regulate their response or resistance to tumor immunity, strategies to systematically discover such genes are lacking.

Loss-of-function genetic screens have been increasingly used to study the functional consequences of gene deletion on tumor cells (Howard et al. (2016) Cold Spring Harb. Symp. Quant. Biol. (2016); Ebert et al. (2008) Nature 451:335-339; Cowley et al. (2014) Scientific Data 1:article number 140035). These approaches include pooled genetic screens using CRISPR-Cas9-mediated genome editing that simultaneously test the role of a large number of genes on tumor cell growth, viability or drug resistance (Wang et al. (2014) Science 343:80-84; Shalem et al. (2014) Science 343:84-87). However, these screens have generally been conducted in vitro, where the contribution of the immune system is absent, or have studied phenotypes such as metastasis that do not directly evaluate the role of tumor immunity (Hart et al. (2015) Cell 163:1515-1526; Yu et al. (2016) Nat. Biotechnol. 34:419-423; Chen et al. (2015) Cell 160:1246-1260).

Accordingly, a great need in the art exists for additional cancer therapeutic strategies, either alone or in combination with a cancer therapy such as modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist) or an immunotherapy like an immune checkpoint inhibitor, and genetic screens to identify cancer therapeutic targets.

SUMMARY OF THE INVENTION

The present invention is based, at least in part, on the discovery that modulating, such as inhibiting or blocking, or enhancing, one or more biomarkers described herein, including those listed in Table 1, provided in the examples, and/or described in the detailed description below, such as one or more regulators of dsRNA editing, sensing and metabolism pathways (e.g., Adar, Zc3hav1, Ppp1r15a, and/or Eif2ak2), either alone or in combination with an immunotherapy (e.g., an immunotherapy disclosed herein, such as a an immunotherapy that inhibits and immune checkpoint or an anti-cancer vaccine and/or virus) and/or modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist), results in a therapeutic benefit for treating cancers. Reference to certain biomarkers useful according to the present invention, such as ADAR, ZC3HAV1, PPP1R15A, and EIF2AK2/PKR, are not to be construed as limiting, but rather to be illustrative of biomarkers described herein that are useful according to the present invention. For example, Adar is a representative, non-limiting biomarker of the present invention. Alternatively, additional biomarkers can include the an interferon response signature such as the Hallmark Response to Interferon Alpha or the Hallmark Response to Interferon Gamma. In some embodiments, the biomarker is a proxy for a response to interferon. In some embodiments, the proxy for response is staining with the an antibody that recognizes dsRNA (e.g., J2 antibody) and/or an antibody that recognizes any member of the STAT family of transcription factors in either phosphorylated or unphosphorylated states. In some embodiments, the proxy for response is STAT1 signaling. The biomarker may be any biomarker that is strongly associated with Type I and Type II IFN signaling. RNA-specific adenosine deaminase (ADAR1) catalyzes adenosine-to-inosine edits on double stranded RNA.

ADAR1 has been shown to edit pre-mRNAs, leading to coding changes, where inosine is read as guanine, as well as pre-miRNAs, lncRNAs, and dsRNAs as low as 36 base pairs. ADAR1 edits endogenous dsRNAs, masking them from intracellular RNA sensors. This editing is thought to detoxify endogenous dsRNAs so they are not mistaken for invading viral RNAs. ADAR1 inhibition activates RNA sensing pathways, which mirrors the cGAS-STING DNA sensing pathway. ADAR1 is an alias of ADAR. As used herein, an ADAR inhibitor includes, but is not limited to, any agent that can decrease the copy number, amount, and/or inhibit the activity of, the at least one Adar variant or isoform listed in Table 1. Mutations in ADAR1 cause Aicardi-Goutières syndrome (AGS) which is associated with a type I interferon signature. AGS is an early onset childhood inflammatory disorder in which symptoms mimic in utero viral infection. AGS patients display chronic increased interferon gene expression signature. In addition, ISG15 is an interferon signaling pathway suppressor and has been ascribed to have an antiviral role.

In one aspect, a method of treating a subject afflicted with a cancer comprising administering to the subject a therapeutically effective amount of an agent that inhibits or enhances the copy number, the expression level, and/or the activity of one or more biomarkers listed in Table 1 or a fragment thereof, is provided.

Numerous embodiments are further provided that can be applied to any aspect of the present invention and/or combined with any other embodiment described herein. For example, in one embodiment, the agent described herein decreases or increases the copy number, the expression level, and/or the activity of Adar, Zc3hav1, Ppp1r15a, and/or Eif2ak2. In another embodiment, the agent described herein selectively decreases the catalytic activity and/or the substrate binding activity of ADAR. In still another embodiment, the agent described herein is a small molecule inhibitor or agonist, CRISPR single-guide RNA (sgRNA), RNA interfering agent, antisense oligonucleotide, peptide or peptidomimetic inhibitor, aptamer, polypeptide agonist, or intrabody. In one embodiment, the RNA interfering agent is a small interfering RNA (siRNA), CRISPR RNA (crRNA), a small hairpin RNA (shRNA), a microRNA (miRNA), or a piwi-interacting RNA (piRNA). In another embodiment, the RNA interfering agent is a CRISPR single-guide RNA (sgRNA). In still another embodiment, the sgRNA comprises a nucleic acid sequence selected from the group consisting of nucleic acid sequence listed in Table 2, Table 3, or Table 5. In yet another embodiment, the agent described herein comprises an intrabody, or an antigen binding fragment thereof, which specifically binds to ADAR and/or a substrate of ADAR. In one embodiment, the intrabody, or antigen binding fragment thereof, is murine, chimeric, humanized, composite, or human. In another embodiment, the intrabody, or antigen binding fragment thereof, is detectably labeled, comprises an effector domain, comprises an Fc domain, and/or is selected from the group consisting of Fv, Fav, F(ab')2, Fab', dsFv, scFv, sc(Fv)2, and diabodies fragments. In still another embodiment, the intrabody, or antigen binding fragment thereof, is conjugated to a cytotoxic agent. In yet another embodiment, the cytotoxic agent is selected from the group consisting of a chemotherapeutic agent, a biologic agent, a toxin, and a radioactive isotope. In one embodiment, the agent described herein increases the sensitivity of the cancer cells to an immunotherapy and/or a modulator of intratumoral interferon, optionally the modulator of intratumoral interferon increases interferon level. In still another embodiment, the method described herein further comprises administering to the subject an immunotherapy and/or a modulator of intratumoral interferon. In another embodiment, the immunotherapy and/or the modulator of intratumoral interferon is administered before, after, or concurrently with the agent. In still another embodiment, the immunotherapy comprises an anti-cancer vaccine and/or virus. In yet another embodiment, the immunotherapy is cell-based. In one embodiment, the immunotherapy inhibits an immune checkpoint, such as an immune checkpoint selected from the group consisting of CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRP, CD47, CD48, 2B4 (CD244), B7.1, B7.2, ILT-2, ILT-4, TIGIT, HHLA2, butyrophilins, IDO, CD39, CD73 and A2aR. In another embodiment, the modulator of intratumoral interferon described herein is selected from the group consisting of radiation, a radiosensitizer, an immunogenic chemotherapy that induce interferon production by the cancer cells or at the site of a tumor, interferon, an interferon-inducing agent, a topical inflammatory agent, and/or a topical TLR agonist. In still another embodiment, the biomarker described herein comprises a nucleic acid sequence having at least 95% identity to a nucleic acid sequence listed in Table 1 and/or encodes an amino acid sequence having at least 95% identity to an amino acid sequence listed in Table 1. In yet another embodiment, the agent described herein reduces the number of proliferating cells in the cancer and/or reduces the volume or size of a tumor comprising the cancer cells. In another embodiment, the agent promotes anti-viral dsRNA editing, sensing, and/or metabolism in the subject. In still another embodiment, the agent increases the sensitivity of the cancer to interferon, such as IFNβ and/or IFNγ. In yet another embodiment, the increase of the sensitivity of the cancer is EIF2AK2-dependent. In one embodiment, the agent described herein increases secretion of interferon of the cancer cells, such as IFNβ. In still another embodiment, the method described herein further comprises administering to the subject interferon and/or another agent or a therapy to increase interferon levels in the microenvironment of the cancer cells. In another embodiment, the agent described herein is administered in a pharmaceutically acceptable formulation.

In another aspect, a method of killing cancer cells comprising contacting the cancer cells with an agent that inhibits or enhances the copy number, the expression level, and/or the activity of one or more biomarkers listed in Table 1 or a fragment thereof, is provided.

As described above, numerous embodiments are further provided that can be applied to any aspect of the present invention and/or combined with any other embodiment described herein. For example, in one embodiment, the agent described herein decreases or increases the copy number, the expression level, and/or the activity of Adar, Zc3hav1, Ppp1r15a, and/or Eif2ak2. In another embodiment, the agent described herein selectively decreases or increases the catalytic activity and/or the substrate binding activity of ADAR. In still another embodiment, the agent is a small molecule inhibitor or agonist, CRISPR single-guide RNA (sgRNA), RNA interfering agent, antisense oligonucleotide, peptide or peptidomimetic inhibitor, aptamer, polypeptide agonist, or intrabody. In yet another embodiment, the RNA interfering agent is a small interfering RNA (siRNA), CRISPR RNA (crRNA), a small hairpin RNA (shRNA), a microRNA (miRNA), or a piwi-interacting RNA (piRNA). In one embodiment, the RNA interfering agent is a CRISPR single-guide RNA (sgRNA). In another embodiment, the sgRNA comprises a nucleic acid sequence selected from the group consisting of nucleic acid sequence listed in Table 2, Table 3, or Table 5. In still another embodiment, the agent described herein comprises an intrabody, or an antigen binding fragment thereof, which specifically binds to ADAR and/or a substrate of ADAR. In one embodiment, the intrabody, or antigen binding fragment thereof, is murine, chimeric, humanized, composite, or human. In another embodiment, the intrabody, or antigen binding fragment thereof, is detectably labeled, comprises an effector domain, comprises an Fc domain, and/or is selected from the group consisting of Fv, Fav, F(ab')2, Fab', dsFv, scFv, sc(Fv)2, and diabodies fragments. In still another embodiment, the intrabody, or antigen binding fragment thereof, is conjugated to a cytotoxic agent. In yet another embodiment, the cytotoxic agent is selected from the group consisting of a chemotherapeutic agent, a biologic agent, a toxin, and a radioactive isotope. In another embodiment, the agent described herein increases the sensitivity of the cancer cells to an immunotherapy and/or a modulator of intratumoral interferon, optionally the modulator of intratumoral interferon increases interferon level. In still embodiment, the method described herein further comprises contacting the cancer cells with an immunotherapy and/or a modulator of intratumoral interferon. In another embodiment, the immunotherapy and/or the modulator of intratumoral interferon is administered before, after, or concurrently with the agent. In still another embodiment, the immunotherapy comprises an anti-cancer vaccine and/or virus. In yet another embodiment, the immunotherapy is cell-based. In one embodiment, the immunotherapy inhibits or enhances an immune checkpoint, such as an immune checkpoint selected from the group consisting of CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRP, CD47, CD48, 2B4 (CD244), B7.1, B7.2, ILT-2, ILT-4, TIGIT, HHLA2, butyrophilins, IDO, CD39, CD73 and A2aR. In another embodiment, the modulator of intratumoral interferon is selected from the group consisting of radiation, a radiosensitizer, an immunogenic chemotherapy that induce interferon production by the cancer cells or at the site of a tumor, interferon, an interferon-inducing agent, a topical inflammatory agent, and/or a topical TLR agonist. In still another embodiment, the biomarker described herein comprises a nucleic acid sequence having at least 95% identity to a nucleic acid sequence listed in Table 1 and/or encodes an amino acid sequence having at least 95% identity to an amino acid sequence listed in Table 1. In another embodiment, the agent described herein reduces the number of proliferating cells in the cancer and/or reduces the volume or size of a tumor comprising the cancer cells. In still another embodiment, the agent described herein promotes anti-viral dsRNA editing, sensing, and/or metabolism by the cancer cells. In yet another embodiment, the agent described herein increases the sensitivity of the cancer cells to interferon, such as IFNβ and/or IFNγ. In one embodiment, the increase of the sensitivity of the cancer cells is EIF2AK2-dependent. In another embodiment, the agent described herein increases secretion of interferon of the cancer cells, such as IFNβ. In still another embodiment, the method described herein further comprises contacting the cancer cells with interferon and/or another agent or a therapy to increase interferon levels in the microenvironment of the cancer cells. In another embodiment, the interferon and/or another agent or a therapy to increase interferon levels in the microenvironment of the cancer cells is administered before, after, or concurrently with the agent. In still another embodiment, the agent described herein is administered in a pharmaceutically acceptable formulation.

In another aspect, a method of determining whether a subject afflicted with a cancer or at risk for developing a cancer would benefit from inhibiting or enhancing the copy number, amount, and/or activity of at least one biomarker listed in Table 1, is provided, the method comprising a) obtaining a biological sample from the subject; b) determining the copy number, amount, and/or activity of at least one biomarker listed in Table 1; c) determining the copy number, amount, and/or activity of the at least one biomarker in a control; and d) comparing the copy number, amount, and/or activity of the at least one biomarker detected in steps b) and c), wherein the presence of, or a significant increase or decrease in, the copy number, amount, and/or activity of, the at least one biomarker listed in Table 1 in the subject sample relative to the control copy number, amount, and/or activity of the at least one biomarker indicates that the subject afflicted with the cancer or at risk for developing the cancer would benefit from inhibiting or enhancing the copy number, amount, and/or activity of the at least one biomarker listed in Table 1. As stated above, numerous embodiments can be applied to any aspect of the present invention. Also, it is clear that inhibiting or blocking Adar increases inflammation and tumor immunity and, for some embodiments, it is believed that inhibiting or blocking Zc3hav1 and/or Ppp1r15a has a similar effect based on certain screening data. For certain embodiments, it is also believed that enhancing of Eif2ak2 (i.e., PKR), such as through agonist stimulation, would act to increase tumor immunity, based on certain screening and ADAR-contextualized data. Accordingly, in certain embodiments of the methods of the present invention, inhibiting/blocking Adar, Zc3hav1, and/or Ppp1r15a and/or promoting Eif2ak, such as by decreasing or increasing, respectively, the biomarker copy number, amount, activity, ability to interact/bind to substrates and/or, increasing or decreasing, respectively, their degradation, stability, interaction with, and/or binding to inhibitors in order to treat cancer, either alone or in combination with additional cancer therapies, such as an immunotherapy. Similarly, it is clear in certain embodiments that methods of screening for biomarker modulators and methods of diagnosing, prognosing, and monitoring cancer involving determining the copy number, amount, activity, ability to interact/bind to substrates of ADAR, ZC3HAV1, PPP1R15A, and/or EIF2AK2/PKR at a point in time, over time, and/or association with an intervention in such embodiments are based on the respective association between immunomodulation based on inhibiting/blocking Adar, Zc3hav1, and/or Ppp1r15a and/or promoting Eif2ak.

For example, in one embodiment, the method described herein further comprises recommending, prescribing, or administering an agent that inhibits or enhances the at least one biomarker listed in Table 1 if the cancer is determined to benefit from the agent. In another embodiment, the method described herein further comprises administering at least one additional cancer therapy that is administered before, after, or concurrently with the agent. In still another embodiment, the method described herein further comprises recommending, prescribing, or administering cancer therapy other than an agent that inhibits or enhances the at least one biomarker listed in Table 1 if the cancer is determined to not benefit from the agent. In yet another embodiment, the cancer therapy is selected from the group consisting of immunotherapy, targeted therapy, chemotherapy, radiation therapy, hormonal therapy, an anti-cancer vaccine, an anti-cancer virus, a checkpoint inhibitor, a radiosensitizer, an immunogenic chemotherapy that induces interferon production by the cancer cells or at the site of a tumor, interferon, an interferon-inducing agent, a topical inflammatory agent, and/or a topical TLR agonist (such as imiquimod). In one embodiment, the control sample is determined from a cancerous or non-cancerous sample from either the patient or a member of the same species to which the patient belongs. In another embodiment, the control sample comprises cells.

In another aspect, a method for predicting the clinical outcome of a subject afflicted with a cancer expressing one or more biomarkers listed in Table 1 or a fragment thereof, is provided, the method comprising a) determining the copy number, amount, and/or activity of at least one biomarker listed in Table 1 in a subject sample; b) determining the copy number, amount, and/or activity of the at least one biomarker in a control having a good clinical outcome; and c) comparing the copy number, amount, and/or activity of the at least one biomarker in the subject sample and in the control, wherein the presence or absence of, or a significant increase or decrease in, the copy number, amount, and/or activity of, the at least one biomarker listed in Table 1 in the subject sample as compared to the copy number, amount and/or activity in the control, is an indication that the subject has a poor clinical outcome.

In another aspect, a method for monitoring the progression of a cancer in a subject, wherein the subject is administered a therapeutically effective amount of an agent that inhibits the copy number, amount, and/or activity of at least one biomarker listed in Table 1, is provided, the method comprising a) detecting in a subject sample at a first point in time the copy number, amount, and/or activity of at least one biomarker listed in Table 1; b) repeating step a) at a subsequent point in time; and c) comparing the amount or activity of at least one biomarker listed in Table 1 detected in steps a) and b) to monitor the progression of the cancer in the subject.

In another aspect, a method of assessing the efficacy of an agent that inhibits or enhances the copy number, amount, and/or activity of at least one biomarker listed in Table 1 for treating a cancer in a subject, is provided, comprising a) detecting in a subject sample at a first point in time the copy number, amount, and/or or activity of at least one biomarker listed in Table 1; b) repeating step a) during at least one subsequent point in time after administration of the agent; and c) comparing the copy number, amount, and/or activity detected in steps a) and b), wherein the absence or presence of, or a significant decrease or increase in, the copy number, amount, and/or activity of, the at least one biomarker listed in Table 1, in the subsequent sample as compared to the copy number, amount, and/or activity in the sample at the first point in time, indicates that the agent treats the cancer in the subject.

As described above, numerous embodiments can be applied to any aspect of the present invention. For example, in one embodiment, between the first point in time and the subsequent point in time, the subject has undergone treatment, completed treatment, and/or is in remission for the cancer. In another embodiment, the cancer treatment is selected from the group consisting of immunotherapy, targeted therapy, chemotherapy, radiation therapy, hormonal therapy, an anti-cancer vaccine, an anti-cancer virus, a checkpoint inhibitor, a radiosensitizer, an immunogenic chemotherapy that induce interferon production by the cancer cells or at the site of a tumor, interferon, an interferon-inducing agent, a topical inflammatory agent, and/or a topical TLR agonist. In still another embodiment, the first and/or at least one subsequent sample is selected from the group consisting of ex vivo and in vivo samples. In yet another embodiment, the first and/or at least one subsequent sample is a portion of a single sample or pooled samples obtained from the subject. In one embodiment, the sample described herein comprises cells, serum, peritumoral tissue, and/or intratumoral tissue obtained from the subject. In another embodiment, the one or more biomarkers listed in Table 1 comprise Adar, Zc3hav1, Ppp1r15a, and/or Eif2ak2. In still another embodiment, the cancer is in a subject and the subject has upregulation of interferon. In yet another embodiment, the cancer cells are in a parainflamed tumor. In one embodiment, the cancer cells produce interferon. In another embodiment, the cancer is selected from the group consisting of melanoma, colorectal cancer, Aicardi Goutieres Syndrome (AGS), gliomas, neuroblastoma, prostate cancer, breast cancer, pancreatic ductal carcinoma, epithelial ovarian cancer, B-CLL, leukemia, B cell lymphoma, and renal cell carcinoma. In still another embodiment, the cancer is in a subject and the subject is an animal model of the cancer. In yet another embodiment, the animal model is a mouse model. In one embodiment, the cancer is in a subject and the subject is a mammal. In another embodiment, the mammal is a mouse or a human. In still another embodiment, the mammal is a human.

In some aspects, the present disclosure provides a method of detecting ADAR1 dependency in a high proliferation cell comprising: (a) contacting the high proliferation cell with an ADAR1 inhibitor; and (b) determining proliferation in the high proliferation cell contacted with the ADAR1 inhibitor, wherein if proliferation is decreased relative to a high proliferation cell not contacted with the ADAR1 inhibitor, the high proliferation cell has ADAR dependency. As described herein, it was found that ADAR1-dependent cell lines and ISG-15 dependent cell lines show a high basal level of interferon signaling pathway activity due to an activated cGAS-STING pathway.

In some embodiments, the ADAR1 inhibitor is a short hairpin RNA (shRNA) targeting ADAR1.

In some embodiments, the ADAR1 inhibitor is a guide RNA (gRNA) targeting ADAR1.

In some aspects, the present disclosure provides a method of detecting ISG15 dependency in a high proliferation cell comprising: (a) contacting the high proliferation cell with an ISG15 inhibitor; and (b) determining proliferation in the high proliferation cell contacted with the ISG15 inhibitor, wherein if the proliferation is decreased relative to a high proliferation cell not contacted with the ISG15 inhibitor, the high proliferation cell has ISG15 dependency.

In some embodiments, the ISG15 inhibitor is a guide RNA (gRNA) targeting ISG15.

In some embodiments, the ISG15 inhibitor is a short hairpin RNA (shRNA) targeting ISG15.

In some embodiments, the high proliferation cell is a cancer cell, and the cancer cell is derived from a biological sample from a subject. In some particular embodiments, the subject has lung cancer or pancreatic cancer. In some particular embodiments, the subject has lung cancer.

In some embodiments, the subject has a cancer caused by a virus. In some particular embodiments, the virus is selected from human papilloma virus (HPV), Epstein-Barr virus (EBV), hepatitis B virus (HBV), hepatitis C virus (HCV), human herpes virus 8 (HHV-8), human T-lymphotrophic virus-1 (HTLV-1), and Merkel cell polyomavirus (MCV).

In some aspects, the present disclosure provides a method of detecting increased interferon signaling pathway activity in a cancer cell comprising detecting the activity of one or more interferon stimulated factors in the cancer cell, wherein if the interferon signaling pathway activity is higher than average in other cancer cells, the cancer cell has increased interferon signaling pathway activity.

In some embodiments, detecting the activity of one or more interferon stimulated factors comprises determining the level of a cyclic dinucleotide in the cancer cell, wherein an elevated level of the cyclic dinucleotide indicates that the cancer cell has increased interferon signaling pathway activity. In some particular embodiments, the cyclic dinucleotide is selected from cyclic guanosine monophosphate-adenosine monophosphate (cGAMP), cyclic di-adenosine monophosphate (c-di-AMP), or cyclic diguanylate (c-di-GMP).

In some embodiments, detecting the activity of one or more interferon stimulated factors comprises determining the expression level and/or phosphorylation of one or more interferon stimulated genes (ISGs) in the cancer cell, wherein an elevated expression level and/or phosphorylation of the one or more ISGs indicates that the cancer cell has increased interferon signaling pathway activity. In some particular embodiments, the one or more interferon stimulated genes (ISGs) is selected from ADAR1, ISG15, USP18, STING, MDA5, PKR, EIF2a, ATF4, IRF9, RIG1, TBK1, IRF3, PD-L1, and a combination thereof. In some particular embodiments, the one or more interferon stimulated genes (ISGs) comprises ADAR1. In some particular embodiments, the expression level of ADAR1 comprises the expression level of the p150 isoform of ADAR1. In some particular embodiments, the one or more interferon stimulated genes (ISGs) comprises ISG15.

In some embodiments, the cancer cell comprises a virus selected from human papilloma virus (HPV), Epstein-Barr virus (EBV), hepatitis B virus (HBV), hepatitis C virus (HCV), human herpes virus 8 (HHV-8), human T-lymphotrophic virus-1 (HTLV-1), and Merkel cell polyomavirus (MCV).

In some embodiments, the cancer cell is a lung cancer cell or a pancreatic cancer cell.

In some embodiments, the method further comprises contacting the cancer cell with an effective amount of an ADAR1 inhibitor.

In some embodiments, the method further comprises contacting the cancer cell with an effective amount of an ISG15 inhibitor.

In some aspects, the present disclosure provides a method of treating a subject in need thereof, the method comprising administering to the subject an effective amount of an ADAR1 inhibitor.

In some embodiments, the ADAR1 inhibitor is a shRNA targeting ADAR1.

In some embodiments, the ADAR1 inhibitor is a gRNA targeting ADAR1.

In some embodiments, the method further comprises administering to the subject an effective amount of an interferon pathway activator.

In some embodiments, the interferon pathway activator is capable of stimulating the expression and/or phosphorylation of one or more genes selected from USP18, STING, cGAS, MDA5, PKR, EIF2α, ATF4, IRF9, RIG1, TBK1, IRF3, and PD-L1. In some particular embodiments, the interferon pathway activator is capable of stimulating the expression of STING.

In some embodiments, the interferon pathway activator is a cyclic dinucleotide. In some particular embodiments, the cyclic dinucleotide is selected from the group consisting of a cyclic guanosine monophosphate-adenosine monophosphate (cGAMP), a cyclic di-adenosine monophosphate (c-di-AMP), a cyclic diguanylate (c-di-GMP), a synthetic cyclic dinucleotide, and an isomer thereof.

In some embodiments, the interferon pathway activator is a DNA methylation inhibitor.

In some particular embodiments, the DNA methylation inhibitor is selected from the group consisting of 5-azacytidine, 5-aza-2'-deoxycytidine, and decitabine. In some particular embodiments, the DNA methylation inhibitor is 5-azacytidine.

In some embodiments, the interferon pathway activator is an interferon. In some particular embodiments, the interferon is a type I interferon. In some particular embodiments, the type I interferon is interferon-β (IFN-β).

In some embodiments, the subject has cancer. In some particular embodiments, the cancer is lung cancer or pancreatic cancer.

In some embodiments, the cancer is caused by a virus. In some particular embodiments, the virus is selected from human papilloma virus (HPV), Epstein-Barr virus (EBV), hepatitis B virus (HBV), hepatitis C virus (HCV), human herpes virus 8 (HHV-8), human T-lymphotrophic virus-1 (HTLV-1), and Merkel cell polyomavirus (MCV).

In some aspects, the present disclosure provides a method of screening to identify a cancer therapy, the method comprising: (a) obtaining a first population of cells and a second population of cells, wherein the first population of cells have elevated interferon signaling pathway activity relative to the second population of cells; (b) contacting the first and second populations of cells with a test agent; and (c) determining the viability of the first and second populations of cells after step (b), wherein the test agent is identified as a cancer therapy if the test agent reduces the viability of the first population of cells more than the viability of the second population of cells.

In some embodiments, wherein an elevated expression level and/or phosphorylation of one or more interferon stimulated genes (ISGs) indicates an elevated interferon signaling pathway activity. In some particular embodiments, the one or more interferon stimulated genes (ISGs) is selected from ADAR1, ISG15, USP18, STING, MDA5, PKR, EIF2α, ATF4, IRF9, RIG1, TBK1, IRF3, PD-L1, and a combination thereof. In some particular embodiments, the one or more interferon stimulated genes (ISGs) comprises ADAR1. In some particular embodiments, the expression level of ADAR1 comprises the expression level of the p150 isoform of ADAR1.

In some embodiments, the first population of cells is cancer cells. In some particular embodiments, the cancer cells are lung cancer cells or pancreatic cancer cells. In some particular embodiments, the cancer cells are lung cancer cells. In some embodiments, the cancer cells are selected from the group consisting of NCI-H196, HCC-366, NCI-H1650, PA-TU-8902, HCC-1438, NCI-H460, NCI-H596, HeLa, and SW-900.

In some embodiments, the cancer cells are caused by a virus. In some particular embodiments, the virus is selected from human papilloma virus (HPV), Epstein-Barr virus (EBV), hepatitis B virus (HBV), hepatitis C virus (HCV), human herpes virus 8 (HHV-8), human T-lymphotrophic virus-1 (HTLV-1), and Merkel cell polyomavirus (MCV).

In some embodiments, the second population of cells are derived from the first population of cells by contacting the first population of cells with an inhibitor of cGAS, STING, IFIT2, IFIT3, IFNAR, IFNAR2, IRF9, JAK1, STAT2, or TYK2. In some particular embodiments, the inhibitor is short hairpin RNA (shRNA) targeting cGAS, STING, IFIT2, IFIT3, IFNAR1, IFNAR2, IRF9, JAK1, STAT2, or TYK2.

In some particular embodiments, the inhibitor is guide RNA (gRNA) targeting cGAS, STING, IFIT2, IFIT3, IFNAR1, IFNAR2, IRF9, JAK1, STAT2, or TYK2. In some embodiments, the second population of cells are selected from the group consisting of A549, NCI-H460, NCI-H1437, NCI-H1299, RERFLCAI, RKN, BT20, and RKO.

In some embodiments, the first population of cells are derived from the second population of cells by contacting the second population of cells with an activator of cGAS, STING, IFIT2, IFIT3, IFNAR1, IFNAR2, IRF9, JAK1, STAT2, or TYK2. In some particular embodiments, the activator is capable of stimulating the expression and/or phosphorylation of one or more genes selected from cGAS, USP18, STING, MDA5, PKR, EIF2α, ATF4, IRF9, RIG1, TBK1, IRF3, and PD-L1. In some particular embodiments, the activator is capable of activating STING.

In some embodiments, the activator is a cyclic dinucleotide. In some particular embodiments, the cyclic dinucleotide is selected from the group consisting of a cyclic guanosine monophosphate-adenosine monophosphate (cGAMP), a cyclic di-adenosine monophosphate (c-di-AMP), a cyclic diguanylate (c-di-GMP), a synthetic cyclic dinucleotide, and an isomer thereof.

In some aspects, the present disclosure provides a method of identifying the likelihood of a cancer in a subject to be responsive to an ADAR1 inhibitor, the method comprising: a) obtaining or providing a subject sample from a patient having cancer; b) measuring the activity of the interferon signaling pathway in the subject sample; and c) comparing said activity of the interferon signaling pathway in a control sample, wherein a significantly increased activity of the interferon signaling pathway in the subject sample relative to the control sample identifies the cancer as being more likely to be responsive to the ADAR1 inhibitor; and wherein a significantly decreased activity of the interferon signaling pathway in the subject sample relative to the control sample identifies the cancer as being less likely to be responsive to the ADAR1 inhibitor.

In some embodiments, detecting the activity of one or more interferon stimulated factors comprises determining the level of a cyclic dinucleotide in the cancer cell, wherein an elevated level of the cyclic dinucleotide indicates that the cancer cell has increased interferon signaling pathway activity. In some particular embodiments, the cyclic dinucleotide is selected from cyclic guanosine monophosphate-adenosine monophosphate (cGAMP), cyclic di-adenosine monophosphate (c-di-AMP), or cyclic diguanylate (c-di-GMP).

In some embodiments, detecting the activity of one or more interferon stimulated factors comprises determining the expression level and/or phosphorylation of one or more interferon stimulated genes (ISGs) in the cancer cell, wherein an elevated expression level and/or phosphorylation of the one or more ISGs indicates that the cancer cell has increased interferon signaling pathway activity. In some particular embodiments, the one or more interferon stimulated genes (ISGs) is selected from ADAR1, ISG15, USP18, STING, MDA5, PKR, EIF2α, ATF4, IRF9, RIG1, TBK1, IRF3, PD-L1, and a combination thereof. In some particular embodiments, the one or more interferon stimulated genes (ISGs) comprises ADAR1. In some particular embodiments, the one or more interferon stimulated genes (ISGs) comprises PKR. In some particular embodiments, the one or more interferon stimulated genes (ISGs) comprises ISG15.f In some embodiments, the method further comprises recommending, prescribing, or administering the ADAR1 inhibitor if the cancer is determined likely to be responsive to the ADAR1 inhibitor.

In some embodiments, the method further comprises recommending, prescribing, or administering anti-cancer therapy other than the ADAR1 inhibitor as a single agent if the cancer is determined less likely to be responsive to the ADAR1 inhibitor. In some embodiments, wherein the anti-cancer therapy is selected from the group consisting of immunotherapy, targeted therapy, chemotherapy, radiation therapy, hormonal therapy, an anti-cancer vaccine, an anti-cancer virus, a checkpoint inhibitor, a localized interferon inducer, and/or an interferon pathway activator, optionally wherein the anti-cancer therapy comprises the ADAR1 inhibitor. In some embodiments, the anti-cancer therapy is administered to the subject in combination with the ADAR1 inhibitor, optionally wherein the anti-cancer therapy is administered before, after, or concurrently with the ADAR1 inhibitor.

In some embodiments, the localized interferon inducer is a STING agonist, chemotherapy, or radiation.

In some embodiments, the interferon pathway activator is capable of stimulating the expression and/or phosphorylation of one or more genes selected from USP18, STING, cGAS, MDA5, PKR, EIF2α, ATF4, IRF9, RIG1, TBK1, IRF3, and PD-L1. In some particular embodiments, the interferon pathway activator is capable of stimulating the expression of STING.

In some embodiments, the interferon pathway activator is a cyclic dinucleotide. In some particular embodiments, the cyclic dinucleotide is selected from the group consisting of a cyclic guanosine monophosphate-adenosine monophosphate (cGAMP), a cyclic di-adenosine monophosphate (c-di-AMP), a cyclic diguanylate (c-di-GMP), a synthetic cyclic dinucleotide, and an isomer thereof.

In some embodiments, the interferon pathway activator is a DNA methylation inhibitor. In some particular embodiments, the DNA methylation inhibitor is selected from the group consisting of 5-azacytidine, 5-aza-2'-deoxycytidine, and decitabine. In some particular embodiments, the DNA methylation inhibitor is 5-azacytidine.

In some embodiments, the interferon pathway activator is an interferon. In some particular embodiments, the interferon is a type I interferon. In some particular embodiments, the type I interferon is interferon-β (IFN-β).

In some embodiments, the cancer is lung cancer or pancreatic cancer. In some embodiments, the cancer is caused by a virus. In some particular embodiments, the virus is selected from human papilloma virus (HPV), Epstein-Barr virus (EBV), hepatitis B virus (HBV), hepatitis C virus (HCV), human herpes virus 8 (HHV-8), human T-lymphotrophic virus-1 (HTLV-1), and Merkel cell polyomavirus (MCV).

In some embodiments, the control sample is determined from a cancerous or non-cancerous sample from either the patient or a member of the same species to which the patient belongs. In some embodiments, the control sample comprises cells or does not comprise cells. In some embodiments, the control sample comprises cancer cells known to be responsive or non-responsive to the ADAR1 inhibitor.

In some aspects, a method of screening to identify an ADAR inhibitor is provided, such as a method comprising (a) obtaining a first population of cells and a second population of cells, wherein the first population of cells has ADAR dependency, and the second population of cells is derived from the first population of cells and has reduced activity of PKR, cGAS, and/or STING, optionally the reduced activity of PKR, cGAS, and/or STING comprises reduced expression level or phosphorylation of PKR, cGAS, and/or STING; (b) contacting the first and second populations of cells with a test agent; and (c) determining the viability of the first and second populations of cells after the contacting step (b), wherein the test agent is an ADAR inhibitor if the test agent reduces the viability of the first population of cells more than the viability of the second population of cells.

In some embodiments, the second population of cells comprises isogenic cells derived from the first population of cells with loss of function of PKR, cGAS, or STING. In certain embodiments, the second population of cells is derived from the first population of cells and has reduced activity of PKR, optionally the reduced activity of PKR comprises reduced expression level or phosphorylation of PKR. In certain embodiments, the second population of cells comprises isogenic cells derived from the first population of cells with loss of function of PKR.

In some embodiments, the method is performed in combination with the method of screening to identify a cancer therapy described herein. In certain embodiments, the method is performed before, after, or concurrently with the method of screening to identify a cancer therapy described herein. In certain embodiment, the test agent has been identified as a potent agent for cancer therapy using the method of screening to identify a cancer therapy described herein.

In some embodiments, an ADAR1 inhibitor or an ISG15 inhibitor may be a molecule that is capable of editing the genome of a cell to knock down or knock out the ADAR1 or ISG15 gene. For example an ADAR1 inhibitor or an ISG15 inhibitor may be nuclease agent that can create site-specific double-strand breaks at desired locations in the genome (e.g., at the ADAR1 or ISG15 loci). In one embodiment, the nuclease agent is a Transcription Activator-Like Effector Nuclease (TALEN). TAL effector nucleases are a class of sequence-specific nucleases that can be used to make double-strand breaks at specific target sequences in the genome of a prokaryotic or eukaryotic organism. TAL effector nucleases are created by fusing a native or engineered transcription activator-like (TAL) effector, or functional part thereof, to the catalytic domain of an endonuclease, such as, for example, FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See, WO 2010/079430; Morbitzer et al. (2010) PNAS 10.1073/pnas.1013133107; Scholze & Boch (2010) Virulence 1:428-432; Christian et al. Genetics (2010) 186:757-761; Li et al. (2010) Nuc. Acids Res. (2010) doi:10.1093/nar/gkg704; and Miller et al. (2011) Nature Biotechnology 29:143-148; all of which are herein incorporated by reference.

Examples of suitable TAL nucleases, and methods for preparing suitable TAL nucleases, are disclosed, e.g., in US Patent Application No. 2011/0239315 A1, 2011/0269234 A1, 2011/0145940 A1, 2003/0232410 A1, 2005/0208489 A1, 2005/0026157 A1, 2005/0064474 A1, 2006/0188987 A1, and 2006/0063231 A1 (each hereby incorporated by reference). In various embodiments, TAL effector nucleases are engineered that cut in or near a target nucleic acid sequence in, e.g., a genomic locus of interest, wherein the target nucleic acid sequence is at or near a sequence to be modified by a targeting vector. The TAL nucleases suitable for use with the various methods and compositions provided herein include those that are specifically designed to bind at or near target nucleic acid sequences to be modified by targeting vectors as described herein.

In one embodiment, each monomer of the TALEN comprises 33-35 TAL repeats that recognize a single base pair via two hypervariable residues. In one embodiment, the nuclease agent is a chimeric protein comprising a TAL repeat-based DNA binding domain operably linked to an independent nuclease. In one embodiment, the independent nuclease is a FokI endonuclease. In one embodiment, the nuclease agent comprises a first TAL-repeat-based DNA binding domain and a second TAL-repeat-based DNA binding domain, wherein each of the first and the second TAL-repeat-based DNA binding domain is operably linked to a FokI nuclease subunit, wherein the first and the second TAL-repeat-based DNA binding domain recognize two contiguous target DNA sequences in each strand of the target DNA sequence separated by a spacer sequence of varying length (12-20 bp), and wherein the FokI nuclease subunits dimerize to create an active nuclease that makes a double strand break at a target sequence.

The nuclease agent employed in the various methods and compositions disclosed herein can further comprise a zinc-finger nuclease (ZFN). In one embodiment, each monomer of the ZFN comprises 3 or more zinc finger-based DNA binding domains, wherein each zinc finger-based DNA binding domain binds to a 3 bp subsite. In other embodiments, the ZFN is a chimeric protein comprising a zinc finger-based DNA binding domain operably linked to an independent nuclease. In one embodiment, the independent endonuclease is a FokI endonuclease. In one embodiment, the nuclease agent comprises a first ZFN and a second ZFN, wherein each of the first ZFN and the second ZFN is operably linked to a FoId nuclease subunit, wherein the first and the second ZFN recognize two contiguous target DNA sequences in each strand of the target DNA sequence separated by about 5-7 bp spacer, and wherein the FokI nuclease subunits dimerize to create an active nuclease that makes a double strand break. See, for example, US20060246567; US20080182332; US20020081614; US20030021776; WO/2002/057308A2; US20130123484; US20100291048; WO/2011/017293A2; and Gaj et al. (2013) Trends in Biotechnology, 31(7):397-405, each of which is herein incorporated by reference.

In one embodiment of the methods provided herein, the nuclease agent comprises (a) a chimeric protein comprising a zinc finger-based DNA binding domain fused to a FoId endonuclease; or, (b) a chimeric protein comprising a Transcription Activator-Like Effector Nuclease (TALEN) fused to a FokI endonuclease.

In still another embodiment, the nuclease agent is a meganuclease. Meganucleases have been classified into four families based on conserved sequence motifs. These motifs participate in the coordination of metal ions and hydrolysis of phosphodiester bonds. HEases are notable for their long recognition sites, and for tolerating some sequence polymorphisms in their DNA substrates. Meganuclease domains, structure and function are known, see for example, Guhan and Muniyappa (2003) Crit Rev Biochem Mol Biol 38:199-248; Lucas et al., (2001) Nucleic Acids Res 29:960-9; Jurica and Stoddard, (1999) Cell Mol Life Sci 55:1304-26; Stoddard, (2006) Q Rev Biophys 38:49-95; and Moure et al., (2002) Nat Struct Biol 9:764. In some examples a naturally occurring variant, and/or engineered derivative meganuclease is used. Methods for modifying the kinetics, cofactor interactions, expression, optimal conditions, and/or recognition site specificity, and screening for activity are known, see for example, Epinat et al., (2003) Nucleic Acids Res 31:2952-62; Chevalier et al., (2002) Mol Cell 10:895-905; Gimble et al., (2003) Mol Biol 334:993-1008; Seligman et al., (2002) Nucleic Acids Res 30:3870-9; Sussman et al., (2004) J Mol Biol 342:31-41; Rosen et al., (2006) Nucleic Acids Res 34:4791-800; Chames et al., (2005) Nucleic Acids Res 33:e178; Smith et al., (2006) Nucleic Acids Res 34:e149; Gruen et al., (2002) Nucleic Acids Res 30:e29; Chen and Zhao, (2005) Nucleic Acids Res 33:e154; WO2005105989; WO2003078619; WO2006097854; WO2006097853; WO2006097784; and WO2004031346.

Any meganuclease can be used herein, including, but not limited to, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, PI-PspI, F-SceI, F-SceII, F-SuvI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NcIIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp6803I, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, I-ZbiIP, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, PI-TliII, or any active variants or fragments thereof.

Nuclease agents can further comprise restriction endonucleases (restriction enzymes), which include Type I, Type II, Type III, and Type IV endonucleases. Type I and Type III restriction endonucleases recognize specific recognition sites, but typically cleave at a variable position from the nuclease binding site, which can be hundreds of base pairs away from the cleavage site (recognition site). In Type II systems the restriction activity is independent of any methylase activity, and cleavage typically occurs at specific sites within or near to the binding site. Most Type II enzymes cut palindromic sequences, however Type IIa enzymes recognize non-palindromic recognition sites and cleave outside of the recognition site, Type IIb enzymes cut sequences twice with both sites outside of the recognition site, and Type IIs enzymes recognize an asymmetric recognition site and cleave on one side and at a defined distance of about 1-20 nucleotides from the recognition site. Type IV restriction enzymes target methylated DNA. Restriction enzymes are further described and classified, for example in the REBASE database (webpage at "rebase.neb"followed by".com"; Roberts et al., (2003) Nucleic Acids Res 31:418-20), Roberts et al., (2003) Nucleic Acids Res 31:1805-12, and Belfort et al., (2002) in Mobile DNA II, pp. 761-783, Eds. Craigie et al., (ASM Press, Washington, D.C.). In specific embodiments, at least two endonuclease enzymes can be selected as the nuclease agents wherein the enzymes create compatible, or complementary, sticky ends.

The nuclease agent employed in the various methods and compositions can also comprise a CRISPR/Cas system. Such systems can employ a Cas9 nuclease, which in some instances, is codon-optimized for the desired cell type in which it is to be expressed. The system further employs a fused crRNA-tracrRNA construct that functions with the codon-optimized Cas9. This single RNA is often referred to as a guide RNA or gRNA. Within a gRNA, the crRNA portion is identified as the "target sequence" for the given recognition site and the tracrRNA is often referred to as the "scaffold." This system has been shown to function in a variety of eukaryotic and prokaryotic cells. Briefly, a short DNA fragment containing the target sequence is inserted into a guide RNA expression plasmid. The gRNA expression plasmid comprises the target sequence (in some embodiments around 20 nucleotides), a form of the tracrRNA sequence (the scaffold) as well as a suitable promoter that is active in the cell and necessary elements for proper processing in eukaryotic cells. Many of the systems rely on custom, complementary oligos that are annealed to form a double stranded DNA and then cloned into the gRNA expression plasmid. The gRNA expression cassette and the Cas9 expression cassette are then introduced into the cell See, for example, Mali P et al. (2013) Science 2013 Feb. 15; 339 (6121):823-6; Jinek M et al. Science 2012 Aug. 17; 337 (6096):816-21; Hwang W Y et al. Nat Biotechnol March 2013; 31(3):227-9; Jiang W et al. Nat Biotechnol March 2013; 31(3):233-9; and, Cong L et al. Science 2013 Feb. 15; 339(6121):819-23, each of which is herein incorporated by reference.

The methods and compositions disclosed herein can utilize Clustered Regularly Interspersed Short Palindromic Repeats (CRISPR)/CRISPR-associated (Cas) systems or components of such systems to modify a genome within a cell. CRISPR/Cas systems include transcripts and other elements involved in the expression of, or directing the activity of, Cas genes. A CRISPR/Cas system can be a type I, a type II, or a type III system. The methods and compositions disclosed herein employ CRISPR/Cas systems by utilizing CRISPR complexes (comprising a guide RNA (gRNA) complexed with a Cas protein) for site-directed cleavage of nucleic acids.

Some CRISPR/Cas systems used in the methods disclosed herein are non-naturally occurring. A "non-naturally occurring" system includes anything indicating the involvement of the hand of man, such as one or more components of the system being altered or mutated from their naturally occurring state, being at least substantially free from at least one other component with which they are naturally associated in nature, or being associated with at least one other component with which they are not naturally associated. For example, some CRISPR/Cas systems employ non-naturally occurring CRISPR complexes comprising a gRNA and a Cas protein that do not naturally occur together.

Active variants and fragments of nuclease agents (i.e., an engineered nuclease agent) are also provided. Such active variants can comprise at least 65%, 70%, 75%, 80%, 85%, 90%, 91%, 92%, 93%, 94%, 95%, 96%, 97%, 98%, 99% or more sequence identity to the native nuclease agent, wherein the active variants retain the ability to cut at a desired recognition site and hence retain nick or double-strand-break-inducing activity. For example, any of the nuclease agents described herein can be modified from a native endonuclease sequence and designed to recognize and induce a nick or double-strand break at a recognition site that was not recognized by the native nuclease agent. Thus, in some embodiments, the engineered nuclease has a specificity to induce a nick or double-strand break at a recognition site that is different from the corresponding native nuclease agent recognition site. Assays for nick or double-strand-break-inducing activity are known and generally measure the overall activity and specificity of the endonuclease on DNA substrates containing the recognition site.

BRIEF DESCRIPTION OF THE DRAWINGS

FIG. 2 shows that deletion of Adar or its related genes sensitizes tumor cells to immunotherapy. A frequency histogram (top) and collapsed histogram (below) of enrichment or depletion (normalized as Z scores) for all sgRNAs in GVAX+PD-1 blockade-treated mice relative to TCRα$^{-/-}$ mice is shown. The dark vertical lines represent sgRNAs targeting Adar, Zc3hav1, or Ppp1r5a.

FIG. 4 shows that ADAR catalyzes adenosine to inosine (A-to-I) editing of dsRNA and is adapted from Pfaller et al. (2011) *Curr. Opin. Immunol.* 23:573-582.

FIG. 5 shows that A-to-I editing by ADAR prevents anti-viral sensing of dsRNA and is adapted from Gantier and Williams (2007) *Cytokine Growth Factor Rev.* 18:363-371.

FIG. 35 shows significant gene ontology (GO) categories for the genes upon which the NCI-H1650 and HCC366 ("HCC-366") cell lines depend for survival.

FIG. 36 is an immunoblot image showing the expression levels of interferon inducible genes in NCI-H196 and control cell line A549.

FIG. 39 shows the relative interferon production of different cell lines. The left panel is a plot of IFN-α and IFN-β mRNA expression level of the cell lines. The right panels are graphs showing the secretion of IFN-α (upper right) and IFN-β (lower right) from a number of cell lines as indicated.

FIG. 40 is a graph showing the effects of ADAR knockout on IFN-β secretion in different cell lines. Two CRISPR sgRNAs, ADAR1 sgRNA-1 and ADAR1 sgRNA-2, were used for ADAR1 knockout. Two sgRNAs targeting GFP were used as negative control.

FIG. 65 includes two panels, identified as panels A and B, which show that co-deletion of genes encoding MAVS, cGAS, or STING do not rescue ADAR knockout lethality in interferon treated A549 cells. Cell viability assessed 3 days after 10 ng/ml IFN-β treatment in double knockout A549 cell lines (Panel A, effect of MA VS knockout; Panel B, effect of TMEM173 (STING) or MB21D1 (cGAS) knockout).

FIG. 66 includes four panels, identified as panels A, B, C, and D, which show the gene expression signature and copy number analysis of interferon genes in human cancer. Panel A and Panel B show the histograms displaying interferon signature z-scores (Panel A, cancer cell lines in the CCLE; Panel B, tumors in TCGA with at least 70% tumor purity). Red line: interferon signature z-score cutoff at 2.26. Panel C shows the copy number plots of the 100 TCGA cancers with the lowest copy numbers for the IFN gene cluster. Schematic represents approximate genomic locations of each gene. Panel D shows a ranked list of genes with homozygous deletion by total sample number across 9,853 TCGA tumors with ABSOLUTE copy number data. Red bars: genes in the IFN gene cluster on chromosome 9p21.3.

FIG. 68 includes four panels, identified as panels A, B, C, and D, and is an exemplary illustration of the signaling pathway in which inhibition of ADAR leads to cell death. Panel A shows that in cells with low, basal interferon signaling, the cGAS-STING pathway is inactive and PKR levels are reduced. Panel B shows that upon cGAS-STING activation, interferon signaling and PKR protein levels are elevated but ADAR1 is still able to suppress PKR activation (FIG. 68, panel B). Panel C shows that once ADAR1 is deleted, the abundant PKR becomes activated and leads to downstream signaling and cell death. Panel D also shows this is also shown in normal cells lines (e.g. A549 and NCI-H1437) once exogenous interferon is introduced.

DETAILED DESCRIPTION OF THE INVENTION

Figure 1:
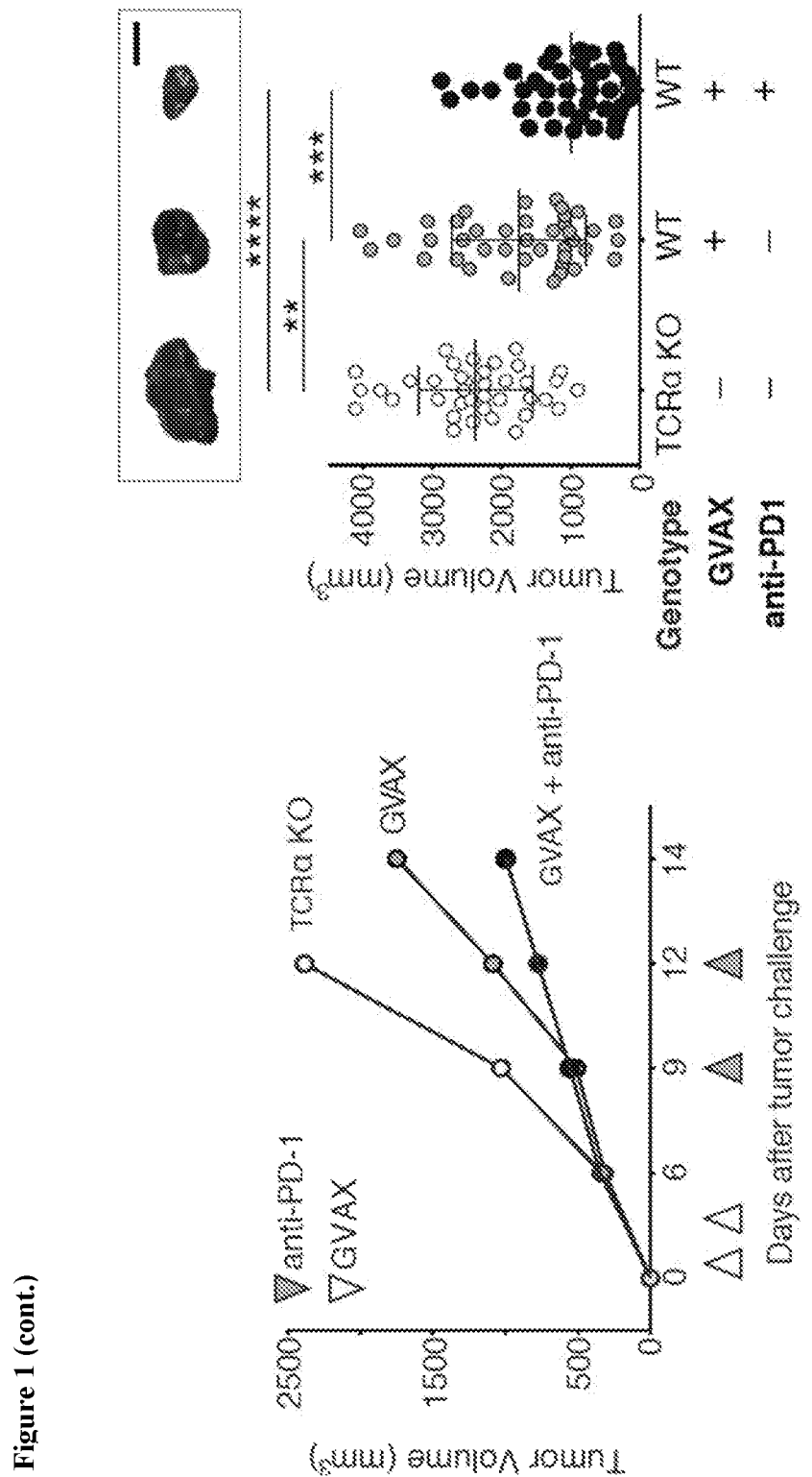
FIG. 1 includes 11 panels, identified as panels A, B, C, D, E, F, G, H, I, J, and K, which show that in vivo pooled loss-of-function screening using CRISPR/Cas9 in tumor cells recovers known mediators of immune evasion. Panel A shows a schematic diagram of the in vivo screening system using the B16 transplantable tumor model. Panel B shows a Western blot of B16 cell lysate for Cas9 and R-ACTIN with or without transduction with a lentiviral vector encoding Cas9. Panel C shows a frequency histogram (top) and collapsed histograms (middle) of enrichment or depletion (normalized as Z scores) for all 9,992 sgRNAs screened. Enrichment/depletion scores are averaged from 10 mice per condition. sgRNAs targeting PD-L1 are indicated by the dark vertical lines (middle). PD-L1 expression is compared among Cas9-expressing B16 tumor cells transfected with one of the four sgRNAs targeting PD-L1 (dark vertical line and shading) or a control sgRNA (grey) (bottom). Panel D shows a pie chart of the fraction of genes targeted in the screening in each of the GO term categories indicated. Panel E shows the results of tumor volumes (in mm$^3$) compared under each conditions, averaged for each group at each time point (left) or for individual animals on the day of sacrifice (right). Bars represent means, while whiskers represent standard deviation. Panel F shows two-dimensional histograms of the pair-wise distribution of sgRNAs abundance (averaged for each condition). Panel G shows the results of saturation analysis of animal replicates from the three in vivo screening conditions. Pearson correlations are calculated for the library distribution in one animal versus any other animal, then for two animals averaged versus any other two averaged, and so on. Saturation approaches r=0.95. Panel H shows a matrix of the Pearson correlations of the library distribution from one animal compared to any other animal for B16 Pool 1. Panel I shows the depletion of CD47 by its specific sgRNAs (indicated in dark vertical line and shading (top and middle) and CD47 expression after CRISPR editing with sgRNAs targeting CD47 (bottom) similar to the manner shown in Panel C. Panel J shows expression of CD47 by B16 cells transfected with either CD47-targeting (left curve) or control (grey) sgRNA. Panel K shows a changes in tumor volumes over time between CD47-null (bottom line; black) and control (top line; gray) tumors growing in mice treated with GVAX and PD-1 blockade (average and standard error of the mean; n=10 animals per group).  $p<0.01$; * $p<0.001$; **** $p<0.0001$.
Figure 1:
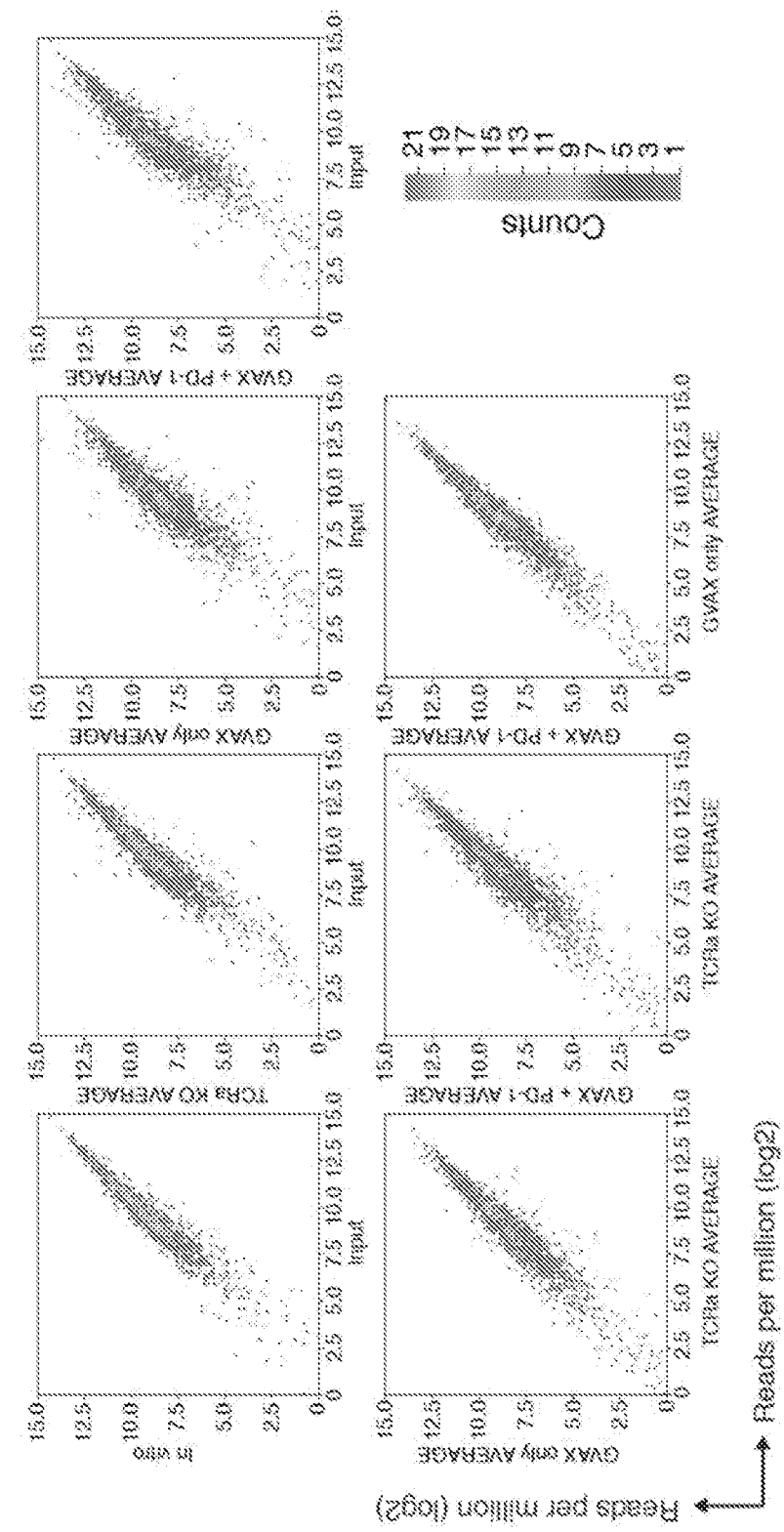
Figure 1:
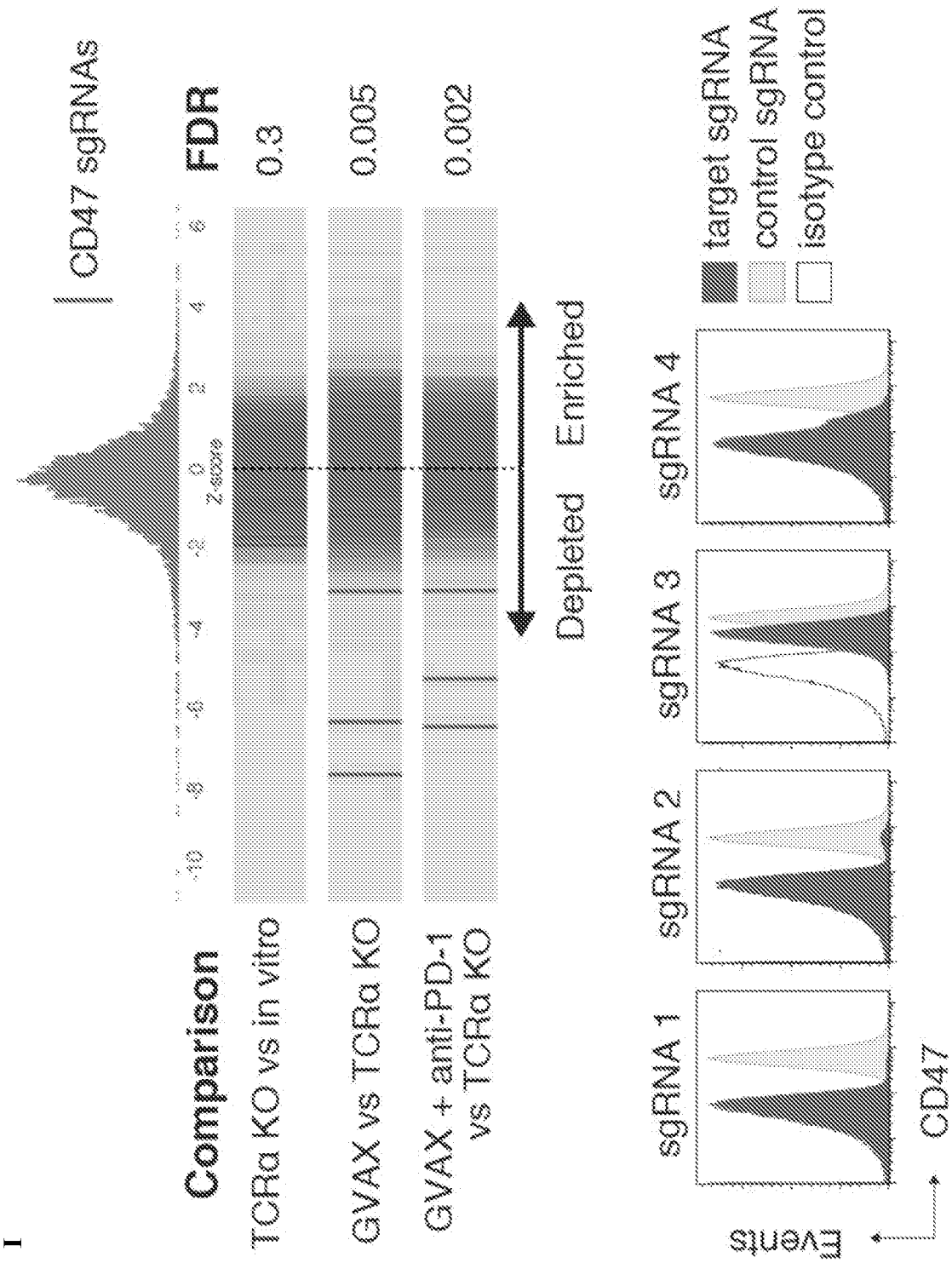

It has been determined herein that modulating (e.g., inhibiting or enhancing) regulators of dsRNA editing, sensing, and/or metabolism (e.g., inhibiting ADAR, ZC3HAV1, and/or PPP1R15A, or enhancing EIF2AK2/PKR, ZC3HAV1, and/or PPP1R15A, and/or modulating one or more biomarkers listed in Table 1, described in the examples, or otherwise described herein) increases dsRNA editing, sensing, and/or metabolism in tumor cells to thereby kill cancer cells and also augment tumor sensitivity to anti-cancer therapies, such as immunotherapies or modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist).

Thus, the instant disclosure provides at least a method of treating cancer, e.g., those cancer types otherwise not responsive or weakly responsive to immunotherapies and/or modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist), with a modulator of certain regulators of dsRNA editing, sensing, and/or metabolism (such as ADAR, ZC3HAV1, PPP1R15A, EIF2AK2/PKR, etc.), either alone or in combination with a cancer therapy such as modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist) or an immunotherapy like an immune checkpoint inhibitor. The results described herein are unexpected given that many cancers have a microenvironment where the cancer cells and/or the non-cancer cells produce interferon but the cancer is not, or at least less optimally, sensitive to the interferon in its microenvironment, as well as the fact that modulating sensitivity to interferon signaling is critical for immunotherapy effects rather than simply modulating interferon availability since interferon therapy is known to not significantly augment immunotherapy effects. Accordingly, the present invention provides methods of inhibiting Adar (or Zc3hav1, Ppp1r15a, etc.) or promoting Eif2ak2 (or Zc3hav1, Ppp1r15a, etc.), such as by inhibiting Adar (or Zc3hav1, Ppp1r15a, etc.) and/or promoting Eif2ak2 (or Zc3hav1, Ppp1r15a, etc.) copy number, amount, activity, ability to interact/bind to substrates and/or, increasing or decreasing, respectively, their degradation, stability, interaction with, and/or binding to inhibitors in order to treat cancer, either alone or in combination with additional cancer therapies, such as an immunotherapy or modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist). Similarly, methods of screening for these inhibitors and methods of diagnosing, prognosing, and monitoring cancer involving ADAR, ZC3HAV1, PPP1R15A, and/or EIF2AK2/PKR modulator monotherapies or combinational therapies are provided. Alternatively, additional biomarkers can include the an interferon response signature such as the Hallmark Response to Interferon Alpha or the Hallmark Response to Interferon Gamma. In some embodiments, the biomarker is a proxy for a response to interferon. In some embodiments, the proxy for response is staining with the an antibody that recognizes dsRNA (e.g., J2 antibody) and/or an antibody that recognizes any member of the STAT family of transcription factors in either phosphorylated or unphosphorylated states.

In some embodiments, the proxy for response is STAT1 signaling. The biomarker may be any biomarker that is associated with Type I and Type II IFN signaling. Inhibiting or blocking Adar increases inflammation and tumor immunity and, for some embodiments, it is believed that inhibiting or blocking Zc3hav1 and/or Ppp1r15a has a similar effect based on certain screening data. Zc3hav1 has a role in degradation of RNA that is believed to be associated with immunotherapy effects such that modulating related dsRNA stability and degradation regulators are believed to modify tumor immunity. Also, for some embodiments, it is believed that enhancing of Eif2ak2 (i.e., PKR), such as through agonist stimulation, would act to increase tumor immunity, based on certain screening and ADAR-contextualized data. Accordingly, in some embodiments, the present invention provides methods of inhibiting/blocking Adar, Zc3hav1, and/or Ppp1r15a and/or promoting Eif2ak, such as by decreasing or increasing, respectively, the biomarker copy number, amount, activity, ability to interact/bind to substrates and/or, increasing or decreasing, respectively, their degradation, stability, interaction with, and/or binding to inhibitors in order to treat cancer, either alone or in combination with additional cancer therapies, such as an immunotherapy or modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist). Similarly, methods of screening for these biomarker modulators and methods of diagnosing, prognosing, and monitoring cancer involving inhibiting/blocking ADAR, ZC3HAV1, PPP1R15A, and/or promoting EIF2AK2/PKR via modulator monotherapies or combinational therapies are provided. Alternatively, additional biomarkers can include the an interferon response signature such as the Hallmark Response to Interferon Alpha or the Hallmark Response to Interferon Gamma. In some embodiments, the biomarker is a proxy for a response to interferon. In some embodiments, the proxy for response is staining with the an antibody that recognizes dsRNA (e.g., J2 antibody) and/or an antibody that recognizes any member of the STAT family of transcription factors in either phosphorylated or unphosphorylated states. In some embodiments, the proxy for response is STAT1 signaling. The biomarker may be any biomarker that is strongly associated with Type I and Type II IFN signaling, The methods and compositions described herein are largely based on the finding that certain high proliferation cells, including cancer cells, are dependent on inhibitors of the interferon pathway in these cells. These inhibitors include ADAR1. These types of cells are sensitive to interferon pathway modulation. This modulation can occur, for example, through the inhibition of the expression or activity of an inhibitor, like ADAR1 or by the activation of an agonist of the pathway, like STING. The disclosure provides methods of detecting these cell types through dependency of these cells on interferon pathway inhibitors or detecting increased interferon pathway activity in high proliferation cells. The disclosure also provides methods of screening of antagonists of the inhibitors of the interferon pathway or agonists of the interferon pathway. In certain embodiments, these agents could be used to reduce the proliferation of high proliferation cells with relatively high interferon pathway activity. These high proliferation cells can include certain types of cancer cells.

I. Definitions

The articles "a" and "an" are used herein to refer to one or to more than one (i.e. to at least one) of the grammatical object of the article. By way of example, "an element" means one element or more than one element.

The term "altered amount" or "altered level" refers to increased or decreased copy number (e.g., germline and/or somatic) of a biomarker nucleic acid, e.g., increased or decreased expression level in a cancer sample, as compared to the expression level or copy number of the biomarker nucleic acid in a control sample. The term "altered amount" of a biomarker also includes an increased or decreased protein level of a biomarker protein in a sample, e.g., a cancer sample, as compared to the corresponding protein level in a normal, control sample. Furthermore, an altered amount of a biomarker protein may be determined by detecting posttranslational modification such as methylation status of the marker, which may affect the expression or activity of the biomarker protein.

The amount of a biomarker in a subject is "significantly" higher or lower than the normal amount of the biomarker, if the amount of the biomarker is greater or less, respectively, than the normal level by an amount greater than the standard error of the assay employed to assess amount, and preferably at least 20%, 30%, 40%, 50%, 60%, 70%, 80%, 90%, 100%, 150%, 200%, 300%, 350%, 400%, 500%, 600%, 700%, 800%, 900%, 1000% or than that amount. Alternately, the amount of the biomarker in the subject can be considered "significantly" higher or lower than the normal amount if the amount is at least about two, and preferably at least about three, four, or five times, higher or lower, respectively, than the normal amount of the biomarker. Such "significance" can also be applied to any other measured parameter described herein, such as for expression, inhibition, cytotoxicity, cell growth, and the like.

The term "altered level of expression" of a biomarker refers to an expression level or copy number of the biomarker in a test sample, e.g., a sample derived from a patient suffering from cancer, that is greater or less than the standard error of the assay employed to assess expression or copy number, and is preferably at least twice, and more preferably three, four, five or ten or more times the expression level or copy number of the biomarker in a control sample (e.g., sample from a healthy subjects not having the associated disease) and preferably, the average expression level or copy number of the biomarker in several control samples. The altered level of expression is greater or less than the standard error of the assay employed to assess expression or copy number, and is preferably at least 20%, 30%, 40%, 50%, 60%, 70%, 80%, 90%, 100%, 150%, 200%, 300%, 350%, 400%, 500%, 600%, 700%, 800%, 900%, 1000% or more times the expression level or copy number of the biomarker in a control sample (e.g., sample from a healthy subjects not having the associated disease) and preferably, the average expression level or copy number of the biomarker in several control samples. In some embodiments, the level of the biomarker refers to the level of the biomarker itself, the level of a modified biomarker (e.g., phosphorylated biomarker), or to the level of a biomarker relative to another measured variable, such as a control (e.g., phosphorylated biomarker relative to an unphosphorylated biomarker).

The term "altered activity" of a biomarker refers to an activity of the biomarker which is increased or decreased in a disease state, e.g., in a cancer sample, as compared to the activity of the biomarker in a normal, control sample. Altered activity of the biomarker may be the result of, for example, altered expression of the biomarker, altered protein level of the biomarker, altered structure of the biomarker, or, e.g., an altered interaction with other proteins involved in the same or different pathway as the biomarker or altered interaction with transcriptional activators or inhibitors.

The term "altered structure" of a biomarker refers to the presence of mutations or allelic variants within a biomarker nucleic acid or protein, e.g., mutations which affect expression or activity of the biomarker nucleic acid or protein, as compared to the normal or wild-type gene or protein. For example, mutations include, but are not limited to substitutions, deletions, or addition mutations. Mutations may be present in the coding or non-coding region of the biomarker nucleic acid.

Unless otherwise specified here within, the terms "antibody" and "antibodies" refers to antigen-binding portions adaptable to be expressed within cells as "intracellular antibodies." (Chen et al. (1994) *Human Gene Ther.* 5:595-601). Methods are well-known in the art for adapting antibodies to target (e.g., inhibit) intracellular moieties, such as the use of single-chain antibodies (scFvs), modification of immunoglobulin VL domains for hyperstability, modification of antibodies to resist the reducing intracellular environment, generating fusion proteins that increase intracellular stability and/or modulate intracellular localization, and the like. Intracellular antibodies can also be introduced and expressed in one or more cells, tissues or organs of a multicellular organism, for example for prophylactic and/or therapeutic purposes (e.g., as a gene therapy) (see, at least PCT Publs. WO 08/020079, WO 94/02610, WO 95/22618, and WO 03/014960; U.S. Pat. No. 7,004,940; Cattaneo and Biocca (1997) *Intracellular Antibodies: Development and Applications* (Landes and Springer-Verlag publs.); Kontermann (2004) *Methods* 34:163-170; Cohen et al. (1998) *Oncogene* 17:2445-2456; Auf der Maur et al. (2001) *FEBSLett.* 508:407-412; Shaki-Loewenstein et al. (2005) *J. Immunol. Meth.* 303:19-39).

Antibodies may be polyclonal or monoclonal; xenogeneic, allogeneic, or syngeneic; or modified forms thereof (e.g. humanized, chimeric, etc.). Antibodies may also be fully human. Preferably, antibodies of the present invention bind specifically or substantially specifically to a biomarker polypeptide or fragment thereof. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

Antibodies may also be "humanized", which is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the present invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

The term "assigned score" refers to the numerical value designated for each of the biomarkers after being measured in a patient sample. The assigned score correlates to the absence, presence or inferred amount of the biomarker in the sample. The assigned score can be generated manually (e.g., by visual inspection) or with the aid of instrumentation for image acquisition and analysis. In certain embodiments, the assigned score is determined by a qualitative assessment, for example, detection of a fluorescent readout on a graded scale, or quantitative assessment. In one embodiment, an "aggregate score," which refers to the combination of assigned scores from a plurality of measured biomarkers, is determined. In one embodiment the aggregate score is a summation of assigned scores. In another embodiment, combination of assigned scores involves performing mathematical operations on the assigned scores before combining them into an aggregate score. In certain, embodiments, the aggregate score is also referred to herein as the "predictive score."

The term "biomarker" refers to a measurable entity of the present invention, such as those in Table 1, including, at least, ADAR, ZC3HAV1, PPP1R15A, and/or EIF2AK2/PKR. Modulators (such as inhibitors or agonists) of these biomarkers can be used to treat cancer and the copy number, amount, and or activity of at least one of these biomarkers has been determined to be predictive of cancer treatment efficacy, including monotherapies (e.g., using at least one of the modulators alone) and/or combination therapies (e.g., using at least two of the modulators or using at least one of the modulators in a combination with modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist) and/or an immunotherapy like an immune checkpoint inhibitor). Biomarkers can include, without limitation, nucleic acids and proteins, including those shown in the Tables, the Examples, the Figures, and otherwise described herein. As described herein, any relevant characteristic of a biomarker can be used, such as the copy number, amount, activity, location, modification (e.g., phosphorylation), and the like.

A "blocking" antibody or an antibody "antagonist" is one which inhibits or reduces at least one biological activity of the antigen(s) it binds. In certain embodiments, the blocking antibodies or antagonist antibodies or fragments thereof described herein substantially or completely inhibit a given biological activity of the antigen(s).

An "agonist" is one which enhances, increases, or promotes at least one biological activity and/or the expression levels of at least one biomarker described herein. In certain embodiments, the agonist described herein substantially or completely enhances or promotes a given biological activity and/or the expression levels of at least one biomarker described herein.

The term "body fluid" refers to fluids that are excreted or secreted from the body as well as fluids that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit).

The terms "cancer" or "tumor" or "hyperproliferative" refer to the presence of cells possessing characteristics typical of cancer-causing cells, such as uncontrolled proliferation, immortality, metastatic potential, rapid growth and proliferation rate, and certain characteristic morphological features. Unless otherwise stated, the terms include metaplasias. In some embodiments, such cells exhibit such characteristics in part or in full due to the expression and activity of the ADAR, ZC3HAV1, PPP1R15A, and/or EIF2AK2/PKR-regulated signaling pathways. In certain embodiments, the cancer cells are capable of responding to interferon because they express functional proteins of the type I interferon signaling pathway and/or type II interferon signaling pathway. In this sense, these cancer cells are "sensitive" to interferon, or their "sensitivity" to interferon is higher than other cells not capable of responding to interferon or having less active activation of interferon signaling pathways upon interferon treatment (e.g., control cells). In some embodiments, the cancer cells described herein are not sensitive to at least one of immunotherapies. Such insensitivity, without limitation, may be related to the inactivation or decreased activation, compared to control cells (e.g., normal and/or wild-type non-cancer cells, and/or cancer cells without this insensitivity to immunotherapies), of interferon signaling (e.g., IFNγ signaling) in such cancer cells and/or other surrounding cells and/or cells localized near to such cancer cells. Such inactivation or decreased activation of interferon signaling, without limitation, may be related to the inhibition of interferon signaling by ADAR, ZC3HAV1, PPP1R15A, and/or EIF2AK2/PKR (e.g., by inhibiting dsRNA editing, sensing, and/or metabolic activities). In some embodiments, the cancer cells are treatable with an agent capable of antagonizing or enhancing ADAR, ZC3HAV1, PPP1R15A, and/or EIF2AK2/PKR, such as inhibiting or enhancing ADAR, ZC3HAV1, PPP1R15A, and/or EIF2AK2/PKR expression and/or function, as described herein. An exemplary agent, without limitation, may relieve the inhibition of interferon (e.g., IFN) signaling and/or dsRNA sensitivity by ADAR, ZC3HAV1, PPP1R15A, and/or EIF2AK2/PKR to such cancer cells and/or other cells surrounding or localized near such cancer cells, thus restoring the IFN signaling and the sensitivity of such cancer cells to immunotherapies, especially those immunotherapies related to interferon signaling pathways. In some embodiments, the treatment with the agent antagonizing or enhancing ADAR, ZC3HAV1, PPP1R15A, and/or EIF2AK2/PKR as described herein would increase IFN signaling in such cancer cells, compared to pre-treatment situations, or would restore IFN signaling in such cancer cells to at least comparable to the levels in control cells, so that such cancer cells would regain sensitivity to immunotherapies. The term "interferon signaling" or "IFN signaling" used herein refers to any cell signaling downstream and/or related to the interaction of interferon (e.g., IFNγ, IFNβ, etc.) and their receptor(s). The receptor specific for IFNγ is IFNγR, comprising two chains, namely IFNγR1 (also known as the IFNγR alpha chain) and IFNγR2 (also known as the IFNγR beta chain). IFNγR1 is the ligand binding receptor and is required but not sufficient for signal transduction, whereas IFNγR2 do not bind IFNγ independently but mainly plays a role in IFNγ signaling and is generally the limiting factor in IFNγ responsiveness. Both IFNγR chains lack intrinsic kinase/phosphatase activity and thus rely on other signaling proteins like Janus-activated kinase 1 (JAK1), JAK2 and signal transducer and activator of transcription 1 (STAT-1) for signal transduction. IFNγR complex in its resting state is a preformed tetramer and upon IFNγ association undergoes a conformational change. This conformational change induces the phosphorylation and activation of JAK1, JAK2, and STAT1 which in turn induces genes containing the gamma-interferon activation sequence (GAS) in the promoter. Many IFNγ functions are mediated by direct activation of immune effector genes by STAT1, including genes encoding antiviral proteins, microbicidal molecules, phagocytic receptors, chemokines, cytokines, and antigen-presenting molecules. Canonical Jak-STAT signaling mechanisms leading to activation of well-characterized STAT1 target genes have been previously reviewed (Stark (2007) *Cytokine Growth Factor Rev.*, 18:419-423). In addition, activation of other STATs and alternative signaling pathways can contribute to IFNγ function in certain cell contexts (reviewed in van Boxel-Dezaire and Stark, 2007 Curr. Top. *Microbiol. Immunol.*, 316:119-154 and Gough et al., 2008 *Cytokine Growth Factor Rev.*, 19:383-394). Importantly, many key IFNγ functions are mediated by cross-regulation of cellular responses to other cytokines and inflammatory factors, such as, at least, tumor necrosis factor-alpha, interleukin-4, type I IFNs, and lipopolysaccharide. The capacity of IFNγ to cross-regulate signaling pathways induced by other endogenous and exogenous factors is less appreciated, and the underlying mechanisms are more recently described. The mechanisms and (patho)physiological impact of IFNγ-mediated cross-regulation of signal transduction is reviewed by Hu and Ivashkiv (2009) *Immunity* 31:539-550. For reviews of multiple IFNγ responsive genes, see Samarajiwa et al. (2009) *Nucl. Acids Res.* 37:D852-D857 and Schneider et al. (2014) *Annu. Rev. Immunol.* 32:513-545. IFNγ signaling can at least promote NK cell activity, increase antigen presentation and lysosome activity of macrophages, activate inducible nitric oxide synthase (iNOS), and induce the production of IgG2a and IgG3 from activated plasma B cells. Many IFN-stimulated genes control viral, bacterial, and parasite infection by directly targeting pathways and functions required during pathogen life cycles. Upregulation of chemokines and chemokine receptors enables cell-to-cell communication, whereas negative regulators of signaling help resolve the IFN-induced state and facilitate the return to cellular homeostasis. Additional IFN-stimulated genes encode for proapoptotic proteins, leading to cell death under certain conditions. IFN signaling, as described herein, include at least activation or inhibition of at least one IFN responsive genes well known in the art. The detection methods for such activation or inhibitor of IFN responsive genes are also well-known in the art. In some embodiments, the cancer cells described herein have growth arrest in response to IFN and/or increased recruitment of immune cells such as in the inflamed tumor microenvironment, preferably due to inhibition by ADAR, ZC3HAV1, PPP1R15A, and/or EIF2AK2/PKR. Upon treatment with the antagonizing or enhancing/activating agent for ADAR, ZC3HAV1, PPP1R15A, and/or EIF2AK2/PKR, as described herein, such cancer cells increase susceptibility to interferons, such as restore IFN signaling. Such defective, reduced, or restored IFN signaling can be detected and/or measured through the expression and/or function of IFN-responsive genes, as described herein, using any known method in the art.

Cancer cells are often in the form of a tumor, but such cells may exist alone within an animal, or may be a non-tumorigenic cancer cell, such as a leukemia cell. As used herein, the term "cancer" includes premalignant as well as malignant cancers. Cancers include, but are not limited to, B cell cancer, e.g., multiple myeloma, Waldenstrom's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithlelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

In some embodiments, a subject in need thereof has cancer. In some cases, the subject in need thereof that has cancer has a cancer that is caused by a virus (e.g., HPV, EBV, HBV, HCV, HHV-8, HTLV-1, and MCV).

In certain embodiments, the cancer encompasses colorectal cancer (e.g., colorectal carcinoma).

The term "colorectal cancer" as used herein, is meant to include cancer of cells of the intestinal tract below the small intestine (e.g., the large intestine (colon), including the cecum, ascending colon, transverse colon, descending colon, and sigmoid colon, and rectum). Additionally, as used herein, the term "colorectal cancer" is meant to further include cancer of cells of the duodenum and small intestine (jejunum and ileum). Colorectal cancer also includes neoplastic diseases involving proliferation of a single clone of cells of the colon and includes adenocarcinoma and carcinoma of the colon whether in a primary site or metastasized.

Colorectal cancer (CRC) is the third most commonly diagnosed cancer and ranks second in cancer mortality. Extensive genetic and genomic analysis of human CRC has uncovered germline and somatic mutations relevant to CRC biology and malignant transformation (Fearon et al. (1990) *Cell* 61, 759-767). These mutations have been linked to well-defined disease stages from aberrant crypt proliferation or hyperplasic lesions to benign adenomas, to carcinoma in situ, and finally to invasive and metastatic disease, thereby establishing a genetic paradigm for cancer initiation and progression. Genetic and genomic instability are catalysts for colon carcinogenesis (Lengauer et al. (1998) *Nature* 396:643-649). CRC can present with two distinct genomic profiles that have been termed (i) chromosomal instability neoplasia (CIN), characterized by rampant structural and numerical chromosomal aberrations driven in part by telomere dysfunction (Artandi et al. (2000) *Nature* 406:641-645; Fodde et al. (2001) *Nat. Rev. Cancer* 1:55-67; Maser and DePinho (2002) *Science* 297:565-569; Rudolph et al. (2001) *Nat. Genet.* 28:155-159) and mitotic aberrations (Lengauer et al. (1998) *Nature* 396:643-649) and (ii) microsatellite instability neoplasia (MIN), characterized by near diploid karyotypes with alterations at the nucleotide level due to mutations in mismatch repair (MN/R) genes (Fishel et al. (1993) *Cell* 75:1027-1038; Ilyas et al. (1999) *Eur. J. Cancer* 35:335-351; Modrich (1991) *Annu. Rev. Genet.* 25:229-253; Parsons et al. (1995) *Science* 268:738-740; Parsons et al. (1993) *Cell* 75:1227-1236). Germline MMR mutations are highly penetrant lesions which drive the MIN phenotype in hereditary nonpolyposis colorectal cancers, accounting for 1-5% of CRC cases (de la Chapelle (2004) *Nat. Rev. Cancer* 4:769-780; Lynch and de la Chapelle (1999) J. Med. Genet. 36:801-818; Umar et al. (2004) *Nat. Rev. Cancer* 4:153-158). While CIN and MIN are mechanistically distinct, their genomic and genetic consequences emphasize the requirement of dominant mutator mechanisms to drive intestinal epithelial cells towards a threshold of oncogenic changes needed for malignant transformation.

A growing number of genetic mutations have been identified and functionally validated in CRC pathogenesis. Activation of the WNT signaling pathway is an early requisite event for adenoma formation. Somatic alterations are present in APC in greater than 70% of nonfamilial sporadic cases and appear to contribute to genomic instability and induce the expression of c-myc and Cyclin D1 (Fodde et al. (2001) *Nat. Rev. Cancer* 1:55-67), while activating β-catenin mutations represent an alternative means of WNT pathway deregulation in CRC (Morin (1997) *Science* 275:1787-1790). K-Ras mutations occur early in neoplastic progression and are present in approximately 50% of large adenomas (Fearon and Gruber (2001) Molecular abnormalities in colon and rectal cancer, ed. J. Mendelsohn, P. H., M. Israel, and L. Liotta, W.B. Saunders, Philadelphia). The BRAF serine/threonine kinase and PIK3CA lipid kinase are mutated in 5-18% and 28% of sporadic CRCs, respectively (Samuels et al. (2004) *Science* 304:554; Davies et al. (2002) *Nature* 417:949-954; Rajagopalan et al. (2002) *Nature* 418: 934; Yuen et al. (2002) *Cancer Res.* 62:6451-6455). BRAF and K-ras mutations are mutually exclusive in CRC, suggesting over-lapping oncogenic activities (Davies et al. (2002) *Nature* 417:949-954; Rajagopalan et al. (2002) *Nature* 418:934). Mutations associated with CRC progression, specifically the adenoma-to-carcinoma transition, target the TP53 and the TGF-β pathways (Markowitz et al. (2002) *Cancer Cell* 1:233-236). Greater than 50% of CRCs harbor TP53 inactivating mutations (Fearon and Gruber (2001) Molecular abnormalities in colon and rectal cancer, ed. J. Mendelsohn, P. H., M. Israel, and L. Liotta, W.B. Saunders, Philadelphia) and 30% of cases possess TGFβ-RII mutations (Markowitz (2000) *Biochim. Biophys. Acta* 1470: M13-M20; Markowitz et al. (1995) *Science* 268:1336-1338). MIN cancers consistently inactivate TGFβ8-RII by frameshift mutations, whereas CIN cancers target the pathway via inactivating somatic mutations in the TGFβ-RII kinase domain (15%) or in the downstream signaling components of the pathway, including SMD4 (15%) or SMAD2 (5%) transcription factors (Markowitz (2000) *Biochim. Biophys. Acta* 1470:M13-M20). In some embodiments, the colorectal cancer is microsatellite instable (MSI) colorectal cancer (Llosa et al. (2014) Cancer Disc. CD-14-0863; published online Oct. 30, 2014). MSI represents about 15% of sporadic CRC and about 5-6% of stage IV CRCs. MSI is caused by epigenetic silencing or mutation of DNA mismatch repair genes and typically presents with lower stage disease than microsatellite stable subset (MSS) CRC. MSI highly express immune checkpoints, such as PD-1, PD-L1, CTLA-4, LAG-3, and IDO. In other embodiments, the colorectal cancer is MSS CRC.

In certain embodiments, the cancer encompasses melanoma. The term "melanoma" as used herein, is generally meant to include cancers that develop from the pigment-containing cells, known as melanocytes, in the basal layer of the epidermis. Melanomas typically occur in the skin but may rarely occur in the mouth, intestines, or eye. In women they most commonly occur on the legs, while in men they are most common on the back. Sometimes they develop from a mole with concerning changes including an increase in size, irregular edges, change in color, itchiness, or skin breakdown. Thus, the term "melanoma" also includes cancers developing from these cells, tissues, and organs.

Melanomas are among the most dangerous forms of skin cancer and develop when unrepaired DNA damage to skin cells (most often caused by ultraviolet radiation from sunshine or tanning beds) triggers gene mutations that lead the skin cells to multiply rapidly and form malignant tumors. The primary cause of melanoma is ultraviolet light (UV) exposure in those with low levels of skin pigment. Melanomas often resemble moles; some develop from moles. Those with many moles, a history of affected family members, and who have poor immune function are at greater risk. A number of rare genetic defects such as xeroderma pigmentosum also increase risk (Azoury and Lange, 2014 *Surg Clin North Am.* 2014 94:945-962).

Melanoma can be divided into different types, including, at least, lentigo maligna, lentigo maligna melanoma, superficial spreading melanoma, acral lentiginous melanoma, mucosal melanoma, nodular melanoma, polypoid melanoma, desmoplastic melanoma, amelanotic melanoma, soft-tissue melanoma, melanoma with small nevus-like cells, melanoma with features of a Spitz nevus, uveal melanoma, etc. (see James, et al., 2006 *Andrews' Diseases of the Skin: clinical Dermatology*. Saunders Elsevier. pp. 694-9)

Diagnosis is by biopsy of any concerning skin lesion, including, at least, shave (tangential) biopsy, punch biopsy, incisional and excisional biopsies, "optical" biopsies (e.g., by reflectance confocal microscopy (RCM)), fine needle aspiration (FNA) biopsy, surgical lymph node biopsy, sentinel lymph node biopsy, etc. In addition, visual inspection may also be used for diagnosis, such as a popular method for the signs and symptoms of melanoma as mnemonic "ABCDE": Asymmetrical skin lesion, Border of the lesion is irregular, Color: melanomas usually have multiple colors, Diameter: moles greater than 6 mm are more likely to be melanomas than smaller moles, and Enlarging: Enlarging or evolving. Another method as the "ugly duckling sign" is also known in the art (Mascaro and Mascaro, 1998 *Arch Dermatol.* 134: 1484-1485).

Treatment of melanoma includes surgery, chemotherapy (such as temozolomide, dacarbazine (also termed DTIC), etc.), radiation therapy, oncolytic virotherapy (e.g., see Forbes et al., 2013 *Front. Genet.* 4:184), and immunotherapy (e.g., interleukin-2 (IL-2), interferon, etc.). Targeted therapies (e.g., as in Maverakis et al., 2015 *Acta Derm Venereol.* 95: 516-524) may include: 1) adoptive cell therapy (ACT) using TILs immune cells (tumor infiltrating lymphocytes) isolated from a person's own melanoma tumor). Cells are grown in large numbers in a laboratory and returned to the patient after a treatment that temporarily reduces normal T cells in the patient's body. TIL therapy following lymphodepletion can result in durable complete response in a variety of setups (Besser et al., 2010 *Clin. Cancer Res.* 16:2646-2655); and 2) adoptive transfer of genetically altered (expressing T cell receptors (TCRs)) autologous lymphocytes into patient's lymphocytes, where the altered lymphocytes recognize and bind to the surface of melanoma cells and kill them. Other therapies include, at least, B-Raf inhibitors (such as vemurafenib, see Chapman et al., 2011 *N. Engl. J. Med.* 364:2507-2516) and ipilimumab (alone or in combination with dacarbazine, see, e.g., Robert et al. (2011) *N. Engl. J. Med.* 364:2517-2526).

The term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control cancer patient (can be stored sample or previous sample measurement) with a known outcome;

normal tissue or cells isolated from a subject, such as a normal patient or the cancer patient, cultured primary cells/tissues isolated from a subject such as a normal subject or the cancer patient, adjacent normal cells/tissues obtained from the same organ or body location of the cancer patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, standard of care cancer therapy). It will be understood by those of skill in the art that such control samples and reference standard expression product levels can be used in combination as controls in the methods of the present invention. In one embodiment, the control may comprise normal or non-cancerous cell/tissue sample. In another preferred embodiment, the control may comprise an expression level for a set of patients, such as a set of cancer patients, or for a set of cancer patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with combination chemotherapy, and cells from patients having benign cancer. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing standard of care therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product levels from cancer control patients with a known outcome, and the expression product levels from the test sample are compared to the control expression product level as the basis for predicting outcome. As demonstrated by the data below, the methods of the present invention are not limited to use of a specific cut-point in comparing the level of expression product in the test sample to the control.

The "copy number" of a biomarker nucleic acid refers to the number of DNA sequences in a cell (e.g., germline and/or somatic) encoding a particular gene product. Generally, for a given gene, a mammal has two copies of each gene. The copy number can be increased, however, by gene amplification or duplication, or reduced by deletion. For example, germline copy number changes include changes at one or more genomic loci, wherein said one or more genomic loci are not accounted for by the number of copies in the normal complement of germline copies in a control (e.g., the normal copy number in germline DNA for the same species as that from which the specific germline DNA and corresponding copy number were determined). Somatic copy number changes include changes at one or more genomic loci, wherein said one or more genomic loci are not accounted for by the number of copies in germline DNA of a control (e.g., copy number in germline DNA for the same subject as that from which the somatic DNA and corresponding copy number were determined).

The "normal" copy number (e.g., germline and/or somatic) of a biomarker nucleic acid or "normal" level of expression of a biomarker nucleic acid or protein is the activity/level of expression or copy number in a biological sample, e.g., a sample containing tissue, whole blood, serum, plasma, buccal scrape, saliva, cerebrospinal fluid, urine, stool, and bone marrow, from a subject, e.g., a human, not afflicted with cancer, or from a corresponding non-cancerous tissue in the same subject who has cancer.

As used herein, the term "costimulate" with reference to activated immune cells includes the ability of a costimulatory molecule to provide a second, non-activating receptor mediated signal (a "costimulatory signal") that induces proliferation or effector function. For example, a costimulatory signal can result in cytokine secretion, e.g., in a T cell that has received a T cell-receptor-mediated signal. Immune cells that have received a cell-receptor mediated signal, e.g., via an activating receptor are referred to herein as "activated immune cells."

The term "determining a suitable treatment regimen for the subject" is taken to mean the determination of a treatment regimen (i.e., a single therapy or a combination of different therapies that are used for the prevention and/or treatment of the cancer in the subject) for a subject that is started, modified and/or ended based or essentially based or at least partially based on the results of the analysis according to the present invention. One example is starting an adjuvant therapy after surgery whose purpose is to decrease the risk of recurrence, another would be to modify the dosage of a particular chemotherapy. The determination can, in addition to the results of the analysis according to the present invention, be based on personal characteristics of the subject to be treated. In most cases, the actual determination of the suitable treatment regimen for the subject will be performed by the attending physician or doctor.

The term "diagnosing cancer" includes the use of the methods, systems, and code of the present invention to determine the presence or absence of a cancer or subtype thereof in an individual. The term also includes methods, systems, and code for assessing the level of disease activity in an individual.

The term "EIF2AK2-dependent sensitivity" refers to a tumor growth defect in the presence of exogenous interferon or immune cells is reversible when EIF2AK2 is blocked, ablated or inhibited. An example of this is demonstrated in FIG. 10, in which concurrent ablation of EIF2AK2 reverses the growth defect associated with interferon-stimulated Adar-null tumor cells.

A molecule is "fixed" or "affixed" to a substrate if it is covalently or non-covalently associated with the substrate such that the substrate can be rinsed with a fluid (e.g. standard saline citrate, pH 7.4) without a substantial fraction of the molecule dissociating from the substrate.

The term "expression signature" or "signature" refers to a group of one or more coordinately expressed biomarkers related to a measured phenotype. For example, the genes, proteins, metabolites, and the like making up this signature may be expressed in a specific cell lineage, stage of differentiation, or during a particular biological response. The biomarkers can reflect biological aspects of the tumors in which they are expressed, such as the cell of origin of the cancer, the nature of the non-malignant cells in the biopsy, and the oncogenic mechanisms responsible for the cancer. Expression data and gene expression levels can be stored on computer readable media, e.g., the computer readable medium used in conjunction with a microarray or chip reading device. Such expression data can be manipulated to generate expression signatures.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

The term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

The term "immunotherapy" or "immunotherapies" refer to any treatment that uses certain parts of a subject's immune system to fight diseases such as cancer. The subject's own immune system is stimulated (or suppressed), with or without administration of one or more agent for that purpose. Immunotherapies that are designed to elicit or amplify an immune response are referred to as "activation immunotherapies." Immunotherapies that are designed to reduce or suppress an immune response are referred to as "suppression immunotherapies." Any agent believed to have an immune system effect on the genetically modified transplanted cancer cells can be assayed to determine whether the agent is an immunotherapy and the effect that a given genetic modification has on the modulation of immune response. In some embodiments, the immunotherapy is cancer cell-specific. In some embodiments, immunotherapy can be "untargeted," which refers to administration of agents that do not selectively interact with immune system cells, yet modulates immune system function. Representative examples of untargeted therapies include, without limitation, chemotherapy, gene therapy, and radiation therapy.

Immunotherapy is one form of targeted therapy that may comprise, for example, the use of cancer vaccines and/or sensitized antigen presenting cells. For example, an oncolytic virus is a virus that is able to infect and lyse cancer cells, while leaving normal cells unharmed, making them potentially useful in cancer therapy. Replication of oncolytic viruses both facilitates tumor cell destruction and also produces dose amplification at the tumor site. They may also act as vectors for anticancer genes, allowing them to be specifically delivered to the tumor site. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). For example, anti-VEGF and mTOR inhibitors are known to be effective in treating renal cell carcinoma. Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

Immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

The term "immunogenic chemotherapy" refers to any chemotherapy that has been demonstrated to induce immunogenic cell death, a state that is detectable by the release of one or more damage-associated molecular pattern (DAMP) molecules, including, but not limited to, calreticulin, ATP and HMGB1 (Kroemer et al. (2013), Annu. Rev. Immunol., 31:51-72). Specific representative examples of consensus immunogenic chemotherapies include anthracyclines, such as doxorubicin and the platinum drug, oxaliplatin, 5'-fluorouracil, among others.

In some embodiments, immunotherapy comprises inhibitors of one or more immune checkpoints. The term "immune checkpoint" refers to a group of molecules on the cell surface of CD4+ and/or CD8+ T cells that fine-tune immune responses by down-modulating or inhibiting an anti-tumor immune response. Immune checkpoint proteins are well-known in the art and include, without limitation, CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRP, CD47, CD48, 2B4 (CD244), B7.1, B7.2, ILT-2, ILT-4, TIGIT, HHLA2, butyrophilins, IDO, CD39, CD73 and A2aR (see, for example, WO 2012/177624). The term further encompasses biologically active protein fragment, as well as nucleic acids encoding full-length immune checkpoint proteins and biologically active protein fragments thereof. In some embodiment, the term further encompasses any fragment according to homology descriptions provided herein. In one embodiment, the immune checkpoint is PD-1.

Immune checkpoints and their sequences are well-known in the art and representative embodiments are described below. For example, the term "PD-1" refers to a member of the immunoglobulin gene superfamily that functions as a coinhibitory receptor having PD-L1 and PD-L2 as known ligands. PD-1 was previously identified using a subtraction cloning based approach to select for genes upregulated during TCR-induced activated T cell death. PD-1 is a member of the CD28/CTLA-4 family of molecules based on its ability to bind to PD-L1. Like CTLA-4, PD-1 is rapidly induced on the surface of T-cells in response to anti-CD3 (Agata et al. 25 (1996) Int. Immunol. 8:765). In contrast to CTLA-4, however, PD-1 is also induced on the surface of B-cells (in response to anti-IgM). PD-1 is also expressed on a subset of thymocytes and myeloid cells (Agata et al. (1996) supra; Nishimura et al. (1996) Int. Immunol. 8:773).

The nucleic acid and amino acid sequences of a representative human PD-1 biomarker is available to the public at the GenBank database under NM_005018.2 and NP_005009.2 and is shown in Table 1 (see also Ishida et al. (1992) 20 EMBO J 11:3887; Shinohara et al. (1994) Genomics 23:704; U.S. Pat. No. 5,698,520). PD-1 has an extracellular region containing immunoglobulin superfamily domain, a transmembrane domain, and an intracellular region including an immunoreceptor tyrosine-based inhibitory motif (ITIM) (Ishida et al. (1992) EMBO J. 11:3887; Shinohara et al. (1994) Genomics 23:704; and U.S. Pat. No. 5,698,520) and an immunoreceptor tyrosine-based switch motif (ITSM). These features also define a larger family of polypeptides, called the immunoinhibitory receptors, which also includes gp49B, PIR-B, and the killer inhibitory receptors (KIRs) (Vivier and Daeron (1997) Immunol. Today 18:286). It is often assumed that the tyrosyl phosphorylated ITIM and ITSM motif of these receptors interacts with SH2-domain containing phosphatases, which leads to inhibitory signals. A subset of these immunoinhibitory receptors bind to MHC polypeptides, for example the KIRs, and CTLA4 binds to B7-1 and B7-2. It has been proposed that there is a phylogenetic relationship between the MHC and B7 genes (Henry et al. (1999) Immunol. Today 20(6):285-8). Nucleic acid and polypeptide sequences of PD-1 orthologs in organisms other than humans are well-known and include, for example, mouse PD-1 (NM_008798.2 and NP_032824.1), rat PD-1 (NM_001106927.1 and NP_001100397.1), dog PD-1 (XM_543338.3 and XP_543338.3), cow PD-1 (NM_001083506.1 and NP_001076975.1), and chicken PD-1 (XM_422723.3 and XP_422723.2).

PD-1 polypeptides are inhibitory receptors capable of transmitting an inhibitory signal to an immune cell to thereby inhibit immune cell effector function, or are capable of promoting costimulation (e.g., by competitive inhibition) of immune cells, e.g., when present in soluble, monomeric form. Preferred PD-1 family members share sequence identity with PD-1 and bind to one or more B7 family members, e.g., B7-1, B7-2, PD-1 ligand, and/or other polypeptides on antigen presenting cells.

The term "PD-1 activity," includes the ability of a PD-1 polypeptide to modulate an inhibitory signal in an activated immune cell, e.g., by engaging a natural PD-1 ligand on an antigen presenting cell. Modulation of an inhibitory signal in an immune cell results in modulation of proliferation of, and/or cytokine secretion by, an immune cell. Thus, the term "PD-1 activity" includes the ability of a PD-1 polypeptide to bind its natural ligand(s), the ability to modulate immune cell costimulatory or inhibitory signals, and the ability to modulate the immune response.

The term "PD-1 ligand" refers to binding partners of the PD-1 receptor and includes both PD-L1 (Freeman et al. (2000) J. Exp. Med. 192:1027-1034) and PD-L2 (Latchman et al. (2001) Nat. Immunol. 2:261). At least two types of human PD-1 ligand polypeptides exist. PD-1 ligand proteins comprise a signal sequence, and an IgV domain, an IgC domain, a transmembrane domain, and a short cytoplasmic tail. Both PD-L1 (See Freeman et al. (2000) for sequence data) and PD-L2 (See Latchman et al. (2001) Nat. Immunol. 2:261 for sequence data) are members of the B7 family of polypeptides. Both PD-L1 and PD-L2 are expressed in placenta, spleen, lymph nodes, thymus, and heart. Only PD-L2 is expressed in pancreas, lung and liver, while only PD-L1 is expressed in fetal liver. Both PD-1 ligands are upregulated on activated monocytes and dendritic cells, although PD-L1 expression is broader. For example, PD-L1 is known to be constitutively expressed and upregulated to higher levels on murine hematopoietic cells (e.g., T cells, B cells, macrophages, dendritic cells (DCs), and bone marrow-derived mast cells) and non-hematopoietic cells (e.g., endothelial, epithelial, and muscle cells), whereas PD-L2 is inducibly expressed on DCs, macrophages, and bone marrow-derived mast cells (see Butte et al. (2007) Immunity 27:111).

PD-1 ligands comprise a family of polypeptides having certain conserved structural and functional features. The term "family" when used to refer to proteins or nucleic acid molecules, is intended to mean two or more proteins or nucleic acid molecules having a common structural domain or motif and having sufficient amino acid or nucleotide sequence homology, as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics. PD-1 ligands are members of the B7 family of polypeptides. The term "B7 family" or "B7 polypeptides" as used herein includes costimulatory polypeptides that share sequence homology with B7 polypeptides, e.g., with B7-1, B7-2, B7h (Swallow et al. (1999) Immunity 11:423), and/or PD-1 ligands (e.g., PD-L1 or PD-L2). For example, human B7-1 and B7-2 share approximately 26% amino acid sequence identity when compared using the BLAST program at NCBI with the default parameters (Blosum62 matrix with gap penalties set at existence 11 and extension 1 (See the NCBI website). The term B7 family also includes variants of these polypeptides which are capable of modulating immune cell function. The B7 family of molecules share a number of conserved regions, including signal domains, IgV domains and the IgC domains. IgV domains and the IgC domains are art-recognized Ig superfamily member domains. These domains correspond to structural units that have distinct folding patterns called Ig folds. Ig folds are comprised of a sandwich of two β sheets, each consisting of anti-parallel R strands of 5-10 amino acids with a conserved disulfide bond between the two sheets in most, but not all, IgC domains of Ig, TCR, and MHC molecules share the same types of sequence patterns and are called the C1-set within the Ig superfamily. Other IgC domains fall within other sets. IgV domains also share sequence patterns and are called V set domains. IgV domains are longer than IgC domains and contain an additional pair of p strands.

Preferred B7 polypeptides are capable of providing costimulatory or inhibitory signals to immune cells to thereby promote or inhibit immune cell responses. For example, B7 family members that bind to costimulatory receptors increase T cell activation and proliferation, while B7 family members that bind to inhibitory receptors reduce costimulation. Moreover, the same B7 family member may increase or decrease T cell costimulation. For example, when bound to a costimulatory receptor, PD-1 ligand can induce costimulation of immune cells or can inhibit immune cell costimulation, e.g., when present in soluble form. When bound to an inhibitory receptor, PD-1 ligand polypeptides can transmit an inhibitory signal to an immune cell. Preferred B7 family members include B7-1, B7-2, B7h, PD-L1 or PD-L2 and soluble fragments or derivatives thereof. In one embodiment, B7 family members bind to one or more receptors on an immune cell, e.g., CTLA4, CD28, ICOS, PD-1 and/or other receptors, and, depending on the receptor, have the ability to transmit an inhibitory signal or a costimulatory signal to an immune cell, preferably a T cell.

Modulation of a costimulatory signal results in modulation of effector function of an immune cell. Thus, the term "PD-1 ligand activity" includes the ability of a PD-1 ligand polypeptide to bind its natural receptor(s) (e.g. PD-1 or B7-1), the ability to modulate immune cell costimulatory or inhibitory signals, and the ability to modulate the immune response.

The term "PD-L1" refers to a specific PD-1 ligand. Two forms of human PD-L1 molecules have been identified. One form is a naturally occurring PD-L1 soluble polypeptide, i.e., having a short hydrophilic domain and no transmembrane domain, and is referred to herein as PD-L1S. The second form is a cell-associated polypeptide, i.e., having a transmembrane and cytoplasmic domain, referred to herein as PD-L1M. The nucleic acid and amino acid sequences of representative human PD-L1 biomarkers regarding PD-L1M are also available to the public at the GenBank database under NM_014143.3 and NP_054862.1. PD-L1 proteins comprise a signal sequence, and an IgV domain and an IgC domain. The signal sequence of PD-L1S is shown from about amino acid 1 to about amino acid 18. The signal sequence of PD-L1M is shown: from about amino acid 1 to about amino acid 18. The IgV domain of PD-L1S is shown from about amino acid 19 to about amino acid 134 and the IgV domain of PD-L1M is shown from about amino acid 19 to about amino acid 134. The IgC domain of PD-L1S is shown from about amino acid 135 to about amino acid 227 and the IgC domain of PD-L1M is shown from about amino acid 135 to about amino acid 227. The hydrophilic tail of the PD-L1 exemplified in PD-L1S comprises a hydrophilic tail shown from about amino acid 228 to about amino acid 245. The PD-L1 polypeptide exemplified in PD-L1M comprises a transmembrane domain shown from about amino acids 239 to about amino acid 259 and a cytoplasmic domain shown from about 30 amino acid 260 to about amino acid 290. In addition, nucleic acid and polypeptide sequences of PD-L1 orthologs in organisms other than humans are well-known and include, for example, mouse PD-L1 (NM_021893.3 and NP_068693.1), rat PD-L1 (NM_001191954.1 and NP_001178883.1), dog PD-L1 (XM_541302.3 and XP_541302.3), cow PD-L1 (NM_001163412.1 and NP_001156884.1), and chicken PD-L1 (XM_424811.3 and XP_424811.3).

The term "PD-L2" refers to another specific PD-1 ligand. PD-L2 is a B7 family member expressed on various APCs, including dendritic cells, macrophages and bone-marrow derived mast cells (Zhong et al. (2007) Eur. J. Immunol. 37:2405). APC-expressed PD-L2 is able to both inhibit T cell activation through ligation of PD-1 and costimulate T cell activation, through a PD-1 independent mechanism (Shin et al. (2005) J. Exp. Med. 201:1531). In addition, ligation of dendritic cell-expressed PD-L2 results in enhanced dendritic cell cytokine expression and survival (Radhakrishnan et al. (2003) J. Immunol. 37:1827; Nguyen et al. (2002) J. Exp. Med. 196:1393). The nucleic acid and amino acid sequences of representative human PD-L2 biomarkers are well-known in the art and are also available to the public at the GenBank database under NM_025239.3 and NP_079515.2. PD-L2 proteins are characterized by common structural elements. In some embodiments, PD-L2 proteins include at least one or more of the following domains: a signal peptide domain, a transmembrane domain, an IgV domain, an IgC domain, an extracellular domain, a transmembrane domain, and a cytoplasmic domain. For example, amino acids 1-19 of PD-L2 comprises a signal sequence. As used herein, a "signal sequence" or "signal peptide" serves to direct a polypeptide containing such a sequence to a lipid bilayer, and is cleaved in secreted and membrane bound polypeptides and includes a peptide containing about 15 or more amino acids which occurs at the N-terminus of secretory and membrane bound polypeptides and which contains a large number of hydrophobic amino acid residues. For example, a signal sequence contains at least about 10-30 amino acid residues, preferably about 15-25 amino acid residues, more preferably about 18-20 amino acid residues, and even more preferably about 19 amino acid residues, and has at least about 35-65%, preferably about 38-50%, and more preferably about 40-45% hydrophobic amino acid residues (e.g., valine, leucine, isoleucine or phenylalanine). In another embodiment, amino acid residues 220-243 of the native human PD-L2 polypeptide and amino acid residues 201-243 of the mature polypeptide comprise a transmembrane domain. As used herein, the term "transmembrane domain" includes an amino acid sequence of about 15 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an alpha-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta, W. N. et al. (1996) Annu. Rev. Neurosci. 19: 235-263. In still another embodiment, amino acid residues 20-120 of the native human PD-L2 polypeptide and amino acid residues 1-101 of the mature polypeptide comprise an IgV domain. Amino acid residues 121-219 of the native human PD-L2 polypeptide and amino acid residues 102-200 of the mature polypeptide comprise an IgC domain. As used herein, IgV and IgC domains are recognized in the art as Ig superfamily member domains. These domains correspond to structural units that have distinct folding patterns called Ig folds. Ig folds are comprised of a sandwich of two β sheets, each consisting of antiparallel (3 strands of 5-10 amino acids with a conserved disulfide bond between the two sheets in most, but not all, domains. IgC domains of Ig, TCR, and MHC molecules share the same types of sequence patterns and are called the C1 set within the Ig superfamily. Other IgC domains fall within other sets. IgV domains also share sequence patterns and are called V set domains. IgV domains are longer than C-domains and form an additional pair of strands. In yet another embodiment, amino acid residues 1-219 of the native human PD-L2 polypeptide and amino acid residues 1-200 of the mature polypeptide comprise an extracellular domain. As used herein, the term "extracellular domain" represents the N-terminal amino acids which extend as a tail from the surface of a cell. An extracellular domain of the present invention includes an IgV domain and an IgC domain, and may include a signal peptide domain. In still another embodiment, amino acid residues 244-273 of the native human PD-L2 polypeptide and amino acid residues 225-273 of the mature polypeptide comprise a cytoplasmic domain. As used herein, the term "cytoplasmic domain" represents the C-terminal amino acids which extend as a tail into the cytoplasm of a cell. In addition, nucleic acid and polypeptide sequences of PD-L2 orthologs in organisms other than humans are well-known and include, for example, mouse PD-L2 (NM_021396.2 and NP_067371.1), rat PD-L2 (NM_001107582.2 and NP_001101052.2), dog PD-L2 (XM_847012.2 and XP_852105.2), cow PD-L2 (XM_586846.5 and XP_586846.3), and chimpanzee PD-L2 (XM_001140776.2 and XP_001140776.1).

The term "PD-L2 activity," "biological activity of PD-L2," or "functional activity of PD-L2," refers to an activity exerted by a PD-L2 protein, polypeptide or nucleic acid molecule on a PD-L2-responsive cell or tissue, or on a PD-L2 polypeptide binding partner, as determined in vivo, or in vitro, according to standard techniques. In one embodiment, a PD-L2 activity is a direct activity, such as an association with a PD-L2 binding partner. As used herein, a "target molecule" or "binding partner" is a molecule with which a PD-L2 polypeptide binds or interacts in nature, such that PD-L2-mediated function is achieved. In an exemplary embodiment, a PD-L2 target molecule is the receptor RGMb. Alternatively, a PD-L2 activity is an indirect activity, such as a cellular signaling activity mediated by interaction of the PD-L2 polypeptide with its natural binding partner (i.e., physiologically relevant interacting macromolecule involved in an immune function or other biologically relevant function), e.g., RGMb. The biological activities of PD-L2 are described herein. For example, the PD-L2 polypeptides of the present invention can have one or more of the following activities: 1) bind to and/or modulate the activity of the receptor RGMb, PD-1, or other PD-L2 natural binding partners, 2) modulate intra- or intercellular signaling, 3) modulate activation of immune cells, e.g., T lymphocytes, and 4) modulate the immune response of an organism, e.g., a mouse or human organism.

"Anti-immune checkpoint therapy" refers to the use of agents that inhibit immune checkpoint nucleic acids and/or proteins. Inhibition of one or more immune checkpoints can block or otherwise neutralize inhibitory signaling to thereby upregulate an immune response in order to more efficaciously treat cancer. Exemplary agents useful for inhibiting immune checkpoints include antibodies, small molecules, peptides, peptidomimetics, natural ligands, and derivatives of natural ligands, that can either bind and/or inactivate or inhibit immune checkpoint proteins, or fragments thereof; as well as RNA interference, antisense, nucleic acid aptamers, etc. that can downregulate the expression and/or activity of immune checkpoint nucleic acids, or fragments thereof. Exemplary agents for upregulating an immune response include antibodies against one or more immune checkpoint proteins block the interaction between the proteins and its natural receptor(s); a non-activating form of one or more immune checkpoint proteins (e.g., a dominant negative polypeptide); small molecules or peptides that block the interaction between one or more immune checkpoint proteins and its natural receptor(s); fusion proteins (e.g. the extracellular portion of an immune checkpoint inhibition protein fused to the Fc portion of an antibody or immunoglobulin) that bind to its natural receptor(s); nucleic acid molecules that block immune checkpoint nucleic acid transcription or translation; and the like. Such agents can directly block the interaction between the one or more immune checkpoints and its natural receptor(s) (e.g., antibodies) to prevent inhibitory signaling and upregulate an immune response. Alternatively, agents can indirectly block the interaction between one or more immune checkpoint proteins and its natural receptor(s) to prevent inhibitory signaling and upregulate an immune response. For example, a soluble version of an immune checkpoint protein ligand such as a stabilized extracellular domain can binding to its receptor to indirectly reduce the effective concentration of the receptor to bind to an appropriate ligand. In one embodiment, anti-PD-1 antibodies, anti-PD-L1 antibodies, and/or anti-PD-L2 antibodies, either alone or in combination, are used to inhibit immune checkpoints. These embodiments are also applicable to specific therapy against particular immune checkpoints, such as the PD-1 pathway (e.g., anti-PD-1 pathway therapy, otherwise known as PD-1 pathway inhibitor therapy).

The term "ADAR," or "ADAR1," a.k.a., adenosine deaminase acting on RNA, refers to a group of enzyme proteinss responsible for binding to double stranded RNA (dsRNA) and converting adenosine (A) to inosine (I) by deamination. ADAR functions in RNA-editing through post-transcriptional modification of mRNA transcripts. Inosine is structurally and functionally similar to guanine (G) in both translation and replication, which leads to I to cytosine (C) binding. As the result, the conversion from A to I in the RNA disrupts the normal A:U pairing which makes the RNA unstable. Most editing sites by ADAR are found in noncoding regions of RNA such as untranslated regions (UTRs), Alu elements and long interspersed nuclear element (LINEs). Mutations in adar have been associated with dyschromatosis symmetrica hereditaria, as well as Aicardi-Goutières syndrome (Rice et al. (2012) *Nature Genetics* 44:1243-1248). ADAR overexpression has been associated with cervical cancer progression and angiogenesis (Chen et al. (2017) *Diagn. Pathol.* 12:12). Expression levels of the ADAR1 protein have shown to be elevated during HIV infection (Weiden et al. (2014) *PloS One.* 9:e08476). Studies of samples from patients with hepatocellular carcinoma (HCC) have shown that ADAR1 is frequently upregulated and ADAR2 is frequently downregulated in the disease. It has been suggested that this is responsible for the disrupted A to I editing pattern seen in HCC and that ADAR1 acts as an oncogene in this context whilst ADAR2 has tumor suppressor activities (Chan et al. (2014) *Gut* 63:832-843). The imbalance of ADAR expression could change the frequency of A to I transitions in the protein coding region of genes, resulting in mutated proteins which drive the disease. The dysregulation of ADAR1 and ADAR2 could be used as a possible poor prognostic marker. In contrast, several research studies have indicated that loss of ADAR1 contributes to melanoma growth and metastasis. ADAR can act on microRNA and affect it's biogenesis, stability and/or it's binding target (Heale et al. (2009) *EMBO J.* 28:3145-3156; Cho et al. (2017) *Int J Mol Sci.* 18:pii:E799). ADAR1 is downregulated by cAMP-response element binding protein (CREB), limiting its ability to act on miRNA (Shoshan et al. (2015) *Nat. Cell Biol.* 17: 311-321). One such example is miR-455-5p which is edited by ADAR1. When ADAR is downregulated by CREB the unedited miR-455-5p down-regulates a tumor suppressor protein called CPEB1, contributing to melanoma progression in an in vivo model (Id.). A Gly1007Arg mutation in ADAR1, as well as other truncated versions, have been implicated as a cause in some cases of Dyschromatosis Symmetrica Hereditaria (DSH1), characterized by hyperpigmentation in the hands and feet and can occur in Japanese and Chinese families (Tojo et al. (2006) *Mov. Disord.* 21:1510-1513). ADAR has also been determined to change the functionality of small RNA molecules. Its is believed that ADAR evolved from ADAT (Adenosine Deaminase Acting on tRNA), a critical protein present in all eukaryotes, early in the metazoan period through the addition of a dsRNA binding domain. This likely occurred in the lineage which leads to the crown Metazoa when a duplicate ADAT gene was coupled to a gene encoding at least one double stranded RNA binding. The ADAR family of genes has been largely conserved over the history of its existence. This, along with its presence in the majority of modern phyla, indicates that RNA editing is an essential regulatory gene for metazoan organisms. ADAR has not been discovered in a variety of non-metazoan eukaryotes, such as plants, fungi and choanoflagellates. In mammals, there are three types of ADARs, ADAR1, ADAR2, and ADAR3 (Savva et al. (2012) *Genome Biology* 13:252). ADAR1 and ADAR2 are found in many tissues in the body while ADAR3 is only found in the brain (Nishikura (2010) *Annu. Rev. Biochem.* 79:321-349). ADAR1 and ADAR2 are known to be catalytically active while ADAR3 is thought to be inactive (Id.). ADAR1 has two known isoforms known as ADAR1p150 and ADAR1p110. ADAR1p110 is only found in the nucleus and ADAR1p150 goes from the nucleus to the cytoplasm (Savva et al. (2012), supra). In humans, the ADAR enzyme's active site has 2-3 amino-terminal dsRNA binding domains (dsRBDs) and one carboxy terminal catalytic deaminase domain (Id.) In the dsRBD domain there is a conserved α-β-β-β-α configuration present (Nishikura (2010), supra). ADAR contains two areas for binding Z-DNA known as Zα and Zβ. ADAR2 and ADAR3 have an arginine rich single stranded RNA (ssRNA) binding domain. A crystal structure of ADAR2 has been solved (Savva et al. (2012), supra). In the enzyme active site, there is a glutamic acid residue (E396) that hydrogen bonds to a $H_2O$ molecule. There is a histidine (H394) and two cysteine restudies (C451 and C516) that coordinates a zinc ion. The zinc activates the water molecule for the nucelophilic hydrolytic deamination. Within the catalytic core there is an inositol hexakisphosphate (IP6), which stabilizes arginine and lysine residues. In mammals, the conversion from A to I requires homodimerization of ADAR1 and ADAR2, but not ADAR3 (Nishikura (2010), supra). In vivo studies have not yet been conclusive if RNA binding is required for dimerization. A study with ADAR1 and 2 mutants which were not able to bind to dsRNA were still able to dimerize, showing they may bind based on protein-protein interactions (Nishikura (2010), supra; Cho et al. (2003) *J. Biol. Chem.* 278:17093-17102). As used herein, Adar is referenced in numerous ways. Adar may be italicized to indicate gene name or may be capitalized to refer to protein name. A person skilled in the art will recognize, depending on context, whether the methods and compositions disclosed herein refer to nucleotides or proteins.

The nucleic acid and amino acid sequences of a representative human ADAR is available to the public at the GenBank database (Gene ID 103) and is shown in Table 1. Human ADAR isoforms include the longest isoform a (GenBank database numbers NM_001111.4 and NP_001102.2, encoded by the longest variant 1, also referred to as ADAR-a), and the shorter isoforms b (NM_015840.3 and NP_056655.2, encoded by a variant 2, also referred to as ADAR-b, which uses an alternate in-frame splice site in the central coding region, compared to variant 1. There are no publicly available full-length transcripts representing this variant; it is represented based on data in PMID:9020165 and annotation on DNA accession U75503.1.), c (NM_015841.3 and NP_056656.2, encoded by a variant 3, also referred to as ADAR-c, which uses two alternate in-frame splice sites in the central coding region, compared to variant 1. There are no publicly available full-length transcripts representing this variant; it is represented based on data in PMID:9020165 and annotation on DNA accession U75503.1.), and d (NM_001025107.2 and NP_001020278.1, or NM_001193495.1 and NP_001180424.1, encoded by a variant 4 and a variant 5, which differ in the 5' UTR, lacks a portion of the 5' coding region, and uses a downstream start codon, compared to variant 1. The resulting isoform d is shorter at the N-terminus, compared to isoform a. Both variants 4 and 5 encode the same isoform, which contains an additional in-frame exon in the middle coding region and an alternate 3' region including a part of the C-terminal coding region, resulting in an additional internal segment and a shorter and distinct C-terminus, as compared to isoform 1). The domain structure of ADAR polypeptide is well known and accessible in UniProtKB database under the accession number P55265, including, in the order from the 5' terminus to the 3' terminus, adenosine deaminase z-alpha domain 1 (DRADA 1, capable of binding Z-DNA rather than B-DNA, e.g., from amino acid 133 to 202 of NP_001102.2), adenosine deaminase z-alpha domain 2 (DRADA 2, e.g., from amino acid 293 to 360 of NP_001102.2), double-stranded RNA binding motif 1 (DRBM 1, e.g., from amino acid 504 to 569 of NP_001102.2), double-stranded RNA binding motif 2 (DRBM 2, e.g., from amino acid 615 to 680 of NP_001102.2), double-stranded RNA binding motif 3 (DRBM 3, e.g., from amino acid 727 to 792 of NP_001102.2), and tRNA-specific and double-stranded RNA adenosine deaminase (RNA-specific editase) domain (e.g., from amino acid 839 to 1222 of NP_001102.2).

Nucleic acid and polypeptide sequences of ADAR orthologs in organisms other than humans are well-known and include, for example, chimpanzee (Pan troglodytes) ADAR (XM_016928010.1 and XP_016783499.1; XM_016928019.1 and XP_016783508.1; XM_009432821.2 and XP_009431096.2; XM_016928034.1 and XP_016783523.1; and XM_016928038.1 and XP_016783527.1), Rhesus monkey ADAR (XM_015110786.1 and XP_014966272.1; XM_015110794.1 and XP 014966280.1; XM_015110801.1 and XP_014966287.1; XM_002801797.2 and XP_002801843.1; and XM_001111902.3 and XP_001111902.2), dog ADAR (XM_005622785.2 and XP_005622842.1), mouse ADAR (NM_019655.3 and NP_062629.3, which is variant 1 using a different splice site, compared to variant 3. The resulting protein (isoform 1) is shorter when it is compared to isoform 3; NM_001038587.4 and NP_001033676.2, which is variant 2 using a different first exon and resulting in the use of a downstream start codon, compared to variant 3. The resulting protein (isoform 2) has a shorter N-terminus when it is compared to isoform 3; and NM_001146296.1 and NP_001139768.1, which is variant 3, encoding the longest protein (isoform 3)), cattle ADAR (XM_015462512.1 and XP_015317998.1; XM_010802967.2 and XP_010801269.1; XM_005203802.3 and XP_005203859.2;

XM_010802969.2 and XP_010801271.1; XM_010802970.2 and XP_010801272.1; XM_010802971.2 and XP_010801273.2; XM_010802972.2 and XP_010801274.1; and XM_002686013.5 and XP_002686059.1), Norway rat (*Rattus norvegicus*) ADAR (NM_031006.1 and NP_112268.1), chicken ADAR (XM_001232161.3 and XP_001232162.2; and XM_004948259.2 and XP_004948316.1), tropical clawed frog (*Xenopus tropicalis*) ADAR (XM_018090325.1 and XP_017945814.1); and zebrafish (*Danio rerio*) ADAR (NM_131596.2 and NP_571671.2).

The term "ADAR activity" includes the ability of an ADAR polypeptide (and its fragments, domains, and/or motifs thereof, discussed herein) to bind RNAs and catalyze the hydrolytic deamination of adenosine to inosine in dsRNA (referred to as A-to-I RNA editing) in a cell (e.g., a cancer cell, and/or an immune cell). ADAR activity may also include one or more of functions, such as affecting gene expression and function in a number of ways, including mRNA translation by changing codons and hence the amino acid sequence of proteins; pre-mRNA splicing by altering splice site recognition sequences; RNA stability by changing sequences involved in nuclease recognition; genetic stability in the case of RNA virus genomes by changing sequences during viral RNA replication; and RNA structure-dependent activities such as microRNA production or targeting or protein-RNA interactions. ADAR can edit both viral and cellular RNAs and can edit RNAs at multiple sites (hyper-editing) or at specific sites (site-specific editing). Its cellular RNA substrates include, e.g., bladder cancer-associated protein (BLCAP), neurotransmitter receptors for glutamate (GRIA2) and serotonin (HTR2C) and GABA receptor (GABRA3). Site-specific RNA editing of transcripts encoding these proteins results in amino acid substitutions which consequently alters their functional activities. ADAR exhibits low-level editing at the GRIA2 Q/R site, but edits efficiently at the R/G site and HOTSPOT1. Its viral RNA substrates include, e.g., hepatitis C virus (HCV), vesicular stomatitis virus (VSV), measles virus (V), hepatitis delta virus (HDV), and human immunodeficiency virus type 1 (HIV-1). ADAR exhibits either a proviral (HDV, MV, VSV and HIV-1) or an antiviral effect (HCV) and this can be editing-dependent (HDV and HCV), editing-independent (VSV and MV) or both (HIV-1). ADAR impairs HCV replication via RNA editing at multiple sites but enhances the replication of MV, VSV and HIV-1 through an editing-independent mechanism via suppression of EIF2AK2/PKR activation and function. ADAR stimulates both the release and infectivity of HIV-1 viral particles by an editing-dependent mechanism where it associates with viral RNAs and edits adenosines in the 5'-UTR and the Rev and Tat coding sequence. ADAR can enhance viral replication of HDV via A-to-I editing at a site designated as amber/W, thereby changing an UAG amber stop codon to an UIG tryptophan (W) codon that permits synthesis of the large delta antigen (L-HDAg) which has a key role in the assembly of viral particles. However, high levels of ADAR1 inhibit HDV replication. Thus, the term "ADAR activity" includes the ability of an ADAR polypeptide to bind its natural substrate(s), the ability to modulate hydrolytic deamination of adenosine on such substrate(s), and the ability to modulate the immune response through such substrate(s) in ADAR-regulated signaling pathways. Homodimerization is essential for ADAR's catalytic activity. For example, the isoform 5 of ADAR can form heterodimers with ADARB1/ADAR2. The isoform 1 interacts with ILF2/NF45 and ILF3/NF90, while binding to ILF3/NF90 up-regulates ILF3-mediated gene expression. Isoform 5 (via the DRBM 3 domain) interacts with TNPO1 and (via DRBM domains) interacts with XPO5. Isoform 1 and isoform 5 can interact with EIF2AK2/PKR and UPF1.

The term "ADAR substrate(s)" refers to binding partners of an ADAR polypeptide (and its fragments, domains, and/or motifs thereof, discussed herein), e.g., the proteins listed above and dsRNAs from which one or more adenosines more be hydrolyticly deaminated into inosine. Such binding partners are usually members in ADAR-regulated signaling pathways, as exemplified herein.

The term "ADAR-regulated signaling pathway(s)" includes signaling pathways in which ADAR (and its fragments, domains, and/or motifs thereof, discussed herein) binds to at least one of its substrate, through which at least one cellular function and/or activity and/or cellular protein profiles is changed. In some embodiments, ADAR hydrolyticly deaminated at least one of its substates which bind to it. ADAR-regulated signaling pathways include at least C6 deamniation of adenosine, cyctokine signaling in immune system, formation of editosome by ADAR proteins (e.g., by ADAR1 and ADAR2 together with the target RNA), interferon signaling (e.g., RIG-I/MDA5 mediated induction of IFN-alpha/beta pathways, Peginterferon alpha-2a/Peginterferon alpha-2b pathway, etc.), mRNA editing, translational control, etc.

The term "ADAR inhibitor(s)" includes any natural or non-natural agent prepared, synthesized, manufactured, and/or purified by human that is capable of reducing, inhibiting, blocking, and/or preventing the ability of an ADAR polypeptide (and its fragments, domains, and/or motifs thereof, discussed herein). In one embodiment, such inhibitors may reduce or inhibit the binding/interaction between ADAR and its substrates or other binding partners. In another embodiment, such inhibitors may reduce or inhibit the catalytic function of ADAR as an adenosine deaminase. In still another embodiment, such inhibitors may increase or promote the turnover rate, reduce or inhibit the expression and/or the stability (e.g., the half-life), and/or change the cellular localization of ADAR, resulting in at least a decrease in ADAR levels and/or activity. Such inhibitors may be any molecule, including but not limited to small molecule compounds, antibodies or intrabodies, RNA interfereing (RNAi) agents (including at least siRNAs, shRNAs, microRNAs (miRNAs), piwi, and other well-known agents). Such inhibitors may be specific to ADAR or also inhibit at least one of other adenosine deaminases. For example, pentostatin (Nipent™) is a nucleoside analog that inhibits the activity of the enzyme adenosine deaminase. EHNA (erythro-9-(2-hydroxy-3-nonyl)adenine) is another potent adenosine deaminase inhibitor, which also acts as a phosphodiesterase inhibitor that selectively inhibits phosphodiesterase type 2 (PDE2) (Podzuweit et al. (1995) *Cell Signal.* 7:733-738; Mery et al. (1995) *Mol Pharmacol.* 48:121-130). It has been demonstrated that EHNA specifically inhibits ADA1, while pentostatin and 1-deazaadenosine can inhibit both ADA1 and ADA2 (Ratech et al. (1981) *Enzyme* 26:74-84; Cristalli et al. (1993) *Drug Dev Res.* 28:253-258; Cristalli et al. (2001) *Med Res Rev.* 21:105-128; Dalla et al. (2013) *Parasitol.* 140:663-671). A helix-threading peptide, which binds to the target dsRNA near the editing site, was reported to inhibit ADAR2 editing (Schirle et al. (2010) *Org. Biomol. Chem.* 8:4898-4904). Naturing products, such as naringin, was also shown as a potent ADA1 inhibitor (Li et al. (2015) *Pharmacol Res Perspect.* 3:e00121). RNA interference for ADAR polypepitdes are also well known and commercially available (e.g., human shRNA (Cat.

TR306828) and siRNA (Cat. #SR300067) products and mouse gene knockout kit via CRISPR (Cat. #KN300874) from Origene (Rockville, MD), siRNA/shRNA products (Cat. #sc-37657, sc-37658, sc-37659, sc-37660, sc-37663, and sc-37664) from Santa Cruz Biotechonology (Dallas, Texas), etc.). Methods for detection, purification, and/or inhibition of ADAR (e.g., by anti-ADAR antibodies) are also well known and commercially available (e.g., multiple anti-ADAR antibodies from Origene (Cat. #TA313422, TA308833, etc.), Cell Signaling Technology (Danvers, MA, Cat. #14175), abcam (Cambridge, MA, Cat. #ab126745, ab206086, ab88574, etc.), EMD Millipore (Billerica, MA, Cat. #MABE516, MABN1061, MABE438, etc.), ThermoFisher Scientific (Waltham, MA, Cat #MA5-17285, PA5-52014, etc.), Santa Cruz Biotechnology (Cat. #sc-73408 and sc-271854), etc.).

The term "ZC3HAV1," a.k.a., Zinc finger CCCH-type antiviral protein 1, refers to a group of a CCCH-type zinc finger (e.g., C-x8-C-x5-C-x3-H) antiviral proteins which inhibit the replication of viruses by recruiting the cellular RNA degradation machineries to degrade the viral mRNAs. ZC3HAV1 binds to a ZAP-responsive element (ZRE) present in the target viral mRNA, recruits cellular poly(A)-specific ribonuclease PARN to remove the poly(A) tail, and the 3-5 exoribonuclease complex exosome to degrade the RNA body from the 3'end. It also recruits the decapping complex DCP1-DCP2 through RNA helicase p72 (DDX17) to remove the cap structure of the viral mRNA to initiate its degradation from the 5-end. Its target viruses belong to families which include retroviridae: human immunodeficiency virus type 1 (HIV-1), moloney and murine leukemia virus (MoMLV) and xenotropic MuLV-related virus (XMRV), filoviridae: ebola virus (EBOV) and marburg virus (MARV), togaviridae: sindbis virus (SINV) and Ross river virus (RRV). ZC3HAV1 specifically targets the multiply spliced but not unspliced or singly spliced HIV-1 mRNAs for degradation. For reports on ZC3HAV1, see Kerns et al. (2008) *PLoS Genet.* 4:E21-E21; Hayakawa et al. (2011) *Nat. Immunol.* 12:37-44; Zhu et al. (2011) *Proc. Natl. Acad. Sci. U.S.A.* 108:15834-15839; and Wang et al. (2012) *PLoS ONE* 7:E39159-E39159. Known functions of ZC3HAV1 include, e.g., cadherin binding, metal ion binding, NAD+ADP-ribosyltransferase activity and RNA binding, etc, involving biological processes such as cellular response to exogenous dsRNA, defense response to virus, innate immune response, negative regulation of viral genome replication, and positive regulation of I-kappaB kinase/NF-kappaB signaling, interferon-alpha production, interferon-beta production, mRNA catabolic process, RIG-1 signaling pathway, and type I interferon production. Isoform 1 of ZC3HAV1 is a more potent viral inhibitor than isoform 2. Isoform 2 acts as a positive regulator of DDX58/RIG-I signaling resulting in activation of the downstream effector IRF3 leading to the expression of type I IFNs and IFN stimulated genes (ISGs). Isoform 1 localizes in the cytoplasm at steady state, but shuttles between nucleus and cytoplasm in a XPO1-dependent manner, while isoform 2 mainly localizes in the cytoplasm.

The nucleic acid and amino acid sequences of a representative human ZC3HAV1 is available to the public at the GenBank database (Gene ID 56829) and is shown in Table 1. Human ZC3HAV1 isoforms include the longer isoform 1 (GenBank database number NP_064504.2), encoded by the longer variant 1 (NM_020119.3), and the shorter isoforms 2 (NP_078901.3), encoded by the shorter variant 2 (NM_024625.3), which uses an alternate splice site in the 3' coding region and lacks several downstream exons, compared to variant 1. It encodes isoform 2, which has a shorter and distinct C-terminus compared to isoform 1. The domain structure of ZC3HAV1 polypeptide is well known and accessible in UniProtKB database under the accession number Q7Z2W4, including, in the order from the 5' terminus to the 3' terminus, a N-terminal domain (e.g., from amino acid 2 to 254 of NP_064504.2), a nuclear export signal motif (e.g., from amino acid 285 to 292 of NP_064504.2), a WWE domain (usually found in those associated with ubiquitination and those associated with poly-ADP ribosylation (PARP) to hold an important function in signal transduction, protein degradation, DNA repair and apoptosis, e.g., from amino acid 594 to 681 of NP_064504.2), and a PARP catalytic domain (e.g., from amino acid 716 to 902 of NP_064504.2). In the N-terminal domain, there is a nuclear localization signal motif (e.g., from amino acid 69 to 76 of NP_064504.2), four C3H1-type zinc finger motifs (e.g., from amino acid 73-86, 88-110, 150-172, and 169-193 of NP_064504.2), and a domain for binding to EXOSC5 (e.g., from amino acid 224-254 of NP_064504.2). ZC3HAV1 proteins can form homodimers or homooligomers. Its homooligomerization is essential for its antiviral activity. ZC3HAV1 interacts (via N-terminal domain) with DDX17 in an RNA-independent manner and with EXOSC3, EXOSC7, DCP2, DCP1A, and PARN, in an RNA-independent manner and interacts with XRN1 in an RNA-dependent manner. Isoform 2 interacts (via zinc-fingers) with DDX58/RIG-I in an RNA-dependent manner and interacts (via N-terminal domain) with DHX30 (via N-terminus) in an RNA-independent manner.

Nucleic acid and polypeptide sequences of ZC3HAV1 orthologs in organisms other than humans are well-known and include, for example, chimpanzee (Pan troglodytes) ZC3HAV1 (XM_009454306.2 and XP_009452581.1; XM_009454307.2 and XP_009452582.1; XM_527904.5 and XP_527904.2; XM_009454309.2 and XP_009452584.1; XM_009454310.2 and XP_009452585.1; XM_009454311.2 and XP_009452586.1; XM_016958231.1 and XP_016813720.1; XM_016958232.1 and XP_016813721.1; and XM_016958233.1 and XP_016813722.1), dog ZC3HAV1 (XM_005629563.2 and XP_005629620.1), cattle ZC3HAV1 (XM_003586006.4 and XP_003586054.1), mouse ZC3HAV1 (NM_001347122.1 and NP_001334051.1, which represent the longest transcript (3) and the longest isoform product (3); NM_028421.1 and NP_082697.1, which represent a variant (1) lacking an exon and its 3' terminal exon extending past a splice site that is used in the longest variant. This results in a novel 3' coding region and 3' UTR, compared to the longest variant 3, encoding an isoform 1 which is shorter and has a distinct C-terminus, compared to isoform 3; and NM_028864.2 and NP_083140.1, which represent a variant (2) lacking several exons and its 3' terminal exon extending past a splice site that is used in variant 3. This results in a novel 3' coding region and 3' UTR, compared to variant 3. It encodes isoform 2 which is shorter and has a distinct C-terminus, compared to isoform 3.), Norway rat (*Rattus norvegicus*) ZC3HAV1 (NM_173045.2 and NP_766633.2), and chicken ZC3HAV1 (XM_015290600.1 and XP_015146086.1; XM_015290605.1 and XP_015146091.1; XM_015290611.1 and XP_015146097.1; XM_015290617.1 and XP_015146103.1; XM_015290625.1 and XP_015146111.1; and XM_015290630.1 and XP_015146116.1).

The term "ZC3HAV1 activity" includes the ability of a ZC3HAV1 polypeptide (and its fragments, domains, and/or motifs thereof, discussed herein) to bind RNAs and proteins and to inhibit virus replication in a cell (e.g., a cancer cell, and/or an immune cell). ZC3HAV1 activity may also include one or more of functions, such as those described herein and/or known by a skilled artisan.

The term "ZC3HAV1 substrate(s)" refers to binding partners of a ZC3HAV1 polypeptide (and its fragments, domains, and/or motifs thereof, discussed herein), e.g., the proteins and RNAs described herein and/or known by a skilled artisan. Such binding partners are usually members in ZC3HAV1-regulated signaling pathways, as exemplified herein.

The term "ZC3HAV1-regulated signaling pathway(s)" includes signaling pathways in which ZC3HAV1 (and its fragments, domains, and/or motifs thereof, discussed herein) binds to at least one of its substrate, through which at least one cellular function and/or activity and/or cellular protein profiles is changed, such as cellular response to exogenous dsRNA, defense response to virus, innate immune response, negative regulation of viral genome replication, and positive regulation of I-kappaB kinase/NF-kappaB signaling, interferon-alpha production, interferon-beta production, mRNA catabolic process, RIG-1 signaling pathway, and type I interferon production, etc.

The term "ZC3HAV1 inhibitor(s)" includes any natural or non-natural agent prepared, synthesized, manufactured, and/or purified by human that is capable of reducing, inhibiting, blocking, and/or preventing the ability of a ZC3HAV1 polypeptide (and its fragments, domains, and/or motifs thereof, discussed herein). In one embodiment, such inhibitors may reduce or inhibit the binding/interaction between ZC3HAV1 and its substrates or other binding partners. In another embodiment, such inhibitors may reduce or inhibit at least one of ZC3HAV1 functions. In still another embodiment, such inhibitors may increase or promote the turnover rate, reduce or inhibit the expression and/or the stability (e.g., the half-life), and/or change the cellular localization of ZC3HAV1, resulting in at least a decrease in ZC3HAV1 levels and/or activity. Such inhibitors may be any molecule, including but not limited to small molecule compounds, antibodies or intrabodies, RNA interfereing (RNAi) agents (including at least siRNAs, shRNAs, microRNAs (miR-NAs), piwi, and other well-known agents). Such inhibitors may be specific to or also inhibit at least one of other proteins having a common domain/motif with ZC3HAV1, e.g., the PARP domain. RNA interference for ZC3HAV1 polypepitdes are well known and commercially available (e.g., human and mouse shRNA (Cat. #TR100001, TL300368, TF512887, etc.) and siRNA (Cat. #SR311205, SR408585, etc.) products and human or mouse gene knockout kit via CRISPR (Cat. #KN208070 and KN319650) from Origene (Rockville, MD), siRNA/shRNA products (Cat. #sc-89362 and sc-155429) and CRISPR knockout product (Cat. #sc-429710) from Santa Cruz Biotechonology (Dallas, Texas), etc.). Methods for detection, purification, and/or inhibition of ZC3HAV1 (e.g., by anti-ZC3HAV1 antibodies) are also well known and commercially available (e.g., multiple anti-ZC3HAV1 antibodies from Origene (Cat. #TA319969), ThermoFisher Scientific (Waltham, MA, Cat #PA5-20986, PA5-31650, etc.), Santa Cruz Biotechnology (Cat. #sc-514958), etc.).

In some embodiments, agents activating, increasing, or enhancing the copy number, amount, and/or activity of ZC3HAV1 are used to modulate dsRNA editing, sensing, and/or metabolism, and thereby to treat cancers described herein. Such agents may include, e.g., ZC3HAV1 agonists. The term "ZC3HAV1 agonist(s)" includes any natural or non-natural agent prepared, synthesized, manufactured, and/or purified by human that is capable of increasing, promoting, enhancing, and/or inducing the biological ability of a ZC3HAV1 polypeptide (and its fragments, domains, and/or motifs thereof, discussed herein). In one embodiment, such agonists may increase or enhance the binding/interaction between ZC3HAV1 and its substrates or other binding partners. In another embodiment, such agonists may increase or enhance at least one of ZC3HAV1 functions. In still another embodiment, such agonists may decrease or inhibit the turnover rate, increase or enhance the expression and/or the stability (e.g., the half-life), and/or change the cellular localization of ZC3HAV1, resulting in at least an increase in ZC3HAV1 levels and/or activity. Such agonists may be any molecule, including but not limited to small molecule compounds, antibodies or intrabodies, polypeptides or fusion proteins (which comprise, e.g., full-length ZC3HAV1, or biologically active fragments thereof, with or without any mutations or modifications to maintain or enhancing ZC3HAV1 expression levels or biological functions. Such agonists may be specific to ZC3HAV1 or also enhance the copy number, amount, and/or activity of at least one of other proteins having a common domain/motif with ZC3HAV1. For example, recombinant ZC3HAV1 proteins are commercially available (e.g., from Origene (Rockville, MD; Cat. #NM_020119) and Vigene Biosciences (Rockville, MD, in adenoviral, lentiviral, and/or AAV vectors, Cat. #VH874516, VH892071, LH874516, and LH892071), etc.

The term "PPP1R15A," a.k.a., protein phosphatase 1 regulatory subunit 15A (also known as growth arrest and DNA damage-inducible protein GADD34), refers to a group of genes whose transcript levels are increased following stressful growth arrest conditions and treatment with DNA-damaging agents. The induction of this gene by ionizing radiation occurs in certain cell lines regardless of p53 status, and its protein response is correlated with apoptosis following ionizing radiation. PPP1R15A is a regulator subunit of protein phosphatase 1 (PP1) and regulates stress-induced eIF2a (the a subunit of eukaryotic translation initiation factor 2). PPP1R15A recruits the serine/threonine-protein phosphatase PP1 to dephosphorylate the translation initiation factor eIF-2A/EIF2S1, thereby reversing the shut-off of protein synthesis initiated by stress-inducible kinases and facilitating recovery of cells from stress. PPP1R15A also down-regulates the TGF-beta signaling pathway by promoting dephosphorylation of TGFB1 by PP1 and may promote apoptosis by inducing TP53 phosphorylation on Ser-15. For reports on PPP1R15A, see Zhan et al. (1994) *Mol. Cell. Biol.* 14:2361-2371; Connor et al. (2001) *Mol. Cell. Biol.* 21:6841-6850; Yagi et al. (2003) *J. Cell. Biochem.* 90:1242-1249; Brush et al. (2003) *Mol. Cell. Biol.* 23:1292-1303; and Shi et al. (2004) *J. Cell Biol.* 164:291-300. PPP1R15A functions in biological processes such as activation of cAMP-dependent PKA signaling, beta-adrenergic signaling (e.g., in erythropoietin pathway, insulin receptor pathway, CDK5 pathway, etc.), downregulation of TGF-beta receptor signaling (e.g., through SMAD), protein processing in endoplasmic reticulum, the GPCR pathway (e.g., breast cancer regulation by Stathmin 1), etc. The known interaction partners for PPP1R15A include, e.g., BAG1 (Hung et al. (2003) *Mol. Cell. Biol.* 23 (10):3477-3486), LYN (Grishin et al. (2001) *Proc. Natl. Acad. Sci. U.S.A.* 98:10172-10177), MILL (Adler et al. (1999) *Mol. Cell. Biol.* 19:7050-7060), PPP1CA (Wu et al. (2002) *J. Biol. Chem.* 277:27706-27715; Connor et al. (2001) *Mol. Cell. Biol.* 21:6841-6850), PPP1CB (Wu et al. (2002), supra; Connor et al. (2001), supra), PPP1CC (Wu et al. (2002), supra; Connor et al.

(2001), supra), SMARCB1 (Adler et al. (1999), supra; Wu et al. (2002), supra), and TSN (Hasegawa and Isobe (1999) *Biochim. Biophys. Acta.* 1428:161-168). PPP1R15A is related to malignant pleural mesothelioma (Prasad et al. (2006) *Cancer Biol. Ther.* 5:48-53).

The nucleic acid and amino acid sequences of a representative human PPP1R15A is available to the public at the GenBank database (Gene ID 23645) and is shown in Table 1. The domain structure of human PPP1R15A (GenBank database number NP_055145.3, encodable by NM_014330.3) polypeptide is well known and accessible in UniProtKB database under the accession number O75807, including, in the order from the 5' terminus to the 3' terminus, a N-terminal region required for localization in the endoplasmic reticulum (e.g., from amino acid 1 to 60 of NP_055145.3), and four repeats (each having approximate 34 amino acids, e.g., from amino acid 337 to 369, 384 to 417, 427 to 460, and 477 to 510 of NP_055145.3). In addition, different regions on PPP1R15A may facilitate its binding to different proteins. For example, a region including, e.g., amino acid 337 to 510 of NP_055145.3, is responsible for the interaction of PPP1R15 with SMAD7 (Shi et al. (2004) *J. Cell Biol.* 164:291-300). In addition, a region including, e.g., amino acid 483 to 555 of NP_055145.3, is responsible for the interaction of PPP1R15 with KMT2A/MLL1 and a region including, e.g., amino acid 536 to 583 of NP_055145.3, is responsible for the interaction of PPP1R15 with SMARCB1.

Nucleic acid and polypeptide sequences of PPP1R15A orthologs in organisms other than humans are well-known and include, for example, chimpanzee (Pan troglodytes) PPP1R15A (XM_009436002.2 and XP_009434277.2, and XM_016936471.1 and XP_016791960.1), Rhesus monkey PPP1R15A (XM_015124498.1 and XP_014979984.1, XM_015124499.1 and XP_014979985.1; and XM_015124496.1 and XP_014979982.1), cattle PPP1R15A (NM_001046178.2 and NP_001039643.1), and mouse PPP1R15A (NM_008654.2 and NP_032680.1).

The term "PPP1R15A activity" includes the ability of a PPP1R15A polypeptide (and its fragments, domains, and/or motifs thereof, discussed herein) to bind other proteins and to regulate signaling pathways (as described herein) in a cell (e.g., a cancer cell, and/or an immune cell). PPP1R15A activity may also include one or more of functions, such as those described herein and/or known by a skilled artisan.

The term "PPP1R15A substrate(s)" refers to binding partners of a PPP1R15A polypeptide (and its fragments, domains, and/or motifs thereof, discussed herein), e.g., the proteins described herein and/or known by a skilled artisan. Such binding partners are usually members in PPP1R15A-regulated signaling pathways, as exemplified herein.

The term "PPP1R15A-regulated signaling pathway(s)" includes signaling pathways in which PPP1R15A (and its fragments, domains, and/or motifs thereof, discussed herein) binds to at least one of its substrates, through which at least one cellular function and/or activity and/or cellular protein profiles is changed, such as activation of cAMP-dependent PKA signaling, beta-adrenergic signaling (e.g., in erythropoietin pathway, insulin receptor pathway, CDK5 pathway, etc.), downregulation of TGF-beta receptor signaling (e.g., through SMAD), protein processing in endoplasmic reticulum, the GPCR pathway (e.g., breast cancer regulation by Stathmin 1), etc.

The term "PPP1R15A inhibitor(s)" includes any natural or non-natural agent prepared, synthesized, manufactured, and/or purified by human that is capable of reducing, inhibiting, blocking, and/or preventing, the ability of a PPP1R15A polypeptide (and its fragments, domains, and/or motifs thereof, discussed herein). In one embodiment, such inhibitors may reduce or inhibit the binding/interaction between PPP1R15A and its substrates or other binding partners. In another embodiment, such inhibitors may reduce or inhibit at least one of PPP1R15A functions. In still another embodiment, such inhibitors may increase or promote the turnover rate, reduce or inhibit the expression and/or the stability (e.g., the half-life), and/or change the cellular localization of PPP1R15A, resulting in at least a decrease in PPP1R15A levels and/or activity. Such inhibitors may be any molecule, including but not limited to small molecule compounds, antibodies or intrabodies, RNA interfereing (RNAi) agents (including at least siRNAs, shRNAs, microRNAs (miRNAs), piwi, and other well-known agents). Such inhibitors may be specific to or also inhibit at least one of other proteins having a common domain/motif with PPP1R15A. For example, Sephin1 (2-(2-chlorobenzylidene) hydrazinecarboximidamide acetate) is a selective inhibitor of PPP1R15A and was granted by the U.S. FDA as an orphan drug to treat Charcot-Marie-Tooth disease (CMT). RNA interference for PPP1R15A polypepitdes are also well known and commercially available (e.g., human and mouse shRNA (Cat. #TG310235, TL501406, TF310235, etc.) and siRNA (Cat. #SR308425, SR418784, etc.) products and human or mouse gene knockout kit via CRISPR (Cat. #KN313736 and KN200581) from Origene (Rockville, MD), siRNA/shRNA products (Cat. #sc-37414 and sc-37415) and CRISPR knockout product (Cat. #sc-421772) from Santa Cruz Biotechonology (Dallas, Texas), Ready-to-package AAV shRNA clones (Cat. #SH891030) from Vigene Biosciences (Rockville, MD), etc.). Methods for detection, purification, and/or inhibition of PPP1R15A (e.g., by anti-PPP1R15A antibodies) are also well known and commercially available (e.g., multiple anti-PPP1R15A antibodies from Origene (Cat. #TA504310, TA504359, CF504310, etc.), abcam (Cambridge, MA, Cat. #ab131402, ab175355, etc.), ThermoFisher Scientific (Waltham, MA, Cat #PA5-20986, PA5-31650, etc.), Santa Cruz Biotechnology (Cat. #sc-373815, sc-46661, sc-8327, etc.), etc.).

In some embodiments, agents activating, increasing, or enhancing the copy number, amount, and/or activity of PPP1R15A are used to modulate dsRNA editing, sensing, and/or metabolism, and thereby to treat cancers described herein. Such agents may include, e.g., PPP1R15A agonists. The term "PPP1R15A agonist(s)" includes any natural or non-natural agent prepared, synthesized, manufactured, and/or purified by human that is capable of increasing, promoting, enhancing, and/or inducing the biological ability of a PPP1R15A polypeptide (and its fragments, domains, and/or motifs thereof, discussed herein). In one embodiment, such agonists may increase or enhance the binding/interaction between PPP1R15A and its substrates or other binding partners. In another embodiment, such agonists may increase or enhance at least one of PPP1R15A functions. In still another embodiment, such agonists may decrease or inhibit the turnover rate, increase or enhance the expression and/or the stability (e.g., the half-life), and/or change the cellular localization of PPP1R15A, resulting in at least an increase in PPP1R15A levels and/or activity. Such agonists may be any molecule, including but not limited to small molecule compounds, antibodies or intrabodies, polypeptides or fusion proteins (which comprise, e.g., full-length PPP1R15A, or biologically active fragments thereof, with or without any mutations or modifications to maintain or enhancing PPP1R15A expression levels or biological functions. Such agonists may be specific to PPP1R15A or also enhance the copy number, amount, and/or activity of at least one of other proteins having a common domain/motif with PPP1R15A. For example, recombinant PPP1R15A proteins are commercially available (e.g., from Origene (Rockville, MD; Cat. #NM_014330 and NM_014330) and Vigene Biosciences (Rockville, MD, in adenoviral, lentiviral, and/or AAV vectors, Cat. #VH891030 and LH891030), etc.

The term "EIF2AK2," a.k.a., Eukaryotic Translation Initiation Factor 2 Alpha Kinase 2 (also known as Protein Phosphatase 1, Regulatory Subunit 83, or PPP1R83), refers to a group of serine/threonine protein kinases that are activated by autophosphorylation after binding to dsRNA. The activated form of the EIF2AK2 protein can phosphorylate the alpha subunit of eukaryotic translation initiation factor EIF2S1, which impairs the recycling of EIF2S1 between successive rounds of initiation leading to inhibition of translation which eventually results in shutdown of cellular and viral protein synthesis. EIF2AK2 is also activated by manganese ions and heparin. Also induced by interferon, EIF2AK2 plays a key role in the innate immune response to viral infection and is involved in the regulation of signal transduction, apoptosis, cell proliferation and differentiation. EIF2AK2 exerts its antiviral activity on a wide range of DNA and RNA viruses including hepatitis C virus (HCV), hepatitis B virus (HBV), measles virus (MV) and herpes simplex virus 1 (HHV-1). Other phosphorylation substrates of EIF2AK2 including p53/TP53, PPP2R5A, DHX9, ILF3, IRS1 and the HHV-1 viral protein US11. In addition to serine/threonine-protein kinase activity, EIF2AK2 also has tyrosine-protein kinase activity and phosphorylates CDK1 at Tyr-4 upon DNA damage, facilitating its ubiquitination and proteosomal degradation. Either as an adapter protein and/or via its kinase activity, EIF2AK2 can regulate various signaling pathways (p38 MAP kinase, NF-kappa-B and insulin signaling pathways, etc.) and transcription factors (JUN, STAT1, STAT3, IRF1, ATF3, etc.) involved in the expression of genes encoding proinflammatory cytokines and IFNs. For example, EIF2AK2 activates the NF-kappa-B pathway via its interaction with IKBKB and TRAF family of proteins and activates the p38 MAP kinase pathway via its interaction with MAP2K6. EIF2AK2 acts as both a positive and negative regulator of the insulin signaling pathway (ISP). For example, EIF2AK2 negatively regulates ISP by inducing the inhibitory phosphorylation of insulin receptor substrate 1 (IRS1) at Ser-312 and positively regulates ISP via phosphorylation of PPP2R5A, which activates FOXO1 and in turn up-regulates the expression of insulin receptor substrate 2 (IRS2). EIF2AK2 regulates NLRP3 inflammasome assembly and the activation of NLRP3, NLRP1, AIM2 and NLRC4 inflammasomes. EIF2AK2 also triggers apoptosis via FADD-mediated activation of CASP8. EIF2AK2 plays a role in the regulation of the cytoskeleton by binding to gelsolin (GSN), sequestering the protein in an inactive conformation away from actin. EIF2AK2 is related to herpes simplex infection (e.g., herpesvirus hominis diseases), hepatitis C infection (e.g., chronic hepatitis c infection), influenza infection, rift valley fever, measles, etc.

The nucleic acid and amino acid sequences of a representative human EIF2AK2 is available to the public at the GenBank database (Gene ID 5610) and is shown in Table 1. Isoforms of human EIF2AK2 include: a transcription variant 1 (NM_002759.3, the longest transcript variant) encoding an isoform a (NP_002750.1), a transcription variant 2 (NM_001135651.2, using a different splice site in the 5' UTR, compared to variant 1) encoding the same isoform a, and a transcription variant 3 (NM_001135652.2, lacking an alternate in-frame exon compared to variant 1) encoding an isoform b (NP_001129124.1), which has the same N- and C-termini but is shorter compared to the isoform a. The 5' UTR splice pattern of the transcript variant 3 has not been determined. The domain structure of human EIF2AK2 polypeptide is well known and accessible in UniProtKB database under the accession number P19525, including, in the order from the 5' terminus to the 3' terminus, a N-terminal double-stranded RNA binding motif (DRBM1) (e.g., from amino acid 9 to 77 of NP_002750.1), a second double-stranded RNA binding motif (DRBM2) (e.g., from amino acid 100 to 167 of NP_002750.1), a protein kinase domain (e.g., from amino acid 267 to 538 of NP_002750.1), and two C-terminal repeats (each having approximately 13 amino acids, e.g., from amino acid 331 to 343 and 345 to 357 of NP_002750.1). In addition, different regions on EIF2AK2 may facilite its binding to different proteins. For example, a region including, e.g., amino acid 266 to 551 of NP_002750.1, is responsible for the interaction of EIF2AK2 with TRAF5 (Gil et al. (2004) *Mol. Cell. Biol.* 24:4502-4512).

Nucleic acid and polypeptide sequences of EIF2AK2 orthologs in organisms other than humans are well-known and include, for example, chimpanzee (Pan troglodytes) EIF2AK2 (NM_001145037.1 amd NP_001138509.1), Rhesus monkey EIF2AK2 (NM_001083948.1 and NP_001077417.1), dog EIF2AK2 (NM_001048135.1 and NP_001041600.1), cattle EIF2AK2 (NM_178109.3 and NP_835210.2), mouse EIF2AK2 (NM_011163.4 and NP_035293.1), rat EIF2AK2 (NM_019335.1 and NP_062208.1), chicken EIF2AK2 (NM_204487.1 and NP_989818.1), tropical clawed frog EIF2AK2 (NM_001079069.1 and NP_001072537.1), and zebrafish EIF2AK2 (NM_001114470.1 and NP_001107942.1).

The term "EIF2AK2 activity" includes the ability of an EIF2AK2 polypeptide (and its fragments, domains, and/or motifs thereof, discussed herein) to bind other proteins and to regulate signaling pathways (as described herein) in a cell (e.g., a cancer cell, and/or an immune cell). EIF2AK2 activity may also include one or more of functions, such as those described herein and/or known by a skilled artisan, such as binding to various RNAs, antiviral activity, and regulation of signal transduction, apoptosis, cell proliferation, differentiation, etc.

The term "EIF2AK2 substrate(s)" refers to binding partners of an EIF2AK2 polypeptide (and its fragments, domains, and/or motifs thereof, discussed herein), e.g., the proteins described herein and/or known by a skilled artisan. Such binding partners are usually members in EIF2AK2-regulated signaling pathways, as exemplified herein.

The term "EIF2AK2-regulated signaling pathway(s)" includes signaling pathways in which EIF2AK2 (and its fragments, domains, and/or motifs thereof, discussed herein) binds to at least one of its substrates, through which at least one cellular function and/or activity and/or cellular protein profiles is changed, such as transport of the SLBP independent mature mRNA (e.g., antiviral mechanism by IFN-stimulated genes, ISG15 antiviral mechanism, etc.), influenza A or herpes simplex infection, peginterferon alpha-2a/peginterferon alpha-2b pathway (Hepatocyte), 4-1BB pathway (e.g., NF-kappaB activation by viruses, PKR pathway, etc.), HIV life cycle, etc.

The term "EIF2AK2 agonist(s)" includes any natural or non-natural agent prepared, synthesized, manufactured, and/or purified by human that is capable of increasing, promoting, enhancing, and/or inducing the ability of an EIF2AK2 polypeptide (and its fragments, domains, and/or motifs thereof, discussed herein). In one embodiment, such agonists may increase or enhance the binding/interaction between EIF2AK2 and its substrates or other binding partners. In another embodiment, such agonists may increase or enhance at least one of EIF2AK2 functions. In still another embodiment, such agonists may decrease or inhibit the turnover rate, increase or enhance the expression and/or the stability (e.g., the half-life), and/or change the cellular localization of EIF2AK2, resulting in at least an increase in EIF2AK2 levels and/or activity. Such agonists may be any molecule, including but not limited to small molecule compounds, antibodies or intrabodies, polypeptides or fusion proteins (which, e.g., comprise full-length EIF2AK2, or biologically active fragments thereof, with or without any mutations or modifications to maintain or enhancing EIF2AK2 expression levels or biological functions. Such agonists may be specific to EIF2AK2 or also enhance copy number, amount, and/or activity of at least one of other proteins having a common domain/motif with EIF2AK2. For example, recombinant EIF2AK2 proteins are commercially available (e.g., from Origene (Rockville, MD; Cat. #NM_001135651 and NM_001135651) and Vigene Biosciences (Rockville, MD, in adenoviral, lentiviral, and/or AAV vectors, Cat. #VH855905 and VH885534), etc.

In some embodiments, agents inhibiting or blocking the copy number, amount, and/or activity of EIF2AK2 are used to modulate dsRNA editing, sensing, and/or metabolism, and thereby to treat cancers described herein. Such agents may include, e.g., EIF2AK2 inhibitors. The term "EIF2AK2 inhibitor(s)" includes any natural or non-natural agent prepared, synthesized, manufactured, and/or purified by human that is capable of reducing, inhibiting, blocking, preventing, and/or that inhibits the ability of a EIF2AK2 polypeptide (and its fragments, domains, and/or motifs thereof, discussed herein). In one embodiment, such inhibitors may reduce or inhibit the binding/interaction between EIF2AK2 and its substrates or other binding partners. In another embodiment, such inhibitors may reduce or inhibit at least one of EIF2AK2 functions. In still another embodiment, such inhibitors may increase or promote the turnover rate, reduce or inhibit the expression and/or the stability (e.g., the half-life), and/or change the cellular localization of EIF2AK2, resulting in at least a decrease in EIF2AK2 levels and/or activity. Such inhibitors may be any molecule, including but not limited to small molecule compounds, antibodies or intrabodies, RNA interfereing (RNAi) agents (including at least siRNAs, shRNAs, microRNAs (miR-NAs), piwi, and other well-known agents). Such inhibitors may be specific to or also inhibit at least one of other proteins having a common domain/motif with EIF2AK2. For example, known small molecule protein kinase inhibitors for EIF2AK2 include 2-Aminopurine (Enzo Life Sciences, Farmingdale, NY, Cat. #BML-CC100-0100), C16 (abcam, Cambridge, MA, Cat. #ab144595), Sal003 (abcam, Cat. #ab142235), 7-Desacetoxy-6,7-dehydrogedunin (7DG, CAS 26927-01-5), and CAS 608512-97-6. RNA interference for EIF2AK2 polypepitdes are also well known and commercially available (e.g., human and mouse shRNA (Cat. #TG320493, TF320493, etc.) and siRNA (Cat. #SR303767, SR416481, etc.) products and human or mouse gene knockout kit via CRISPR (Cat. #KN210792 and KN305092) from Origene (Rockville, MD), siRNA/shRNA products (Cat. #sc-36263 and sc-36264) and CRISPR knockout product (Cat. #sc-422410) from Santa Cruz Biotechonology (Dallas, Texas), Ready-to-package AAV shRNA clones (Cat. #SH885534 and SH855905) from Vigene Biosciences (Rockville, MD), etc.). Methods for detection, purification, and/or inhibition of EIF2AK2 (e.g., by anti-EIF2AK2 antibodies) are also well known and commercially available (e.g., multiple anti-EIF2AK2 antibodies from Origene (Cat. #TA300449, TA325442, TA332778, etc.), abcam (Cambridge, MA, Cat. #ab32506, ab184257, ab58301, etc.), Cell Signaling Technology (Danvers, MA, Cat #12297, 3072, 2766, etc.), Santa Cruz Biotechnology (Cat. #sc-136038, sc-136352, sc-6282, etc.), etc.).

Methods of detecting the activation or inhibition of IFN-responsive genes and/or the corresponding cellular functionality are well-known in the art and taught throughout the instant disclosure. For example, different cell growth rates are associated with cells with normal or defective interferon (e.g., IFN) signaling in response to TNF, IFNγ and/or IFNβ. Thus, cell growth can be measured and compared before and after treatment with ADAR, ZC3HAV1, PPP1R15A, and/or EIF2AK2/PKR modulators with well known techniques, such as an in vitro competition assay. While IFN-pathway deficient cells (e.g., cancer cells) may have a significant growth advantage over wild type cancer cells or non-cancer cells, when exposed to IFNγ or IFNβ, an effective ADAR, ZC3HAV1, and/or PPP1R15A inhibitor, and/or an EIF2AK2/PKR modulator may ameliorate such growth advantage or cause growth disadvantages, relative to controls. Other readouts for testing the function of such ADAR, ZC3HAV1, PPP1R15A, and/or EIF2AK2/PKR modulators may include the expression and/or function of IFNγ-responsive genes and/or cellular functions. For example, the activation of IFNγ-responsive genes may be detected and such ADAR, ZC3HAV1, PPP1R15A, and/or EIF2AK2/PKR modulators may increase or restore the expression of such responsive genes, such as increased expression of Granzyme B in CCD8+ T cells, MIHC-I on tumor cell surface, cytokines (e.g., at least Cxcl9, Cxcl10, Cxcl11, Ccl5, B2m, Cdkn1a, Casp4, Casp8, Ifit2, and Bak1), etc. Other readouts on cellular function for such ADAR, ZC3HAV1, and/or PPP1R15A inhibitors, and/or EIF2AK2/PKR agonistsmay include, e.g., tumor size, responsiveness to immunotherapies, overall survival, dsRNA editing, sensitivity, and/or metabolism, antigen presentation, T cell recognition of tumors, CD8+ T cell and γδ+ T cell numbers, apoptosis, T cell infiltration into tumors, or other methods taught in the instant disclosure.

The term "immune response" includes T cell mediated and/or B cell mediated immune responses. Exemplary immune responses include T cell responses, e.g., cytokine production and cellular cytotoxicity. In addition, the term immune response includes immune responses that are indirectly effected by T cell activation, e.g., antibody production (humoral responses) and activation of cytokine responsive cells, e.g., macrophages.

The term "immunotherapeutic agent" can include any molecule, peptide, antibody or other agent which can stimulate a host immune system to generate an immune response to a tumor or cancer in the subject. Various immunotherapeutic agents are useful in the compositions and methods described herein.

The term "inhibit" includes the decrease, limitation, or blockage, of, for example a particular action, function, or interaction. In some embodiments, cancer is "inhibited" if at least one symptom of the cancer is alleviated, terminated, slowed, or prevented. As used herein, cancer is also "inhibited" if recurrence or metastasis of the cancer is reduced, slowed, delayed, or prevented.

The term "interaction", when referring to an interaction between two molecules, refers to the physical contact (e.g., binding) of the molecules with one another. Generally, such an interaction results in an activity (which produces a biological effect) of one or both of said molecules.

The term "interferon-inducing agent" used herein refers to any agent capable of inducing interferon production, release, and/or at least one of interferon functions, including, e.g., inteferon-related cell signaling. Generally, in response to microbes, such as viruses and bacteria, and their products, the interferons are produced after molecules uniquely found in microbes, such as viral glycoproteins, viral RNA, bacterial endotoxin (lipopolysaccharide), bacterial flagella, CpG motifs, are recognized by and bound to pattern recognition receptors, such as membrane bound Toll like receptors or the cytoplasmic receptors RIG-I or MDA5. For example, Toll Like Receptors (TLRs), e.g., TLR3 is important for inducing interferons in response to the presence of double-stranded RNA viruses, with double-stranded RNA (dsRNA) as its ligand. After binding dsRNA, this receptor activates the transcription factors IRF3 and NF-κB, which are important for initiating synthesis of many inflammatory proteins. RNA interference technology tools such as siRNA or vector-based reagents can either silence or stimulate interferon pathways (Whitehead et al. (2011) *Annu Rev Chem Biomol Eng.* 2:77-96). Release of IFN from cells (specifically IFN-γ in lymphoid cells) is also induced by mitogens. Other cytokines, such as interleukin 1, interleukin 2, interleukin-12, tumor necrosis factor and colony-stimulating factor, can also enhance interferon production (Haller et al. (2007) *Cytokine Growth Factor Rev.* 18:425-433). Toll Like Receptors (TLRs) are single, membrane-spanning, non-catalytic receptors usually expressed in sentinel cells such as macrophages and dendritic cells. TLRs are a type of pattern recognition receptor (PRR) and recognize structurally conserved molecules derived from microbes and activate immune cell responses. TLR superfamily, including at least TLR1-TLR13, are well-known in the art. TLRs can form dimers (homodimers and/or heterodimers) to function in multiple cell signaling pathways, such as MyD88-dependent pathway and TIR-domain-containing adapter-inducing interferon-β (TRIF)-dependent pathway.

The term "TLR agonists" used herein refers to any agent capable of increasing the production, release, protein superstructure (e.g., dimerization), stability/half-life, and/or at least one of the functions of at least one TLR protein, including those agents capable of increasing TLR-related cell signaling and/or antagonizing TLR inhibitors. The agonist can be a naturally occurring activator of a TLR, such as LPS, a ligand for TLR4; flagellin, a ligand of TLR5; double-stranded RNA, a ligand for TLR3; and viral RNA, a ligand for TLR7. The agonist can also be a synthetic activator for a TLR, such as an LPS-mimetic (Corixa Corporation, Seattle, Wash.) that activates TLR4; and imiquimode that activates TLR7. Several small molecule agonists of TLRs have been identified to shape adaptive immune responses to clear pathogens as well as to circumvent the process of carcinogenesis (Adams et al. (2009) *Immunotherapy* 1:949-964; Rakoff-Nahoum and Medzhitov (2009) *Nat. Rev. Cancer* 9:57-63). Agonists for TLR2 (Zhang et al. (2011) *J. Immunol.* 186:1963-1969), TLR3 (Salaun et al. (2011) *Cancer Res.* 71:1607-1614), TLR4 (Garay et al. (2007) *Eur. J. Pharmacol.* 563:1-17), TLR7 or TLR8 (Schon and Schon (2004) *Apoptosis* 9:291-298) and TLR9 (Krieg et al. (2008) *Oncogene* 27:161-167) have shown promise as anti-cancer treatments.

The TLR1 agonists include, but are not limited to, tri-acylated lipopeptides (LPs), phenol-soluble modulin, *Mycobacterium tuberculosis* LP, S-(2,3-bis(palmitoyloxy)-(2-RS)-propyl)-N-palmitoyl-(R)-Cys-(S)-Ser-(S)-Lys(4)-OH, trihydrochloride (Pam3Cys) LP which mimics the acetylated amino terminus of a bacterial lipoprotein and OspA LP from *Borrelia burgdorferi*.

TLR2 is the most ubiquitous of the TLRs found expressed on the surface of all cells of the immune system, including monocytes, macrophages, dendritic cells, and B cells. TLR2 recognizes a large set of structurally diverse ligands including peptidoglycan, lipoteichoic acid and lipoprotein from gram-positive bacteria, lipoarabinomannan from mycobacteria, and zymosan from yeast cell wall. The agonist of TLR2 can be a lipoteichoic acid, a peptidoglycan, lipoprotein, outer-surface lipoprotein (OspA), a synthetic lipopeptide Pam3Cys-Lip, zymoson or mannan. Lipoproteins/lipopeptides are the major agonists for TLR2 (Zahringer et al. (2008) *Immunobiology* 213:205-224). TLR2 dimerization with TLR1 recognizes tri-acylated lipopeptides, whereas TLR2/TLR6 heterodimers recognize di-acylated lipopeptides. TLR2 agonists have been shown to induce tumor regression or prolong survival in cancer patients (Garay et al. (2007) *Eur. J. Pharmacol.* 563:1-17; Curtin et al. (2009) *PLOS Medicine* 6:E10; Zhang et al. (2011) *J. Immunol.* 186:1963-1969). A number of small molecule agonists of TLR2 have recently been described that specifically activate human TLR2 (Agnihotri et al. (2011) *Cancer Res.* 71:5123-5133).

The TLR-3 agonists include, but are not limited to, double stranded RNA (dsRNA), and polyinosinic-polycytidylic acid (Poly IC), a molecular nucleic acid pattern associated with viral infection.

Synthetic derivatives of lipid A are known to be TLR 4 agonists including, but not limited to: 3D-MPL (GaxoSmithKline Biologicals North America), OM174 (2-deoxy-6-o-[2-deoxy-2-[(R)-3-dodecanoyloxytetra-decanoylamino]-4-o-phosphono-p-D-glucopyranosyl]-2-[(R)-3-hydroxytetradecanoylamino]-a-D-glucopyranosyldihydrogenphosphate) (WO 95/14026), OM 294 DP (3S, 9R)-3-[(R)-dodecanoyloxytetradecanoylamino]-4-oxo-5-aza-9(R)-[(R)-3-hydroxytetradecanoylamino]decan-1,10-diol,1,10-bis(dihydrogenophosphate) (WO 99/64301 and WO 00/0462), and OM 197 MP-Ac DP (3S-, 9R)-3-[(R)-dodecanoyloxytetradecanoylamino]-4-oxo-5-aza-9-[(R)-3-hydroxytetradecanoylamino]decan-1, 10-diol,1-dihydrogenophosphate 10-(6-aminohexanoate) (WO 01/46127). Other TLR4 agonists include, but are not limited to, alkyl Glucosaminide phosphates (AGPs), CRX524 or CRX527 (see U.S. Pat. No. 6,113,918; WO 2006/012425; WO 2006/016997), lipopolysaccharide from gram-negative bacteria and its derivatives or fragments thereof, heat shock protein (HSP) 10, 60, 65, 70, 75 or 90, surfactant Protein A, hyaluronan oligosaccharides, heparan sulphate fragments, fibronectin fragments, fibrinogen peptides and b-defensin-2, muramyl dipeptide (MDP) or F protein of respiratory syncitial virus.

TLR7 and TLR8 play a major role in the anti-viral response during viral infection by their ability to recognize single stranded RNA PAMPs. Several low molecular weight activators of TLR7 have been identified, which can be classified into three groups imidazoquinolines, nucleoside analogs of purines and 3-deazapurine derivatives (Hemmi et al. (2002) *Nat. Immunol.* 3:196-200; Lee et al. (2003) *Proc. Natl. Acad. Sci. U.S.A.* 100:6646-6651; Jones et al. (2011) *Bioorganic Med. Chem. Lett.* 21:5939-5943). Imidazoquinoline derivatives include 1H-imidazo[4,5-c]quinolones (described in U.S. Pat. No. 4,689,338 (Riker)) and imiquimod (3M-Aldara™, R-837, -26308). Other members of imidazoquinolines are Resiquimod (R-848, S-28609), Gardiquimod, and CL097 (InvivoGen), which in contrast to imiquimod are also ligands for the TLR8 receptor. Aldara™ is a cream formulation of imiquimod licensed for the topical treatment of anogenital warts, actinic keratosis and superficial basal cell carcinoma in humans. Nucleoside analogs of purines include 8-hydroxyadenines, such as 9-benzyl-8-hydroxy-2-(2-methoxyethoxy) adenine (SM-360320) (Kurimoto et al. (2004) Bioorganic Med. Chem. 12:1091-1099) and the compound CL264 (InvivoGen), which is derived from SM-360320 by incorporating the amino-acid glycine, on the benzyl group. The third class of TLR7 agonists is 3-deazapurines, which are purine derivatives that include an amine functional group on the benzyl moiety (WO Pat. No. 2007/093901 (Pfizer)).

TLR7 and TLR8 are targets for anti-cancer therapy (Smits et al. (2008) The oncologist 13: 859-875; Bourquin et al. (2011) Cancer Res. 71: 5123-5133; Hotz and Bourquin (2012) Oncoimmunology 1:227-228). A variety of different small molecule compounds that are TLR7 modulators, either purine or imidazoquinoline derivatives, have been reported for the treatment of infections and diseases, in particular to treat cancer of the skin and bladder, autoimmune diseases, allergic diseases and as adjuvants for vaccines (US Pat. No. 2011/0053893; U.S. Pat. Nos. 8,044,056; 7,485,432; US Pat. No. 2011/0070575; US Pat. No. 2011/0282061; US Pat. No. 2011/0229500; US Pat. No. 2010/0240623; US Pat. No. 2010/0210598). More recently, efficacy of TLR7 agonists have been reported in renal cell carcinoma (Kauffman et al. (2012) J. Oncol. 103:298).

Further examples of TLR agonists are described in U.S. Pat. No. 7,993,659, US Application No. 2005/0163764, U.S. Pat. No. 9,567,336, and WO Application No. 2011/151431, which are incorporated by references herein.

An "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of a biomarker polypeptide or fragment thereof, in which the protein is separated from cellular components of the cells from which it is isolated or recombinantly produced. In one embodiment, the language "substantially free of cellular material" includes preparations of a biomarker protein or fragment thereof, having less than about 30% (by dry weight) of non-biomarker protein (also referred to herein as a "contaminating protein"), more preferably less than about 20% of non-biomarker protein, still more preferably less than about 10% of non-biomarker protein, and most preferably less than about 5% non-biomarker protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

As used herein, the term "isotype" refers to the antibody class (e.g., IgM, IgG1, IgG2C, and the like) that is encoded by heavy chain constant region genes.

As used herein, the term "$K_D$" is intended to refer to the dissociation equilibrium constant of a particular antibody-antigen interaction. The binding affinity of antibodies of the disclosed invention may be measured or determined by standard antibody-antigen assays, for example, competitive assays, saturation assays, or standard immunoassays such as ELISA or RIA.

A "kit" is any manufacture (e.g. a package or container) comprising at least one reagent, e.g. a probe or small molecule, for specifically detecting and/or affecting the expression of a marker of the present invention. The kit may be promoted, distributed, or sold as a unit for performing the methods of the present invention. The kit may comprise one or more reagents necessary to express a composition useful in the methods of the present invention. In certain embodiments, the kit may further comprise a reference standard, e.g., a nucleic acid encoding a protein that does not affect or regulate signaling pathways controlling cell growth, division, migration, survival or apoptosis. One skilled in the art can envision many such control proteins, including, but not limited to, common molecular tags (e.g., green fluorescent protein and beta-galactosidase), proteins not classified in any of pathway encompassing cell growth, division, migration, survival or apoptosis by GeneOntology reference, or ubiquitous housekeeping proteins. Reagents in the kit may be provided in individual containers or as mixtures of two or more reagents in a single container. In addition, instructional materials which describe the use of the compositions within the kit can be included.

The term "neoadjuvant therapy" refers to a treatment given before the primary treatment. Examples of neoadjuvant therapy can include chemotherapy, radiation therapy, and hormone therapy. For example, in treating breast cancer, neoadjuvant therapy can allows patients with large breast cancer to undergo breast-conserving surgery.

The "normal" level of expression of a biomarker is the level of expression of the biomarker in cells of a subject, e.g., a human patient, not afflicted with a cancer. An "over-expression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples.

An "over-expression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples.

The term "pre-determined" biomarker amount and/or activity measurement(s) may be a biomarker amount and/or activity measurement(s) used to, by way of example only, evaluate a subject that may be selected for a particular treatment, evaluate a response to a treatment such as ADAR, ZC3HAV1, PPP1R15A, and/or EIF2AK2/PKR modulators, either alone or in combination with a cancer therapy such as modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist) or an immunotherapy like an immune checkpoint inhibitor, and/or evaluate the disease state. A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements. In another embodiment, the amounts determined and/or compared in a method described herein are based on relative measurements, such as ratios (e.g., serum biomarker normalized to the expression of housekeeping or otherwise generally constant biomarker). The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

The term "predictive" includes the use of a biomarker nucleic acid and/or protein status, e.g., over- or underactivity, emergence, expression, growth, remission, recurrence or resistance of tumors before, during or after therapy, for determining the likelihood of response of a cancer to ADAR, ZC3HAV1, PPP1R15A, and/or EIF2AK2/PKR modulators, either alone or in combination with a cancer therapy such as modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist) or an immunotherapy like an immune checkpoint inhibitor. Such predictive use of the biomarker may be confirmed by, e.g., (1) increased or decreased copy number (e.g., by FISH, FISH plus SKY, single-molecule sequencing, e.g., as described in the art at least at J. Biotechnol., 86:289-301, or qPCR), overexpression or underexpression of a biomarker nucleic acid (e.g., by ISH, Northern Blot, or qPCR), increased or decreased biomarker protein (e.g., by IHC), or increased or decreased activity, e.g., in more than about 5%, 6%, 7%, 8%, 9%, 10%, 11%, 12%, 13%, 14%, 15%, 20%, 25%, 30%, 40%, 50%, 60%, 70%, 80%, 90%, 95%, 100%, or more of assayed human cancers types or cancer samples; (2) its absolute or relatively modulated presence or absence in a biological sample, e.g., a sample containing tissue, whole blood, serum, plasma, buccal scrape, saliva, cerebrospinal fluid, urine, stool, or bone marrow, from a subject, e.g. a human, afflicted with cancer; (3) its absolute or relatively modulated presence or absence in clinical subset of patients with cancer (e.g., those responding to a particular ADAR, ZC3HAV1, PPP1R15A, and/or EIF2AK2/PKR modulator, either alone or in combination with a cancer therapy such as modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist) or an immunotherapy like an immune checkpoint inhibitor or those developing resistance thereto).

The term "pre-malignant lesions" as described herein refers to a lesion that, while not cancerous, has potential for becoming cancerous. It also includes the term "pre-malignant disorders" or "potentially malignant disorders." In particular this refers to a benign, morphologically and/or histologically altered tissue that has a greater than normal risk of malignant transformation, and a disease or a patient's habit that does not necessarily alter the clinical appearance of local tissue but is associated with a greater than normal risk of precancerous lesion or cancer development in that tissue (leukoplakia, erythroplakia, erytroleukoplakia lichen planus (lichenoid reaction) and any lesion or an area which histological examination showed atypia of cells or dysplasia. In one embodiment, a metaplasia is a pre-malignant lesion.

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

The term "probe" refers to any molecule which is capable of selectively binding to a specifically intended target molecule, for example, a nucleotide transcript or protein encoded by or corresponding to a biomarker nucleic acid. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

The term "prognosis" includes a prediction of the probable course and outcome of cancer or the likelihood of recovery from the disease. In some embodiments, the use of statistical algorithms provides a prognosis of cancer in an individual. For example, the prognosis can be surgery, development of a clinical subtype of cancer (e.g., solid tumors, such as esophageal cancer and gastric cancer), development of one or more clinical factors, or recovery from the disease.

The term "response to inhibitor or therapy" relates to any response of the hyperproliferative disorder (e.g., cancer) to an anti-cancer agent, such as an ADAR, ZC3HAV1, PPP1R15A, and/or EIF2AK2/PKR modulator, either alone or in combination with a cancer therapy such as modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist) or an immunotherapy like an immune checkpoint inhibitor, preferably to a change in tumor mass and/or volume after initiation of neoadjuvant or adjuvant therapy. Hyperproliferative disorder response may be assessed, for example for efficacy or in a neoadjuvant or adjuvant situation, where the size of a tumor after systemic intervention can be compared to the initial size and dimensions as measured by CT, PET, mammogram, ultrasound or palpation. Responses may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular cancer therapeutic regimen is at least 25%, 30%, 35%, 40%, 45%, 50%, 55%, 60%, 65%, 70%, 75%, 80%, 85%, or more. Additional criteria for evaluating the response to cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence. For example, in order to determine appropriate threshold values, a particular cancer therapeutic regimen can be administered to a population of subjects and the outcome can be correlated to biomarker measurements that were determined prior to administration of any cancer therapy. The outcome measurement may be pathologic response to therapy given in the neoadjuvant setting. Alternatively, outcome measures, such as overall survival and disease-free survival can be monitored over a period of time for subjects following cancer therapy for which biomarker measurement values are known. In certain embodiments, the doses administered are standard doses known in the art for cancer therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of a cancer therapy can be determined using well-known methods in the art, such as those described in the Examples section.

The term "resistance" refers to an acquired or natural resistance of a cancer sample or a mammal to a cancer therapy (i.e., being nonresponsive to or having reduced or limited response to the therapeutic treatment), such as having a reduced response to a therapeutic treatment by 25% or more, for example, 30%, 40%, 50%, 60%, 70%, 80%, or more, to 2-fold, 3-fold, 4-fold, 5-fold, 10-fold, 15-fold, 20-fold or more. The reduction in response can be measured by comparing with the same cancer sample or mammal before the resistance is acquired, or by comparing with a different cancer sample or a mammal that is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multi-drug-resistant microorganism or a combination of microorganisms. The determination of resistance to a therapeutic treatment is routine in the art and within the skill of an ordinarily skilled clinician, for example, can be measured by cell proliferative assays and cell death assays as described herein as "sensitizing." In some embodiments, the term "reverses resistance" means that the use of a second agent in combination with a primary cancer therapy (e.g., chemotherapeutic or radiation therapy) is able to produce a significant decrease in tumor volume at a level of statistical significance (e.g., $p<0.05$) when compared to tumor volume of untreated tumor in the circumstance where the primary cancer therapy (e.g., chemotherapeutic or radiation therapy) alone is unable to produce a statistically significant decrease in tumor volume compared to tumor volume of untreated tumor. This generally applies to tumor volume measurements made at a time when the untreated tumor is growing log rhythmically.

The terms "response" or "responsiveness" refers to an anti-cancer response, e.g. in the sense of reduction of tumor size or inhibiting tumor growth. The terms can also refer to an improved prognosis, for example, as reflected by an increased time to recurrence, which is the period to first recurrence censoring for second primary cancer as a first event or death without evidence of recurrence, or an increased overall survival, which is the period from treatment to death from any cause. To respond or to have a response means there is a beneficial endpoint attained when exposed to a stimulus. Alternatively, a negative or detrimental symptom is minimized, mitigated or attenuated on exposure to a stimulus. It will be appreciated that evaluating the likelihood that a tumor or subject will exhibit a favorable response is equivalent to evaluating the likelihood that the tumor or subject will not exhibit favorable response (i.e., will exhibit a lack of response or be non-responsive).

An "RNA interfering agent" as used herein, is defined as any agent which interferes with or inhibits expression of a target biomarker gene by RNA interference (RNAi). Such RNA interfering agents include, but are not limited to, nucleic acid molecules including RNA molecules which are homologous to the target biomarker gene of the present invention, or a fragment thereof, short interfering RNA (siRNA), and small molecules which interfere with or inhibit expression of a target biomarker nucleic acid by RNA interference (RNAi).

"RNA interference (RNAi)" is an evolutionarily conserved process whereby the expression or introduction of RNA of a sequence that is identical or highly similar to a target biomarker nucleic acid results in the sequence specific degradation or specific post-transcriptional gene silencing (PTGS) of messenger RNA (mRNA) transcribed from that targeted gene (see Coburn and Cullen (2002) *J. Virol.* 76:9225), thereby inhibiting expression of the target biomarker nucleic acid. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target biomarker nucleic acids. As used herein, "inhibition of target biomarker nucleic acid expression" or "inhibition of marker gene expression" includes any decrease in expression or protein activity or level of the target biomarker nucleic acid or protein encoded by the target biomarker nucleic acid. The decrease may be of at least 30%, 40%, 50%, 60%, 70%, 80%, 90%, 95% or 99% or more as compared to the expression of a target biomarker nucleic acid or the activity or level of the protein encoded by a target biomarker nucleic acid which has not been targeted by an RNA interfering agent.

The term "sample" used for detecting or determining the presence or level of at least one biomarker is typically brain tissue, cerebrospinal fluid, whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In certain instances, the method of the present invention further comprises obtaining the sample from the individual prior to detecting or determining the presence or level of at least one marker in the sample.

The term "sensitize" means to alter cancer cells or tumor cells in a way that allows for more effective treatment of the associated cancer with a cancer therapy (e.g., anti-immune checkpoint, chemotherapeutic, and/or radiation therapy). In some embodiments, normal cells are not affected to an extent that causes the normal cells to be unduly injured by the therapies. An increased sensitivity or a reduced sensitivity to a therapeutic treatment is measured according to a known method in the art for the particular treatment and methods described herein below, including, but not limited to, cell proliferative assays (Tanigawa N, Kern D H, Kikasa Y, Morton D L, Cancer Res 1982; 42: 2159-2164), cell death assays (Weisenthal L M, Shoemaker R H, Marsden J A, Dill P L, Baker J A, Moran E M, Cancer Res 1984; 94: 161-173; Weisenthal L M, Lippman M E, Cancer Treat Rep 1985; 69: 615-632; Weisenthal L M, In: Kaspers G J L, Pieters R, Twentyman P R, Weisenthal L M, Veerman A J P, eds. Drug Resistance in Leukemia and Lymphoma. Langhorne, P A: Harwood Academic Publishers, 1993: 415-432; Weisenthal L M, Contrib Gynecol Obstet 1994; 19: 82-90). The sensitivity or resistance may also be measured in animal by measuring the tumor size reduction over a period of time, for example, 6 month for human and 4-6 weeks for mouse. A composition or a method sensitizes response to a therapeutic treatment if the increase in treatment sensitivity or the reduction in resistance is 25% or more, for example, 30%, 40%, 50%, 60%, 70%, 80%, or more, to 2-fold, 3-fold, 4-fold, 5-fold, 10-fold, 15-fold, 20-fold or more, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of a cancer therapy can be equally applied to methods for sensitizing hyperproliferative or otherwise cancerous cells (e.g., resistant cells) to the cancer therapy.

"Short interfering RNA" (siRNA), also referred to herein as "small interfering RNA" is defined as an agent which functions to inhibit expression of a target biomarker nucleic acid, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) *RNA* April; 9(4):493-501 incorporated by reference herein).

RNA interfering agents, e.g., siRNA molecules, may be administered to a patient having or at risk for having cancer, to inhibit expression of a biomarker gene which is overexpressed in cancer and thereby treat, prevent, or inhibit cancer in the subject.

The term "small molecule" is a term of the art and includes molecules that are less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., polyketides) (Cane et al. (1998) *Science* 282:63), and natural product extract libraries. In another embodiment, the compounds are small, organic non-peptidic compounds. In a further embodiment, a small molecule is not biosynthetic.

The term "specific binding" refers to antibody binding to a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE® assay instrument using an antigen of interest as the analyte and the antibody as the ligand, and binds to the predetermined antigen with an affinity that is at least 1.1-, 1.2-, 1.3-, 1.4-, 1.5-, 1.6-, 1.7-, 1.8-, 1.9-, 2.0-, 2.5-, 3.0-, 3.5-, 4.0-, 4.5-, 5.0-, 6.0-, 7.0-, 8.0-, 9.0-, or 10.0-fold or greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen." Selective binding is a relative term referring to the ability of an antibody to discriminate the binding of one antigen over another.

The term "subject" refers to any healthy animal, mammal or human, or any animal, mammal or human afflicted with a cancer, e.g., brain, lung, ovarian, pancreatic, liver, breast, prostate, and/or colorectal cancers, melanoma, multiple myeloma, and the like. The term "subject" is interchangeable with "patient."

The term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

The term "synergistic effect" refers to the combined effect of two or more anti-cancer agents (e.g., at least two of ADAR, ZC3HAV1, PPP1R15A, and/or EIF2AK2/PKR modulators, or at least one ADAR, ZC3HAV1, PPP1R15A, and/or EIF2AK2/PKR modulator combined with another cancer therapy, such as immunotherapy like an immune checkpoint inhibitor) can be greater than the sum of the separate effects of the anti-cancer agents/therapies alone.

The term "T cell" includes $CD4^+$ T cells and $CD8^+$ T cells. The term T cell also includes both T helper 1 type T cells and T helper 2 type T cells. The term "antigen presenting cell" includes professional antigen presenting cells (e.g., B lymphocytes, monocytes, dendritic cells, Langerhans cells), as well as other antigen presenting cells (e.g., keratinocytes, endothelial cells, astrocytes, fibroblasts, and oligodendrocytes).

The term "therapeutic effect" refers to a local or systemic effect in animals, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods of the present invention may be administered in a sufficient amount to produce a reasonable benefit/risk ratio applicable to such treatment.

The terms "therapeutically-effective amount" and "effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. In some embodiments, the $LD_{50}$ (lethal dosage) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more reduced for the agent relative to no administration of the agent. Similarly, the $ED_{50}$ (i.e., the concentration which achieves a half-maximal inhibition of symptoms) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. Also, Similarly, the $IC_{50}$ (i.e., the concentration which achieves half-maximal cytotoxic or cytostatic effect on cancer cells) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. In some embodiments, cancer cell growth in an assay can be inhibited by at least about 10%, 15%, 20%, 25%, 30%, 35%, 40%, 45%, 50%, 55%, 60%, 65%, 70%, 75%, 80%, 85%, 90%, 95%, or even 100%. In another embodiment, at least about a 10%, 15%, 20%, 25%, 30%, 35%, 40%, 45%, 50%, 55%, 60%, 65%, 70%, 75%, 80%, 85%, 90%, 95%, or even 100% decrease in a solid malignancy can be achieved.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a biomarker nucleic acid and normal post-transcriptional processing (e.g. splicing), if any, of the RNA transcript, and reverse transcription of the RNA transcript.

As used herein, the term "unresponsiveness" includes refractivity of cancer cells to therapy or refractivity of therapeutic cells, such as immune cells, to stimulation, e.g., stimulation via an activating receptor or a cytokine. Unresponsiveness can occur, e.g., because of exposure to immunosuppressants or exposure to high doses of antigen. As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory polypeptide) results in failure to produce cytokines and, thus, failure to proliferate. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the APi sequence that can be found within the enhancer (Kang et al. (1992) Science 257:1134).

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well-known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA encoding a biomarker nucleic acid (or any portion thereof) can be used to derive the polypeptide amino acid sequence, using the genetic code to translate the DNA or RNA into an amino acid sequence. Likewise, for polypeptide amino acid sequence, corresponding nucleotide sequences that can encode the polypeptide can be deduced from the genetic code (which, because of its redundancy, will produce multiple nucleic acid sequences for any given amino acid sequence). Thus, description and/or disclosure herein of a nucleotide sequence which encodes a polypeptide should be considered to also include description and/or disclosure of the amino acid sequence encoded by the nucleotide sequence. Similarly, description and/or disclosure of a polypeptide amino acid sequence herein should be considered to also include description and/or disclosure of all possible nucleotide sequences that can encode the amino acid sequence.

Finally, nucleic acid and amino acid sequence information for the loci and biomarkers of the present invention (e.g., biomarkers listed in Table 1) are well-known in the art and readily available on publicly available databases, such as the National Center for Biotechnology Information (NCBI). For example, exemplary nucleic acid and amino acid sequences derived from publicly available sequence databases are provided below and include, for example, PCT Publ. WO 2014/022759, which is incorporated herein in its entirety by this reference.

TABLE 1

SEQ ID NO: 1 Human ADAR Variant 1 cDNA Sequence (NM_001111.4, CDS region from position 243-3923)

```
  1   gccctcctc ttggccaaac tttccggagg ggaaggcttt ccgaggaaac gaaagcgaaa 61   ttgaaccgga gccatcttgg gcccggcgcg cagacccgcg gagtttcccg tgccgacgcc 121   ccggggccac ttccagtgcg gagtagcgga ggcgtggggg cctcgagggg ctggcgcggc 181   ccagcggtcg ggccagggtc gtgccgccgg cgggtcgggc cgggcaatgc ctcgcgggcg 241   caatgaatcc gcggcagggg tattccctca gcggatacta cacccatcca tttcaaggct 301   atgagcacag acagctcagg taccagcagc ctgggccagg atcttccccc agtagtttcc 361   tgcttaagca aatagaattt ctcaaggggc agctcccaga agcaccggtg attggaaagc 421   agacaccgtc actgccacct tccctcccag gactccggcc aaggtttcca gtactacttg 481   cctccagtac cagaggcagg caagtggaca tcagggggtgt ccccagggggc gtgcatctcg 541   gaagtcaggg gctccagaga gggttccagc atccttcacc acgtggcagg agtctgccac 601   agagaggtgt tgattgcctt tcctcacatt tccaggaact gagtatctac caagatcagg 661   aacaaaggat cttaaagttc ctggaagagc ttggggaagg gaaggccacc acagcacatg
```

TABLE 1-continued

```
 721  atctgtctgg gaaacttggg actccgaaga aagaaatcaa tcgagtttta tactccctgg
 781  caaagaaggg caagctacag aaagaggcag gaacaccccc tttgtggaaa atcgcggtct
 841  ccactcaggc ttggaaccag cacagcggag tggtaagacc agacggtcat agccaaggag
 901  ccccaaactc agacccgagt ttggaaccgg aagacagaaa ctccacatct gtctcagaag
 961  atcttcttga gccttttatt gcagtctcag ctcaggcttg gaaccagcac agcggagtgg
1021  taagaccaga cagtcatagc caaggatccc caaactcaga cccaggtttg gaacctgaag
1081  acagcaactc cacatctgcc ttggaagatc ctcttgagtt tttagacatg gccgagatca
1141  aggagaaaat ctgcgactat ctcttcaatg tgtctgactc ctctgccctg aatttggcta
1201  aaaatattgg ccttaccaag gcccgagata taaatgctgt gctaattgac atggaaaggc
1261  aggggatgt ctatagacaa gggacaaccc ctcccatatg gcatttgaca gacaagaagc
1321  gagagaggat gcaaatcaag agaaatacga acagtgttcc tgaaaccgct ccagctgcaa
1381  tccctgagac caaagaaac gcagagttcc tcacctgtaa tatacccaca tcaaatgcct
1441  caaataacat ggtaaccaca gaaaaagtgg agaatgggca ggaacctgtc ataaagttag
1501  aaaacaggca agaggccaga ccagaaccag caagactgaa accacctgtt cattacaatg
1561  gcccctcaaa agcagggtat gttgactttg aaaatggcca gtgggccaca gatgacatcc
1621  cagatgactt gaatagtatc cgcgcagcac caggtgagtt tcgagccatc atggagatgc
1681  cctccttcta cagtcatggc ttgccacggt gttcacccta caagaaactg acagagtgcc
1741  agctgaagaa ccccatcagc gggctgttag aatatgccca gttcgctagt caaacctgtg
1801  agttcaacat gatagagcag agtggaccac cccatgaacc tcgatttaaa ttccaggttg
1861  tcatcaatgg ccgagagttt cccccagctg aagctggaag caagaaagtg gccaagcagg
1921  atgcagctat gaaagccatg acaattctgc tagaggaagc caaagccaag gacagtggaa
1981  aatcagaaga atcatcccac tattccacag agaaagaatc agagaagact gcagagtccc
2041  agaccccac cccttcagcc acatccttct tttctgggaa gagccccgtc accacactgc
2101  ttgagtgtat gcacaaattg gggaactcct gcgaattccg tctcctgtcc aaagaaggcc
2161  ctgcccatga acccaagttc caatactgtg ttgcagtggg agcccaaact ttccccagtg
2221  tgagtgctcc cagcaagaaa gtggcaaagc agatggccgc agaggaagcc atgaaggccc
2281  tgcatgggga ggcgaccaac tccatggctt ctgataacca gcctgaaggt atgatctcag
2341  agtcacttga taacttggaa tccatgatgc caacaaggt caggaagatt ggcgagctcg
2401  tgagatacct gaacaccaac cctgtgggtg gccttttgga gtacgcccgc tcccatggct
2461  ttgctgctga attcaagttg gtcgaccagt ccggacctcc tcacgagccc aagttcgttt
2521  accaagcaaa agttggggt cgctggttcc cagccgtctg cgcacacagc aagaagcaag
2581  gcaagcagga agcagcagat gcggctctcc gtgtcttgat tggggagaac gagaaggcag
2641  aacgcatggg tttcacagag gtaacccag tgacagggc cagtctcaga gaactatgc
2701  tcctcctctc aaggtcccca gaagcacagc caaagacact ccctctcact ggcagcacct
2761  tccatgacca gatagccatg ctgagccacc ggtgcttcaa cactctgact aacagcttcc
2821  agccctcctt gctcggccgc aagattctgg ccgccatcat tatgaaaaaa gactctgagg
2881  acatgggtgt cgtcgtcagc ttgggaacag ggaatcgctg tgtgaaagga gattctctca
2941  gcctaaaagg agaaactgtc aatgactgcc atgcagaaat aatctcccgg agaggcttca
3001  tcaggtttct ctacagtgag ttaatgaaat acaactccca gactgcgaag gatagtatat
3061  ttgaacctgc taagggagga gaaaagctcc aaataaaaaa gactgtgtca ttccatctgt
```

TABLE 1-continued

```
3121  atatcagcac tgctccgtgt ggagatggcg ccctctttga caagtcctgc agcgaccgtg
3181  ctatggaaag cacagaatcc cgccactacc ctgtcttcga aatcccaaa caaggaaagc
3241  tccgcaccaa ggtggagaac ggagaaggca caatccctgt ggaatccagt gacattgtgc
3301  ctacgtggga tggcattcgg ctcggggaga gactccgtac catgtcctgt agtgacaaaa
3361  tcctacgctg gaacgtgctg ggcctgcaag gggcactgtt gacccacttc ctgcagccca
3421  tttatctcaa atctgtcaca ttgggttacc ttttcagcca agggcatctg acccgtgcta
3481  tttgctgtcg tgtgacaaga gatgggagtg catttgagga tggactacga catcccttta
3541  ttgtcaacca ccccaaggtt ggcagagtca gcatatatga ttccaaaagg caatccggga
3601  agactaagga gacaagcgtc aactggtgtc tggctgatgg ctatgacctg gagatcctgg
3661  acggtaccag aggcactgtg gatgggccac ggaatgaatt gtcccgggtc tccaaaaaga
3721  acattttttct tctatttaag aagctctgct ccttccgtta ccgcagggat ctactgagac
3781  tctcctatgg tgaggccaag aaagctgccc gtgactacga gacggccaag aactacttca
3841  aaaaaggcct gaaggatatg ggctatggga actggattag caaaccccag gaggaaaaga
3901  acttttatct ctgcccagta tagtatgctc cagtgacaga tggattaggg tgtgtcatac
3961  tagggtgtga gagaggtagg tcgtagcatt cctcatcaca tggtcagggg atttttttttt
4021  ctccttttttt tttctttttta agccataatt ggtgatactg aaaactttgg gttcccattt
4081  atcctgcttt ctttgggatt gctaggcaag gtctggccag gccccccttt tttccccccaa
4141  gtgaagaggc agaaacctaa gaagttatct tttctttcta cccaaagcat acatagtcac
4201  tgagcacctg cggtccattt cctcttaaaa gttttgtttt gatttgtttc catttccttt
4261  cccttttgtgt ttgctacact gacctcttgc ggtcttgatt aggtttcagt caactctgga
4321  tcatgtcagg gactgataat ttcatttgtg gattacgcag accctctac ttcccctctt
4381  tcccttctga gattctttcc ttgtgatctg aatgtctcct ttcccctc agagggcaaa
4441  gaggtgaaca taaggatttt ggtgaaacat ttgtaagggt aggagttgaa aactgcagtt
4501  cccagtgcca cggaagtgtg attggagcct gcagataatg cccagccatc ctcccatcct
4561  gcactttagc cagctgcagg gcgggcaagg caaggaaagc tgcttccctg gaagtgtatc
4621  actttctccg gcagctggga agtctagaac cagccagact gggttaaggg agctgctcaa
4681  gcaatagcag aggtttcacc cggcaggatg acacagacca cttcccaggg agcacgggca
4741  tgccttggaa tattgccaag cttccagctg cctcttctcc taaagcattc ctaggaatat
4801  tttccccgcc aatgctgggc gtacacccta gccaacggga caaatcctag agggtataaa
4861  atcatctctg ctcagataat catgacttag caagaataag ggcaaaaaat cctgttggct
4921  taacgtcact gttccacccg gtgtaatatc tctcatgaca gtgacaccaa gggaagttga
4981  ctaagtcaca tgtaaattag gagtgtttta aagaatgcca tagatgttga ttcttaactg
5041  ctacagataa cctgtaattg agcagattta aaattcaggc atacttttcc atttatccaa
5101  gtgctttcat ttttccagat ggcttcagaa gtaggctcgt gggcagggcg cagacctgat
5161  ctttataggg ttgacataga aagcagtagt tgtgggtgaa agggcaggtt gtcttcaaac
5221  tctgtgaggt agaatccttt gtctatacct ccatgaacat tgactcgtgt gttcagagcc
5281  tttggcctct ctgtggagtc tggctctctg gctcctgtgc attctttgaa tagtcactcg
5341  taaaaactgt cagtgcttga aactgttttcc tttactcatg ttgaagggac tttgttggct
5401  tttagagtgt tggtcatgac tccaagagca gagcagggaa gagcccaagc atagacttgg
5461  tgccgtggtg atggctgcag tccagttttg tgatgctgct tttacgtgtc cctcgataac
```

TABLE 1-continued

```
5521  agtcagctag acacactcag gaggactact gaggctctgc gaccttcagg agctgagcct
5581  gcctctctcc tttagatgac agaccttcat ctgggaacgt gctgagccag caccctcaga
5641  tgatttccct ccaaactgct gactaggtca tcctctgtct ggtagagaca ttcacatctt
5701  tgcttttatt ctatgctctc tgtacttttg accaaaaatt gaccaaagta agaaaatgca
5761  agttctaaaa atagactaag gatgcctttg cagaacacca aagcatccca aggaactggt
5821  agggaagtgg cgcctgtctc ctggagtgga agaggcctgc tccctggctc tgggtctgct
5881  gggggcacag taaatcagtc ttggcaccca catccagggc agagaggtct gtggttctca
5941  gcatcagaag gcagcgcagc ccctctcctc ttcaggctac agggttgtca cctgctgagt
6001  cctcaggttg tttggcctct ctggtccatc ttgggcatta ggttctccag cagagctctg
6061  gccagctgcc tcttctttaa ctgggaacac aggctctcac aagatcagaa ccccactca
6121  cccccaagat cttatctagc aagcctgtag tattcagttt ctgttgtagg aagagagcga
6181  ggcatccctg aattccacgc atctgctgga aacgagccgt gtcagatcgc acatccctgc
6241  gccccatgc ccctctgagt cacacaggac agaggaggca gagcttctgc ccactgttat
6301  cttcactttc ttttgtccagt cttttgtttt taataagcag tgaccctccc tactcttctt
6361  tttaatgatt tttgtagttg atttgtctga actgtggcta ctgtgcattc cttgaataat
6421  cacttgtaaa aattgtcagt gcttgaagct gtttccttta ctcacattga agggacttcg
6481  ttggtttttt ggagtcttgg ttgtgactcc aagagcagag tgaggaagac ccccaagcat
6541  agactcgggt actgtgatga tggctgcagt ccagttttat gattctgctt ttatgtgtcc
6601  cttgataaca gtgacttaac aatatacatt cctcataaat aaaaaaaaaa caagaatctg
6661  aattcttaga aaaaaaaaaa aaaaaaaaaa aa
```

SEQ ID NO: 2 Human ADAR isoform a Amino Acid Sequence (NP_001102.2)

```
   1  mnprqgysls gyythpfqgy ehrqlryqqp gpgssspssfl lkqieflkgq lpeapvigkq
  61  tpslppslpg lrprfpvlla sstrgrqvdi rgvprgvhlg sqglqrgfqh psprgrslpq
 121  rgvdclsshf qelsiyqdqe qrilkfleel gegkattahd lsgklgtpkk einrvlysla
 181  kkgklqkeag tpplwkiavs tqawnqhsgv vrpdghsqga pnsdpslepe drnstsvsed
 241  llepfiavsa qawnqhsgvv rpdshsqgsp nsdpgleped snstsaledp lefldmaeik
 301  ekicdylfnv sdssalnlak nigltkardi navlidmerq gdvyrqgttp piwhltdkkr
 361  ermqikrntn svpetapaai petkrnaefl tcniptsnas nnmvttekve ngqepvikle
 421  nrqearpepa rlkppvhyng pskagyvdfe ngqwatddip ddlnsiraap gefraimemp
 481  sfyshglprc spykkltecq lknpisglle yaqfasqtce fnmieqsgpp heprfkfqvv
 541  ingrefppae agskkvakqd aamkamtill eeakakdsgk seesshyste kesektaesq
 601  tptpsatsff sgkspvttll ecmhklgnsc efrllskegp ahepkfqycv avgaqtfpsv
 661  sapskkvakq maaeeamkal hgeatnsmas dnqpegmise sldnlesmmp nkvrkigelv
 721  rylntnpvgg lleyarshgf aaefklvdqs gpphepkfvy qakvggrwfp avcahskkqg
 781  kqeaadaalr vligenekae rmgftevtpv tgaslrrtml llsrspeaqp ktlpltgstf
 841  hdqiamlshr cfntltnsfq psllgrkila aiimkkdsed mgvvvslgtg nrcvkgdsls
 901  lkgetvndch aeiisrrgfi rflyselmky nsqtakdsif epakggeklq ikktvsfhly
 961  istapcgdga lfdkscsdra mestesrhyp vfenpkqgkl rtkvengegt ipvessdivp
1021  twdgirlger lrtmscsdki lrwnvlglqg allthflqpi ylksvtlgyl fsqghltrai
1081  ccrvtrdgsa fedglrhpfi vnhpkvgrvs iydskrqsgk tketsvnwcl adgydleild
```

TABLE 1-continued

```
1141 gtrgtvdgpr nelsrvskkn ifllfkklcs fryrrdllrl sygeakkaar dyetaknyfk 1201 kglkdmgygn wiskpqeekn fylcpv
```

SEQ ID NO: 3 Human ADAR Variant 2 cDNA Sequence (NM_015840.3, CDS region from position 243-3845)

```
   1 gccctcctc ttggccaaac tttccggagg ggaaggcttt ccgaggaaac gaaagcgaaa 61 ttgaaccgga gccatcttgg gcccggcgcg cagacccgcg gagtttcccg tgccgacgcc 121 ccggggccac ttccagtgcg gagtagcgga ggcgtggggg cctcgagggg ctggcgcggc 181 ccagcggtcg ggccagggtc gtgccgccgg cgggtcgggc cgggcaatgc ctcgcgggcg 241 caatgaatcc gcggcagggg tattccctca gcggatacta cacccatcca tttcaaggct 301 atgagcacag acagctcagg taccagcagc ctgggccagg atcttccccc agtagtttcc 361 tgcttaagca aatagaattt ctcaaggggc agctcccaga agcaccggta attggaaagc 421 agacaccgtc actgccacct tccctcccag gactccggcc aaggttttca gtactacttg 481 cctccagtac cagaggcagg caagtggaca tcaggggtgt ccccaggggc gtgcatctcg 541 gaagtcaggg gctccagaga gggttccagc atccttcacc acgtggcagg agtctgccac 601 agagaggtgt tgattgcctt tcctcacatt tccaggaact gagtatctac caagatcagg 661 aacaaaggat cttaaagttc ctggaagagc ttggggaagg gaaggccacc acagcacatg 721 atctgtctgg gaaacttggg actccgaaga aagaaatcaa tcgagtttta tactccctgg 781 caaagaaggg caagctacag aaagaggcag gaacacccc tttgtggaaa atcgcggtct 841 ccactcaggc ttggaaccag cacagcggag tggtaagacc agacggtcat agccaaggag 901 ccccaaactc agacccgagt ttggaaccgg aagacagaaa ctccacatct gtctcagaag 961 atcttcttga gccttttatt gcagtctcag ctcaggcttg gaaccagcac agcggagtgg 1021 taagaccaga cagtcatagc caaggatccc caaactcaga cccaggtttg gaacctgaag 1081 acagcaactc cacatctgcc ttggaagatc ctcttgagtt tttagacatg gccgagatca 1141 aggagaaaat ctgcgactat ctcttcaatg tgtctgactc ctctgccctg aatttggcta 1201 aaaatattgg ccttaccaag gcccgagata taaatgctgt gctaattgac atggaaaggc 1261 agggggatgt ctatagacaa gggacaaccc ctcccatatg gcatttgaca gacaagaagc 1321 gagagaggat gcaaatcaag agaaatacga acagtgttcc tgaaaccgct ccagctgcaa 1381 tccctgagac caaaagaaac gcagagttcc tcacctgtaa tacccaca tcaaatgcct 1441 caaataacat ggtaaccaca gaaaaagtgg agaatgggca ggaacctgtc ataaagttag 1501 aaaacaggca agaggccaga ccagaaccag caagactgaa accacctgtt cattacaatg 1561 gcccctcaaa agcagggtat gttgactttg aaaatggcca gtgggccaca gatgacatcc 1621 cagatgactt gaatagtatc cgcgcagcac caggtgagtt tcgagccatc atggagatgc 1681 cctccttcta cagtcatggc ttgccacggt gttcacccta caagaaactg acagagtgcc 1741 agctgaagaa ccccatcagc gggctgttag aatatgccca gttcgctagt caaacctgtg 1801 agttcaacat gatagagcag agtggaccac cccatgaacc tcgatttaaa ttccaggttg 1861 tcatcaatgg ccgagagttt cccccagctg aagctggaag caagaaagtg gccaagcagg 1921 atgcagctat gaaagccatg acaattctgc tagaggaagc caaagccaag gacagtggaa 1981 aatcagaaga atcatcccac tattccacag agaaagaatc agagaagact gcagagtccc 2041 agacccccac cccttcagcc acatccttct ttctgggaa gagcccgtc accacactgc 2101 ttgagtgtat gcacaaattg gggaactcct gcgaattccg tctcctgtcc aaagaaggcc 2161 ctgcccatga acccaagttc caatactgtg ttgcagtggg agcccaaact ttccccagtg
```

TABLE 1-continued

```
2221  tgagtgctcc cagcaagaaa gtggcaaagc agatggccgc agaggaagcc atgaaggccc
2281  tgcatgggga ggcgaccaac tccatggctt ctgataacca gcctgaaggt atgatctcag
2341  agtcacttga taacttggaa tccatgatgc ccaacaaggt caggaagatt ggcgagctcg
2401  tgagatacct gaacaccaac cctgtgggtg ccttttgga gtacgcccgc tcccatggct
2461  ttgctgctga attcaagttg gtcgaccagt ccggacctcc tcacgagccc aagttcgttt
2521  accaagcaaa agttgggggt cgctggttcc cagccgtctg cgcacacagc aagaagcaag
2581  gcaagcagga agcagcagat gcggctctcc gtgtcttgat tggggagaac gagaaggcag
2641  aacgcatggg tttcacagag ctccctctca ctggcagcac cttccatgac cagatagcca
2701  tgctgagcca ccggtgcttc aacactctga ctaacagctt ccagccctcc ttgctcggcc
2761  gcaagattct ggccgccatc attatgaaaa aagactctga ggacatgggt gtcgtcgtca
2821  gcttgggaac agggaatcgc tgtgtgaaag gagattctct cagcctaaaa ggagaaactg
2881  tcaatgactg ccatgcagaa ataatctccc ggagaggctt catcaggttt ctctacagtg
2941  agttaatgaa atacaactcc cagactgcga aggatagtat atttgaacct gctaagggag
3001  gagaaaagct ccaaataaaa aagactgtgt cattccatct gtatatcagc actgctccgt
3061  gtggagatgg cgccctcttt gacaagtcct gcagcgaccg tgctatggaa agcacagaat
3121  cccgccacta ccctgtcttc gagaatccca acaaggaaa gctccgcacc aaggtggaga
3181  acggagaagg cacaatccct gtggaatcca gtgacattgt gcctacgtgg gatggcattc
3241  ggctcgggga gagactccgt accatgtcct gtagtgacaa atcctacgc tggaacgtgc
3301  tgggcctgca aggggcactg ttgacccact tcctgcagcc catttatctc aaatctgtca
3361  cattgggtta cctttcagc caagggcatc tgacccgtgc tatttgctgt cgtgtgacaa
3421  gagatgggag tgcatttgag gatggactac gacatcctt tattgtcaac caccccaagg
3481  ttggcagagt cagcatatat gattccaaaa ggcaatccgg gaagactaag gagacaagcg
3541  tcaactggtg tctggctgat ggctatgacc tggagatcct ggacggtacc agaggcactg
3601  tggatgggcc acggaatgaa ttgtcccggg tctccaaaaa gaacatttt cttctattta
3661  agaagctctg ctccttccgt taccgcaggg atctactgag actctcctat ggtgaggcca
3721  agaaagctgc ccgtgactac gagacggcca agaactactt caaaaaaggc ctgaaggata
3781  tgggctatgg gaactggatt agcaaaccc aggaggaaaa gaactttat ctctgcccag
3841  tatagtatgc tccagtgaca gatggattag ggtgtgtcat actagggtgt gagagaggta
3901  ggtcgtagca ttcctcatca catggtcagg ggatttttt ttctccttt ttttcttt
3961  taagccataa ttggtgatac tgaaaacttt gggttcccat ttatcctgct ttctttggga
4021  ttgctaggca aggtctggcc aggccccct ttttccccc aagtgaagag gcagaaacct
4081  aagaagttat cttttcttc tacccaaagc atacatagtc actgagcacc tgcggtccat
4141  ttcctcttaa aagttttgtt ttgatttgtt tccatttcct ttcccttgt gtttgctaca
4201  ctgacctctt gcggtcttga ttaggtttca gtcaactctg gatcatgtca gggactgata
4261  atttcatttg tggattacgc agacccctct acttcccctc tttcccttct gagattcttt
4321  ccttgtgatc tgaatgtctc cttttccccc tcagagggca aagaggtgaa cataaaggat
4381  ttggtgaaac atttgtaagg gtaggagttg aaaactgcag ttcccagtgc cacggaagtg
4441  tgattggagc ctgcagataa tgcccagcca tcctcccatc ctgcacttta gccagctgca
4501  gggcgggcaa ggcaaggaaa gctgcttccc tggaagtgta tcactttctc cggcagctgg
4561  gaagtctaga accagccaga ctgggttaag ggagctgctc aagcaatagc agaggtttca
```

TABLE 1-continued

```
4621  cccggcagga tgacacagac cacttcccag ggagcacggg catgccttgg aatattgcca 4681  agcttccagc tgcctcttct cctaaagcat tcctaggaat attttccccg ccaatgctgg 4741  gcgtacaccc tagccaacgg acaaatcct agagggtata aaatcatctc tgctcagata 4801  atcatgactt agcaagaata agggcaaaaa atcctgttgg cttaacgtca ctgttccacc 4861  cggtgtaata tctctcatga cagtgacacc aagggaagtt gactaagtca catgtaaatt 4921  aggagtgttt taaagaatgc catagatgtt gattcttaac tgctacagat aacctgtaat 4981  tgagcagatt taaaattcag gcatactttt ccatttatcc aagtgctttc attttccag 5041  atggcttcag aagtaggctc gtgggcaggg cgcagacctg atctttatag ggttgacata 5101  gaaagcagta gttgtgggtg aaagggcagg ttgtcttcaa actctgtgag gtagaatcct 5161  ttgtctatac ctccatgaac attgactcgt gtgttcagag cctttggcct ctctgtggag 5221  tctggctctc tggctcctgt gcattctttg aatagtcact cgtaaaaact gtcagtgctt 5281  gaaactgttt cctttactca tgttgaaggg actttgttgg cttttagagt gttggtcatg 5341  actccaagag cagagcaggg aagagcccaa gcatagactt ggtgccgtgg tgatggctgc 5401  agtccagttt tgtgatgctg cttttacgtg tccctcgata acagtcagct agacacactc 5461  aggaggacta ctgaggctct gcgaccttca ggagctgagc ctgcctctct cctttagatg 5521  acagaccttc atctgggaac gtgctgagcc agcaccctca gatgattccc ctccaaactg 5581  ctgactaggt catcctctgt ctggtagaga cattcacatc tttgctttta ttctatgctc 5641  tctgtacttt tgaccaaaaa ttgaccaaag taagaaaatg caagttctaa aaatagacta 5701  aggatgcctt tgcagaacac caaagcatcc caaggaactg gtagggaagt ggcgcctgtc 5761  tcctggagtg gaagaggcct gctccctggc tctgggtctg ctgggggcac agtaaatcag 5821  tcttggcacc cacatccagg gcagagaggt ctgtggttct cagcatcaga aggcagcgca 5881  gccctctcc tcttcaggct acagggttgt cacctgctga gtcctcaggt tgtttggcct 5941  ctctggtcca tcttgggcat taggttctcc agcagagctc tggccagctg cctcttcttt 6001  aactgggaac acaggctctc acaagatcag aacccccact caccccaag atcttatcta 6061  gcaagcctgt agtattcagt ttctgttgta ggaagagagc gaggcatccc tgaattccac 6121  gcatctgctg gaaacgagcc gtgtcagatc gcacatccct gcgccccat gccctctga 6181  gtcacacagg acagaggagg cagagcttct gcccactgtt atcttcactt tcttgtcca 6241  gtcttttgtt tttaataagc agtgaccctc cctactcttc ttttaatga ttttgtagt 6301  tgatttgtct gaactgtggc tactgtgcat tccttgaata atcacttgta aaaattgtca 6361  gtgcttgaag ctgtttcctt tactcacatt gaagggactt cgttggtttt ttggagtctt 6421  ggttgtgact ccaagagcag agtgaggaag accccaagc atagactcgg tactgtgat 6481  gatggctgca gtccagtttt atgattctgc ttttatgtgt cccttgataa cagtgactta 6541  acaatataca ttcctcataa ataaaaaaa aacaagaatc tgaattctta gaaaaaaaa 6601  aaaaaaaaaa aaaa
```

SEQ ID NO: 4 Human ADAR isoform b Amino Acid Sequence (NP_056655.2)

```
  1  mnprqgysls gyythpfqgy ehrqlryqqp gpgsspssfl lkqieflkgq lpeapvigkq 61  tpslppslpg lrprfpvlla sstrgrqvdi rgvprgvhlg sqglqrgfqh psprgrslpq 121  rgvdclsshf gelslyqdqe qrilkfleel gegkattahd lsgklgtpkk einrvlysla 181  kkgklqkeag tpplwkiavs tqawnqhsgv vrpdghsqga pnsdpslepe drnstsvsed 241  llepfiavsa qawnqhsgvv rpdshsqgsp nsdpgleped snstsaledp lefldmaeik 301  ekicdylfnv sdssalnlak nigltkardi navlidmerq gdvyrqgttp piwhltdkkr
```

TABLE 1-continued

```
 361 ermqikrntn svpetapaai petkrnaefl tcniptsnas nnmvttekve ngqepvikle
 421 nrqearpepa rlkppvhyng pskagyvdfe ngqwatddip ddlnsiraap gefraimemp
 481 sfyshglprc spykkltecq lknpisglle yaqfasqtce fnmieqsgpp heprfkfqvv
 541 ingrefppae agskkvakqd aamkamtill eeakakdsgk seesshyste kesektaesq
 601 tptpsatsff sgkspvttll ecmhklgnsc efrllskegp ahepkfqycv avgaqtfpsv
 661 sapskkvakq maaeeamkal hgeatnsmas dnqpegmise sldnlesmmp nkvrkigelv
 721 rylntnpvgg lleyarshgf aaefklvdqs gpphepkfvy qakvggrwfp avcahskkqg
 781 kqeaadaalr vligenekae rmgftelplt gstfhdqiam lshrcfntlt nsfqpsllgr
 841 kilaalimkk dsedmgvvvs lgtgnrcvkg dslslkgetv ndchaelisr rgfirflyse
 901 lmkynsqtak dsifepakgg eklqikktvs fhlyistapc gdgalfdksc sdramestes
 961 rhypvfenpk qgklrtkven gegtipvess divptwdgir lgerlrtmsc sdkilrwnvl
1021 glqgallthf lqpiylksvt lgylfsqghl traiccrvtr dgsafedglr hpfivnhpkv
1081 grvsiydskr qsgktketsv nwcladgydl eildgtrgtv dgprnelsrv skkniflllfk
1141 klcsfryrrd llrlsygeak kaardyetak nyfkkglkdm gygnwiskpq eeknfylcpv
```

SEQ ID NO: 5 Human ADAR Variant 3 cDNA Sequence (NM_015841.3, CDS region from position 243-3788)

```
   1 gccctcctc ttggccaaac tttccggagg ggaaggcttt ccgaggaaac gaaagcgaaa
  61 ttgaaccgga gccatcttgg gcccggcgcg cagacccgcg gagtttcccg tgccgacgcc
 121 ccggggccac ttccagtgcg gagtagcgga ggcgtgggg cctcgagggg ctggcgcggc
 181 ccagcggtcg ggccagggtc gtgccgccgg cgggtcgggc gggcaatgc ctcgcgggcg
 241 caatgaatcc gcggcagggg tattccctca gcggatacta cacccatcca tttcaaggct
 301 atgagcacag acagctcagg taccagcagc ctgggccagg atcttccccc agtagtttcc
 361 tgcttaagca aatagaattt ctcaaggggc agctcccaga agcaccggta attggaaagc
 421 agacaccgtc actgccacct tccctcccag gactccggcc aaggtttcca gtactacttg
 481 cctccagtac cagaggcagg caagtgaaca tcagggtgtg tgcccagggg cgtgcatctcg
 541 gaagtcaggg gctccagaga gggttccagc atccttcacc acgtggcagg agtctgccac
 601 agagaggtgt tgattgcctt tcctcacatt tccaggaact gagtatctac caagatcagg
 661 aacaaaggat cttaaagttc ctggaagagc ttggggaagg gaaggccacc acagcacatg
 721 atctgtctgg gaaacttggg actccgaaga aagaaatcaa tcgagtttta tactccctgg
 781 caaagaaggg caagctacag aaagaggcag gaacacccc tttgtggaaa atcgcggtct
 841 ccactcaggc ttggaaccag cacagcggag tggtaagacc agacggtcat agccaaggag
 901 ccccaaactc agacccgagt ttggaaccgg aagacagaaa ctccacatct gtctcagaag
 961 atcttcttga gccttttatt gcagtctcag ctcaggcttg gaaccagcac agcggagtgg
1021 taagaccaga cagtcatagc caaggatccc caaactcaga cccaggtttg gaacctgaag
1081 acagcaactc cacatctgcc ttggaagatc tcttgagtt tttagacatg gccgagatca
1141 aggagaaaat ctgcgactat ctcttcaatg tgtctgactc ctctgccctg aatttggcta
1201 aaaatattgg ccttaccaag gcccgagata aaatgctgt gctaattgac atggaaaggc
1261 aggggggatgt ctatagacaa gggacaaccc ctcccatatg gcatttgaca gacaagaagc
1321 gagagaggat gcaaatcaag agaaatacga acagtgttcc tgaaaccgct ccagctgcaa
1381 tccctgagac caaaagaaac gcagagttcc tcacctgtaa tatcccaca tcaaatgcct
1441 caaataacat ggtaaccaca gaaaaagtgg agaatgggca ggaacctgtc ataaagttag
```

TABLE 1-continued

```
1501  aaaacaggca agaggccaga ccagaaccag caagactgaa accacctgtt cattacaatg
1561  gcccctcaaa agcagggtat gttgactttg aaaatggcca gtgggccaca gatgacatcc
1621  cagatgactt gaatagtatc cgcgcagcac caggtgagtt tcgagccatc atggagatgc
1681  cctccttcta cagtcatggc ttgccacggt gttcacccta caagaaactg acagagtgcc
1741  agctgaagaa ccccatcagc gggctgttag aatatgccca gttcgctagt caaacctgtg
1801  agttcaacat gatagagcag agtggaccac cccatgaacc tcgatttaaa ttccaggttg
1861  tcatcaatgg ccgagagttt cccccagctg aagctggaag caagaaagtg gccaagcagg
1921  atgcagctat gaaagccatg acaattctgc tagaggaagc caaagccaag gacagtggaa
1981  aatcagaaga atcatcccac tattccacag agaaagaatc agagaagact gcagagtccc
2041  agacccccac cccttcagcc acatccttct tttctgggaa gagcccgtc accacactgc
2101  ttgagtgtat gcacaaattg gggaactcct gcgaattccg tctcctgtcc aaagaaggcc
2161  ctgcccatga acccaagttc caatactgtg ttgcagtggg agcccaaact tccccagtg
2221  tgagtgctcc cagcaagaaa gtggcaaagc agatggccgc agaggaagcc atgaaggccc
2281  tgcatgggga ggcgaccaac tccatggctt ctgataacca ggtcaggaag attggcgagc
2341  tcgtgagata cctgaacacc aaccctgtgg gtggccttt ggagtacgcc cgctcccatg
2401  gctttgctgc tgaattcaag ttggtcgacc agtccggacc tcctcacgag cccaagttcg
2461  tttaccaagc aaaagttggg ggtcgctggt tcccagccgt ctgcgcacac agcaagaagc
2521  aaggcaagca ggaagcagca gatgcggctc tccgtgtctt gattggggag aacgagaagg
2581  cagaacgcat gggtttcaca gagctccctc tcactggcag caccttccat gaccagatag
2641  ccatgctgag ccaccggtgc ttcaacactc tgactaacag cttccagccc tccttgctcg
2701  gccgcaagat tctggccgcc atcattatga aaaaagactc tgaggacatg ggtgtcgtcg
2761  tcagcttggg aacagggaat cgctgtgtga aggagattc tctcagccta aaaggagaaa
2821  ctgtcaatga ctgccatgca gaaataatct cccggagagg cttcatcagg tttctctaca
2881  gtgagttaat gaaatacaac tcccagactg cgaaggatag tatatttgaa cctgctaagg
2941  gaggagaaaa gctccaaata aaaaagactg tgtcattcca tctgtatatc agcactgctc
3001  cgtgtggaga tggcgccctc tttgacaagt cctgcagcga ccgtgctatg gaaagcacag
3061  aatcccgcca ctaccctgtc ttcgagaatc ccaaacaagg aaagctccgc accaaggtgg
3121  agaacggaga aggcacaatc cctgtggaat ccagtgacat tgtgcctacg tgggatggca
3181  ttcggctcgg ggagagactc cgtaccatgt cctgtagtga caaaatccta cgctggaacg
3241  tgctgggcct gcaagggca ctgttgaccc acttcctgca gcccatttat ctcaaatctg
3301  tcacattggg ttacctttc agccaagggc atctgacccg tgctatttgc tgtcgtgtga
3361  caagagatgg gagtgcattt gaggatggac tacgacatcc ctttattgtc aaccacccca
3421  aggttggcag agtcagcata tatgattcca aaaggcaatc cgggaagact aaggagacaa
3481  gcgtcaactg tgtgtctggc tgatggctatg acctggagat cctggacggt accagaggca
3541  ctgtggatgg gccacggaat gaattgtccc gggtctccaa aaagaacatt tttcttctat
3601  ttaagaagct ctgctccttc cgttaccgca gggatctact gagactctcc tatggtgagg
3661  ccaagaaagc tgcccgtgac tacgagacgc caagaactta cttcaaaaaa ggcctgaagg
3721  atatgggcta tgggaactgg attagcaaac cccaggagga aaagaacttt atctctgcc
3781  cagtatagta tgctccagtg acagatggat tagggtgtgt catactaggg tgtgagagag
3841  gtaggtcgta gcattcctca tcacatggtc aggggatttt ttttttctcct tttttttct
```

TABLE 1-continued

```
3901  ttttaagcca taattggtga tactgaaaac tttgggttcc catttatcct gctttctttg
3961  ggattgctag gcaaggtctg gccaggcccc cctttttcc cccaagtgaa gaggcagaaa
4021  cctaagaagt tatcttttct ttctacccaa agcatacata gtcactgagc acctgcggtc
4081  catttcctct taaaagtttt gttttgattt gtttccattt ccttcccctt tgtgtttgct
4141  acactgacct cttgcggtct tgattaggtt tcagtcaact ctggatcatg tcagggactg
4201  ataatttcat tgtggatta cgcagacccc tctacttccc ctctttccct tctgagattc
4261  tttccttgtg atctgaatgt ctccttttcc ccctcagagg gcaaagaggg gaacataaag
4321  gatttggtga aacatttgta agggtaggag ttgaaaactg cagttcccag tgccacggaa
4381  gtgtgattgg agcctgcaga taatgcccag ccatcctccc atcctgcact ttagccagct
4441  gcagggcggg caaggcaagg aaagctgctt ccctggaagt gtatcacttt ctccggcagc
4501  tgggaagtct agaaccagcc agactgggtt aagggagctg ctcaagcaat gcagaggtt
4561  tcacccggca ggatgacaca gaccacttcc cagggagcac gggcatgcct tggaatattg
4621  ccaagcttcc agctgcctct tctcctaaag cattcctagg aatattttcc ccgccaatgc
4681  tgggcgtaca ccctagccaa cgggacaaat cctagagggt ataaaatcat ctctgctcag
4741  ataatcatga cttagcaaga ataagggcaa aaaatcctgt tggcttaacg tcactgttcc
4801  acccggtgta atatctctca tgacagtgac accaagggaa gttgactaag tcacatgtaa
4861  attaggagtg ttttaaagaa tgccatagat gttgattctt aactgctaca gataacctgt
4921  aattgagcag atttaaaatt caggcatact tttccattta tccaagtgct ttcattttc
4981  cagatggctt cagaagtagg ctcgtgggca gggcgcagac ctgatcttta tagggttgac
5041  atagaaagca gtagttgtgg gtgaaagggc aggttgtctt caaactctgt gaggtagaat
5101  cctttgtcta tacctccatg aacattgact cgtgtgttca gagcctttgg cctctctgtg
5161  gagtctggct ctctggctcc tgtgcattct ttgaatagtc actcgtaaaa actgtcagtg
5221  cttgaaactg tttcctttac tcatgttgaa gggactttgt tggcttttag agtgttggtc
5281  atgactccaa gagcagagca gggaagagcc caagcataga cttggtgccg tggtgatggc
5341  tgcagtccag ttttgtgatg ctgcttttac gtgtccctcg ataacagtca gctagacaca
5401  ctcaggagga ctactgaggc tctgcgacct tcaggagctg agcctgcctc tctcctttag
5461  atgacagacc ttcatctggg aacgtgctga gccagcaccc tcagatgatt tccctccaaa
5521  ctgctgacta ggtcatcctc tgtctggtag agacattcac atctttgctt ttattctatg
5581  ctctctgtac ttttgaccaa aaattgacca aagtaagaaa atgcaagttc taaaaataga
5641  ctaaggatgc ctttgcagaa caccaaagca tcccaaggaa ctggtaggga agtggcgcct
5701  gtctcctgga gtggaagagg cctgctccct ggctctgggt ctgctggggg cacagtaaat
5761  cagtcttggc acccacatcc agggcagaga ggtctgtggt tctcagcatc agaaggcagc
5821  gcagcccctc tcctcttcag gctacagggt tgtcacctgc tgagtcctca ggttgtttgg
5881  cctctctggt ccatcttggg cattaggttc tccagcagag ctctggccag ctgcctcttc
5941  tttaactggg aacacaggct ctcacaagat cagaaccccc actcaccccc aagatcttat
6001  ctagcaagcc tgtagtattc agtttctgtt gtaggaagag agcgaggcat ccctgaattc
6061  cacgcatctg ctggaaacga gccgtgtcag atcgcacatc cctgcgcccc catgcccctc
6121  tgagtcacac aggacagagg aggcagagct tctgcccact gttatcttca ctttctttgt
6181  ccagtctttt gttttaata agcagtgacc ctccctactc ttcttttaa tgatttttgt
6241  agttgatttg tctgaactgt ggctactgtg cattccttga ataatcactt gtaaaaattg
```

TABLE 1-continued

```
6301 tcagtgcttg aagctgtttc ctttactcac attgaaggga cttcgttggt tttttggagt
6361 cttggttgtg actccaagag cagagtgagg aagaccccca agcatagact cgggtactgt
6421 gatgatggct gcagtccagt tttatgattc tgcttttatg tgtcccttga taacagtgac
6481 ttaacaatat acattcctca taaataaaaa aaaaacaaga atctgaattc ttagaaaaaa
6541 aaaaaaaaaa aaaaaaa
```

SEQ ID NO: 6 Human ADAR isoform c Amino Acid Sequence (NP_056656.2)
```
   1 mnprqgysls gyythpfqgy ehrqlryqqp gpgsspssfl lkqieflkgq lpeapvigkq
  61 tpslppslpg lrprfpvlla sstrgrqvdi rgvprgvhlg sqglqrgfqh psprgrslpq
 121 rgvdclsshf qelsiyqdqe qrilkfleel gegkattahd lsgklgtpkk einrvlysla
 181 kkgklqkeag tpplwkiavs tqawnqhsgv vrpdghsqga pnsdpslepe drnstsvsed
 241 llepfiavsa qawnqhsgvv rpdshsqgsp nsdpgleped snstsaledp lefldmaeik
 301 ekicdylfnv sdssalnlak nigltkardi navlidmerq gdvyrqgttp piwhltdkkr
 361 ermqikrntn svpetapaai petkrnaefl tcniptsnas nnmvttekve ngqepvikle
 421 nrqearpepa rlkppvhyng pskagyvdfe ngqwatddip ddlnsiraap gefraimemp
 481 sfyshglprc spykkltecq lknpisglle yaqfasqtce fnmieqsgpp heprfkfqvv
 541 ingrefppae agskkvakqd aamkamtill eeakakdsgk seesshyste kesektaesq
 601 tptpsatsff sgkspvttll ecmhklgnsc efrllskegp ahepkfqycv avgaqtfpsv
 661 sapskkvakq maaeeamkal hgeatnsmas dnqvrkigel vrylntnpvg glleyarshg
 721 faaefklvdq sgpphepkfv yqakvggrwf pavcahskkq gkqeaadaal rvligeneka
 781 ermgftelpl tgstfhdqia mlshrcfntl tnsfqpsllg rkilaaiimk kdsedmgvvv
 841 slgtgnrcvk gdslslkget vndchaeiis rrgfirflys elmkynsqta kdsifepakg
 901 geklqikktv sfhlyistap cgdgalfdks csdrameste srhypvfenp kqgklrtkve
 961 ngegtipves sdivptwdgi rlgerlrtms csdkilrwnv lglqgallth flqpiylksv
1021 tlgylfsqgh ltraiccrvt rdgsafedgl rhpfivnhpk vgrvsiydsk rqsgktkets
1081 vnwcladgyd leildgtrgt vdgprnelsr vskknifllf kklcsfryrr dllrlsygea
1141 kkaardyeta knyfkkglkd mgygnwiskp qeeknfylcp v
```

SEQ ID NO: 7 Human ADAR Variant 4 cDNA Sequence (NM_001025107.2, CDS region from position 997-3792)
```
   1 gaccagacca ttgattcccg actgaaggta gagaaggcta cgtggtgggg gagggtgggg
  61 ggagggtcgc ggccgcactg gcagcctccg ggtgtccggc cgtgtcccga ggaagtgcaa
 121 gacccggggt attccctcag cggatactac acccatccat ttcaaggcta tgagcacaga
 181 cagctcaggt accagcagcc tgggccagga tcttccccca gtagtttcct gcttaagcaa
 241 atagaatttc tcaaggggca gctcccagaa gcaccggtga ttggaaagca gacaccgtca
 301 ctgccacctt ccctcccagg actccggcca aggtttccag tactacttgc ctccagtacc
 361 agaggcaggc aagtggacat caggggtgtc cccaggggcg tgcatctcgg aagtcagggg
 421 ctccagagag ggttccagca tccttcacca cgtggcagga gtctgccaca gagaggtgtt
 481 gattgccttt cctcacattt ccaggaactg agtatctacc aagatcagga acaaaggatc
 541 ttaaagttcc tggaagagct tggggaaggg aaggccacca cagcacatga tctgtctggg
 601 aaacttggga ctccgaagaa agaaatcaat cgagttttat actccctggc aaagaagggc
 661 aagctacaga aagaggcagg aacaccccct tgtgtgaaaa tcgcggtctc cactcaggct
 721 tggaaccagc acagcggagt ggtaagacca gacggtcata gccaaggagc cccaaactca
```

TABLE 1-continued

```
 781   gacccgagtt tggaaccgga agacagaaac tccacatctg tctcagaaga tcttcttgag
 841   ccttttattg cagtctcagc tcaggcttgg aaccagcaca gcggagtggt aagaccagac
 901   agtcatagcc aaggatcccc aaactcagac ccaggtttgg aacctgaaga cagcaactcc
 961   acatctgcct tggaagatcc tcttgagttt ttagacatgg ccgagatcaa ggagaaaatc
1021   tgcgactatc tcttcaatgt gtctgactcc tctgccctga atttggctaa aaatattggc
1081   cttaccaagg cccgagatat aaatgctgtg ctaattgaca tggaaaggca ggggatgtc
1141   tatagacaag ggacaacccc tcccatatgg catttgacag acaagaagcg agagaggatg
1201   caaatcaaga gaaatacgaa cagtgttcct gaaaccgctc cagctgcaat ccctgagacc
1261   aaaagaaacg cagagttcct cacctgtaat atacccacat caaatgcctc aaataacatg
1321   gtaaccacag aaaaagtgga gaatgggcag gaacctgtca taagttaga aaacaggcaa
1381   gaggccagac cagaaccagc aagactgaaa ccacctgttc attacaatgg cccctcaaaa
1441   gcagggtatg ttgactttga aaatggccag tgggccacag atgacatccc agatgacttg
1501   aatagtatcc gcgcagcacc aggtgagttt cgagccatca tggagatgcc ctccttctac
1561   agtcatggct tgccacggtg ttcaccctac aagaaactga cagagtgcca gctgaagaac
1621   cccatcagcg ggctgttaga atatgcccag ttcgctagtc aaacctgtga gttcaacatg
1681   atagagcaga gtggaccacc ccatgaacct cgatttaaat tccaggttgt catcaatggc
1741   cgagagtttc ccccagctga agctggaagc aagaaagtgg ccaagcagga tgcagctatg
1801   aaagccatga caattctgct agaggaagcc aaagccaagg acagtggaaa atcagaagaa
1861   tcatcccact attccacaga gaaagaatca gagaagactg cagagtccca gacccccacc
1921   ccttcagcca catccttctt ttctgggaag agccccgtca ccacactgct tgagtgtatg
1981   cacaaattgg ggaactcctg cgaattccgt ctcctgtcca agaaggccc tgcccatgaa
2041   cccaagttcc aatactgtgt tgcagtggga gcccaaactt tccccagtgt gagtgctccc
2101   agcaagaaag tggcaaagca gatggccgca gaggaagcca tgaaggccct gcatggggag
2161   gcgaccaact ccatggcttc tgataaccag cctgaaggta tgatctcaga gtcacttgat
2221   aacttggaat ccatgatgcc caacaaggtc aggaagattg gcgagctcgt gagatacctg
2281   aacaccaacc ctgtgggtgg ccttttggag tacgcccgct cccatggctt tgctgctgaa
2341   ttcaagttgg tcgaccagtc cggacctcct cacgagccca gttcgttta ccaagcaaaa
2401   gttgggggtc gctggttccc agccgtctgc gcacacagca agaagcaagg caagcaggaa
2461   gcagcagatg cggctctccg tgtcttgatt ggggagaacg agaaggcaga acgcatgggt
2521   ttcacagagg taaccccagt gacagggggcc agtctcagaa gaactatgct cctcctctca
2581   aggtccccag aagcacagcc aaagacactc cctctcactg gcagcacctt ccatgaccag
2641   atagccatgc tgagccaccg gtgcttcaac actctgacta acagcttcca gccctccttg
2701   ctcggccgca agattctggc cgccatcatt atgaaaaaag actctgagga catgggtgtc
2761   gtcgtcagct gggaacagg gaatcgctgt gtgaaggag attctctcag cctaaaagga
2821   gaaactgtca atgactgcca tgcagaaata atctcccgga gaggcttcat caggtttctc
2881   tacagtgagt taatgaaata caactcccag actgcgaagg atagtatatt tgaacctgct
2941   aagggaggag aaaagctcca aataaaaaag actgtgtcat tccatctgta tatcagcact
3001   gctccgtgtg gagatggcgc cctcttttgac aagtcctgca gcgaccgtgc tatggaaagc
3061   acagaatccc gccactaccc tgtcttcgaa atcccaaac aaggaaagct ccgcaccaag
3121   gtggagaacg gagaaggcac aatccctgtg gaatccagtg acattgtgcc tacgtgggat
```

TABLE 1-continued

```
3181  ggcattcggc tcggggagag actccgtacc atgtcctgta gtgacaaaat cctacgctgg
3241  aacgtgctgg gcctgcaagg ggcactgttg acccacttcc tgcagcccat ttatctcaaa
3301  tctgtcacat tgggttacct tttcagccaa gggcatctga cccgtgctat ttgctgtcgt
3361  gtgacaagag atgggagtgc atttgaggat ggactacgac atccctttat tgtcaaccac
3421  cccaaggttg gcagagtcag catatatgat tccaaaaggc aatccgggaa gactaaggag
3481  acaagcgtca actggtgtct ggctgatggc tatgacctgg agatcctgga cggtaccaga
3541  ggcactgtgg atgggccacg gaatgaattg tcccgggtct ccaaaaagaa cattttctt
3601  ctatttaaga agctctgctc cttccgttac cgcagggatc tactgagact ctcctatggt
3661  gaggccaaga aagctgcccg tgactacgag acggccaaga actacttcaa aaaaggcctg
3721  aaggatatgg gctatgggaa ctggattagc aaaccccagg aggaaaagaa ctttatctc
3781  tgcccagtat agtatgctcc agtgacagat ggattagggt gtgtcatact agggtgtgag
3841  agaggtaggt cgtagcattc ctcatcacat ggtcagggga tttttttttc tccttttttt
3901  ttcttttaa gccataattg gtgatactga aaactttggg ttcccattta tcctgctttc
3961  tttgggattg ctaggcaagg tctggccagg cccccctttt ttcccccaag tgaagaggca
4021  gaaacctaag aagttatctt ttctttctac ccaaagcata catagtcact gagcacctgc
4081  ggtccatttc ctcttaaaag ttttgttttg atttgtttcc atttccttc cctttgtgtt
4141  tgctacactg acctcttgcg gtcttgatta ggtttcagtc aactctggat catgtcaggg
4201  actgataatt tcatttgtgg attacgcaga cccctctact tcccctcttt cccttctgag
4261  attctttcct tgtgatctga atgtctcctt ttccccctca gagggcaaag aggtgaacat
4321  aaaggatttg gtgaaacatt tgtaagggta ggagttgaaa actgcagttc ccagtgccac
4381  ggaagtgtga ttggagcctg cagataatgc ccagccatcc tcccatcctg cactttagcc
4441  agctgcaggg cgggcaaggc aaggaaagct gcttccctgg aagtgtatca ctttctccgg
4501  cagctgggaa gtctagaacc agccagactg ggttaaggga gctgctcaag caatagcaga
4561  ggtttcaccc ggcaggatga cacagaccac ttcccaggga gcacgggcat gccttggaat
4621  attgccaagc ttccagctgc ctcttctcct aaagcattcc taggaatatt ttccccgcca
4681  atgctgggcg tacaccctag ccaacgggac aaatcctaga gggtataaaa tcatctctgc
4741  tcagataatc atgacttagc aagaataagg gcaaaaatc ctgttggctt aacgtcactg
4801  ttccacccgg tgtaatatct ctcatgacag tgacaccaag ggaagttgac taagtcacat
4861  gtaaattagg agtgttttaa agaatgccat agatgttgat tcttaactgc tacagataac
4921  ctgtaattga gcagatttaa aattcaggca tacttttcca tttatccaag tgctttcatt
4981  tttccagatg gcttcagaag taggctcgtg ggcagggcgc agacctgatc tttatagggt
5041  tgacatagaa agcagtagtt gtgggtgaaa gggcaggttg tcttcaaact ctgtgaggta
5101  gaatcctttg tctataccctc catgaacatt gactcgtgtg ttcagagcct ttggcctctc
5161  tgtggagtct ggctctctgg ctcctgtgca ttctttgaat agtcactcgt aaaaactgtc
5221  agtgcttgaa actgtttcct ttactcatgt tgaagggact tgttggcttt tagagtgtt
5281  ggtcatgact ccaagagcag agcagggaag agcccaagca tagacttggt gccgtggtga
5341  tggctgcagt ccagtttttgt gatgctgctt ttacgtgtcc ctcgataaca gtcagctaga
5401  cacactcagg aggactactg aggctctgcg accttcagga gctgagcctg cctctctcct
5461  ttagatgaca gaccttcatc tgggaacgtg ctgagccagc accctcagat gatttccctc
5521  caaactgctg actaggtcat cctctgtctg gtagagacat tcacatcttt gcttttattc
```

TABLE 1-continued

```
5581  tatgctctct gtactttgga ccaaaaattg accaaagtaa gaaaatgcaa gttctaaaaa
5641  tagactaagg atgcctttgc agaacaccaa agcatcccaa ggaactggta gggaagtggc
5701  gcctgtctcc tggagtggaa gaggcctgct ccctggctct gggtctgctg ggggcacagt
5761  aaatcagtct tggcacccac atccagggca gagaggtctg tggttctcag catcagaagg
5821  cagcgcagcc cctctcctct tcaggctaca gggttgtcac ctgctgagtc ctcaggttgt
5881  ttggcctctc tggtccatct tgggcattag gttctccagc agagctctgg ccagctgcct
5941  cttctttaac tgggaacaca ggctctcaca agatcagaac ccccactcac ccccaagatc
6001  ttatctagca agcctgtagt attcagtttc tgttgtagga agagagcgag gcatccctga
6061  attccacgca tctgctggaa acgagccgtg tcagatcgca catccctgcg cccccatgcc
6121  cctctgagtc acacaggaca gaggaggcag agcttctgcc cactgttatc ttcactttct
6181  ttgtccagtc ttttgttttt aataagcagt gaccctccct actcttcttt ttaatgattt
6241  ttgtagttga tttgtctgaa ctgtggctac tgtgcattcc ttgaataatc acttgtaaaa
6301  attgtcagtg cttgaagctg tttcctttac tcacattgaa gggacttcgt tggttttttg
6361  gagtcttggt tgtgactcca agagcagagt gaggaagacc cccaagcata gactcgggta
6421  ctgtgatgat ggctgcagtc cagttttatg attctgcttt tatgtgtccc ttgataacag
6481  tgacttaaca atatacattc ctcataaata aaaaaaaaac aagaatctga attcttagaa
6541  aaaaaaaaaa aaaaaaaaaa a
```

SEQ ID NO: 8 Human ADAR isoform d Amino Acid Sequence (NP_001180424.1)
```
  1  maeikekicd ylfnvsdssa lnlakniglt kardinavli dmerqgdvyr qgttppiwhl
 61  tdkkrermqi krntnsvpet apaaipetkr naefltcnip tsnasnnmvt tekvengqep
121  viklenrqea rpeparlkpp vhyngpskag yvdfengqwa tddipddlns iraapgefra
181  imempsfysh glprcspykk ltecqlknpi sglleyaqfa sqtcefnmie qsgpphepfr
241  kfqvvingre fppaeagskk vakqdaamka mtilleeaka kdsgkseess hystekesek
301  taesqtptps atsffsgksp vttllecmhk lgnscefrll skegpahepk fqycvavgaq
361  tfpsvsapsk kvakqmaaee amkalhgeat nsmasdnqpe gmisesldnl esmmpnkvrk
421  igelvrylnt npvgglleya rshgfaaefk lvdqsgpphe pkfvyqakvg grwfpavcah
481  skkqgkqeaa daalrvlige nekaermgft evtpvtgasl rrtmlllsrs peaqpktlpl
541  tgstfhdqia mlshrcfntl tnsfqpsllg rkilaaiimk kdsedmgvvv slgtgnrcvk
601  gdslslkget vndchaelis rrgfirflys elmkynsqta kdsifepakg geklqikktv
661  sfhlyistap cgdgalfdks csdrameste srhypvfenp kqgklrtkve ngegtipves
721  sdivptwdgi rlgerlrtms csdkilrwnv lglqgallth flqpiylksv tlgylfsqgh
781  ltraiccrvt rdgsafedgl rhpfivnhpk vgrvsiydsk rqsgktkets vnwcladgyd
841  leildgtrgt vdgprnelsr vskkniflllf kklcsfryrr dllrlsygea kkaardyeta
901  knyfkkglkd mgygnwiskp qeeknfylcp v
```

SEQ ID NO: 9 Human ADAR Variant 5 cDNA Sequence (NM_001193495.1, CDS region from position 1166-3961)
```
  1  cagcactttg ggaggccgag gagggcggat caggagatcg acaccatcct ggccagcatg
 61  gtgaaacccc atctctacta aaaatacaaa aattagctgg gtgtggtggc gtgcgcctgt
121  aatcccagct actccggagg ctgaggcagg agaatcactt gaacccggga ggcggagatt
181  gcagtgagct gagatcacac tgcactccag cctgattgca gtgagccgag atcatgccac
241  tgcactccag cttggcaaca gagcgagact ccgtctcaca gaaaaaaaa taaccgggta
301  ttccctcagc ggatactaca cccatccatt tcaaggctat gagcacagac agctcaggta
```

TABLE 1-continued

```
 361   ccagcagcct gggccaggat cttcccccag tagtttcctg cttaagcaaa tagaatttct
 421   caaggggcag ctcccagaag caccggtgat tggaaagcag acaccgtcac tgccaccttc
 481   cctcccagga ctccggccaa ggtttccagt actacttgcc tccagtacca gaggcaggca
 541   agtggacatc aggggtgtcc ccaggggcgt gcatctcgga agtcaggggc tccagagagg
 601   gttccagcat ccttcaccac gtggcaggag tctgccacag agaggtgttg attgcctttc
 661   ctcacatttc caggaactga gtatctacca agatcaggaa caaaggatct taaagttcct
 721   ggaagagctt ggggaaggga aggccaccac agcacatgat ctgtctggga aacttgggac
 781   tccgaagaaa gaaatcaatc gagttttata ctccctggca agaagggca agctacagaa
 841   agaggcagga acaccccctt tgtggaaaat cgcggtctcc actcaggctt ggaaccagca
 901   cagcggagtg gtaagaccag acggtcatag ccaaggagcc ccaaactcag acccgagttt
 961   ggaaccggaa gacagaaact ccacatctgt ctcagaagat cttcttgagc cttttattgc
1021   agtctcagct caggcttgga accagcacag cggagtggta agaccagaca gtcatagcca
1081   aggatcccca aactcagacc caggtttgga acctgaagac agcaactcca catctgcctt
1141   ggaagatcct cttgagtttt tagacatggc cgagatcaag gagaaaatct gcgactatct
1201   cttcaatgtg tctgactcct ctgccctgaa tttggctaaa atattggcc ttaccaaggc
1261   ccgagatata aatgctgtgc taattgacat ggaaaggcag ggggatgtct atagacaagg
1321   gacaaccct cccatatggc atttgacaga caagaagcga gagggatgc aaatcaagag
1381   aaatacgaac agtgttcctg aaaccgctcc agctgcaatc cctgagacca aagaaacgc
1441   agagttcctc acctgtaata tacccacatc aaatgcctca ataacatgg taaccacaga
1501   aaaagtggag aatgggcagg aacctgtcat aaagttagaa acaggcaag aggccagacc
1561   agaaccagca agactgaaac cacctgttca ttacaatggc ccctcaaaag cagggtatgt
1621   tgactttgaa aatggccagt gggccacaga tgcatccca gatgacttga atagtatccg
1681   cgcagcacca ggtgagtttc gagccatcat ggagatgccc tccttctaca gtcatggctt
1741   gccacggtgt tcaccctaca agaaactgac agagtgccag ctgaagaacc ccatcagcgg
1801   gctgttagaa tatgcccagt tcgctagtca aacctgtgag ttcaacatga tagagcagag
1861   tggaccaccc catgaacctc gatttaaatt ccaggttgtc atcaatggcc gagagtttcc
1921   cccagctgaa gctggaagca agaaagtggc caagcaggat gcagctatga agccatgac
1981   aattctgcta gaggaagcca agccaagga cagtggaaaa tcagaagaat catcccacta
2041   ttccacagag aaagaatcag agaagactgc agagtcccag accccaccc cttcagccac
2101   atccttcttt tctgggaaga gcccgtcac cacactgctt gagtgtatgc acaaattggg
2161   gaactcctgc gaattccgtc tcctgtccaa agaaggccct gcccatgaac ccaagttcca
2221   atactgtgtt gcagtgggag cccaaacttt ccccagtgtg agtgctccca gcaagaaagt
2281   ggcaaagcag atggccgcag aggaagccat gaaggccctg catggggagg cgaccaactc
2341   catggcttct gataaccagc ctgaaggtat gatctcagag tcacttgata acttggaatc
2401   catgatgccc aacaaggtca ggaagattgg cgagctcgtg agatacctga acaccaaccc
2461   tgtgggtggc cttttggagt acgcccgctc ccatggcttt gctgctgaat tcaagttggt
2521   cgaccagtcc ggacctcctc acgagcccaa gttcgtttac caagcaaaag ttggggtcg
2581   ctggttccca gccgtctgcg cacacagcaa gaagcaaggc aagcaggaag cagcagatgc
2641   ggctctccgt gtcttgattg gggagaacga gaaggcagaa cgcatgggtt tcacagaggt
2701   aacccagtg acagggggcca gtctcagaag aactatgctc ctcctctcaa ggtccccaga
```

TABLE 1-continued

```
2761  agcacagcca aagacactcc ctctcactgg cagcaccttc catgaccaga tagccatgct
2821  gagccaccgg tgcttcaaca ctctgactaa cagcttccag ccctccttgc tcggccgcaa
2881  gattctggcc gccatcatta tgaaaaaaga ctctgaggac atgggtgtcg tcgtcagctt
2941  gggaacaggg aatcgctgtg tgaaaggaga ttctctcagc ctaaaaggag aaactgtcaa
3001  tgactgccat gcagaaataa tctcccggag aggcttcatc aggtttctct acagtgagtt
3061  aatgaaatac aactcccaga ctgcgaagga tagtatattt gaacctgcta agggaggaga
3121  aaagctccaa ataaaaaaga ctgtgtcatt ccatctgtat atcagcactg ctccgtgtgg
3181  agatggcgcc ctctttgaca agtcctgcag cgaccgtgct atggaaagca cagaatcccg
3241  ccactaccct gtcttcgaga atcccaaaca aggaaagctc cgcaccaagg tggagaacgg
3301  agaaggcaca atccctgtgg aatccagtga cattgtgcct acgtgggatg cattcggct
3361  cggggagaga ctccgtacca tgtcctgtag tgacaaaatc ctacgctgga acgtgctggg
3421  cctgcaaggg gcactgttga cccacttcct gcagcccatt tatctcaaat ctgtcacatt
3481  gggttacctt ttcagccaag ggcatctgac ccgtgctatt tgctgtcgtg tgacaagaga
3541  tgggagtgca tttgaggatg gactacgaca tcccttatt gtcaaccacc ccaaggttgg
3601  cagagtcagc atatatgatt ccaaaaggca atccgggaag actaaggaga caagcgtcaa
3661  ctggtgtctg gctgatggct atgacctgga gatcctggac ggtaccgagg cactgtggga
3721  tgggccacgg aatgaattgt cccgggtctc caaaaagaac atttttcttc tatttaagaa
3781  gctctgctcc ttccgttacc gcagggatct actgagactc tcctatggtg aggccaagaa
3841  agctgcccgt gactacgaga cggccaagaa ctacttcaaa aaaggcctga aggatatggg
3901  ctatgggaac tggattagca aaccccagga ggaaaagaac ttttatctct gcccagtata
3961  gtatgctcca gtgacagatg gattagggtg tgtcatacta gggtgtgaga gaggtaggtc
4021  gtagcattcc tcatcacatg gtcaggggat ttttttttct cctttttttt tcttttttaag
4081  ccataattgg tgatactgaa actttgggt tcccatttat cctgctttct ttgggattgc
4141  taggcaaggt ctggccaggc ccccctttt tcccccaagt gaagaggcag aaacctaaga
4201  agttatcttt tctttctacc caaagcatac atagtcactg agcacctgcg gtccatttcc
4261  tcttaaaagt tttgttttga tttgtttcca tttcctttcc ctttgtgttt gctacactga
4321  cctcttgcgg tcttgattag gtttcagtca actctggatc atgtcaggga ctgataattt
4381  catttgtgga ttacgcagac ccctctactt cccctctttc ccttctgaga ttctttcctt
4441  gtgatctgaa tgtctccttt tccccctcag agggcaaaga ggtgaacata aaggatttgg
4501  tgaaacattt gtaagggtag gagttgaaaa ctgcagttcc cagtgccacg gaagtgtgat
4561  tggagcctgc agataatgcc cagccatcct cccatcctgc actttagcca gctgcagggc
4621  gggcaaggca aggaaagctg cttccctgga agtgtatcac tttctccggc agctgggaag
4681  tctagaacca gccagactgg gttaagggag ctgctcaagc aatagcagag gtttcacccg
4741  gcaggatgac acagaccact tcccagggag cacgggcatg ccttggaata ttgccaagct
4801  tccagctgcc tcttctccta aagcattcct aggaatattt tccccgccaa tgctgggcgt
4861  acaccctagc aacgggaca atcctagag ggtataaaat catctctgct cagataatca
4921  tgacttagca agaataaggg caaaaaatcc tgttggctta acgtcactgt tccacccggt
4981  gtaatatctc tcatgacagt gacaccaagg gaagttgact aagtcacatg taaattagga
5041  gtgttttaaa gaatgccata gatgttgatt cttaactgct acagataacc tgtaattgag
5101  cagatttaaa attcaggcat acttttccat ttatccaagt gctttcattt ttccagatgg
```

TABLE 1-continued

```
5161   cttcagaagt aggctcgtgg gcagggcgca gacctgatct ttatagggtt gacatagaaa
5221   gcagtagttg tgggtgaaag ggcaggttgt cttcaaactc tgtgaggtag aatcctttgt
5281   ctatacctcc atgaacattg actcgtgtgt tcagagcctt tggcctctct gtggagtctg
5341   gctctctggc tcctgtgcat tctttgaata gtcactcgta aaaactgtca gtgcttgaaa
5401   ctgtttcctt tactcatgtt aagggactt tgttggcttt tagagtgttg gtcatgactc
5461   caagagcaga gcagggaaga gcccaagcat agacttggtg ccgtggtgat ggctgcagtc
5521   cagttttgtg atgctgcttt tacgtgtccc tcgataacag tcagctagac acactcagga
5581   ggactactga ggctctgcga ccttcaggag ctgagcctgc ctctctcctt tagatgacag
5641   accttcatct gggaacgtgc tgagccagca ccctcagatg atttccctcc aaactgctga
5701   ctaggtcatc ctctgtctgg tagagacatt cacatctttg cttttattct atgctctctg
5761   tacttttgac caaaaattga ccaaagtaag aaaatgcaag ttctaaaaat agactaagga
5821   tgcctttgca gaacaccaaa gcatcccaag gaactggtag ggaagtggcg cctgtctcct
5881   ggagtggaag aggcctgctc cctggctctg gtctgctgg gggcacagta aatcagtctt
5941   ggcacccaca tccagggcag agaggtctgt ggttctcagc atcagaaggc agcgcagccc
6001   ctctcctctt caggctacag ggttgtcacc tgctgagtcc tcaggttgtt tggcctctct
6061   ggtccatctt gggcattagg ttctccagca gagctctggc cagctgcctc ttctttaact
6121   gggaacacag gctctcacaa gatcagaacc cccactcacc cccaagatct tatctagcaa
6181   gcctgtagta ttcagtttct gttgtaggaa gagagcgagg catccctgaa ttccacgcat
6241   ctgctggaaa cgagccgtgt cagatcgcac atccctgcgc cccatgccc ctctgagtca
6301   cacaggacag aggaggcaga gcttctgccc actgttatct tcactttctt tgtccagtct
6361   tttgtttta ataagcagtg accctcccta ctcttctttt taatgatttt tgtagttgat
6421   ttgtctgaac tgtggctact gtgcattcct tgaataatca cttgtaaaaa ttgtcagtgc
6481   ttgaagctgt ttcctttact cacattgaag ggacttcgtt ggttttttgg agtcttggtt
6541   gtgactccaa gagcagagtg aggaagaccc ccaagcatag actcgggtac tgtgatgatg
6601   gctgcagtcc agttttatga ttctgctttt atgtgtccct tgataacagt gacttaacaa
6661   tatacattcc tcataaataa aaaaaaaca agaatctgaa ttcttagaaa aaaaaaaaa
6721   aaaaaaaaaa
```

SEQ ID NO: 10 Mouse ADAR Variant 1 cDNA Sequence (NM_019655.3, CDS region from position 94-3552)

```
  1   aacagttggg cggggaagcc ttttcaagga aacgaaagtg aactctgggg agccagccat
 61   cttacggcca caggtgcggg ccttgccggc actatgtctc aagggttcag gggacccaca
121   ggggtgttcc ctcaccagac acagtcgtac ttggaccccta gtcatgagca tagcaagtgg
181   agatacccgc agccacaggg gccggagtct taccctagga gtttccagct tcagcagata
241   gagtttctca aagggcggct cccagaagca cccttgattg aatacaaac ccagtcactg
301   ccgccattcc tcccaggaca ctggccaaga ttcccagggc cacctgccca agacaggcaa
361   ctggaaatct gggagttccc caggagtgtg actctcagaa atcagggggtt ccacatagga
421   ccccacttc ctcccccaca cagcaggggt acaccatgga gaggtgctga cgggctttgc
481   tcacacttcc gggagctgag catcagtcag agtccggagc agaaggttct aaaccgcctg
541   gaaagagcttg gggagggaa ggccaccact gcccatgtgc tagccagaga gctcagaatc
601   cccaaaaggg acatcaatcg tattttgtac tccctggaaa agaagggaaa gctgcacaga
661   ggaaggggga aacctccttt gtggagcctt gtgcccttga gtcaggcttg gactcagccc
```

TABLE 1-continued

```
 721   cctggagttg tgaatccaga tagttgtatc caggaattcc ctagaggaga gcctggtttg
 781   gacagtgagg acggagaccc tgcctctgac ttagaaggac cttctgagcc tcttgacatg
 841   gctgaaatca aggagaagat ctgtgactat ctgttcaatg tgtcaaactc ctctgccctg
 901   aacctggcta agaacattgg cctcaccaag gcccgagatg tgacctcagt gctgattgac
 961   ttggaaaggc aaggcgatgt ctacaggcaa ggggcaactc ctcccatctg gtacttgacg
1021   gacaagaagc gtgagaggct gcagatgaag agaagtacac acagtgctcc tgcccctacc
1081   ccgacagctg tcccagaggc cactagaagc ccctcattcc ctgcctgcca cccgccccca
1141   gcaggtgcct caagcagtgt ggcagcctcc aagagagtgg agaatgggca ggagcctgcg
1201   ataaagcatg aaagtaggca tgaggccaga ccaggaccaa tgagactgcg gcctcacgct
1261   tatcacaatg gcccctctag agcagggtat gtggcctctg aaaatggcca gtgggccaca
1321   gatgacatcc cagataactt gaatagtatc cacacagcac caggtgagtt tcgagccatc
1381   atggagatgc cctccttcta cagcccctacc ttgccacggt gttcacccta caagaagcta
1441   actgagtgcc agctgaagaa ccctgtcagc gggttgttag agtatgctca gttcactagt
1501   cagacctgtg atttcaacct gatagagcag agtggaccgt cccatgaacc tcgatttaaa
1561   ttccaggttg tcatcaatgg gcgggaattt cccccagctg aggctggcag caagaaagta
1621   gccaagcagg acgcagcagt gaaagccatg gcgattctgc ttcgggaagc caaagccaaa
1681   gacagtggtc aaccagaaga cttgtcccac tgtcccatgg aagaagactc ggagaaacca
1741   gcagaggctc aggcccccag ctcctcagca acatccttgt tctctgggaa gagcccagtt
1801   actacactgc ttgagtgcat gcacaaacta gggaactcct gtgaattccg tctcctgtcc
1861   aaagaaggcc ctgctcatga ccccaagttc cagtactgtg tagcagtagg agcccagacc
1921   ttccccccctg tgagcgcccc cagcaagaag gtagcaaagc agatggccgc agaggaagcc
1981   atgaaggcgc tgcaggagga ggcagccagt tcagcggatg accagtctgg aggtgcgaac
2041   acagactcac ttgatgaatc tatggctccc aacaagatca ggaggattgg tgagctcgtc
2101   aggtacctga acaccaaccc cgtaggcggc ttgttggagt acgcccgatc tcatggcttt
2161   gctgctgagt tcaagctcat tgaccagtct ggacctcctc acgaacccaa gtttgtttac
2221   caagcaaaag ttgggggccg ctggttttcca gccgtgtgtg cacacagcaa gaaacagggc
2281   aagcaggatg cagcggatgc agccctccgg gtcttgatcg gggagagcga aaggcagag
2341   cagttgggtt tcgcagagct tcctctctct ggcagcacct tccacgacca gatagctatg
2401   ctgagccaca ggtgcttcaa tgctctgacc aacagtttcc agccctccct gctcggccgc
2461   aagatcctgg ctgccattat tatgaaaaga gatccagagg acatgggtgt tgtcgtgagt
2521   ttggggacag gcaatcgctg tgtgaaaggg gactctctca gcctgaaggg agagacggtc
2581   aatgactgcc atgccgaaat catctcccgg aggggcttca tcaggttttct ctacagtgaa
2641   ctgatgaagt acaaccacca cactgccaag aacagcatat ttgagcttgc caggggagga
2701   gagaagctgc agataaagaa gacggtttct tttcatctct acatcagcac ggcgccatgt
2761   ggagatgggg ccctcttttga caaatcctgc agtgaccgtg ccgtggaaag cacagagtcc
2821   cgccattacc ctgtctttga aaatcccaag caaggcaagc ttcgcaccaa ggtggagaat
2881   ggggaaggca caattcctgt ggagtccagt gatattgtac ccacgtggga tggcatccgc
2941   cttggggaaa gactccgtac catgtcctgt agtgacaaaa tcctacgctg gaatgtgctg
3001   ggcctgcaag gggcgttgtt gacgcacttc ctacagcctg tgtacctgaa atctgtaacc
3061   ttaggttacc ttttcagcca agggcatctg acccgtgcta tttgctgccg cgtgaccaga
```

TABLE 1-continued

```
3121  gatgggaaag catttgagga tggactacgc tatcccttta ttgtcaacca ccccaaggtc
3181  ggccgagtca gtgtttatga ttccaaaaga cagtccggaa agaccaagga aacaagcgtc
3241  aactggtgca tggctgatgg ctatgaccta gagatcctgg atggcaccag aggcactgtg
3301  gatggaccag ggaaagagtt gtctcgggtg tccaagaaga atattttcct tcagtttaag
3361  aagctctgct ccttccgagc ccgcagagat ttactgcagc tctcttatgt gaagccaag
3421  aaagctgccc gtgactatga cttagccaag aactacttca agaaaagcct gcgagacatg
3481  ggctatggga attggatcag caaaccccag gaggaaaaga acttttacct ctgtccagta
3541  cccaatgact gatagtgggg cgcgtttctc ctggggtcag agggcggtca tggcattcct
3601  catcacaccg ggccagagga taggagcttt ttttacccac tccccccttt tttaatggta
3661  gaaccataat agatggtacc aagaactgct ttctttggga tttcaaggtg gggtccagcc
3721  aagtccccac ctcccttttc tcaaggaag aggccaagat taaggaaat ggaaatgcta
3781  ccattccata tgtagcacag acagttcttg gtcacatgga gcccaggccc ctcgggcttc
3841  gttttgcgga ggttttttc atctccttt cctttgctgc actggcctct tgtgggttg
3901  attccatccc atcagttctc tgtaaatgat gtcaggggcc agtgatgtca cctgcagatg
3961  cgcaggcagg cccctgctct gtcatccttc cctcctagga tgccttcctg tgatgaggtt
4021  tctccttccc caccccagag gatagaggtg aacataaagg attggtgaaa tgtttacaag
4081  ggcaggagtt gacaaccgtg gtcagggatt gtcgaacaac aggaatgtgg taaactgtgg
4141  ttgggacagg caagccctac ccagtaacag gccgtgctgg cccaccaagg aacttcctt
4201  cctgggcagc agggaagttg agaatcggcc agtgggaccg aggaaggtac ccaaaccaag
4261  cacgtcccag tagggtcca caagcactaa ctagagtgca ccagcattcc atggaatgtc
4321  gctatgcctc catctgcccc tccatgagca ctcccagaag ctggccctgg gcacgtgtgg
4381  tgttggcccc aggccccagc tgtttgtgaa aagcagaggg tgagcatagt gggcagagca
4441  gctttgccca gacggcaaag gtaaaggcag agcatcctgc cggtgcactg ggattcttct
4501  ggtctcagca gaagtgacaa agccctgcat agaattaatg tttctaaaag gccagaggca
4561  ttgattctga actgcatcaa agactggaga tgcaaatatt acttctccat tagtaaatgt
4621  actttcattc tatcagatgg cttcagaagc tgggtcacgg acagggcaca gggccctgga
4681  atctctgccc tgctcctttg aggatcttca tttacataca agtgttgtag gtggcagggc
4741  aggctggcct cccactctgg gatgggcttc tttgactcct cccctctga cagtgacttg
4801  tgggtatgtg ggagcctctg tagaatctgg ttctagcatc agatcaacca gccagaccct
4861  gctccattct gccctctag gaccaagccc acctctttcc tctgaatggt gtggctccat
4921  ctggagacag ctggccagtg tgttcaacag tttcctgcac ccccttgctt aaccctcaga
4981  gctgcctggt tcccccaccc tctggcccac tgccaacagc aaacatcaca ttcgtacttc
5041  aagtctaatg ctactgcct cctcaatcta tgaacagatc tggccaacac aagaacctgt
5101  gtcttcacaa tacactgggg atgtctttgc acagccaaat catcctatga aactccagcg
5161  tctgtggaag tgagaaagca gcaccatgct tgtggtgtcg gctggaggcg tgtcaccctc
5221  cggcaactgc atctgaagca gagcccttgt ggtttccagg cctggacagg gagctcttcc
5281  cctgggtct aaaggacaga gatgtctctc cctttgattc ctttggtccc tctggtcctc
5341  cctgggtatt cacacatacc ccaatcctgt ctagacaacg agtggttctg ggtttctgca
5401  gatggaagag agcaaggtgt ccctgagttc tgtggacttg accccgcat cccaccctga
5461  ccctgcctcc agtcccgctg gccgagggca gagcctcctc ccactgtgct tccttcacgt
```

TABLE 1-continued

```
5521  ttactttaag aagcagggcc tccctccaca ccgtctctta atactttctg tagttgattt
5581  gtctgaaccg tggctgtctt gcattccttg aataatcatg tgtaagaatt gtcaatgctt
5641  gaaactattt cctgtactca agttgaaggg actttgttgg ccttgggggtt ttagcagtga
5701  ctccaagagc agagtgggga agcacccagg catagcctttg cgctgtgat ggatgcagtc
5761  cctccctctg tcccttaca agtgacagta tacattccta aaaataaaaa cactgaagca
5821  tcaggactgt taaaaaaaaa aaaaaaaaa
```

SEQ ID NO: 11 Mouse ADAR isoform 1 Amino Acid Sequence (NP_062629.3)

```
   1  msqgfrgptg vfphqtqsyl dpshehskwr ypqpqgpesy prsfqlqqie flkgrlpeap
  61  ligiqtqslp pflpghwprf pgppaqdrql eiwefprsvt lrnqgfhigp plppphsrgt
 121  pwrgadglcs hfrelsisqs peqkvlnrle elgegkatta hvlarelrip krdinrilys
 181  lekkgklhrg rgkpplwslv plsqawtqpp gvvnpdsciq efprgepgld sedgdpasdl
 241  egpsepldma eikekicdyl fnvsnssaln laknigltka rdvtsvlidl erqgdvyrqg
 301  atppiwyltd kkrerlqmkr sthsapaptp tavpeatrsp sfpachpppa gasssvaask
 361  rvengqepai khesrhearp gpmrlrphay hngpsragyv asengqwatd dipdnlnsih
 421  tapgefraim empsfysptl prcspykklt ecqlknpvsg lleyaqftsq tcdfnlieqs
 481  gpsheprfkf qvvingrefp paeagskkva kqdaavkama illreakakd sgqpedlshc
 541  pmeedsekpa eaqapssssat slfsgkspvt tllecmhklg nscefrllsk egpandpkfq
 601  ycvavgaqtf ppvsapskkv akqmaaeeam kalqeeaass addqsggant dsldesmapn
 661  kirrigelvr ylntnpvggl leyarshgfa aefklidqsg pphepkfvyq akvggrwfpa
 721  vcahskkqgk qdaadaalrv ligesekaeq lgfaelplsg stfhdqiaml shrcfnaltn
 781  sfqpsllgrk ilaaiimkrd pedmgvvvsl gtgnrcvkgd slslkgetvn dchaelisrr
 841  gfirflysel mkynhhtakn sifelargge klqikktvsf hlyistapcg dgalfdkscs
 901  dravestesr hypvfenpkq gklrtkveng egtipvessd ivptwdgirl gerlrtmscs
 961  dkilrwnvlg lqgallthfl qpvylksvtl gylfsqghlt raiccrvtrd gkafedglry
1021  pfivnhpkvg rvsvydskrq sgktketsvn wcmadgydle ildgtrgtvd gpgkelsrvs
1081  kkniflqfkk lcsfrarrdl lqlsygeakk aardydlakn yfkkslrdmg ygnwiskpqe
1141  eknfylcpvp nd
```

SEQ ID NO: 12 Mouse ADAR Variant 2 cDNA Sequence (NM_001038587.4, CDS region from position 846-3638)

```
   1  agtgatgtca ccaatctgcg ccctaaccat tgattcctga ctgaaggtgg aagactacgc
  61  gttgggacta gccgggaagg gcgcagcctt gggctcacga gtgggcagcg tccgaggaat
 121  cgcgcgcggg ggtgttccct caccagacac agtcgtactt ggaccctagt catgagcata
 181  gcaagtggag ataccccgcag ccacaggggc cggagtctta ccctaggagt ttccagcttc
 241  agcagataga gtttctcaaa gggcggctcc cagaagcacc cttgattgga atacaaaccc
 301  agtcactgcc gccattcctc ccaggacact ggccaagatt cccagggcca cctgcccaag
 361  acaggcaact ggaaatctgg gagttcccca ggagtgtgac tctcagaaat caggggttcc
 421  acataggacc cccacttcct cccccacaca gcagggtac accatggaga ggtgctgacg
 481  ggctttgctc acacttccgg gagctgagca tcagtcagag tccggagcag aaggttctaa
 541  accgcctgga gagcttggg gaggggaagg ccaccactgc ccatgtgcta gccagagagc
 601  tcagaatccc caaaaggggac atcaatcgta tttttgtactc cctggaaaag aagggaaagc
 661  tgcacagagg aaggggggaaa cctcctttgt ggagccttgt gcccttgagt caggcttgga
```

TABLE 1-continued

```
 721  ctcagccccc tggagttgtg aatccagata gttgtatcca ggaattccct agaggagagc
 781  ctggtttgga cagtgaggac ggagaccctg cctctgactt agaaggacct tctgagcctc
 841  ttgacatggc tgaaatcaag gagaagatct gtgactatct gttcaatgtg tcaaactcct
 901  ctgccctgaa cctggctaag aacattggcc tcaccaaggc ccagatgtg acctcagtgc
 961  tgattgactt ggaaaggcaa ggcgatgtct acaggcaagg gcaactcct cccatctggt
1021  acttgacgga caagaagcgt gagaggctgc agatgaagag aagtacacac agtgctcctg
1081  cccctacccc gacagctgtc ccagaggcca ctagaagccc tcattccct gcctgccacc
1141  cgcccccagc aggtgcctca agcagtgtgg cagcctccaa gagagtggag aatgggcagg
1201  agcctgcgat aaagcatgaa agtaggcatg aggccagacc aggaccaatg agactgcggc
1261  ctcacgctta tcacaatggc ccctctagag cagggtatgt ggcctctgaa aatggccagt
1321  gggccacaga tgacatccca gataacttga atagtatcca cacagcacca ggtgagtttc
1381  gagccatcat ggagatgccc tccttctaca gccctacctt gccacggtgt tcaccctaca
1441  agaagctaac tgagtgccag ctgaagaacc ctgtcagcgg gttgttagag tatgctcagt
1501  tcactagtca gacctgtgat ttcaacctga tagagcagag tggaccgtcc catgaacctc
1561  gatttaaatt ccaggttgtc atcaatgggc gggaatttcc cccagctgag gctggcagca
1621  agaaagtagc caagcaggac gcagcagtga aagccatggc gattctgctt cgggaagcca
1681  aagccaaaga cagtggtcaa ccagaagact tgtcccactg tccatggaa gaagactcgg
1741  agaaaccagc agaggctcag gcccccagct cctcagcaac atccttgttc tctgggaaga
1801  gcccagttac tacactgctt gagtgcatgc acaaactagg gaactcctgt gaattccgtc
1861  tcctgtccaa agaaggccct gctcatgacc ccaagttcca gtactgtgta gcagtaggag
1921  cccagacctt cccccctgtg agcgccccca gcaagaaggt agcaaagcag atggccgcag
1981  aggaagccat gaaggcgctg caggaggagg cagccagttc agcggatgac cagtctggag
2041  gtgcgaacac agactcactt gatgaatcta tggctcccaa caagatcagg aggattggtg
2101  agctcgtcag gtacctgaac accaaccccg taggcggctt gttggagtac gcccgatctc
2161  atggctttgc tgctgagttc aagctcattg accagtctgg acctcctcac gaacccaagt
2221  ttgtttacca agcaaaagtt gggggccgct ggtttccagc cgtgtgtgca cacagcaaga
2281  aacagggcaa gcaggatgca gcggatgcag ccctccgggt cttgatcggg gagagcgaga
2341  aggcagagca gttgggtttc gcagaggtaa ccccagtaac aggggccagt ctcagaagaa
2401  ctatgctcct cctttccagg tccccagatg cacatccaaa gacacttcct ctctctggca
2461  gcaccttcca cgaccagata gctatgctga gccacaggtg cttcaatgct ctgaccaaca
2521  gtttccagcc ctccctgctc ggccgcaaga tcctggctgc cattattatg aaaagagatc
2581  cagaggacat gggtgttgtc gtgagtttgg ggacaggcaa tcgctgtgtg aaaggggact
2641  ctctcagcct gaaggagag acggtcaatg actgccatgc cgaaatcatc tcccggaggg
2701  gcttcatcag gtttctctac agtgaactga tgaagtacaa ccaccacact gccaagaaca
2761  gcatatttga gcttgccagg ggaggagaga agctgcagat aaagaagacg gtttcttttc
2821  atctctacat cagcacggcg ccatgtggag atgggccct ctttgacaaa tcctgcagtg
2881  accgtgccgt ggaaagcaca gagtcccgcc attaccctgt ctttgaaaat cccaagcaag
2941  gcaagcttcg caccaaggtg gagaatgggg aaggcacaat tcctgtggag tccagtgata
3001  ttgtacccac gtgggatggc atccgccttg gggaaagact ccgtaccatg tcctgtagtg
3061  acaaaatcct acgctggaat gtgctgggcc tgcaaggggc gttgttgacg cacttcctac
```

TABLE 1-continued

```
3121  agcctgtgta cctgaaatct gtaaccttag gttaccttt  cagccaaggg catctgaccc
3181  gtgctattg  ctgccgcgtg accagagatg ggaaagcatt tgaggatgga ctacgctatc
3241  cctttattgt caaccacccc aaggtcggcc gagtcagtgt ttatgattcc aaaagacagt
3301  ccggaaagac caaggaaaca agcgtcaact ggtgcatggc tgatggctat gacctagaga
3361  tcctggatgg caccagaggc actgtggatg gaccagggaa agagttgtct cgggtgtcca
3421  agaagaatat tttccttcag tttaagaagc tctgctcctt ccgagcccgc agagatttac
3481  tgcagctctc ttatggtgaa gccaagaaag ctgcccgtga ctatgactta gccaagaact
3541  acttcaagaa aagcctgcga gacatgggct atgggaattg gatcagcaaa ccccaggagg
3601  aaaagaactt ttacctctgt ccagtaccca atgactgata gtggggcgcg tttctcctgg
3661  ggtcagaggg cggtcatggc attcctcatc acaccgggcc agaggatagg agcttttttt
3721  acccactccc ccctttttta atggtagaac cataatagat ggtaccaaga actgctttct
3781  ttgggatttc aaggtggggt ccagccaagt ccccacctcc cttttctcaa gggaagaggc
3841  caagattaaa ggaaatggaa atgctaccat tccatatgta gcacagacag ttcttggtca
3901  catggagccc aggcccctcg ggcttcgttt tgcggaggtt tttttcatct ccttttcctt
3961  tgctgcactg gcctcttgtg ggtttgattc catcccatca gttctctgta aatgatgtca
4021  ggggccagtg atgtcacctg cagatgcgca ggcaggcccc tgctctgtca tccttccctc
4081  ctaggatgcc ttcctgtgat gaggtttctc cttccccacc ccagaggata gaggtgaaca
4141  taaaggattg gtgaaatgtt tacaagggca ggagttgaca accgtggtca gggattgtcg
4201  aacaacagga atgtggtaaa ctgtggttgg gacaggcaag ccctacccag taacaggccg
4261  tgctggccca ccaaggaact tcccttcctg ggcagcaggg aagttgaaga tcggccagtg
4321  ggaccgagga aggtacccaa accaagcacg tcccagtagg ggtccacaag cactaactag
4381  agtgcaccag cattccatgg aatgtcgcta tgcctccatc tgcccctcca tgagcactcc
4441  cagaagctgg ccctgggcac gtgtggtgtt ggcccaggc  cccagctgtt tgtgaaaagc
4501  agagggtgag catagtgggc agagcagctt tgcccagacg gcaaaggtaa aggcagagca
4561  tcctgccggt gcactgggat tcttctggtc tcagcagaag tgacaaagcc ctgcatagaa
4621  ttaatgtttc taaaaggcca gaggcattga ttctgaactg catcaaagac tggagatgca
4681  aatattactt ctccattagt aaatgtactt tcattctatc agatggcttc agaagctggg
4741  tcacggacag ggcacagggc cctggaatct ctgccctgct cctttgagga tcttcattta
4801  catacaagtg ttgtaggtgg cagggcaggc tggcctccca ctctgggatg ggcttctttg
4861  actcctcccc ctctgacagt gacttgtggg tatgtgggag cctctgtaga atctggttct
4921  agcatcagat caaccagcca gaccctgctc cattctgccc ctctaggacc aagcccacct
4981  ctttcctctg aatggtgtgg ctccatctgg agacagctgg ccagtgtgtt caacagtttc
5041  ctgcaccccc ttgcttaacc ctcagagctg cctggttccc ccaccctctg gcccactgcc
5101  aacagcaaac atcacattcg tacttcaagt ctaatggcta ctgcctcctc aatctatgaa
5161  cagatctggc caacacaaga acctgtgtct tcacaataca ctgggatgt  ctttgcacag
5221  ccaaatcatc ctatgaaact ccagcgtctg tggaagtgag aaagcagcac catgcttgtg
5281  gtgtcggctg gaggcgtgtc acctccggc  aactgcatct gaagcagagc ccttgtggtt
5341  tccaggcctg gacagggagc tcttcccctg gggtctaaag gacagagatg tctctcctt
5401  tgattccttt ggtccctctg gtcctccctg ggtattcaca catacccaa  tcctgtctag
5461  acaacgagtg gttctgggtt tctgcagatg gaagagagca aggtgtccct gagttctgtg
```

TABLE 1-continued

```
5521  gacttgaccc ccgcatccca ccctgaccct gcctccagtc ccgctggccg agggcagagc 5581  ctcctcccac tgtgcttcct tcacgtttac tttaagaagc agggcctccc tccacaccgt 5641  ctcttaatac tttctgtagt tgatttgtct gaaccgtggc tgtcttgcat tccttgaata 5701  atcatgtgta agaattgtca atgcttgaaa ctatttcctg tactcaagtt gaagggactt 5761  tgttggcctt ggggttttag cagtgactcc aagagcagag tggggaagca cccaggcata 5821  gccttggcgc tgtgatggat gcagtccctc cctctgtccc tttacaagtg acagtataca 5881  ttcctaaaaa taaaaacact gaagcatcag gactgttaaa aaaaaaaaaa aaaaaa
```

SEQ ID NO: 13 Mouse ADAR isoform 2 Amino Acid Sequence (NP_001033676.2)
```
  1  maeikekicd ylfnvsnssa lnlakniglt kardvtsvli dlerqgdvyr qgatppiwyl 61  tdkkrerlqm krsthsapap tptavpeatr spsfpachpp pagasssvaa skrvengqep 121  aikhesrhea rpgpmrlrph ayhngpsrag yvasengqwa tddipdnlns ihtapgefra 181  imempsfysp tlprcspykk ltecqlknpv sglleyaqft sqtcdfnlie qsgpsheprf 241  kfqvvingre fppaeagskk vakqdaavka maillreaka kdsgqpedls hcpmeedsek 301  paeaqapsss atslfsgksp vttllecmhk lgnscefrll skegpahdpk fqycvavgaq 361  tfppvsapsk kvakqmaaee amkalqeeaa ssaddqsgga ntdsldesma pnkirrigel 421  vrylntnpvg glleyarshg faaefklidq sgpphepkfv yqakvggrwf pavcahskkq 481  gkqdaadaal rvligeseka eqlgfaevtp vtgaslrrtm lllsrspdah pktlplsgst 541  fhdqiamlsh rcfnaltnsf qpsllgrkil aaiimkrdpe dmgvvvslgt gnrcvkgdsl 601  slkgetvndc haeiisrrgf irflyselmk ynhhtaknsi felarggekl qikktvsfhl 661  yistapcgdg alfdkscsdr avestesrhy pvfenpkqgk lrtkvengeg tipvessdiv 721  ptwdgirlge rlrtmscsdk ilrwnvlglq gallthflqp vylksvtlgy lfsqghltra 781  iccrvtrdgk afedglrypf ivnhpkvgrv svydskrqsg ktketsvnwc madgydleil 841  dgtrgtvdgp gkelsrvskk niflqfkklc sfrarrdllq lsygeakkaa rdydlaknyf 901  kkslrdmgyg nwiskpqeek nfylcpvpnd
```

SEQ ID NO: 14 Mouse ADAR Variant 3 cDNA Sequence (NM_001146296.1, CDS region from position 94-3630)
```
  1  aacagttggg cggggaagcc ttttcaagga aacgaaagtg aactctgggg agccagccat 61  cttacggcca caggtgcggg ccttgccggc actatgtctc aagggttcag gggacccaca 121  ggggtgttcc ctcaccagac acagtcgtac ttggaccta gtcatgagca tagcaagtgg 181  agatacccgc agccacaggg gccggagtct tacccctagga gtttccagct tcagcagata 241  gagtttctca aagggcggct cccagaagca cccttgattg aatacaaac ccagtcactg 301  ccgccattcc tcccaggaca ctggccaaga ttcccagggc cacctgccca agacaggcaa 361  ctggaaatct gggagttccc caggagtgtg actctcagaa atcagggtt ccacatagga 421  cccccacttc ctcccccaca cagcagggt acaccatgga gaggtgctga cgggctttgc 481  tcacacttcc gggagctgag catcagtcag agtccggagc agaaggttct aaaccgcctg 541  gaagagcttg ggagggaa ggccaccact gcccatgtgc tagccagaga gctcagaatc 601  cccaaaaggg acatcaatcg tatttttgtac tccctggaaa agaagggaaa gctgcacaga 661  ggaaggggga aacctccttt gtggagcctt gtgcccttga gtcaggcttg gactcagccc 721  cctggagttg tgaatccaga tagttgtatc caggaattcc ctagaggaga gcctggtttg 781  gacagtgagg acggagaccc tgcctctgac ttagaaggac cttctgagcc tcttgacatg 841  gctgaaatca aggagaagat ctgtgactat ctgttcaatg tgtcaaactc ctctgccctg 901  aacctggcta agaacattgg cctcaccaag gcccgagatg tgacctcagt gctgattgac
```

TABLE 1-continued

```
 961 ttggaaaggc aaggcgatgt ctacaggcaa ggggcaactc ctcccatctg gtacttgacg
1021 gacaagaagc gtgagaggct gcagatgaag agaagtacac acagtgctcc tgccctacc
1081 ccgacagctg tcccagaggc cactagaagc ccctcattcc ctgcctgcca cccgcccca
1141 gcaggtgcct caagcagtgt ggcagcctcc aagagagtgg agaatgggca ggagcctgcg
1201 ataaagcatg aaagtaggca tgaggccaga ccaggaccaa tgagactgcg gcctcacgct
1261 tatcacaatg gcccctctag agcagggtat gtggcctctg aaaatggcca gtgggccaca
1321 gatgacatcc cagataactt gaatagtatc cacacagcac caggtgagtt tcgagccatc
1381 atggagatgc cctccttcta cagccctacc ttgccacggt gttcacccta caagaagcta
1441 actgagtgcc agctgaagaa ccctgtcagc gggttgttag agtatgctca gttcactagt
1501 cagacctgtg atttcaacct gatagagcag agtggaccgt cccatgaacc tcgatttaaa
1561 ttccaggttg tcatcaatgg gcgggaattt cccccagctg aggctggcag caagaaagta
1621 gccaagcagg acgcagcagt gaaagccatg gcgattctgc ttcgggaagc caaagccaaa
1681 gacagtggtc aaccagaaga cttgtcccac tgtcccatgg aagaagactc ggagaaacca
1741 gcagaggctc aggcccccag ctcctcagca acatccttgt tctctgggaa gagcccagtt
1801 actacactgc ttgagtgcat gcacaaacta gggaactcct gtgaattccg tctcctgtcc
1861 aaagaaggcc ctgctcatga ccccaagttc cagtactgtg tagcagtagg agcccagacc
1921 ttcccccctg tgagcgcccc cagcaagaag gtagcaaagc agatggccgc agaggaagcc
1981 atgaaggcgc tgcaggagga ggcagccagt tcagcggatg accagtctgg aggtgcgaac
2041 acagactcac ttgatgaatc tatggctccc aacaagatca ggaggattgg tgagctcgtc
2101 aggtacctga acaccaaccc cgtaggcggc ttgttggagt acgcccgatc tcatggcttt
2161 gctgctgagt tcaagctcat tgaccagtct ggacctcctc acgaacccaa gtttgtttac
2221 caagcaaaag ttgggggccg ctggttttcca gccgtgtgtg cacacagcaa gaaacagggc
2281 aagcaggatg cagcggatgc agccctccgg gtcttgatcg gggagagcga gaaggcagag
2341 cagttgggtt tcgcagaggt aacccccagta acaggggcca gtctcagaag aactatgctc
2401 ctcctttcca ggtccccaga tgcacatcca aagacacttc ctctctctgg cagcaccttc
2461 cacgaccaga tagctatgct gagccacagg tgcttcaatg ctctgaccaa cagtttccag
2521 ccctccctgc tcggccgcaa gatcctggct gccattatta tgaaaagaga tccagaggac
2581 atgggtgttg tcgtgagttt ggggacaggc aatcgctgtg tgaaagggga ctctctcagc
2641 ctgaagggag agacggtcaa tgactgccat gccgaaatca tctcccggag gggcttcatc
2701 aggtttctct acagtgaact gatgaagtac aaccaccaca ctgccaagaa cagcatattt
2761 gagcttgcca ggggaggaga gaagctgcag ataaagaaga cggtttcttt tcatctctac
2821 atcagcacgg cgccatgtgg agatgggggcc ctcttttgaca aatcctgcag tgaccgtgcc
2881 gtggaaagca cagagtcccg ccattaccct gtctttgaaa atcccaagca aggcaagctt
2941 cgcaccaagg tggagaatgg ggaaggcaca attcctgtgg agtccagtga tattgtaccc
3001 acgtgggatg gcatccgcct tggggaaaga ctccgtacca tgtcctgtag tgacaaaatc
3061 ctacgctgga atgtgctggg cctgcaaggg gcgttgttga cgcacttcct acagcctgtg
3121 tacctgaaat ctgtaacctt aggttacctt ttcagccaag gcatctgac ccgtgctatt
3181 tgctgccgcg tgaccagaga tgggaaagca tttgaggatg gactacgcta tccctttatt
3241 gtcaaccacc ccaaggtcgg ccgagtcagt gtttatgatt ccaaaagaca gtccggaaag
3301 accaaggaaa caagcgtcaa ctggtgcatg gctgatggct atgacctaga gatcctggat
```

TABLE 1-continued

```
3361  ggcaccagag gcactgtgga tggaccaggg aaagagttgt ctcgggtgtc caagaagaat
3421  attttccttc agtttaagaa gctctgctcc ttccgagccc gcagagattt actgcagctc
3481  tcttatggtg aagccaagaa agctgcccgt gactatgact tagccaagaa ctacttcaag
3541  aaaagcctgc gagacatggg ctatgggaat tggatcagca aaccccagga ggaaaagaac
3601  ttttacctct gtccagtacc caatgactga tagtggggcg cgtttctcct ggggtcagag
3661  ggcggtcatg gcattcctca tcacaccggg ccagaggata ggagcttttt ttacccactc
3721  ccccctttt taatggtaga accataatag atggtaccaa gaactgcttt ctttgggatt
3781  tcaaggtggg gtccagccaa gtccccacct cccttttctc aagggaagag gccaagatta
3841  aaggaaatgg aaatgctacc attccatatg tagcacagac agttcttggg cacatggagc
3901  ccaggcccct cgggcttcgt tttgcggagg ttttttttcat ctccttttcc tttgctgcac
3961  tggcctcttg tgggtttgat tccatcccat cagttctctg taaatgatgt caggggccag
4021  tgatgtcacc tgcagatgcg caggcaggcc cctgctctgt catccttccc tcctaggatg
4081  ccttcctgtg atgaggtttc tccttcccca ccccagagga tagaggtgaa cataaaggat
4141  tggtgaaatg tttacaaggg caggagttga caaccgtggt cagggattgt cgaacaacag
4201  gaatgtggta aactgtggtt gggacaggca agccctaccc agtaacaggc cgtgctggcc
4261  caccaaggaa cttcccttcc tgggcagcag ggaagttgag aatcggccag tgggaccgag
4321  gaaggtaccc aaaccaagca cgtcccagta ggggtccaca agcactaact agagtgcacc
4381  agcattccat ggaatgtcgc tatgcctcca tctgcccctc catgagcact cccagaagct
4441  ggccctgggc acgtgtggtg ttggccccag gccccagctg tttgtgaaaa gcagagggtg
4501  agcatagtgg gcagagcagc tttgcccaga cggcaaaggt aaaggcagag catcctgccg
4561  gtgcactggg attcttctgg tctcagcaga agtgacaaag ccctgcatag aattaatgtt
4621  tctaaaaggc cagaggcatt gattctgaac tgcatcaaag actggagatg caaatattac
4681  ttctccatta gtaaatgtac tttcattcta tcagatggct tcagaagctg ggtcacggac
4741  agggcacagg gccctggaat ctctgccctg ctccttttgag gatcttcatt tacatacaag
4801  tgttgtaggt ggcagggcag gctggcctcc cactctggga tgggcttctt tgactcctcc
4861  ccctctgaca gtgacttgtg ggtatgtggg agcctctgta gaatctggtt ctagcatcag
4921  atcaaccagc cagaccctgc tccattctgc ccctctagga ccaagcccac ctctttcctc
4981  tgaatggtgt ggctccatct ggagacagct ggccagtgtg ttcaacagtt cctgcaccc
5041  ccttgcttaa ccctcagagc tgcctggttc ccccacccct tggcccactg ccaacagcaa
5101  acatcacatt cgtacttcaa gtctaatggc tactgcctcc tcaatctatg aacagatctg
5161  gccaacacaa gaacctgtgt cttcacaata cactggggat gtctttgcac agccaaatca
5221  tcctatgaaa ctccagcgtc tgtggaagtg agaaagcagc accatgcttg tggtgtcggc
5281  tggaggcgtg tcaccctccg gcaactgcat ctgaagcaga gcccttgtgg tttccaggcc
5341  tggacaggga gctcttcccc tggggtctaa aggacagaga tgtctctccc tttgattcct
5401  ttggtccctc tggtcctccc tgggtattca cacataccc aatcctgtct agacaacgag
5461  tggttctggg tttctgcaga tggaagagag caaggtgtcc ctgagttctg tggacttgac
5521  ccccgcatcc caccctgacc ctgcctccag tcccgctggc cgagggcaga gcctcctccc
5581  actgtgcttc cttcacgttt actttaagaa gcagggcctc cctccacacc gtctcttaat
5641  actttctgta gttgatttgt ctgaaccgtg gctgtcttgc attccttgaa taatcatgtg
5701  taagaattgt caatgcttga aactatttcc tgtactcaag ttgaagggac tttgttggcc
```

TABLE 1-continued

```
5761 ttggggtttt agcagtgact ccaagagcag agtggggaag cacccaggca tagccttggc 5821 gctgtgatgg atgcagtccc tccctctgtc cctttacaag tgacagtata cattcctaaa 5881 aataaaaaca ctgaagcatc aggactgtta aaaaaaaaaa aaaaaaa
```

SEQ ID NO: 15 Mouse ADAR isoform 3 Amino Acid Sequence (NP_001139768.1)
```
   1 msqgfrgptg vfphqtqsyl dpshehskwr ypqpqgpesy prsfqlqqie flkgrlpeap
  61 ligiqtqslp pflpghwprf pgppaqdrql eiwefprsvt lrnqgfhigp plppphsrgt
 121 pwrgadglcs hfrelsisqs peqkvlnrle elgegkatta hvlarelrip krdinrilys
 181 lekkgklhrg rgkpplwslv plsqawtqpp gvvnpdsciq efprgepgld sedgdpasdl
 241 egpsepldma eikekicdyl fnvsnssaln laknigltka rdvtsvlidl erqgdvyrqg
 301 atppiwyltd kkrerlqmkr sthsapaptp tavpeatrsp sfpachpppa gasssvaask
 361 rvengqepai khesrhearp gpmrlrphay hngpsragyv asengqwatd dipdnlnsih
 421 tapgefraim empsfysptl prcspykklt ecqlknpvsg lleyaqftsq tcdfnlieqs
 481 gpsheprfkf qvvingrefp paeagskkva kqdaavkama illreakakd sgqpedlshc
 541 pmeedsekpa eaqapsssat slfsgkspvt tllecmhklg nscefrllsk egpandpkfq
 601 ycvavgaqtf ppvsapskkv akqmaaeeam kalqeeaass addqsggant dsldesmapn
 661 kirrigelvr ylntnpvggl leyarshgfa aefklidqsg pphepkfvyq akvggrwfpa
 721 vcahskkqgk qdaadaalrv ligesekaeq lgfaevtpvt gaslrrtmll lsrspdahpk
 781 tlplsgstfh dqiamlshrc fnaltnsfqp sllgrkilaa iimkrdpedm gvvvslgtgn
 841 rcvkgdslsl kgetvndcha eiisrrgfir flyselmkyn hhtaknsife larggeklqi
 901 kktvsfhlyi stapcgdgal fdkscsdrav estesrhypv fenpkqgklr tkvengegti
 961 pvessdivpt wdgirlgerl rtmscsdkil rwnvlglqga llthflqpvy lksvtlgylf
1021 sqghltraic crvtrdgkaf edglrypfiv nhpkvgrvsv ydskrqsgkt ketsvnwcma
1081 dgydleildg trgtvdgpgk elsrvskkni flqfkklcsf rarrdllqls ygeakkaard
1141 ydlaknyfkk slrdmgygnw iskpqeeknf ylcpvpnd
```

SEQ ID NO: 16 Human ZC3HAV1 Variant 1 cDNA Sequence (NM_020119.3, CDS region from position 389-3097)
```
   1 cttttagttt ctcttctttc taaagaaggc tcgcggagcc cggctggaga acctcaccct
  61 cgccgagcct agaaccgaga gggggccacc ccaggcggtc accagcagat ttgcccgcgc
 121 gttctctttc tttccaccca gttgcccttg cggccggctg taaacctgcc actaggaccc
 181 ggtcggtgag atctagcctc ttgacctgag agccgagagt ggatcgctgg gctgggctaa
 241 cggcgacgga gagcgcgccc tcgctgactc cgggcgcgcc cagcagtagc accgcccgcg
 301 cccgcccctg gacacttgta agtttcgatt tccgatttcc gcggaaccga gtcccgcgcc
 361 gcggcagagc cagcacagcc agcgcgccat ggcggacccg gaggtgtgct gcttcatcac
 421 caaaatcctg tgcgcccacg ggggccgcat ggccctggac gcgctgctcc aggagatcgc
 481 gctgtctgag ccgcagctct gtgaggtgct gcaggtggcc gggcccgacc gctttgtggt
 541 gttggagacc ggcggcgagg ccgggatcac ccgatcggtg gtggccacca ctcgagcccg
 601 ggtctgccgt cgcaagtact gccagagacc ctgcgataac ctgcatctct gcaaactcaa
 661 cttgctgggc cggtgcaact attcgcagtc cgagcggaat ttatgcaaat attctcatga
 721 ggttctctca aagagaaact tcaaagtcct gaaaaatcac gaactctctg gactgaacaa
 781 agaggaatta gcagtgctcc tcctccaaag tgatcctttt tttatgcccg agatatgcaa
 841 aagttataag ggagagggtc ggcagcagat ttgtaaccag cagccaccgt gttcaagact
```

TABLE 1-continued

```
 901  ccacatctgt gaccacttca cccgagggaa ctgtcgtttt cccaactgcc tccggtccca
 961  taacctgatg gacagaaagg tgctggccat catgagggag cacgggctga accccgacgt
1021  ggtccagaac atccaggaca tctgcaacag caagcacatg cagaagaatc ccccagggcc
1081  cagagctcct tcttcacatc gtagaaacat ggcatatagg gctagaagca agagtagaga
1141  tcggttcttt cagggcagcc aagaatttct tgcgtctgct tcagcgtctg ctgagaggtc
1201  ctgcacacct agtccagatc agatcagcca cagggcttcc ctggaggacg cgcctgtgga
1261  cgatctcacc cgcaagttca cgtatctggg gagtcaggat cgcgctcggc ctccctcagg
1321  ctcgtccaag gctactgatc ttggaggaac aagtcaggcc gggacaagcc agaggttttt
1381  agagaacggc agtcaagagg acctcttgca tggaaatcca ggcagcactt accttgcttc
1441  caattcaaca tcagccccca actggaagag cctcacatcc tggacgaatg accaaggcgc
1501  caggagaaag actgtgtttt ctcccacgct acctgccgcc cgctcttctc ttggctctct
1561  gcaaacacct gaagctgtga ccaccagaaa gggcacaggc ttgctttcct cagactacag
1621  gatcatcaat ggcaaaagtg gaactcagga catccagcct ggccctcttt ttaataataa
1681  tgctgatgga gtggccacag atataacttc taccagatcc ttaaattaca aaagcactag
1741  cagcggtcac agagaaatat catcacctag gattcaggat gctggacctg cttcccgaga
1801  tgtccaggcc actggcagaa tcgcagatga tgctgaccca agagtagcac ttgttaacga
1861  ttctttatct gatgtcacaa gtaccacatc ttctagggtg gatgatcatg actcagagga
1921  aatttgtctt gaccatctgt gtaagggttg tccgcttaat ggtagctgca gcaaagtcca
1981  cttccatctg ccttaccggt ggcagatgct tattggtaaa acctggacgg acttttgagca
2041  catggagacg atcgagaaag gctactgtaa ccccggaatc cacctctgtt ctgtaggaag
2101  ttatacaatc aattttcggg taatgagttg tgattccttt cccatccgac gcctctccac
2161  tccttcttct gtcaccaagc cagccaattc tgtcttcacc accaaatgga tttggtattg
2221  gaagaatgaa tctggcacat ggattcagta tggagaagag aaagacaaac ggaaaaattc
2281  aaacgtcgac tcttcatacc tggagtctct ctatcaatcc tgtccgaggg gagttgtgcc
2341  atttcaggcg ggctcacgga actatgagct gagtttccaa gggatgattc agacaaacat
2401  agcttccaaa actcaaaagg atgtcatcag aagaccaaca tttgtgcctc agtggtatgt
2461  gcagcagatg aagagagggc cagaccatca gccagcaaag acctcgtcag tgtctttaac
2521  tgcgaccttt cgtcctcagg aggacttttg cttcctatcc tcaaagaaat ataagttgtc
2581  agagatccat cacctacatc cagaatatgt cagagtaagt gagcatttta aagcttccat
2641  gaaaaatttc aagattgaaa agataaagaa gatcgagaac tcagagctcc tggataaatt
2701  tacatggaag aaatcgcaga tgaaggaaga aggaaaactc ctattttatg cgacaagccg
2761  tgcctatgtg gaatctatct gttcgaataa ttttgacagt ttcctacatg aaactcatga
2821  aaacaaatac ggaaaaggaa tttactttgc aaaagatgcc atctattccc acaaaaattg
2881  cccgtatgat gccaaaaacg tcgttatgtt tgtagcccaa gttctggttg aaagtttac
2941  tgaaggaaat ataacgtaca cgagccctcc tccacagttc gacagctgtg tggataccag
3001  atcgaatccc tccgtttttg tcatctttca gaaagatcag gtttacccac aatatgtgat
3061  tgaatatact gaagacaaag cctgcgtgat tagttagaac cgatgaatac agcgtcagaa
3121  ggatgccata accattctgt tcctttacag aactaaattg ccgcagacag gagttaaagt
3181  tttatatttt cctgctcagt tatctaatgt cttagatcag tggtcccaa attttgctac
3241  atattagaat catctgggag gttttaaaca aattctgatg cccaggttgc accccatgcc
```

TABLE 1-continued

```
3301  aatgaaatca tttctgggcg tcagcgccag gcagttgtat tttttttttt tttttttttt
3361  ttgagactga atctcactcc atcgtccagg ctggagtgca gtggcgcgat ctcggctcac
3421  tgcaacctct gcctcccggg ttcaagcaat tctcctgcct cagcctcccg agtagctgga
3481  actacaggca cacactgccg cgcccagcta ttttttgta tttttagta gagacagggt
3541  ttcactgtgt tgcccaggct ggtctcaaac tcctgagctc aggcaatctg cccgccttgg
3601  cctcccaaag tgctaggatt acaggtatga gccaccatgc ccggctggca gttgtatttt
3661  ttaaagccct tctgatgatt ccaatgtgtt ggaaagttta ccttgtctca gatgtaactg
3721  gtaaaggctg atttctaaat tttctgtaat tgcagcaacc tttctctcct gtctacccctt
3781  ttagtttact gtatgccatg gttttgtttt ggttacattg aaagaaagtt aatttggaaa
3841  atttgggaga aatctaatca tgcctattaa ggatgtaaga cattacagcc ttagaagaaa
3901  gattgtgaaa agctggggag aaaatgctta aggacatgct aggggaaaaa aaagtaaaat
3961  tgaagtgcta ttgcagacat ggctgcagta ctgtaccttta tcattctgat gaaactgatt
4021  tggagcaccc ttttctttat cgctacattt atttagggga caaactccat ccaggttgac
4081  tctctctgga atgcggtaat aagagctggc aagtaaggct cagagagaag caaccaactg
4141  gagttaattg cccatttggg ctctttgtat aattatggca aagtagacat ttatgttcta
4201  attaatatga ttacagagaa ggctttttct caggtcaggc ttttcatgaa agtattttga
4261  gaacaatgaa ttgcaataac cagcttcaca caagcataac tgataaacgc gagtgctatt
4321  gtagtcttgg caagtgagcc aagaacctag gagcagggcc attcctactg aaggacgggc
4381  cccctacgga gatgaaattt gtttcctggt gagcacagaa tcagaacaaa gaacaatatc
4441  ccaaagaggc cctgtgtcta ccaggagctt ctttttccaa atgtaatgga ttatgtggaa
4501  ttgtagtgcc atcggttttt acttagagcc cttgacgtgc ttggaccaat atttccttcc
4561  ttcttatgaa ccaggttttt ccttctgatt ttcccttttc aacattcctt accagtcacc
4621  aaagtttcct gttataattt cttttagcag acaagttata agtcagattt aattagcatc
4681  agagttgatt ttatattagt cagattttgg atcatcacag agatctccac aactccttgg
4741  cttaaacagc tccaccggta aaaaaaaaa aaaaaaaaa aaaaaaaat agttttttta
4801  gagtagagtt attttctggg agagttacta caaatgctta ttctcattga cttatttctt
4861  tcatggtaac tttcgttttg gagtgttcat tttctgaact tgaccctcac attgtagggg
4921  tgcagtttgt ccaactcttt ccaacagccc attagacacc actagctgga tatttcacag
4981  gcatctttga ttcaatatgt ccaaagtgga actctccatc tacctccctc acatgaacct
5041  gttcctctct caggatctgt atgtaagtga aaagcatcac catctaccca ttggctcaag
5101  cagaaatctg gaagtcatct ttgactcctt cctctcccctc ctgataaaca tctaagcagt
5161  ttctaagtct agttttacct cttaaatatc tctgttccct tctaagttgt ttgctgtgtt
5221  ttcttcagag caagaaggtt atatttttta aaatttactt agtaatgcac attcaaaaca
5281  cacatcaagt cttcaggata aagttcaaaa ccgctgtcat ggccccatgt gatctctccc
5341  tcccctaccc ctctatcatt tagtttcttc tgcgcaagcc actctggctt cctttcagtt
5401  ttgtggttcc catttttagc tagttcagtg gttttcaatg ggcatttctg cctttttttt
5461  tctaaacgac aaatagaaat acatcttctt tattatcctc caaatccaat tcagaggtaa
5521  tatgctccac ctacacacaa ttttagaaat aaattaaaaa ttaaataaaa ctaatatgaa
5581  cataaagagg aaataaaagg tacctaactt gggcacagct gtaactgaag acctaatgaa
5641  gtagtcagat gcttacaact atttataatg catcaatttg aacttagaag gtaggagatc
```

TABLE 1-continued

```
5701  agatcatatg tgggaaaatg taaaagcagg gatatcagtg ggcattagaa taaaaactag
5761  ggatacaata acttctttgc atatgacaat acttatttgt atataagaga agaacgaaa
5821  taacctttat tgaaataaag atactatgca agaaaatgta cagttgtcga agtggagaaa
5881  atgaggatat attccttgcag acgagctata ggtcatacat gaatgtctag tgagacattc
5941  aaaattcgta tagggtgcag agtaatttct tattgtgagg aactgtccaa tgtattgcaa
6001  gatgttctgc atacttggct ctcacatact aaatgctagt agcgcccca ccccacgcc
6061  cagtcacggt gacaaccaca aaccctatca gatctattca ccttttcag agcagatatt
6121  ttgtaacatt ctctttgctg acctgaaatg actcatagat aatacaatct acttacacac
6181  atgaatttct taaaaaaatc aatttaatgc cctaactctc ttattaagga gaaatagaaa
6241  agaagaaatt tataatgaaa agaagatgaa tttcattatg taaacgctca ggcatgacta
6301  cgctgtttga aacagacaga tgtttactct tccttgtaat gagtaggttt ggatttaaga
6361  gccgattaga ggctacttcc tgtaaacaag tacaggaaaa tgaaactaga cgggtggggg
6421  acactagaat gaaaaccagt gttagggtaa agacaaaaca gactatgtac ataatctgta
6481  tatgggaaaa gaaagagcga aattacctta cttaaggata ataggacaag acaaattaca
6541  gattgtctca gagaaaacaa atgagttact ctctcggaca agctgtaggt cctacctaaa
6601  tgtccagcag gacattagac agtcgtacag ggtacagaat aattcttcgt tgtgtggcac
6661  taacccacac actgcaggac atcgttctcc ctggctgcat ccactcagtg ctgggagtag
6721  tccccagtta ttatgaaacc accaataacc cactgaccac agtgagaacc actgattttt
6781  tccactgacc tactgaatat ctagcatcct tagattggct caactgttac tttcctaagg
6841  agtccttcta cagaataggt cagatcttgg cctcccaaac cccttatttt taaaatactt
6901  tgcgccttgc tttgataatt tgtattatgt atccaaactg aaattatctg ctttctgcat
6961  tagaatgtaa gccccctgag ggttgagtca gtctgtcttg tttgctgtgc cacgcctgat
7021  gcccagccca gcagcatgct ttgtacactg atatattggg taaattttgt tgaataaatt
7081  aagctcaact atttgtattt caatagttga gttgtattgc ttcctgttct tcaagcttaa
7141  tttgaactgt ctaataaaaa gaagtaatta aaaaaaaaa aaaaaaaaa
```

SEQ ID NO: 17 Human ZC3HAV1 isoform 1 Amino Acid Sequence (NP_064504.2)
```
  1  madpevccfi tkilcahggr maldallqei alsepqlcev lqvagpdrfv vletggeagi
 61  trsvvattra rvcrrkycqr pcdnlhlckl nllgrcnysq sernlckysh evlseenfkv
121  lknhelsgln keelavllq sdpffmpeic ksykgegrqq icnqqppcsr lhicdhftrg
181  ncrfpnclrs hnlmdrkvla imrehglnpd vvqniqdicn skhmqknppg prapsshrrn
241  mayrarsksr drffqgsqef lasasasaer sctpspdqis hrasledapv ddltrkftyl
301  gsqdrarpps gsskatdlgg tsqagtsqrf lengsqedll hgnpgstyla snstsapnwk
361  sltswtndqg arrktvfspt lpaarsslgs lqtpeavttr kgtgllssdy riingksgtq
421  diqpgplfnn nadgvatdit strslnykst ssghreissp riqdagpasr dvqatgriad
481  dadprvalvn dslsdvtstt ssrvddhdse eicldhlckg cplngscskv hfhlpyrwqm
541  ligktwtdfe hmetiekgyc npgihlcsvg sytinfrvms cdsfpirrls tpssvtkpan
601  svfttkwiwy wknesgtwiq ygeekdkrkn snvdssyles lyqscprgvv pfqagsrnye
661  lsfqgmiqtn iasktqkdvi rrptfvpqwy vqqmkrgpdh qpaktssvsl tatfrpqedf
721  cflsskkykl seihhlhpey vrvsehfkas mknfkiekik kiensellkdk ftwkksqmke
```

| | |
|---|---|
| 781 | egkllfyats rayvesicsn nfdsflheth enkygkgiyf akdaiyshkn cpydaknvvm |
| 841 | fvaqvlvgkf tegnitytsp ppqfdscvdt rsnpsvfvif qkdqvypqyv ieytedkacv |
| 901 | is |

SEQ ID NO: 18 Human ZC3HAV1 Variant 2 cDNA Sequence (NM_024625.3, CDS region from position 389-2488)

| | |
|---|---|
| 1 | cttttagttt ctcttctttc taaagaaggc tcgcggagcc cggctggaga acctcaccct |
| 61 | cgccgagcct agaaccgaga gggggccacc ccaggcggtc accagcagat ttgcccgcgc |
| 121 | gttctctttc tttccaccca gttgcccttg cggccggctg taaacctgcc actaggaccc |
| 181 | ggtcggtgag atctagcctc ttgacctgag agccgagagt ggatcgctgg gctgggctaa |
| 241 | cggcgacgga gagcgcgccc tcgctgactc cgggcgcgcc cagcagtagc accgcccgcg |
| 301 | cccgcccctg gacacttgta agtttcgatt tccgatttcc gcggaaccga gtcccgcgcc |
| 361 | gcggcagagc cagcacagcc agcgcgccat ggcggacccg gaggtgtgct gcttcatcac |
| 421 | caaaatcctg tgcgcccacg ggggccgcat ggccctggac gcgctgctcc aggagatcgc |
| 481 | gctgtctgag ccgcagctct gtgaggtgct gcaggtggcc gggcccgacc gctttgtggt |
| 541 | gttggagacc ggcggcgagg ccgggatcac ccgatcggtg gtggccacca ctcgagcccg |
| 601 | ggtctgccgt cgcaagtact gccagagacc ctgcgataac ctgcatctct gcaaactcaa |
| 661 | cttgctgggc cggtgcaact attcgcagtc cgagcggaat ttatgcaaat attctcatga |
| 721 | ggttctctca gaagagaact tcaaagtcct gaaaaatcac gaactctctg gactgaacaa |
| 781 | agaggaatta gcagtgctcc tcctccaaag tgatcctttt tttatgcccg agatatgcaa |
| 841 | aagttataag ggagagggtc ggcagcagat ttgtaaccag cagccaccgt gttcaagact |
| 901 | ccacatctgt gaccacttca cccgagggaa ctgtcgtttt cccaactgcc tccggtccca |
| 961 | taacctgatg gacagaaagg tgctggccat catgagggag cacgggctga accccgacgt |
| 1021 | ggtccagaac atccaggaca tctgcaacag caagcacatg cagaagaatc ccccagggcc |
| 1081 | cagagctcct tcttcacatc gtagaaacat ggcatatagg ctagaagca agagtagaga |
| 1141 | tcggttcttt cagggcagcc aagaatttct tgcgtctgct tcagcgtctg ctgagaggtc |
| 1201 | ctgcacacct agtccagatc agatcagcca cagggcttcc ctggaggacg cgcctgtgga |
| 1261 | cgatctcacc cgcaagttca cgtatctggg gagtcaggat cgcgctcggc ctccctcagg |
| 1321 | ctcgtccaag gctactgatc ttggaggaac aagtcaggcc gggacaagcc agaggttttt |
| 1381 | agagaacggc agtcaagagg acctcttgca tggaaatcca ggcagcactt accttgcttc |
| 1441 | caattcaaca tcagccccca actggaagag cctcacatcc tggacgaatg accaaggcgc |
| 1501 | caggagaaag actgtgtttt ctcccacgct acctgccgcc cgctcttctc ttggctctct |
| 1561 | gcaaacacct gaagctgtga ccaccagaaa gggcacaggc ttgctttcct cagactacag |
| 1621 | gatcatcaat ggcaaaagtg gaactcagga catccagcct ggccctcttt taataataa |
| 1681 | tgctgatgga gtggccacag atataacttc taccagatcc ttaaattaca aaagcactag |
| 1741 | cagcggtcac agagaaatat catcacctag gattcaggat gctggacctg cttcccgaga |
| 1801 | tgtccaggcc actggcagaa tcgcagatga tgctgaccca agagtagcac ttgttaacga |
| 1861 | ttctttatct gatgtcacaa gtaccacatc ttctagggtg gatgatcatg actcagagga |
| 1921 | aatttgtctt gaccatctgt gtaagggttg tccgcttaat ggtagctgca gcaaagtcca |
| 1981 | cttccatctg ccttaccggt ggcagatgct tattggtaaa acctggacgg actttgagca |
| 2041 | catggagacg atcgagaaag gctactgtaa ccccggaatc cacctctgtt ctgtaggaag |
| 2101 | ttatacaatc aattttcggg taatgagttg tgattccttt cccatccgac gcctctccac |

TABLE 1-continued

```
2161 tccttcttct gtcaccaagc cagccaattc tgtcttcacc accaaatgga tttggtattg 2221 gaagaatgaa tctggcacat ggattcagta tggagaagag aaagacaaac ggaaaaattc 2281 aaacgtcgac tcttcatacc tggagtctct ctatcaatcc tgtccgaggg gagttgtgcc 2341 atttcaggcg ggctcacgga actatgagct gagtttccaa gggatgattc agacaaacat 2401 agcttccaaa actcaaaagg atgtcatcag aagaccaaca tttgtgcctc agtggtatgt 2461 gcagcagatg aagagagggc cagagtaagt gttctgaagc agctgtttgc tgacagatgc 2521 ttgagatgtt catgccctgg gctcatcaag tcactcgtga atctggagcc tgttttcctg 2581 aaaagttcct gtttgcatta ctctgcagtt tccatttgca ttatcgatga gtaagatgct 2641 tgttaagcag catggtgtga ctgaaaggat actagatcgg aaaatgaatt ttctttctga 2701 aagggaagtc tgagcgagtc tcctaaatac tctgggcttt agcttctcca gctgtgaaga 2761 gctggattga tgcagtacac ctaaggaata atcatatata ctgggttttt gttttgctgt 2821 ggattcttt tttttttttt tttttagag ggggtctcac tttgttgccc aggctggtct 2881 tgaactcctg agctcaagtg atcctcctac ctcagtctcc caaagtgctg ggattacagg 2941 catgagccac cgtgcctggc tttgctgtgg attcttttgg gtgtcttttg ttttcctaca 3001 cgatttatag aggatgaggg gcggagaaag agatagaaaa aagggatgag ctagctgtta 3061 gagcaagggt tttggtgaga gataatattg attgaaggga ttttaaagga aatgttgctg 3121 tggggattc attgtaactc tccttgtgaa ctgctcagta aactctacat tgttcatgaa 3181 caaaaaaaa aaaaaaaaa aaaaaaaaa aaaaaaa
```

SEQ ID NO: 19 Human ZC3HAV1 isoform 2 Amino Acid Sequence (NP_078901.3)
```
  1 madpevccfi tkilcahggr maldallqei alsepqlcev lqvagpdrfv vletggeagi 61 trsvvattra rvcrrkycqr pcdnlhlckl nllgrcnysq sernlckysh evlseenfkv 121 lknhelsgln keelavlllq sdpffmpeic ksykgegrqq icnqqppcsr lhicdhftrg 181 ncrfpnclrs hnlmdrkvla imrehglnpd vvqniqdicn skhmqknppg prapsshrrn 241 mayrarsksr drffqgsqef lasasasaer sctpspdqls hrasledapv ddltrkftyl 301 gsqdrarpps gsskatdlgg tsqagtsqrf lengsqedll hgnpgstyla snstsapnwk 361 sltswtndqg arrktvfspt lpaarsslgs lqtpeavttr kgtgllssdy riingksgtq 421 diqpgplfnn nadgvatdit strslnykst ssghreissp riqdagpasr dvqatgriad 481 dadprvalvn dslsdvtstt ssrvddhdse eicldhlckg cplngscskv hfhlpyrwqm 541 ligktwtdfe hmetiekgyc npgihlcsvg sytinfrvms cdsfpirrls tpssvtkpan 601 svfttkwiwy wknesgtwiq ygeekdkrkn snvdssyles lyqscprgvv pfqagsrnye 661 lsfqgmiqtn lasktqkdvi rrptfvpqwy vqqmkrgpe 601 svfttkwiwy wknesgtwiq
```

SEQ ID NO: 20 Mouse ZC3HAV1 Variant 1 cDNA Sequence (NM_028421.1, CDS
region from position 382-3222)
```
  1 actctcctca ggctcatcaa aactccaccc gagcctcacg aacgtcctta cttcctctct 61 tcctggtagc agccttgcag tcccgagctc gggggaccct acgtctagcc tggaaccgag 121 ggtaccgcgc cgcggcggac ctgcccgcct aacgtcgctc gcttcccatt cgctctcccg 181 cgcggctgac tttaaatctg accccaggac ctcgtcgtcg aggtcgggcc tcgcgacacc 241 accgccggag ttggaaagcg aaaccgctct gctctgcgag cggcaccgcc cgcgtccgcc 301 cctgggaccg cgcgtaagtt tcgattctcc gtgaagccga gtcccgcgca gcggccggag 361 cagcggcagc catagcgcgc catgacggat cccgaggtat tctgtttcat caccaagatc
```

TABLE 1-continued

```
 421  ctgtgcgctc acgggggccg catgaccctg gaggaactgc tgggtgagat cagcctcccc
 481  gaagcgcaac tctacgagct gctgaaggca gcagggcccg atcgctttgt gctattggag
 541  actggagacc aggccgggat cactcggtcg gtggtggcta ctactcgagc ccgcgtctgc
 601  cgtcgcaagt actgccagag accctgcgac agcctgcacc tttgcaagct taatctgctc
 661  ggccggtgcc actatgcaca gtcccagcgg aacctctgca atatctctca cgatgttctc
 721  tcggaacaga acttccaggt cctgaagaat catgagctct ccgggcttaa ccaagaggag
 781  ctggcggtcc tcctggtcca aagcgaccct ttcttcatgc tgagatatg caagagttac
 841  aaaggagagg gccgcaaaca gatctgcggg cagccgcagc cctgcgagag actccacatc
 901  tgtgagcact tcacccgggg caactgcagt tacctcaact gtctcaggtc tcataacctg
 961  atggacagga aggtgttggc catcatgagg gagcatgggc tgagttctga tgtggtccag
1021  aacatccagg atatctgcaa caacaaacac actcggagga accccctag catgagagct
1081  ccccacccac atcgcagagg cggggcacac agggacagaa gcaaaagcag agaccgcttc
1141  catcacaaca gtctagaggt tctctcaacg gtctcacctc tgggatctgg tcccctagc
1201  ccagatgtca ccggctgtaa ggatcccctg gaggatgtgt ctgcagatgt cacccagaag
1261  ttcaagtacc tggggactca ggaccgtgca cagctttcct ccgtctcatc taaggccgct
1321  ggtgtccgag gacccagtca atgagagca agccaggagt ttttggagga tggggatcca
1381  gatggcttgt tttctaggaa tcgttctgat tcgtccacaa gtcgaacctc tgctgctggc
1441  tttcctctcg ttgcggcaca aagaaatgaa gctggggcca tgaaaatggg catgccttca
1501  ggacaccacg tcgaggtcaa gggcaagaac gaggacattg atcgcgtccc gttttaaat
1561  agttatattg atggggtaac aatggaagaa gcaacagtct caggaattct aggtaaaagg
1621  gccacagaca acggtctgga agaaatgata ctatctagca accatcagaa gagtgtggct
1681  aagacccagg atccccagac cgctggcaga atcactgaca gtggccaaga cacggcattc
1741  ctgcatagta aatatgaaga aaacccagcg tggccaggta catctaccca taacggccca
1801  aatggcttta gtcaaattat ggatgaaacg cctaatgtct ctaaaagtag tcccactggt
1861  tttggcataa aatcagcagt cactggagga aaagaagcag tctattctgg agttcagagt
1921  ctgagaagcc atgtcctggc tatgcctggg gagaccacta ctcctgtaca gggcagcaat
1981  aggctgcctc cgtcacctct gtcttcttcc acaagccaca gagttgcagc ctctgggagc
2041  cctggcaaga gctccaccca tgcctctgtg agcccagcca gtgagccctc gaggatgatg
2101  atgatgatgt cagaccctgc tgagtattcc ctatgctaca tcgtaaatcc tgtatctcct
2161  aggatggatg atcatggcct gaaggaaatc tgtctggatc atctgtacag gggctgtcag
2221  caggtcaact gcaacaagaa ccacttccat ctgccctacc ggtggcagct gttcatattg
2281  cccacttgga tggactttca ggacatggag tatatcgagc gggcctattg tgatccccaa
2341  attgaaatca ttgtgataga aaaacatcgg atcaatttca gaaaaatgac ttgtgattcc
2401  tacccccatcc gtcgcctctc cactccttca tttgtcgaaa aaacacttaa ttctgtcttc
2461  accaccaagt ggctttggta ttggaggaat gaattgaatg aatatactca gtatgggcat
2521  gagagcccaa gccataccag ctccgaaatt aattctgcat acctggagtc tttcttccac
2581  tcctgtccca ggggagtttt gcagttccac gctggttcac agaattacga gttaagcttt
2641  caagggatga ttcagacgaa tatagcttcc aagactcaaa ggcatgttgt gagaaggcca
2701  gttttgtttt cttcgaagga tgtggagcag aagagaagag gtccagacca tcagccagtg
2761  atgccccagg cagatgctct gaccctgttt tcttctcccc agaggaatgc tagcactgtt
```

TABLE 1-continued

```
2821 tcttctaacg aatatgagtt tatagagctc aataaccagg atgaggagta tgccaaaata
2881 agtgaacagt ttaaagcatc catgaaacaa ttcaagattg tgacgataaa gaggatatgg
2941 aaccagaagc tctgggacac ttttgagaga aagaagcaaa agatgaaaaa caagactgag
3001 atgttcctat ttcacgcggt gggccggatt catatggatt acatctgtaa gaataatttc
3061 gagtggatcc tacatggaaa ccgggagatc agatatggaa aaggtttgtg ctggaggaga
3121 gagaactgtg actccagcca tgcgcatggt ttccttgaga tgcccttggc atcacttggt
3181 agaactgcat ctctggactc cagtggcctt cagagaaaat aagctgagtt accttgttag
3241 gacagctcca ttgtcttgag ggtgctttgc cttggcccta gggctccttg tctgtttgtc
3301 tttttctctg gaacaactc aagatcttcc tatttgtaaa ctgttccgtc tgctggctat
3361 gttctctgcc attgctgttt actagagatg gcttttcctg atcgctgtct gtggctgcag
3421 agctattcaa agtagctttc taattaatgc cactgatggt tccaggggag agtggggaga
3481 agcccgttct catctcaggg ctctgccctc acacagaatg cttttttttt tatgaaccct
3541 tcattctttg tgggtgttta aggaataaga tatggtcaga cctgacagtg caggcttagg
3601 aggccgaggc aggaagattt atttagtcca aggctagtgt gtactacaaa gctagctcaa
3661 agctagccac aacaacttag taagaccaag tcttaaaata gaaagaaaaa aggttggggc
3721 tatttcttaa tggtagaggc ctggtctagc ctgagagagg ccccacaggt ttagctacag
3781 tacc
```

SEQ ID NO: 21 Mouse ZC3HAV1 isoform 1 Amino Acid Sequence (NP_082697.1)
```
  1 mtdpevfcfi tkilcahggr mtleellgei slpeaqlyel lkaagpdrfv lletgdqagi
 61 trsvvattra rvcrrkycqr pcdslhlckl nllgrchyaq sqrnlckysh dvlseqnfqv
121 lknhelsgln qeelavllvq sdpffmpeic ksykgegrkq icgqpqpcer lhicehftrg
181 ncsylnclrs hnlmdrkvla imrehglssd vvqniqdicn nkhtrrnpps mraphphrrg
241 gahrdrsksr drfhhnslev lstvsplgsg ppspdvtgck dpledvsadv tqkfkylgtq
301 draqlssvss kaagvrgpsq mrasqefled gdpdglfsrn rsdsstsrts aagfplvaaq
361 rneagamkmg mpsghhvevk gknedidrvp flnsyidgvt meeatvsgil gkratdngle
421 emilssnhqk svaktqdpqt agritdsgqd taflhskyee npawpgtsth ngpngfsqim
481 detpnvskss ptgfgiksav tggkeavysg vqslrshvla mpgetttpvq gsnrlppspl
541 ssstshrvaa sgspgkssth asvspaseps rmmmmmsdpa eyslcyivnp vsprmddhgl
601 keicldhlyr gcqqvncnkn hfhlpyrwql filptwmdfq dmeyierayc dpqieiivie
661 khrinfkkmt cdsypirrls tpsfvektln svftrtkwlwy wrnelneytq yghespshts
721 seinsayles ffhscprgvl qfhagsqnye lsfqgmiqtn iasktqrhvv rrpvfvsskd
781 veqkrrgpdh qpvmpqadal tlfsspqrna stvssneyef ielnnqdeey akiseqfkas
841 mkqfkivtik riwnqklwdt ferkkqkmkn ktemflfhav grihmdyick nnfewilhgn
901 reirygkglc wrrencdssh ahgflempla slgrtaslds sglqrk
```

SEQ ID NO: 22 Mouse ZC3HAV1 Variant 2 cDNA Sequence (NM_028864.2, CDS region from position 382-2751)
```
  1 actctcctca ggctcatcaa aactccaccc gagcctcacg aacgtccta cttcctctct
 61 tcctggtagc agccttgcag tcccgagctc ggggaccctc acgtctagcc tggaaccgag
121 ggtaccgcgc cgcggcggac ctgcccgcct aacgtcgctc gcttccattc gctctcccg
181 cgcggctgac tttaaatctg accccaggac ctcgtcgtcg aggtcgggcc tcgcgacacc
241 accgcggag ttgaaagcg aaaccgctct gctctgcgag cggcaccgcc cgcgtccgcc
301 cctgggaccg cgcgtaagtt tcgattctcc gtgaagccga gtcccgcgca gcggccggag
```

TABLE 1-continued

```
 361  cagcggcagc catagcgcgc catgacggat cccgaggtat tctgtttcat caccaagatc
 421  ctgtgcgctc acgggggccg catgaccctg gaggaactgc tgggtgagat cagcctcccc
 481  gaagcgcaac tctacgagct gctgaaggca gcagggcccg atcgctttgt gctattggag
 541  actggagacc aggccgggat cactcggtcg gtggtggcta ctactcgagc ccgcgtctgc
 601  cgtcgcaagt actgccagag accctgcgac agcctgcacc tttgcaagct taatctgctc
 661  ggccggtgcc actatgcaca gtcccagcgg aacctctgca atattctca cgatgttctc
 721  tcggaacaga acttccaggt cctgaagaat catgagctct ccgggcttaa ccaagaggag
 781  ctggcggtcc tcctggtcca aagcgaccct ttcttcatgc tgagatatg caagagttac
 841  aaaggagagg gccgcaaaca gatctgcggg cagccgcagc cctgcgagag actccacatc
 901  tgtgagcact tcacccgggg caactgcagt tacctcaact gtctcaggtc tcataacctg
 961  atggacagga aggtgttggc catcatgagg gagcatgggc tgagttctga tgtggtccag
1021  aacatccagg atatctgcaa caacaaacac actcggagga acccccctag catgagagct
1081  ccccacccac atcgcagagg cggggcacac agggacagaa gcaaaagcag agaccgcttc
1141  catcacaaca gtctagaggt tctctcaacg gtctcacctc tgggatctgg tcccctagc
1201  ccagatgtca ccggctgtaa ggatcccctg gaggatgtgt ctgcagatgt cacccagaag
1261  ttcaagtacc tggggactca ggaccgtgca cagcttttcct ccgtctcatc taaggccgct
1321  ggtgtccgag acccagtca aatgagagca agccaggagt ttttggagga tggggatcca
1381  gatggcttgt tttctaggaa tcgttctgat tcgtccacaa gtcgaacctc tgctgctggc
1441  tttcctctcg ttgcggcaca aagaaatgaa gctggggcca tgaaaatggg catgccttca
1501  ggacaccacg tcgaggtcaa gggcaagaac gaggacattg atcgcgtccc gttttttaaat
1561  agttatattg atggggtaac aatggaagaa gcaacagtct caggaattct aggtaaaagg
1621  gccacagaca acggtctgga agaaatgata ctatctagca accatcagaa gagtgtggct
1681  aagacccagg atccccagac cgctggcaga atcactgaca gtggccaaga cacggcattc
1741  ctgcatagta aatatgaaga aaacccagcg tggccaggta catctaccca taacggccca
1801  aatggctta gtcaaattat ggatgaaacg cctaatgtct ctaaaagtag tcccactggt
1861  tttggcataa aatcagcagt cactggagga aaagaagcag tctattctgg agttcagagt
1921  ctgagaagcc atgtcctggc tatgcctggg gagaccacta ctcctgtaca gggcagcaat
1981  aggctgcctc cgtcacctct gtcttcttcc acaagccaca gagttgcagc ctctgggagc
2041  cctggcaaga gctccaccca tgcctctgtg agcccagcca gtgagccctc gaggatgatg
2101  atgatgatgt cagaccctgc tgagtattcc ctatgctaca tcgtaaatct tgtatctcct
2161  aggatggatg atcatggcct gaaggaaatc tgtctggatc atctgtacag gggctgtcag
2221  caggtcaact gcaacaagaa ccacttccat ctgccctacc ggtggcagct gttcatattg
2281  cccacttgga tggactttca ggacatggag tatatcgagc gggcctattg tgatccccaa
2341  attgaaatca ttgtgataga aaaacatcgg atcaatttca agaaaatgac ttgtgattcc
2401  tacccatcc gtcgcctctc cactccttca tttgtcgaaa aaacacttaa ttctgtcttc
2461  accaccaagt ggctttggta ttggaggaat gaattgaatg aatatactca gtatgggcat
2521  gagagcccaa gccataccag ctccgaaatt aattctgcat acctggagtc tttcttccac
2581  tcctgtccca ggggagtttt gcagttccac gctggttcac agaattacga gttaagcttt
2641  caagggatga ttcagacgaa tatagcttcc aagactcaaa ggcatgttgt gagaaggcca
2701  gttttttgtt cttcgaagga tgtggagcag aagagaagag gtccagagta agtgttcagc
```

TABLE 1-continued

```
2761  agctgttagc tcaggccatg atcttgctgc gtcatgctgc gtcatgctgt gtcatgcatc
2821  tggaggtctg tgttcttggg aagttcctgc ctctgtctta ctgtagtttc tgtttgattt
2881  atctatgagt aaggaaattg ttaagcagtg tgacataact gaaagtttcc tggccagggg
2941  actagggagt gcaagcactt ggttaagctt tgtgtaacag atacaaggcc ttgggtttag
3001  agtgtaggag aagggatgc tataccatga aaccagcatc cgcctttagc ttacaggcta
3061  tttagctgct cgctctcatc tgcactctgg gccttacttg ctccagctgc gactggctgg
3121  atcaaggagt gtacaagtgt atacactgga tttttgtttt gttggggtc ctctctgtgt
3181  ctttggttgt gctgagagga caggaggctg agaaagaggc ttaagttagt agcctgggga
3241  aagagctgga gagatgaagt tcactaaagg cattggtgtt agatttaatc gacttgtaat
3301  cattgtaccc atgggcatt tcaaggtggg ttttgctgtg gggaattcat tgtaacttgc
3361  ctgtctctat gaaactcagt aaaatctcat tgttcg
```

SEQ ID NO: 23 Mouse ZC3HAV1 isoform 2 Amino Acid Sequence (NP_083140.1)

```
  1  mtdpevfcfi tkilcahggr mtleellgei slpeaqlyel lkaagpdrfv lletgdqagi
 61  trsvvattra rvcrrkycqr pcdslhlckl nllgrchyaq sqrnlckysh dvlseqnfqv
121  lknhelsgln qeelavllvq sdpffmpeic ksykgegrkq icgqpqpcer lhicehftrg
181  ncsylnclrs hnlmdrkvla imrehglssd vvqniqdicn nkhtrrnpps mraphphrrg
241  gahrdrsksr drfhhnslev lstvsplgsg ppspdvtgck dpledvsadv tqkfkylgtq
301  draqlssvss kaagvrgpsq mrasqefled gdpdglfsrn rsdsstsrts aagfplvaaq
361  rneagamkmg mpsghhvevk gknedidrvp flnsyidgvt meeatvsgil gkratdngle
421  emilssnhqk svaktqdpqt agritdsgqd taflhskyee npawpgtsth ngpngfsqlm
481  detpnvskss ptgfgiksav tggkeavysg vqslrshvla mpgetttpvq gsnrlppspl
541  ssstshrvaa sgspgkssth asyspaseps rmmmmmsdpa eyslcyivnp vsprmddhgl
601  keicldhlyr gcqqvncnkn hfhlpyrwql filptwmdfq dmeyierayc dpqieiivie
661  khrinfkkmt cdsypirrls tpsfvektln svfttkwlwy wrnelneytq yghespshts
721  seinsayles ffhscprgvl qfhagsqnye lsfqgmiqtn iasktqrhvv rrpvfvsskd
781  veqkrrgpe
```

SEQ ID NO: 24 Mouse ZC3HAV1 Variant 3 cDNA Sequence (NM_001347122.1, CDS region from position 382-3372)

```
  1  actctcctca ggctcatcaa aactccaccc gagcctcacg aacgtcctta cttcctctct
 61  tcctggtagc agccttgcag tcccgagctc gggggacctc acgtctagcc tggaaccgag
121  ggtaccgcgc gcgcggcggac ctgcccgcct aacgtcgctc gcttcccatt cgctctcccg
181  cgcggctgac tttaaatctg acccaggac ctcgtcgtcg aggtcgggcc tcgcgacacc
241  accgccggag ttggaaagcg aaaccgctct gctctgcgag cggcaccgcc cgcgtccgcc
301  cctgggaccg cgcgtaagtt tcgattctcc gtgaagccga gtcccgcgca gcggccggag
361  cagcggcagc catagcgcgc catgacggat cccgaggtat tctgtttcat caccaagatc
421  ctgtgcgctc acggggggccg catgaccctg gaggaactgc tgggtgagat cagcctcccc
481  gaagcgcaac tctacgagct gctgaaggca gcagggcccg atcgctttgt gctattggag
541  actggagacc aggccgggat cactcggtcg gtggtggcta ctactcgagc ccgcgtctgc
601  cgtcgcaagt actgccagag accctgcgac agcctgcacc tttgcaagct taatctgctc
661  ggccggtgcc actatgcaca gtcccagcgg aacctctgca atattctca cgatgttctc
721  tcggaacaga acttccaggt cctgaagaat catgagctct ccgggcttaa ccaagaggag
```

TABLE 1-continued

```
 781  ctggcggtcc tcctggtcca aagcgaccct ttcttcatgc ctgagatatg caagagttac
 841  aaaggagagg gccgcaaaca gatctgcggg cagccgcagc cctgcgagag actccacatc
 901  tgtgagcact tcacccgggg caactgcagt tacctcaact gtctcaggtc tcataacctg
 961  atggacagga aggtgttggc catcatgagg gagcatgggc tgagttctga tgtggtccag
1021  aacatccagg atatctgcaa caacaaacac actcggagga accccctag catgagagct
1081  ccccacccac atcgcagagg cggggcacac agggacagaa gcaaaagcag agaccgcttc
1141  catcacaaca gtctagaggt tctctcaacg gtctcacctc tgggatctgg tcccctagc
1201  ccagatgtca ccggctgtaa ggatcccctg gaggatgtgt ctgcagatgt cacccagaag
1261  ttcaagtacc tggggactca ggaccgtgca cagctttcct ccgtctcatc taaggccgct
1321  ggtgtccgag acccagtca atgagagca agccaggagt ttttggagga tggggatcca
1381  gatggcttgt tttctaggaa tcgttctgat tcgtccacaa gtcgaacctc tgctgctggc
1441  tttcctctcg ttgcggcaca agaaatgaa gctggggcca tgaaaatggg catgccttca
1501  ggacaccacg tcgaggtcaa gggcaagaac gaggacattg atcgcgtccc gttttaaat
1561  agttatattg atggggtaac aatggaagaa gcaacagtct caggaattct aggtaaaagg
1621  gccacagaca acggtctgga agaaatgata ctatctagca accatcagaa gagtgtggct
1681  aagacccagg atccccagac cgctggcaga atcactgaca gtggccaaga cacggcattc
1741  ctgcatagta aatatgaaga aaacccagcg tggccaggta catctaccca taacggccca
1801  aatggctta gtcaaattat ggatgaaacg cctaatgtct ctaaaagtag tcccactggt
1861  tttggcataa aatcagcagt cactggagga aaagaagcag tctattctgg agttcagagt
1921  ctgagaagcc atgtcctggc tatgcctggg gagaccacta ctcctgtaca gggcagcaat
1981  aggctgcctc cgtcacctct gtcttcttcc acaagccaca gagttgcagc ctctgggagc
2041  cctggcaaga gctccaccca tgcctctgtg agcccagcca gtgagccctc gaggatgatg
2101  atgatgatgt cagaccctgc tgagtattcc ctatgctaca tcgtaaatcc tgtatctcct
2161  aggatggatg atcatggcct gaaggaaatc tgtctggatc atctgtacag gggctgtcag
2221  caggtcaact gcaacaagaa ccacttccat ctgccctacc ggtggcagct gttcatattg
2281  cccacttgga tggactttca ggacatggag tatatcgagc gggcctattg tgatccccaa
2341  attgaaatca ttgtgataga aaaacatcgg atcaatttca agaaaatgac ttgtgattcc
2401  tacccatcc gtcgcctctc cactccttca tttgtcgaaa aaacacttaa ttctgtcttc
2461  accaccaagt ggctttggta ttggaggaat gaattgaatg aatatactca gtatgggcat
2521  gagagcccaa gccataccag ctccgaaatt aattctgcat acctggagtc tttcttccac
2581  tcctgtccca ggggagtttt gcagttccac gctggttcac agaattacga gttaagcttt
2641  caagggatga ttcagacgaa tatagcttcc aagactcaaa ggcatgttgt gagaaggcca
2701  gttttttgttt cttcgaagga tgtggagcag aagagaagag gtccagacca tcagccagtg
2761  atgccccagg cagatgctct gaccctgttt tcttctcccc agaggaatgc tagcactgtt
2821  tcttctaacg aatatgagtt tatagagctc aataaccagg atgaggagta tgccaaaata
2881  agtgaacagt ttaaagcatc catgaaacaa ttcaagattg tgacgataaa gaggatatgg
2941  aaccagaagc tctgggacac ttttgagaga aagaagcaaa agatgaaaaa caagactgag
3001  atgttcctat ttcacgcggt gggccggatt catatggatt acatctgtaa gaataatttc
3061  gagtggatcc tacatggaaa ccggagatc agatatggaa aaggaaatta ttttacaaaa
3121  gaagccatgt attcacacaa gagttgttca tatgattcca gaggcactgt catgttcgta
```

TABLE 1-continued

```
3181  gcccgagtcc tggttggaag tgtcattgaa ggaaatatga cattaagtag ccctcccgcg
3241  ctctatgaca gctgtgtgga caccaggctg aatccgtccg tctttgtcat tttccggaaa
3301  gaacagattt acccagagta tgtgattgag tatatggagt tagagaaaga gaaaggatgc
3361  ataattagtt agaaaggatg tataccatgc tgaaaccatt ctgttgctat ttaggaccaa
3421  aacattttca gacagtaggt aggcttttac attcccttgc tccgttacct aacgacttaa
3481  accagttcct tgcttccccc atccctacac attgttccta agtctgattt tacctcccca
3541  ataccagcca gtatcaggtg ttcttatagt ccttggcgcc tttgcatcta attcattggt
3601  tctagacgaa ctattctgtc agttttacc acctagtagg caatacctgt tttgtctaat
3661  attcaaagtg caattcgcgt ctagattatc cacacaattt cactaattga aaaatatcaa
3721  atttactatt ataatgtaag agagaaatat aggtcataac ttcggcacga ctttaagtac
3781  taagcaataa tggagtcgtc agacgcctcc gcttaccgtg aaccagtatg agcttgggag
3841  aaaggaactg gaagaacatg aaaaagcagg gcatgtgta  gacattagtg aaaattaaca
3901  atgcacgtta tttgcaaatg tcagcaatta tctgtacatg gtaagaacga aaaataccatt
3961  cattgaaata aagctacagc acaagacaac ttacagattg tgaaacagcg agaatgaaga
4021  gctacattct tgcagacgag ctgtaggtcg tacacgaatg tctaaagaga cattcaaaac
4081  tcgaataggg tgcagagtaa tttcttactg tgaggaattg cccaatgtat ggaaagatgc
4141  atagttggct ctcacatgct aaatgccagt agcgccctcc ttcgcttgaa gtcatgacaa
4201  ccacagtccc tactagacct gttcatcttt tttttttttt tttttttttt ttttggtgtt
4261  tttgagacag ggtttctctg cgtagtccta gctgtcctgg aactcacttt gtagaccagg
4321  ctggcctcga actcagaaat ccgcctgcct ctgcctcccg agtgctggga ttaaaggcgt
4381  gcgccaccac gcccggctct gttcatcctt ttaaaggtag atcttttata acatcctttg
4441  ccaccttgag atgatttata ggtaatataa tctacatttg agtttattca gacttaattt
4501  agtgccctac ttgtgttata atggaaactt agaaggtcag aactctgtaa tggacataaa
4561  ctgttaagta ctcaggcatg actacgctat cagctacgaa acatgttaac tctcactagg
4621  aatagctttg cttaagagt  ccagcagggg caacttcctg agatgaatga agtacaggaa
4681  aatgaaagat tagagggatg tgtgacggaa tacagtatta gggttcacca tagcagactc
4741  tgcgctttat ctgtctatgg tgaaggatag ggcgcaatca ctttaattgt aatgatagat
4801  aaataagaca ggacaaacta cagtttgtct cagaggaatc caaggattct ttttcagaca
4861  agttgtaggt cccgcataca tgtccaccag gacattagac agtcgtaaag atgcagaacg
4921  aacagtttgt gtgtgggact gacccaccca cacacagcag ggcacttgtt ctgcctcagg
4981  ctgcatctac tcagtgccgt taataaactt tagatacaaa ccaacaacca ccattctcca
5041  gtatactaca gtgggaatca ctgatctagt taacggcagc actcttggat taattcaatt
5101  gttatttcta ctctttaaca acagaataag ccagatccctt gactctcaag cccccagttt
5161  ttaaaaacaa ggtgttcctt gatttataat ccttcttgtt tatgctgtgt tctttgattt
5221  ataatccttg tttgctcaat aaaaagaaaa aataatttga ttcatttgcc ctca
```

SEQ ID NO: 25 Mouse ZC3HAV1 isoform 3 Amino Acid Sequence (NP_083140.1)

```
  1  mtdpevfcfi tkilcahggr mtleellgei slpeaqlyel lkaagpdrfv lletgdqagi
 61  trsvvattra rvcrrkycqr pcdslhlckl nllgrchyaq sqrnlckysh dvlseqnfqv
121  lknhelsgln qeelavllvq sdpffmpeic ksykgegrkq icgqpqpcer lhicehftrg
181  ncsylnclrs hnlmdrkvla imrehglssd vvqniqdicn nkhtrrnpps mraphphrrg
241  gahrdrsksr drfhhnslev lstvsplgsg ppspdvtgck dpledvsadv tqkfkylgtq
```

TABLE 1-continued

```
301  draqlssvss kaagvrgpsq mrasqefled gdpdglfsrn rsdsstsrts aagfplvaaq 361  rneagamkmg mpsghhvevk gknedidrvp flnsyidgvt meeatvsgil gkratdngle 421  emilssnhqk svaktqdpqt agritdsgqd taflhskyee npawpgtsth ngpngfsqim 481  detpnvskss ptgfgiksav tggkeavysg vqslrshvla mpgetttpvq gsnrlppspl 541  ssstshrvaa sgspgkssth asyspaseps rmmmmmsdpa eyslcyivnp vsprmddhgl 601  keicldhlyr gcqqvncnkn hfhlpyrwql filptwmdfq dmeyierayc dpqieiivie 661  khrinfkkmt cdsypirrls tpsfvektln svfttkwlwy wrnelneytq yghespshts 721  seinsayles ffhscprgvl qfhagsqnye lsfqgmiqtn iasktqrhvv rrpvfvsskd 781  veqkrrgpdh qpvmpqadal tlfsspqrna stvssneyef ielnnqdeey akiseqfkas 841  mkqfkivtik riwnqklwdt ferkkqkmkn ktemflfhav grihmdyick nnfewilhgn 901  reirygkgny ftkeamyshk scsydsrgtv mfvarvlvgs viegnmtlss ppalydscvd 961  trlnpsvfvi frkeqiypey vieymeleke kgciis
```

SEQ ID NO: 26 Human PPP1R15A cDNA Sequence (NM_014330.3, CDS region from position 270-2294)

```
   1  ataaaagcct agtggccatt gtgttcgttg ctcttatcgg ttcccatccc agttgttgat 61  cttatgcaag acgctgcacg accccgcgcc cgcttgtcgc acggcactt gaggcagccg 121  gagatactct gagttactcg gagcccgacg cctgagggtg agatgaacgc gctggcctcc 181  ctaaccgtcc ggacctgtga tcgcttctgg cagaccgaac cggcgctcct gccccgggg 241  tgacgcgcag ctcccagccg cccagacaca tggccccagg ccaagcaccc catcaggcta 301  ccccgtggag ggatgcccac cctttcttcc tcctgtcccc agtgatgggc ctcctcagcc 361  gcgcctggag ccgcctgagg ggcctgggac tctagagcc ctggctggtg aagcagtaa 421  aaggagcagc tctggtagaa gctggcctgg agggagaagc taggactcct ctggcaatcc 481  cccataccc ttggggcaga cgccctgaag aggaggctga agacagtgga ggccctggag 541  aggacagaga aacactgggg ctgaaaacca gcagttccct tcctgaagcc tggggacttt 601  tggatgatga tgatggcatg tatggtgagc gagaggcaac cagtgtccct agagggcagg 661  gaagtcaatt tgcagatggc cagcgtgctc ccctgtctcc cagccttctg ataaggacac 721  tgcaaggttc tgataagaac ccaggggagg agaaagccga ggaagaggga gttgctgaag 781  aggagggagt taacaagttc tcttatccac catcacaccg ggagtgttgt ccagccgtgg 841  aggaggagga cgatgaagaa gctgtaaaga aagaagctca cagaacctct acttctgcct 901  tgtctccagg atccaagccc agcacttggg tgtcttgccc aggggaggaa gagaatcaag 961  ccacggagga taaaagaaca gaaagaagta aaggagccag gaagacctcc gtgtccccc 1021  gatcttcagg ctccgacccc aggtcctggg agtatcgttc aggagaggcg tccgaggaga 1081  aggaggaaaa ggcacacaaa gaaactggga aggagaaagc tgccccaggg ccgcaatcct 1141  cagccccagc ccagaggccc cagctcaagt cctggtggtg ccaacccagt gatgaagagg 1201  agggtgaggt caaggctttg ggggcagctg agaaggatgg agaagctgag tgtcctccct 1261  gcatcccccc accaagtgcc ttcctgaagg cctgggtgta ttggccagga gaggacacag 1321  aggaagagga agatgaggaa gaagatgagg acagtgactc tggatcagat gaggaagagg 1381  gagaagctga ggcttcctct tccactcctg ctacaggtgt cttcttgaag tcctgggtct 1441  atcagccagg agaggacaca gaggaggagg aagatgagga cagtgataca ggatcagccg 1501  aggatgaaag agaagctgag acttctgctt ccacacccc tgcaagtgct ttccttgaagg 1561  cctgggtgta tcggccagga gaggacacgg aggaggagga agatgaggat gtggatagtg
```

TABLE 1-continued

```
1621 aggataagga agatgattca gaagcagcct tgggagaagc tgagtcagac ccacatccct
1681 cccacccgga ccagagggcc cacttcaggg gctggggata tcgacctgga aaagagacag
1741 aggaagagga agctgctgag gactggggag aagctgagcc ctgcccsttc cgagtggcca
1801 tctatgtacc tggagagaag ccaccgcctc cctgggctcc tcctaggctg ccctccgac
1861 tgcaaaggcg gctcaagcgc ccagaaaccc ctactcatga tccggaccct gagactcccc
1921 taaaggccag aaaggtgcgc ttctccgaga aggtcactgt ccatttcctg gctgtctggg
1981 cagggccggc ccaggccgcc cgccagggcc cctgggagca gcttgctcgg gatcgcagcc
2041 gcttcgcacg ccgcatcacc caggcccagg aggagctgag cccctgcctc acccctgctg
2101 cccgggccag agcctgggca cgcctcagga acccacctt agcccccatc cctgccctca
2161 cccagacctt gccttcctcc tctgtcccit cgtccccagt ccagaccacg cccttgagcc
2221 aagctgtggc cacaccttcc cgctcgtctg ctgctgcagc ggctgccctg gacctcagtg
2281 ggaggcgtgg ctgagaccaa ctggtttgcc tataatttat taactattta ttttttctaa
2341 gtgtgggttt atataaggaa taaagccttt tgatttgtag cgaaaaaaaa aaaaaaaa
```

SEQ ID NO: 27 Human PPP1R15A amino acid Sequence (NP_055145.3)
```
  1 mapgqaphqa tpwrdahpff llspvmglls rawsrlrglg plepwlveav kgaalveagl
 61 egeartplai phtpwgrrpe eeaedsggpg edretlglkt ssslpeawgl lddddgmyge
121 reatsvprgq gsqfadgqra plspsllirt lqgsdknpge ekaeeegvae eegvnkfsyp
181 pshreccpav eeeddeeavk keahrtstsa lspgskpstw vscpgeeenq atedkrters
241 kgarktsysp rssgsdprsw eyrsgeasee keekahketg kgeaapgpqs sapaqrpqlk
301 swwcqpsdee egevkalgaa ekdgeaecpp cipppsaflk awvywpgedt eeeedeeede
361 dsdsgsdeee geaeasssstp atgvflkswv yqpgedteee ededsdtgsa edereaetsa
421 stppasaflk awvyrpgedt eeeededvds edkeddseaa lgeaesdphp shpdqrahfr
481 gwgyrpgket eeeeaaedwg eaepcpfrva iyvpgekppp pwapprlplr lqrrlkrpet
541 pthdpdpetp lkarkvrfse kvtvhflavw agpaqaarqg pweqlardrs rfarritqaq
601 eelspcltpa ararawarlr npplapipal tqtlpsssvp sspvqttpls qavatpsrss
661 aaaaaaldls grrg
```

SEQ ID NO: 28 Mouse PPP1R15A cDNA Sequence (NM_008654.2, CDS region from position 284-2257)
```
  1 agcgccgcgt cagggtataa aagccgcgtg gacgatgttg gcgcagattg agtcagctct
 61 gagtttgtgg aagattacat gcgatatccc gcgcgacccc gcatcccttt gccggccggg
121 acagcctttg ctacagcctg tgaaacattg cgtccccgag ccccacgcct gagggcgaca
181 tgaacccgct ggcttcgcga gcagtccgga cccacgatcg cttttggcaa ccagaaccgg
241 cgcttcagcc cccggggtga cgtgcagccc gccgcccaga cacatggccc cgagcccaag
301 accccagcat gtcctgcact ggagggacgc ccacaacttc tatctcctgt ccccactgat
361 gggcttgctc agtcgggcct ggagccgcct gaggggccca gaagtcccag aggcatggct
421 ggcaaaaaca gtaacaggag cagatcagat agaagctgcg gctctgctga cacctacccc
481 tgtctctggt aacctcctcc ctcatgggga gactgaagaa agtggatctc ctgaacagag
541 tcaagcagcc cagaggctct gccttgtgga agctgaaagt tcccctcctg aaacttgggg
601 acttttcaaat gttgatgagt acaatgcaaa gccaggacaa gatgacctta gagagaagga
661 aatggaacgc acagctgcaa aggccacact cagcccgct ggcctgcaag ggctgataa
721 gaggcttggg gaggtggtgg ctagagaaga gggagtggct gagcccgctt atcccacatc
```

TABLE 1-continued

```
 781  acagctggag ggtggtccag ctgagaatga agaggatgga gaaacagtga agacttacca
 841  agcttctgct gcttccatag ctccgggata caaacccagc acccctgtgc ctttcttggg
 901  ggaggcagaa catcaagcca cggaagaaaa aggaacagaa aacaaggctg accctccaa
 961  ctctccttct tcaggctccc actccagagc ctgggagtac tactctagag agaagcctaa
1021  gcaggaggga gaagccaagg tagaggcaca cagggcaggg cagggtcacc cttgtcggaa
1081  tgctgaggct gaggaaggag gacctgagac aacttttgtc tgtactgaa atgccttcct
1141  gaaggcctgg gtgtatcgcc caggagagga cacagaggaa gaagacaaca gcgattcgga
1201  ttcagctgag gaagacacag ctcagaccgg tgccaccccc catacaagtg ccttcctgaa
1261  ggcctgggtg tatcgccag gagaggacac agaggaagaa gacagcgatt cggattcagc
1321  tgaggaagac acagctcaga ccggtgccac cccccataca agtgccttcc tgaaggcctg
1381  ggtgtatcgc ccaggagagg acacagagga gaaaacagc gatttggatt cagctgagga
1441  agacacagct cagaccggtg ccaccccca tacaagtgcc ttcctgaagg cctgggtgta
1501  tcgcccagga gaggacacag aggaagaaaa cagcgatttg gattcagctg aggaagacac
1561  agctcagacc ggtgccaccc cacatacaag tccctttcctg aaggcctggg tgtatcgccc
1621  aggagaggac acagaagatg acacagaaga ggaagaggac agtgagaatg tggccccagg
1681  tgactcagaa acagctgact caagccagag tccctgcctt cagccccagc gttgtctacc
1741  aggagagaag accaagggac gtggggaaga gcccctctc ttccaggtgg ccttctattt
1801  acccggagag aagccagaat caccttgggc tgcacctaag ctgccccttc gactgcagag
1861  gcggctcaga ttgttcaaag ccccacccg gatcaggac cccgagattc ctctaaaagc
1921  tcggaaggta cacttcgctg agaaagtcac agtccatttc cttgctgtct gggcaggacc
1981  agcccaagct gcccgtcgag gtccctggga gcagtttgca cgagatcgaa gccgctttgc
2041  tcgacgcatt gcccaggcag aggaagagct gggtccctac cttacccctg attccagggc
2101  cagagcatgg gcacgcctta gaaacccatc tcttccacag tccgagcctc gctcttcctc
2161  tgaggccact cccttgaccc aagatgtgac cacaccctct cccttccca gtgaaacccc
2221  ttcgcccagc ctgtacttgg gagggaggcg gggctaagcc tgagtagttt cctattattt
2281  atttatttat ttatttgaat aagaaataaa gccttttaat ttgtagtgat aaaaaaaaaa
2341  aaaaa
```

SEQ ID NO: 29 Mouse PPP1R15A amino acid Sequence (NP_032680.1)
```
   1  mapsprpqhv lhwrdahnfy llsplmglls rawsrlrgpe vpeawlaktv tgadqieaaa
  61  lltptpvsgn llphgetees gspeqsqaaq rlclveaess ppetwglsnv deynakpgqd
 121  dlrekemert agkatlqpag lqgadkrlge vvareegvae payptsqleg gpaeneedge
 181  tvktyqasaa siapgykpst pvpflgeaeh qateekgten kadpsnspss gshsraweyy
 241  srekpkqege akveahragq ghpcrnaeae eggpettfvc tgnaflkawv yrpgedteee
 301  dnsdsdsaee dtaqtgatph tsaflkawvy rpgedteeed sdsdsaeedt aqtgatphts
 361  aflkawvyrp gedteeensd ldsaeedtaq tgatphtsaf lkawvyrpge dteeensdld
 421  saeedtaqtg atphtspflk awvyrpgedt eddteeeeds envapgdset adssqspclq
 481  pqrclpgekt kgrgeepplf qvafylpgek pespwaapkl plrlqrrlrl fkaptrdqdp
 541  eiplkarkvh faekvtvhfl avwagpaqaa rrgpweqfar drsrfarria qaeeeklgpyl
 601  tpdsrarawa rlrnpslpqs eprssseatp ltqdvttpsp lpsetpspsl ylggrrg
```

TABLE 1-continued

SEQ ID NO: 30 Human EIF2AK2 cDNA Sequence Variant 1 (NM_002759.3, CDS region from position 558-2213)

```
   1 agcagacgag ggcttgtgcg agaggggggcc gggcggctgc agggaaggcg gagtccaagg
  61 ggaaaacgaa actgagaacc agctctcccg aagccgcggg tctccggccg gcggcggcgg
 121 cggcggcggc ggcggcgcag tttgctcata ctttgtgact tgcggtcaca gtggcattca
 181 gctccacact tggtagaacc acaggcacga caagcataga acatcctaa acaatcttca
 241 tcgaggcatc gaggtccatc ccaataaaaa tcaggagacc ctggctatca tagaccttag
 301 tcttcgctgg tatcactcgt ctgtctgaac cagcggttgc attttttta gccttctttt
 361 ttctcttta ccagtttctg gagcaaattc agtttgcctt cctggatttg taaattgtaa
 421 tgacctcaaa actttagcag ttcttccatc tgactcaggt ttgcttctct ggcggtcttc
 481 agaatcaaca tccacacttc cgtgattatc tgcgtgcatt ttggacaaag cttccaacca
 541 ggatacggga agaagaaatg gctggtgatc tttcagcagg tttcttcatg gaggaactta
 601 atacataccg tcagaagcag ggagtagtac ttaaatatca agaactgcct aattcaggac
 661 ctccacatga taggaggttt acatttcaag ttataataga tggaagagaa tttccagaag
 721 gtgaaggtag atcaaagaag gaagcaaaaa atgccgcagc caaattagct gttgagatac
 781 ttaataagga aaagaaggca gttagtcctt tattattgac aacaacgaat tcttcagaag
 841 gattatccat ggggaattac ataggcctta tcaatagaat tgcccagaag aaaagactaa
 901 ctgtaaatta tgaacagtgt gcatcggggg tgcatgggcc agaaggattt cattataaat
 961 gcaaaatggg acagaaagaa tatagtattg gtacaggttc tactaaacag gaagcaaaac
1021 aattggccgc taaacttgca tatcttcaga tattatcaga agaaacctca gtgaaatctg
1081 actacctgtc ctctggttct tttgctacta cgtgtgagtc ccaaagcaac tctttagtga
1141 ccagcacact cgcttctgaa tcatcatctg aaggtgactt ctcagcagat acatcagaga
1201 taaattctaa cagtgacagt ttaaacagtt cttcgttgct tatgaatggt ctcagaaata
1261 atcaaaggaa ggcaaaaaga tctttggcac ccagatttga ccttcctgac atgaaagaaa
1321 caaagtatac tgtggacaag aggtttggca tggattttaa agaaatagaa ttaattggct
1381 caggtggatt tggccaagtt ttcaaagcaa aacacagaat tgacggaaag acttacgtta
1441 ttaaacgtgt taaatataat aacgagaagg cggagcgtga agtaaaagca ttggcaaaac
1501 ttgatcatgt aaatattgtt cactacaatg gctgttggga tggatttgat tatgatcctg
1561 agaccagtga tgattctctt gagagcagtg attatgatcc tgagaacagc aaaaatagtt
1621 caaggtcaaa gactaagtgc cttttcatcc aaatggaatt ctgtgataaa gggaccttgg
1681 aacaatggat tgaaaaaaga agaggcgaga actagacaa agttttggct ttggaactct
1741 ttgaacaaat aacaaagggg gtggattata cattcaaa aaaattaatt catagagatc
1801 ttaagccaag taatatattc ttagtagata caaaacaagt aaagattgga gactttggac
1861 ttgtaacatc tctgaaaaat gatggaaagc gaacaaggag taagggaact tgcgataca
1921 tgagcccaga acagatttct tcgcaagact atggaaagga agtggacctc tacgctttgg
1981 ggctaattct tgctgaactt cttcatgtat gtgacactgc ttttgaaaca tcaaagtttt
2041 tcacagacct acgggatggc atcatctcag atatatttga taaaaaagaa aaaactcttc
2101 tacagaaatt actctcaaag aaacctgagg atcgacctaa cacatctgaa atactaagga
2161 ccttgactgt gtggaagaaa agcccagaga aaaatgaacg acacacatgt tagagcccttt
2221 ctgaaaaagt atcctgcttc tgatatgcag ttttccttaa attatctaaa atctgctagg
2281 gaatatcaat agatatttac cttttatttt aatgtttcct ttaatttttt actatttta
```

TABLE 1-continued

```
2341 ctaatctttc tgcagaaaca gaaaggtttt cttcttttg cttcaaaaac attcttacat
2401 tttactttt cctggctcat ctctttattc ttttttttt tttaaagaca gagtctcgct
2461 ctgttgccca ggctggagtg caatgacaca gtcttggctc actgcaactt ctgcctcttg
2521 ggttcaagtg attctcctgc ctcagcctcc tgagtagctg gattacaggc atgtgccacc
2581 cacccaacta ttttgtgt ttaataaa gacagggttt caccatgttg gccaggctgg
2641 tctcaaactc ctgacctcaa gtaatccacc tgcctcggcc tcccaaagtg ctgggattac
2701 agggatgagc caccgcgccc agcctcatct ctttgttcta aagatggaaa aaccacccc
2761 aaattttctt tttatactat taatgaatca atcaattcat atctatttat taaatttcta
2821 ccgcttttag gccaaaaaaa tgtaagatcg ttctctgcct cacatagctt acaagccagc
2881 tggagaaata tggtactcat taaaaaaaaa aaaaaaagtg atgtacaacc acttcggaaa
2941 acaatttggc attatctagt aaagttgaat ccatgtatac ccacatagct atcaattcta
3001 ttcctacata cgtgcttaca agaatgtcca taaaccctg tttataatag ccaaaagaac
3061 agggaacaac cataatgcac atcaaaagaa gaatggatta aaaaaattat attcacacac
3121 aggagtacta tatagtattg aaaacaattg aagtacagct aaatgtaata acgtaacaca
3181 atacaactct cagaaacata atgttaagcg aacaaagcag gttttcagaa aatatatgca
3241 gaataattcc atttatataa agttccagag catgcaaaac taatcatttt tgtataaaaa
3301 acccaacaaa tgtgatgaga caataatggg aaggaaggga atgagaaata ttaaattctg
3361 gatggtggtt atctttgagg gaggggaatg atgtgattgg ggaaatggac tttcaaaggt
3421 aatggtaact tccttaagct ggatggtagg tccactagtg tttgctgcat agttatacct
3481 tttatcttaa atacatttg tatctattgt aacaaccact ttaaagacaa ccgtgctgta
3541 aggcagtagc taaaaacaga aaatagtcca tcgggaaggg taagatggct ttctgctgag
3601 cacagggcta gaagtgacag cccagtgggc cttccaacta tatgccaggg tgttagatga
3661 gtagagagga gaccacccag gaagtctgga caagggtct ggcatgagct ctggagaaga
3721 tatatttgag gaacatgggg tatgctagtt tgttgtcctg aattgctgta gagaagataa
3781 tttaaattgc atcttagaag acgaccctga gggtgaattt caacttaggg caattgtttt
3841 agtttgtttc ttattggttt aaatggatac ttgaagctgg ataatttata aggaaaagag
3901 atttatatga cttacagttc tgcaggctgt acaagaaaca tggcaccagc atctgcttct
3961 tccccggctg cttccactca tggtggaagg tgaaggggag ccggatgtgc agagatcata
4021 tggcaagaga ggaagcaaga gagcgaggga gaaggtgcca ggctctttt aaataaccgg
4081 ctcttgaggg aactaataga ttgagaactc cttgcttctc ctccccagca caccccaccc
4141 ccagggacgg cattaatgta ttcatgaggg gtcttccccc atgacccaaa cacctcccat
4201 caggccccac ctccaacact gggatcaaat ttcaacatga gattttgggg gacaaacatg
4261 caaactatag cagcaaccag ctaccattct aaaactgcca tatgatttta ggatttttaa
4321 aaagggccaa atttaggtta agcaaaaaaa aaaaaaaaa a
```

SEQ ID NO: 31 Human EIF2AK2 Amino Acid Sequence Isoform a (NP_002750.1)

```
  1 magdlsagff meelntyrqk qgvvlkyqel pnsgpphdrr ftfqviidgr efpegegrsk
 61 keaknaaakl aveilnkekk aysplllttt nsseglsmgn yiglinriaq kkrltvnyeq
121 casgvhgpeg fhykckmgqk eysigtgstk qeakqlaakl aylqilseet svksdylssg
181 sfattcesqs nslvtstlas esssegdfsa dtseinsnsd slnssllmn glrnnqrkak
241 rslaprfdlp dmketkytvd krfgmdfkei eligsggfgq vfkakhridg ktyvikrvky
```

| | |
|---|---|
| 301 | nnekaerevk alakldhvni vhyngcwdgf dydpetsdds lessdydpen sknssrsktk |
| 361 | clfiqmefcd kgtleqwiek rrgekldkvl alelfeqitk gvdyihskkl ihrdlkpsni |
| 421 | flvdtkqvki gdfglvtslk ndgkrtrskg tlrymspeqi ssqdygkevd lyalglilae |
| 481 | llhvcdtafe tskfftdlrd giisdifdkk ektllqklls kkpedrpnts eilrtltvwk |
| 541 | kspeknerht c |

SEQ ID NO: 32 Human EIF2AK2 cDNA Sequence Variant 2 (NM_001135651.2, CDS region from position 324-1979)

```
   1 agcagacgag ggcttgtgcg agaggggggcc gggcggctgc agggaaggcg gagtccaagg
  61 ggaaaacgaa actgagaacc agctctcccg aagccgcggg tctccggccg gcggcggcgg
 121 cggcggcggc ggcggcgcag tttctggagc aaattcagtt tgccttcctg gatttgtaaa
 181 ttgtaatgac ctcaaaactt tagcagttct tccatctgac tcaggtttgc ttctctggcg
 241 gtcttcagaa tcaacatcca cacttccgtg attatctgcg tgcattttgg acaaagcttc
 301 caaccaggat acgggaagaa gaaatggctg gtgatctttc agcaggtttc ttcatggagg
 361 aacttaatac ataccgtcag aagcagggag tagtacttaa atatcaagaa ctgcctaatt
 421 caggacctcc acatgatagg aggtttacat ttcaagttat aatagatgga agagaatttc
 481 cagaaggtga aggtagatca aagaaggaag caaaaaatgc cgcagccaaa ttagctgttg
 541 agatacttaa taaggaaaag aaggcagtta gtcctttatt attgacaaca acgaattctt
 601 cagaaggatt atccatgggg aattacatag gccttatcaa tagaattgcc cagaagaaaa
 661 gactaactgt aaattatgaa cagtgtgcat cggggggtgca tgggccagaa ggatttcatt
 721 ataaatgcaa aatgggacag aaagaatata gtattggtac aggttctact aaacaggaag
 781 caaaacaatt ggccgctaaa cttgcatatc ttcagatatt atcagaagaa acctcagtga
 841 aatctgacta cctgtcctct ggttcttttg ctactacgtg tgagtcccaa agcaactctt
 901 tagtgaccag cacactcgct tctgaatcat catctgaagg tgacttctca gcagatacat
 961 cagagataaa ttctaacagt gacagtttaa acagttcttc gttgcttatg aatggtctca
1021 gaaataatca aggaaggca aaaagatctt tggcacccag atttgacctt cctgacatga
1081 aagaaacaaa gtatactgtg acaagaggt ttggcatgga ttttaaagaa atagaattaa
1141 ttggctcagg tggatttggc caagttttca agcaaaaaca cagaattgac ggaaagactt
1201 acgttattaa acgtgttaaa tataataacg agaaggcgga gcgtgaagta aaagcattgg
1261 caaaacttga tcatgtaaat attgttcact acaatggctg ttgggatgga tttgattatg
1321 atcctgagac cagtgatgat tctcttgaga gcagtgatta tgatcctgag aacagcaaaa
1381 atagttcaag gtcaaagact aagtgccttt tcatccaaat ggaattctgt gataaaggga
1441 ccttggaaca atggattgaa aaagaagag gcgagaaact agacaaagtt ttggctttgg
1501 aactctttga acaaataaca aaggggtgg attatataca ttcaaaaaaa ttaattcata
1561 gagatcttaa gccaagtaat atattcttag tagatacaaa acaagtaaag attggagact
1621 ttggacttgt aacatctctg aaaaatgatg gaaagcgaac aaggagtaag ggaactttgc
1681 gatacatgag cccagaacag atttcttcgc aagactatgg aaaggaagtg gacctctacg
1741 ctttggggct aattcttgct gaacttcttc atgtatgtga cactgctttt gaaacatcaa
1801 agtttttcac agacctacgg gatggcatca tctcagatat atttgataaa aagaaaaaa
1861 ctcttctaca gaaattactc tcaaagaaac ctgaggatcg acctaacaca tctgaaatac
1921 taaggacctt gactgtgtgg aagaaaagcc cagagaaaaa tgaacgacac acatgttaga
1981 gcccttctga aaagtatcc tgcttctgat atgcagtttt ccttaaatta tctaaaatct
```

TABLE 1-continued

```
2041  gctagggaat atcaatagat atttaccttt tattttaatg tttcctttaa ttttttacta
2101  ttttttactaa tctttctgca gaaacagaaa ggttttcttc ttttgcttc aaaaacattc
2161  ttacatttta cttttcctg gctcatctct ttattctttt ttttttttta aagacagagt
2221  ctcgctctgt tgcccaggct ggagtgcaat gacacagtct tggctcactg caacttctgc
2281  ctcttgggtt caagtgattc tcctgcctca gcctcctgag tagctggatt acaggcatgt
2341  gccacccacc caactaattt ttgtgttttt aataaagaca gggtttcacc atgttggcca
2401  ggctggtctc aaactcctga cctcaagtaa tccacctgcc tcggcctccc aaagtgctgg
2461  gattacaggg atgagccacc gcgcccagcc tcatctcttt gttctaaaga tggaaaaacc
2521  accccaaat tttctttta tactattaat gaatcaatca attcatatct atttattaaa
2581  tttctaccgc ttttaggcca aaaaatgta agatcgttct ctgcctcaca tagcttacaa
2641  gccagctgga gaaatatggt actcattaaa aaaaaaaa aaagtgatgt acaaccactt
2701  cggaaaacaa tttggcatta tctagtaaag ttgaatccat gtatacccac atagctatca
2761  attctattcc tacatacgtg cttacaagaa tgtccataaa accctgttta taatagccaa
2821  aagaacaggg aacaaccata atgcacatca aaagaagaat ggattaaaaa aattatattc
2881  acacacagga gtactatata gtattgaaaa caattgaagt acagctaaat gtaataacgt
2941  aacacaatac aactctcaga aacataatgt taagcgaaca aagcaggttt tcagaaaata
3001  tatgcagaat aattccattt atataaagtt ccagagcatg caaaactaaa tcatttgta
3061  taaaaaaccc aacaaatgtg atgagacaat aatgggaagg aagggaatga gaaatattaa
3121  attctggatg gtggttatct ttgagggagg ggaatgatgt gattggggaa atggactttc
3181  aaaggtaatg gtaacttcct taagctggat ggtaggtcca ctagtgtttg ctgcatagtt
3241  ataccttta tcttaaatac attttgtatc tattgtaaca accactttaa agacaaccgt
3301  gctgtaaggc agtagctaaa aacagaaat agtccatcgg gaagggtaag atggctttct
3361  gctgagcaca gggctagaag tgacagccca gtgggccttc caactatatg ccagggtgtt
3421  agatgagtag agaggagacc acccaggaag tctggacaag gggtctggca tgagctctgg
3481  agaagatata tttgaggaac atggggtatg ctagtttgtt gtcctgaatt gctgtagaga
3541  agataattta aattgcatct tagaagacga ccctgagggt gaatttcaac ttagggcaat
3601  tgtttagtt tgtttcttat tggtttaaat ggatacttga agctggataa tttataagga
3661  aaagagattt atatgactta cagttctgca ggctgtacaa gaaacatggc accagcatct
3721  gcttcttccc cggctgcttc cactcatggt ggaaggtgaa ggggagccgg atgtgcagag
3781  atcatatggc aagagaggaa gcaagagagc gagggagaag gtgccaggct cttttaaat
3841  aaccggctct tgagggaact aatagattga gaactccttg cttctcctcc ccagcacacc
3901  ccaccccag ggacggcatt aatgtattca tgagggtct tccccatga cccaaacacc
3961  tcccatcagg ccccacctcc aacactggga tcaaatttca acatgagatt tgggggaca
4021  aacatgcaaa ctatagcagc aaccagctac cattctaaaa ctgccatatg atttaggat
4081  ttttaaaaag ggccaaattt aggttaagca aaaaaaaaaa aaaaaaa
```

SEQ ID NO: 33 Human EIF2AK2 cDNA Sequence Variant 3 (NM_001135652.2, CDS region from position 17-1549)

```
   1  gatacgggaa gaagaaatgg ctggtgatct ttcagcaggt ttcttcatgg aggaacttaa
  61  tacataccgt cagaagcagg gagtagtact taaatatcaa gaactgccta attcaggacc
 121  tccacatgat aggaggttta catttcaagt tataatagat ggaagagaat ttccagaagg
 181  tgaaggtaga tcaaagaagg aagcaaaaaa tgccgcagcc aaattagctg ttgagatact
```

TABLE 1-continued

```
 241  taataaggaa aagaaggcag ttagtccttt attattgaca caacgaatt cttcagaagg
 301  attatccatg gggaattaca taggccttat caatagaatt gcccagaaga aaagactaac
 361  tgtaaattat gaacagtgtg catcggggt gcatgggcca gaaggatttc attataaatg
 421  caaaatggga cagaaagaat atagtattgg tacaggttct actaaacagg aagcaaaaca
 481  attggccgct aaacttgcat atcttcagat attatcagaa gaaacctcag tgaaatctga
 541  ctacctgtcc tctggttctt ttgctactac gtgtgagtcc caaagcaact ctttagtgac
 601  cagcacactc gcttctgaat catcatctga aggtgacttc tcagcagata catcagagat
 661  aaattctaac agtgacagtt taaacagttc ttcgttgctt atgaatggtc tcagaaataa
 721  tcaaaggaag gcaaaaagat ctttggcacc cagatttgac cttcctgaca tgaaagaaac
 781  aaagtatact gtggacaaga ggaaggcgga gcgtgaagta aaagcattgg caaaacttga
 841  tcatgtaaat attgttcact acaatggctg ttgggatgga tttgattatg atcctgagac
 901  cagtgatgat tctcttgaga gcagtgatta tgatcctgag aacagcaaaa atagttcaag
 961  gtcaaagact aagtgccttt tcatccaaat ggaattctgt gataaaggga ccttggaaca
1021  atggattgaa aaagaagag gcgagaaact agacaaagtt ttggctttgg aactctttga
1081  acaaataaca aaagggggtgg attatataca ttcaaaaaaa ttaattcata gagatcttaa
1141  gccaagtaat atattcttag tagatacaaa acaagtaaag attggagact tggacttgt
1201  aacatctctg aaaaatgatg gaaagcgaac aaggagtaag ggaactttgc gatacatgag
1261  cccagaacag atttcttcgc aagactatgg aaaggaagtg gacctctacg ctttggggct
1321  aattcttgct gaacttcttc atgtatgtga cactgctttt gaaacatcaa agttttcac
1381  agacctacgg gatggcatca tctcagatat atttgataaa aagaaaaaa ctcttctaca
1441  gaaattactc tcaaagaaac ctgaggatcg acctaacaca tctgaaatac taaggacctt
1501  gactgtgtgg aagaaaagcc cagagaaaaa tgaacgacac acatgttaga gcccttctga
1561  aaaagtatcc tgcttctgat atgcagtttt ccttaaatta tctaaaatct gctagggaat
1621  atcaatagat atttacctt tatttaatg tttcctttaa ttttttacta tttttactaa
1681  tctttctgca gaaacagaaa ggttttcttc tttttgcttc aaaaacattc ttacatttta
1741  cttttccctg gctcatctct ttattctttt tttttttta aagacagagt ctcgctctgt
1801  tgcccaggct ggagtgcaat gacacagtct ggctcactg caacttctgc ctcttgggtt
1861  caagtgattc tcctgcctca gcctcctgag tagctggatt acaggcatgt gccacccacc
1921  caactaattt ttgtgttttt aataaagaca gggtttcacc atgttggcca ggctggtctc
1981  aaactcctga cctcaagtaa tccacctgcc tcggcctccc aaagtgctgg gattacaggg
2041  atgagccacc gcgcccagcc tcatctcttt gttctaaaga tggaaaaacc accccccaaat
2101  tttcttttta tactattaat gaatcaatca attcatatct atttattaaa tttctaccgc
2161  ttttaggcca aaaaaatgta agatcgttct ctgcctcaca tagcttacaa gccagctgga
2221  gaaatatggt actcattaaa aaaaaaaaaa aaagtgatgt acaaccactt cggaaaacaa
2281  tttggcatta tctagtaaag ttgaatccat gtatacccac atagctatca attctattcc
2341  tacatacgtg cttacaagaa tgtccataaa accctgttta taatagccaa agaacaggg
2401  aacaaccata atgcacatca aagaagaat ggattaaaaa aattatattc acacacagga
2461  gtactatata gtattgaaaa caattgaagt acagctaaat gtaataacgt aacacaatac
2521  aactctcaga acataatgt taagcgaaca aagcaggttt tcagaaaata tatgcagaat
2581  aattccattt atataaagtt ccagagcatg caaaactaaa tcattttgta taaaaaaccc
```

TABLE 1-continued

```
2641  aacaaatgtg atgagacaat aatgggaagg aagggaatga gaaatattaa attctggatg 2701  gtggttatct ttgagggagg ggaatgatgt gattggggaa atggactttc aaaggtaatg 2761  gtaacttcct taagctggat ggtaggtcca ctagtgtttg ctgcatagtt ataccttta 2821  tcttaaatac attttgtatc tattgtaaca accactttaa agacaaccgt gctgtaaggc 2881  agtagctaaa aacagaaaat agtccatcgg gaagggtaag atggctttct gctgagcaca 2941  gggctagaag tgacagccca gtgggccttc caactatatg ccagggtgtt agatgagtag 3001  agaggagacc acccaggaag tctggacaag gggtctggca tgagctctgg agaagatata 3061  tttgaggaac atggggtatg ctagtttgtt gtcctgaatt gctgtagaga agataattta 3121  aattgcatct tagaagacga ccctgagggt gaatttcaac ttagggcaat tgttttagtt 3181  tgtttcttat tggtttaaat ggatacttga agctggataa tttataagga aaagagattt 3241  atatgactta cagttctgca ggctgtacaa gaaacatggc accagcatct gcttcttccc 3301  cggctgcttc cactcatggt ggaaggtgaa ggggagccgg atgtgcagag atcatatggc 3361  aagagaggaa gcaagagagc gagggagaag gtgccaggct cttttaaat aaccggctct 3421  tgagggaact aatagattga gaactccttg cttctcctcc ccagcacacc ccacccccag 3481  ggacggcatt aatgtattca tgaggggtct tcccccatga cccaaacacc tcccatcagg 3541  ccccacctcc aacactggga tcaaatttca acatgagatt tgggggaca aacatgcaaa 3601  ctatagcagc aaccagctac cattctaaaa ctgccatatg attttaggat ttttaaaaag 3661  ggccaaattt aggttaagca aaaaaaaaaa aaaaaaa
```

SEQ ID NO: 34 Human EIF2AK2 Amino Acid Sequence Isoform b (NP_001129124.1)

```
  1  magdlsagff meelntyrqk qgvvlkyqel pnsgpphdrr ftfqviidgr efpegegrsk 61  keaknaaakl aveilnkekk avsplllttt nsseglsmgn yiglinriaq kkrltvnyeq 121  casgvhgpeg fhykckmgqk eysigtgstk qeakqlaakl aylqilseet svksdylssg 181  sfattcesqs nslvtstlas esssegdfsa dtseinsnsd slnssllmn glrnnqrkak 241  rslaprfdlp dmketkytvd krkaerevka lakldhvniv hyngcwdgfd ydpetsddsl 301  essdydpens knssrsktkc lfiqmefcdk gtleqwiekr rgekldkvla lelfeqitkg 361  vdyihskkli hrdlkpsnif lvdtkqvkig dfglvtslkn dgkrtrskgt lrymspeqis 421  sqdygkevdl yalglilael lhvcdtafet skfftdlrdg iisdifdkke ktllqkllsk 481  kpedrpntse ilrtltvwkk speknerhtc
```

SEQ ID NO: 35 Mouse EIF2AK2 cDNA Sequence (NM_011163.4, CDS region from position 190-1737)

```
  1  gaaggcggag tccgccggga aaacgaaaca gaagagaacc ggccaggccc ggacttccat 61  gggcagcagc agcggcaggg aacggagggc gaatagattt cagagcctgc acctgaagta 121  caattcgaat cctgctccag ggagcgagcc actgtccgga tccagaaact ttggccactg 181  ggaggaaaaa tggccagtga taccccaggt ttctacatgg acaaacttaa taaataccgc 241  cagatgcacg gagtagccat tacgtataaa gaacttagta cttcgggacc tccacatgac 301  agaaggttta catttcaagt tttaatagat gagaaggaat ttccagaagc caaaggtaga 361  tcaaagcagg aggcaagaaa cgctgcagcc aaattagctg ttgatatact tgataacgaa 421  aacaaggtgg attgtcacac gagtgcatct gagcaaggct tgttcgttgg taactacata 481  ggccttgtca atagctttgc ccagaagaaa aagctgtctg taaattatga acagtgtgag 541  cccaactctg agttgcctca agatttatt tgtaaatgca aaattgggca gacaatgtat 601  ggtactggtt caggtgtcac caaacaggag gcaaagcagt tggctgcgaa agaagcctat 661  cagaagctgt taaagagccc gccgaaaact gccggaacat cctctagcgt tgtcacatct
```

TABLE 1-continued

```
 721  acattcagtg gcttttccag cagctcgtct atgacaagta atggtgtttc ccagtcagca
 781  cctggaagtt tttcctcaga gaacgtgttt acgaacggtc tcggagaaaa taaaaggaaa
 841  tcaggagtaa aagtatcccc tgatgatgtg caaagaaata aatatacctt ggacgccagg
 901  tttaacagcg attttgaaga catagaagaa attggcttag gtggatttgg tcaagttttc
 961  aaagcgaaac acagaattga tggaaagaga tacgctatta agcgcgttaa atataacacg
1021  gagaaggcgg agcacgaagt acaagcgctg gcagaactca atcacgtcaa cattgtccaa
1081  taccatagtt gttgggaggg agttgactat gatcctgagc acagcatgag tgatacaagt
1141  cgatacaaaa cccggtgcct ctttattcaa atggaattct gtgataaagg aactttggag
1201  caatggatga gaaacagaaa tcagagtaaa gtggacaaag ctttgatttt ggacttatat
1261  gaacaaatcg tgaccggagt ggagtatata cactcgaaag ggttaattca cagagatctt
1321  aagccaggta atatattttt agtagatgaa agacacatta agatcggaga ctttggcctt
1381  gcaacagccc tggaaaatga tggaaaatcc cgaacaagga gaacaggaac tcttcaatac
1441  atgagtccag aacagttatt tttaaagcac tatggaaaag aagtggacat cttgctttg
1501  ggccttattc tagctgaact tcttcacacg tgcttcacgg agtcagagaa aataaagttt
1561  ttcgaaagtc taagaaaagg cgacttctct aatgatatat tcgacaacaa agaaaaaagc
1621  cttctaaaaa aactactctc agagaaaccc aaggaccgac ctgagacatc tgaaatcctg
1681  aagaccttgg ctgaatggag gaacatctca gagaaaaaga aagaaacac atgttagggc
1741  ctttctgaga aaacattcct ctgccgtggt tttcctttaa cgatctgcag tctgagggga
1801  gtatcagtga atattatcct tcttttctta ataccactct cccagacagg ttttggttag
1861  ggtgacccac agacattgta tttattaggc tatgaaaaag tatgcccatt tcctcaattg
1921  ttaattgctg ggcctgtggc tggctagcta gccaaatatg taaatgcttg tttctcgtct
1981  gcccaaagag aaaggcaggc tcctgtgtgg gaagtcacag agcccccaaa gccaactgga
2041  tgaggaagga ctctggcttt tggcataaaa aagagctggt agtcagagct ggggcagaag
2101  gtcctgcaga cagacagaca gacagacaga cagacagaca gacagacaga gacacaaaga
2161  catggactag aatggaggag ggagggagga agggagggag ggagagagag agagagaaag
2221  aaagagagag agaccacatg gagagacaaa atggcttaag ttagctgggc tacctgagag
2281  actgtcccag aaaacaggcc aacaaccttc cttatgctat atagatgtct cagtgtcttt
2341  atcattaaac accaagcagg actgctaaaa actctgcaat agggttttt tttcctgtt
2401  acttcaaaag caatcttaca aagttatttt tttgacaatt ccatacatgc attgtgttct
2461  gatcccactc tgaaccctct gccattcatg ccttgtctgt catgtgaact gttgcctctg
2521  aatgtggggg tccaaattaa ccctctgccc ttgagtggct tctctcaggt agtgattgtg
2581  atgagaaaag taatgagatg ctggcaaaga tgtgcagaaa gaagaacact tctccactgc
2641  tggtaggatt gcaagctggt acaaccaccc tggaaatcag actggaggtt cctcagaaac
2701  acagtactac ctgaggaccc aacaatacca ctactggtca tatcccaga agatggtcca
2761  acatgtaata tggacacatg cgccactatg ttcatagtag ccttatttat aatagccagg
2821  agctggaaag aacccagatg tccctcagca gaggaatgga tacagaaaat gtggcacatt
2881  tacacaatgg agtactactc agctattaaa aatgaattca tgaaattctt agacaaatgg
2941  atggatctgg aggatatcat cttgagtgag gtaacccaat cgcaaaagaa cacacatgat
3001  atgcactcac tgataagtgg atattagccc aaaagctcca aataaccaag atacaattca
3061  cagactacat gaagctcaag aagaaggaag accaaagtgt gggtgctttg gtccctctta
```

TABLE 1-continued

```
3121  gaaggggaac aaagtactca caggagcaaa tatggagata gagtgtagag cagagactga
3181  aggaaaggcc atccagagac tgtcccatat acagagactg ggaattcatc ccatacacag
3241  ttaccaaacc cagacactat tgtggatgcc aagacattca tgctgacagg agcctgatat
3301  ggctgtctcc tgagaggtcc tgccagagcc ttacaataca gagactgatg ctcacagcca
3361  accactggac tgagtgtggg gtccccaata gaggagttag agaaaggact gaaggagttg
3421  aagggggtttg caaccccata agaacaacaa tatcaaccaa gcagacccc cagagctccc
3481  agtgactaag ccatcaacca aggagtacac atggctccag ctgcatatgt agcagaggat
3541  ggccttgtca tgtatcaaaa ggaggagagg tccttggtcc tatgaaggtg cgatagatgc
3601  cccagtatag gggaatcaag ggcagatagg tgggttggag gaacaccctc atagaagcag
3661  ggggagtaag gaaggatatg gggatttctg ggaggggtgg aaactaggaa aggggggtaac
3721  atttgaaatg taaataaaga aaatatccaa ttaaaaaaaa aagaaaaaga aaaagaaaa
3781  gaatagtaat aaaatggtac aggaagtaga gttatattgc aataaaccta ctgttgggct
3841  ttcaggactg gtttgtggga ggaatgtgaa aaagtttgaa gccccaggtt agagaagtcc
3901  tcaaatggta tacgtcaaac ttactgtggt agctcaaaag tctcctgaga ggccctgctt
3961  ggagttagcc ttgtagaggt ccagtctttc cttgttgttc tttcagactt gctttgtaga
4021  atattggtag ttactttgtg cctttgtatg ctgtaatagt tgttttatag ggcctcacag
4081  ctaagagttt ctcgctgctt ctcaaagcac tttggacctt tgcatggagt tgagtattaa
4141  gattatggga atttctgagg tgggactgaa agcatttgc attatgagat ggccatgagc
4201  caacagagac ttggacacac tcctccactg tcaaccgagg cttctgccaa atcttccctg
4261  tcatgaagga ttgtatcatc tgaaattgag tctaaataga taaataaata agtaaataaa
4321  tctctcaaaa aaaaaaaaaa aaa
```

SEQ ID NO: 36 Mouse EIF2AK2 Amino Acid Sequence (NP_035293.1)

```
  1  masdtpgfym dklnkyrqmh gvaitykels tsgpphdrrf tfqvlideke fpeakgrskq
 61  earnaaakla vdildnenkv dchtsaseqg lfvgnyiglv nsfaqkkkls vnyeqcepns
121  elpqrfickc kigqtmygtg sgvtkqeakq laakeayqkl lksppktagt sssvvtstfs
181  gfssssmts ngvsqsapgs fssenvftng lgenkrksgv kvspddvqrn kytldarfns
241  dfedieeigl ggfgqvfkak hridgkryai krvkynteka ehevqalael nhvnivqyhs
301  cwegvdydpe hsmsdtsryk trclfiqmef cdkgtleqwm rnrnqskvdk alildlyeqi
361  vtgveyihsk glihrdlkpg niflvderhi kigdfglata lendgksrtr rtgtlqymsp
421  eqlflkhygk evdifalgli laellhtcft esekikffes lrkgdfsndi fdnkeksllk
481  kllsekpkdr petseilktl aewrnisekk krntc
```

\* Included in Table 1 are RNA nucleic acid molecules (e.g., thymines replaced with uredines), nucleic acid molecules encoding orthologs of the encoded proteins, as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO listed in Table 1, or a portion thereof. Such nucleic acid molecules can have a function of the full-length nucleic acid as described further herein.

\* Included in Table 1 are orthologs of the proteins, as well as polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO listed in Table 1, or a portion thereof. Such polypeptides can have a function of the full-length polypeptide as described further herein.

\* Included in Table 1 are any known components of double-stranded RNA (dsRNA) editing, sensing, and/or metabolism pathways, including any known nucleic acid sequence and amino acid sequence, as well as variants and isoforms, of Adar, Zc3hav1, Ppp1R5a, and Eif2AK2/Pkr, including orthologs of the pathway components and nucleic acid and amino acid variants having the recited homology described in the immediately preceding paragraphs and elsewhere herein.

II. Subjects

In one embodiment, the subject for whom predicted likelihood of efficacy of an ADAR, ZC3HAV1, PPP1R15A, and/or EIF2AK2/PKR modulators, either alone or in combination with a cancer therapy such as modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist) or an immunotherapy like an immune checkpoint inhibitor is determined, is a mammal (e.g., mouse, rat, primate, non-human mammal, domestic animal, such as a dog, cat, cow, horse, and the like), and is preferably a human. In another embodiment, the subject is an animal model of cancer. For example, the animal model can be an orthotopic xenograft animal model of a human-derived cancer.

In another embodiment of the methods of the present invention, the subject has not undergone treatment, such as chemotherapy, radiation therapy, targeted therapy, and/or immunotherapies. In still another embodiment, the subject has undergone treatment, such as chemotherapy, radiation therapy, targeted therapy, and/or immunotherapies.

In certain embodiments, the subject has had surgery to remove cancerous or precancerous tissue. In other embodiments, the cancerous tissue has not been removed, e.g., the cancerous tissue may be located in an inoperable region of the body, such as in a tissue that is essential for life, or in a region where a surgical procedure would cause considerable risk of harm to the patient.

The methods of the present invention can be used to determine the responsiveness to ADAR, ZC3HAV1, PPP1R15A, and/or EIF2AK2/PKR modulators, either alone or in combination with a cancer therapy such as modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist) or an immunotherapy like an immune checkpoint inhibitor, of many different cancers in subjects such as those described herein.

III. Sample Collection, Preparation and Separation

In some embodiments, biomarker amount and/or activity measurement(s) in a sample from a subject is compared to a predetermined control (standard) sample. The sample from the subject is typically from a diseased tissue, such as cancer cells or tissues. The control sample can be from the same subject or from a different subject. The control sample is typically a normal, non-diseased sample. However, in some embodiments, such as for staging of disease or for evaluating the efficacy of treatment, the control sample can be from a diseased tissue. The control sample can be a combination of samples from several different subjects. In some embodiments, the biomarker amount and/or activity measurement(s) from a subject is compared to a pre-determined level. This pre-determined level is typically obtained from normal samples. As described herein, a "pre-determined" biomarker amount and/or activity measurement(s) may be a biomarker amount and/or activity measurement(s) used to, by way of example only, evaluate a subject that may be selected for treatment (e.g., based on the number of genomic mutations and/or the number of genomic mutations causing non-functional proteins for DNA repair genes), evaluate a response to an ADAR, ZC3HAV1, PPP1R15A, and/or EIF2AK2/PKR modulator, either alone or in combination with a cancer therapy such as modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist) or an immunotherapy like an immune checkpoint inhibitor, and/or evaluate a response to an ADAR, ZC3HAV1, PPP1R15A, and/or EIF2AK2/PKR modulator, either alone or in combination with a cancer therapy such as modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist) or an immunotherapy like an immune checkpoint inhibitor, with one or more additional anti-cancer therapies. A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements.

In another embodiment, the amounts determined and/or compared in a method described herein are based on relative measurements, such as ratios (e.g., biomarker copy numbers, level, and/or activity before a treatment vs. after a treatment, such biomarker measurements relative to a spiked or man-made control, such biomarker measurements relative to the expression of a housekeeping gene, and the like). For example, the relative analysis can be based on the ratio of pre-treatment biomarker measurement as compared to post-treatment biomarker measurement. Pre-treatment biomarker measurement can be made at any time prior to initiation of anti-cancer therapy. Post-treatment biomarker measurement can be made at any time after initiation of anti-cancer therapy. In some embodiments, post-treatment biomarker measurements are made 1, 2, 3, 4, 5, 6, 7, 8, 9, 10, 11, 12, 13, 14, 15, 16, 17, 18, 19, 20 weeks or more after initiation of anti-cancer therapy, and even longer toward indefinitely for continued monitoring. Treatment can comprise anti-cancer therapy, such as a therapeutic regimen comprising one or more ADAR, ZC3HAV1, PPP1R15A, and/or EIF2AK2/PKR modulator, either alone or in combination with a cancer therapy such as modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist) or an immunotherapy like an immune checkpoint inhibitor, with other anti-cancer agents.

The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

In some embodiments of the present invention the change of biomarker amount and/or activity measurement(s) from the pre-determined level is about 0.1, 0.2, 0.3, 0.4, 0.5, 0.6, 0.7, 0.8, 0.9, 1.0, 1.5, 2.0, 2.5, 3.0, 3.5, 4.0, 4.5, or 5.0 fold or greater, or any range in between, inclusive. Such cutoff values apply equally when the measurement is based on relative changes, such as based on the ratio of pre-treatment biomarker measurement as compared to post-treatment biomarker measurement.

Biological samples can be collected from a variety of sources from a patient including a body fluid sample, cell sample, or a tissue sample comprising nucleic acids and/or proteins. "Body fluids" refer to fluids that are excreted or secreted from the body as well as fluids that are normally not (e.g., amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit). In a preferred embodiment, the subject and/or control sample is selected from the group consisting of cells, cell lines, histological slides, paraffin embedded tissues, biopsies, whole blood, nipple aspirate, serum, plasma, buccal scrape, saliva, cerebrospinal fluid, urine, stool, and bone marrow. In one embodiment, the sample is serum, plasma, or urine. In another embodiment, the sample is serum.

The samples can be collected from individuals repeatedly over a longitudinal period of time (e.g., once or more on the order of days, weeks, months, annually, biannually, etc.). Obtaining numerous samples from an individual over a period of time can be used to verify results from earlier detections and/or to identify an alteration in biological pattern as a result of, for example, disease progression, drug treatment, etc. For example, subject samples can be taken and monitored every month, every two months, or combinations of one, two, or three month intervals according to the present invention. In addition, the biomarker amount and/or activity measurements of the subject obtained over time can be conveniently compared with each other, as well as with those of normal controls during the monitoring period, thereby providing the subject's own values, as an internal, or personal, control for long-term monitoring.

Sample preparation and separation can involve any of the procedures, depending on the type of sample collected and/or analysis of biomarker measurement(s). Such procedures include, by way of example only, concentration, dilution, adjustment of pH, removal of high abundance polypeptides (e.g., albumin, gamma globulin, and transferrin, etc.), addition of preservatives and calibrants, addition of protease inhibitors, addition of denaturants, desalting of samples, concentration of sample proteins, extraction and purification of lipids.

The sample preparation can also isolate molecules that are bound in non-covalent complexes to other protein (e.g., carrier proteins). This process may isolate those molecules bound to a specific carrier protein (e.g., albumin), or use a more general process, such as the release of bound molecules from all carrier proteins via protein denaturation, for example using an acid, followed by removal of the carrier proteins.

Removal of undesired proteins (e.g., high abundance, uninformative, or undetectable proteins) from a sample can be achieved using high affinity reagents, high molecular weight filters, ultracentrifugation and/or electrodialysis. High affinity reagents include antibodies or other reagents (e.g., aptamers) that selectively bind to high abundance proteins. Sample preparation could also include ion exchange chromatography, metal ion affinity chromatography, gel filtration, hydrophobic chromatography, chromatofocusing, adsorption chromatography, isoelectric focusing and related techniques. Molecular weight filters include membranes that separate molecules on the basis of size and molecular weight. Such filters may further employ reverse osmosis, nanofiltration, ultrafiltration and microfiltration.

Ultracentrifugation is a method for removing undesired polypeptides from a sample. Ultracentrifugation is the centrifugation of a sample at about 15,000-60,000 rpm while monitoring with an optical system the sedimentation (or lack thereof) of particles. Electrodialysis is a procedure which uses an electromembrane or semipermeable membrane in a process in which ions are transported through semi-permeable membranes from one solution to another under the influence of a potential gradient. Since the membranes used in electrodialysis may have the ability to selectively transport ions having positive or negative charge, reject ions of the opposite charge, or to allow species to migrate through a semipermable membrane based on size and charge, it renders electrodialysis useful for concentration, removal, or separation of electrolytes.

Separation and purification in the present invention may include any procedure known in the art, such as capillary electrophoresis (e.g., in capillary or on-chip) or chromatography (e.g., in capillary, column or on a chip). Electrophoresis is a method which can be used to separate ionic molecules under the influence of an electric field. Electrophoresis can be conducted in a gel, capillary, or in a microchannel on a chip. Examples of gels used for electrophoresis include starch, acrylamide, polyethylene oxides, agarose, or combinations thereof. A gel can be modified by its cross-linking, addition of detergents, or denaturants, immobilization of enzymes or antibodies (affinity electrophoresis) or substrates (zymography) and incorporation of a pH gradient. Examples of capillaries used for electrophoresis include capillaries that interface with an electrospray.

Capillary electrophoresis (CE) is preferred for separating complex hydrophilic molecules and highly charged solutes. CE technology can also be implemented on microfluidic chips. Depending on the types of capillary and buffers used, CE can be further segmented into separation techniques such as capillary zone electrophoresis (CZE), capillary isoelectric focusing (CIEF), capillary isotachophoresis (cITP) and capillary electrochromatography (CEC). An embodiment to couple CE techniques to electrospray ionization involves the use of volatile solutions, for example, aqueous mixtures containing a volatile acid and/or base and an organic such as an alcohol or acetonitrile.

Capillary isotachophoresis (cITP) is a technique in which the analytes move through the capillary at a constant speed but are nevertheless separated by their respective mobilities.

Capillary zone electrophoresis (CZE), also known as free-solution CE (FSCE), is based on differences in the electrophoretic mobility of the species, determined by the charge on the molecule, and the frictional resistance the molecule encounters during migration which is often directly proportional to the size of the molecule. Capillary isoelectric focusing (CIEF) allows weakly-ionizable amphoteric molecules, to be separated by electrophoresis in a pH gradient. CEC is a hybrid technique between traditional high performance liquid chromatography (HPLC) and CE.

Separation and purification techniques used in the present invention include any chromatography procedures known in the art. Chromatography can be based on the differential adsorption and elution of certain analytes or partitioning of analytes between mobile and stationary phases. Different examples of chromatography include, but not limited to, liquid chromatography (LC), gas chromatography (GC), high performance liquid chromatography (HPLC), etc.

IV. Biomarker Nucleic Acids and Polypeptides

One aspect of the present invention pertains to the use of isolated nucleic acid molecules that correspond to biomarker nucleic acids that encode a biomarker polypeptide or a portion of such a polypeptide. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

A biomarker nucleic acid molecule of the present invention can be isolated using standard molecular biology techniques and the sequence information in the database records described herein. Using all or a portion of such nucleic acid sequences, nucleic acid molecules of the present invention can be isolated using standard hybridization and cloning techniques (e.g., as described in Sambrook et al., ed., *Molecular Cloning: A Laboratory Manual,* 2nd ed., Cold Spring Harbor Laboratory Press, Cold Spring Harbor, N.Y., 1989).

A nucleic acid molecule of the present invention can be amplified using cDNA, mRNA, or genomic DNA as a template and appropriate oligonucleotide primers according to standard PCR amplification techniques. The nucleic acid molecules so amplified can be cloned into an appropriate vector and characterized by DNA sequence analysis. Furthermore, oligonucleotides corresponding to all or a portion of a nucleic acid molecule of the present invention can be prepared by standard synthetic techniques, e.g., using an automated DNA synthesizer.

Moreover, a nucleic acid molecule of the present invention can comprise only a portion of a nucleic acid sequence, wherein the full length nucleic acid sequence comprises a marker of the present invention or which encodes a polypeptide corresponding to a marker of the present invention. Such nucleic acid molecules can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a biomarker nucleic acid sequence. Probes based on the sequence of a biomarker nucleic acid molecule can be used to detect transcripts or genomic sequences corresponding to one or more markers of the present invention. The probe comprises a label group attached thereto, e.g., a radioisotope, a fluorescent compound, an enzyme, or an enzyme co-factor.

A biomarker nucleic acid molecules that differ, due to degeneracy of the genetic code, from the nucleotide sequence of nucleic acid molecules encoding a protein which corresponds to the biomarker, and thus encode the same protein, are also contemplated.

In addition, it will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

The term "allele," which is used interchangeably herein with "allelic variant," refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene or allele. For example, biomarker alleles can differ from each other in a single nucleotide, or several nucleotides, and can include substitutions, deletions, and insertions of nucleotides. An allele of a gene can also be a form of a gene containing one or more mutations.

The term "allelic variant of a polymorphic region of gene" or "allelic variant", used interchangeably herein, refers to an alternative form of a gene having one of several possible nucleotide sequences found in that region of the gene in the population. As used herein, allelic variant is meant to encompass functional allelic variants, non-functional allelic variants, SNPs, mutations and polymorphisms.

The term "single nucleotide polymorphism" (SNP) refers to a polymorphic site occupied by a single nucleotide, which is the site of variation between allelic sequences. The site is usually preceded by and followed by highly conserved sequences of the allele (e.g., sequences that vary in less than 1/100 or 1/1000 members of a population). A SNP usually arises due to substitution of one nucleotide for another at the polymorphic site. SNPs can also arise from a deletion of a nucleotide or an insertion of a nucleotide relative to a reference allele. Typically the polymorphic site is occupied by a base other than the reference base. For example, where the reference allele contains the base "T" (thymidine) at the polymorphic site, the altered allele can contain a "C" (cytidine), "G" (guanine), or "A" (adenine) at the polymorphic site. SNP's may occur in protein-coding nucleic acid sequences, in which case they may give rise to a defective or otherwise variant protein, or genetic disease. Such a SNP may alter the coding sequence of the gene and therefore specify another amino acid (a "missense" SNP) or a SNP may introduce a stop codon (a "nonsense" SNP). When a SNP does not alter the amino acid sequence of a protein, the SNP is called "silent." SNP's may also occur in noncoding regions of the nucleotide sequence. This may result in defective protein expression, e.g., as a result of alternative spicing, or it may have no effect on the function of the protein.

As used herein, the terms "gene" and "recombinant gene" refer to nucleic acid molecules comprising an open reading frame encoding a polypeptide corresponding to a marker of the present invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the present invention.

In another embodiment, a biomarker nucleic acid molecule is at least 7, 15, 20, 25, 30, 40, 60, 80, 100, 150, 200, 250, 300, 350, 400, 450, 550, 650, 700, 800, 900, 1000, 1100, 1200, 1300, 1400, 1500, 1600, 1700, 1800, 1900, 2000, 2200, 2400, 2600, 2800, 3000, 3500, 4000, 4500, or more nucleotides in length and hybridizes under stringent conditions to a nucleic acid molecule corresponding to a marker of the present invention or to a nucleic acid molecule encoding a protein corresponding to a marker of the present invention. As used herein, the term "hybridizes under stringent conditions" is intended to describe conditions for hybridization and washing under which nucleotide sequences at least 60% (65%, 70%, 75%, 80%, preferably 85%) identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

In addition to naturally-occurring allelic variants of a nucleic acid molecule of the present invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the present invention pertains to nucleic acid molecules encoding a polypeptide of the present invention that contain changes in amino acid residues that are not essential for activity. Such polypeptides differ in amino acid sequence from the naturally-occurring proteins which correspond to the markers of the present invention, yet retain biological activity. In one embodiment, a biomarker protein has an amino acid sequence that is at least about 40% identical, 50%, 60%, 70%, 75%, 80%, 83%, 85%, 87.5%, 90%, 91%, 92%, 93%, 94%, 95%, 96%, 97%, 98%, 99% or identical to the amino acid sequence of a biomarker protein described herein.

An isolated nucleic acid molecule encoding a variant protein can be created by introducing one or more nucleotide substitutions, additions or deletions into the nucleotide sequence of nucleic acids of the present invention, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

In some embodiments, the present invention further contemplates the use of anti-biomarker antisense nucleic acid molecules, i.e., molecules which are complementary to a sense nucleic acid of the present invention, e.g., complementary to the coding strand of a double-stranded cDNA molecule corresponding to a marker of the present invention or complementary to an mRNA sequence corresponding to a marker of the present invention. Accordingly, an antisense nucleic acid molecule of the present invention can hydrogen bond to (i.e. anneal with) a sense nucleic acid of the present invention. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a polypeptide of the present invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been sub-cloned in an antisense orientation (i.e., RNA transcribed from the inserted nucleic acid will be of an antisense orientation to a target nucleic acid of interest, described further in the following subsection).

The antisense nucleic acid molecules of the present invention are typically administered to a subject or generated in situ such that they hybridize with or bind to cellular mRNA and/or genomic DNA encoding a polypeptide corresponding to a selected marker of the present invention to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules of the present invention includes direct injection at a tissue site or infusion of the antisense nucleic acid into a blood- or bone marrow-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the present invention can be an u-anomeric nucleic acid molecule. An u-anomeric nucleic acid molecule forms specific double-stranded hybrids with complementary RNA in which, contrary to the usual a-units, the strands run parallel to each other (Gaultier et al., 1987, *Nucleic Acids Res.* 15:6625-6641). The antisense nucleic acid molecule can also comprise a 2'-o-methylribonucleotide (Inoue et al., 1987, *Nucleic Acids Res.* 15:6131-6148) or a chimeric RNA-DNA analogue (Inoue et al., 1987, *FEBS Lett.* 215:327-330).

The present invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes as described in Haselhoff and Gerlach, 1988, *Nature* 334:585-591) can be used to catalytically cleave mRNA transcripts to thereby inhibit translation of the protein encoded by the mRNA. A ribozyme having specificity for a nucleic acid molecule encoding a polypeptide corresponding to a marker of the present invention can be designed based upon the nucleotide sequence of a cDNA corresponding to the marker. For example, a derivative of a Tetrahymena L-19 IVS RNA can be constructed in which the nucleotide sequence of the active site is complementary to the nucleotide sequence to be cleaved (see Cech et al. U.S. Pat. No. 4,987,071; and Cech et al. U.S. Pat. No. 5,116,742). Alternatively, an mRNA encoding a polypeptide of the present invention can be used to select a catalytic RNA having a specific ribonuclease activity from a pool of RNA molecules (see, e.g., Bartel and Szostak, 1993, *Science* 261:1411-1418).

The present invention also encompasses nucleic acid molecules which form triple helical structures. For example, expression of a biomarker protein can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) *Anticancer Drug Des.* 6(6):569-84; Helene (1992) *Ann. N.Y. Acad. Sci.* 660:27-36; and Maher (1992) *Bioassays* 14(12):807-15.

In various embodiments, the nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acid molecules (see Hyrup et al., 1996, *Bioorganic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Nat. Acad. Sci. USA* 93:14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup, 1996, supra; Perry-O'Keefe et al., 1996, *Proc. Nat. Acad. Sci. USA* 93:14670-675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNASE H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) *Nucleic Acids Res.* 24(17):3357-63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., 1989, *Nucleic Acids Res.* 17:5973-88). PNA monomers are then coupled in a step-wise manner to produce a chimeric molecule with a 5' PNA segment and a 3' DNA segment (Finn et al., 1996, *NucleicAcids Res.* 24(17):3357-63). Alternatively, chimeric molecules can be synthesized with a 5' DNA segment and a 3' PNA segment (Peterser et al., 1975, *Bioorganic Med. Chem. Lett.* 5:1119-11124).

In other embodiments, the oligonucleotide can include other appended groups such as peptides (e.g., for targeting host cell receptors in vivo), or agents facilitating transport across the cell membrane (see, e.g., Letsinger et al., 1989, *Proc. Nat. Acad. Sci. USA* 86:6553-6556; Lemaitre et al., 1987, *Proc. Nat. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, *Bio/Techniques* 6:958-976) or intercalating agents (see, e.g., Zon, 1988, *Pharm. Res.* 5:539-549). To this end, the oligonucleotide can be conjugated to another molecule, e.g., a peptide, hybridization triggered cross-linking agent, transport agent, hybridization-triggered cleavage agent, etc.

Another aspect of the present invention pertains to the use of biomarker proteins and biologically active portions thereof. In one embodiment, the native polypeptide corresponding to a marker can be isolated from cells or tissue sources by an appropriate purification scheme using standard protein purification techniques. In another embodiment, polypeptides corresponding to a marker of the present invention are produced by recombinant DNA techniques. Alternative to recombinant expression, a polypeptide corresponding to a marker of the present invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a biomarker polypeptide include polypeptides comprising amino acid sequences sufficiently identical to or derived from a biomarker protein amino acid sequence described herein, but which includes fewer amino acids than the full length protein, and exhibit at least one activity of the corresponding full-length protein. Typically, biologically active portions comprise a domain or motif with at least one activity of the corresponding protein. A biologically active portion of a protein of the present invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the present invention.

Preferred polypeptides have an amino acid sequence of a biomarker protein encoded by a nucleic acid molecule described herein. Other useful proteins are substantially identical (e.g., at least about 40%, preferably 50%, 60%, 70%, 75%, 80%, 83%, 85%, 88%, 90%, 91%, 92%, 93%, 94%, 95%, 96%, 97%, 98%, or 99%) to one of these sequences and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to a nucleic acid molecules of the present invention. BLAST protein searches can be performed with the XBLAST program, score=50, wordlength=3 to obtain amino acid sequences homologous to a protein molecules of the present invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See ncbi.nlm.nih.gov. Another preferred, non-limiting example of a mathematical algorithm utilized for the comparison of sequences is the algorithm of Myers and Miller, (1988) *Comput Appl Biosci,* 4:11-7. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Nat. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The present invention also provides chimeric or fusion proteins corresponding to a biomarker protein. As used herein, a "chimeric protein" or "fusion protein" comprises all or part (preferably a biologically active part) of a polypeptide corresponding to a marker of the present invention operably linked to a heterologous polypeptide (i.e., a polypeptide other than the polypeptide corresponding to the marker). Within the fusion protein, the term "operably linked" is intended to indicate that the polypeptide of the present invention and the heterologous polypeptide are fused in-frame to each other. The heterologous polypeptide can be fused to the amino-terminus or the carboxyl-terminus of the polypeptide of the present invention.

One useful fusion protein is a GST fusion protein in which a polypeptide corresponding to a marker of the present invention is fused to the carboxyl terminus of GST sequences. Such fusion proteins can facilitate the purification of a recombinant polypeptide of the present invention.

In another embodiment, the fusion protein contains a heterologous signal sequence, immunoglobulin fusion protein, toxin, or other useful protein sequence. Chimeric and fusion proteins of the present invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the present invention can be cloned into such an expression vector such that the fusion moiety is linked in-frame to the polypeptide of the present invention.

A signal sequence can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the present invention pertains to the described polypeptides having a signal sequence, as well as to polypeptides from which the signal sequence has been proteolytically cleaved (i.e., the cleavage products). In one embodiment, a nucleic acid sequence encoding a signal sequence can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present invention also pertains to variants of the biomarker polypeptides described herein. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a biomarker protein which function as either agonists (mimetics) or as antagonists can be identified by screening combinatorial libraries of mutants, e.g., truncation mutants, of the protein of the present invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the present invention from a degenerate oligonucleotide sequence. Methods for synthesizing degenerate oligonucleotides are known in the art (see, e.g., Narang, 1983, *Tetrahedron* 39:3; Itakura et al., 1984, *Annu. Rev. Biochem.* 53:323; Itakura et al., 1984, *Science* 198:1056; Ike et al., 1983 *Nucleic Acid Res.* 11:477).

In addition, libraries of fragments of the coding sequence of a polypeptide corresponding to a marker of the present invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the present invention (Arkin and Yourvan, 1992, *Proc. Nat. Acad. Sci. USA* 89:7811-7815; Delgrave et al., 1993, *Protein Engineering* 6(3):327-331). An isolated polypeptide or a fragment thereof (or a nucleic acid encoding such a polypeptide) corresponding to one or more biomarkers of the present invention, including the biomarkers listed in Table 1 or fragments thereof, can be used as an immunogen to generate antibodies that bind to said immunogen, using standard techniques for polyclonal and monoclonal antibody preparation according to well-known methods in the art. An antigenic peptide comprises at least 8 amino acid residues and encompasses an epitope present in the respective full length molecule such that an antibody raised against the peptide forms a specific immune complex with the respective full length molecule. Preferably, the antigenic peptide comprises at least 10 amino acid residues. In one embodiment such epitopes can be specific for a given polypeptide molecule from one species, such as mouse or human (i.e., an antigenic peptide that spans a region of the polypeptide molecule that is not conserved across species is used as immunogen; such non conserved residues can be determined using an alignment such as that provided herein).

In some embodiments, the immunotherapy utilizes an inhibitor of at least one immune checkpoint, such as an antibody binds substantially specifically to an immune checkpoint, such as PD-1, and inhibits or blocks its immunoinhibitory function, such as by interrupting its interaction with a binding partner of the immune checkpoint, such as PD-L1 and/or PD-L2 binding partners of PD-1. In one embodiment, an antibody, especially an intrabody, binds substantially specifically to ADAR, ZC3HAV1, PPP1R15A, and/or EIF2AK2/PKR and inhibits, blocks, or enhances its biological function, such as by interrupting or enhancing its interaction with a substrate like STAT or JAK proteins. In another embodiment, an antibody, especially an intrbody, binds substantially specifically to an ADAR, ZC3HAV1, PPP1R15A, and/or EIF2AK2/PKR binding partner, such as ADAR, ZC3HAV1, PPP1R15A, and/or EIF2AK2/PKR substrates described herein, and inhibits, blocks, or enhances its biological function, such as by interrupting or enhancing its interaction to ADAR, ZC3HAV1, PPP1R15A, and/or EIF2AK2/PKR.

For example, a polypeptide immunogen typically is used to prepare antibodies by immunizing a suitable subject (e.g., rabbit, goat, mouse or other mammal) with the immunogen. A preferred animal is a mouse deficient in the desired target antigen. For example, a PD-1 knockout mouse if the desired antibody is an anti-PD-1 antibody, may be used. This results in a wider spectrum of antibody recognition possibilities as antibodies reactive to common mouse and human epitopes are not removed by tolerance mechanisms. An appropriate immunogenic preparation can contain, for example, a recombinantly expressed or chemically synthesized molecule or fragment thereof to which the immune response is to be generated. The preparation can further include an adjuvant, such as Freund's complete or incomplete adjuvant, or similar immunostimulatory agent. Immunization of a suitable subject with an immunogenic preparation induces a polyclonal antibody response to the antigenic peptide contained therein.

Polyclonal antibodies can be prepared as described above by immunizing a suitable subject with a polypeptide immunogen. The polypeptide antibody titer in the immunized subject can be monitored over time by standard techniques, such as with an enzyme linked immunosorbent assay (ELISA) using immobilized polypeptide. If desired, the antibody directed against the antigen can be isolated from the mammal (e.g., from the blood) and further purified by well-known techniques, such as protein A chromatography, to obtain the IgG fraction. At an appropriate time after immunization, e.g., when the antibody titers are highest, antibody-producing cells can be obtained from the subject and used to prepare monoclonal antibodies by standard techniques, such as the hybridoma technique (originally described by Kohler and Milstein (1975) *Nature* 256:495-497) (see also Brown et al. (1981) *J. Immunol.* 127:539-46; Brown et al. (1980) *J. Biol. Chem.* 255:4980-83; Yeh et al. (1976) *Proc. Nat. Acad. Sci.* 76:2927-31; Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985) *Monoclonal Antibodies and Cancer Therapy*, Alan R. Liss, Inc., pp. 77-96) or trioma techniques. The technology for producing monoclonal antibody hybridomas is well-known (see generally Kenneth, R. H. in *Monoclonal Antibodies: A New Dimension In Biological Analyses*, Plenum Publishing Corp., New York, New York (1980); Lerner, E. A. (1981) *Yale J. Biol. Med.* 54:387-402; Gefter, M. L. et al. (1977) *Somatic Cell Genet.* 3:231-36). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptide antigen, preferably specifically. In some embodiments, the immunization is performed in a cell or animal host that has a knockout of a target antigen of interest (e.g., does not produce the antigen prior to immunization).

Any of the many well-known protocols used for fusing lymphocytes and immortalized cell lines can be applied for the purpose of generating a monoclonal antibody against one or more biomarkers of the present invention, including the biomarkers listed in Table 1, or a fragment thereof (see, e.g., Galfre, G. et al. (1977) *Nature* 266:55052; Gefter et al. (1977) supra; Lerner (1981) supra; Kenneth (1980) supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, MD Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the present invention are detected by screening the hybridoma culture supernatants for antibodies that bind a given polypeptide, e.g., using a standard ELISA assay.

As an alternative to preparing monoclonal antibody-secreting hybridomas, a monoclonal specific for one of the above described polypeptides can be identified and isolated by screening a recombinant combinatorial immunoglobulin library (e.g., an antibody phage display library) with the appropriate polypeptide to thereby isolate immunoglobulin library members that bind the polypeptide. Kits for generating and screening phage display libraries are commercially available (e.g., the Pharmacia *Recombinant Phage Antibody System*, Catalog No. 27-9400-01; and the Stratagene SurfZAP™ Phage Display Kit, Catalog No. 240612). Additionally, examples of methods and reagents particularly amenable for use in generating and screening an antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Biotechnology* (NY) 9:1369-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clarkson et al. (1991) *Nature* 352:624-628; Gram et al. (1992) *Proc. Nat. Acad. Sci. USA* 89:3576-3580; Garrard et al. (1991) *Biotechnology* (NY) 9:1373-1377; Hoogenboom et al. (1991) *Nucleic Acids Res.* 19:4133-4137; Barbas et al. (1991) *Proc. Nat. Acad. Sci. USA* 88:7978-7982; and McCafferty et al. (1990) *Nature* 348:552-554.

Since it is well-known in the art that antibody heavy and light chain CDR3 domains play a particularly important role in the binding specificity/affinity of an antibody for an antigen, the recombinant monoclonal antibodies of the present invention prepared as set forth above preferably comprise the heavy and light chain CDR3s of variable regions of the antibodies described herein and well-known in the art. Similarly, the antibodies can further comprise the CDR2s of variable regions of said antibodies. The antibodies can further comprise the CDR1s of variable regions of said antibodies. In other embodiments, the antibodies can comprise any combinations of the CDRs.

The CDR1, 2, and/or 3 regions of the engineered antibodies described above can comprise the exact amino acid sequence(s) as those of variable regions of the present invention described herein. However, the ordinarily skilled artisan will appreciate that some deviation from the exact CDR sequences may be possible while still retaining the ability of the antibody, especially an introbody, to bind a desired target, such as ADAR, ZC3HAV1, PPP1R15A, and/or EIF2AK2/PKR and/or a binding partner thereof, either alone or in combination with an immunotherapy, such as immune checkpoint inhibitors, their binding partners/substrates, or another immunotherapy effectively (e.g., conservative sequence modifications). Accordingly, in another embodiment, the engineered antibody may be composed of one or more CDRs that are, for example, 50%, 60%, 70%, 80%, 85%, 90%, 91%, 92%, 93%, 94%, 95%, 96%, 97%, 98%, 99%, or 99.5% identical to one or more CDRs of the present invention described herein or otherwise publicly available.

For example, the structural features of non-human or human antibodies (e.g., a rat anti-mouse/anti-human antibody) can be used to create structurally related human antibodies, especially introbodies, that retain at least one functional property of the antibodies of the present invention, such as binding to ADAR, ZC3HAV1, PPP1R15A, and/or EIF2AK2/PKR, ADAR, ZC3HAV1, PPP1R15A, and/or EIF2AK2/PKR-binding partners/substrates, and/or an immune checkpoint. Another functional property includes inhibiting binding of the original known, non-human or human antibodies in a competition ELISA assay.

Antibodies, immunoglobulins, and polypeptides of the present invention can be used in an isolated (e.g., purified) form or contained in a vector, such as a membrane or lipid vesicle (e.g. a liposome). Moreover, amino acid sequence modification(s) of the antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce binding activity and can be corrected by replacing the amino acids with amino acid residues of the original antibody derived from a non-human animal.

Similarly, modifications and changes may be made in the structure of the antibodies described herein, and in the DNA sequences encoding them, and still obtain a functional molecule that encodes an antibody and polypeptide with desirable characteristics. For example, antibody glycosylation patterns can be modulated to, for example, increase stability. By "altering" is meant deleting one or more carbohydrate moieties found in the antibody, and/or adding one or more glycosylation sites that are not present in the antibody. Glycosylation of antibodies is typically N-linked. "N-linked" refers to the attachment of the carbohydrate moiety to the side chain of an asparagine residue. The tripeptide sequences asparagine-X-serine and asparagines-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites). Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, orhydroxyproline, (e) aromatic residues such as those of phenylalanine, tyrosine, or tryptophan, or (f) the amide group of glutamine. For example, such methods are described in WO87/05330.

Similarly, removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr et al. (1987) and by Edge et al. (1981). Enzymatic cleavage of carbohydrate moieties on antibodies can be achieved by the use of a variety of endo- and exo-glycosidases as described by Thotakura et al. (1987).

Other modifications can involve the formation of immunoconjugates. For example, in one type of covalent modification, antibodies or proteins are covalently linked to one of a variety of non proteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Conjugation of antibodies or other proteins of the present invention with heterologous agents can be made using a variety of bifunctional protein coupling agents including but not limited to N-succinimidyl (2-pyridyldithio) propionate (SPDP), succinimidyl (N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6diisocyanate), and bis-active fluorine compounds (such as 1,5-difluoro-2,4-dinitrobenzene). For example, carbon labeled 1-isothiocyanatobenzyl methyldiethylene triaminepentaacetic acid (MX-DTPA) is an exemplary chelating agent for conjugation of radionucleotide to the antibody (WO 94/11026).

In another aspect, the present invention features antibodies conjugated to a therapeutic moiety, such as a cytotoxin, a drug, and/or a radioisotope. When conjugated to a cytotoxin, these antibody conjugates are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). An antibody of the present invention can be conjugated to a radioisotope, e.g., radioactive iodine, to generate cytotoxic radiopharmaceuticals for treating a related disorder, such as a cancer.

Conjugated antibodies, in addition to therapeutic utility, can be useful for diagnostically or prognostically to monitor polypeptide levels in tissue as part of a clinical testing procedure, e.g., to determine the efficacy of a given treatment regimen. Detection can be facilitated by coupling (i e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, P-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate (FITC), rhodamine, dichlorotriazinylamine fluorescein, dansyl chloride or phycoerythrin (PE); an example of a luminescent material includes luminol; examples of bioluminescent materials include luciferase, luciferin, and aequorin, and examples of suitable radioactive material include $^{125}$I, $^{131}$I, $^{35}$S, or $^{3}$H. [0134] As used herein, the term "labeled", with regard to the antibody, is intended to encompass direct labeling of the antibody by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody, as well as indirect labeling of the antibody by reactivity with a detectable substance.

The antibody conjugates of the present invention can be used to modify a given biological response. The therapeutic moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *Pseudomonas* exotoxin, or diphtheria toxin; a protein such as tumor necrosis factor or interferon-.gamma.; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other cytokines or growth factors.

In one embodiment, an antibody for use in the instant invention is a bispecific or multispecific antibody. A bispecific antibody has binding sites for two different antigens within a single antibody polypeptide. Antigen binding may be simultaneous or sequential. Triomas and hybrid hybridomas are two examples of cell lines that can secrete bispecific antibodies. Examples of bispecific antibodies produced by a hybrid hybridoma or a trioma are disclosed in U.S. Pat. No. 4,474,893. Bispecific antibodies have been constructed by chemical means (Staerz et al. (1985) *Nature* 314:628, and Perez et al. (1985) *Nature* 316:354) and hybridoma technology (Staerz and Bevan (1986) *Proc. Nat. Acad. Sci. USA*, 83:1453, and Staerz and Bevan (1986) *Immunol. Today* 7:241). Bispecific antibodies are also described in U.S. Pat. No. 5,959,084. Fragments of bispecific antibodies are described in U.S. Pat. No. 5,798,229.

Bispecific agents can also be generated by making heterohybridomas by fusing hybridomas or other cells making different antibodies, followed by identification of clones producing and co-assembling both antibodies. They can also be generated by chemical or genetic conjugation of complete immunoglobulin chains or portions thereof such as Fab and Fv sequences. The antibody component can bind to a polypeptide or a fragment thereof of one or more biomarkers of the present invention, including one or more biomarkers listed in Table 1, or a fragment thereof. In one embodiment, the bispecific antibody could specifically bind to both a polypeptide or a fragment thereof and its natural binding partner(s) or a fragment(s) thereof.

Techniques for modulating antibodies, such as humanization, conjugation, recombinant techniques, and the like are well-known in the art.

In another aspect of this invention, peptides or peptide mimetics can be used to antagonize the activity of one or more biomarkers of the present invention, including one or more biomarkers listed in Table 1, or a fragment(s) thereof. In one embodiment, variants of one or more biomarkers listed in Table 1 which function as a modulating agent for the respective full length protein, can be identified by screening combinatorial libraries of mutants, e.g., truncation mutants, for antagonist activity. In one embodiment, a variegated library of variants is generated by combinatorial mutagenesis at the nucleic acid level and is encoded by a variegated gene library. A variegated library of variants can be produced, for instance, by enzymatically ligating a mixture of synthetic oligonucleotides into gene sequences such that a degenerate set of potential polypeptide sequences is expressible as individual polypeptides containing the set of polypeptide sequences therein. There are a variety of methods which can be used to produce libraries of polypeptide variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential polypeptide sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a polypeptide coding sequence can be used to generate a variegated population of polypeptide fragments for screening and subsequent selection of variants of a given polypeptide. In one embodiment, a library of coding sequence fragments can be generated by treating a double stranded PCR fragment of a polypeptide coding sequence with a nuclease under conditions wherein nicking occurs only about once per polypeptide, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the polypeptide.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of polypeptides. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of interest (Arkin and Youvan (1992) *Proc. Natl. Acad. Sci. USA* 89:7811-7815; Delagrave et al. (1993) *Protein Eng.* 6(3): 327-331). In one embodiment, cell based assays can be exploited to analyze a variegated polypeptide library. For example, a library of expression vectors can be transfected into a cell line which ordinarily synthesizes one or more biomarkers of the present invention, including one or more biomarkers listed in Table 1, or a fragment thereof. The transfected cells are then cultured such that the full length polypeptide and a particular mutant polypeptide are produced and the effect of expression of the mutant on the full length polypeptide activity in cell supernatants can be detected, e.g., by any of a number of functional assays. Plasmid DNA can then be recovered from the cells which score for inhibition, or alternatively, potentiation of full length polypeptide activity, and the individual clones further characterized.

Systematic substitution of one or more amino acids of a polypeptide amino acid sequence with a D-amino acid of the same type (e.g., D-lysine in place of L-lysine) can be used to generate more stable peptides. In addition, constrained peptides comprising a polypeptide amino acid sequence of interest or a substantially identical sequence variation can be generated by methods known in the art (Rizo and Gierasch (1992) *Annu. Rev. Biochem.* 61:387, incorporated herein by reference); for example, by adding internal cysteine residues capable of forming intramolecular disulfide bridges which cyclize the peptide.

The amino acid sequences described herein will enable those of skill in the art to produce polypeptides corresponding peptide sequences and sequence variants thereof. Such polypeptides can be produced in prokaryotic or eukaryotic host cells by expression of polynucleotides encoding the peptide sequence, frequently as part of a larger polypeptide. Alternatively, such peptides can be synthesized by chemical methods. Methods for expression of heterologous proteins in recombinant hosts, chemical synthesis of polypeptides, and in vitro translation are well-known in the art and are described further in Maniatis et al. *Molecular Cloning: A Laboratory Manual* (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Merrifield, J. (1969) *J.*

Am. Chem. Soc. 91:501; Chaiken I. M. (1981) *CRC Crit. Rev. Biochem.* 11: 255; Kaiser et al. (1989) *Science* 243:187; Merrifield, B. (1986) *Science* 232:342; Kent, S. B. H. (1988) *Annu. Rev. Biochem.* 57:957; and Offord, R. E. (1980) *Semisynthetic Proteins*, Wiley Publishing, which are incorporated herein by reference).

Peptides can be produced, typically by direct chemical synthesis. Peptides can be produced as modified peptides, with nonpeptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal-modifications such as amidation, as well as other terminal modifications, including cyclization, can be incorporated into various embodiments of the present invention. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Peptides described herein can be used therapeutically to treat disease, e.g., by altering costimulation in a patient.

Peptidomimetics (Fauchere (1986) *Adv. Drug Res.* 15:29; Veber and Freidinger (1985) TINS p. 392; and Evans et al. (1987) *J. Med. Chem.* 30:1229, which are incorporated herein by reference) are usually developed with the aid of computerized molecular modeling. Peptide mimetics that are structurally similar to therapeutically useful peptides can be used to produce an equivalent therapeutic or prophylactic effect. Generally, peptidomimetics are structurally similar to a paradigm polypeptide (i.e., a polypeptide that has a biological or pharmacological activity), but have one or more peptide linkages optionally replaced by a linkage selected from the group consisting of: —CH2NH—, —CH$_2$S—, —CH2-CH2-, —CH═CH— (cis and trans), —COCH2-, —CH(OH)CH2-, and —CH2SO—, by methods known in the art and further described in the following references: Spatola, A. F. in "*Chemistry and Biochemistry of Amino Acids, Peptides, and Proteins*" Weinstein, B., ed., Marcel Dekker, New York, p. 267 (1983); Spatola, A. F., Vega Data (March 1983), Vol. 1, Issue 3, "Peptide Backbone Modifications" (general review); Morley, J. S. (1980) *Trends Pharm. Sci.* pp. 463-468 (general review); Hudson, D. et al. (1979) *Int. J. Pept. Prot. Res.* 14:177-185 (—CH2NH—, CH2CH2-); Spatola, A. F. et al. (1986) *Life Sci.* 38:1243-1249 (—CH2-S); Hann, M. M. (1982) *J. Chem. Soc. Perkin Trans. I.* 307-314 (—CH—CH—, cis and trans); Almquist, R. G. et al. (190) *J. Med. Chem.* 23:1392-1398 (—COCH2-); Jennings-White, C. et al. (1982) *Tetrahedron Lett.* 23:2533 (—COCH2-); Szelke, M. et al. European Appln. EP 45665 (1982) CA: 97:39405 (1982)(—CH(OH) CH2-); Holladay, M. W. et al. (1983) *Tetrahedron Lett.* (1983) 24:4401-4404 (—C(OH)CH2-); and Hruby, V. J. (1982) *Life Sci.* (1982) 31:189-199 (—CH2-S—); each of which is incorporated herein by reference. A particularly preferred non-peptide linkage is —CH2NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macropolypeptides(s) to which the peptidomimetic binds to produce the therapeutic effect. Derivatization (e.g., labeling) of peptidomimetics should not substantially interfere with the desired biological or pharmacological activity of the peptidomimetic.

Also encompassed by the present invention are small molecules which can modulate (either enhance or inhibit) interactions, e.g., between biomarkers described herein or listed in Table 1 and their natural binding partners. The small molecules of the present invention can be obtained using any of the numerous approaches in combinatorial library methods known in the art, including: spatially addressable parallel solid phase or solution phase libraries; synthetic library methods requiring deconvolution; the 'one-bead one-compound' library method; and synthetic library methods using affinity chromatography selection. (Lam, K. S. (1997) *Anticancer Drug Des.* 12:145).

Examples of methods for the synthesis of molecular libraries can be found in the art, for example in: DeWitt et al. (1993) *Proc. Nat. Acad. Sci. USA* 90:6909; Erb et al. (1994) *Proc. Nat. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner USP '409), plasmids (Cull et al. (1992) *Proc. Nat. Acad. Sci. USA* 89:1865-1869) or on phage (Scott and Smith (1990) *Science* 249:386-390); (Devlin (1990) *Science* 249:404-406); (Cwirla et al. (1990) *Proc. Natl. Acad. Sci. USA* 87:6378-6382); (Felici (1991) *J. Mol. Biol.* 222:301-310); (Ladner supra.). Compounds can be screened in cell based or non-cell based assays. Compounds can be screened in pools (e.g. multiple compounds in each testing sample) or as individual compounds.

Chimeric or fusion proteins can be prepared for the ADAR, ZC3HAV1, PPP1R15A, and/or EIF2AK2/PKR modulators and/or agents for the immunotherapies described herein, such as modulators to the biomarkers of the present invention, including the biomarkers listed in Table 1, or fragments thereof. As used herein, a "chimeric protein" or "fusion protein" comprises one or more biomarkers of the present invention, including one or more biomarkers listed in Table 1, or a fragment thereof, operatively linked to another polypeptide having an amino acid sequence corresponding to a protein which is not substantially homologous to the respective biomarker. In a preferred embodiment, the fusion protein comprises at least one biologically active portion of one or more biomarkers of the present invention, including one or more biomarkers listed in Table 1, or fragments thereof. Within the fusion protein, the term "operatively linked" is intended to indicate that the biomarker sequences and the non-biomarker sequences are fused in-frame to each other in such a way as to preserve functions exhibited when expressed independently of the fusion. The "another" sequences can be fused to the N-terminus or C-terminus of the biomarker sequences, respectively.

Such a fusion protein can be produced by recombinant expression of a nucleotide sequence encoding the first peptide and a nucleotide sequence encoding the second peptide. The second peptide may optionally correspond to a moiety that alters the solubility, affinity, stability or valency of the first peptide, for example, an immunoglobulin constant region. In another preferred embodiment, the first peptide consists of a portion of a biologically active molecule (e.g. the extracellular portion of the polypeptide or the ligand binding portion). The second peptide can include an immunoglobulin constant region, for example, a human Cγ1 domain or Cγ 4 domain (e.g., the hinge, CH2 and CH3 regions of human IgCγ1, or human IgCγ4, see e.g., Capon et al. U.S. Pat. Nos. 5,116,964; 5,580,756; 5,844,095 and the like, incorporated herein by reference). Such constant regions may retain regions which mediate effector function (e.g. Fc receptor binding) or may be altered to reduce effector function. A resulting fusion protein may have altered solubility, binding affinity, stability and/or valency (i.e., the number of binding sites available per polypeptide) as compared to the independently expressed first peptide, and may increase the efficiency of protein purification. Fusion proteins and peptides produced by recombinant techniques can be secreted and isolated from a mixture of cells and medium containing the protein or peptide. Alternatively, the protein or peptide can be retained cytoplasmically and the cells harvested, lysed and the protein isolated. A cell culture typically includes host cells, media and other byproducts. Suitable media for cell culture are well-known in the art. Protein and peptides can be isolated from cell culture media, host cells, or both using techniques known in the art for purifying proteins and peptides. Techniques for transfecting host cells and purifying proteins and peptides are known in the art.

Preferably, a fusion protein of the present invention is produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992).

The fusion proteins of the present invention can be used as immunogens to produce antibodies in a subject. Such antibodies may be used to purify the respective natural polypeptides from which the fusion proteins were generated, or in screening assays to identify polypeptides which inhibit the interactions between one or more biomarkers polypeptide or a fragment thereof and its natural binding partner(s) or a fragment(s) thereof.

Also provided herein are compositions comprising one or more nucleic acids comprising or capable of expressing at least 1, 2, 3, 4, 5, 10, 20 or more small nucleic acids or antisense oligonucleotides or derivatives thereof, wherein said small nucleic acids or antisense oligonucleotides or derivatives thereof in a cell specifically hybridize (e.g., bind) under cellular conditions, with cellular nucleic acids (e.g., small non-coding RNAS such as miRNAs, pre-miRNAs, pri-miRNAs, miRNA*, anti-miRNA, a miRNA binding site, a variant and/or functional variant thereof, cellular mRNAs or a fragments thereof). In one embodiment, expression of the small nucleic acids or antisense oligonucleotides or derivatives thereof in a cell can inhibit expression or biological activity of cellular nucleic acids and/or proteins, e.g., by inhibiting transcription, translation and/or small nucleic acid processing of, for example, one or more biomarkers of the present invention, including one or more biomarkers listed in Table 1, or fragment(s) thereof. In one embodiment, the small nucleic acids or antisense oligonucleotides or derivatives thereof are small RNAs (e.g., microRNAs) or complements of small RNAs. In another embodiment, the small nucleic acids or antisense oligonucleotides or derivatives thereof can be single or double stranded and are at least six nucleotides in length and are less than about 1000, 900, 800, 700, 600, 500, 400, 300, 200, 100, 50, 40, 30, 25, 24, 23, 22, 21, 20, 19, 18, 17, 16, 15, or 10 nucleotides in length. In another embodiment, a composition may comprise a library of nucleic acids comprising or capable of expressing small nucleic acids or antisense oligonucleotides or derivatives thereof, or pools of said small nucleic acids or antisense oligonucleotides or derivatives thereof. A pool of nucleic acids may comprise about 2-5, 5-10, 10-20, 10-30 or more nucleic acids comprising or capable of expressing small nucleic acids or antisense oligonucleotides or derivatives thereof.

In one embodiment, binding may be by conventional base pair complementarity, or, for example, in the case of binding to DNA duplexes, through specific interactions in the major groove of the double helix. In general, "antisense" refers to the range of techniques generally employed in the art, and includes any process that relies on specific binding to oligonucleotide sequences.

It is well-known in the art that modifications can be made to the sequence of a miRNA or a pre-miRNA without disrupting miRNA activity. As used herein, the term "functional variant" of a miRNA sequence refers to an oligonucleotide sequence that varies from the natural miRNA sequence, but retains one or more functional characteristics of the miRNA (e.g. cancer cell proliferation inhibition, induction of cancer cell apoptosis, enhancement of cancer cell susceptibility to chemotherapeutic agents, specific miRNA target inhibition). In some embodiments, a functional variant of a miRNA sequence retains all of the functional characteristics of the miRNA. In certain embodiments, a functional variant of a miRNA has a nucleobase sequence that is a least about 60%, 65%, 70%, 75%, 80%, 85%, 90%, 91%, 92%, 93%, 94%, 95%, 96%, 97%, 98% or 99% identical to the miRNA or precursor thereof over a region of about 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases, or that the functional variant hybridizes to the complement of the miRNA or precursor thereof under stringent hybridization conditions. Accordingly, in certain embodiments the nucleobase sequence of a functional variant is capable of hybridizing to one or more target sequences of the miRNA.

miRNAs and their corresponding stem-loop sequences described herein may be found in miRBase, an online searchable database of miRNA sequences and annotation, found on the world wide web at microrna.sanger.ac.uk. Entries in the miRBase Sequence database represent a predicted hairpin portion of a miRNA transcript (the stem-loop), with information on the location and sequence of the mature miRNA sequence. The miRNA stem-loop sequences in the database are not strictly precursor miRNAs (pre-miRNAs), and may in some instances include the pre-miRNA and some flanking sequence from the presumed primary transcript. The miRNA nucleobase sequences described herein encompass any version of the miRNA, including the sequences described in Release 10.0 of the miRBase sequence database and sequences described in any earlier Release of the miRBase sequence database. A sequence database release may result in the re-naming of certain miRNAs. A sequence database release may result in a variation of a mature miRNA sequence.

In some embodiments, miRNA sequences of the present invention may be associated with a second RNA sequence that may be located on the same RNA molecule or on a separate RNA molecule as the miRNA sequence. In such cases, the miRNA sequence may be referred to as the active strand, while the second RNA sequence, which is at least partially complementary to the miRNA sequence, may be referred to as the complementary strand. The active and complementary strands are hybridized to create a double-stranded RNA that is similar to a naturally occurring miRNA precursor. The activity of a miRNA may be optimized by maximizing uptake of the active strand and minimizing uptake of the complementary strand by the miRNA protein complex that regulates gene translation. This can be done through modification and/or design of the complementary strand.

In some embodiments, the complementary strand is modified so that a chemical group other than a phosphate or hydroxyl at its 5' terminus. The presence of the 5' modification apparently eliminates uptake of the complementary strand and subsequently favors uptake of the active strand by the miRNA protein complex. The 5' modification can be any of a variety of molecules known in the art, including $NH_2$, $NHCOCH_3$, and biotin.

In another embodiment, the uptake of the complementary strand by the miRNA pathway is reduced by incorporating nucleotides with sugar modifications in the first 2-6 nucleotides of the complementary strand. It should be noted that such sugar modifications can be combined with the 5' terminal modifications described above to further enhance miRNA activities.

In some embodiments, the complementary strand is designed so that nucleotides in the 3' end of the complementary strand are not complementary to the active strand. This results in double-strand hybrid RNAs that are stable at the 3' end of the active strand but relatively unstable at the 5' end of the active strand. This difference in stability enhances the uptake of the active strand by the miRNA pathway, while reducing uptake of the complementary strand, thereby enhancing miRNA activity.

Small nucleic acid and/or antisense constructs of the methods and compositions presented herein can be delivered, for example, as an expression plasmid which, when transcribed in the cell, produces RNA which is complementary to at least a unique portion of cellular nucleic acids (e.g., small RNAs, mRNA, and/or genomic DNA). Alternatively, the small nucleic acid molecules can produce RNA which encodes mRNA, miRNA, pre-miRNA, pri-miRNA, miRNA*, anti-miRNA, or a miRNA binding site, or a variant thereof. For example, selection of plasmids suitable for expressing the miRNAs, methods for inserting nucleic acid sequences into the plasmid, and methods of delivering the recombinant plasmid to the cells of interest are within the skill in the art. See, for example, Zeng et al. (2002) *Mol. Cell* 9:1327-1333; Tuschl (2002), *Nat. Biotechnol.* 20:446-448; Brummelkamp et al. (2002) *Science* 296:550-553; Miyagi-shi et al. (2002) *Nat. Biotechnol.* 20:497-500; Paddison et al. (2002) *Genes Dev.* 16:948-958; Lee et al. (2002) *Nat. Biotechnol.* 20:500-505; and Paul et al. (2002) *Nat. Biotechnol.* 20:505-508, the entire disclosures of which are herein incorporated by reference.

Alternatively, small nucleic acids and/or antisense constructs are oligonucleotide probes that are generated ex vivo and which, when introduced into the cell, results in hybridization with cellular nucleic acids. Such oligonucleotide probes are preferably modified oligonucleotides that are resistant to endogenous nucleases, e.g., exonucleases and/or endonucleases, and are therefore stable in vivo. Exemplary nucleic acid molecules for use as small nucleic acids and/or antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) BioTechniques 6:958-976; and Stein et al. (1988) Cancer Res 48:2659-2668.

Antisense approaches may involve the design of oligonucleotides (either DNA or RNA) that are complementary to cellular nucleic acids (e.g., complementary to biomarkers listed in Table 1). Absolute complementarity is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a nucleic acid (e.g., RNA) it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well (Wagner (1994) *Nature* 372: 333). Therefore, oligonucleotides complementary to either the 5' or 3' untranslated, non-coding regions of genes could be used in an antisense approach to inhibit translation of endogenous mRNAs. Oligonucleotides complementary to the 5' untranslated region of the mRNA may include the complement of the AUG start codon. Antisense oligonucleotides complementary to mRNA coding regions are less efficient inhibitors of translation but could also be used in accordance with the methods and compositions presented herein. Whether designed to hybridize to the 5', 3' or coding region of cellular mRNAs, small nucleic acids and/or antisense nucleic acids should be at least six nucleotides in length, and can be less than about 1000, 900, 800, 700, 600, 500, 400, 300, 200, 100, 50, 40, 30, 25, 24, 23, 22, 21, 20, 19, 18, 17, 16, 15, or 10 nucleotides in length.

Regardless of the choice of target sequence, it is preferred that in vitro studies are first performed to quantitate the ability of the antisense oligonucleotide to inhibit gene expression. In one embodiment these studies utilize controls that distinguish between antisense gene inhibition and non-specific biological effects of oligonucleotides. In another embodiment these studies compare levels of the target nucleic acid or protein with that of an internal control nucleic acid or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

Small nucleic acids and/or antisense oligonucleotides can be DNA or RNA or chimeric mixtures or derivatives or modified versions thereof, single-stranded or double-stranded. Small nucleic acids and/or antisense oligonucleotides can be modified at the base moiety, sugar moiety, or phosphate backbone, for example, to improve stability of the molecule, hybridization, etc., and may include other appended groups such as peptides (e.g., for targeting host cell receptors), or agents facilitating transport across the cell membrane (see, e.g., Letsinger et al. (1989) Proc. Natl. Acad. Sci. U.S.A. 86:6553-6556; Lemaitre et al. (1987) Proc. Natl. Acad. Sci. U.S.A. 84:648-652; PCT Publication No. WO88/09810) or the blood-brain barrier (see, e.g., PCT Publication No. WO89/10134), hybridization-triggered cleavage agents. (See, e.g., Krol et al. (1988) BioTech. 6:958-976) or intercalating agents. (See, e.g., Zon (1988) Pharm. Res. 5:539-549). To this end, small nucleic acids and/or antisense oligonucleotides may be conjugated to another molecule, e.g., a peptide, hybridization triggered cross-linking agent, transport agent, hybridization-triggered cleavage agent, etc.

Small nucleic acids and/or antisense oligonucleotides may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxyti-ethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Small nucleic acids and/or antisense oligonucleotides may also comprise at least one modified sugar moiety selected from the group including but not limited to arabinose, 2-fluoroarabinose, xylulose, and hexose.

In certain embodiments, a compound comprises an oligonucleotide (e.g., a miRNA or miRNA encoding oligonucleotide) conjugated to one or more moieties which enhance the activity, cellular distribution or cellular uptake of the resulting oligonucleotide. In certain such embodiments, the moiety is a cholesterol moiety (e.g., antagomirs) or a lipid moiety or liposome conjugate. Additional moieties for conjugation include carbohydrates, phospholipids, biotin, phenazine, folate, phenanthridine, anthraquinone, acridine, fluoresceins, rhodamines, coumarins, and dyes. In certain embodiments, a conjugate group is attached directly to the oligonucleotide. In certain embodiments, a conjugate group is attached to the oligonucleotide by a linking moiety selected from amino, hydroxyl, carboxylic acid, thiol, unsaturations (e.g., double or triple bonds), 8-amino-3,6-dioxaoctanoic acid (ADO), succinimidyl 4-(N-maleimidomethyl) cyclohexane-1-carboxylate (SMCC), 6-aminohexanoic acid (AHEX or AHA), substituted C1-C10 alkyl, substituted or unsubstituted C2-C10 alkenyl, and substituted or unsubstituted C2-C10 alkynyl. In certain such embodiments, a substituent group is selected from hydroxyl, amino, alkoxy, carboxy, benzyl, phenyl, nitro, thiol, thioalkoxy, halogen, alkyl, aryl, alkenyl and alkynyl.

In certain such embodiments, the compound comprises the oligonucleotide having one or more stabilizing groups that are attached to one or both termini of the oligonucleotide to enhance properties such as, for example, nuclease stability. Included in stabilizing groups are cap structures. These terminal modifications protect the oligonucleotide from exonuclease degradation, and can help in delivery and/or localization within a cell. The cap can be present at the 5'-terminus (5'-cap), or at the 3'-terminus (3'-cap), or can be present on both termini. Cap structures include, for example, inverted deoxy abasic caps.

Suitable cap structures include a 4', 5'-methylene nucleotide, a 1-(beta-D-erythrofuranosyl) nucleotide, a 4'-thio nucleotide, a carbocyclic nucleotide, a 1,5-anhydrohexitol nucleotide, an L-nucleotide, an alpha-nucleotide, a modified base nucleotide, a phosphorodithioate linkage, a threo-pentofuranosyl nucleotide, an acyclic 3', 4'-seco nucleotide, an acyclic 3,4-dihydroxybutyl nucleotide, an acyclic 3,5-dihydroxypentyl nucleotide, a 3'-3'-inverted nucleotide moiety, a 3'-3'-inverted abasic moiety, a 3'-2'-inverted nucleotide moiety, a 3'-2'-inverted abasic moiety, a 1,4-butanediol phosphate, a 3'-phosphoramidate, a hexylphosphate, an aminohexyl phosphate, a 3'-phosphate, a 3'-phosphorothioate, a phosphorodithioate, a bridging methylphosphonate moiety, and a non-bridging methylphosphonate moiety 5'-aminoalkyl phosphate, a 1,3-diamino-2-propyl phosphate, 3-aminopropyl phosphate, a 6-aminohexyl phosphate, a 1,2-aminododecyl phosphate, a hydroxypropyl phosphate, a 5'-5'-inverted nucleotide moiety, a 5'-5'-inverted abasic moiety, a 5'-phosphoramidate, a 5'-phosphorothioate, a 5'-amino, a bridging and/or non-bridging 5'-phosphoramidate, a phosphorothioate, and a 5'-mercapto moiety.

Small nucleic acids and/or antisense oligonucleotides can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, small nucleic acids and/or antisense oligonucleotides comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In a further embodiment, small nucleic acids and/or antisense oligonucleotides are a-anomeric oligonucleotides. An u-anomeric oligonucleotide forms specific double-stranded hybrids with complementary RNA in which, contrary to the usual b-units, the strands run parallel to each other (Gautier et al. (1987) Nucl. Acids Res. 15:6625-6641). The oligonucleotide is a 2'-O-methylribonucleotide (Inoue et al. (1987) Nucl. Acids Res. 15:6131-6148), or a chimeric RNA-DNA analogue (Inoue et al. (1987) FEBS Lett. 215: 327-330).

Small nucleic acids and/or antisense oligonucleotides of the methods and compositions presented herein may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988) Nucl. Acids Res. 16:3209, methylphosphonate oligonucleotides can be prepared by use of controlled pore glass polymer supports (Sarin et al. (1988) Proc. Natl. Acad. Sci. U.S.A. 85:7448-7451), etc. For example, an isolated miRNA can be chemically synthesized or recombinantly produced using methods known in the art. In some instances, miRNA are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), Cruachem (Glasgow, UK), and Exiqon (Vedbaek, Denmark).

Small nucleic acids and/or antisense oligonucleotides can be delivered to cells in vivo. A number of methods have been developed for delivering small nucleic acids and/or antisense oligonucleotides DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

In one embodiment, small nucleic acids and/or antisense oligonucleotides may comprise or be generated from double stranded small interfering RNAs (siRNAs), in which sequences fully complementary to cellular nucleic acids (e.g. mRNAs) sequences mediate degradation or in which sequences incompletely complementary to cellular nucleic acids (e.g., mRNAs) mediate translational repression when expressed within cells, or piwiRNAs. In another embodiment, double stranded siRNAs can be processed into single stranded antisense RNAs that bind single stranded cellular RNAs (e.g., microRNAs) and inhibit their expression. RNA interference (RNAi) is the process of sequence-specific, post-transcriptional gene silencing in animals and plants, initiated by double-stranded RNA (dsRNA) that is homologous in sequence to the silenced gene. in vivo, long dsRNA is cleaved by ribonuclease III to generate 21- and 22-nucleotide siRNAs. It has been shown that 21-nucleotide siRNA duplexes specifically suppress expression of endogenous and heterologous genes in different mammalian cell lines, including human embryonic kidney (293) and HeLa cells (Elbashir et al. (2001) Nature 411:494-498). Accordingly, translation of a gene in a cell can be inhibited by contacting the cell with short double stranded RNAs having a length of about 15 to 30 nucleotides or of about 18 to 21 nucleotides or of about 19 to 21 nucleotides. Alternatively, a vector encoding for such siRNAs or short hairpin RNAs (shRNAs) that are metabolized into siRNAs can be introduced into a target cell (see, e.g., McManus et al. (2002) RNA 8:842; Xia et al. (2002) Nat. Biotechnol. 20:1006; and Brummelkamp et al. (2002) Science 296:550). Vectors that can be used are commercially available, e.g., from OligoEngine under the name pSuper RNAi System™.

Ribozyme molecules designed to catalytically cleave cellular mRNA transcripts can also be used to prevent translation of cellular mRNAs and expression of cellular polypeptides, or both (See, e.g., PCT International Publication WO90/11364, published Oct. 4, 1990; Sarver et al. (1990) Science 247:1222-1225 and U.S. Pat. No. 5,093,246). While ribozymes that cleave mRNA at site specific recognition sequences can be used to destroy cellular mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well-known in the art and is described more fully in Haseloff and Gerlach (1988) Nature 334:585-591. The ribozyme may be engineered so that the cleavage recognition site is located near the 5' end of cellular mRNAs; i.e., to increase efficiency and minimize the intracellular accumulation of non-functional mRNA transcripts.

The ribozymes of the methods presented herein also include RNA endoribonucleases (hereinafter "Cech-type ribozymes") such as the one which occurs naturally in Tetrahymena thermophila (known as the IVS, or L-19 IVS RNA) and which has been extensively described by Thomas Cech and collaborators (Zaug et al. (1984) Science 224:574-578; Zaug et al. (1986) Science 231:470-475; Zaug et al. (1986) Nature 324:429-433; WO 88/04300; and Been et al. (1986) Cell 47:207-216). The Cech-type ribozymes have an eight base pair active site which hybridizes to a target RNA sequence whereafter cleavage of the target RNA takes place. The methods and compositions presented herein encompasses those Cech-type ribozymes which target eight base-pair active site sequences that are present in cellular genes.

As in the antisense approach, the ribozymes can be composed of modified oligonucleotides (e.g., for improved stability, targeting, etc.). A preferred method of delivery involves using a DNA construct "encoding" the ribozyme under the control of a strong constitutive pol III or pol II promoter, so that transfected cells will produce sufficient quantities of the ribozyme to destroy endogenous cellular messages and inhibit translation. Because ribozymes unlike antisense molecules, are catalytic, a lower intracellular concentration is required for efficiency.

Nucleic acid molecules to be used in triple helix formation for the inhibition of transcription of cellular genes are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Small nucleic acids (e.g., miRNAs, pre-miRNAs, pri-miRNAs, miRNA*, anti-miRNA, or a miRNA binding site, or a variant thereof), antisense oligonucleotides, ribozymes, and triple helix molecules of the methods and compositions presented herein may be prepared by any method known in the art for the synthesis of DNA and RNA molecules. These include techniques for chemically synthesizing oligodeoxyribonucleotides and oligoribonucleotides well-known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone. One of skill in the art will readily understand that polypeptides, small nucleic acids, and antisense oligonucleotides can be further linked to another peptide or polypeptide (e.g., a heterologous peptide), e.g., that serves as a means of protein detection. Non-limiting examples of label peptide or polypeptide moieties useful for detection in the invention include, without limitation, suitable enzymes such as horseradish peroxidase, alkaline phosphatase, beta-galactosidase, or acetylcholinesterase; epitope tags, such as FLAG, MYC, HA, or HIS tags; fluorophores such as green fluorescent protein; dyes; radioisotopes; digoxygenin; biotin; antibodies; polymers; as well as others known in the art, for example, in Principles of Fluorescence Spectroscopy, Joseph R. Lakowicz (Editor), Plenum Pub Corp, 2nd edition (July 1999).

The modulatory agents described herein (e.g., antibodies, small molecules, peptides, fusion proteins, or small nucleic acids) can be incorporated into pharmaceutical compositions and administered to a subject in vivo. The compositions may contain a single such molecule or agent or any combination of agents described herein. "Single active agents" described herein can be combined with other pharmacologically active compounds ("second active agents") known in the art according to the methods and compositions provided herein.

The production and use of biomarker nucleic acid and/or biomarker polypeptide molecules described herein can be facilitated by using standard recombinant techniques. In some embodiments, such techniques use vectors, preferably expression vectors, containing a nucleic acid encoding a biomarker polypeptide or a portion of such a polypeptide. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the present invention is intended to include such other forms of expression vectors, such as viral vectors (e.g., replication defective retroviruses, adenoviruses and adeno-associated viruses), which serve equivalent functions.

The recombinant expression vectors of the present invention comprise a nucleic acid of the present invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Methods in Enzymology: Gene Expression Technology* vol. 185, Academic Press, San Diego, CA (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the present invention can be introduced into host cells to thereby produce proteins or peptides, including fusion proteins or peptides, encoded by nucleic acids as described herein.

The recombinant expression vectors for use in the present invention can be designed for expression of a polypeptide corresponding to a marker of the present invention in prokaryotic (e.g., *E. coli*) or eukaryotic cells (e.g., insect cells {using baculovirus expression vectors}, yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:31-40), pMAL (New England Biolabs, Beverly, MA) and pRIT5 (Pharmacia, Piscataway, NJ) which fuse glutathione S-transferase (GST), maltose E binding protein, or protein A, respectively, to the target recombinant protein.

Examples of suitable inducible non-fusion E. coli expression vectors include pTrc (Amann et al., 1988, Gene 69:301-315) and pET 11d (Studier et al., p. 60-89, In Gene Expression Technology: Methods in Enzymology vol. 185, Academic Press, San Diego, CA, 1991). Target biomarker nucleic acid expression from the pTrc vector relies on host RNA polymerase transcription from a hybrid trp-lac fusion promoter. Target biomarker nucleic acid expression from the pET 11d vector relies on transcription from a T7 gn10-lac fusion promoter mediated by a co-expressed viral RNA polymerase (T7 gn1). This viral polymerase is supplied by host strains BL21 (DE3) or HMS174(DE3) from a resident prophage harboring a T7 gn1 gene under the transcriptional control of the lacUV 5 promoter.

One strategy to maximize recombinant protein expression in E. coli is to express the protein in a host bacterium with an impaired capacity to proteolytically cleave the recombinant protein (Gottesman, p. 119-128, In Gene Expression Technology: Methods in Enzymology vol. 185, Academic Press, San Diego, CA, 1990. Another strategy is to alter the nucleic acid sequence of the nucleic acid to be inserted into an expression vector so that the individual codons for each amino acid are those preferentially utilized in E. coli (Wada et al., 1992, Nucleic Acids Res. 20:2111-2118). Such alteration of nucleic acid sequences of the present invention can be carried out by standard DNA synthesis techniques.

In another embodiment, the expression vector is a yeast expression vector. Examples of vectors for expression in yeast S. cerevisiae include pYepSec1 (Baldari et al., 1987, EMBO J. 6:229-234), pMFa (Kurjan and Herskowitz, 1982, Cell 30:933-943), pJRY88 (Schultz et al., 1987, Gene 54:113-123), pYES2 (Invitrogen Corporation, San Diego, CA), and pPicZ (Invitrogen Corp, San Diego, CA).

Alternatively, the expression vector is a baculovirus expression vector. Baculovirus vectors available for expression of proteins in cultured insect cells (e.g., Sf 9 cells) include the pAc series (Smith et al., 1983, Mol. Cell Biol. 3:2156-2165) and the pVL series (Lucklow and Summers, 1989, Virology 170:31-39).

In yet another embodiment, a nucleic acid of the present invention is expressed in mammalian cells using a mammalian expression vector. Examples of mammalian expression vectors include pCDM8 (Seed, 1987, Nature 329:840) and pMT2PC (Kaufman et al., 1987, EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, Genes Dev. 1:268-277), lymphoid-specific promoters (Calame and Eaton, 1988, Adv. Immunol. 43:235-275), in particular promoters of T cell receptors (Winoto and Baltimore, 1989, EMBO J. 8:729-733) and immunoglobulins (Banerji et al., 1983, Cell 33:729-740; Queen and Baltimore, 1983, Cell 33:741-748), neuron-specific promoters (e.g., the neurofilament promoter; Byrne and Ruddle, 1989, Proc. Natl. Acad. Sci. USA 86:5473-5477), pancreas-specific promoters (Edlund et al., 1985, Science 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990, Science 249:374-379) and the a-fetoprotein promoter (Camper and Tilghman, 1989, Genes Dev. 3:537-546).

The present invention further provides a recombinant expression vector comprising a DNA molecule cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the present invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes (see Weintraub et al., 1986, Trends in Genetics, Vol. 1(1)).

Another aspect of the present invention pertains to host cells into which a recombinant expression vector of the present invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., E. coli) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

V. Analyzing Biomarker Nucleic Acids and Polypeptides

Biomarker nucleic acids and/or biomarker polypeptides can be analyzed according to the methods described herein and techniques known to the skilled artisan to identify such genetic or expression alterations useful for the present invention including, but not limited to, 1) an alteration in the level of a biomarker transcript or polypeptide, 2) a deletion or addition of one or more nucleotides from a biomarker gene, 4) a substitution of one or more nucleotides of a biomarker gene, 5) aberrant modification of a biomarker gene, such as an expression regulatory region, and the like.

a. Methods for Detection of Copy Number

Methods of evaluating the copy number of a biomarker nucleic acid are well-known to those of skill in the art. The presence or absence of chromosomal gain or loss can be evaluated simply by a determination of copy number of the regions or markers identified herein.

In one embodiment, a biological sample is tested for the presence of copy number changes in genomic loci containing the genomic marker. A copy number of at least 3, 4, 5, 6, 7, 8, 9, or 10 is predictive of poorer outcome of ADAR, ZC3HAV1, PPP1R15A, and/or EIF2AK2/PKR.

Methods of evaluating the copy number of a biomarker locus include, but are not limited to, hybridization-based assays. Hybridization-based assays include, but are not limited to, traditional "direct probe" methods, such as Southern blots, in situ hybridization (e.g., FISH and FISH plus SKY) methods, and "comparative probe" methods, such as comparative genomic hybridization (CGH), e.g., cDNA-based or oligonucleotide-based CGH. The methods can be used in a wide variety of formats including, but not limited to, substrate (e.g. membrane or glass) bound methods or array-based approaches.

In one embodiment, evaluating the biomarker gene copy number in a sample involves a Southern Blot. In a Southern Blot, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid. Alternatively, a Northern blot may be utilized for evaluating the copy number of encoding nucleic acid in a sample. In a Northern blot, mRNA is hybridized to a probe specific for the target region. Comparison of the intensity of the hybridization signal from the probe for the target region with control probe signal from analysis of normal RNA (e.g., a non-amplified portion of the same or related cell, tissue, organ, etc.) provides an estimate of the relative copy number of the target nucleic acid. Alternatively, other methods well-known in the art to detect RNA can be used, such that higher or lower expression relative to an appropriate control (e.g., a non-amplified portion of the same or related cell tissue, organ, etc.) provides an estimate of the relative copy number of the target nucleic acid.

An alternative means for determining genomic copy number is in situ hybridization (e.g., Angerer (1987) *Meth. Enzymol* 152: 649). Generally, in situ hybridization comprises the following steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application. In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained. The probes are typically labeled, e.g., with radioisotopes or fluorescent reporters. In one embodiment, probes are sufficiently long so as to specifically hybridize with the target nucleic acid(s) under stringent conditions. Probes generally range in length from about 200 bases to about 1000 bases. In some applications it is necessary to block the hybridization capacity of repetitive sequences. Thus, in some embodiments, tRNA, human genomic DNA, or Cot-I DNA is used to block non-specific hybridization.

An alternative means for determining genomic copy number is comparative genomic hybridization. In general, genomic DNA is isolated from normal reference cells, as well as from test cells (e.g., tumor cells) and amplified, if necessary. The two nucleic acids are differentially labeled and then hybridized in situ to metaphase chromosomes of a reference cell. The repetitive sequences in both the reference and test DNAs are either removed or their hybridization capacity is reduced by some means, for example by prehybridization with appropriate blocking nucleic acids and/or including such blocking nucleic acid sequences for said repetitive sequences during said hybridization. The bound, labeled DNA sequences are then rendered in a visualizable form, if necessary. Chromosomal regions in the test cells which are at increased or decreased copy number can be identified by detecting regions where the ratio of signal from the two DNAs is altered. For example, those regions that have decreased in copy number in the test cells will show relatively lower signal from the test DNA than the reference compared to other regions of the genome. Regions that have been increased in copy number in the test cells will show relatively higher signal from the test DNA. Where there are chromosomal deletions or multiplications, differences in the ratio of the signals from the two labels will be detected and the ratio will provide a measure of the copy number. In another embodiment of CGH, array CGH (aCGH), the immobilized chromosome element is replaced with a collection of solid support bound target nucleic acids on an array, allowing for a large or complete percentage of the genome to be represented in the collection of solid support bound targets. Target nucleic acids may comprise cDNAs, genomic DNAs, oligonucleotides (e.g., to detect single nucleotide polymorphisms) and the like. Array-based CGH may also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays. Methods of preparing immobilized chromosomes or arrays and performing comparative genomic hybridization are well-known in the art (see, e.g., U.S. Pat. Nos. 6,335, 167; 6,197,501; 5,830,645; and 5,665,549 and Albertson (1984) *EMBO J.* 3: 1227-1234; Pinkel (1988) *Proc. Nat. Acad. Sci. USA* 85: 9138-9142; EPO Pub. No. 430,402; Methods in Molecular Biology, Vol. 33: In situ Hybridization Protocols, Choo, ed., Humana Press, Totowa, N.J. (1994), etc.). In another embodiment, the hybridization protocol of Pinkel, et al. (1998) *Nature Genetics* 20: 207-211, or of Kallioniemi (1992) *Proc. Natl Acad Sci USA* 89:5321-5325 (1992) is used.

In still another embodiment, amplification-based assays can be used to measure copy number. In such amplification-based assays, the nucleic acid sequences act as a template in an amplification reaction (e.g., Polymerase Chain Reaction (PCR). In a quantitative amplification, the amount of amplification product will be proportional to the amount of template in the original sample. Comparison to appropriate controls, e.g. healthy tissue, provides a measure of the copy number.

Methods of "quantitative" amplification are well-known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the present invention. In fluorogenic quantitative PCR, quantitation is based on amount of fluorescence signals, e.g., TaqMan and SYBR green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

Loss of heterozygosity (LOH) and major copy proportion (MCP) mapping (Wang, Z. C., et al. (2004) *Cancer Res* 64(1):64-71; Seymour, A. B., et al. (1994) *Cancer Res* 54, 2761-4; Hahn, S. A., et al. (1995) *Cancer Res* 55, 4670-5; Kimura, M., et al. (1996) *Genes Chromosomes Cancer* 17, 88-93; Li et al., (2008) *MBC Bioinform.* 9, 204-219) may also be used to identify regions of amplification or deletion.

b. Methods for Detection of Biomarker Nucleic Acid Expression

Biomarker expression may be assessed by any of a wide variety of well-known methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In preferred embodiments, activity of a particular gene is characterized by a measure of gene transcript (e.g. mRNA), by a measure of the quantity of translated protein, or by a measure of gene product activity. Marker expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In another embodiment, detecting or determining expression levels of a biomarker and functionally similar homologs thereof, including a fragment or genetic alteration thereof (e.g., in regulatory or promoter regions thereof) comprises detecting or determining RNA levels for the marker of interest. In one embodiment, one or more cells from the subject to be tested are obtained and RNA is isolated from the cells. In a preferred embodiment, a sample of breast tissue cells is obtained from the subject.

In one embodiment, RNA is obtained from a single cell. For example, a cell can be isolated from a tissue sample by laser capture microdissection (LCM). Using this technique, a cell can be isolated from a tissue section, including a stained tissue section, thereby assuring that the desired cell is isolated (see, e.g., Bonner et al. (1997) Science 278: 1481; Emmert-Buck et al. (1996) Science 274:998; Fend et al. (1999) Am. J. Path. 154: 61 and Murakami et al. (2000) Kidney Int. 58:1346). For example, Murakami et al., supra, describe isolation of a cell from a previously immunostained tissue section.

It is also be possible to obtain cells from a subject and culture the cells in vitro, such as to obtain a larger population of cells from which RNA can be extracted. Methods for establishing cultures of non-transformed cells, i.e., primary cell cultures, are known in the art.

When isolating RNA from tissue samples or cells from individuals, it may be important to prevent any further changes in gene expression after the tissue or cells has been removed from the subject. Changes in expression levels are known to change rapidly following perturbations, e.g., heat shock or activation with lipopolysaccharide (LPS) or other reagents. In addition, the RNA in the tissue and cells may quickly become degraded. Accordingly, in a preferred embodiment, the tissue or cells obtained from a subject is snap frozen as soon as possible.

RNA can be extracted from the tissue sample by a variety of methods, e.g., the guanidium thiocyanate lysis followed by CsCl centrifugation (Chirgwin et al., 1979, Biochemistry 18:5294-5299). RNA from single cells can be obtained as described in methods for preparing cDNA libraries from single cells, such as those described in Dulac, C. (1998) Curr. Top. Dev. Biol. 36, 245 and Jena et al. (1996) J. Immunol. Methods 190:199. Care to avoid RNA degradation must be taken, e.g., by inclusion of RNAsin.

The RNA sample can then be enriched in particular species. In one embodiment, poly(A)+RNA is isolated from the RNA sample. In general, such purification takes advantage of the poly-A tails on mRNA. In particular and as noted above, poly-T oligonucleotides may be immobilized within on a solid support to serve as affinity ligands for mRNA. Kits for this purpose are commercially available, e.g., the MessageMaker kit (Life Technologies, Grand Island, NY).

In a preferred embodiment, the RNA population is enriched in marker sequences. Enrichment can be undertaken, e.g., by primer-specific cDNA synthesis, or multiple rounds of linear amplification based on cDNA synthesis and template-directed in vitro transcription (see, e.g., Wang et al. (1989) *Proc. Natl. Acad. Sci. U.S.A.* 86: 9717; Dulac et al., supra, and Jena et al., supra).

The population of RNA, enriched or not in particular species or sequences, can further be amplified. As defined herein, an "amplification process" is designed to strengthen, increase, or augment a molecule within the RNA. For example, where RNA is mRNA, an amplification process such as RT-PCR can be utilized to amplify the mRNA, such that a signal is detectable or detection is enhanced. Such an amplification process is beneficial particularly when the biological, tissue, or tumor sample is of a small size or volume.

Various amplification and detection methods can be used. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall, et al., PCR Methods and Applications 4: 80-84 (1994). Real time PCR may also be used.

Other known amplification methods which can be utilized herein include but are not limited to the so-called "NASBA" or "3SR" technique described in PNAS USA 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., Clin. Chem. 42: 9-13 (1996) and European Patent Application No. 684315; target mediated amplification, as described by PCT Publication WO9322461; PCR; ligase chain reaction (LCR) (see, e.g., Wu and Wallace, Genomics 4, 560 (1989), Landegren et al., Science 241, 1077 (1988)); self-sustained sequence replication (SSR) (see, e.g., Guatelli et al., Proc. Nat. Acad. Sci. USA, 87, 1874 (1990)); and transcription amplification (see, e.g., Kwoh et al., Proc. Natl. Acad. Sci. USA 86, 1173 (1989)).

Many techniques are known in the state of the art for determining absolute and relative levels of gene expression, commonly used techniques suitable for use in the present invention include Northern analysis, RNase protection assays (RPA), microarrays and PCR-based techniques, such as quantitative PCR and differential display PCR. For example, Northern blotting involves running a preparation of RNA on a denaturing agarose gel, and transferring it to a suitable support, such as activated cellulose, nitrocellulose or glass or nylon membranes. Radiolabeled cDNA or RNA is then hybridized to the preparation, washed and analyzed by autoradiography.

In situ hybridization visualization may also be employed, wherein a radioactively labeled antisense RNA probe is hybridized with a thin section of a biopsy sample, washed, cleaved with RNase and exposed to a sensitive emulsion for autoradiography. The samples may be stained with hematoxylin to demonstrate the histological composition of the sample, and dark field imaging with a suitable light filter shows the developed emulsion. Non-radioactive labels such as digoxigenin may also be used.

Alternatively, mRNA expression can be detected on a DNA array, chip or a microarray. Labeled nucleic acids of a test sample obtained from a subject may be hybridized to a solid surface comprising biomarker DNA. Positive hybridization signal is obtained with the sample containing biomarker transcripts. Methods of preparing DNA arrays and their use are well-known in the art (see, e.g., U.S. Pat. Nos. 6,618,796; 6,379,897; 6,664,377; 6,451,536; 548,257; U.S. 20030157485 and Schena et al. (1995) *Science* 20, 467-470; Gerhold et al. (1999) *Trends In Biochem. Sci.* 24, 168-173; and Lennon et al. (2000) *Drug Discovery Today* 5, 59-65, which are herein incorporated by reference in their entirety). Serial Analysis of Gene Expression (SAGE) can also be performed (See for example U.S. Patent Application 20030215858).

To monitor mRNA levels, for example, mRNA is extracted from the biological sample to be tested, reverse transcribed, and fluorescently-labeled cDNA probes are generated. The microarrays capable of hybridizing to marker cDNA are then probed with the labeled cDNA probes, the slides scanned and fluorescence intensity measured. This intensity correlates with the hybridization intensity and expression levels.

Types of probes that can be used in the methods described herein include cDNA, riboprobes, synthetic oligonucleotides and genomic probes. The type of probe used will generally be dictated by the particular situation, such as riboprobes for in situ hybridization, and cDNA for Northern blotting, for example. In one embodiment, the probe is directed to nucleotide regions unique to the RNA. The probes may be as short as is required to differentially recognize marker mRNA transcripts, and may be as short as, for example, 15 bases; however, probes of at least 17, 18, 19 or 20 or more bases can be used. In one embodiment, the primers and probes hybridize specifically under stringent conditions to a DNA fragment having the nucleotide sequence corresponding to the marker. As herein used, the term "stringent conditions" means hybridization will occur only if there is at least 95% identity in nucleotide sequences. In another embodiment, hybridization under "stringent conditions" occurs when there is at least 97% identity between the sequences.

The form of labeling of the probes may be any that is appropriate, such as the use of radioisotopes, for example, $^{32}P$ and $^{35}S$. Labeling with radioisotopes may be achieved, whether the probe is synthesized chemically or biologically, by the use of suitably labeled bases.

In one embodiment, the biological sample contains polypeptide molecules from the test subject. Alternatively, the biological sample can contain mRNA molecules from the test subject or genomic DNA molecules from the test subject.

In another embodiment, the methods further involve obtaining a control biological sample from a control subject, contacting the control sample with a compound or agent capable of detecting marker polypeptide, mRNA, genomic DNA, or fragments thereof, such that the presence of the marker polypeptide, mRNA, genomic DNA, or fragments thereof, is detected in the biological sample, and comparing the presence of the marker polypeptide, mRNA, genomic DNA, or fragments thereof, in the control sample with the presence of the marker polypeptide, mRNA, genomic DNA, or fragments thereof in the test sample.

c. Methods for Detection of Biomarker Protein Expression

The activity or level of a biomarker protein can be detected and/or quantified by detecting or quantifying the expressed polypeptide. The polypeptide can be detected and quantified by any of a number of means well-known to those of skill in the art. Aberrant levels of polypeptide expression of the polypeptides encoded by a biomarker nucleic acid and functionally similar homologs thereof, including a fragment or genetic alteration thereof (e.g., in regulatory or promoter regions thereof) are associated with the likelihood of response of a cancer to ADAR, ZC3HAV1, PPP1R15A, and/or EIF2AK2/PKR modulators, alone or in combination with an immunotherapy and/or modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist). Any method known in the art for detecting polypeptides can be used. Such methods include, but are not limited to, immunodiffusion, immunoelectrophoresis, radioimmunoassay (RIA), enzyme-linked immunosorbent assays (ELISAs), immunofluorescent assays, Western blotting, binder-ligand assays, immunohistochemical techniques, agglutination, complement assays, high performance liquid chromatography (HPLC), thin layer chromatography (TLC), hyperdiffusion chromatography, and the like (e.g., Basic and Clinical Immunology, Sites and Terr, eds., Appleton and Lange, Norwalk, Conn. pp 217-262, 1991 which is incorporated by reference). Preferred are binder-ligand immunoassay methods including reacting antibodies with an epitope or epitopes and competitively displacing a labeled polypeptide or derivative thereof.

For example, ELISA and RIA procedures may be conducted such that a desired biomarker protein standard is labeled (with a radioisotope such as $^{125}I$ or $^{35}S$, or an assayable enzyme, such as horseradish peroxidase or alkaline phosphatase), and, together with the unlabeled sample, brought into contact with the corresponding antibody, whereon a second antibody is used to bind the first, and radioactivity or the immobilized enzyme assayed (competitive assay). Alternatively, the biomarker protein in the sample is allowed to react with the corresponding immobilized antibody, radioisotope- or enzyme-labeled anti-biomarker protein antibody is allowed to react with the system, and radioactivity or the enzyme assayed (ELISA-sandwich assay). Other conventional methods may also be employed as suitable.

The above techniques may be conducted essentially as a "one-step" or "two-step" assay. A "one-step" assay involves contacting antigen with immobilized antibody and, without washing, contacting the mixture with labeled antibody. A "two-step" assay involves washing before contacting, the mixture with labeled antibody. Other conventional methods may also be employed as suitable.

In one embodiment, a method for measuring biomarker protein levels comprises the steps of contacting a biological specimen with an antibody or variant (e.g., fragment) thereof which selectively binds the biomarker protein, and detecting whether said antibody or variant thereof is bound to said sample and thereby measuring the levels of the biomarker protein.

Enzymatic and radiolabeling of biomarker protein and/or the antibodies may be effected by conventional means. Such means will generally include covalent linking of the enzyme to the antigen or the antibody in question, such as by glutaraldehyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labeling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labeled antibody with the substrate under controlled conditions well-known in the art.

Other techniques may be used to detect biomarker protein according to a practitioner's preference based upon the present disclosure. One such technique is Western blotting (Towbin et at., Proc. Nat. Acad. Sci. 76:4350 (1979)), wherein a suitably treated sample is run on an SDS-PAGE gel before being transferred to a solid support, such as a nitrocellulose filter. Anti-biomarker protein antibodies (unlabeled) are then brought into contact with the support and assayed by a secondary immunological reagent, such as labeled protein A or anti-immunoglobulin (suitable labels including $^{125}I$, horseradish peroxidase and alkaline phosphatase). Chromatographic detection may also be used.

Immunohistochemistry may be used to detect expression of biomarker protein, e.g., in a biopsy sample. A suitable antibody is brought into contact with, for example, a thin layer of cells, washed, and then contacted with a second, labeled antibody. Labeling may be by fluorescent markers, enzymes, such as peroxidase, avidin, or radiolabeling. The assay is scored visually, using microscopy.

Anti-biomarker protein antibodies, such as intrabodies, may also be used for imaging purposes, for example, to detect the presence of biomarker protein in cells and tissues of a subject. Suitable labels include radioisotopes, iodine ($^{125}I$, $^{121}I$), carbon ($^{14}C$), sulphur ($^{35}S$), tritium ($^3H$), indium ($^{112}In$), and technetium ($^{99}mTc$), fluorescent labels, such as fluorescein and rhodamine, and biotin.

For in vivo imaging purposes, antibodies are not detectable, as such, from outside the body, and so must be labeled, or otherwise modified, to permit detection. Markers for this purpose may be any that do not substantially interfere with the antibody binding, but which allow external detection. Suitable markers may include those that may be detected by X-radiography, NMR or MRI. For X-radiographic techniques, suitable markers include any radioisotope that emits detectable radiation but that is not overtly harmful to the subject, such as barium or cesium, for example. Suitable markers for NMR and MRI generally include those with a detectable characteristic spin, such as deuterium, which may be incorporated into the antibody by suitable labeling of nutrients for the relevant hybridoma, for example.

The size of the subject, and the imaging system used, will determine the quantity of imaging moiety needed to produce diagnostic images. In the case of a radioisotope moiety, for a human subject, the quantity of radioactivity injected will normally range from about 5 to 20 millicuries of technetium-99. The labeled antibody or antibody fragment will then preferentially accumulate at the location of cells which contain biomarker protein. The labeled antibody or antibody fragment can then be detected using known techniques.

Antibodies that may be used to detect biomarker protein include any antibody, whether natural or synthetic, full length or a fragment thereof, monoclonal or polyclonal, that binds sufficiently strongly and specifically to the biomarker protein to be detected. An antibody may have a $K_d$ of at most about $10^{-6}$ M, $10^{-7}$ M, $10^{-8}$ M, $10^{-9}$ M, $10^{-10}$ M, $10^{-11}$ M, $10^{-12}$ M. The phrase "specifically binds" refers to binding of, for example, an antibody to an epitope or antigen or antigenic determinant in such a manner that binding can be displaced or competed with a second preparation of identical or similar epitope, antigen or antigenic determinant. An antibody may bind preferentially to the biomarker protein relative to other proteins, such as related proteins.

Antibodies are commercially available or may be prepared according to methods known in the art.

Antibodies and derivatives thereof that may be used encompass polyclonal or monoclonal antibodies, chimeric, human, humanized, primatized (CDR-grafted), veneered or single-chain antibodies as well as functional fragments, i.e., biomarker protein binding fragments, of antibodies. For example, antibody fragments capable of binding to a biomarker protein or portions thereof, including, but not limited to, Fv, Fab, Fab' and F(ab') 2 fragments can be used. Such fragments can be produced by enzymatic cleavage or by recombinant techniques. For example, papain or pepsin cleavage can generate Fab or F(ab') 2 fragments, respectively. Other proteases with the requisite substrate specificity can also be used to generate Fab or F(ab') 2 fragments. Antibodies can also be produced in a variety of truncated forms using antibody genes in which one or more stop codons have been introduced upstream of the natural stop site. For example, a chimeric gene encoding a F(ab') 2 heavy chain portion can be designed to include DNA sequences encoding the CH, domain and hinge region of the heavy chain.

Synthetic and engineered antibodies are described in, e.g., Cabilly et al., U.S. Pat. No. 4,816,567 Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0451216 B1; and Padlan, E. A. et al., EP 0519596 A1. See also, Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single-chain antibodies. Antibodies produced from a library, e.g., phage display library, may also be used.

In some embodiments, agents that specifically bind to a biomarker protein other than antibodies are used, such as peptides. Peptides that specifically bind to a biomarker protein can be identified by any means known in the art. For example, specific peptide binders of a biomarker protein can be screened for using peptide phage display libraries.

d. Methods for Detection of Biomarker Structural Alterations

The following illustrative methods can be used to identify the presence of a structural alteration in a biomarker nucleic acid and/or biomarker polypeptide molecule in order to, for example, identify ADAR, ZC3HAV1, PPP1R15A, and/or EIF2AK2/PKR, or other biomarkers used in the immunotherapies described herein that are overexpressed, overfunctional, and the like.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in a biomarker nucleic acid such as a biomarker gene (see Abravaya et al. (1995) Nucleic Acids Res. 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a biomarker gene under conditions such that hybridization and amplification of the biomarker gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self-sustained sequence replication (Guatelli, J. C. et al. (1990) Proc. Natl. Acad. Sci. USA 87:1874-1878), transcriptional amplification system (Kwoh, D. Y. et al. (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well-known to those of skill in the art. These detection schemes are especially useful for the detection of nucleic acid molecules if such molecules are present in very low numbers.

In an alternative embodiment, mutations in a biomarker nucleic acid from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in biomarker nucleic acid can be identified by hybridizing a sample and control nucleic acids, e.g., DNA or RNA, to high density arrays containing hundreds or thousands of oligonucleotide probes (Cronin, M. T. et al. (1996) Hum. Mutat. 7:244-255; Kozal, M. J. et al. (1996) Nat. Med. 2:753-759). For example, biomarker genetic mutations can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene. Such biomarker genetic mutations can be identified in a variety of contexts, including, for example, germline and somatic mutations.

In yet another embodiment, any of a variety of sequencing reactions known in the art can be used to directly sequence a biomarker gene and detect mutations by comparing the sequence of the sample biomarker with the corresponding wild-type (control) sequence. Examples of sequencing reactions include those based on techniques developed by Maxam and Gilbert (1977) *Proc. Natl. Acad. Sci. USA* 74:560 or Sanger (1977) *Proc. Natl. Acad Sci. USA* 74:5463. It is also contemplated that any of a variety of automated sequencing procedures can be utilized when performing the diagnostic assays (Naeve (1995) *Biotechniques* 19:448-53), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in a biomarker gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes formed by hybridizing (labeled) RNA or DNA containing the wild-type biomarker sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with SI nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl. Acad. Sci. USA 85:4397 and Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in biomarker cDNAs obtained from samples of cells. For example, the mutY enzyme of E. coi cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on a biomarker sequence, e.g., a wild-type biomarker treated with a DNA mismatch repair enzyme, and the cleavage products, if any, can be detected from electrophoresis protocols or the like (e.g., U.S. Pat. No. 5,459,039.)

In other embodiments, alterations in electrophoretic mobility can be used to identify mutations in biomarker genes. For example, single strand conformation polymorphism (SSCP) may be used to detect differences in electrophoretic mobility between mutant and wild type nucleic acids (Orita et al. (1989) *Proc Nat. Acad. Sci USA* 86:2766; see also Cotton (1993) *Mutat. Res.* 285:125-144 and Hayashi (1992) *Genet. Anal. Tech. AppL.* 9:73-79). Single-stranded DNA fragments of sample and control biomarker nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163; Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

VI. Anti-Cancer Therapies and Methods of Treatment

The efficacy of therapy to inhibit or enhance ADAR, ZC3HAV1, PPP1R15A, and/or EIF2AK2/PKR, either alone or in combination with another therapy such as modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist) or an immunotherapy like immune checkpoint blockade, is predicted according to biomarker amount and/or activity associated with a cancer in a subject according to the methods described herein. In one embodiment, such ADAR, ZC3HAV1, PPP1R15A, and/or EIF2AK2/PKR modulators, alone or in combination with an immunotherapy (e.g., immune checkpoint inhibitors) and/or modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist) can be administered, particularly if a subject has first been indicated as being a likely responder to ADAR, ZC3HAV1, PPP1R15A, and/or EIF2AK2/PKR modulators, alone or in combination with an immunotherapy and/or modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist). In another embodiment, such ADAR, ZC3HAV1, PPP1R15A, and/or EIF2AK2/PKR modulators, alone or in combination with an immunotherapy and/or radiation therapy can be avoided once a subject is indicated as not being a likely responder to ADAR, ZC3HAV1, PPP1R15A, and/or EIF2AK2/PKR modulators, alone or in combination with an immunotherapy and/or modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist), and an alternative treatment regimen, such as targeted and/or untargeted anti-cancer therapies can be administered. Combination therapies are also contemplated and can comprise, for example, one or more chemotherapeutic agents and radiation, one or more chemotherapeutic agents and immunotherapy, or one or more chemotherapeutic agents, radiation and chemotherapy, each combination of which can be with anti-immune checkpoint therapy. In addition, any representative embodiment of an agent to modulate a particular target can be adapted to any other target described herein by the ordinarily skilled artisn (e.g., direct and indirect PD-1 inhibitors described herein can be applied to other immune checkpoint inhibitors and/or ADAR, ZC3HAV1, PPP1R15A, and/or EIF2AK2/PKR modulators, such as monospecific antibodies, bispecific antibodies, non-activiting forms, small molecules, peptides, interfering nucleic acids, and the like).

The present disclosure provides a method of treating a subject in need thereof, the method including administering to the subject an effective amount of an ADAR1 inhibitor. The present disclosure also provides a method of treating a subject in need thereof, the method including administering to the subject an effective amount of an ISG15 inhibitor. In some embodiments, a method of treating a subject in need thereof may include administering to the subject an effective amount of an inhibitor of a regulator of the interferon signaling pathway (e.g., a suppressor or negative regulator of the interferon signaling pathway). The present disclosure provides a method of treating a subject in need thereof, including administering to the subject an effective amount of an ADAR1 inhibitor or ISG15 inhibitor, and further administering to the subject an effective amount of an interferon pathway activator. As used herein, the term "interferon pathway activator" refers to a molecule (e.g., small molecule, biomolecule) that is capable of stimulating the expression of one or more genes in the interferon signaling pathway. The genes in the interferon signaling pathway include without limitation USP18, STING, MDA5, PKR, EIF2α, ATF4, IRF9, RIG1, TBK1, IRF3, PD-L1, and a combination thereof. Cell death following ATF4 activation of the ER stress response and the unfolded protein response results in immunogenic cell death. Other genes are known to those ordinarily skilled in the art. In a particular embodiment, an interferon pathway activator that finds use in the methods of treatment of the present disclosure is an interferon pathway activator that is capable of stimulating the expression of STING (e.g., is capable of activating STING). STING is also known in the art as ERIS, MITA, MPYS, and TMEM173.

The interferon pathway activator can be any molecule (e.g., small molecule, biomolecule) that stimulates the activation or expression of an interferon signaling pathway gene. Various methods of detecting the activation or expression of an interferon signaling pathway gene are known in the art. For example, the biological activity of an interferon pathway activator of the invention can be confirmed using, e.g., a virus-plaque-reduction assay, assays that measure the inhibition of cell proliferation, the regulation of functional cellular activities, the regulation of cellular differentiation, and immunomodulation, as well as a reporter gene assay, in which the promoter region of IFN responsive genes is linked with a heterologous reporter gene, for example, firefly luciferase or alkaline phosphatase, and transfected into an IFN-sensitive cell line such that stably transfected cell lines exposed to an interferon pathway activator increase expression of the reporter gene product. Other assays for measuring an interferon pathway activator include measuring the upregulation or activity of the double-stranded RNA (dsRNA)-dependent protein kinase R (PKR), the 2'-5'-oligoadenylate synthetase (2'-5'-OAS), IFN-inducible Mx proteins, a tryptophan-degrading enzyme (see, e.g., Pfefferkorn, Proc. Natl. Acad. Sci. USA 81:908-912, 1984), IFN-stimulated gene 20 (ISG20), p56, ISG15, mGBP2, GBP-1, the APOBEC proteins, viperin, or other factors (see, e.g., Zhang et al., J. Virol., 81:11246-11255, 2007, and U.S. Pat. No. 7,442,527). Where activation of an interferon signaling pathway is mediated by activation of STING, aggregation of STING, which can be detected by immunostaining, native gel electrophoresis, or other methods known in the art, also indicates an activation of an interferon signaling pathway.

In some embodiments, an interferon pathway activator for use in a method of treatment as described herein is a cyclic dinucleotide that activates STING. Cyclic dinucleotides have been described herein, e.g., without limitation, a cyclic guanosine monophosphate-adenosine monophosphate (cGAMP), a cyclic di-adenosine monophosphate (c-di-AMP) (e.g., bis-(3', 5')-cyclic dimeric adenosine monophosphate), or a cyclic diguanylate (c-di-GMP) (e.g., bis-(3', 5')-cyclic dimeric guanosine monophosphate). In some cases, a cyclic dinucleotide that finds use in a method of treatment as described herein is a synthetic cyclic dinucleotide. Synthetic cyclic dinucleotides may include, for example, without limitation, 2'2'-cGAMP, 2'3'-cGAMP, 2'3'-cGAM(PS)2 (Rp/Sp), 3'3'-cGAMP, c-di-AMP, 2'3'-c-di-AMP, 2'3'-c-di-AM(PS)2 (Rp,Rp), c-di-GMP, 2'3'-c-di-GMP, c-di-IMP, c-di-UMP, or an analog thereof. In some cases, a cyclic dinucleotide that finds use in a method of treatment as described herein is the xanthenone analog DMXAA, which is also known in the art as Vadimezan or ASA404. A cyclic dinucleotide for use in a method of treatment as described herein may be an isomer of a cyclic dinucleotide already described herein.

In other embodiments, an interferon pathway activator for use in a method of treatment as described herein is a DNA methylation inhibitor (e.g., a DNA methyltransferase inhibitor). DNA methylation inhibitors have recently been shown to trigger interferon signaling pathway components by inducing a phenomenon called viral mimicry. See, e.g., Roulois et al. Cell 2015, 162(5):961-973 and Chiappinelli et al. Cell 2015, 162(5):974-986. There are two classes of DNA methyltransferase inhibitors, nucleoside analogues and non-nucleosides. Examples of DNA methyltransferase inhibitors that are nucleoside analogues, without limitation, include azacitidine (5-azacytidine), decitabine (5-aza-2'-deoxycytidine), 5-fluoro-2'-deoxycitidine, 5,6-dihydro-5-azacytidine (DHAC), zebularine (2'-O-t-butyldimethylsilyl-3'-O-[(diisopropylamino)(2-cyanoethoxy)phosphi-no]-5'-O-(4,4'-dimethoxytrityl)-2(1H)-pyrimidinone-1-j-D-riboside), fazarabine (1-β-D-arabinofuranosyl-5-azacytosine). Examples of non-nucleoside DNA methyltransferase inhibitors include, without limitation, hydralizine, procaine, procainamide, epigallocatechin gallate, psammaplin A, and RG108 ((S)-2-(1,3-dioxo-1,3-dihydro-isoindol-2-yl)-3-(1H-indol-3-yl)-propionic acid). Accordingly, in a particular embodiment, a method of treating a subject in need thereof, includes administering to the subject an effective amount of an ADAR1 inhibitor or ISG15 inhibitor, and administering to the subject an effective amount of azacytidine (5'-azacytidine).

In other embodiments, an interferon pathway activator for use in a method of treatment as described herein is an interferon. There are three types of interferons, where type I and type II are in general responsible for regulating and activating the immune response, and type III interferon signals through a receptor complex that includes IL10R2 and IFNLR1. In particular embodiments, the effective amount of interferon is an effective amount of a type I interferon. In mammals, type I interferons include IFN-α (alpha), IFN-β (beta), IFN-κ (kappa), IFN-δ (delta), IFN-ε (epsilon), IFN-τ (tau), IFN-ω (omega), and TFN-ζ (zeta, also known as limuitin). In particular embodiments, the effective amount of interferon is an effective amount of human IFN-a (e.g., IFN-α-1a, IFN-α-1b, IFN-α-2a, IFN-α-2b, and consensus IFN-α (conIFN-α) (as described in the art), a human IFN-β (e.g., IFN-β-1a and IFN-β-1b), a human IFN-γ), or an IFN-τ or a polypeptide that demonstrates the same or similar biological activity to an interferon as described herein. In particular embodiments, an effective amount of interferon for use in a method of treating a subject in need thereof, is an effective amount of interferon-β (IFN-β).

Any combination of treatment methods as described herein may be used. The treatment methods may be combined simultaneously, or performed one after another, in no particular order. For example, a method of treating a subject in need thereof, includes administering an effective amount of an ADAR1 inhibitor or ISG15 inhibitor, and administering an effective amount of interferon pathway activator, and administering an effective amount of interferon. In one embodiment, a method of treating a subject in need thereof, includes administering an effective amount of an ADAR1 inhibitor, and administering an effective amount of interferon pathway activator. In one embodiment, a method of treating a subject in need thereof, includes administering an effective amount of an ISG15 inhibitor, and administering an effective amount of interferon pathway activator. In one embodiment, a method of treating a subject in need thereof, includes administering an effective amount of an ADAR1 inhibitor, and administering an effective amount of interferon. In one embodiment, a method of treating a subject in need thereof, includes administering an effective amount of an ISG15 inhibitor, and administering an effective amount of interferon. In one embodiment, a method of treating a subject in need thereof, includes administering an effective amount of an ADAR1 inhibitor, administering an effective amount of an interferon pathway activator, and administering an effective amount of interferon. In one embodiment, a method of treating a subject in need thereof, includes administering an effective amount of an ISG15 inhibitor, administering an effective amount of an interferon pathway activator, and administering an effective amount of interferon.

The ADAR1 inhibitor or ISG15 inhibitor can be administered to the subject before or after the administration of the interferon pathway activator. Also, the ADAR1 inhibitor or ISG15 inhibitor can be administered simultaneously with the interferon pathway activator (e.g., in a single composition, or in separate compositions administered within an hour, two hours, four hours, or during the same doctor visit). Those ordinarily skilled in the art would be able to recognize the optimal way in performing a treatment including the use of an effective amount of an interferon pathway activator and an effective amount of an ADAR1 inhibitor or ISG15 inhibitor.

In such embodiments, administering of an ADAR1 inhibitor or ISG15 inhibitor together with an interferon pathway activator (e.g., simultaneous administration or one after another), may provide a synergistic effect on the subject in need thereof. For example, simultaneously administering an ADAR1 inhibitor or ISG15 inhibitor together with an interferon pathway activator may further decrease the proliferation of a high proliferation cell (e.g., cancer cell) from the patient. As another example, simultaneously administering an ADAR1 inhibitor or ISG15 inhibitor together with an interferon pathway activator may kill a high proliferation cell, whereas administration of an ADAR1 inhibitor or ISG15 inhibitor alone may only decrease the proliferation of a high proliferation cell.

The term "targeted therapy" refers to administration of agents that selectively interact with a chosen biomolecule to thereby treat cancer. One example includes immunotherapies such as immune checkpoint inhibitors, which are well-known in the art. For example, anti-PD-1 pathway agents, such as therapeutic monoclonal blocking antibodies, which are well-known in the art and described above, can be used to target tumor microenvironments and cells expressing unwanted components of the PD-1 pathway, such as PD-1, PD-L1, and/or PD-L2.

For example, the term "PD-1 pathway" refers to the PD-1 receptor and its ligands, PD-L1 and PD-L2. "PD-1 pathway inhibitors" block or otherwise reduce the interaction between PD-1 and one or both of its ligands such that the immunoinhibitory signaling otherwise generated by the interaction is blocked or otherwise reduced. Anti-immune checkpoint inhibitors can be direct or indirect. Direct anti-immune checkpoint inhibitors block or otherwise reduce the interaction between an immune checkpoint and at least one of its ligands. For example, PD-1 inhibitors can block PD-1 binding with one or both of its ligands. Direct PD-1 combination inhibitors are well-known in the art, especially since the natural binding partners of PD-1 (e.g., PD-L1 and PD-L2), PD-L1 (e.g., PD-1 and B7-1), and PD-L2 (e.g., PD-1 and RGMb) are known.

For example, agents which directly block the interaction between PD-1 and PD-L1, PD-1 and PD-L2, PD-1 and both PD-L1 and PD-L2, such as a bispecific antibody, can prevent inhibitory signaling and upregulate an immune response (i.e., as a PD-1 pathway inhibitor). Alternatively, agents that indirectly block the interaction between PD-1 and one or both of its ligands can prevent inhibitory signaling and upregulate an immune response. For example, B7-1 or a soluble form thereof, by binding to a PD-L1 polypeptide indirectly reduces the effective concentration of PD-L1 polypeptide available to bind to PD-1. Exemplary agents include monospecific or bispecific blocking antibodies against PD-1, PD-L1, and/or PD-L2 that block the interaction between the receptor and ligand(s); a non-activating form of PD-1, PD-L1, and/or PD-L2 (e.g., a dominant negative or soluble polypeptide), small molecules or peptides that block the interaction between PD-1, PD-L1, and/or PD-L2; fusion proteins (e.g. the extracellular portion of PD-1, PD-L1, and/or PD-L2, fused to the Fc portion of an antibody or immunoglobulin) that bind to PD-1, PD-L1, and/or PD-L2 and inhibit the interaction between the receptor and ligand(s); a non-activating form of a natural PD-1, PD-L2, and/or PD-L2 ligand, and a soluble form of a natural PD-1, PD-L2, and/or PD-L2 ligand.

Indirect anti-immune checkpoint inhibitors block or otherwise reduce the immunoinhibitory signaling generated by the interaction between the immune checkpoint and at least one of its ligands. For example, an inhibitor can block the interaction between PD-1 and one or both of its ligands without necessarily directly blocking the interaction between PD-1 and one or both of its ligands. For example, indirect inhibitors include intrabodies that bind the intracellular portion of PD-1 and/or PD-L1 required to signal to block or otherwise reduce the immunoinhibitory signaling. Similarly, nucleic acids that reduce the expression of PD-1, PD-L1, and/or PD-L2 can indirectly inhibit the interaction between PD-1 and one or both of its ligands by removing the availability of components for interaction. Such nucleic acid molecules can block PD-L1, PD-L2, and/or PD-L2 transcription or translation.

Similarly, agents which indirectly block or enhance the interaction between ADAR, ZC3HAV1, PPP1R15A, and/or EIF2AK2/PKR and their binding partners/substrates, and the like, can inhibit or enhance ADAR, ZC3HAV1, PPP1R15A, and/or EIF2AK2/PKR and promote downstream signaling and immune responses, such as increasing sensitivity to interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist) signaling, dsRNA editing, sensing, and/or metabolism, and immunotherapies. For example, a truncated or dominant negative form of ADAR, ZC3HAV1, and/or PPP1R15A, and/or a full-length or dominant positive form of EIF2AK2/PKR, by binding to an ADAR, ZC3HAV1, PPP1R15A, and/or EIF2AK2/PKR substrate indirectly reduces or increase the effective concentration of such substrate available to bind to ADAR, ZC3HAV1, PPP1R15A, and/or EIF2AK2/PKR. Exemplary agents include monospecific or bispecific antibodies, especially intrabodies, against ADAR, ZC3HAV1, PPP1R15A, and/or EIF2AK2/PKR and/or ADAR, ZC3HAV1, PPP1R15A, and/or EIF2AK2/PKR substrate(s) that block or enhance the interaction between the ADAR, ZC3HAV1, PPP1R15A, and/or EIF2AK2/PKR and its substrate(s); a non-active form of ADAR, ZC3HAV1, and/or PPP1R15A, and/or an active form of EIF2AK2/PKR, or ADAR, ZC3HAV1, PPP1R15A, and/or EIF2AK2/PKR substrate(s) (e.g., a dominant negative or dominant positive polypeptide), small molecules or peptides that block the interaction between ADAR, ZC3HAV1, and/or PPP1R15A, and/or enhance the interaction between EIF2AK2/PKR, and its substrate(s) or the catalytic activity of ADAR, ZC3HAV1, PPP1R15A, and/or EIF2AK2/PKR; and a non-activating form of a natural ADAR, ZC3HAV1, and.or PPP1R15A, and/or a constitutively active form of EIF2AK2/PKR, or its substrate(s).

Immunotherapies that are designed to elicit or amplify an immune response are referred to as "activation immunotherapies." Immunotherapies that are designed to reduce or suppress an immune response are referred to as "suppression immunotherapies." Any agent believed to have an immune system effect on the genetically modified transplanted cancer cells can be assayed to determine whether the agent is an immunotherapy and the effect that a given genetic modification has on the modulation of immune response. In some embodiments, the immunotherapy is cancer cell-specific. In some embodiments, immunotherapy can be "untargeted," which refers to administration of agents that do not selectively interact with immune system cells, yet modulates immune system function. Representative examples of untargeted therapies include, without limitation, chemotherapy, gene therapy, and radiation therapy.

Immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

In one embodiment, immunotherapy comprises adoptive cell-based immunotherapies. Well-known adoptive cell-based immunotherapeutic modalities, including, without limitation, irradiated autologous or allogeneic tumor cells, tumor lysates or apoptotic tumor cells, antigen-presenting cell-based immunotherapy, dendritic cell-based immunotherapy, adoptive T cell transfer, adoptive CAR T cell therapy, autologous immune enhancement therapy (AIET), cancer vaccines, and/or antigen presenting cells. Such cell-based immunotherapies can be further modified to express one or more gene products to further modulate immune responses, such as expressing cytokines like GM-CSF, and/or to express tumor-associated antigen (TAA) antigens, such as Mage-1, gp-100, patient-specific neoantigen vaccines, and the like.

In another embodiment, immunotherapy comprises non-cell-based immunotherapies. In one embodiment, compositions comprising antigens with or without vaccine-enhancing adjuvants are used. Such compositions exist in many well-known forms, such as peptide compositions, oncolytic viruses, recombinant antigen comprising fusion proteins, and the like. In still another embodiment, immunomodulatory interleukins, such as IL-2, IL-6, IL-7, IL-12, IL-17, IL-23, and the like, as well as modulators thereof (e.g., blocking antibodies or more potent or longer lasting forms) are used. In yet another embodiment, immunomodulatory cytokines, such as interferons, G-CSF, imiquimod, TNFalpha, and the like, as well as modulators thereof (e.g., blocking antibodies or more potent or longer lasting forms) are used. In another embodiment, immunomodulatory chemokines, such as CCL3, CCL26, and CXCL7, and the like, as well as modulators thereof (e.g., blocking antibodies or more potent or longer lasting forms) are used. In another embodiment, immunomodulatory molecules targeting immunosuppression, such as STAT3 signaling modulators, NFkappaB signaling modulators, and immune checkpoint modulators, are used. The terms "immune checkpoint" and "anti-immune checkpoint therapy" are described above.

In still another embodiment, immunomodulatory drugs, such as immunocytostatic drugs, glucocorticoids, cytostatics, immunophilins and modulators thereof (e.g., rapamycin, a calcineurin inhibitor, tacrolimus, ciclosporin (cyclosporin), pimecrolimus, abetimus, gusperimus, ridaforolimus, everolimus, temsirolimus, zotarolimus, etc.), hydrocortisone (cortisol), cortisone acetate, prednisone, prednisolone, methylprednisolone, dexamethasone, betamethasone, triamcinolone, beclometasone, fludrocortisone acetate, deoxycorticosterone acetate (doca) aldosterone, a non-glucocorticoid steroid, a pyrimidine synthesis inhibitor, leflunomide, teriflunomide, a folic acid analog, methotrexate, anti-thymocyte globulin, anti-lymphocyte globulin, thalidomide, lenalidomide, pentoxifylline, bupropion, curcumin, catechin, an opioid, an IMPDH inhibitor, mycophenolic acid, myriocin, fingolimod, an NF-xB inhibitor, raloxifene, drotrecogin alfa, denosumab, an NF-xB signaling cascade inhibitor, disulfiram, olmesartan, dithiocarbamate, a proteasome inhibitor, bortezomib, MG132, Prol, NPI-0052, curcumin, genistein, resveratrol, parthenolide, thalidomide, lenalidomide, flavopiridol, non-steroidal anti-inflammatory drugs (NSAIDs), arsenic trioxide, dehydroxymethylepoxyquinomycin (DHMEQ), I3C(indole-3-carbinol)/DIM(di-indolmethane) (13C/DIM), Bay 11-7082, luteolin, cell permeable peptide SN-50, IKBa.-super repressor overexpression, NFKB decoy oligodeoxynucleotide (ODN), or a derivative or analog of any thereo, are used. In yet another embodiment, immunomodulatory antibodies or protein are used. For example, antibodies that bind to CD40, Toll-like receptor (TLR), OX40, GITR, CD27, or to 4-1BB, T-cell bispecific antibodies, an anti-IL-2 receptor antibody, an anti-CD3 antibody, OKT3 (muromonab), otelixizumab, teplizumab, visilizumab, an anti-CD4 antibody, cleneliximab, keliximab, zanolimumab, an anti-CD11 a antibody, efalizumab, an anti-CD18 antibody, erlizumab, rovelizumab, an anti-CD20 antibody, afutuzumab, ocrelizumab, ofatumumab, pascolizumab, rituximab, an anti-CD23 antibody, lumiliximab, an anti-CD40 antibody, teneliximab, toralizumab, an anti-CD40L antibody, ruplizumab, an anti-CD62L antibody, aselizumab, an anti-CD80 antibody, galiximab, an anti-CD147 antibody, gavilimomab, a B-Lymphocyte stimulator (BLyS) inhibiting antibody, belimumab, an CTLA4-Ig fusion protein, abatacept, belatacept, an anti-CTLA4 antibody, ipilimumab, tremelimumab, an anti-eotaxin 1 antibody, bertilimumab, an anti-a4-integrin antibody, natalizumab, an anti-IL-6R antibody, tocilizumab, an anti-LFA-1 antibody, odulimomab, an anti-CD25 antibody, basiliximab, daclizumab, inolimomab, an anti-CD5 antibody, zolimomab, an anti-CD2 antibody, siplizumab, nerelimomab, faralimomab, atlizumab, atorolimumab, cedelizumab, dorlimomab aritox, dorlixizumab, fontolizumab, gantenerumab, gomiliximab, lebrilizumab, maslimomab, morolimumab, pexelizumab, reslizumab, rovelizumab, talizumab, telimomab aritox, vapaliximab, vepalimomab, aflibercept, alefacept, rilonacept, an IL-1 receptor antagonist, anakinra, an anti-IL-5 antibody, mepolizumab, an IgE inhibitor, omalizumab, talizumab, an IL12 inhibitor, an IL23 inhibitor, ustekinumab, and the like.

Nutritional supplements that enhance immune responses, such as vitamin A, vitamin E, vitamin C, and the like, are well-known in the art (see, for example, U.S. Pat. Nos. 4,981,844 and 5,230,902 and PCT Publ. No. WO 2004/004483) can be used in the methods described herein.

Similarly, agents and therapies other than immunotherapy or in combination thereof can be used with in combination with ADAR, ZC3HAV1, PPP1R15A, and/or EIF2AK2/PKR modulators, alone or in combination with an immunotherapy, to stimulate an immune response to thereby treat a condition that would benefit therefrom. For example, chemotherapy, radiation, epigenetic modifiers (e.g., histone deacetylase (HDAC) modifiers, methylation modifiers, phosphorylation modifiers, and the like), targeted therapy, and the like are well-known in the art.

The term "untargeted therapy" refers to administration of agents that do not selectively interact with a chosen biomolecule yet treat cancer. Representative examples of untargeted therapies include, without limitation, chemotherapy, gene therapy, and radiation therapy.

In one embodiment, chemotherapy is used. Chemotherapy includes the administration of a chemotherapeutic agent. Such a chemotherapeutic agent may be, but is not limited to, those selected from among the following groups of compounds: platinum compounds, cytotoxic antibiotics, antimetabolites, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2) inhibitors are used and such inhibitors are well-known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al.). The mechanism of action is generally related to the ability of PARP inhibitors to bind PARP and decrease its activity. PARP catalyzes the conversion of .beta.-nicotinamide adenine dinucleotide (NAD+) into nicotinamide and poly-ADP-ribose (PAR). Both poly (ADP-ribose) and PARP have been linked to regulation of transcription, cell proliferation, genomic stability, and carcinogenesis (Bouchard V. J. et. al. Experimental Hematology, Volume 31, Number 6, June 2003, pp. 446-454(9); Herceg Z.; Wang Z.-Q. Mutation Research/Fundamental and Molecular Mechanisms of Mutagenesis, Volume 477, Number 1, 2 Jun. 2001, pp. 97-110(14)). Poly(ADP-ribose) polymerase 1 (PARP1) is a key molecule in the repair of DNA single-strand breaks (SSBs) (de Murcia J. et al. 1997. Proc Natl Acad Sci USA 94:7303-7307; Schreiber V, Dantzer F, Ame J C, de Murcia G (2006) Nat Rev Mol Cell Biol 7:517-528; Wang Z Q, et al. (1997) Genes Dev 11:2347-2358). Knockout of SSB repair by inhibition of PARP1 function induces DNA double-strand breaks (DSBs) that can trigger synthetic lethality in cancer cells with defective homology-directed DSB repair (Bryant H E, et al. (2005) *Nature* 434:913-917; Farmer H, et al. (2005) *Nature* 434:917-921). The foregoing examples of chemotherapeutic agents are illustrative, and are not intended to be limiting.

In another embodiment, radiation therapy is used. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In another embodiment, surgical intervention can occur to physically remove cancerous cells and/or tissues.

In still another embodiment, hormone therapy is used. Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

In yet another embodiment, hyperthermia, a procedure in which body tissue is exposed to high temperatures (up to 106° F.) is used. Heat may help shrink tumors by damaging cells or depriving them of substances they need to live. Hyperthermia therapy can be local, regional, and whole-body hyperthermia, using external and internal heating devices. Hyperthermia is almost always used with other forms of therapy (e.g., radiation therapy, chemotherapy, and biological therapy) to try to increase their effectiveness. Local hyperthermia refers to heat that is applied to a very small area, such as a tumor. The area may be heated externally with high-frequency waves aimed at a tumor from a device outside the body. To achieve internal heating, one of several types of sterile probes may be used, including thin, heated wires or hollow tubes filled with warm water; implanted microwave antennae; and radiofrequency electrodes. In regional hyperthermia, an organ or a limb is heated. Magnets and devices that produce high energy are placed over the region to be heated. In another approach, called perfusion, some of the patient's blood is removed, heated, and then pumped (perfused) into the region that is to be heated internally. Whole-body heating is used to treat metastatic cancer that has spread throughout the body. It can be accomplished using warm-water blankets, hot wax, inductive coils (like those in electric blankets), or thermal chambers (similar to large incubators). Hyperthermia does not cause any marked increase in radiation side effects or complications. Heat applied directly to the skin, however, can cause discomfort or even significant local pain in about half the patients treated. It can also cause blisters, which generally heal rapidly.

In still another embodiment, photodynamic therapy (also called PDT, photoradiation therapy, phototherapy, or photochemotherapy) is used for the treatment of some types of cancer. It is based on the discovery that certain chemicals known as photosensitizing agents can kill one-celled organisms when the organisms are exposed to a particular type of light. PDT destroys cancer cells through the use of a fixed-frequency laser light in combination with a photosensitizing agent. In PDT, the photosensitizing agent is injected into the bloodstream and absorbed by cells all over the body. The agent remains in cancer cells for a longer time than it does in normal cells. When the treated cancer cells are exposed to laser light, the photosensitizing agent absorbs the light and produces an active form of oxygen that destroys the treated cancer cells. Light exposure must be timed carefully so that it occurs when most of the photosensitizing agent has left healthy cells but is still present in the cancer cells. The laser light used in PDT can be directed through a fiber-optic (a very thin glass strand). The fiber-optic is placed close to the cancer to deliver the proper amount of light. The fiber-optic can be directed through a bronchoscope into the lungs for the treatment of lung cancer or through an endoscope into the esophagus for the treatment of esophageal cancer. An advantage of PDT is that it causes minimal damage to healthy tissue. However, because the laser light currently in use cannot pass through more than about 3 centimeters of tissue (a little more than one and an eighth inch), PDT is mainly used to treat tumors on or just under the skin or on the lining of internal organs. Photodynamic therapy makes the skin and eyes sensitive to light for 6 weeks or more after treatment. Patients are advised to avoid direct sunlight and bright indoor light for at least 6 weeks. If patients must go outdoors, they need to wear protective clothing, including sunglasses. Other temporary side effects of PDT are related to the treatment of specific areas and can include coughing, trouble swallowing, abdominal pain, and painful breathing or shortness of breath. In December 1995, the U.S. Food and Drug Administration (FDA) approved a photosensitizing agent called porfimer sodium, or Photofrin®, to relieve symptoms of esophageal cancer that is causing an obstruction and for esophageal cancer that cannot be satisfactorily treated with lasers alone. In January 1998, the FDA approved porfimer sodium for the treatment of early non-small cell lung cancer in patients for whom the usual treatments for lung cancer are not appropriate. The National Cancer Institute and other institutions are supporting clinical trials (research studies) to evaluate the use of photodynamic therapy for several types of cancer, including cancers of the bladder, brain, larynx, and oral cavity.

In yet another embodiment, laser therapy is used to harness high-intensity light to destroy cancer cells. This technique is often used to relieve symptoms of cancer such as bleeding or obstruction, especially when the cancer cannot be cured by other treatments. It may also be used to treat cancer by shrinking or destroying tumors. The term "laser" stands for light amplification by stimulated emission of radiation. Ordinary light, such as that from a light bulb, has many wavelengths and spreads in all directions. Laser light, on the other hand, has a specific wavelength and is focused in a narrow beam. This type of high-intensity light contains a lot of energy. Lasers are very powerful and may be used to cut through steel or to shape diamonds. Lasers also can be used for very precise surgical work, such as repairing a damaged retina in the eye or cutting through tissue (in place of a scalpel). Although there are several different kinds of lasers, only three kinds have gained wide use in medicine: Carbon dioxide ($CO_2$) laser—This type of laser can remove thin layers from the skin's surface without penetrating the deeper layers. This technique is particularly useful in treating tumors that have not spread deep into the skin and certain precancerous conditions. As an alternative to traditional scalpel surgery, the $CO_2$ laser is also able to cut the skin. The laser is used in this way to remove skin cancers. Neodymium:yttrium-aluminum-garnet (Nd:YAG) laser—Light from this laser can penetrate deeper into tissue than light from the other types of lasers, and it can cause blood to clot quickly. It can be carried through optical fibers to less accessible parts of the body. This type of laser is sometimes used to treat throat cancers. Argon laser—This laser can pass through only superficial layers of tissue and is therefore useful in dermatology and in eye surgery. It also is used with light-sensitive dyes to treat tumors in a procedure known as photodynamic therapy (PDT). Lasers have several advantages over standard surgical tools, including: Lasers are more precise than scalpels. Tissue near an incision is protected, since there is little contact with surrounding skin or other tissue. The heat produced by lasers sterilizes the surgery site, thus reducing the risk of infection. Less operating time may be needed because the precision of the laser allows for a smaller incision. Healing time is often shortened; since laser heat seals blood vessels, there is less bleeding, swelling, or scarring. Laser surgery may be less complicated. For example, with fiber optics, laser light can be directed to parts of the body without making a large incision. More procedures may be done on an outpatient basis. Lasers can be used in two ways to treat cancer: by shrinking or destroying a tumor with heat, or by activating a chemical—known as a photosensitizing agent—that destroys cancer cells. In PDT, a photosensitizing agent is retained in cancer cells and can be stimulated by light to cause a reaction that kills cancer cells. $CO_2$ and Nd:YAG lasers are used to shrink or destroy tumors. They may be used with endoscopes, tubes that allow physicians to see into certain areas of the body, such as the bladder. The light from some lasers can be transmitted through a flexible endoscope fitted with fiber optics. This allows physicians to see and work in parts of the body that could not otherwise be reached except by surgery and therefore allows very precise aiming of the laser beam. Lasers also may be used with low-power microscopes, giving the doctor a clear view of the site being treated. Used with other instruments, laser systems can produce a cutting area as small as 200 microns in diameter—less than the width of a very fine thread. Lasers are used to treat many types of cancer. Laser surgery is a standard treatment for certain stages of glottis (vocal cord), cervical, skin, lung, vaginal, vulvar, and penile cancers. In addition to its use to destroy the cancer, laser surgery is also used to help relieve symptoms caused by cancer (palliative care). For example, lasers may be used to shrink or destroy a tumor that is blocking a patient's trachea (windpipe), making it easier to breathe. It is also sometimes used for palliation in colorectal and anal cancer. Laser-induced interstitial thermotherapy (LITT) is one of the most recent developments in laser therapy. LITT uses the same idea as a cancer treatment called hyperthermia; that heat may help shrink tumors by damaging cells or depriving them of substances they need to live. In this treatment, lasers are directed to interstitial areas (areas between organs) in the body. The laser light then raises the temperature of the tumor, which damages or destroys cancer cells.

The duration and/or dose of treatment with therapies may vary according to the particular therapeutic agent or combination thereof. An appropriate treatment time for a particular cancer therapeutic agent will be appreciated by the skilled artisan. The present invention contemplates the continued assessment of optimal treatment schedules for each cancer therapeutic agent, where the phenotype of the cancer of the subject as determined by the methods of the present invention is a factor in determining optimal treatment doses and schedules.

Any means for the introduction of a polynucleotide into mammals, human or non-human, or cells thereof may be adapted to the practice of this invention for the delivery of the various constructs of the present invention into the intended recipient. In one embodiment of the present invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126-139, 1995). Formulation of DNA, e.g. with various lipid or liposome materials, may then be effected using known methods and materials and delivered to the recipient mammal. See, e.g., Canonico et al. Am J Respir Cell Mol Biol 10:24-29, 1994; Tsan et al, Am J Physiol 268; Alton et al., Nat Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well-known and any can be selected for a particular application. In one embodiment of the present invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the a- and p-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Felgner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide of the present invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al. (1990) J. Virol., 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In other embodiments, recombinant biomarker polypeptides, and fragments thereof, can be administered to subjects. In some embodiments, fusion proteins can be constructed and administered which have enhanced biological properties. In addition, the biomarker polypeptides, and fragment thereof, can be modified according to well-known pharmacological methods in the art (e.g., pegylation, glycosylation, oligomerization, etc.) in order to further enhance desirable biological activities, such as increased bioavailability and decreased proteolytic degradation.

VII. Clinical Efficacy

Clinical efficacy can be measured by any method known in the art. For example, the response to a therapy, such as ADAR, ZC3HAV1, PPP1R15A, and/or EIF2AK2/PKR modulators, alone or in combination with an immunotherapy and/or modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist), relates to any response of the cancer, e.g., a tumor, to the therapy, preferably to a change in tumor mass and/or volume after initiation of neoadjuvant or adjuvant chemotherapy. Tumor response may be assessed in a neoadjuvant or adjuvant situation where the size of a tumor after systemic intervention can be compared to the initial size and dimensions as measured by CT, PET, mammogram, ultrasound or palpation and the cellularity of a tumor can be estimated histologically and compared to the cellularity of a tumor biopsy taken before initiation of treatment. Response may also be assessed by caliper measurement or pathological examination of the tumor after biopsy or surgical resection. Response may be recorded in a quantitative fashion like percentage change in tumor volume or cellularity or using a semi-quantitative scoring system such as residual cancer burden (Symmans et al., *J. Cin. Oncol.* (2007) 25:4414-4422) or Miller-Payne score (Ogston et al., (2003) Breast (Edinburgh, Scotland) 12:320-327) in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of tumor response may be performed early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed.

In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular anti-immune checkpoint therapeutic regimen is at least 25%, 30%, 35%, 40%, 45%, 50%, 55%, 60%, 65%, 70%, 75%, 80%, 85%, or more.

Additional criteria for evaluating the response to immunotherapies, such as anti-immune checkpoint therapies, are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence.

For example, in order to determine appropriate threshold values, a particular anti-cancer therapeutic regimen can be administered to a population of subjects and the outcome can be correlated to biomarker measurements that were determined prior to administration of any immunotherapy, such as anti-immune checkpoint therapy. The outcome measurement may be pathologic response to therapy given in the neoadjuvant setting. Alternatively, outcome measures, such as overall survival and disease-free survival can be monitored over a period of time for subjects following immunotherapies for whom biomarker measurement values are known. In certain embodiments, the same doses of immunotherapy agents, if any, are administered to each subject. In related embodiments, the doses administered are standard doses known in the art for those agents used in immunotherapies. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of an immunotherapy can be determined using methods such as those described in the Examples section.

VIII. Further Uses and Methods of the Present Invention

The compositions described herein can be used in a variety of diagnostic, prognostic, and therapeutic applications. In any method described herein, such as a diagnostic method, prognostic method, therapeutic method, or combination thereof, all steps of the method can be performed by a single actor or, alternatively, by more than one actor. For example, diagnosis can be performed directly by the actor providing therapeutic treatment. Alternatively, a person providing a therapeutic agent can request that a diagnostic assay be performed. The diagnostician and/or the therapeutic interventionist can interpret the diagnostic assay results to determine a therapeutic strategy. Similarly, such alternative processes can apply to other assays, such as prognostic assays.

a. Screening Methods

One aspect of the present invention relates to screening assays, including non-cell based assays and xenograft animal model assays. In one embodiment, the assays provide a method for identifying whether a cancer is likely to respond to an ADAR, ZC3HAV1, PPP1R15A, and/or EIF2AK2/PKR modulators, alone or in combination with an immunotherapy and/or modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist), such as in a human by using a xenograft animal model assay, and/or whether an agent can inhibit the growth of or kill a cancer cell that is unlikely to respond to ADAR, ZC3HAV1, PPP1R15A, and/or EIF2AK2/PKR modulators, alone or in combination with an immunotherapy and/or modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist).

In one embodiment, the present invention relates to assays for screening test agents which bind to, or modulate the biological activity of, at least one biomarker described herein (e.g., in the tables, figures, examples, or otherwise in the specification). In one embodiment, a method for identifying such an agent entails determining the ability of the agent to modulate, e.g. inhibit, the at least one biomarker described herein.

In one embodiment, an assay is a cell-free or cell-based assay, comprising contacting at least one biomarker described herein, with a test agent, and determining the ability of the test agent to modulate (e.g., inhibit) the enzymatic activity of the biomarker, such as by measuring direct binding of substrates or by measuring indirect parameters as described below.

For example, in a direct binding assay, biomarker protein (or their respective target polypeptides or molecules) can be coupled with a radioisotope or enzymatic label such that binding can be determined by detecting the labeled protein or molecule in a complex. For example, the targets can be labeled with $^{125}$I, $^{35}$S, $^{14}$C, or $^{3}$H, either directly or indirectly, and the radioisotope detected by direct counting of radioemmission or by scintillation counting. Alternatively, the targets can be enzymatically labeled with, for example, horseradish peroxidase, alkaline phosphatase, or luciferase, and the enzymatic label detected by determination of conversion of an appropriate substrate to product. Determining the interaction between biomarker and substrate can also be accomplished using standard binding or enzymatic analysis assays. In one or more embodiments of the above described assay methods, it may be desirable to immobilize polypeptides or molecules to facilitate separation of complexed from uncomplexed forms of one or both of the proteins or molecules, as well as to accommodate automation of the assay.

Binding of a test agent to a target can be accomplished in any vessel suitable for containing the reactants. Non-limiting examples of such vessels include microtiter plates, test tubes, and micro-centrifuge tubes. Immobilized forms of the antibodies described herein can also include antibodies bound to a solid phase like a porous, microporous (with an average pore diameter less than about one micron) or macroporous (with an average pore diameter of more than about 10 microns) material, such as a membrane, cellulose, nitrocellulose, or glass fibers; a bead, such as that made of agarose or polyacrylamide or latex; or a surface of a dish, plate, or well, such as one made of polystyrene.

In an alternative embodiment, determining the ability of the agent to modulate the interaction between the biomarker and a substrate or a biomarker and its natural binding partner can be accomplished by determining the ability of the test agent to modulate the activity of a polypeptide or other product that functions downstream or upstream of its position within the signaling pathway (e.g., feedback loops). Such feedback loops are well-known in the art (see, for example, Chen and Guillemin (2009) Int. J. Tryptophan Res. 2:1-19).

The present invention further pertains to novel agents identified by the above-described screening assays. Accordingly, it is within the scope of this invention to further use an agent identified as described herein, such as in an appropriate animal model. For example, an agent identified as described herein can be used in an animal model to determine the efficacy, toxicity, or side effects of treatment with such an agent. Alternatively, an antibody identified as described herein can be used in an animal model to determine the mechanism of action of such an agent.

In some embodiments, the present disclosure also provides a method of screening to identify an agent, for use in a therapy. In some embodiments, the agent is further developed into a therapeutic agent for use in a cancer therapy. An agent identified by methods of screening of the present disclosure may be further developed into a therapeutic agent for use in treating subjects having cancer (e.g., lung or pancreatic cancer, or a cancer caused by a virus).

In one embodiment, a method of screening as provided herein includes (a) obtaining a first population of cells and a second population of cells; (b) contacting the first and second populations of cells with a test agent; and (c) determining the viability of the first and second populations of cells after the contacting step (b). In some cases, step (a) includes obtaining a first population of cells and a second population of cells, wherein the first population of cells have elevated interferon signaling pathway activity relative to the second population of cells. Methods of determining whether a cell has an elevated interferon signaling pathway activity are described herein. For example, an elevated expression level and/or phosphorylation of one or more interferon stimulated genes may indicate an elevated interferon signaling pathway activity. In some embodiments, an elevated interferon signaling pathway activity is indicated by an elevated expression level and/or phosphorylation of one or more of the genes ADAR1, ISG15, USP18, STING, MDA5, PKR, EIF2α, ATF4, IRF9, RIG1, TBK1, IRF3, PD-L1, and a combination thereof. A database of interferon regulated genes can be found at "www.interferome"followed by".org", and as described in Samarajiwa et al., Nucleic Acids Res. 2009, 37(database issue):D852-857. Those ordinarily skilled in the art would be able to access a database of interferon regulated genes and select further interferon stimulated genes for use in the methods described herein. In some cases, an elevated interferon signaling pathway activity is indicated by an elevated expression level of one or more interferon stimulated genes, wherein the one or more interferon stimulated genes comprises ADAR. In such cases, an elevated interferon signaling pathway activity is indicated by an elevated expression level of the p150 isoform of ADAR1.

In some embodiments, the first population of cells having an elevated interferon signaling pathway activity relative to the second population of cells, has an interferon signaling pathway activity that is, for example, at least 5% elevated, at least 10% elevated, at least 15% elevated, at least 20% elevated, at least 25% elevated, at least 30% elevated, at least 35% elevated, at least 40% elevated, at least 45% elevated, at least 50% elevated, at least 60% elevated, at least 70% elevated, at least 80% elevated, at least 90% elevated, at least 100% elevated, relative to the interferon signaling pathway activity of the second population of cells. In some embodiments, the first population of cells has an interferon signaling pathway activity that is, for example, at least two times, at least three times, at least four times, at least five times, at least six times, at least seven times, at least eight times, at least nine times, at least ten times or more, the interferon signaling pathway activity of the second population of cells.

In one embodiment, a method of screening as provided herein includes (a) obtaining a first population of cells and a second population of cells; (b) contacting the first and second populations of cells with a test agent; and (c) determining the viability of the first and second populations of cells after the contacting step (b), wherein the test agent is a potential therapeutic agent for use in a cancer therapy if the test agent reduces the viability of the first population of cells more than the viability of the second population of cells. A method of screening as provided in the present disclosure may be particularly useful in identifying an inhibitor of ADAR1 or an inhibitor of ISG15, which may further be developed into a therapeutic agent for use in a cancer therapy.

In some embodiments, the first population of cells that has an elevated interferon signaling pathway activity relative to the second population of cells includes cancer cells. In some cases, the first population of cells includes lung cancer cells or pancreatic cancer cells. In some cases, the first population of cells includes cancer cells that are caused by a virus. In such cases, a method of screening may include infecting a first population of cells with a virus that causes cancer. For example, HPV, EBV, HBV, HCV, HHV-8, HTLV-1, and MCV are known in the art to cause cancer in cells. In some embodiments, the first population of cells is, without limitation, derived from the following cell lines: NCI-H196, HCC-366, NCI-H1650, PA-TU-8902, HCC-1438, NCI-H196, NCI-H460, NCI-H596, HeLa, and SW-900. Other cell lines known to those ordinarily skilled in the art may find use as a first population of cells in methods of screening described herein. For example, cell lines with elevated basal interferon signaling pathway activity may be suitable for use as a first population of cells in methods of screening described herein.

In some embodiments, the second population of cells that have a lower level of interferon signaling pathway activity as compared to the first population of cells are non-cancer cells. In some embodiments, the second population of cells may be derived from the first population of cells by contacting the first population of cells with an inhibitor of cGAS, STING, IFIT2, IFIT3, IFNAR1, IFNAR2, IRF9, JAK1, STAT2, or TYK2. Such inhibitors may be a chemical or molecule that reduces the activity of cGAS, STING, IFIT2, IFIT3, IFNAR1, IFNAR2, IRF9, JAK1, STAT2, or TYK2. For example, the inhibitor can be a short hairpin RNA (shRNA) or guide RNA (gRNA) that targets cGAS, STING, IFIT2, IFIT3, IFNAR1, IFNAR2, IRF9, JAK1, STAT2, or TYK2. Other genes that can be targeted for use in a screening method described herein are readily known in the art. For example, those of skill in the art can access a database of interferon regulated genes at "www.interferome-"followed by".org", and as described in Samarajiwa et al., Nucleic Acids Res. 2009, 37(database issue):D852-857. Those ordinarily skilled in the art would be able to further select suitable genes for use in the methods of screening described herein. In some embodiments, the second population of cells is, without limitation, derived from the following cell lines: A549, NCI-H460, NCI-H1437, NCI-H1299, RERFLCAI, and RKO. As such, a first population of cells and a second population of cells derived from the first population of cells can be examined, for example, for response to a test agent, at the same time.

In some embodiments, the first population of cells may be derived from the second population of cells by contacting the second population of cells with an activator of cGAS, STING, IFIT2, IFIT3, IFNAR1, IFNAR2, IRF9, JAK1, STAT2, or TYK2. Activators of cGAS and STING include without limitation cyclic dinucleotides described herein. In some embodiments, the cyclic dinucleotide is selected from the group consisting of a cyclic guanosine monophosphate-adenosine monophosphate (cGAMP), a cyclic di-adenosine monophosphate (c-di-AMP), a cyclic diguanylate (c-di-GMP), a synthetic cyclic dinucleotide, and an isomer thereof. As used herein, the terms of "first population of cells" and "second population of cells" encompass the cells, the progeny of the cells, and the parent cells from which the cells divide from. As such, a second population of cells and a first population of cells derived from the second population of cells can be examined, for example, for response to a test agent, at the same time.

Other cell lines known to those ordinarily skilled in the art may find use as a second population of cells in methods of screening described herein. For example, cell lines that have not been infected by a cancer-causing virus may be suitable for use as a second population of cells in methods of screening described herein. Accordingly, the second population of cells may be derived from the first population of cells by infecting the first population of cells with a virus that is known to cause cancer (as described herein).

In some embodiments, methods of screening to identify an ADAR inhibitor are provided herein, including methods comprising (a) obtaining a first population of cells and a second population of cells; (b) contacting the first and second populations of cells with a test agent; and (c) determining the viability of the first and second populations of cells after the contacting step (b), wherein the test agent is a potential therapeutic agent for use in a cancer therapy if the test agent reduces the viability of the first population of cells more than the viability of the second population of cells.

In one embodiments, the first population of cells has ADAR1 dependency. A method of detecting ADAR1 dependency in a high proliferation cell is provided in other sections of the present invention. In another embodiment, the second cell population is derived from the first population but has a reduced activity of PKR, cGAS, and/or STING, optionally wherein the reduced activity of PKR, cGAS, and/or STING comprises reduced expression level or phosphorylation of PKR, cGAS, and/or STING. For example, the second cell population may be isogenic cells derived from the first population with loss of function of PKR, cGAS, and/or STING. In yet another embodiment, the test agent has been screened with any other method of screening disclosed herein and identified as an agent for cancer therapy. The first and/or second cell population may be used in any other method of screening disclosed in the present invention.

b. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining the amount and/or activity level of a biomarker described herein in the context of a biological sample (e.g., blood, serum, cells, or tissue) to thereby determine whether an individual afflicted with a cancer is likely to respond to ADAR, ZC3HAV1, PPP1R15A, and/or EIF2AK2/PKR modulators, alone or in combination with an immunotherapy and/or modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist), such as in a cancer. Such assays can be used for prognostic or predictive purpose alone, or can be coupled with a therapeutic intervention to thereby prophylactically treat an individual prior to the onset or after recurrence of a disorder characterized by or associated with biomarker polypeptide, nucleic acid expression or activity. The skilled artisan will appreciate that any method can use one or more (e.g., combinations) of biomarkers described herein, such as those in the tables, figures, examples, and otherwise described in the specification.

Another aspect of the present invention pertains to monitoring the influence of agents (e.g., drugs, compounds, and small nucleic acid-based molecules) on the expression or activity of a biomarker described herein. These and other agents are described in further detail in the following sections.

The skilled artisan will also appreciated that, in certain embodiments, the methods of the present invention implement a computer program and computer system. For example, a computer program can be used to perform the algorithms described herein. A computer system can also store and manipulate data generated by the methods of the present invention which comprises a plurality of biomarker signal changes/profiles which can be used by a computer system in implementing the methods of this invention. In certain embodiments, a computer system receives biomarker expression data; (ii) stores the data; and (iii) compares the data in any number of ways described herein (e.g., analysis relative to appropriate controls) to determine the state of informative biomarkers from cancerous or pre-cancerous tissue. In other embodiments, a computer system (i) compares the determined expression biomarker level to a threshold value; and (ii) outputs an indication of whether said biomarker level is significantly modulated (e.g., above or below) the threshold value, or a phenotype based on said indication. Or, for example, a computer system can also store and manipulate data generated by the methods of the present invention which comprises a plurality of interferon stimulated factors (ISGs) signal changes/profiles which can be used by a computer system in implementing the methods of this invention. In certain embodiments, a computer system receives one or more interferon stimulated factors (ISGs) activity data; (ii) stores the data; and (iii) compares the data in any number of ways described herein (e.g., analysis relative to appropriate controls) to determine the state of informative ISGs from cancerous or pre-cancerous tissue. In other embodiments, a computer system (i) compares the determined activity of one or more interferon stimulated genes (ISGs) to a threshold value; and (ii) outputs an indication of whether said ISG activity is significantly modulated (e.g., above or below) the threshold value, or a phenotype based on said indication.

In certain embodiments, such computer systems are also considered part of the present invention. Numerous types of computer systems can be used to implement the analytic methods of this invention according to knowledge possessed by a skilled artisan in the bioinformatics and/or computer arts. Several software components can be loaded into memory during operation of such a computer system. The software components can comprise both software components that are standard in the art and components that are special to the present invention (e.g., dCHIP software described in Lin et al. (2004) *Bioinformatics* 20, 1233-1240; radial basis machine learning algorithms (RBM) known in the art).

The methods of the present invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.).

In certain embodiments, the computer comprises a database for storage of biomarker data. Such stored profiles can be accessed and used to perform comparisons of interest at a later point in time. For example, biomarker expression profiles of a sample derived from the non-cancerous tissue of a subject and/or profiles generated from population-based distributions of informative loci of interest in relevant populations of the same species can be stored and later compared to that of a sample derived from the cancerous tissue of the subject or tissue suspected of being cancerous of the subject.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

c. Diagnostic Assays

The present invention provides, in part, methods, systems, and code for accurately classifying whether a biological sample is associated with a cancer that is likely to respond to ADAR, ZC3HAV1, PPP1R15A, and/or EIF2AK2/PKR modulators, alone or in combination with an immunotherapy and/or modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist). In some embodiments, the present invention is useful for classifying a sample (e.g., from a subject) as associated with or at risk for responding to or not responding to ADAR, ZC3HAV1, PPP1R15A, and/or EIF2AK2/PKR modulators, alone or in combination with an immunotherapy and/or modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist) using a statistical algorithm and/or empirical data (e.g., the amount or activity of a biomarker described herein, such as in the tables, figures, examples, and otherwise described in the specification).

An exemplary method for detecting the amount or activity of a biomarker described herein, and thus useful for classifying whether a sample is likely or unlikely to respond to ADAR, ZC3HAV1, PPP1R15A, and/or EIF2AK2/PKR modulators, alone or in combination with an immunotherapy and/or modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist) involves obtaining a biological sample from a test subject and contacting the biological sample with an agent, such as a protein-binding agent like an antibody or antigen-binding fragment thereof, or a nucleic acid-binding agent like an oligonucleotide, capable of detecting the amount or activity of the biomarker in the biological sample. In some embodiment, measuring the activity of the interferon signaling pathway comprises detecting the activity of one or more interferon stimulated factors (ISGs). An exemplary method for detecting the amount or activity of an interferon stimulated factor, and thus useful for classifying whether a sample is likely or unlikely to respond to an ADAR involves obtaining a biological sample from a test subject and contacting the biological sample with an agent, such as a protein-binding agent like an antibody or antigen-binding fragment thereof, or a nucleic acid-binding agent like an oligonucleotide, capable of detecting the amount or activity of the interferon stimulated factor in the biological sample. In some embodiments, at least one antibody or antigen-binding fragment thereof is used, wherein two, three, four, five, six, seven, eight, nine, ten, or more such antibodies or antibody fragments can be used in combination (e.g., in sandwich ELISAs) or in serial. In certain instances, the statistical algorithm is a single learning statistical classifier system. For example, a single learning statistical classifier system can be used to classify a sample as a based upon a prediction or probability value and the presence or level of the biomarker. The use of a single learning statistical classifier system typically classifies the sample as, for example, a likely immunotherapy responder or progressor sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well-known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method of the present invention further comprises sending the sample classification results to a clinician, e.g., an oncologist.

In another embodiment, the diagnosis of a subject is followed by administering to the individual a therapeutically effective amount of a defined treatment based upon the diagnosis.

In one embodiment, the methods further involve obtaining a control biological sample (e.g., biological sample from a subject who does not have a cancer or whose cancer is susceptible to ADAR, ZC3HAV1, PPP1R15A, and/or EIF2AK2/PKR modulators, alone or in combination with an immunotherapy and/or modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist), a biological sample from the subject during remission, or a biological sample from the subject during treatment for developing a cancer progressing despite ADAR, ZC3HAV1, PPP1R15A, and/or EIF2AK2/PKR modulators, alone or in combination with an immunotherapy and/or modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist)).

d. Prognostic Assays

The diagnostic methods described herein can furthermore be utilized to identify subjects having or at risk of developing a cancer that is likely or unlikely to be responsive to ADAR, ZC3HAV1, PPP1R15A, and/or EIF2AK2/PKR modulators, alone or in combination with an immunotherapy and/or modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist). The assays described herein, such as the preceding diagnostic assays or the following assays, can be utilized to identify a subject having or at risk of developing a disorder associated with a misregulation of the amount or activity of at least one biomarker described herein, such as in cancer. Alternatively, the prognostic assays can be utilized to identify a subject having or at risk for developing a disorder associated with a misregulation of the at least one biomarker described herein, such as in cancer. Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with the aberrant biomarker expression or activity.

e. Treatment Methods

The therapeutic compositions described herein, such as ADAR, ZC3HAV1, PPP1R15A, and/or EIF2AK2/PKR modulators, alone or in combination with an immunotherapy and/or modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist), can be used in a variety of in vitro and in vivo therapeutic applications using the formulations and/or combinations described herein. In one embodiment, the therapeutic agents can be used to treat cancers determined to be responsive thereto. For example, single or multiple agents that inhibit or block ADAR, ZC3HAV1, and/or PPP1R15A, and/or activate or enhance EIF2AK2/PKR, alone or in combination with an immunotherapy and/or modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist) can be used to treat cancers in subjects identified as likely responders thereto.

Modulatory methods of the present invention involve contacting a cell, such as an immune cell with an agent that inhibits, blocks, or enhance the expression and/or activity of ADAR, ZC3HAV1, PPP1R15A, and/or EIF2AK2/PKR, alone or in combination with modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist) and/or an immunotherapy, such as an immune checkpoint inhibitor (e.g., PD-1). Exemplary agents useful in such methods are described above. Such agents can be administered in vitro or ex vivo (e.g., by contacting the cell with the agent) or, alternatively, in vivo (e.g., by administering the agent to a subject). As such, the present invention provides methods useful for treating an individual afflicted with a condition that would benefit from an increased immune response, such as an infection or a cancer like colorectal cancer.

Agents that upregulate immune responses can be in the form of enhancing an existing immune response or eliciting an initial immune response. Thus, enhancing an immune response using the subject compositions and methods is useful for treating cancer, but can also be useful for treating an infectious disease (e.g., bacteria, viruses, or parasites), a parasitic infection, and an immunosuppressive disease.

Exemplary infectious disorders include viral skin diseases, such as Herpes or shingles, in which case such an agent can be delivered topically to the skin. In addition, systemic viral diseases, such as influenza, the common cold, and encephalitis might be alleviated by systemic administration of such agents. In one preferred embodiment, agents that upregulate the immune response described herein are useful for modulating the arginase/iNOS balance during *Trypanosoma cruzi* infection in order to facilitate a protective immune response against the parasite.

Immune responses can also be enhanced in an infected patient through an ex vivo approach, for instance, by removing immune cells from the patient, contacting immune cells in vitro with an agent described herein and reintroducing the in vitro stimulated immune cells into the patient.

In certain instances, it may be desirable to further administer other agents that upregulate immune responses, for example, forms of other B7 family members that transduce signals via costimulatory receptors, in order to further augment the immune response. Such additional agents and therapies are described further below.

Agents that upregulate an immune response can be used prophylactically in vaccines against various polypeptides (e.g., polypeptides derived from pathogens). Immunity against a pathogen (e.g., a virus) can be induced by vaccinating with a viral protein along with an agent that upregulates an immune response, in an appropriate adjuvant.

In another embodiment, upregulation or enhancement of an immune response function, as described herein, is useful in the induction of tumor immunity.

In another embodiment, the immune response can be stimulated by the methods described herein, such that pre-existing tolerance, clonal deletion, and/or exhaustion (e.g., T cell exhaustion) is overcome. For example, immune responses against antigens to which a subject cannot mount a significant immune response, e.g., to an autologous antigen, such as a tumor specific antigens can be induced by administering appropriate agents described herein that upregulate the immune response. In one embodiment, an autologous antigen, such as a tumor-specific antigen, can be coadministered. In another embodiment, the subject agents can be used as adjuvants to boost responses to foreign antigens in the process of active immunization.

In one embodiment, immune cells are obtained from a subject and cultured ex vivo in the presence of an agent as described herein, to expand the population of immune cells and/or to enhance immune cell activation. In a further embodiment the immune cells are then administered to a subject. Immune cells can be stimulated in vitro by, for example, providing to the immune cells a primary activation signal and a costimulatory signal, as is known in the art. Various agents can also be used to costimulate proliferation of immune cells. In one embodiment immune cells are cultured ex vivo according to the method described in PCT Application No. WO 94/29436. The costimulatory polypeptide can be soluble, attached to a cell membrane, or attached to a solid surface, such as a bead.

IX. Administration of Agents

The immune modulating agents of the present invention are administered to subjects in a biologically compatible form suitable for pharmaceutical administration in vivo, to enhance immune cell mediated immune responses. By "biologically compatible form suitable for administration in vivo" is meant a form to be administered in which any toxic effects are outweighed by the therapeutic effects. The term "subject" is intended to include living organisms in which an immune response can be elicited, e.g., mammals. Examples of subjects include humans, dogs, cats, mice, rats, and transgenic species thereof. Administration of an agent as described herein can be in any pharmacological form including a therapeutically active amount of an agent alone or in combination with a pharmaceutically acceptable carrier.

Administration of a therapeutically active amount of the therapeutic composition of the present invention is defined as an amount effective, at dosages and for periods of time necessary, to achieve the desired result. For example, a therapeutically active amount of an agent may vary according to factors such as the disease state, age, sex, and weight of the individual, and the ability of peptide to elicit a desired response in the individual. Dosage regimens can be adjusted to provide the optimum therapeutic response. For example, several divided doses can be administered daily or the dose can be proportionally reduced as indicated by the exigencies of the therapeutic situation.

Inhibiting or blocking ADAR, ZC3HAV1, and/or PPP1R15A, and/or enhancing or activating EIF2AK2/PKR, alone or in combination with an immunotherapy and/or modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist), can be accomplished by combination therapy with the modulatory agents described herein. Combination therapy describes a therapy in which ADAR, ZC3HAV1, PPP1R15A, and/or EIF2AK2/PKR is inhibited, blocked, or enhanced with an immunotherapy simultaneously. This may be achieved by administration of the modulatory agent described herein swith the immunotherapy imultaneously (e.g., in a combination dosage form or by simultaneous administration of single agents) or by administration of single inhibitory or activating agent for ADAR, ZC3HAV1, PPP1R15A, and/or EIF2AK2/PKR, or in combination with an immunotherapy and/or modulators of intratumoral interferon (e.g., radiation, a radiosensitizer, an immunogenic chemotherapy that induce interferon production by the cancer cells or at the site of a tumor, interferon, an interferon-inducing agent, a topical inflammatory agent, and/or a topical TLR agonist), according to a schedule that results in effective amounts of each modulatory agent present in the patient at the same time. Accordingly, the modulators (e.g., ADAR1 inhibitors or ISG15 inhibitors) of the present invention can be incorporated into pharmaceutical compositions suitable for administration. Such compositions typically comprise the nucleic acid molecule, protein, antibody, modulatory compound, or modulatory molecule and a pharmaceutically acceptable carrier.

The therapeutic agents described herein can be administered in a convenient manner such as by injection (subcutaneous, intravenous, etc.), oral administration, inhalation, transdermal application, or rectal administration. Depending on the route of administration, the active compound can be coated in a material to protect the compound from the action of enzymes, acids and other natural conditions which may inactivate the compound. For example, for administration of agents, by other than parenteral administration, it may be desirable to coat the agent with, or co-administer the agent with, a material to prevent its inactivation.

An agent can be administered to an individual in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEEP) and trasylol. Liposomes include water-in-oil-in-water emulsions as well as conventional liposomes (Sterna et al. (1984) *J. Neuroimmunol.* 7:27).

As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that modulates (e.g., inhibits) biomarker expression and/or activity, or expression and/or activity of the complex, or composition comprising an agent that modulates (e.g., inhibits) biomarker expression and/or activity, or expression and/or activity of the complex, which is effective for producing some desired therapeutic effect, e.g., cancer treatment, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., inhibits) biomarker expression and/or activity, or expression and/or activity of the complex encompassed by the present invention. These salts can be prepared in situ during the final isolation and purification of the therapeutic agents, or by separately reacting a purified therapeutic agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", J. Pharm. Sci. 66:1-19).

In other cases, the agents useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates (e.g., inhibits) biomarker expression and/or activity, or expression and/or activity of the complex. These salts can likewise be prepared in situ during the final isolation and purification of the therapeutic agents, or by separately reacting the purified therapeutic agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well-known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that modulates (e.g., inhibits) biomarker expression and/or activity, with the carrier and, optionally, one or more accessory ingredients. In general, the formulations are prepared by uniformly and intimately bringing into association a therapeutic agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a therapeutic agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well-known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more therapeutic agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., inhibits) biomarker expression and/or activity include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a therapeutic agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., inhibits) biomarker expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., inhibits) biomarker expression and/or activity, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a therapeutic agent to the body.

Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more therapeutic agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the present invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., inhibits) biomarker expression and/or activity, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the therapeutic agents of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be determined by the methods of the present invention so as to obtain an amount of the active ingredient, which is effective to achieve the desired therapeutic response for a particular subject, composition, and mode of administration, without being toxic to the subject.

The nucleic acid molecules of the present invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

In one embodiment, an agent of the present invention is an antibody. As defined herein, a therapeutically effective amount of antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of diagnostic assays.

X. Methods of Detecting Dependency

The RNA-specific adenosine deaminase (ADAR1) catalyzes adenosine-to-inosine edits on double stranded RNA.

ADAR1 inhibition activates RNA sensing pathways, which mirrors the cGAS-STING DNA sensing pathway. Both DNA and RNA sensing axes activate the same downstream pathway. See, e.g., Corrales et al., Cell Reports 2015, 11:1018-1030 and review by Deng et al., Clin. Cancer Res. 2016, 22(1):20-25. In addition, ISG15 is an interferon signaling pathway suppressor and has been ascribed to have an antiviral role. The inventors have discovered, and as provided herein, that ADAR1-dependent cell lines and ISG15-dependent cell lines show a high basal level of interferon signaling pathway activity due to an activated cGAS-STING pathway.

The term "STING" or "stimulator of interferon genes", also known as transmembrane protein 173 (TMEM173), refers to a five transmembrane protein that functions as a major regulator of the innate immune response to viral and bacterial infections. STING is a cytosolic receptor that senses both exogenous and endogenous cytosolic cyclic dinucleotides (CDNs), activating TBK1/IRF3 (interferon regulatory factor 3), NF-κB (nuclear factor KB), and STAT6 (signal transducer and activator of transcription 6) signaling pathways to induce robust type I interferon and proinflammatory cytokine responses. The term "STING" is intended to include fragments, variants (e.g., allelic variants) and derivatives thereof. Representative human STING cDNA and human STING protein sequences are well-known in the art and are publicly available from the National Center for Biotechnology Information (NCBI). Human STING isoforms include the longer isoform 1 (NM_198282.3 and NP_938023.1), and the shorter isoform 2 (NM_001301738.1 and NP_001288667.1; which has a shorter 5' UTR and lacks an exon in the 3' coding region which results in a shorter and distinct C-terminus compared to variant 1). Nucleic acid and polypeptide sequences of STING orthologs in organisms other than humans are well-known and include, for example, chimpanzee STING (XM_016953921.1 and XP_016809410.1; XM_009449784.2 and XP_009448059.1; XM_001135484.3 and XP_001135484.1), monkey STING (XM_015141010.1 and XP_014996496.1), dog STING (XM_022408269.1 and XP_022263977.1; XM_005617260.3 and XP_005617317.1; XM_022408249.1 and XP_022263957.1; XM_005617262.3 and XP_005617319.1; XM_005617258.3 and XP_005617315.1; XM_022408253.1 and XP_022263961.1; XM_005617257.3 and XP_005617314.1; XM_022408240.1 and XP_022263948.1; XM_005617259.3 and XP_005617316.1; XM_022408259.1 and XP_022263967.1; XM_022408265.1 and XP_022263973.1), cattle STING (NM_001046357.2 and NP_001039822.1), mouse STING (NM_001289591.1 and NP_001276520.1; NM_001289592.1 and NP_001276521.1; NM_028261.1 and NP_082537.1), and rat STING (NM_001109122.1 and NP_001102592.1).

STING agonists have been shown as useful therapies to treat cancer. Agonists of STING well-known in the art and include, for example, MK-1454, STING agonist-1 (MedChem Express Cat No. HY-19711), cyclic dinucleotides (CDNs) such as cyclic di-AMP (c-di-AMP), cyclic-di-GMP (c-di-GMP), cGMP-AMP (2'3'cGAMP or 3'3'cGAMP), or 10-carboxymethyl-9-acridanone (CMA) (Ohkuri et al. (2015) *Oncoimmunology* 4(4):e999523), rationally designed synthetic CDN derivative molecules (Fu et al. (2015) *Sci Transl Med.* 7(283):283ra52. doi: 10.1126/scitranslmed.aaa4306), and 5,6-dimethyl-xanthenone-4-acetic acid (DMXAA) (Corrales et al. (2015) *Cell Rep.* 11(7):1018-1030). These agonists bind to and activate STING, leading to a potent type I IFN response. On the other hand, targeting the cGAS-STING pathway with small molecule inhibitors would benefit for the treatment of severe debilitating diseases such as inflammatory and autoimmune diseases associated with excessive type I IFNs production due to aberrant DNA sensing and signaling. STING inhibitors are also known and include, for example, CCCP (MedChem Express, Cat No. HY-100941) and 2-bromopalmitate (Tao et al. (2016) *IUBMB Life.* 68(11):858-870). It is to be noted that the term can further be used to refer to any combination of features described herein regarding STING molecules. For example, any combination of sequence composition, percentage identify, sequence length, domain structure, functional activity, etc. can be used to describe a STING molecule of the present invention.

The term "cGAS", also known as cyclic GMP-AMP synthase, refers to a Nucleotidyltransferase that catalyzes the formation of cyclic GMP-AMP (cGAMP) from ATP and GTP. The catalysis involves both the formation of a 2,5 phosphodiester linkage at the GpA step and the formation of a 3,5 phosphodiester linkage at the ApG step, producing c[G(2,5)pA(3,5)p]. cGAS has antiviral activity by acting as a key cytosolic DNA sensor, the presence of double-stranded DNA (dsDNA) in the cytoplasm being a danger signal that triggers the immune responses. CGAS binds cytosolic DNA directly, leading to activation and synthesis of cGAMP, a second messenger that binds to and activates TMEM173/STING, thereby triggering type-I interferon production. cGAMP can be transferred between cells by virtue of packaging within viral particles contributing to IFN-induction in newly infected cells in a cGAS-independent but TMEM173/STING-dependent manner. Upon *M. tuberculosis* infection THP-1 cells knocked-out for this gene have impaired type-I interferon production (IF-1 beta), nor do they produce type-I IFN upon transfection with dsDNA. Diseases associated with cGAS include Aicardi-Goutieres Syndrome and Renpenning Syndrome. cGAS is involved in the cytosolic sensors of pathogen-associated DNA and RIG-I/MDA5 mediated induction of IFN-α/P pathways.

The term "cGAS" is intended to include fragments, variants (e.g., allelic variants) and derivatives thereof. Representative human cGAS cDNA and human cGAS protein sequences are well-known in the art and are publicly available from the National Center for Biotechnology Information (NCBI). At least one human cGAS isoform is known (NM_138441.2 and NP_612450.2). Nucleic acid and polypeptide sequences of cGAS orthologs in organisms other than humans are well-known and include, for example, chimpanzee cGAS (XM_009451553.2 and XP_009449828.1; XM_009451552.2 and XP_009449827.1), monkey cGAS (NM_001318175.1 and NP_001305104.1), cattle cGAS (XM_005210662.3 and XP_005210719.1; XM_002690020.5 and XP_002690066.2), mouse cGAS (NM_173386.5 and NP_775562.2), rat cGAS (XM_006243439.3 and XP_006243501.2), and chicken cGAS (XM_419881.5 and XP_419881.4).

The term "STING pathway" or "cGAS-STING pathway" refers to a STING-regulated innate immune pathway, which mediates cytosolic DNA-induced signaling events. Cytosolic DNA binds to and activates cGAS, which catalyzes the synthesis of 2'3'-cGAMP from ATP and GTP. 2'3'-cGAMP binds to the ER adaptor STING, which traffics to the ER-Golgi intermediate compartment (ERGIC) and the Golgi apparatus. STING then activates IKK and TBK1. TBK1 phosphorylates STING, which in turn recruits IRF3 for phosphorylation by TBK1. Phosphorylated IRF3 dimerizes and then enters the nucleus, where it functions with NF-kB to turn on the expression of type I interferons and other immunomodulatory molecules. The cGAS-STING pathway not only mediates protective immune defense against infection by a large variety of DNA-containing pathogens but also detects tumor-derived DNA and generates intrinsic antitumor immunity. However, aberrant activation of the cGAS-STING pathway by self DNA can also lead to autoimmune and inflammatory disease.

In one aspect, the present disclosure provides a method of detecting ADAR dependency in a cell. In some embodiments, a method for detecting ADAR1 dependency includes contacting the cell with an ADAR1 inhibitor, and determining proliferation in the cell contacted with the ADAR1 inhibitor. ADAR1 dependency is indicated if the cell contacted with the ADAR1 inhibitor exhibits a decreased proliferation level relative to the proliferation level of a cell not contacted with the ADAR1 inhibitor. In some embodiments, the method is for detecting ADAR1 dependency in a high proliferation cell. Accordingly, in some embodiments, a method for detecting ADAR1 dependency in a high proliferation cell includes contacting the high proliferation cell with an ADAR1 inhibitor, and determining proliferation in the high proliferation cell contacted with the ADAR1 inhibitor. ADAR1 dependency is indicated if the high proliferation cell contacted with the ADAR1 inhibitor exhibits a decreased proliferation level relative to the proliferation level of a cell not contacted with the ADAR1 inhibitor.

In another aspect, the present disclosure provides a method of detecting ISG15 dependency in a cell. In some embodiments, a method for detecting ISG15 dependency includes contacting the cell with an ISG15 inhibitor, and determining proliferation in the cell contacted with the ISG15 inhibitor. ISG15 dependency is indicated if the cell contacted with the ISG15 inhibitor exhibits a decreased proliferation level relative to the proliferation level of a cell not contacted with the ISG15 inhibitor.

In some embodiments, a method for detecting ISG15 dependency in a high proliferation cell includes contacting the high proliferation cell with an ISG15 inhibitor, and determining proliferation in the high proliferation cell contacted with the ISG15 inhibitor. ISG15 dependency is indicated if the high proliferation cell contacted with the ISG15 inhibitor exhibits a decreased proliferation level relative to the proliferation level of a cell not contacted with the ISG15 inhibitor.

The term "ISG15", also known as ISG15 ubiquitin-like modifier, refers to an ubiquitin-like protein that is conjugated to intracellular target proteins upon activation by interferon-alpha and interferon-beta. Several functions have been ascribed to the encoded protein, including chemotactic activity towards neutrophils, direction of ligated target proteins to intermediate filaments, cell-to-cell signaling, and antiviral activity during viral infections. While conjugates of this protein have been found to be noncovalently attached to intermediate filaments, this protein is sometimes secreted. ISG15 plays a key role in the innate immune response to viral infection either via its conjugation to a target protein (isgylation) or via its action as a free or unconjugated protein. Isgylation involves a cascade of enzymatic reactions involving E1, E2, and E3 enzymes which catalyze the conjugation of ISG15 to a lysine residue in the target protein. Its target proteins include IFIT1, MX1/MxA, PPM1B, UBE2L6, UBA7, CHMP5, CHMP2A, CHMP4B and CHMP6. ISG15 can also isgylate EIF2AK2/PKR which results in its activation, DDX58/RIG-I which inhibits its function in antiviral signaling response, EIF4E2 which enhances its cap structure-binding activity and translation-inhibition activity, UBE2N and UBE2E1 which negatively regulates their activity, IRF3 which inhibits its ubiquitination and degradation and FLNB which prevents its ability to interact with the upstream activators of the JNK cascade thereby inhibiting IFNA-induced JNK signaling. ISG15 exhibits antiviral activity towards both DNA and RNA viruses, including influenza A, HIV-1 and Ebola virus. ISG15 restricts HIV-1 and ebola virus via disruption of viral budding. ISG15 inhibits the ubiquitination of HIV-1 Gag and host TSG101 and disrupts their interaction, thereby preventing assembly and release of virions from infected cells. ISG15 inhibits Ebola virus budding mediated by the VP40 protein by disrupting ubiquitin ligase activity of NEDD4 and its ability to ubiquitinate VP40. ISG15 isgylates influenza A virus NS1 protein which causes a loss of function of the protein and the inhibition of virus replication. The secreted form of ISG15 can induce natural killer cell proliferation, act as a chemotactic factor for neutrophils and act as an IFN-gamma-inducing cytokine playing an essential role in anti-mycobacterial immunity.

The term "ISG15" is intended to include fragments, variants (e.g., allelic variants) and derivatives thereof. Representative human ISG15 cDNA and human ISG15 protein sequences are well-known in the art and are publicly available from the National Center for Biotechnology Information (NCBI). At least one human ISG15 isoform is known (NM_005101.3 and NP_005092.1). Nucleic acid and polypeptide sequences of ISG15 orthologs in organisms other than humans are well-known and include, for example, chimpanzee ISG15 (XM_009454678.2 and XP_009452953.1), monkey ISG15 (NM_001266806.1 and NP_001253735.1), dog ISG15 (XM_003639053.4 and XP_003639101.1), cattle ISG15 (NM_174366.1 and NP_776791.1), mouse ISG15 (NM_015783.3 and NP_056598.2), and rat ISG15 (NM_001106700.1 and NP_001100170.1).

As used herein, a "high proliferation cell" refers to a cell that is highly proliferative. Cell proliferation is the process that results in an increase of the number of cells, and may be defined by cell divisions that exceed cell loss through cell death or differentiation. Decreased proliferation may refer to cells in which the number of cell divisions is lower than the number of cell loss.

In some embodiments, cell proliferation can be determined by the number of viable cells counted at a first time point and a second time point. For example, if the number of viable cells counted at the second time point is increased relative to the number of viable cells counted at the first time point, then the cells are proliferative. Accordingly, if the level of increase of the number of viable cells of a first cell type is higher than the increase of the number of viable cells of a second cell type, the first cell type has a higher proliferation level than the second cell type. Accordingly, if the level of increase of the number of viable cells of a first cell type is lower than the increase of the number of viable cells of a second cell type, the first cell type has a lower proliferation level than the second cell type.

In some embodiments, cell proliferation can be determined using a variety of assays that are known in the art. For example, cell proliferation can be measured by performing DNA synthesis cell proliferation assays, performing metabolic cell proliferation assays, detecting markers of cell proliferation, measuring the concentration of a certain molecule (e.g., intracellular ATP within the cell), and other methods that are known in the art. Those ordinarily skilled in the art will be able to choose a suitable method for determining cell proliferation.

In some cases, cell proliferation is high in a cell that, for example, has lost its ability to control its growth. For example, a high proliferation cell may refer to a cancer cell. Cancer cells of interest in the methods provided by present disclosure can include, without limitation, breast cancer cells, prostate cancer cells, skin cancer cells, brain cancer cells, colon cancer cells, lung cancer cells, blood cancer cells, lymphatic cancer cells, pancreatic cancer cells, and more. In some embodiments, cancer cells of the methods provided by the present disclosure are lung cancer cells or pancreatic cancer cells. In some embodiments, cancer cells include cells obtained from a cancer that has been caused by viral infection. Both DNA and RNA viruses have been shown to be capable of causing cancer. DNA viruses that are known to cause cancer include, without limitation, Epstein-Barr virus (EBV), human papilloma virus (HPV), hepatitis B virus (HBV), Merkel cell polyomavirus (MCV) and human herpes virus-8 (HHV-8). RNA viruses that are known to cause cancer include, without limitation, human T-lymphotrophic virus-1 (HTLV-1) and hepatitis C virus (HCV). In some embodiments, cancer cells include cells obtained from a cancer that has been caused by a bacterial infection. For example, Helicobacter pylori and Chlamydia trachomatis are known to cause cancer. In some embodiments, cancer cells include cells obtained from a cancer that has been caused by a parasite. For example, Opisthorchis viverrini, Clonorchis sinensis and Schistosoma haematobium are parasites known to cause cancer.

In some embodiments, a high proliferation cell is a cancer cell that is derived from a biological sample from a subject. A "biological sample" is a sample that contains cells or cellular material. Non-limiting examples of biological samples include urine, blood, cerebrospinal fluid (CSF), pleural fluid, sputum, and peritoneal fluid, bladder washings, secretions (e.g., breast secretion), oral washings, tissue samples, touch preps, or fine-needle aspirates. Depending on the type of cancer a subject has, the type of biological sample will vary. As used herein, a "subject" may be a human subject, e.g., a human subject having cancer, a mammal, a rodent, etc. Accordingly, a high proliferation cell in the methods of the present disclosure may be, for example, a human cancer cell derived from a biological sample from a human having cancer.

In some embodiments, a method of detecting ADAR1 dependency in a cell includes contacting the cell with an ADAR1 inhibitor. In some embodiments, a method of detecting ISG15 dependency in a cell includes contacting the cell with an ISG15 inhibitor. As used herein, an "ADAR1 inhibitor" or "ISG15 inhibitor" refers to any molecule (e.g., small molecule, biomolecule) that can inhibit ADAR1 or ISG15.

In some embodiments, an ADAR1 inhibitor or an ISG15 inhibitor may be an RNA silencing agent targeting ADAR1 or ISG15. As used herein, the term "RNA silencing" refers to a group of sequence-specific regulatory mechanisms (e.g., RNA interference (RNAi), transcriptional gene silencing (TGS), post-transriptional gene silencing (PTGS), quelling, co-suppression, and translational repression) mediated by RNA molecules which result in the inhibition or "silencing" of the expression of a corresponding protein-coding gene. As used herein, the term "target gene" is a gene whose expression is to be substantially inhibited or "silenced." While not wishing to be bound by theory, it is hypothesized that RNA silencing can be achieved by cleaving the mRNA of the target gene or translational repression of the target gene.

In some embodiments, an ADAR1 inhibitor or an ISG15 inhibitor may be a molecule that is capable of editing the genome of a cell to knock down or knock out the ADAR1 or ISG15 gene. For example an ADAR1 inhibitor or an ISG15 inhibitor may be nuclease agent that can create site-specific double-strand breaks at desired locations in the genome (e.g., at the ADAR1 or ISG15 loci). Particular examples of nuclease agents for use in the methods disclosed herein include RNA-guided CRISPR-Cas9 system, zinc finger proteins, meganucleases, TAL domains, TALENs, yeast assembly, recombinases, leucine zippers, CRISPR/Cas, endonucleases, and other nuclease agents known to those in the art and disclosed herein.

XI. Identifying Cells Suitable for Inhibition

The present disclosure provides methods of detecting increased interferon signaling pathway activity in a cell. The methods include detecting the activity of one or more interferon stimulated factors in the cell, and if the detected activity is higher than average in other cells, the cell has increased interferon signaling pathway activity. In some embodiments, the cell is a high proliferation cell and the detected activity is higher than average of different high proliferation cells. In some embodiments, the cell is a cancer cell and the detected activity is higher than average of different cancer cells. Accordingly, in one embodiment, a method of detecting increased interferon signaling pathway activity in a cancer includes detecting the activity of one or more interferon stimulated factors in the cancer cell, wherein if the interferon signaling pathway activity is higher than average in other cancer cells, the cancer cell has increased interferon signaling pathway activity. In some embodiments, the cancer cell is of a particular cancer cell type (e.g., lung cancer or pancreatic cancer), and has a higher than average interferon signaling pathway activity relative to a different cancer cell type (e.g., non-lung cancer or non-pancreatic cancer).

The interferon signaling pathway plays a critical role in the human immune response. For example, after viral infection, the human body triggers a complex regulatory system of innate and adaptive immune responses designed to defend against the virus. One of the many responses to viral invasion includes the induction of the interferon signaling pathway, which when induced, can lead to increased cellular resistance to viral infection. As used herein, the term "interferon stimulated factor" refers to a molecule (e.g., a small molecule, an RNA, or a protein) that is induced by the interferon signaling pathway. Accordingly, detecting the activity of one or more interferon stimulated factors includes, for example, detecting the level of a chemical or molecule that is stimulated by the interferon signaling pathway.

Accordingly, in some embodiments, detecting the activity of one or more interferon stimulated factors in a cell includes determining the level of a cyclic dinucleotide in the cell, wherein an elevated level of the cyclic dinucleotide indicates that the cell has increased interferon signaling pathway activity. Prokaryotic as well as eukaryotic cells use various small molecules for cell signaling and intra- and intercellular communication. Cyclic nucleotides like cGMP, cAMP, etc. are known to have regulatory and initiating activity in pro- and eukaryotic cells. Prokaryotic cells also use cyclic purine dinucleotides as regulatory molecules. In prokaryotes, the condensation of two GTP molecules is catalyst by the enzyme diguanylate cyclase (DGC) to give c-diGMP, which represents an important regulator in bacteria. For example, without limitation, cytosolic bacterial pathogens can modulate innate immune responses through the cyclic dinucleotides they produce. Recent work suggests that cyclic diGMP or analogs thereof can also stimulate or enhance immune or inflammatory response in a patient or can enhance the immune response to a vaccine by serving as an adjuvant in mammals. Cytosolic detection of pathogen-derived DNA requires signaling through TANK binding kinase 1 (TBK1) and its downstream transcription factor, IFN-regulatory factor 3 (IRF3). A transmembrane protein called STING (stimulator of IFN genes; also known as MITA, ERIS, MPYS and TMEM173) functions as the signaling receptor for these cyclic purine dinucleotides, causing stimulation of the TBK1-IRF3 signalling axis and a STING-dependent type I interferon response. See, e.g., FIG. 1. Burdette et al., Nature 478: 515-18, 2011 demonstrated that STING binds directly to cyclic diguanylate monophosphate, but not to other unrelated nucleotides or nucleic acids.

In some embodiments, a method of the present disclosure that includes determining the level of a cyclic dinucleotide, includes determining the level of, without limitation, a cyclic guanosine monophosphate-adenosine monophosphate (cGAMP), a cyclic di-adenosine monophosphate (c-di-AMP) (e.g., bis-(3', 5')-cyclic dimeric adenosine monophosphate), or a cyclic diguanylate (c-di-GMP) (e.g., bis-(3', 5')-cyclic dimeric guanosine monophosphate). Other naturally occurring cyclic dinucleotides will be known to those ordinarily skilled in the art.

In other embodiments, detecting the activity of one or more interferon stimulated factors in a cell includes determining the expression level and/or phosphorylation of one or more interferon stimulated genes in the cell. Accordingly, an elevated expression level and/or phosphorylation of the one or more interferon stimulated genes indicates that the cell has increased interferon signaling pathway activity. As used herein, the term "interferon stimulated gene" refers to a gene that is expressed or upregulated in response to interferon. Without limitation, examples of interferon stimulated genes include ADAR1, ISG15, USP18, STING, MDA5, PKR, EIF2α, ATF4, IRF9, RIG, TBK1, IRF3, PD-L1 and others that will be recognized by a person ordinarily skilled in the art. A database of interferon regulated genes can be found at "www.interferome"followed by".org", and as described in Samarajiwa et al., Nucleic Acids Res. 2009, 37(database issue):D852-857. Those ordinarily skilled in the art would be able to access a database of interferon regulated genes and select further interferon stimulated genes for use in the methods described herein.

In some embodiments, determining the expression level of one or more interferon stimulated genes in the cell includes determining the expression level of a combination of any interferon stimulated genes. In such embodiments, an increased interferon signaling pathway activity in a cell is indicated when the average expression level of the combination of interferon stimulated genes in the cell is elevated compared to the average expression level of the same combination of interferon stimulated genes in a different cell. In particular embodiments, determining the expression level of one or more interferon stimulated genes in the cell includes determining the expression level of ADAR1 or ISG15, or the combination of ADAR1 and ISG15. In some embodiments, determining the expression level of one or more interferon stimulated genes in the cell includes determining the expression level of the p150 isoform of ADAR1.

A method of detecting increased interferon signaling pathway activity in a cell finds use in the present disclosure because the inventors made the discovery that a cell with an elevated basal level of interferon signaling pathway activity is suitable for ADAR1 inhibition or ISG15 inhibition, wherein the ADAR1 inhibition or ISG15 inhibition will kill the cell, or in the case of a high proliferation cell, decrease the proliferation of the high proliferation cell. Accordingly, upon detecting increased interferon signaling pathway activity in a cell, the method may further include contacting the cell with an effective amount of an ADAR1 inhibitor or ISG15 inhibitor. In some embodiments, the cell is in a subject (e.g., mammalian subject, human subject), and the ADAR1 inhibitor or ISG15 inhibitor is administered to the subject in an effective amount. ADAR1 inhibitors and ISG15 inhibitors are described in the present disclosure (e.g., shRNAs or gRNAs targeting ADAR1 and ISG15 respectively). As used herein, an "effective amount" refers to an amount that provides, in this case, sufficient inhibition of, e.g., ADAR1 or ISG15, to kill, or decrease the proliferation of a cell.

XII. Kits

The present invention also encompasses kits for detecting and/or modulating biomarkers described herein. A kit of the present invention may also include instructional materials disclosing or describing the use of the kit or an antibody of the disclosed invention in a method of the disclosed invention as provided herein. A kit may also include additional components to facilitate the particular application for which the kit is designed. For example, a kit may additionally contain means of detecting the label (e.g., enzyme substrates for enzymatic labels, filter sets to detect fluorescent labels, appropriate secondary labels such as a sheep anti-mouse-HRP, etc.) and reagents necessary for controls (e.g., control biological samples or standards). A kit may additionally include buffers and other reagents recognized for use in a method of the disclosed invention. Non-limiting examples include agents to reduce non-specific binding, such as a carrier protein or a detergent.

EXAMPLES

Example 1: Materials and Methods for Examples 2-5 a. In Vivo CRISPR Screening in B16 Tumor Cells

A Cas9-expressing version of the B16 melanoma cell line was created and confirmed that it could edit DNA efficiently with CRISPR using sgRNAs targeting the PD-L1 gene. For screening the B16-Cas9 cell line, a library of 9,992 optimized sgRNAs was created to target 2,398 genes, selected from the GO term categories: kinase, phosphatase, cell surface, plasma membrane, antigen processing and presentation, immune system process, and chromatin remodeling. The transcript abundance of the genes in these categories were then filtered to include only those that were expressed >RPKM (log 2)=0.9. These genes were then ranked for expression in the B16 cell line using RNAseq to select for the top 2,398 expressed genes. The library was divided into 4 sub-pools, each containing one sgRNA per gene and 100 non-targeting control sgRNAs. The 4 sub-pools were screened individually and sgRNAs were delivered to B16-Cas9 cells via lentiviral infection at an infection rate of 30%. Transduced B16 cells were purified using a hCD19 reporter by positive magnetic selection (Miltenyi Biotech, Cambridge, MA) and then expanded in vitro before being implanted into animals. For each sub-pool, B16 cells were implanted into 10 TCRα$^{-/-}$ mice, 10 WT mice treated with GVAX, and 10 WT mice treated with GVAX and PD-1 blockade (see below for treatment protocols). B16 cells transduced with libraries were also grown in vitro at approximately 2000× library coverage for the same time period as the animal experiment. Mice were sacrificed 12-14 days after tumor implantation tumor genomic DNA was prepared from whole tumor tissue using the Qiagen DNA Blood Midi kit (Qiagen, Hilden, Germany). PCR was used to amplify the sgRNA region and sequencing to determine sgRNA abundance was performed on an Illumina HiSeq system (Illumina, San Diego, CA). Significantly enriched or depleted sgRNAs from any comparison of conditions were identified using the STARS algorithm (Abbas & Dutta (2009) Nat. Rev. Cancer 9:400-414; Doench et al. (2014) Nat. Biotechnol. 32:1262-1267).

B16F10 mleanoma and B16-GM-CSF cells were a gift form Dr. Glenn Dranoff B16 cells were grown in DMEM (Gibco) with 10% fetal bovine serum (Gemini biosciences)

and antibiotics. All cell lines were subject to periodic testing for *mycoplasma* using the LookOut® Mycoplasma PCR detection kit (Sigma).

b. Animal Treatment and Tumor Challenges

The designs of these animal studies and procedures were approved by the Dana Farber Cancer Institute IACUC committee. Dana Farber's specific-pathogen free facility was used for the storage and care of all mice. Seven-week old wild-type female C57BL/6J mice were obtained from Jackson laboratories (Bar Harbor, ME). A colony of B6.129S2-Tcra$^{tm1Mom}$/J (Tcra) T cell-deficient mice were bred on site. Mice were aged matched to be 7-12 weeks old at the time of tumor inoculation. For screening, $2.0 \times 10^6$ library-transduced B16-Cas9 cells resuspended in Hanks Balanced Salt Solution (Gibco, Thermo Fisher Scientific, Waltham, MA) were mixed 1:1 by volume with Matrigel® (Corning, Corning, NY) and subcutaneously injected into the right flank on day 0. Mice were vaccinated with $1.0 \times 10^6$ GM-CSF-secreting B16 (GVAX) cells that had been irradiated with 3500 Gy on days 1 and 4 to elicit an anti-tumor immune response. Subsequently, mice were treated with 100 µg of rat monoclonal anti-PD1 antibody (clone: 29F.1A12) on days 9 and 12 via intraperitoneal injection. For validation assays, $1.0 \times 10^6$ tumor cells were subcutaneously injected into the right flank without matrigel. Tumors were measured every 3 days beginning on day 6 after challenge until time of death. Measurements were taken manually by collecting the longest dimension (length) and the longest perpendicular dimension (width). Tumor volume was estimated with the formula: $(L \times W^2)/2$. $CO_2$ inhalation was used to euthanize mice on the day of sacrifice.

c. Creation of CRISPR Edited Tumor Cell Lines

Transient transfection of Cas9-sgRNA plasmid (pX459, Addgene, Cambridge, MA) was used to edit B16 and Braf/Pten melanoma cell lines. pX459 was digested with the enzyme Bpil (Thermo Fisher Scientific) as per the manufacturer's instructions and sgRNA oligos were cloned in using standard molecular cloning. For B16 cells, $5 \times 10^5$ cells were plated in a well of a 6-well plate and were transfected the following day using 2 µg of pX459 plasmid DNA and Turbofect™ (3:1 ratio, Thermo Fisher Scientific). Twenty-four hours after transfection, transfectants were selected in puromycin (6 µg/mL, Thermo Fisher Scientific). For Braf/Pten melanoma cells, $5 \times 10^5$ cells were plated in a well of a 6-well plate and were transfected the following day using 4 µg of pX459 plasmid DNA and Turbofect™ (3:1 ratio). After selection, cells were grown for 14 days in vitro before being implanted into mice.

d. Flow Cytometry Analysis of B16 Tumor Cells

B16 cells were trypsinized and washed in PBS+2% FBS, stained with antibodies for cell surface proteins as per the manufacturer's instructions, and then analyzed on an Accuri™ C6 flow cytometry system (BD Biosciences).

e. RNAseg Analysis of Tumor Cells

Adar-null or control sgRNA-transfected B16 cells were stimulated with IFNγ (100 ng/mL, Cell Signaling Technology), TNFα (10 ng/mL, Peprotech) or both for 48 hours. RNA was extracted from cell pellets using the Qiagen RNeasy® Mini kit according to manufacturer's instructions. First-strand Illumina-barcoded libraries were generated using the NEB RNA Ultra™ Directional kit according to manufacturer's instructions, including a 12-cycle PCR enrichment. Libraries were sequenced on an Illumina NextSeq™ 500 instrument using paired-end 37 bp reads. Data were trimmed for quality using the Trimmomatic pipeline with the following parameters: LEADING:15 TRAILING:15 SLIDINGWINDOW4:15 MINLEN:16. Data were aligned to mouse reference genome mm10 using the Bowtie 2 aligning sequencing tool (available at the World Wide Web website of Johns Hopkins University). HTSeq was used to map aligned reads to genes and to generate a gene count matrix and it is available at the World Wide Web address of huber.embl.de/users/anders/HTSeq/doc/overview.html.

Normalized counts and differential expression analysis was performed using the DESeq2 R package. The gene set enrichment analysis was performed as described previously in Abbas & Dutta (2009) *Nat. Rev. Cancer* 9:400-414 and Todd et al. (2007) *Nat. Genet.* 39:857-864. Principle Components Analysis (PCA) was performed on the normalized gene counts including all genes that passed a minimal expression filter. Signature scores for the individual samples were generated using FastProject (available at the World Wide Web address of bmcbioinformatics.biomedcentral-.com/articles/10.1186/s2859-016-1176-5) and the Hallmark gene signature collection (Liberzon et al. (2015) *Cell Sys.* 1:417-425). Pearson correlation coefficients were calculated between the Hallmark gene signatures and PC1 and PC2. Selected signatures were plotted on a normalized PCA projection of the dataset.

f. Western Blotting

Whole cell lysates were prepared in lysis buffer (60 mM Tris HC, 2% SDS, 10% glycerol, complete EDTA-free protease-inhibitor (Roche, Basel, Switzerland), and 500 U/mL benzonase nuclease (Novagen, Merck, Darmstadt, Germany)). Samples were boiled at 100° C. and clarified by centrifugation. Protein concentration was measured with a BCA protein assay kit (Pierce, Dallas, Texas). Fifty to one hundred and fifty micrograms of protein was loaded on 4-12% Bolt® Bis-Tris Plus gels (Life Technologies, Carlsbad, CA) in MES buffer (Life Technologies). Protein was transferred to 0.45 µm nitrocellulose membranes (Bio-Rad, Hercules, CA). Membranes were blocked in Tris-buffered saline plus 0.1% Tween 20 (TBS-T) containing 5% non-fat dry milk for 1 hour at room temperature followed by overnight incubation with primary antibody at 4° C. Membranes were washed with TBS-T and incubated with HRP-conjugated secondary antibodies for 1 hour at room temperature. HRP was activated with Supersignal® West Dura Extended Duration Substrate (Pierce) and visualized with a chemiluminscent detection system using Fuji ImageQuante LAS4000 (GE Healthcare Life Sciences, Pittsburgh, PA). Blots were then analyzed using ImageJ and Adobe® Photoshop® software.

g. Antibodies

For Western blotting, primary antibodies against R-ACTIN (Abcam, Cambridge, UK, Cat. #8227), and FLAG (clone M2, Sigma Aldrich) were used. Peroxidase-conjugated secondaries against Rabbit-IgG (Cat. #111-035-046) and Mouse-IgG (Cat. #115-035-174) were purchased from Jackson Laboratories (Bar Harbor, ME).

For flow cytometry, the following anti-mouse (m) fluorochrome-conjugated antibodies were used: H2K(b)/H2D (b) (clone 28-8-6, Biolegend), CD47 (clone miap301, Biolegend), SIINFEKL-H2K(b) (clone 25-D1.16, Biolegend), Granzyme B (clone GB11, Biolegend), TNF (clone MP6-XT22, Biolegend), IFNγ (clone XMG1.2, Biolegend), CD8a (clone 53-6.7, Biolegend), CD4 (clone RM4-5 or GK15, Biolegend), TCR-P (clone H57-597, Biolegend), PD-1 (clone RPMI-30, Biolegend), Tim-3 (clone TMR3-2.3, Biolegend), CD45 (clone 104 or 30-F11, Biolegend), Ly6C (clone HK1.4, Biolegend), I-A/I-E (clone M5/114.15.2, Biolegend), F4/80 (clone BM8, Biolegend), CD11c (clone N418, Biolegend), CD24 (clone M1/69, Biolegend), CD11b (clone M/70, Biolegend), CD103 (clone 2E7, Biolegend), CD3E (clone 145-2C11, Biolegend), TCRγ/δ (clone GL3, Biolegend), NK1.1 (clone PK136, Biolegend), CD44 (clone IM7, Biolegend), Ki-67 (clone B56, BD Biosciences), CD274 (clone MIH5, BD Biosciences), and Foxp3 (clone JFK-16s, eBioscience).

h. CRISPR sgRNA Sequences

CRISPR sgRNA sequences used are described in Table 2 below.

TABLE 2

| Gene Name/sg# | sgRNA Sequence |
|---|---|
| Cd274 sgRNA 1: | GCCTGCTGTCACTTGCTACG (SEQ ID NO: 37) |
| Cd274 sgRNA 2: | AATCAACCAGAGAATTTCCG (SEQ ID NO: 38) |
| Cd274 sgRNA 3: | GGTCCAGCTCCCGTTCTACA (SEQ ID NO: 39) |
| Cd274 sgRNA 4: | GTATGGCAGCAACGTCACGA (SEQ ID NO: 40) |
| Cd47 sgRNA 1: | TATAGAGCTGAAAAACCGCA (SEQ ID NO: 41) |
| Cd47 sgRNA 2: | CCACATTACGGACGATGCAA (SEQ ID NO: 42) |
| Cd47 sgRNA 3: | TCTTACGAGGAGGAGAAAGG (SEQ ID NO: 43) |
| Cd47 sgRNA 4: | GCAAGTGTAGTTTCCCACCA (SEQ ID NO: 44) |
| control sgRNA 1: | GCGAGGTATTCGGCTCCGCG (SEQ ID NO: 45) |
| control sgRNA 2: | GCTTTCACGGAGGTTCGACG (SEQ ID NO: 46) |
| control sgRNA 3: | ATGTTGCAGTTCGGCTCGAT (SEQ ID NO: 47) |
| control sgRNA 4: | ACGTGTAAGGCGAACGCCTT (SEQ ID NO: 48) |
| control sgRNA 5: | ATTGTTCGACCGTCTACGGG (SEQ ID NO: 49) |
| Mouse Adar sgRNA 1 (P150 only) forward: | CACCGTCTGGATTCACAACTCCAGG (SEQ ID NO: 50) |
| Mouse Adar sgRNA 1 (P150 only) reverse: | AAACCCTGGAGTTGTGAATCCAGAC (SEQ ID NO: 51) |
| Mouse Adar sgRNA 2 (P110 and P150) forward: | CACCGTCTACAGCCCTACCTTGCCA (SEQ ID NO: 52) |
| Mouse Adar sgRNA 2 (P110 and P150) reverse: | AAACTGGCAAGGTAGGGCTGTAGAC (SEQ ID NO: 53) |
| Mouse Adar sgRNA 3 (P150 only) forward: | CACCGTGTGACTCTCAGAAATCAG (SEQ ID NO: 54) |
| Mouse Adar sgRNA 3 (P150 only) reverse: | AAACCTGATTTCTGAGAGTCACAC (SEQ ID NO: 55) |
| Mouse Adar sgRNA 4 forward: | CACCGTTCCAAGTCAATCAGCACTG (SEQ ID NO: 56) |
| Mouse Adar sgRNA 4 reverse: | AAACCAGTGCTGATTGACTTGGAAC (SEQ ID NO: 57) |
| Mouse Adar sgRNA 5 (P150 only) forward: | CACCGCACACAGCAGGGGTACACCA (SEQ ID NO: 58) |
| Mouse Adar sgRNA 5 (P150 only) reverse: | AAACTGGTGTACCCCTGCTGTGTGC (SEQ ID NO: 59) |
| Mouse Adar sgRNA 6 forward: | CACCGTCCGTCAAGTACCAGATGGG (SEQ ID NO: 60) |
| Mouse Adar sgRNA 6 reverse: | AAACCCCATCTGGTACTTGACGGAC (SEQ ID NO: 61) |
| Human Adar sgRNA 1 (P150 only) forward: | CACCGATGGGTGTAGTATCCGCTGA (SEQ ID NO: 62) |

TABLE 2-continued

| Gene Name/sg# | sgRNA Sequence |
|---|---|
| Human Adar sgRNA 1 (P150 only) reverse: | AAACTCAGCGGATACTACACCCATC (SEQ ID NO: 63) |
| Human Adar sgRNA 2 (P150 only) forward: | CACCGTGTGGCAGACTCCTGCCACG (SEQ ID NO: 64) |
| Human Adar sgRNA 2 (P150 only) reverse: | AAACCGTGGCAGGAGTCTGCCACAC (SEQ ID NO: 65) |
| Human Adar sgRNA 3 (P110 and P150) forward: | CACCGAGGGGATGTCTATAGACAA (SEQ ID NO: 66) |
| Human Adar sgRNA 3 (P110 and P150) reverse: | AAACTTGTCTATAGACATCCCCCTC (SEQ ID NO: 67) |
| Human Adar sgRNA 4 forward: | CACCGTTCTTGTAGGGTGAACACCG (SEQ ID NO: 68) |
| Human Adar sgRNA 4 reverse: | AAACCGGTGTTCACCCTACAAGAAC (SEQ ID NO: 69) |

Examples 2-5 disclose the development of a pooled loss-of-function in vivo genetic screening approach that uses CRISPR-Cas9 genome editing to discover genes that increase sensitivity or cause resistance to immunotherapy in a mouse transplantable tumor model. About 2,400 genes expressed by tumor cells were screened in the B16 murine melanoma model to identify those that increase or decrease sensitivity to immunotherapy with tumor vaccination and PD-1 checkpoint blockade. The screen identified known immune evasion molecules PD-L1 (also known as CD274) and CD47, as tumor cells bearing sgRNAs for these targets were significantly depleted in animals treated with immunotherapy. It was discovered and further validated that modulating multiple new genes, such as those involved in dsRNA editing, sensing, and/or metabolisms (e.g., Adar, Zc3hav1, Ppp1r15a, or Eif2ak2), sensitizes tumor cells to immunotherapy. These findings reveal that this screening approach can discover new immunotherapy targets and prioritize their combination with existing immunotherapies.

Example 2: A Pooled Loss-of-Function In Vivo Genetic Screen Recovers Known Immune Evasion Molecules Expressed by Tumors In order to systematically identify new cancer immunotherapy targets and resistance mechanisms, a pooled genetic screening approach was developed to identify genes that increase or decrease the fitness of tumor cells growing in vivo in animals treated with immunotherapy (FIG. 1A). First, a B16 melanoma cell line was engineered to express Cas9 (FIG. 1B), confirmed of efficient DNA editing using sgRNAs targeting PD-L1 (FIG. 1C, bottom). Next, a library of lentiviral vectors was created to encode 9,992 sgRNAs targeting 2,398 genes from relevant functional classes that were expressed at detectable levels in the tumor cell line (FIG. 1D). After transduction and in vitro passage to allow gene editing to take place, the tumor cells were transplanted into animals that were then treated with either a GM-CSF-secreting, irradiated tumor cell vaccine (GVAX) or GVAX plus PD-1 blockade using a monoclonal antibody for PD-1, in order to apply immune selective pressure on the tumor cells (FIG. 1E) (see Dranoff (2003) Oncogene 22:3188-3192; Dranoff et al. (1993) Proc. Natl. Acad. Sci. U.S.A. 90:3539-3543; and Duraiswamy et al. (2013) Cancer Res. 73:3591-3603; Curran & Allison (2009) Cancer Res 69:7747-7755; Curran et al. (2010) Proc. Natl. Acad. Sci. U.S.A. 107:4275-4280). In parallel, the library-transduced tumor cells were transplanted into TCRα$^{-/-}$ mice, which lack CD4$^+$ and CD8$^+$ T cells and were therefore unable to apply adaptive immune selective pressure on the tumors. This allowed to distinguish the effect of immune selective pressure on library representation from nonspecific effects on tumor cell viability. After 12-14 days, tumors were harvested (FIG. 1E), with all sgRNAs recovered from each animal with good inter-animal reproducibility (FIGS. 1F-1H).

The library representation in tumors from immunotherapy-treated wild-type (WT) animals were compared with that found in tumors growing in TCRα$^{-/-}$ mice. Deletion of genes that result in resistance to immunotherapy would be expected to increase tumor sgRNA representation in WT animals, while deletion of genes that result in increased sensitivity of tumors to immunotherapy would decrease sgRNA representation.

It was first determined whether genes that scored in the screen recovered known immune evasion molecules (indicated by depletion of sgRNAs) or resistance mechanisms (which would result in enrichment of targeting sgRNAs). Inspection of the list of genes targeted by sgRNAs depleted from tumors treated with immunotherapy revealed the known immune evasion molecule PD-L1 (also known as CD247), indicating that loss of PD-L1 increased the sensitivity of tumor cells to immune attack. sgRNAs targeting PD-L1 were not depleted from tumors in TCRα$^{-/-}$ mice relative to cells growing in vitro, presumably due to the absence of T cell-mediated selective pressure (FIG. 1I), but were significantly depleted in WT mice treated with GVAX relative to TCRα$^{-/-}$ mice (FDR=0.004). However, the depletion of PD-L1-targeting sgRNAs seen in GVAX-treated tumors was not observed in tumors treated with GVAX and anti-PD-1, indicating that loss of PD-L1 does not confer a selective disadvantage to tumors when PD-L1:PD-1 interactions are blocked (FIG. 1C).

It was also found that sgRNAs targeting CD47, which enables immune evasion by impairing engulfment of tumors cells by phagocytes (as in Liu et al. (2015) Nat. Med. 21:1209-1215; Weiskopf et al. (2016) J. Clin. Invest. 126: 2610-2620; and Tseng et al. (2013) Proc. Nat. Acad. Sci. U.S.A. 110: 11103-11108), were markedly depleted in tumors treated with either GVAX or with GVAX plus PD-1 blockade (FDR=0.005, 0.002 respectively) (FIG. 1I). To confirm that CD47-null tumors were more susceptible to GVAX and PD-1 blockade, CD47-null B16 melanoma cells were generated using transient transfection of a Cas9-sgRNA plasmid (as in Ran et al. (2013) Nat. Protoc. 8:2281-2308)(FIG. 1J). It was found that loss of CD47 significantly improved control of tumor growth mediated by GVAX plus anti-PD-1 immunotherapy (FIG. 1K, p<0.01).

Thus, in vivo genetic screening recovered genes known to confer tumor evasion properties on cancer cells.

Figure 2:
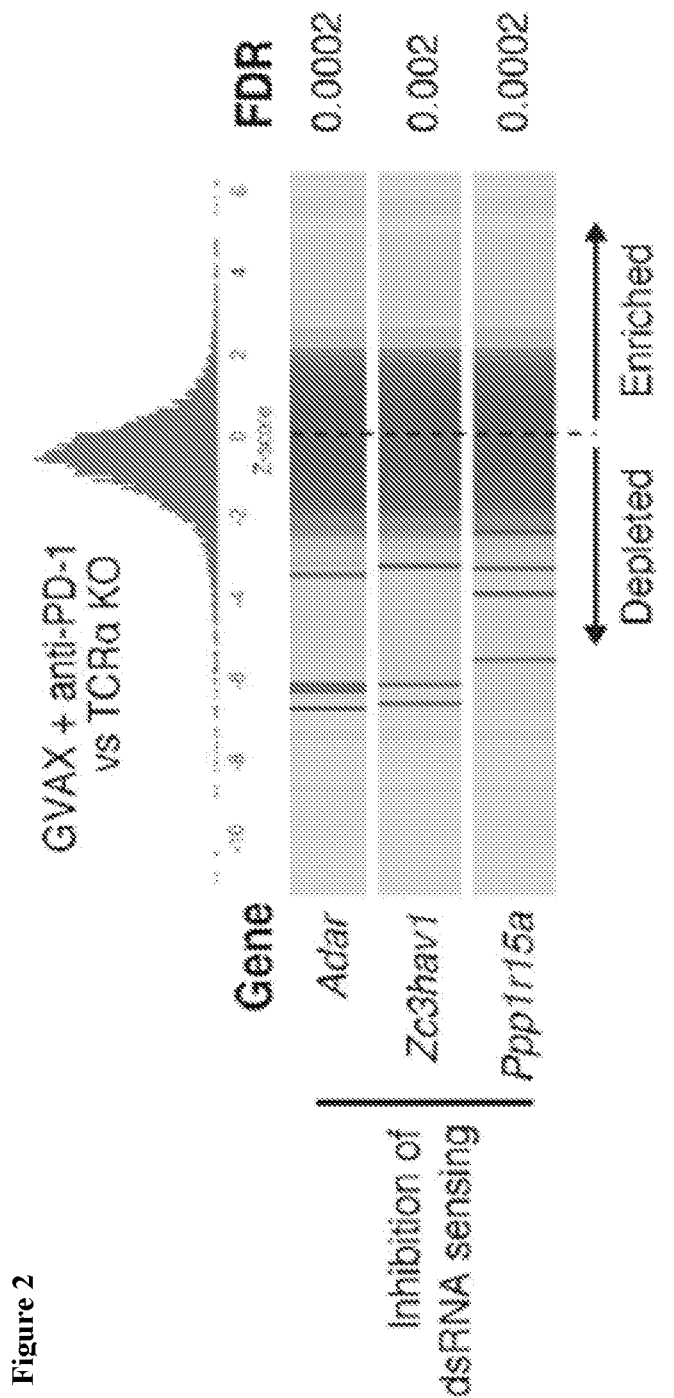
Figure 3:
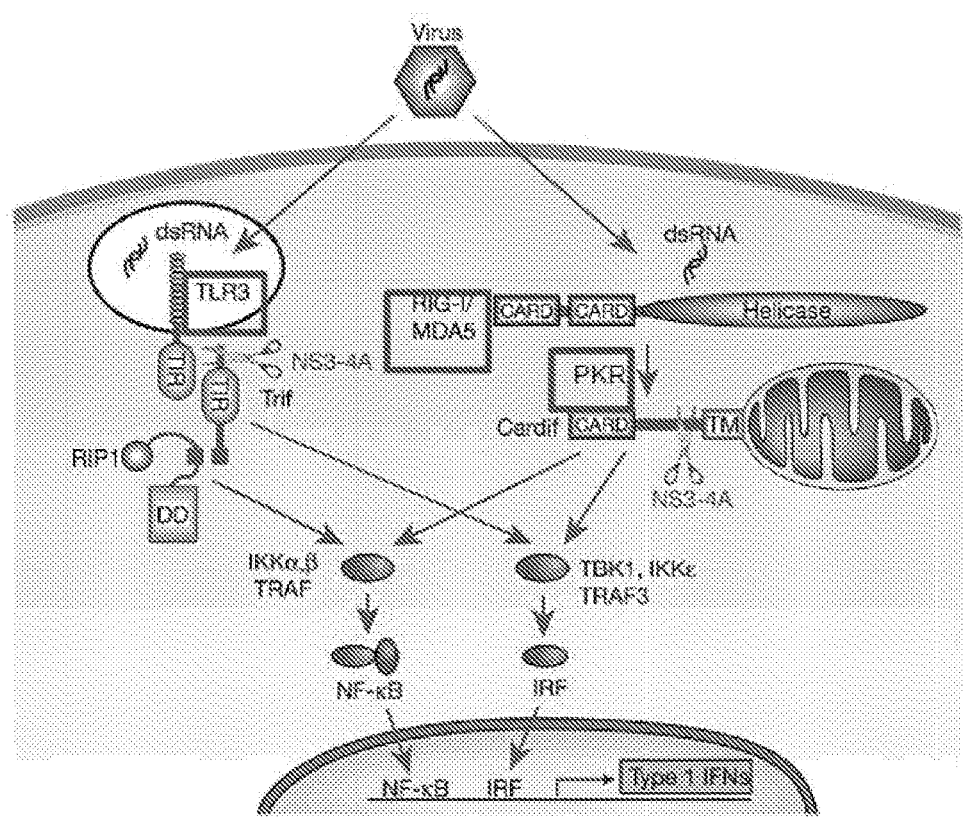
FIG. 3 shows that recognition of dsRNA drives interferon (IFN) production and anti-viral transcriptional programs and is adapted from Meylan et al. (2006) *Nature* 442:39-44.
Figure 6:
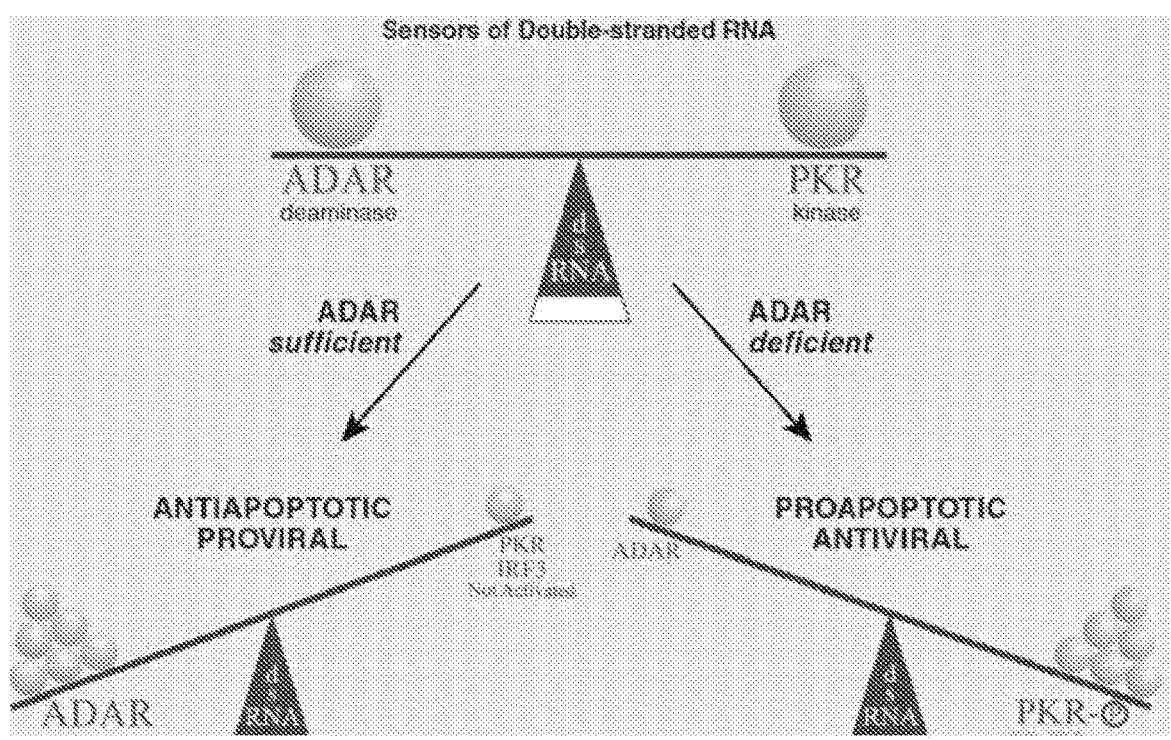
FIG. 6 shows that the balance between ADAR and PKR controls the inflammatory and apoptotic response to dsRNA and is adapted from Pfaller et al. (2011) *Curr. Opin. Immunol.* 23:573-582.
Figure 7:
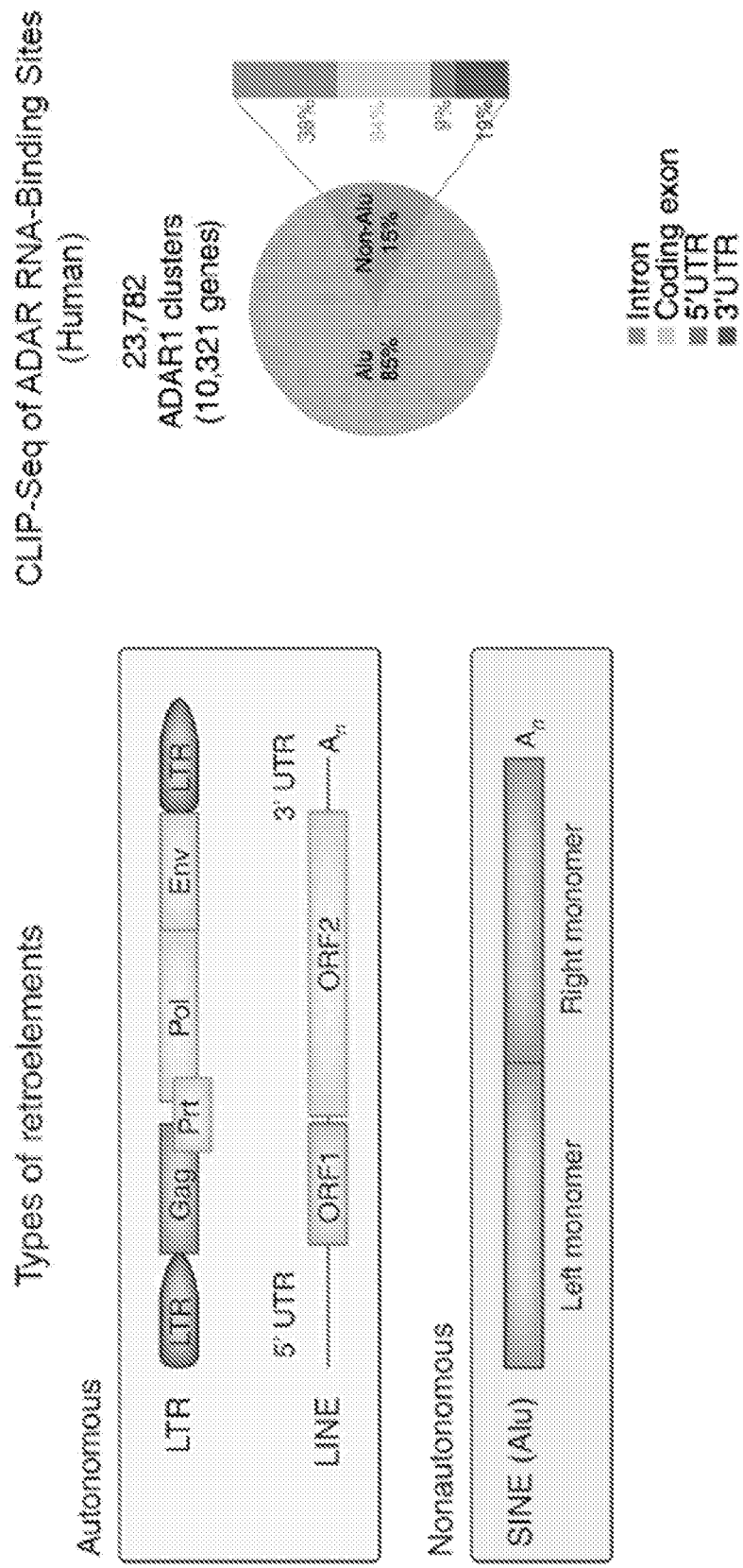
FIG. 7 shows that ADAR edits both endogenous retroelements and endogenous host mRNA and is adapted from Bahn et al. (2015) *Nat. Commun.* 6:6355.

Example 3: Discovery of New Gene Targets to Increase the Efficacy of Immunotherapy Deletion of novel candidate immunotherapy targets was found to increase sensitivity of tumor cells to immunotherapy. sgRNAs targeting genes involved in dsRNA editing, sensing, and/or metabolism (e.g., Adar) were markedly depleted in mice treated with GVAX and PD-1 blockade (FIG. 2) relative to growth in TCRα$^{-/-}$ mice. In many cases, multiple members of the same pathway or even the same multi-protein complex were depleted under immune selective pressure, underscoring the importance of diverse biological pathways, such as the dsRNA editing, sensing, and/or metabolism pathway (FIGS. 3-7).

Figure 8:
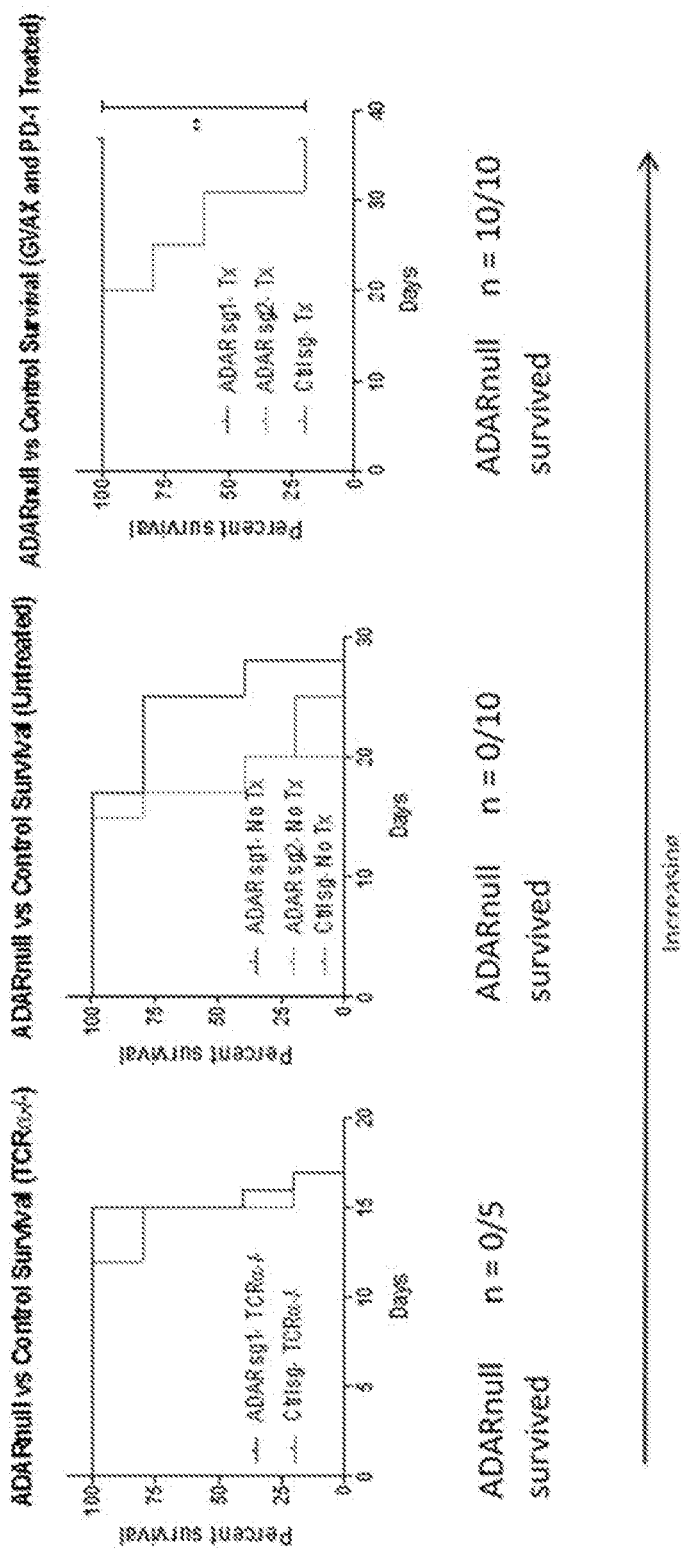
FIG. 8 includes 5 panels, identified as panels A, B, C, D, and E, which show the in vivo validation of ADAR as an anti-cancer target, either alone or in combination with immunotherapy. Panel A shows the results of Western blot analyses using anti-ADAR primary and anti-mouse-HRP secondary antibodies to detect ADAR and an anti-beta-actin antibody to detect the positive control protein. Mouse Adar sgRNA1 (targeting P150 only) effectively depleted the P150 isoform of ADAR, but not the P110 isoform of ADAR, while sgRNA2 (targeting P110 and P150) effectively depleted both isoforms, with or without IFNβ addition. Panel B shows that Adar deficiency improves responses to immunotherapy in the B16 model. Adar null B16 cells were made by transfection of Adar guides/Cas9 or control guide/Cas9 in PLX459 plasmid. Panel C shows that Adar deficiency in B16 tumors enhances the survival advantage conferred by immunotherapy. Adar null B16 cells were injected as above into either TCRα or control mice (treated or untreated). Panel D shows that Adar deficiency in MC38 tumors improves responses to immunotherapy. Adar null MC38 cells were made by infection of Cas9+ MC38 cells with Lentivirus derived from PXPR24 plasmid with Adar guides. Panel E shows that single-cell cloned Adar-deficient B16 tumors are rejected even with minimal immune pressure. Single cell clones were derived from bulk B16 transfected populations as described in previous panels.
Figure 8:
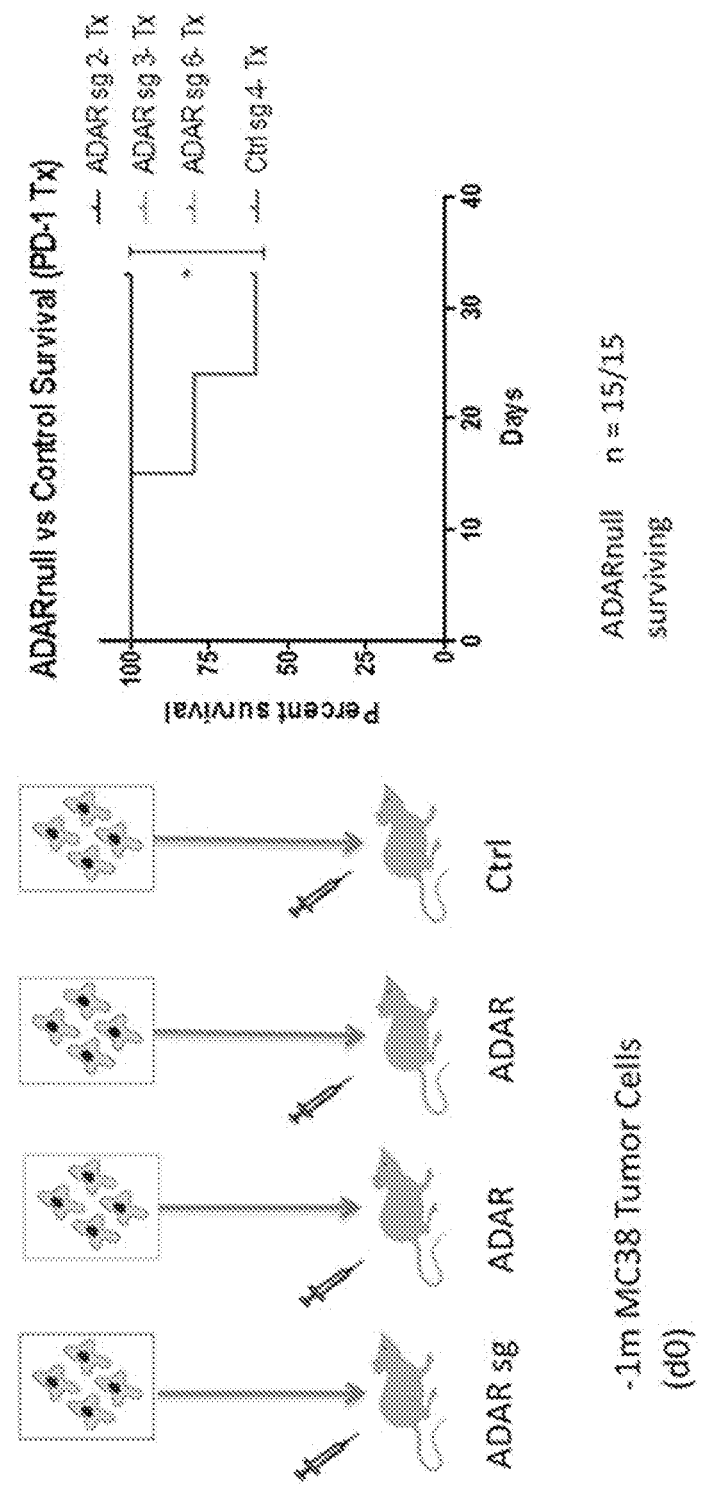
Figure 8:
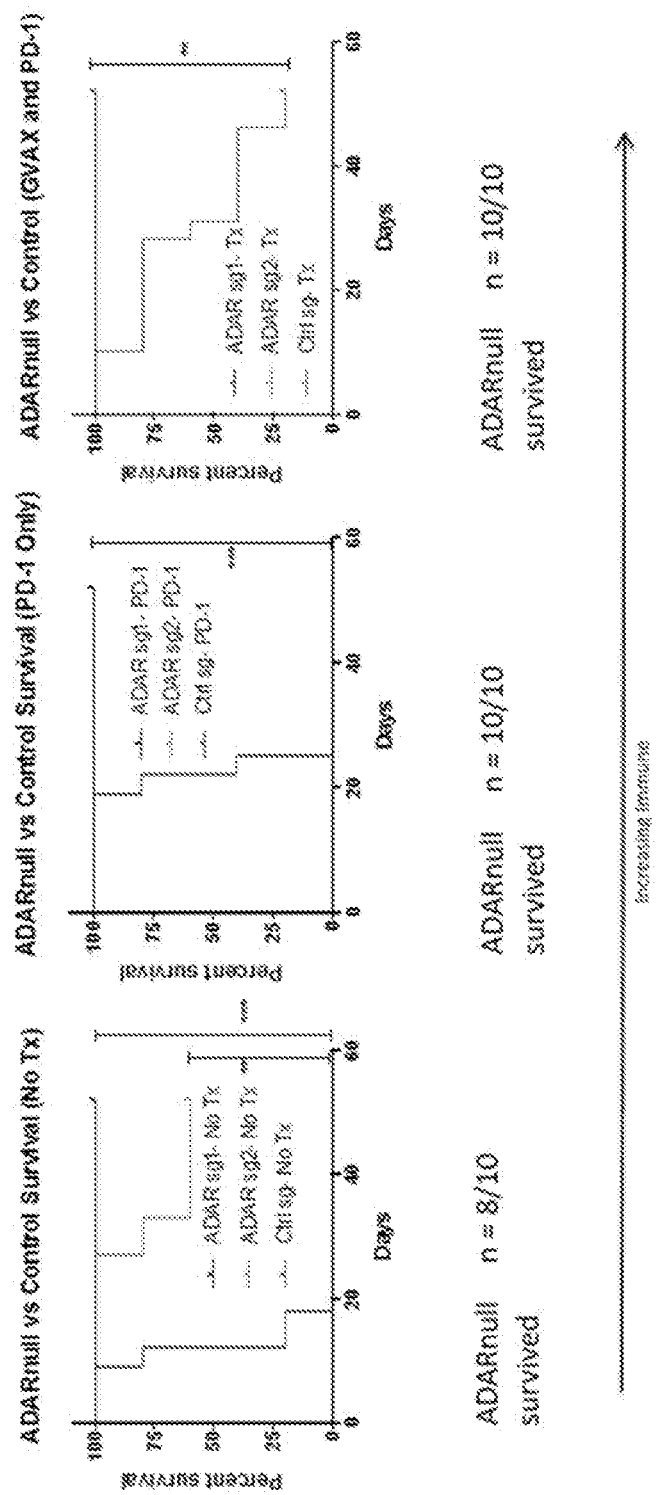

Example 4: In Vivo Validation of ADAR as a Target, Including as a Target for Combination with Immunotherapy Representative genes, e.g., Adar, were selected to validate based on their highest cumulative score as ranked by the STARS algorithm (Doench et al. (2014) Nat. Biotechnol. 32:1262-1267). sgRNAs were designed against Adar and were used to effectively deplete either the p150 isoform, or both the p110 and the p150 isoforms, of ADAR (FIG. 8A).

In vivo effects of knocking out Adar were further tested by injecting mice with B16 tumor cells transfected with anti-Adar or control sgRNA/Cas9. As a result, knocking out Adar by sgRNAs effectively improved mice survival up to at least 50 days, resulting in a 19/20 surviving rate, compared to the 4/10 survival rate of the control (FIG. 8B). Similarly, CRISPR-mediated ADAR deficient B16 tumor cells were administered to either TCRα$^{-/-}$ or control mice with or without immunotherapy treatment (GVAX+anti-PD-1 antibody). Knocking out Adar was able to improve the survival of control mice without treatment or with GVAX+anti-PD-1 antibody treatment, but not that of TCRα$^{-/-}$ mice or control mice without treatment (FIG. 8C). Similar knock-out experiments using MC38 tumor cells also showed the survival improvement of mice receiving anti-PD-1 antibody treatment (FIG. 8D). When using single cell clones derived from bulk B16, knocking out Adar improved mice survival with or without immunotherapy treatment, while the tumors were rejected even with minimal immune pressure (FIG. 8E). These results demonstrate that both 1) bulk-transfected CRISPR sg/CAS9 cell populations (with a high percentage of Adar-null cells) and 2) the bulk-transfected cell populations can be single-cell cloned and recombined into mixes with 100% knockout of Adar. Using the cells of 1) leads to improved survival in immunotherapy-treated mice but not in untreated mice. Using the cells of 2) leads to both untreated and treated mice having improved survival, whereas TCRalpha mice do not have improved survival. The data shown in FIG. 8C (bulk-transfected cells) and FIG. 8E (single cell clone mixes of 3 single cell clones with confirmed knockout) illustrates these differences in effect.

Thus, loss of Adar sensitizes tumor cells to the effect of immunotherapy. Further evidence shows that Adar-loss in tumor cells independently promotes anti-tumor immunity and increases the immune infiltrate of tumors. The single-cell data above and data produced with lentivirus constructs for CRISPR-induced Adar loss also indicate that Adar loss alone produces at least some survival advantage in untreated mice.

Example 5: Mechanism Studies of ADAR-Induced Sensitivity to Checkpoint Blockade

Figure 9:
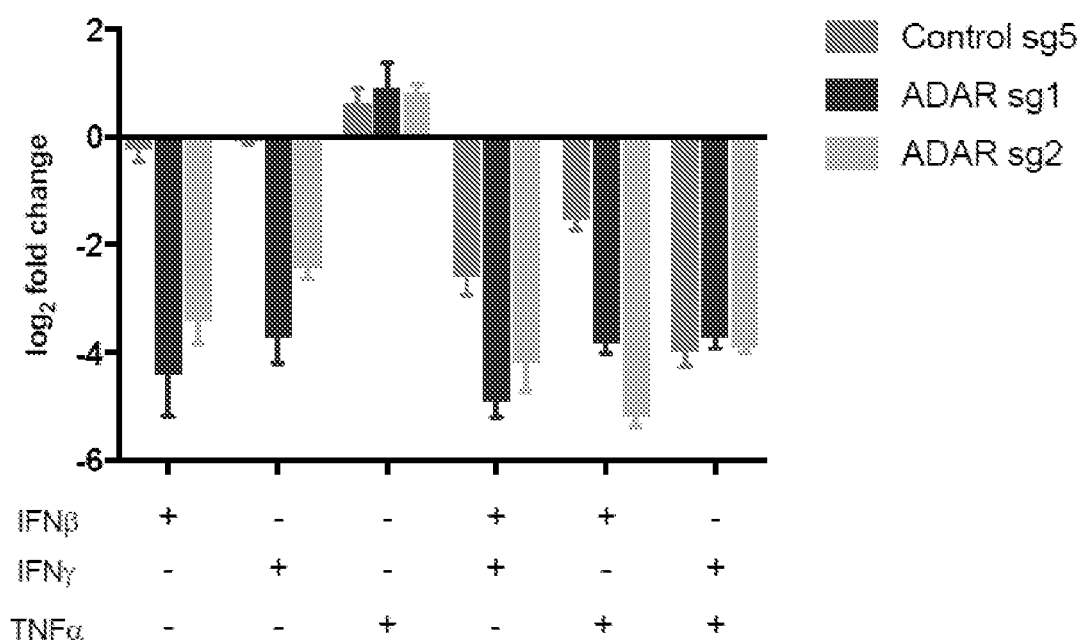
FIG. 9 includes 3 panels, identified as panels A, B, and C, which provide exemplary mechanisms of ADAR-induced sensitivity to checkpoint blockade. Panel A shows that Adar deficiency in B16 tumor cells increases IFNβ and IFNγ-induced growth arrest in vitro. A certain number of B16 tumor cells (50 k; Adar null or control) were stimulated in vitro with cytokine for 72 hours and the cell numbers were then counted. Panel B shows that Adar-deficient cells produce IFNβ in response to IFN stimulation. A certain number of B16 tumor cells (50 k; Adar null or control) were stimulated with cytokine in vitro, washed to remove cytokine (for IFNβ), and evaluated via IFNβ ELISA. Panel C shows that expression of PD-L1 and Class I MHC are similar in Adar$^{-/-}$ and control cells following cytokine stimulation. A certain number of B16 tumor cells (50 k; Adar null or control) were stimulated in vitro with cytokine for 72 hours and stained for Class I MHC and PD-L1.
Figure 9:
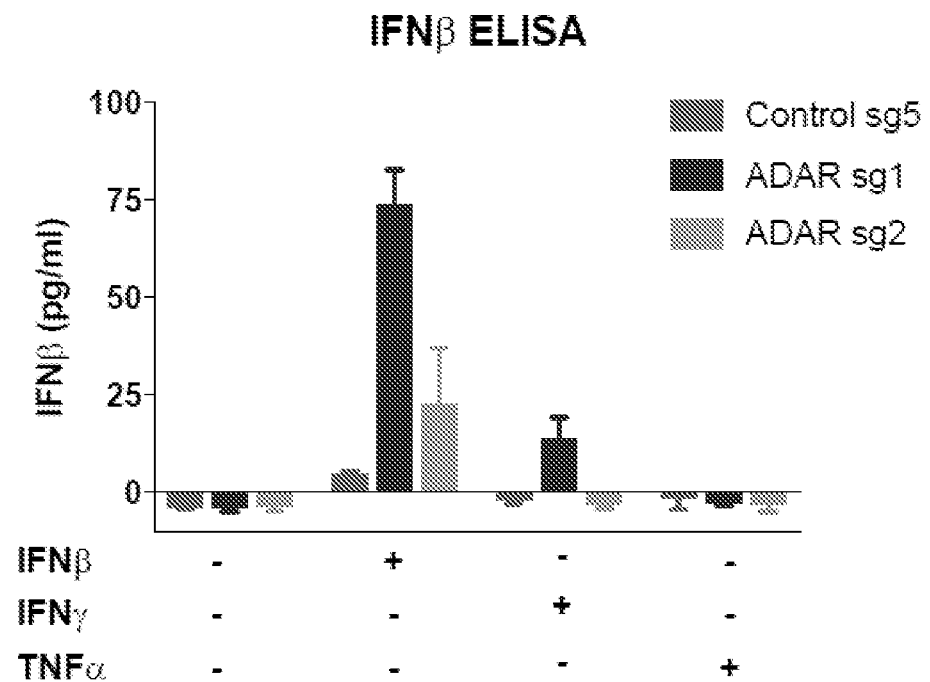
Figure 9:
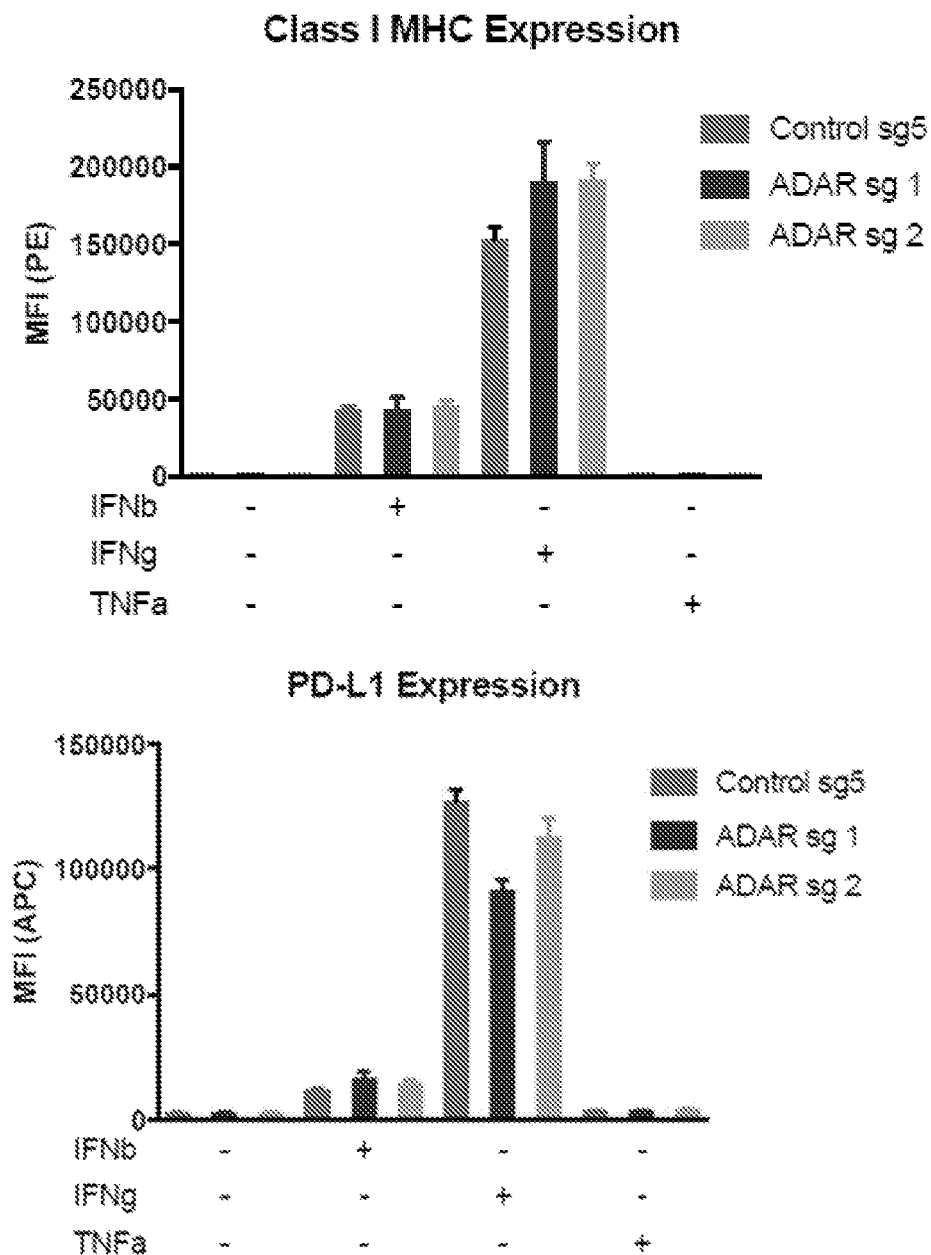
Figure 16:
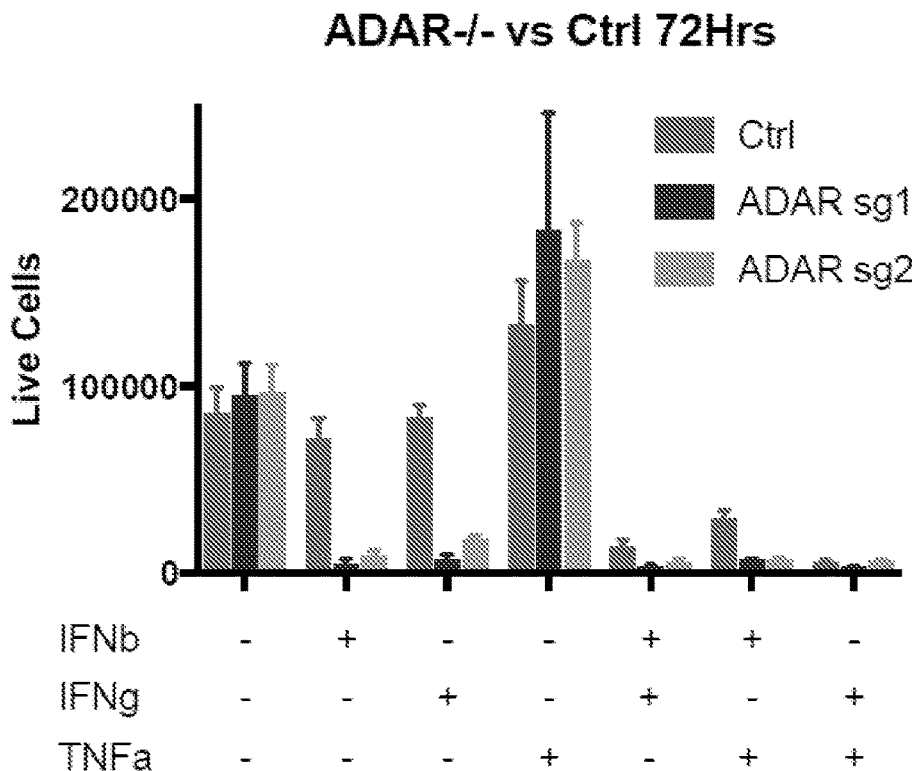
FIG. 16 shows that Adar knockout increases IFNβ and IFNγ-induced growth arrest in vitro.

To identify the mechanism by which loss of Adar enhanced the efficacy of immunotherapy, the growth rate and the cytokine/protein expression profiles of immune cell subsets in the tumor microenvironment of control and Adar null tumors was compared. Adar deficiency in B16 tumor cells increased IFNβ and IFNγ-induced growth arrest in vitro (FIG. 9A and FIG. 16). In addition, Adar-deficient cells produced IFNβ in response to IFN stimulation (FIG. 9B). Expression of PD-L1 and Class I MHC was similar in Adar$^{-/-}$ and control cells following cytokine stimulation (FIG. 9C). Thus, without limitation, exemplary mechanisms for rejection of Adar null tumors may include: 1) growth arrest in response to IFNβ (a.k.a., innate engraftment failure) as an intrinsic effect; 2) growth arrest in response to IFNγ (a.k.a., T-cell/NK cytokine sensitivity) as an intrinsic effect; 3) increased recruitment of immune cells (a.k.a., inflamed tumor microenvironment) as an extrinsic effect; or 4) any combination of the above.

Figure 10:
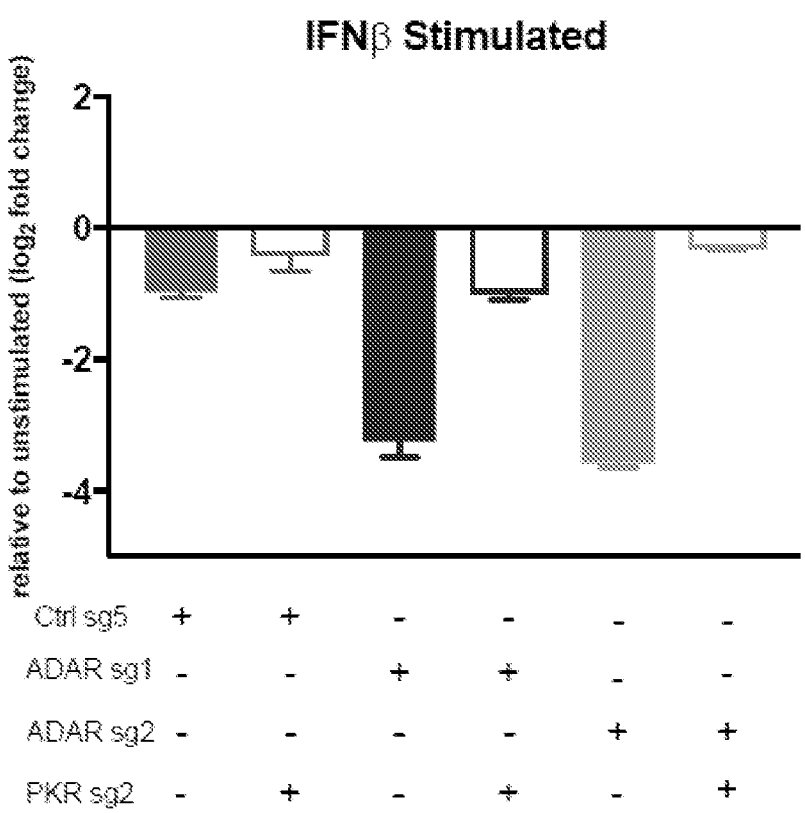
FIG. 10 shows that the increased IFN-induced arrest in Adar-deficient tumor cells is PKR-dependent. A certain number of B16 tumor cells (50 k; Adar null or control) were stimulated in vitro with cytokine for 72 hours and the cell numbers were then counted.
Figure 10:
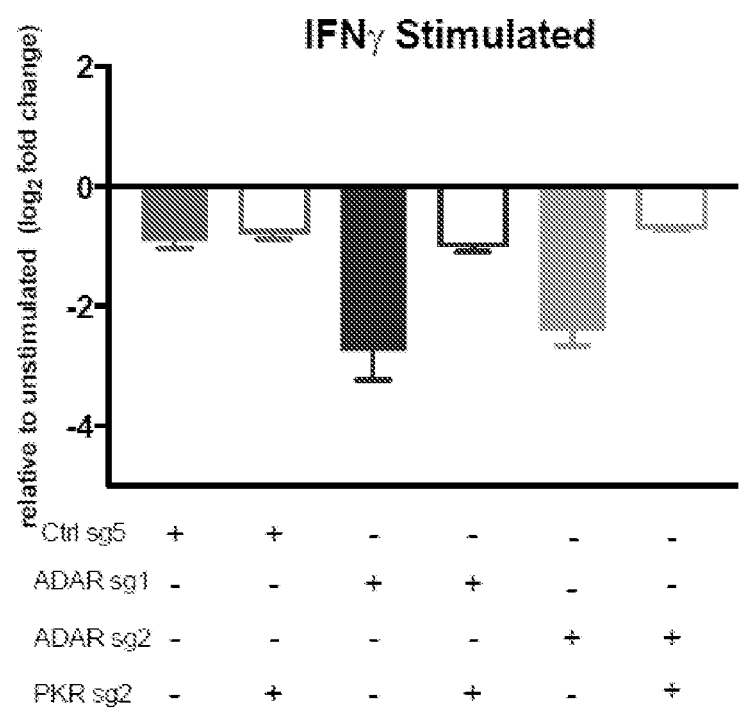
Figure 12:
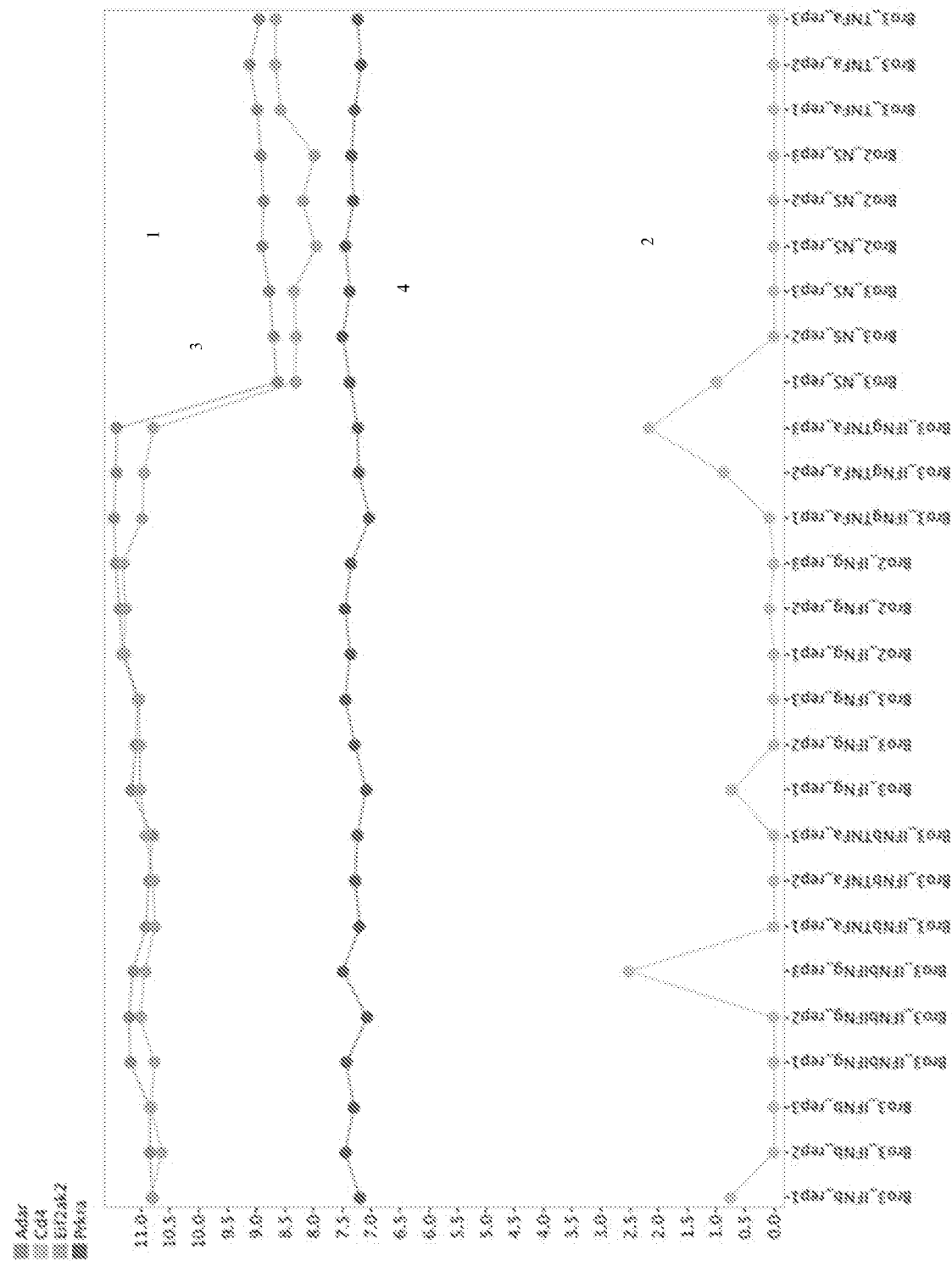
FIG. 12 shows that ADAR and PKR are coordinately regulated by Type I and Type II IFNs.

Interestingly, increased IFN-induced arrest in Adar-deficient tumor cells was found to be PKR-dependent. As shown in FIG. 10, the induced cell arrest (shown in cell numbers) by knocking out Adar in tumor cells stimulated with either IFN was dramatically ameliorated when PKR was knocked out by CRISPR. The data also show that Adar and PKR/Eif2ak2 are coordinately regulated by Type I and Type II IFNs (FIG. 12).

Figure 17:
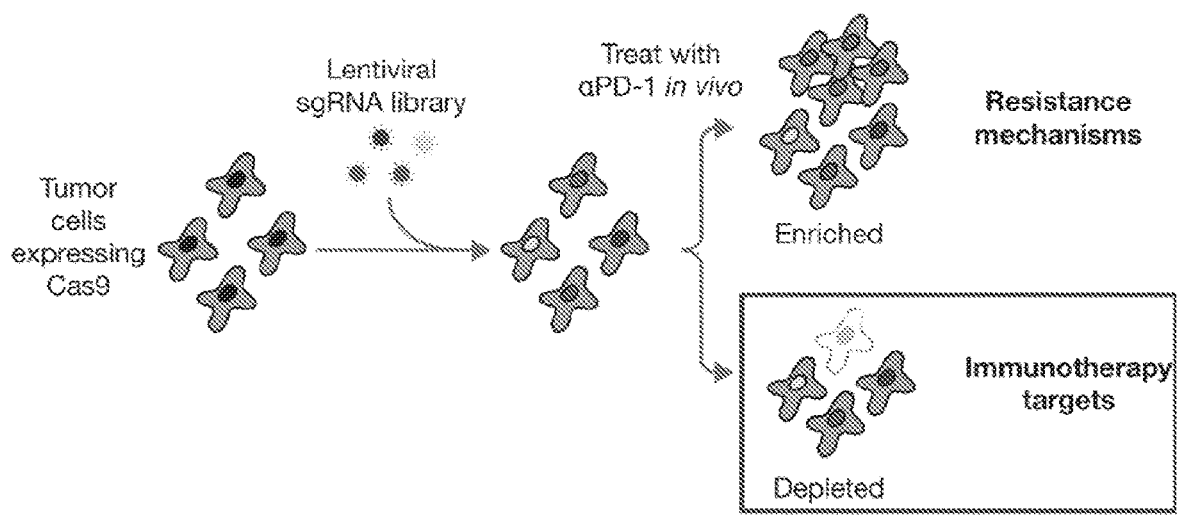
FIG. 17 shows a schematic diagram illustrating pooled screen approaches to discovering and identifying cancer immunotherapy.

Immunotherapy, e.g., through checkpoint blockade, is rapidly becoming a cornerstone of cancer therapy (Reck et al. (2016) N. Engl. J. Med. 375:1823-1833; Hodi et al. (2010) N. Engl. J. Med. 363:711-723; Postow et al. (2015) N. Engl. J. Med. 372:2006-2017; Wolchok et al. (2013) N. Engl. J. Med. 369:122-133; Ferris et al. (2016) N. Engl. J. Med. 375:1856-1867; Brahmer et al. (2012) N. Engl. J. Med. 366:2455-2465; Nghiem et al. (2016) N. Engl. J. Med. 374:2542-2552; Topalian et al. (2012) N. Engl. J. Med. 366:2443-2454); and Motzer et al. (2015) N. Engl. J. Med. 373:1803-1813). However, incomplete clinical response and the development of resistance limit its efficacy (Tumeh et al. (2014) Nature 515:568-571; Kelderman et al. (2014) Mol. Oncol. 8:1132-1139; Zaretsky et al. (2016) N. Engl. J. Med. 375:819-829). Here, it was demonstrated that pooled loss-of-function genetic screens in vivo can identify genes that modulate the efficacy of immunotherapy and therefore represent potential new therapeutic targets (FIG. 17 and FIG. 1A). The screening approach identified genes that, when deleted, make cells more sensitive to immunotherapy. These genetic dependencies included known targets that are currently the focus of intense therapeutic development: PD-L1, which inhibits T cells via PD-1 (Freeman et al. (2000) J. Exp. Med. 192:1027-1034; and Dong et al. (2002) Nat. Med. 8:793-800) and CD47, which inhibits tumor cell phagocytosis via SIRPα (Liu et al. (2015) Nat. Med. 21:1209-1215; Weiskopf et al. (2016) J. Clin. Invest. 126:2610-2620; Tseng et al. (2013) Proc. Natl. Acad. Sci. U.S.A. 110: 11103-11108). As the number of emerging immunotherapies, such as blockade of CD47, increases, it is becoming more challenging to select those that should be prioritized for combination therapy with PD-1 checkpoint blockade. Genetic screens can identify genes that cause synthetic lethality with specific immunotherapies, providing a rational means to identify effective combinations.

Figure 11:
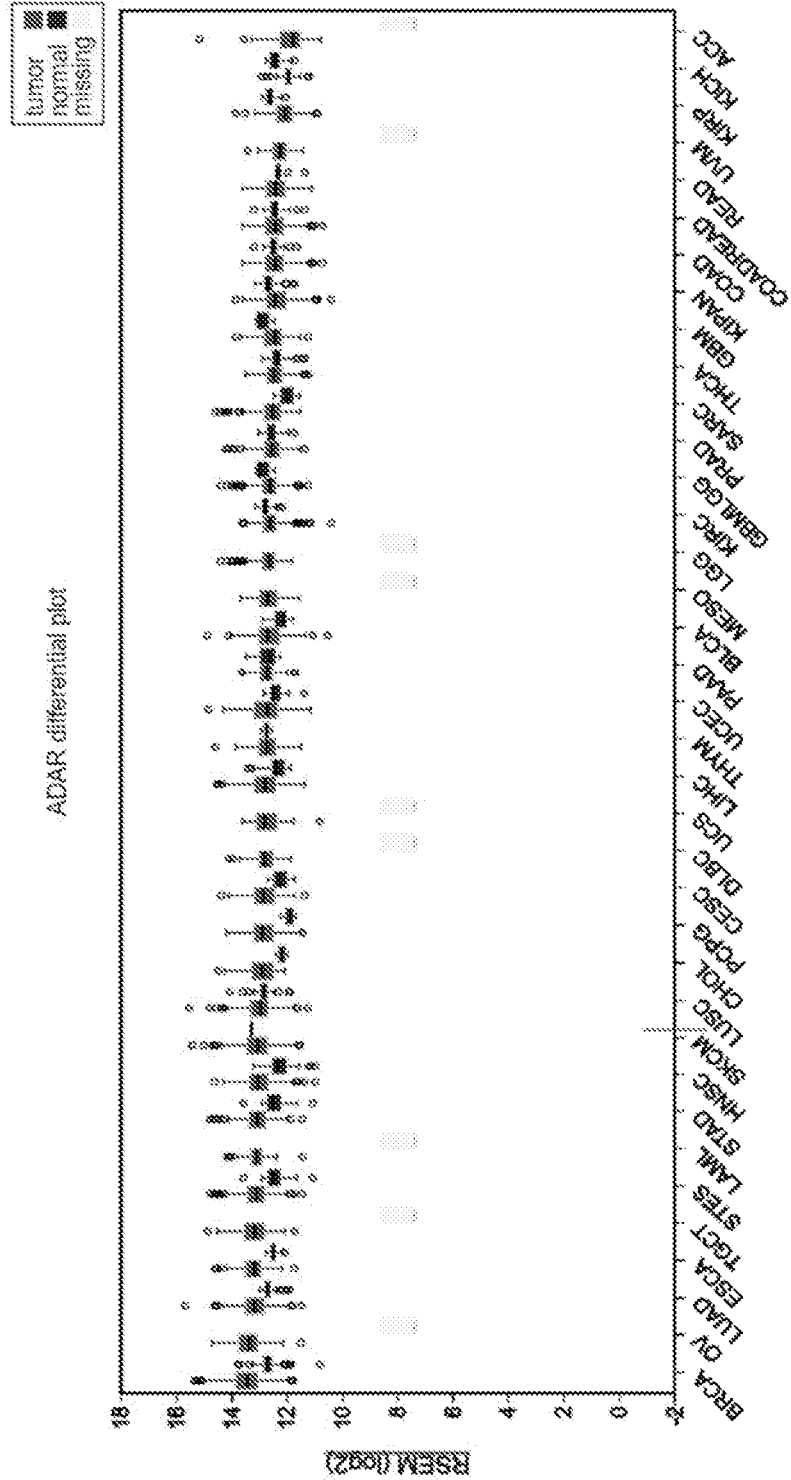
FIG. 11 shows that Adar is broadly expressed in normal and malignant tissues and is adapted from the World Wide Web address of firebrowse.org/viewGene.html?gene=ADAR.

Adar has been demonstrated to encode two broadly expressed isoforms of approximately 110 kDa and 150 kDa in both mice and humans. The p110 isoform is expressed constitutively in the nucleus, while the p150 isoform is induced by exposure to interferon and predominantly localized within the cytoplasm (Bass and Weintraub (1988) *Cell* 55:1089-1098; Nishikura (2010) *Annu. Rev. Biochem.* 79:321-349). ADAR has several characterized functional domains including a Z-DNA-binding domain, a double-stranded RNA-binding domain and an RNA-editing catalytic domain (Herbert et al. (1997) *Proc. Natl. Acad. Sci. USA* 94:8421-8426; Kim et al. (1994) *Proc. Natl. Acad. Sci. USA* 91:11457-11461). ADAR's best studied role is to catalyze adenosine-inosine (A to I) editing of endogenously produced double-stranded RNA (dsRNA). Through this mechanism, ADAR has been suggested to: 1) mediate critical pathways during embryogenesis and development, 2) modulate the expression and function of microRNAs and 3) prevent the recognition of endogenous retroelements and endogenous RNA secondary structures such as hairpins as exogenous viral infections (Nishikura (2016) *Nat. Rev. Mol. Cell Biol.* 17:83-96) (FIG. 3-7). As shown in FIG. 11, ADAR is broadly expressed in normal and malignant tissues.

Cells that lack ADAR have an inflammatory phenotype due to elevated interferon-signaling and activation of dsRNA sensing through the RIG-I-like Receptors (RLRs) RIG-I, MDA5 and PKR (Yang et al. (2014) *J. Immunol.* 193:3436-3445; Liddicoat et al. (2015) *Science* 349:1115-1120; Pestal et al. (2015) *Immunity* 43:933-944). Studies of the targets of ADAR editing have suggested that both coding and non-coding dsRNAs are edited, but that the majority of edited sites derive from the short-interspersed nuclear elements known as Alu, which are the remnants of ancient viral infections that integrated into the genome thousands to millions of years ago and currently represent approximately 10% of the human genome (Bahn et al. (2015) *Nat. Commun.* 6:6355). In the absence of the ADAR protein, the inflammatory phenotype described above can be severe, and complete genetic ablation, which induces the inflammatory phenotype as well as the loss of the developmental and micro-RNA-modulating roles, is embryonic lethal in mouse models (Mannion et al. (2014) *Cell Rep.* 9:1482-1494; Hartner et al. (2004) *J. Biol. Chem.* 279:4894-4902; Hartner et al. (2009) *Nat. Immunol.* 10:109-115). Notably, however, a human correlate of this inflammatory phenotype has been described as a cause of the type I interferonopathy (i.e., any disease or disorder in which a subject has upregulated interferon) known as Aicardi Goutiere Syndrome (AGS), which can be caused by mutation in the Adar gene (Rice et al. (2012) *Nat. Genet.* 44:1243-1248). Patients with ADAR-associated Aicardi Goutiere Syndrome in most cases demonstrate an autosomal recessive inheritance pattern of Adar mutation clustered within the catalytic (A to I editing) domain. Gene expression patterns suggestive of elevated interferon/anti-viral signaling are detectable both in the blood of patients and in the blood of their asymptomatic parents (Rice et al. (2012), supra). Clinical features of Aicardi Goutieres Syndrome include, at least, syndromic type I interferonopathy, presentation often in infancy or childhood with microcephaly, neonatal seizures, poor feeding, cerebral calcifications and atrophy, chillblain lesions, Dystonia, or other disorders, and neonatal cases which may resemble transplacental viral infection with intermittent fever, hepatosplenomegaly and thrombocytopenia. Laboratory features of Aicardi Goutieres Syndrome include, at least, increased WBC in the CSF, elevated IFNα within the CSF, elevated IFN gene transcripts in patients (also detectable in parents in ADAR-related cases), etc.

Thus, the available human data support both the relevance of the inflammatory phenotype described in model systems and the existence of a safe therapeutic window for immunologically relevant ADAR inhibition.

The data and results provided herein indicate that the therapeutic inhibition, impairment of gene expression, and/or genetic ablation of Adar (Adenosine Deaminase Acting on RNA) are strategies for treating cancer, either alone or in combination with an immunotherapy. For example, the data and results provided herein demonstrate that loss of expression of the ADAR protein by genetic ablation of Adar improves responses to immunotherapy by triggering antiviral sensing of endogenous dsRNAs and further show that 1) ADAR deficiency in tumor cells improves responses to immunotherapy in B16 and MC38 models; 2) ADAR deficiency in B16 tumor cells increases susceptibility to IFNβ and IFNγ in a PKR-dependent manner; 3) ADAR-deficient B16 tumor cells make IFNβ when stimulated with IFNβ; 4) ADAR deficiency in tumor cells may permit the sensing of EREs and endogenous hairpin structures as "non-self" in the setting of type I or type II IFN; and 5) IFN-dependence of phenotype may suggest a therapeutic window for cancers with suboptimal immune responses, particularly in combination with interferon-producing therapies.

The data suggest a hitherto unexpected therapeutic strategy that leverages the interferon-high inflammatory phenotype described above to produce anti-tumor effects. In vivo pooled CRISPR screens were used to find a dramatic and selective depletion of Adar$^{-/-}$ cells under immunologic pressure. In addition, individual tumor challenges in B16 and MC38 transplantable mouse tumor cell lines demonstrated improved responses to immunotherapy in Adar$^{-/-}$ tumors compared to control tumors. Following exposure to interferon stimulus, Adar$^{-/-}$ tumor cells were also shown to have both an increased sensitivity to interferon and an elaboration of type I interferon.

Figure 13:
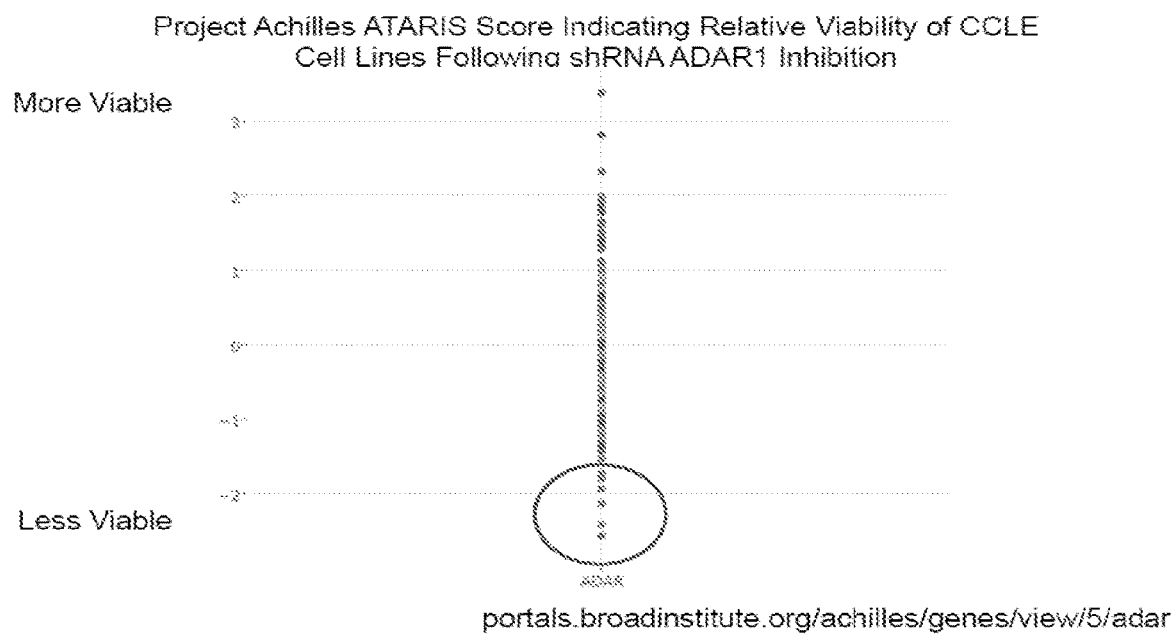
FIG. 13 shows that shRNA inhibition results in synthetic lethality of ADAR in a subset of human tumors and is adapted from the Wordl Wide Web address of portals.broadinstitute.org/Achilles/genes/view/5/adar.
Figure 14:
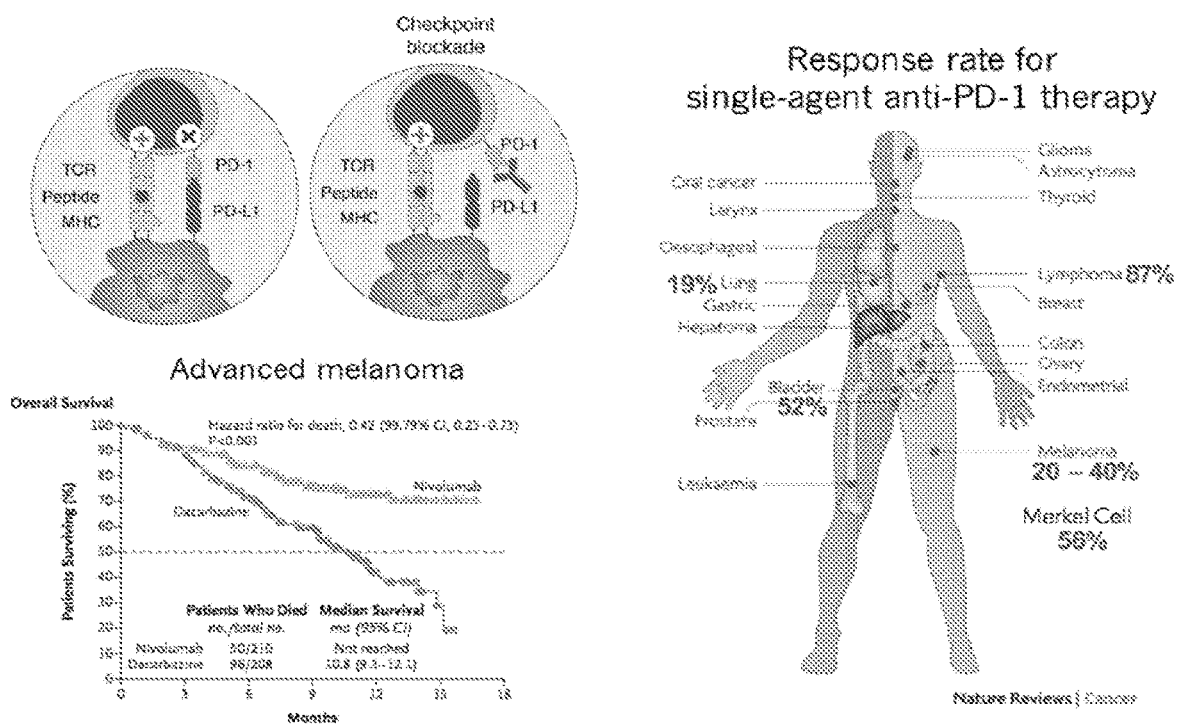
FIG. 14 provides a summary of clinical impact of immunotherapy using checkpoint blockade with anti-PD-1 antibodies.
Figure 15:
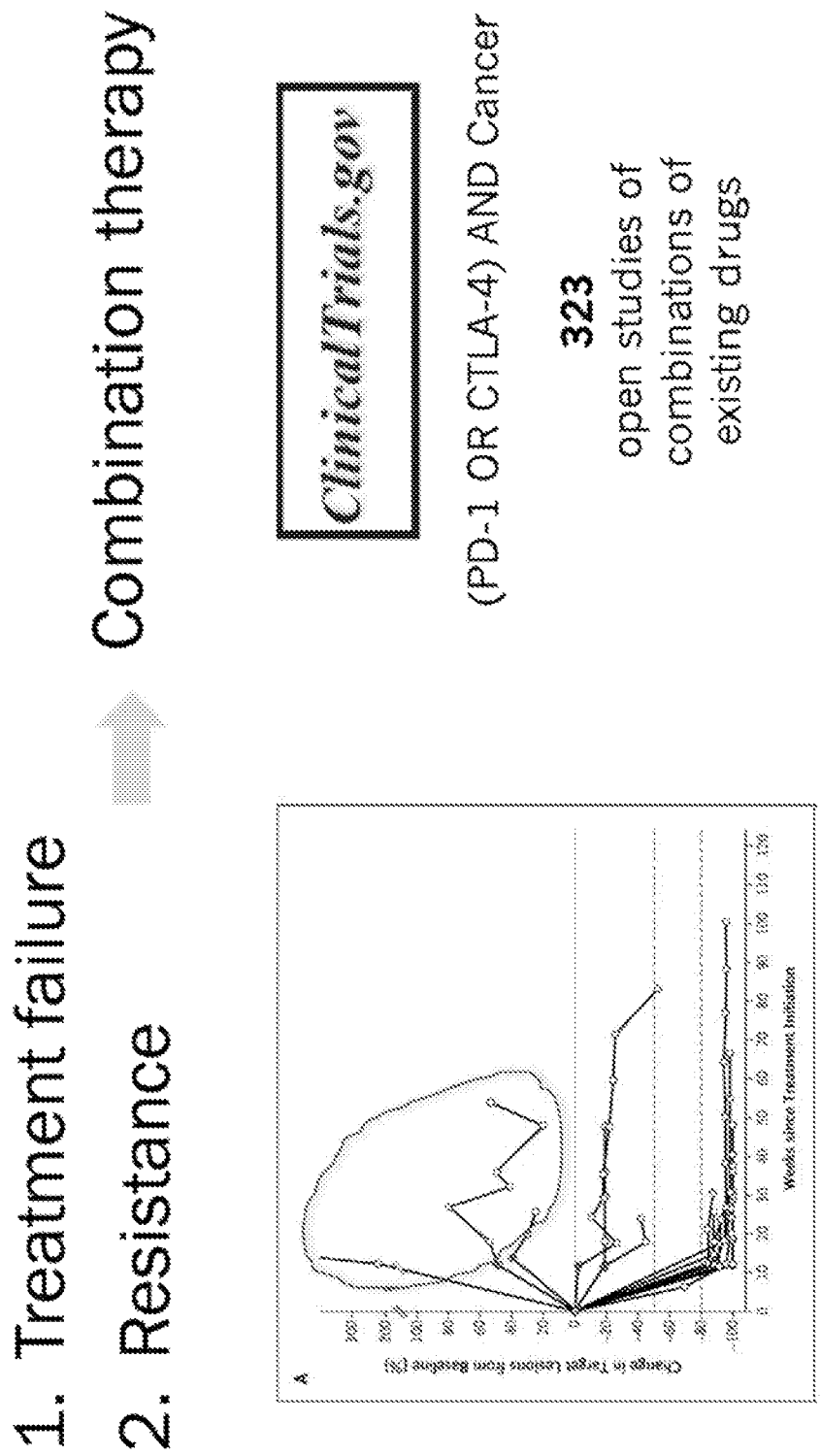
FIG. 15 provides a summary of improving current immunotherapy by increasing response rates and managing acquired resistance.

Adar is yet an unreported target for immunotherapy. Rational design approaches are possible for Adar given existence of crystal structures, known substrate and adenosine deaminase inhibitors. Adar-targeting therapies may include, at least, monotherapies for inflamed/parainflamed tumors and immunotherapy combinations (e.g., combination with immunogenic/interferon-producing chemotherapies, with locally delivered interferon or interferon-inducing agents (e.g., TLR agonists), or with targeted therapeutic radiation (or as a radiation sensitizer)) (FIGS. 14-15). Possible toxicity for such therapies may still exist since complete Adar knockout in mouse models is embryonic lethal with inflammatory, hematologic, and liver abnormalities. Data also suggest synthetic lethality of Adar inhibition through shRNA in a subset of human tumors (FIG. 13). In addition, research on Aicardi Goutieres Syndrome (interferonopathy with brain and skin manifestations and a range of severity) suggests a window of tolerability, which may be determined by local IFN-concentrations.

There is a potential benefit in numerous possible therapeutic approaches that involve targeting of ADAR including, e.g., combination with immune checkpoint blockade and/or vaccination strategies, a monotherapy or combination in parainflamed tumors that express or induce interferon (Aran et al. (2016) *Genome Biol.* 17:145), a combination with targeted radiation and/or use as a radiosensitizer, a combination with immunogenic chemotherapeutics that induce the production of interferon at the site of the tumor, a combination with locally delivered interferon or interferon-inducing agents, a combination with topical inflammatory agents such as imiquimod, etc. In each described exemplary combination, the non-ADAR-specific intervention may result in the production of interferon at the site of the tumor, thereby magnifying the effects of ADAR inhibition at that site. Broadly stated, an intervention, situation, or strategy that leads to a locally increased concentration of interferon within the tumor or area proximal to the tumor is believed to create a similarly localized increase in sensitivity to ADAR inhibition or ablation. Notably, some tumors will either produce interferon themselves or induce production of the interferon locally by the immune system. In this case, utilization of ADAR inhibition as a monotherapy, even in the absence of combination strategies, is particularly useful. Subjects or cancer cells amenable to such monotherapy can be stratified or identified, respectively, by using biomarkers indicating locally available interferon, such as interferon gene expression signatures, genomic characterization of mutations that lead to direct interferon production, a direct assay for interferon content following tumor biopsy, and the like.

It is believed that additional experiments, such as testing the responses to immunotherapy of $Adar^{-/-}$ tumors in additional mouse tumor models; testing increased susceptibility of human tumor cells to interferons in vitro; providing mechanistic RNA-sequencing data supporting increased activation of anti-viral programs in $Adar^{-/-}$ tumor cells; evaluating the immune infiltration of $Adar^{-/-}$ versus control tumor cells by flow cytometry; assessing the number and functionality of antigen-specific T-cells from $Adar^{-/-}$ tumors compared to control tumors; and evaluating the response of $Adar^{-/-}$ versus control tumor cells to additional therapeutic modalities, including further immunotherapies and therapeutic radiation, will further confirm that the therapeutic inhibition, impairment of gene expression, and/or genetic ablation of Adar (Adenosine Deaminase Acting on RNA) are strategies for treating cancer, either alone or in combation with an immunotherapy.

In summary, targeting ADAR1 in tumor cells produces an antiviral state that potentiates anti-tumor immune responses and the effects of immunotherapy, likely by unblinding the immune system to the remnants of ancient infections that have persisted within the genome. There is a strong rationale for the development of therapeutics targeting ADAR to trigger anti-viral RNA editing, sensing, and metabolism.

Example 6: Loss of Adar Induces Inflammation within Tumor Microenvironments and Enhances Responses to Checkpoint Blockade and Interferon-Producing Therapies Despite the remarkable advance of checkpoint blockade into the clinic, the majority of patients still fail to respond. Tumors without significant inflammation (i.e., "cold tumors") often respond poorly to immunotherapies such as PD-1 checkpoint blockade. Innate sensing of RNA and DNA within tumors can increase inflammation, but how this process is regulated to promote effective anti-tumor immunity remains unclear. Major mechanisms of resistance include a failure to recruit and polarize anti-tumor immune cells and a failure to respond to the cytotoxic and cytostatic mechanisms elaborated by those cells. The RNA-editing enzyme, Adar, was identified herein as a target for cancer immunotherapy and interferon-producing therapies sensitization with the ability to overcome these two major barriers to response. It is demonstrated herein that loss of RNA editing by deletion of the adenosine deaminase Adar in vivo results in increased responses to checkpoint blockade (e.g., PD-1 checkpoint blockade) and other therapies that increase interferon within the tumor microenvironment, such as therapeutic radiation and topical TLR agonists in multiple tumor models that are otherwise resistant to these interventions. Deletion of Adar within tumor cells reduced A-to-I editing of endogenous double-stranded RNA, increased its detection by multiple dsRNA-sensors, leading to increased interferon secretion, local inflammation and enhanced response to checkpoint blockade. The data showed that loss of Adar increased inflammation within non-inflamed tumor microenvironments, as well as recruitment of T-cells, NK cells and dendritic cells. In addition, deletion of Adar sensitized tumors to the anti-proliferative and pro-apoptotic effects of interferon. It is shown that Adar loss resulted in dramatically enhanced responses to both type I and type II interferons secondary to both PKR-dependent translational arrest and increased apoptosis.

Accordingly, Adar deficiency within tumors increased the efficacy of other therapies that increase interferon within the tumor microenvironment, such as radiation and topical TLR agonists. The results provide functional data demonstrating that Adar-deficiency increased the efficacy of immunotherapy and the mechanistic insight into this phenomenon including the demonstration of an increased sensitivity in Adar-deficient cells to type I and type II interferons, which are often produced by immune cells including those that are believed to produce responses to immunotherapy and the elaboration of type I interferons by the Adar-deficient tumor cells themselves, which are believed to modulate the tumor microenvironment. Taken together, these mechanisms are believed to simultaneously overcome multiple mechanisms of resistance to interferon-producing therapies, thereby allowing targeted synergy with both checkpoint blockade and interferon-producing therapies, such as therapeutic irradiation and topical TLR agonists.

Example 7: The RNA Editing Enzyme Adar1 Functions as a Checkpoint that Constrains Innate Activation of Tumor Immunity Cancer immunotherapy is effective in only a minority of patients. Tumors that fail to respond to checkpoint blockade often show scant pre-existing inflammation. Efforts to increase tumor inflammation have focused on delivering exogenous ligands for DNA or RNA pattern recognition receptors to the tumor microenvironment. Whether inhibitory mechanisms that limit the sensing of innate ligands could also be targeted to increase tumor immunity is not known. Here it is shown that loss of function of the RNA editing enzyme ADAR1 profoundly sensitizes tumors to immunotherapy. Deletion of Adar1 in tumor cells increased the efficacy of PD-1 checkpoint blockade and resulted in the spontaneous accumulation and inflammatory polarization of immune cells in untreated tumors. ADAR1 loss reduced adenosine to inosine (A-to-I) editing of endogenous double-stranded RNA (dsRNA) in tumor cells, providing more immunostimulatory ligands for detection by RNA sensors. Genetic epistasis experiments in vitro and in vivo showed that Adar1 loss sensitized tumors through two mechanisms: i) interferon β secretion from tumor cells, mediated by the sensor Mda5; and ii) interferon-induced growth arrest and apoptosis of tumor cells, mediated by the protein kinase regulated by RNA (Pkr). Both mechanisms required initial interferon exposure in order to upregulate RNA sensors. Consistent with this, Adar1-deficient tumors were also sensitized to other therapies that increase local interferon levels, including irradiation and treatment with toll-like receptor agonists. Therapeutic inhibition of Adar1 may therefore potentiate a broad range of anti-cancer therapies that depend on tumor inflammation.

Despite remarkable clinical successes of immunotherapy, the majority of patients do not respond to checkpoint inhibition, often because of a lack of immune infiltration or because of the presence of immunosuppressive cell types in the tumor microenvironment.

Figure 18:
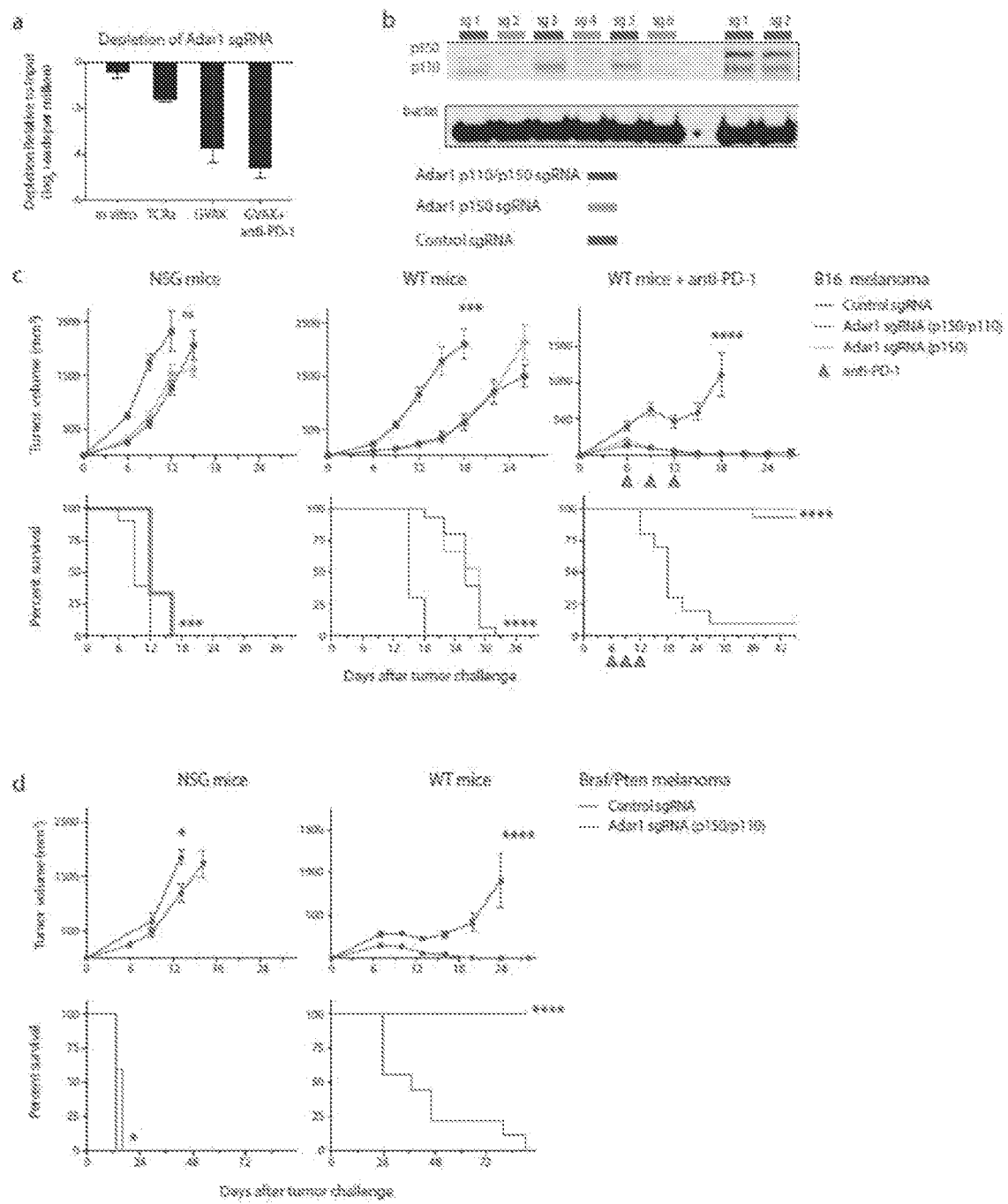
FIG. 18 includes four panels, identified as panels A, B, C, and D, which show that loss of Adar1 in tumor cells enhances anti-tumor immunity and responses to PD-1 checkpoint blockade. Panel A shows relative depletion of Adar1 sgRNAs from a pool targeting 2,368 genes expressed by B16 tumor cells under increasing immune pressure. Panel B shows expression of Adar1 protein following in control or Adar1-null B16 tumor cells. Panel C shows tumor volume (upper panel) and survival analysis (lower panel) of control (grey), Adar1 p150 null (orange) or Adar1 p110/p150 null (red) B16 tumors in NSG, WT and WT anti-PD-1 treated C57BL/6 mice. Data represent the mean of 5 animals per guide with 2 separate guides for the control group and 3 separate guides for each Adar1 null group. Panel D shows tumor volume and survival analysis of control (grey) or Adar1 p110/p150 null (red) Braf/Pten tumors (n=10 animals per group) in NSG or WT C57BL/6 mice. * P<0.05;  P<0.01; * P<0.001; **** P<0.0001.

The following results further confirm the results described in the Examples above. For example, a pooled in vivo CRISPR screen was conducted to identify genes expressed by the B16 transplantable melanoma model that, when deleted, confer sensitivity to immunotherapy. This screen identified a number of genes with the potential to modify the response to endogenous RNA species (FIG. 22, panel A), including Adar1, an adenosine deaminase acting on dsRNA that limits sensing of endogenous dsRNA (FIG. 18, panel A). Adar1-targeting guides were markedly depleted from the sgRNA pool in tumors in immunocompetent treated with a GM-CSF-secreting vaccine (GVAX) and PD-1 (FDR=0.002), but too much lesser extent in tumors growing in immunodeficient animals, and not at all in cells grown in vitro (FIG. 18, panel A).

Figure 22:
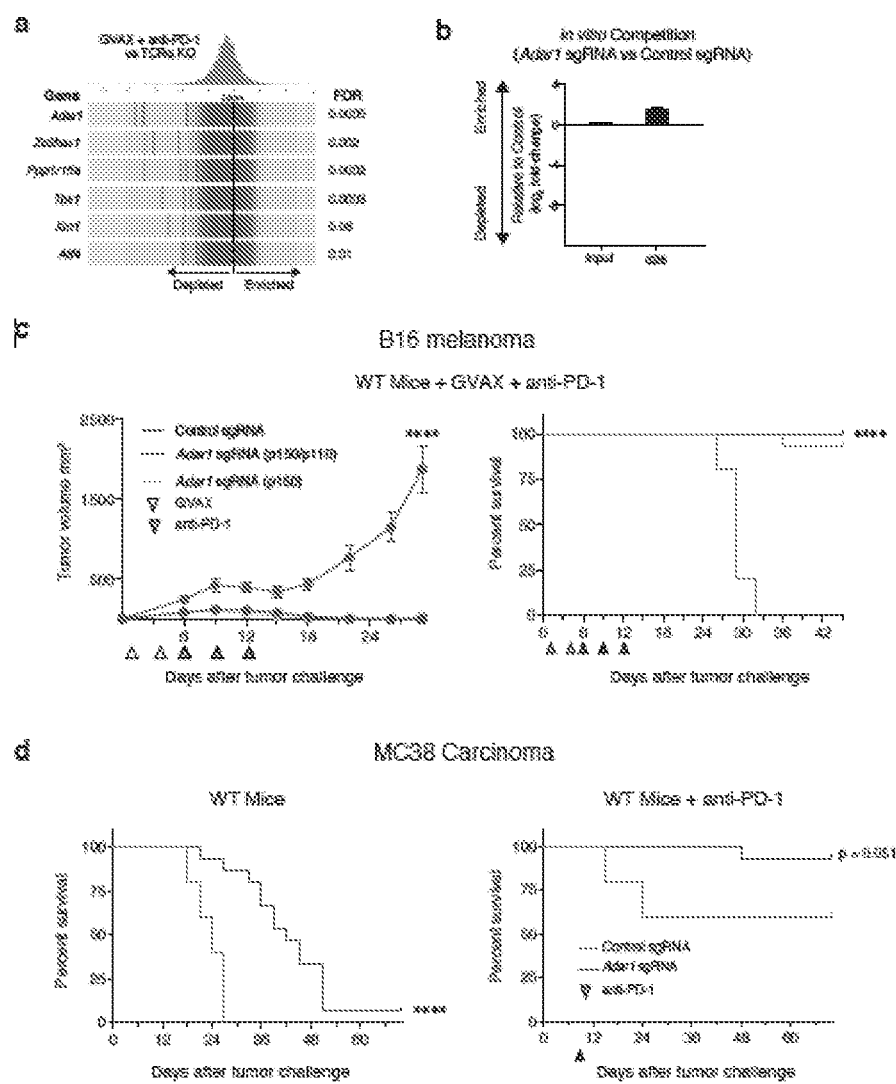
FIG. 22 includes four panels, identified as panels A, B, C, and D, which provide further validation that Adar1 loss enhances the response to immunotherapy. Panel A shows relative depletion of sgRNA targeting genes related to the anti-viral response to RNA in WT mice treated with GVAX+ anti-PD-1 compared to untreated TCR-/- mice from a previously published pooled in vivo CRISPR screen to identify novel immunotherapy targets. Panel B shows in vitro competition assay results showing the relative depletion/enrichment of an Adar1 null (GFP+) relative to a control (TdTomato+) population of B16 tumor both before and after 28 days of co-culture. Panel C shows tumor volume (left) and survival analysis (right) results of control (grey), Adar1 p150 null (orange) or Adar1 p110/p150 null (red) B16 tumors in GVAX and anti-PD-1 treated wild-type C57BL/6 mice. Data represent the mean of 5 animals per guide with 2 separate guides for the control group and at least 2 separate guides for each Adar1 null group. Panel D shows survival analysis results of control (grey) and Adar p150 or p110/p150 null (red) MC38 tumors in WT or WT and anti-PD-1-treated C57BL/6 mice. Data represent the mean of 5 animals per guide with 2 separate guides for the control group and 3 separate guides for the Adar1 null group. * P<0.05;  P<0.01; * P<0.001; **** P<0.0001.

To test whether deletion of Adar1 sensitized tumors to immune attack, B16 tumor cell lines were generated that lacked either the interferon (IFN)-inducible p150 isoform of Adar1 or both the constitutive p110 and inducible p150 isoforms. Tumor cells lacking Adar1 p150 or Adar1 p110/p150 (each isoform targeted by three sgRNAs, FIG. 18, Panel B; hereafter termed Adar1 null tumors) did not show a growth disadvantage in vitro (FIG. 22, panel B) suggesting that neither isoform is essential for cell viability. Adar null tumors implanted in NOD SCID IL2RG−/− mice (NSG mice), which lack functional innate and adaptive immunity, showed only a minimal decrease in tumor size and increase in survival relative to control sgRNA transduced tumors (FIG. 18, panel C). However, in immunocompetent animals Adar1 null tumors grew significantly more slowly than control tumors, leading to increased animal survival. PD-1 antibody treatment, which had minimal effect on control B16 tumors, cured nearly all animals bearing Adar1 null tumors (FIG. 18, panel C, P<0.0001, Log-rank test), as did treatment with PD-1 and GVAX (FIG. 22, panel C). Similarly, loss of Adar also significantly increased survival in the Braf/Pten melanoma transplantable tumor model in immunocompetent animals, but had a minimal effect in animals that lacked functioning immunity (FIG. 18, panel D; P<0.0001, Log-rank test). Moreover, Adar1 deletion improved response to PD-1 checkpoint blockade in the MC38 colon carcinoma model (FIG. 22, panel D). Thus, deletion of Adar1 markedly sensitizes multiple transplantable tumor models to immune attack.

Figure 19:
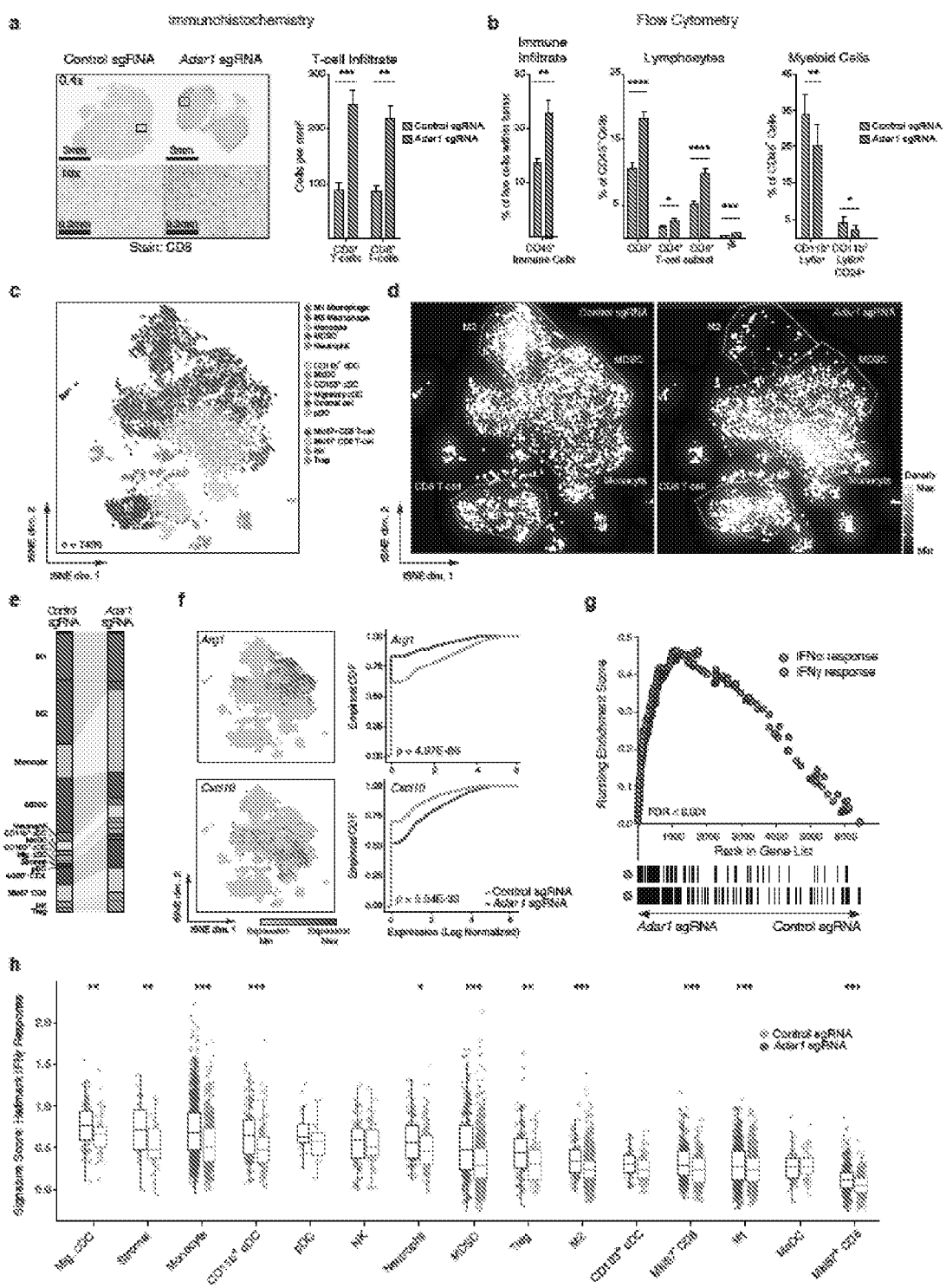
FIG. 19 includes eight panels, identified as panels A, B, C, D, E, F, G, and H, which show that the tumor immune microenvironment is reshaped by loss of Adar1 in tumor cells. Panel A shows immunohistochemistry for CD3+ and CD8+ cells in untreated control or Adar null B16 tumors (n=8 mice per group). Panel B shows flow cytometry of immune populations from untreated control (grey) and Adar1 null (red) B16 tumors (representative results from two experiments; n=8-10 mice per group per experiment). A t-SNE plot (Panel C) and density plots (Panel D) of 7,406 RNA-sequenced single CD45+ cells from Adar1 null and control B16 tumors (n=2 biological replicates for each population) are shown. Panel E shows a stacked bar graph from representing the differential composition of immune subpopulations in Adar1 null and control B16 tumors. Panel F shows differential expression of Arg1 and Cxcl10 within myeloid subpopulations and between Adar1 null (red) and control (grey) B16 tumors (cumulative distribution frequency, Kolmogorov-Smirnov test). Panel G shows the results of gene set enrichment analysis of interferon response signatures in immune cells from Adar1 null and control tumors. Panel H shows single-cell enrichment scores of an IFN response signature within individual immune subpopulations from Adar1 null and control tumors (Kolmogorov-Smirnov test).* P<0.05;  P<0.01; * P<0.001; **** P<0.0001.
Figure 23:
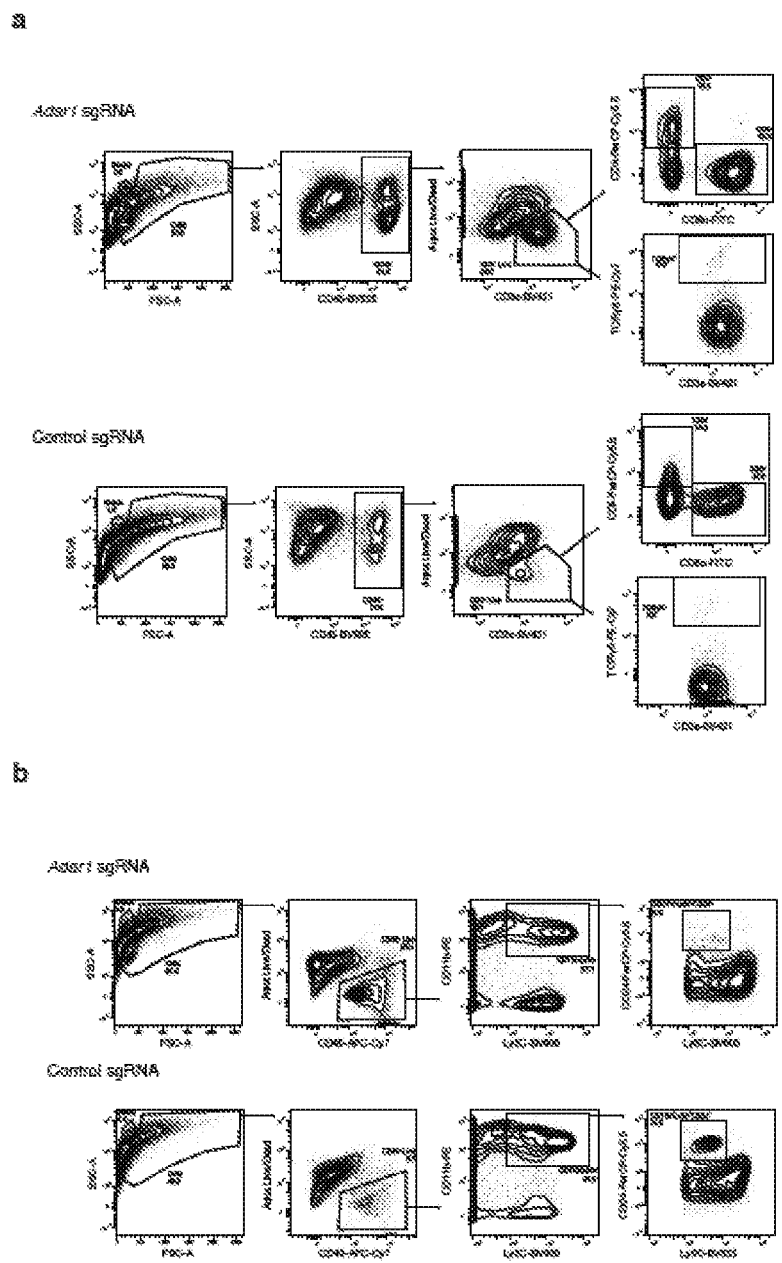
FIG. 23 includes two panels, identified as panels A and B, which show flow cytometry extended data and gating strategies. Panel A shows a gating strategy and representative flow cytometry plots for the quantification of CD4+, CD8+ and T cells. Panel B shows a gating strategy and representative flow cytometry plots for CD11b+Ly6c+ and CD11b+ Ly6cloCD24+ cells.
Figure 24:
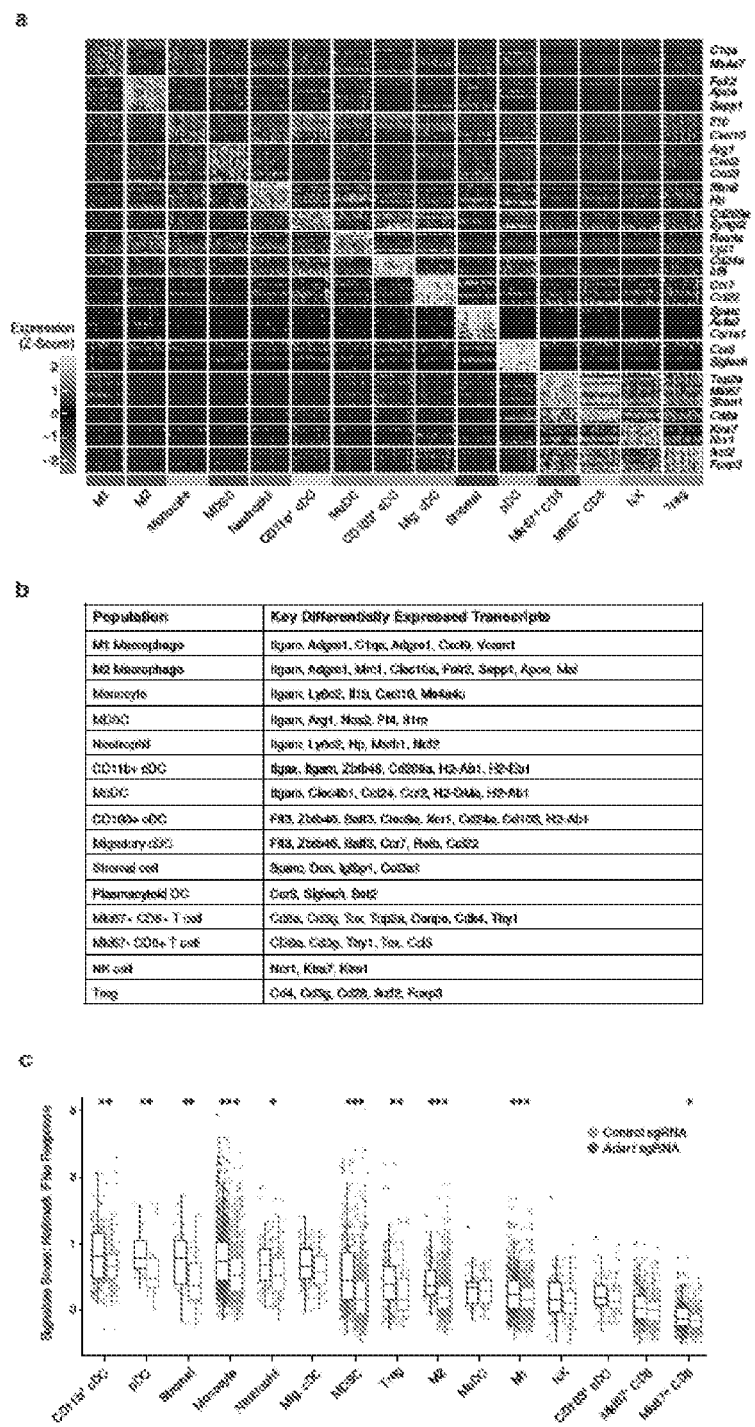
FIG. 24 includes three panels, identified as panels A, B, and C, which provide single-cell RNAseq extended data. Panel A shows gene expression matrix from single-cell RNAseq experiment characterizing expression of lineage-defining genes in cell clusters. Panel B shows key differentially expressed transcripts that distinguish cell clusters in FIG. 2. Panel C shows single-cell enrichment scores of an IFN response signature score within individual immune subpopulations from Adar1 null and control tumors (Kolmogorov-Smirnov test). * P<0.05;  P<0.01; * P<0.001.

To determine the nature of the immune response that was responsible for the increased sensitivity of Adar1-deficient tumors, the immune microenvironment of Adar1 null tumor was compared with control tumors from untreated wild-type (WT) mice. First, using immunohistochemistry, a significant increase in CD8+ T cells was found in Adar1 null tumors (FIG. 19, P<0.005, Student's t test), which were diffusely infiltrated throughout the tumor. Next, using flow cytometry (FIG. 23), it was found that Adar null tumors had significantly increased CD45+ immune infiltration compared with control tumors (FIG. 19, Panel b, P<0.01, Student's t test). Adar1-null tumors had significantly increased proportions of CD3+ T cells, CD8+ T cells and T cells compared to control tumors (FIG. 19, panel B, P<0.005 in all cases, Student's t test). Significant decreases in the proportions of CD11b+ Ly6c+ and CD11b+Ly6cloCD24+ cells in the Adar null tumors compared to the controls (P<0.01 and P<0.05, Student's t test) were also observed, suggesting a decrease in immunosuppressive myeloid-derived suppressor cells (MDSC) and tumor-associated neutrophils (FIG. 19, panel B). Lastly, a single-cell RNA sequencing on 7,406 CD45+ cells from Adar1 null and control B16 tumors was performed (FIG. 19, panels C-H). In addition to increased CD8+ T cell infiltration, a striking repolarization of the myeloid compartment of Adar1 null tumors was found (FIG. 19, panel D-F, FIG. 24, panels A-B). The fraction of M2 macrophages and MDSC was decreased in Adar1-null tumors, and myeloid cells had a marked decrease in expression of genes associated with a suppressive phenotype, such as Arg1 (P=2.63e, Kolmogorov-Smirnov test) and increased expression of inflammatory genes, such as Cxcl10 (P=1.53e, Kolmogorov-Smirnov test, FIG. 19, panel F, FIG. 24, panels A-B).

It was reasoned that inflammatory polarization of the myeloid compartment in Adar1 null tumors may be due to inflammatory cytokines and chemokines including type I and type II IFNs. The expression of signatures of IFN and IFN response was measured in the immune cells from Adar1 null tumors (FIG. 19, panel G) and found that virtually all immune cell types showed a significant increase in the expression of IFN and IFN response genes relative to control tumors (FIG. 19, panel H; FIG. 24, panel C). Deletion of Adar1 therefore caused a global reshaping of the tumor immune compartment, increasing the number of effector cells, enhancing IFN signaling and reducing the frequency of suppressive myeloid populations.

Figure 20:
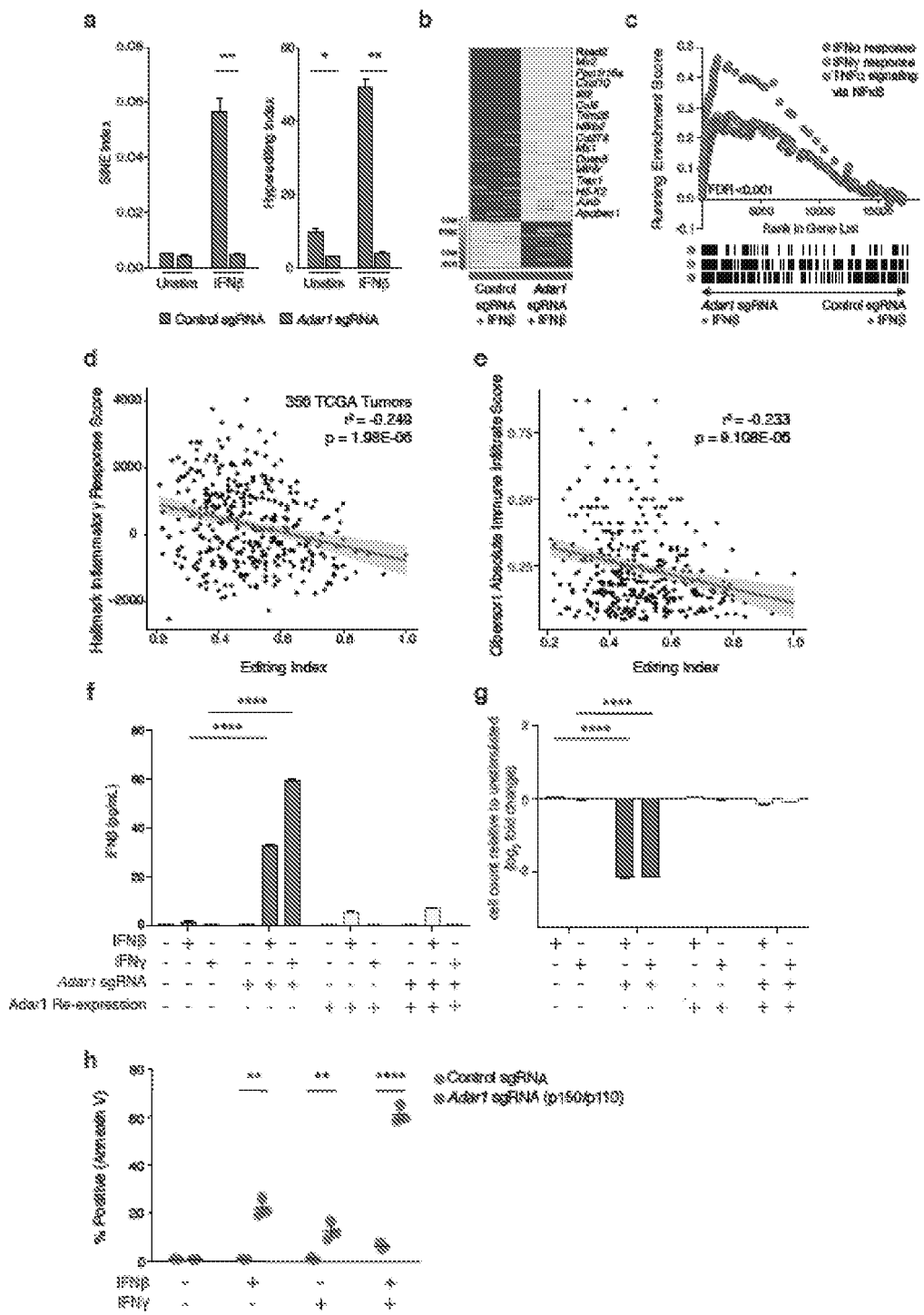
FIG. 20 includes eight panels, identified as panels A, B, C, D, E, F, G, and H, which show that Adar1 null tumor cells show impaired A-to-I editing, increased interferon secretion, and impaired growth in response to interferon stimulation. Panel A shows quantification of A-to-I editing in SINEs (right panel) and hyper-editing (left panel) in control (grey) and Adar1 null (red) B16 tumors before or following stimulation with interferon (n=3). Panel B shows a heat map showing differentially expressed genes from Adar1 null and control tumor cells 36 hours after IFN stimulation in vitro (n=3). Panel C shows the results of gene set enrichment analysis of signatures of IFN, IFN and TNF signaling via NFB in Adar1 null compared to control B16 tumors cells 36 hours following IFN stimulation in vitro. Panels D and E show the correlation between SINE (Alu) editing index and Hallmark Inflammatory Response gene signature (Panel D) and Cibersort Absolute score for immune infiltration (Panel E) in 356 tumors from TCGA. Panel F shows IFN ELISA results of supernatant from control (grey), Adar1 null (red), Adar null with full-length re-expression construct (red outline) and control with Adar1 re-expression construct (grey outline) B16 tumor cells in the unstimulated state and following stimulation with IFN and IFN (n=3 for each condition). Panel G shows relative growth of control (grey), Adar p150/p110-null (red), Adar1 null with full-length Adar1 re-expression construct (red outline) and control with Adar1 re-expression construct (grey outline) B16 tumor cells in cytokine-stimulated relative to unstimulated conditions (n=3 for each condition). Panel H shows annexin V staining in control (grey) and Adar1 p110/p150 null tumors (red) following stimulation with IFN, IFN, or a combination of both. * P<0.05;  P<0.01; * P<0.001, **** P<0.0001.

A-to-I editing of dsRNA species by Adar1 has been found to limit the induction of IFN-induced genes in somatic cells. It was therefore asked whether the interferon-induced reshaping of the immune microenvironment in Adar1 null tumors was related to sensing of un-edited dsRNA in tumor cells. Adar null tumor cells demonstrated a significant decrease in A-to-I RNA editing and hyperediting in vitro, particularly in the small interspersed nuclear elements (SINEs; FIG. 20, panel A, FIG. 25, panel A). This defect was pronounced following IFN stimulation, consistent with previous reports that IFN-mediated upregulation of Adar expression increases dsRNA editing. To test whether reduced dsRNA A-to-I editing resulted in an increased IFN response in tumor cells, gene expression profiles of Adar1 null and wild-type tumor cells was compared in vitro following interferon stimulation. Significant upregulation of gene signatures associated with IFN response, IFN response and TNF signaling via NFB, as well as upregulation of cytokine and chemokine genes, including IFNB1, IL-6, CCL5, CXCL9 and CXCL10, were found (FIG. 20, panels B and C).

Many human tumors have amplifications of the ADAR1 locus and increased A-to-I editing levels compared to non-malignant tissues that might prevent immunostimulatory dsRNA from eliciting an inflammatory response. To determine whether increased A-to-I editing of dsRNA in human tumors was associated with reduced inflammation in human cancer, levels of RNA editing were compared with previously characterized levels within The Cancer Genome Atlas (TCGA) to gene expression signatures of inflammatory response and immune infiltration. It was found that increased A-to-I editing within SINEs (Alu) was negatively correlated with expression signatures of inflammation (P=1.98e-6, Kolmogorov-Smirnov test), response to IFN (P=0.012) evidence of apoptosis (P=1.113e-7), as well as two measurements of inferred immune infiltration (FIG. 20, panels D and E, FIG. 25, panel B and C, P=9.108e-6 and 0.0029), suggesting that human tumors with the lowest levels of RNA editing (and correspondingly the greatest amount of immunostimulatory dsRNA) have the highest levels of immune infiltration and inflammatory gene expression.

Figure 26:
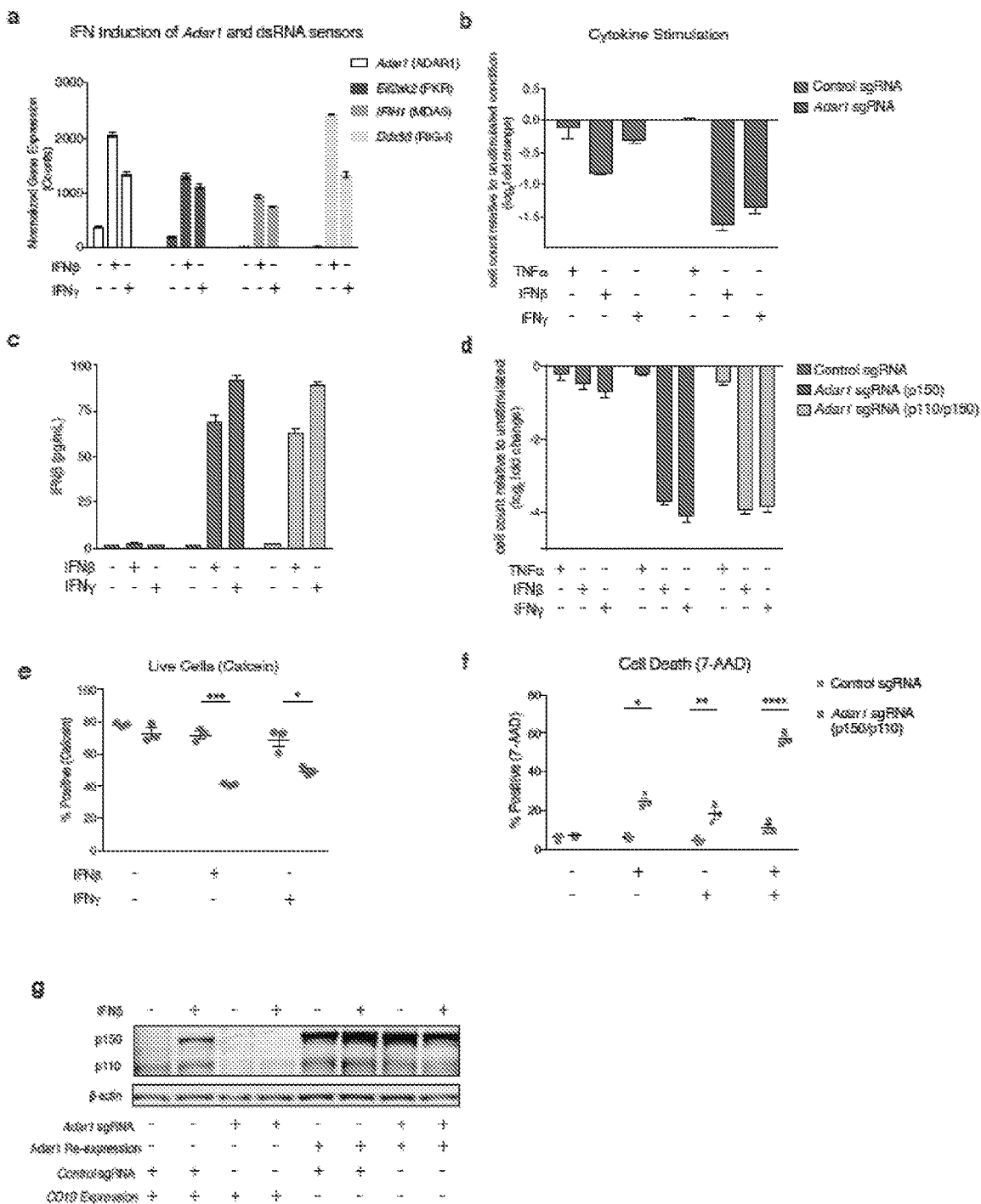
FIG. 26 includes seven panels, identified as panels A, B, C, D, E, F, and G, which provide corroborating study results of Adar1-null tumor cells in vitro. Panel A shows upregulation of Adar1 and dsRNA sensors following stimulation with IFN or IFN as measured in RNAseq experiments. Panel B shows growth inhibition of Adar1 null (red) and control (grey) Braf/Pten tumor cells following stimulation with TNF, IFN, or IFN relative to the unstimulated state. Panel C shows IFN ELISA of control (grey), Adar1 p150/p110 null (red) and Adar1 p150 null (orange) following stimulation with IFN or IFN. Data represent the mean of 3 replicates for each guide with 2 control guides, 3 guides targeting Adar1 p150/p110 and 3 guides targeting Adar1 p150 alone. Panel D shows growth inhibition of Adar1 p150/p110 null (red) and Adar p150 null (orange) following stimulation with IFN or IFN. Data represent the mean of 3 replicates for each guide with 2 control guides, 3 guides targeting Adar1 p150/p110 and 3 guides targeting Adar1 p150 alone. Panels E and F shows calcein cell viability (Panel E) and 7-AAD cell death (Panel F) staining of control (grey) or Adar1 p150/p110 null (red) B16 tumor cells following stimulation with IFN, IFN or a combination of both. Data are representative of 3 separate experiments with 3 replicates for each condition. Panel G shows Western blot results of B16Adar1 null tumor cells following re-expression of WT Adar1 or an irrelevant control (CD19) protein.

To confirm that impaired A-to-I editing was associated with increased IFN expression, IFN secretion was measured in control and Adar1 null B16 tumor cells. Under unstimulated conditions, neither Adar1 null nor control tumor cells expressed IFN. However, following stimulation with exogenous IFN or IFN, Adar1 null tumors secreted IFN, whereas control cells did not (FIG. 20, panel F). Re-expression of Adar1 in Adar1 null tumors suppressed the IFN secretion demonstrating that this effect was unlikely to be an off target effect of gene editing (FIG. 20, panel F; FIG. 26, panel G). IFN secretion from Adar null tumor cells persisted after exogenous IFN in the medium had been removed, suggesting a positive feedback loop in which exogenous IFN stimulation upregulates RNA sensors that detect the increased quantities of unedited dsRNA in Adar1 null tumor cells, resulting in autocrine IFN stimulation. Consistent with this model, B16 tumor cells significantly upregulated dsRNA sensors including Ifih1, Ddx58 and Eif2ak2 upon IFN stimulation (FIG. 26, panel A).

Loss of Adar1 has been associated with translational arrest and apoptosis. In order to determine whether Adar1 loss also induced growth arrest and apoptosis in tumor cells, cell growth and apoptosis in Adar1 null and control tumors were studied. Growth of control B16 or Braf/Pten tumor cells in vitro was only modestly impaired by IFN or IFN (FIG. 20, panel G, FIG. 26, panel B, C and D). However Adar null cells showed significant inhibition of growth (P<0.0001, Student's t test) associated with elevated levels of apoptosis (FIG. 20, panel H, FIG. 26, panel E and F) relative to control tumor cells. Re-expression of Adar1 reverted the growth inhibition by IFN to wild-type levels (FIG. 20, panel G, FIG. 26, panel G).

Figure 21:
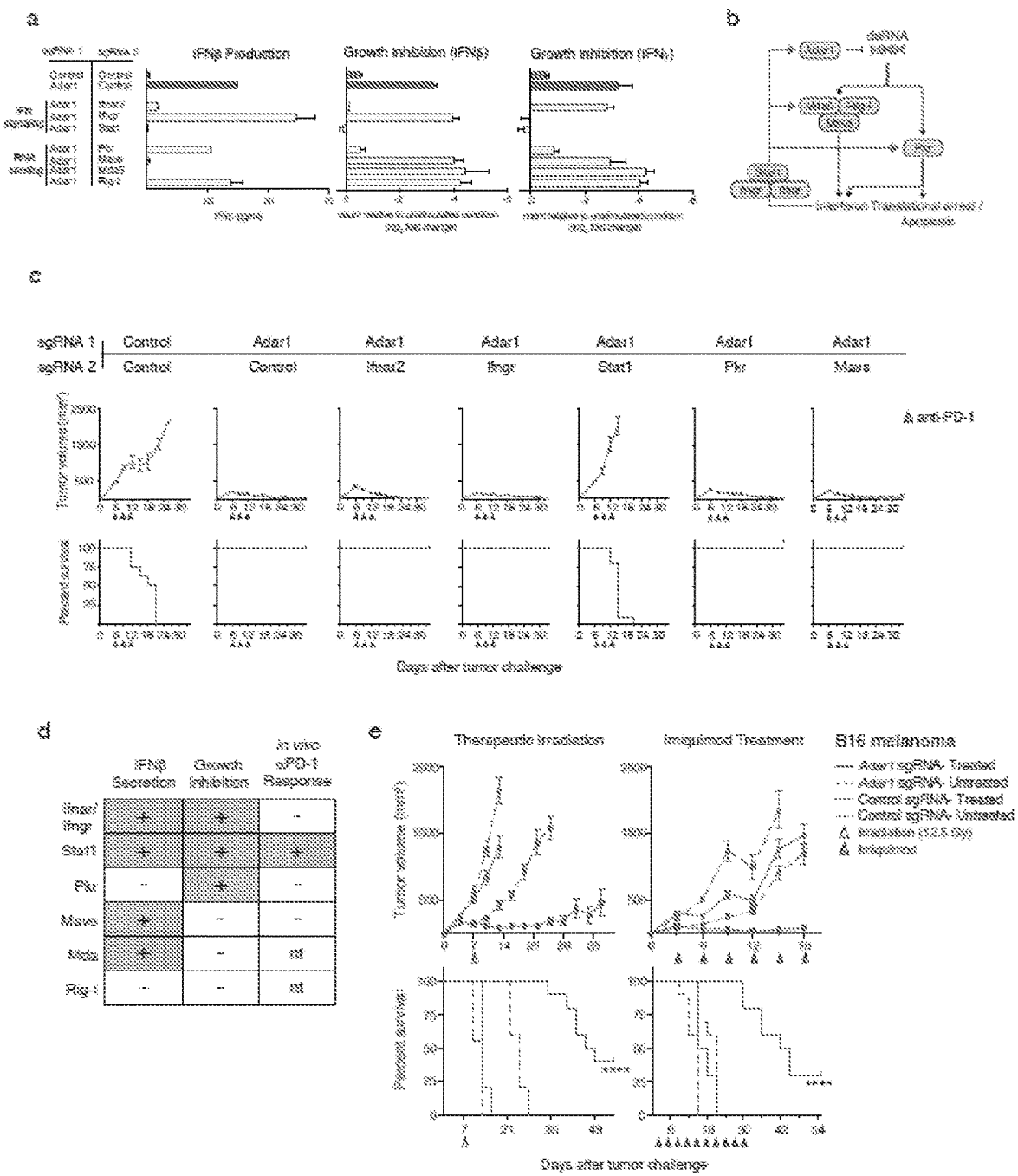
FIG. 21 includes five panels, identified as panels A, B, C, D, and E, which show that Adar1 null tumors are sensitized to immunotherapy due to increased Mda5-dependent interferon release and Pkr-dependent growth inhibition. Panel A shows genetic dependencies of IFN secretion (left) and cytokine growth inhibition (right) in Adar1 null B16 tumor cells for the genes indicated (n=3 for each condition). Panel B shows a schema of the genes required for interferon release and growth arrest in Adar1 null cells. Panel C shows B16 tumor volume and survival analysis results demonstrating genetic dependencies for sensitivity to PD-1 checkpoint in vivo for the genes indicated (n=5 mice in each group). Panel D shows a summary of in vitro and in vivo epistatic results. Panel E shows tumor volume and survival analysis results of control (grey) and Adar1 null (red) B16 tumors following therapeutic irradiation and imiquimod treatment. Data are representative of two separate experiments (n=5 mice in each treatment group). * P<0.05;  P<0.01; * P<0.001; **** P<0.0001.
Figure 27:
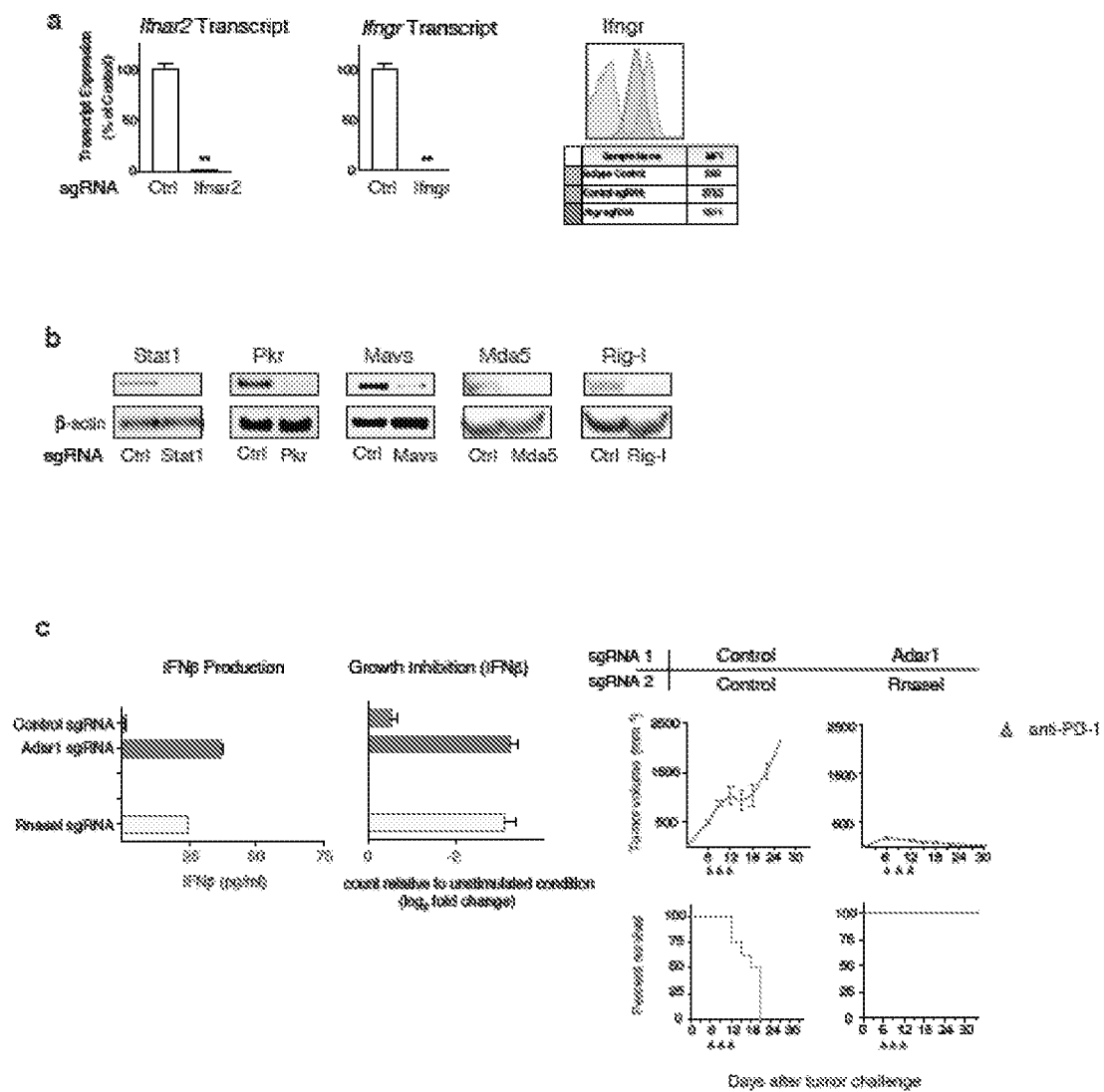
FIG. 27 includes three panels, identified as panels A, B, and C, which provide further epistasis study results. Panel A shows expression of Ifnar2 and Ifngr transcripts and Ifngr protein from control and Adar1/Ifnar2 and Adar1/Ifngr null B16 tumor cells as measured by quantitative real-time PCR and flow cytometry. Panel B shows Western blot results of Stat1, Pkr, Mavs, Mda5 and Rig-I in control and Adar1 double-deletion tumor cells. Panel C shows evaluation results of the epistatic relationship between Adar1 and Rnase1 in B16 tumor cells in vitro and in vivo.

Genetic studies in the mouse model of Adar deficiency have shown an embryonic lethal phenotype that requires the activity of Mavs or Mda5, but not Pkr or Stat. In contrast, studies in human cells have demonstrated that PKR is required for translational arrest and apoptosis following Adar1 deletion. To identify which RNA sensing pathways are necessary to elicit the IFN response, apoptosis, and the enhanced immunotherapy response observed in Adar1 null tumors, double-deleted B16 tumor cell lines was generated that lacked Adar1 and each member of the IFN signaling or dsRNA sensing pathway shown in FIG. 21, panel B (FIG. 21, panels A and B, FIG. 27). The requirement for each pathway member for three phenotypes was tested: i) enhanced IFN production in vitro; ii) growth inhibition/apoptosis in vitro; and iii) sensitivity to PD-1 checkpoint blockade in vivo. The in vitro phenotypes showed genetic dependencies distinct from those suggested by the mouse knockout: IFN secretion by Adar1 null cells was suppressed by epistatic loss of Mda5 and Mavs but not by loss of Pkr; however the growth inhibition/apoptosis phenotype was abolished by loss of Pkr, but not Mda5, Mavs, Rig-I or Rnase1. Moreover, loss of IFN receptor recognition or Stat1 prevented both the increase in IFN secretion and inhibition of growth in Adar1 null tumors (FIG. 21, panel C) in response to IFN stimulation (while these genes are dispensable for the Adar1 knockout mouse phenotype). Thus, Adar1 deficient cells have distinct dsRNA sensing dependencies for IFN production and for growth inhibition, and an absolute dependence on IFN exposure to trigger either phenotype (FIG. 21, panel C).

Figure 25:
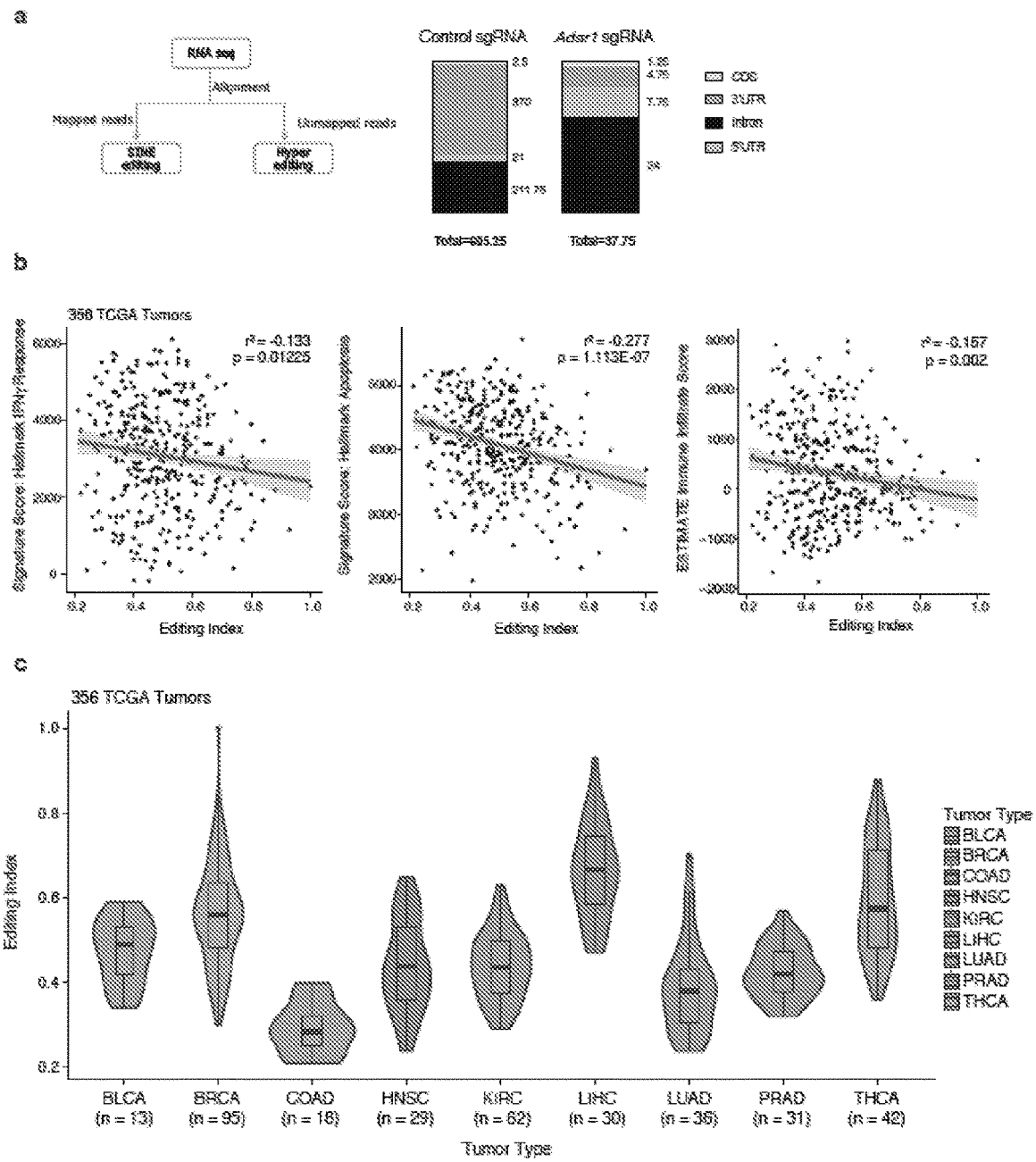
FIG. 25 includes three panels, identified as panels A, B, and C, which show extended analysis results correlating RNA editing and signatures of immune infiltration in TCGA. Panel A shows RNA editing pipeline (left) and transcript localization within the genome of discovered edits (right). Panel B shows correlations between SINE (Alu) editing index and signatures for IFN, apoptosis and immune infiltrate using the ESTIMATE method from 356 tumors in TCGA. Panel C shows correlations between Alu editing index and tumor type in the same tumors from TCGA.

The distinct genetic dependencies of IFN secretion and apoptosis in Adar1 null tumor cells in vitro allowed us to dissect which of these phenotypes was required for the increased sensitivity to checkpoint blockade in vivo (FIG. 21, panel C and D, FIG. 25, panel C). Neither loss of Pkr nor Mavs reduced the sensitivity of Adar null tumors to immunotherapy. This suggests that either growth inhibition and apoptosis (mediated by Pkr) or interferon secretion (mediated by Mavs) is sufficient to increase the sensitivity of Adar1-null tumors to PD-1 checkpoint blockade. However, Stat1 deletion completely abrogated the sensitivity of Adar null tumors demonstrating that IFN stimulation of Adar1 null tumor cells was absolutely required to initiate the cellular feedback loop that increases sensitivity to immunotherapy. Neither deletion of Ifnar2 (the receptor for Type I IFN) nor of Ifngr (Type II IFN receptor) in Adar1 null tumors was sufficient to suppress the enhanced response to PD-1 checkpoint blockade, suggesting that signaling by either Type I or Type II IFN in vivo could serve to initiate the enhanced immunotherapy response.

Given that either type I or type II IFN could sensitize Adar1 null tumors to immunotherapy, it was reasoned that loss of Adar1 may sensitize tumors to other anti-tumor therapies that have been shown to elicit the production of type I IFN within the microenvironment, such as radiation or toll-like receptor agonists. Neither radiation (12.5 Gy), nor topical therapy with imiquimod, a TLR7 agonist, increased the survival of animals bearing control B16 tumors. However, both treatments significantly slowed tumor growth and enhanced survival in animals bearing Adar1 null tumors, in some cases leading to complete tumor clearance (FIG. 21, panel E, P<0.0001 for survival in both cases, log-rank test). Thus, Adar1 loss increases the efficacy of irradiation and imiquimod therapy, suggesting that inhibiting RNA editing may enhance the effects of therapies that produce local IFN-mediated inflammation.

Three main conclusions emerge from these studies. First, Adar1 deletion remodels the immune microenvironment of tumors and sensitizes them to immunotherapy. Second, the mechanisms by which Adar1 null tumors are sensitized involves activation of distinct Mda5-dependent IFN secretion and Pkr-dependent growth inhibition phenotypes as well as an absolute requirement for exogenous IFN that would not have been predicted by the phenotype of Adar1 knockout mice. A reasonable concern about Adar as a therapeutic target is that its inhibition would lead to autoimmunity through generalized triggering of the interferon response in healthy tissues. However, the dependence on exogenous IFN to trigger the sensitivity of Adar deficient tumors may provide a therapeutic window for targeting ADAR1 clinically, by combining ADAR1 inhibition with anti-tumor therapies that increase IFN abundance in the tumor. Third, current strategies to improve the outcome of immunotherapy assume that increasing delivery or expression of innate ligands are believed to be required to increase immune infiltration of non-inflamed tumors. In contrast, these results indicate that cancer cells already contain sufficient quantities of immunostimulatory nucleic acids to elicit therapeutic inflammation, if the innate checkpoints that limit their detection—such as Adar1—can be overcome.

Methods for Example 7

Creation of CRISPR Edited Tumor Cell Lines.

Adar1 was deleted in Cas9-expressing B16 tumor cell lines for validation experiments using a lentiviral delivery system (pXPR_BRD024, Addgene) to express sgRNAs using puromycin selection as previously described. For further validation experiments, epistasis and re-expression/rescue experiments, Adar1 was deleted in B16 cells using transient transfection of a Cas9-sgRNA plasmid (pX459, Addgene) with the Turbofect transfection reagent (Thermo Fisher Scientific, R0531) and puromycin selection. For epistasis experiments, Cas9 was expressed using the pLX311 backbone and epistasis guides were expressed using the pXPR_BRD024 lentiviral expression system. For in vitro re-expression/rescue experiments, Adar1 or an irrelevant control protein (CD19) was expressed using the pLX311 backbone used in prior work to express Cas9.

Animal Treatment and Tumor Challenges.

The designs of animal studies and procedures were approved by the Dana Farber Cancer Institute IACUC and the Broad Institute IACUC committees. Specific pathogen-free facilities at the Dana Farber and the Broad Institute were used for the storage and care of all mice. Six-week old wild-type female C57BL/6J mice were obtained from Jackson laboratories, Bar Harbor ME A colony of B6.129S2-Tcra$^{tm1Mom}$/J (Tcra) T cell-deficient mice were bred on site at the Dana Farber. A colony of NOD.Cg-Prkd$^{scid}$ Il2rg$^{tm1Wjl}$/SzJ (NSG) were bred on site at the Broad Institute. Mice were aged matched to be 6-12 weeks old at the time of tumor inoculation. For tumor challenges, $2.0 \times 10^6$ tumor B16, Braf/Pten or MC38 cells resuspended in Hanks Balanced Salt Solution (Gibco) were mixed 1:1 by volume with matrigel (Corning) and subcutaneously injected into the right flank on day 0. Where indicated, mice were vaccinated with $1.0 \times 10^6$ GM-CSF-secreting B16 (GVAX) cells (kindly provided by Dr. Glenn Dranoff) that had been irradiated with 3500 Gy on days 1 and 4 to elicit an anti-tumor immune response. Subsequently, where indicated mice were treated with 100 mg of rat monoclonal anti-PD1 (clone: 29F.1A12) on days 6, 9 and 12 (for B16) and day 9 (for MC38) via intraperitoneal injection. Tumors were measured every 3 days beginning on day 6 after challenge until time of death. Measurements were taken manually by collecting the longest dimension (length) and the longest perpendicular dimension (width). Tumor volume was estimated with the formula: $(L \times W2)/2$. $CO_2$ inhalation was used to euthanize mice on the day of sacrifice. For irradiation experiments, the Dana Farber Small Animal Radiation Research Platform was utilized. Briefly, mice were anesthetized via isoflurane inhalation for the duration of each treatment. For each treatment, tumors were visualized using cone beam computed tomography (CT) using 60 kVp and 0.8 mA photons. Tumors were treated using a 10×10 mm square shaped collimator selected to give 0.25-0.5 cm margins around gross tumor, using 220 kVp and 13 mA photons given with a lateral en face field prescribed to a depth of 5 mm. The small animal radiation research platform was calibrated and maintained as previously described. For imiquimod experiments, 5% imiquimod cream was obtained through the Dana-Farber Cancer Institute animal facility. A thin film of imiquimod cream was applied to the skin overlying tumors every three days following tumor inoculation until tumor outgrowth or disappearance.

Immunohistochemistry.

Immunohistochemical (IHC) staining was performed at the Dana-Farber/Harvard Cancer Center Specialized Histopathology Core using a Leica Bond automated staining platform with anti-CD3 (Abcam, clone ab16669; 1:150 dilution) and anti-CD8 (eBio, clone 14-0808; 1:100 dilution) antibodies. Slides were visualized using Aperio software. CD3+ and CD8+ cells staining with strong membranous positivity were enumerated in five separate areas at 20× magnification in a blinded fashion by G.K.G. for each slide.

Analysis of Tumor-Infiltrating Lymphocytes by Flow Cytometry.

$2 \times 10^6$ control guide or Adar1 null tumor cells (Adar sgRNA 2) were implanted in matrigel into BL6 female mice at 5-8 weeks of age. On day 14 following implantation, tumors were dissected from the surrounding fascia, weighed, mechanically minced, and treated with collagenase P (2 mg/mL, Sigma) and DNAse I (50 mcg/mL, Sigma) for 10 minutes at 37° C. Cells were passed through a 70 micron filter to remove clumps, diluted in media, and a small aliquot taken directly for flow cytometry. Cell surface staining was performed with the indicated antibodies prior to fixation/permeabilization of the cells (Intracellular Fixation & Permeabilization Buffer Set, eBiosciences) for intracellular staining. Sphero™ AccuCount Fluorescent Particles (Spherotech) were added to each tube to allow cell counting prior to analysis on a LSR II flow cytometer (BD Biosciences). All analysis was done with FlowJo software (FlowJo). Cell counts were determined by normalizing cell numbers to beads recorded, divided by the amount of tumor aliquot taken and the mass of the tumor.

Analysis of Tumor-Infiltrating Lymphocytes by Single Cell RNAseq.

Adar1 null (sgRNA2) or control tumor cells ($2 \times 10^6$) were implanted in matrigel into the right flank of C57BL/6 female mice. On day 14, tumors were dissected from the surrounding fascia, mechanically minced, and treated with collagenase P (2 mg/mL, Sigma) and DNAse I (50 mcg/mL, Sigma) for 10 minutes at 37° C. Tumor-infiltrating leukocytes were enriched using Optiprep (Sigma) density gradient followed by CD45+ MACS positive selection (Miltenyi). B16 tumor cells grown in culture were added to each sample at a 5% ratio as a spike-in control for assessing sample to sample variability. Cells were counted and loaded onto the 10× device (10× Genomics). Samples were processed per the manufacturer's protocol and sequenced on an Illumina NextSeq sequencer. Sample demultiplexing, barcode processing, alignment, filtering, UMI counting, and aggregation of sequencing runs were performed using the Cell Ranger analysis pipeline (v1.2). Downstream analyses were performed in R using the Seurat package.

For each cell, two quality control metrics were calculated: (1) the total number of genes detected and (2) the proportion of UMIs contributed by mitochondrially encoded transcripts. Cells in which fewer than 200 genes were detected and in which mitochondrially encoded transcripts constituted greater than 10% of the total library were excluded from downstream analysis. Genes detected in fewer than three cells across the dataset were also excluded, yielding a preliminary expression matrix of 8,834 cells (comprised of both infiltrating immune cells and spiked-in tumor cells) by 17,190 genes. To assess technical variability between samples, an initial tSNE projection was generated using all 8,834 cells; co-clustering of spiked-in tumor cells expressing Pmel and Mlana (transcriptional markers of melanoma) from all four experiments demonstrated minimal sample to sample variability. 1,428 tumor cells were subsequently removed from the total expression matrix, leaving only infiltrating immune cells for downstream analysis.

Mean and dispersion values were calculated for each gene across the remaining 7,406 cells, and a subset of 1,494 highly variable genes were selected for principal components analysis (PCA). Following PCA, the first 55 PCs were determined to be significant (P<0.01) using the jackstraw method and tSNE was performed on these significant PCs using default parameters for 1000 iterations for visualization in two dimensions. Unsupervised clustering using a shared nearest neighbor modularity optimization based algorithm (resolution parameter 0.8) identified 15 distinct clusters. For classification of immune cell populations, differential expression analysis was performed between each cluster and all other cells using a Wilcoxon rank sum test. Top differential expression results for each cluster were cross-referenced with canonical markers for a comprehensive range of immune cell populations, yielding a consensus panel of transcriptional markers for each of the 15 clusters (FIG. 24, panel B).

For pre-ranked GSEA, differential expression analysis was performed between all infiltrating immune cells from Adar1 null tumors and control tumors using a Wilcoxon rank sum test, and a ranking metric was calculated for each gene as R=−log 10 (q), where q is the FDR-adjusted P-value. Pre-ranked GSEA was performed using a curated collection of gene-sets consisting of sets from the Hallmark and Gene Ontology collections in the MSigDB database. Single-cell signature scoring using FastProject was also performed using this curated collection.

RNAseq Analysis of Tumor Cells.

Adar1 null or control sgRNA-transfected B16 cells were stimulated with IFNγ (100 ng/mL, Cell Signaling Technology) or IFNβ (1000 U/mL, PBL) for 36 hours. RNA was extracted from cell pellets using the Qiagen RNeasy® Mini kit according to the manufacturer's instructions. First-strand Illumina-barcoded libraries were generated using the NEB RNA Ultra™ Directional kit according to manufacturer's instructions, using ribosomal RNA depletion and including a 12-cycle PCR enrichment. Libraries were sequenced on an Illumina NextSeq 500 instrument using paired-end 37 bp reads. Data were trimmed for quality using the Trimmomatic pipeline with the following parameters: LEADING:15 TRAILING:15 SLIDINGWINDOW:4:15 MINLEN:16. Data were aligned to mouse reference genome mm10 using Bowtie2. HTSeq was used to map aligned reads to genes and to generate a gene count matrix. Normalized counts and differential expression analysis was performed using the DESeq2 R package. Gene set enrichment analysis was performed as previously described, using the Hallmark gene signature collection.

RNA Editing Analysis of Tumor Cells

All editing analysis was performed using tumor cell RNAseq data, which was generated as indicated above. The quality of the sequence reads was confirmed using the FastQC (https://www.bioinformatics.barbaraham.ac.uk) quality control tool with default parameters. Duplicated reads were removed using prinseq54. Next, sequence reads were aligned using the STAR55 aligner to the mm9 reference genome with parameters that accept only uniquely aligned reads (outFilterMultimapNmax=1) and limit the number of mismatches to 0.05 of the mapped length (outFilterMismatchNoverLmax=0.05).

In order to generate the SINE index measurements, a previously published human Alu-specific editing detection algorithm was adjusted to screen three mouse SINE subfamilies: B1, B2 and B4. Similar to the Alu editing index, the SINE editing index is defined as the number of guanosines that were aligned to genomic adenosines that reside in SINE element, divided by the total number of nucleotides within the reads that align to SINE adenosine positions.

Hyper-editing analysis is another global estimate of RNA editing levels. This analysis quantifies heavily edited reads (hyper-edited) which fail to align to the corresponding genome using standard alignment tools, and are hence traditionally overlooked. In order to align these hyper-edited reads, all adenosines were transformed to guanosines in both the unmapped reads and the reference genome and realigned, and then transformed back to the nucleotide to identify all mismatches. For each sample, the number of hyper-edited reads per million mapped reads is used to quantify the level of hyper-editing.

TCGA Analysis.

SINE (Alu) editing index was obtained from a previously published study characterizing primary tumor samples from 356 patients with publically available RNAseq data in the TCGA collection (see cancergenome.nih.gov/. Gene signature scores for Hallmark gene sets were assigned to these primary tumor samples using single sample gene set enrichment analysis (ssGSEA) and the GenePattern interface (see genepattern.broadinstitute.org). CIBERSOR was used to calculate an absolute immune infiltrate score for all primary tumor samples. ESTIMATE was used to independently quantitate immune infiltrate for each primary tumor sample (see bioinformatics.mdanderson.org/estimate/). For samples without a publically available ESTIMATE score, scores were calculated using the ESTIMATE R package. Pearson correlation tests were performed using R.

In Vitro Cytokine Stimulations and Growth Inhibition Assays.

Tumor cells were engineered as noted above and plated in DMEM+10% FBS containing the indicated combinations of cytokines: IFN (1,000 U/ml, PBL), IFN (100 ng/ml, Cell Signaling Technologies), TNF (10 ng/ml, PreproTech). For rescue/re-expression experiments, 10,000 cells were plated in 96-well plates and viable cells were enumerated after 72 hours using Cell Titer-Glo® (Promega, G7570). For all other growth inhibition assays, 50,000 cells were plated in 12-well plates and viable cells were counted after 72 hours using the Countess automated cell counting system (Thermo Fisher Scientific, C10227).

Cell Death Assays

Three sets of transfected B16 cells (control sgRNA5, Adar1 sg1 and Adar1 sg2) were plated in separate 6-well plates at a concentration of 100,000 cells per well and incubated for 72 hours with DMEM+10% FBS containing one of the following combinations of cytokines: IFNβ, IFNγ, IFNβ and IFNγ, 5% D MSO and 25% DMSO. Cytokine or DMSO treated B16 cells, following trypsinization and washes in PBS+2% FBS, were stained for 20 minutes on ice using manufacturer-recommended concentrations of Annexin-V PE and 7-AAD from the PE Annexin V Apoptosis Detection Kit 1(BD Pharmingen) and with Calcein-AM (ThermoFisher Scientific). Staining of cell surface markers was then analyzed using an Accuri C6 flow cytometry system. Analysis was carried out using FlowJo software.

IFN ELISA

Cells were seeded at a density of 10,000 cells per well in a 96-well plate. Mouse interferon beta (pbl assay science) was then added. After 24 hrs of incubation at 37° C., the supernatant was aspirated from the wells to remove the mouse interferon beta. The wells were then gently washed once with media. Fresh warm media was then replaced in the wells. After 48 hrs of incubation at 37° C., the supernatant was collected, and the concentration of interferon beta was determined using The VeriKine Mouse Interferon Beta ELISA Kit (pbl assay science).

Western Blotting

Whole cell lysates were prepared in lysis buffer (60 mM Tris HCl, 2% SDS, 10% glycerol, complete EDTA-free protease-inhibitor (Roche), and 500 U/mL benzonase nuclease (Novagen)). Samples were boiled at 100° C. and clarified by centrifugation. Protein concentration was measured with a BCA protein assay kit (Pierce). 30-150 µg of protein was loaded on 4-12% Bolt Bis-Tris Plus gels (Life Technologies) in MES buffer (Life Technologies). Protein was transferred to 0.45 mm nitrocellulose membranes (Bio-Rad). Membranes were blocked in Tris-buffered saline plus 0.1% Tween 20 (TBS-T) containing 5% non-fat dry milk for 1 hour at room temperature followed by overnight incubation with primary antibody at 4° C. Membranes were washed with TBS-T and incubated with HRP-conjugated secondary antibodies for 1 hour at room temperature. HRP was activated with SuperSignal™ West Dura Extended Duration Substrate (Pierce) and visualized with a chemiluminscent detection system using Fuji ImageQuant LAS4000 (GE Healthcare Life Sciences). Blots were then analyzed using ImageJ and Adobe Photoshop software.

Antibodies

Flow cytometry antibodies are listed in below and immunohistochemistry antibodies are listed above. For Western blotting, primary antibodies against Adar1 (15.8.6, Santa Cruz Biotechnology), Pkr (EPR19374, Abcam), Rig-I (D14G6, Cell Signaling Technology), Mda5 (D74E4, Cell Signaling Technology), Stat1 (p91, Polyclonal Goat IgG, R&D Systems), Mavs (Rabbit Polyclonal IgG, Abcam), and RNaseL (E-9, Santa Cruz) were used. Peroxidase-conjugated secondary antibodies against rabbit IgG, mouse IgG or goat IgG were purchased from Jackson Laboratories.

| Antigen | Fluorophore | Clone | Company |
| --- | --- | --- | --- |
| CD8a | PC | 53_6.7 | Biolegend |
| CD4 | BV421 | RM4-5 | Biolegend |
| TCR-b | APC-Cy7 | H57-597 | Biolegend |
| Granzyme B | FITC | IM7 | Biolegend |
| PD-1 | Pe-Cy7 | RMPI-30 | Biolegend |
| Tim-3 | APC | RMT3-2.3 | Biolegend |
| Ki-67 | PerCP-Cy5.5 | B56 | BD Biosciences |
| CD45 | BV605 | 104 | Biolegend |
| CD45 | APC-Cy7 | 30-F11 | Biolegend |
| Ly6C | BV605 | HK1.4 | Biolegend |
| MHC II | PECy7 | M5/114.152 | Biolegend |
| F4/60 | APC | BM8 | Biolegend |
| CD11c | FITC | N418 | Biolegend |
| CD24 | PerCP/Cy5.5 | M1/69 | Biolegend |
| CD11b | PE | M1/70 | Biolegend |
| CD103 | BV421 | 2E7 | Biolegend |
| CD3e | BV421 | 124-2C11 | Biolegend |
| TCRgd | PE-Cy7 | GL3 | Biolegend |
| NK1.1 | PE | PK136 | Biolegend |
| CD4 | PerCP-Cy5.5 | GK15 | Biolegend |
| CD6 | FITC | 53-6.7 | Biolegend |
| CD44 | APC-Cy7 | IM7 | Biolegend |
| Foxp3 | APC | FJK-16s | eBioscience |
| Aqua Live/Dead Fixable | N/A | NA | Invitrogen |
| IFNGR | PE | 2E2 | eBioscience |

Quantitative Real-Time PCR (qPCR)

For each replicate, one million tumor cells were collected and resuspended in buffer RLT (Qiagen, 79216). RNA was extracted using an RNeasy® Mini Kit (Qiagen, 74104) as per manufacturer's instructions. RNA was converted to cDNA using the Improm-II™ Reverse Transcription System (Promega, A3800). qPCR reactions were carried out in 20 reaction volumes with 10 ul of the TaqMan® Gene Expression Master Mix (Thermo Fisher Scientific, 4369016), 5 ul of nuclease free H2O, 1 ul of each probe, and 3 ul of each cDNA sample. The qPCR reaction was run using a ViiA 7 Real-Time PCR System (Thermo Fisher Scientific) in a 96-well plate. FAM-tagged targets were quantitated using the CT method relative to—actin, which was VIC-tagged.

TABLE 5

CRISPR sgRNA Sequences

| | |
| --- | --- |
| Adar sgRNA1 | CACCGTCTGGATTCACAACTCCAGG |
| Adar sgRNA2 | CACCGTCACAGCCCTACCTTGCCA |
| Adar sgRNA 3 | CACCGTGTGACTCTCAGAAATCAG |
| Adar sgRNA4 | ACCGTTCCAAGTCAATCAGCACTG |
| Adar sgRNA5 | CACCGCACACAGCAGGGGTACACCA |
| Adar sgRNA6 | CACCGTCCGTCAAGTACCAGATGGG |
| Ddx58 sgRNA1 | CACCGCGTTGGAGATGCTAAGACCG |
| Ddx58 sgRNA2 | CACCGTCCGCCAGAGATGAACGAAG |
| Eif2ak2 sgRNA1 | CACCGTGGCTACTCCGTGCATCTGG |
| Eif2ak2 sgRNA2 | CACCGCTCGTCTATGACAAGTAAT |
| Ifih1 sgRNA1 | CACCGTGTGGGTTTGACATAGCGCG |
| Ifih1 sgRNA2 | CACCGCCTGAGGGTGAACGTCCCAG |
| Ifnar2 sgRNA 1 | CACCGTACCAGAGGGTGTAGTTAG |
| Ifnar2 sgRNA 2 | CACCACACAAGCTGAGGAGACCGA |
| Ifngr1 sgRNA 1 | CACCCGACTTCAGGGTGAAATACG |
| Ifngr1 sgRNA 2 | CACCGGTATTCCCAGCATACGACA |
| Mavs sgRNA1 | CACCGCCGGTTCCCGATCTGCCTGT |
| Mavs sgRNA2 | CACCGGGAACCGGGACACACTCTG |
| Stat1 sgRNA 1 | CACCGATCATCTACAACTGTCTGA |
| Stat1 sgRNA 2 | CACCGTACGATGACAGTTTCCCCA |
| control sgRNA 1 | CACCGCGAGGTATTCGGCTCCGCG |
| control sgRNA 2 | CACCGCTTTCACGGAGGTTCGACG |
| control sgRNA 3 | CACCATGTTGCAGTTCGGCTCGAT |
| control sgRNA 4 | CACCACGTGTAAGGCGAACGCCTT |
| control sgRNA 5 | CACCATTGTTCGACCGTCTACGGG |

Statistics

Statistical tests employed with number of replicates and independent experiments are listed inline with text and figure legends. All graphs report mean s.e.m. values except where indicated. ttests were two-tailed in all cases. For box-plot elements, centerline represents the median value, box limits represent upper and lower quartiles and whiskers represent minimum and maximum values. PRISM was used for basic statistical analysis and plotting (http://www.graphpad.com), and the Rlanguage and programming environment (https://wwwr-proect.org) was used for the remainder of the statistical analysis.

Data Availability

All data presented in this manuscript are available from the corresponding author upon reasonable request. Bulk tumor cell RNA sequencing has been deposited at the GEO (http://www.ncbi.nim.nih.gov/geo) under the accession number GSE110708. Single cell RNA sequencing of tumor cells were also deposited at the GFO under the accession number GSE110746.

the HCC366, NCI-H1650 ("H1650") and NCI-H196 ("H196") cell lines, with no effect on control cells ("A549").

Similar patterns were observed after knockdown of other suppressors of interferon signaling, such as ISG15. As

| NAME | SIZE | ES | NES | NOM p-val |
|---|---|---|---|---|
| HALLMARK_INTERFERON_ALPHA_RESPONSE | 91 | 0.464342 | 5.2162766 | 0 |
| HALLMARK_INTERFERON_GAMMA_RESPONSE | 181 | 0.2796316 | 4.4897733 | 0 |
| HALLMARK_TNFA_SIGNALING_VIA_NFKB | 186 | 0.2513026 | 3.8252308 | 0 |
| HALLMARK_UNFOLDED_PROTEIN_RESPONSE | 110 | 0.2741036 | 3.301307 | 0 |
| HALLMARK_P53_PATHWAY | 185 | 0.1724229 | 2.6934104 | 0 |
| HALLMARK_MYC_TARGETS_V2 | 58 | 0.2500267 | 2.241947 | 0 |
| HALLMARK_IL6_JAK_STAT3_SIGNALING | 76 | 0.1821964 | 1.8833364 | 0.011494253 |
| HALLMARK_KRAS_SIGNALING_DN | 141 | 0.1227702 | 1.6867998 | 0.02366864 |
| HALLMARK_NOTCH_SIGNALING | 30 | 0.2103566 | 1.3925092 | 0.11434109 |
| HALLMARK_TGF_BETA_SIGNALING | 52 | 0.1383464 | 1.1498951 | 0.26640928 |
| HALLMARK_INFLAMMATORY_RESPONSE | 160 | 0.0731223 | 1.0879765 | 0.33266532 |
| HALLMARK_ALLOGRAFT_REJECTION | 160 | 0.0711711 | 1.026139 | 0.40246406 |

| FDR q-val | FWER p-val | RANK AT MAX | LEADING EDGE |
|---|---|---|---|
| 0 | 0 | 1315 | tags = 54%, list = 8%, signal = 58% |
| 0 | 0 | 2365 | tags = 41%, list = 14%, signal = 48% |
| 0 | 0 | 4412 | tags = 51%, list = 26%, signal = 67% |
| 0 | 0 | 1724 | tags = 37%, list = 10%, signal = 41% |
| 0 | 0 | 2920 | tags = 34%, list = 17%, signal = 41% |
| 0.001295369 | 0.017 | 4013 | tags = 48%, list = 23%, signal = 63% |
| 0.01595127 | 0.209 | 2987 | tags = 36%, list = 17%, signal = 43% |
| 0.04179405 | 0.509 | 11557 | tags = 79%, list = 67%, signal = 241% |
| 0.14544195 | 0.949 | 4410 | tags = 47%, list = 26%, signal = 63% |
| 0.3275033 | 0.999 | 1264 | tags = 21%, list = 7%, signal = 23% |
| 0.36572328 | 1 | 10891 | tags = 71%, list = 63%, signal = 191% |
| 0.40600365 | 1 | 10602 | tags = 69%, list = 62%, signal = 178% |

Figure 28:
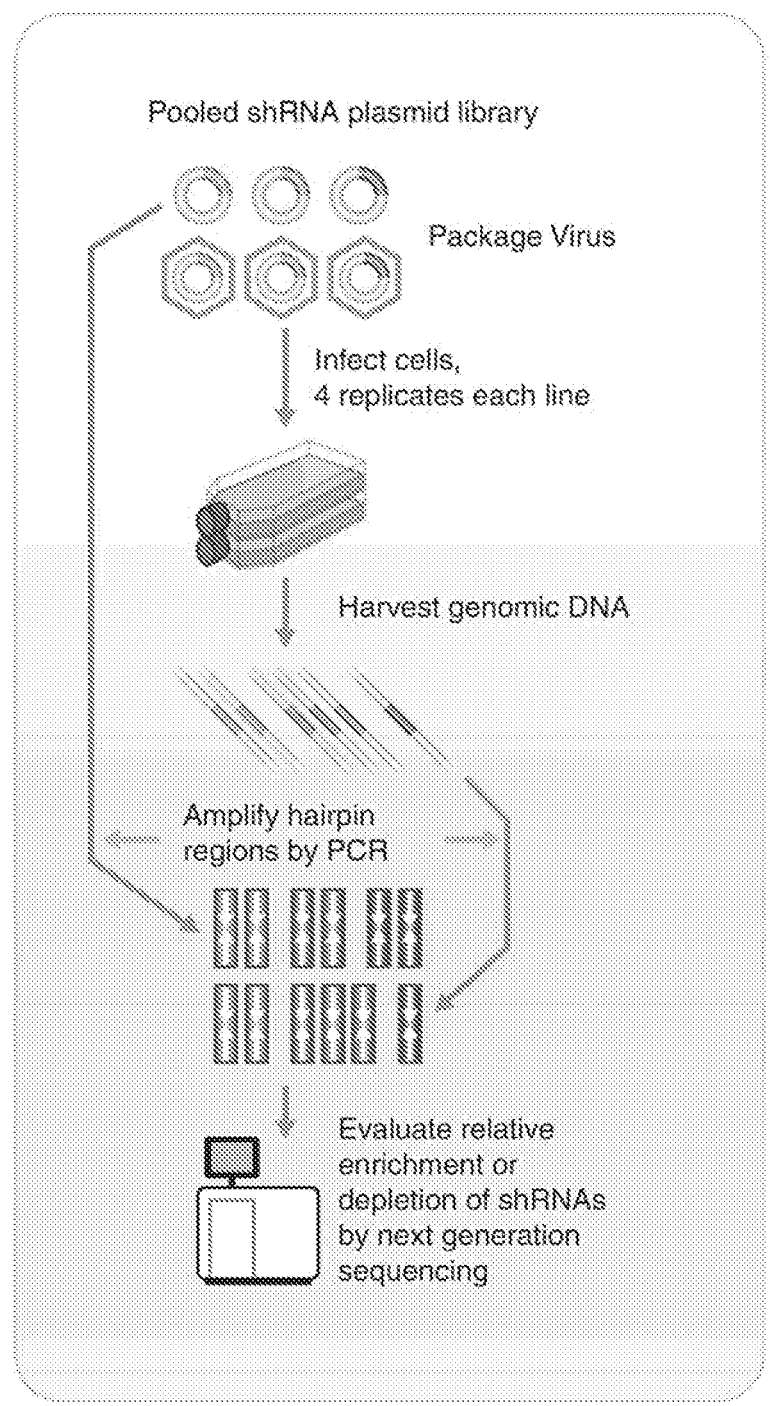
FIG. 28 shows a schematic flow chart showing a screen for cell survival using a pooled shRNA library.

Example 8: Identification of Cancer Cell Lines that are Dependent on the Negative Interferon Signaling Regulators ADAR1 and ISG15 for Survival ADAR1 is an RNA editing enzyme that suppresses interferon signaling by masking endogenous double-stranded RNA from intracellular innate immune RNA sensors. To investigate cancer cell lines that are acutely dependent on ADAR1 expression for survival, shRNA knockdown data obtained from was mined. As depicted in FIG. 28, a pooled shRNA plasmid library was packaged into viruses that were used to infect cell lines with 4 replicates per line. After 16 population doublings, genomic DNA was harvested and hairpin regions were amplified by polymerase chain reaction (PCR). The relative enrichment or depletion of shRNAs was evaluated by next generation sequencing, and the Knockdown Dependence Score of each gene was calculated in data mining. The experimental flowchart was similar to previously published screens, see, e.g., Cowley et al (2014) *Scientific Data* 1:140035.

Figure 29:
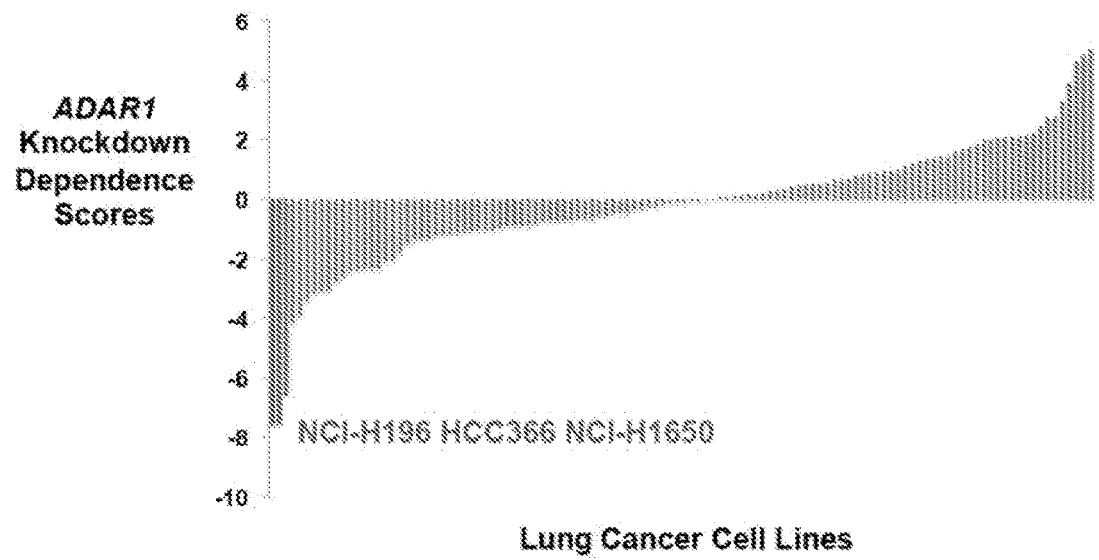
FIG. 29 shows a plot of ADAR1 knockdown dependence scores of various lung cancer cell lines.
Figure 30:
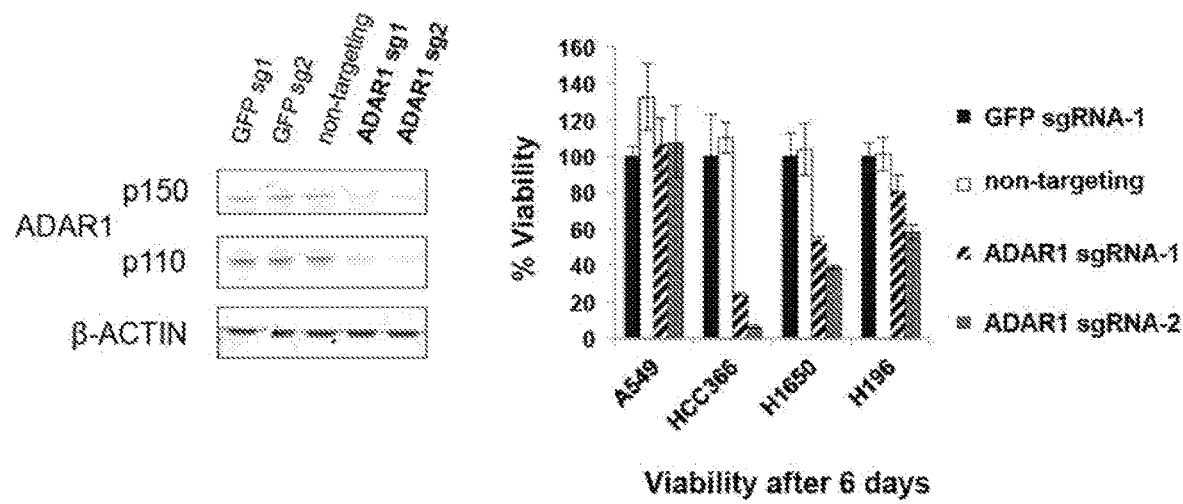
FIG. 30 shows the effects of ADAR1 sg1 and ADAR1 sg2 on ADAR1 expression and on the viability of various cell lines.
Figure 31:
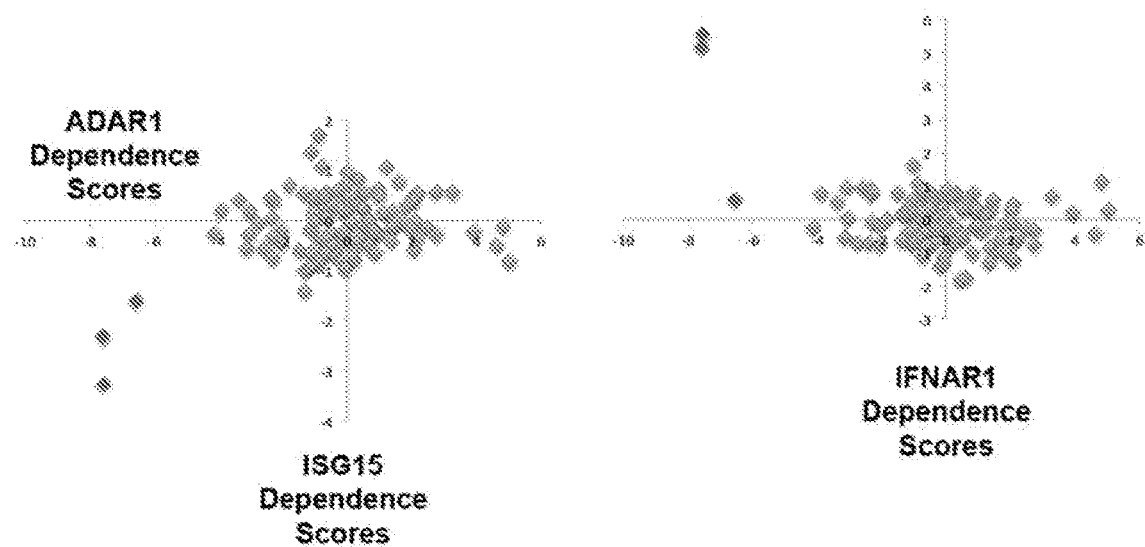
FIG. 31 plots ADAR1 dependence scores against ISG15 dependence scores and IFNAR1 dependence scores of lung cancer cell lines.

Using the mined screening data, the ADAR1 Knockdown Dependence Scores of more than a hundred lung cancer cell lines were calculated and plotted (FIG. 29). The data revealed three cell lines that were highly dependent on ADAR1: NCI-H196, HCC366 and NCI-H1650 (FIG. 29). The HCC366 cell line was found to harbor an ADAR1 D897N mutation. To validate the shRNA knockdown findings, lentiviral CRISPR-Cas9 knockout of ADAR1 was performed on the three lung cancer cell lines. FIG. 30, left panel, shows knockout of ADAR1 isoforms p150 and p110 using ADAR1 sg1 and ADAR1 sg2 in A549 cells. CRISPR-Cas9 controls were two GFP-targeting sgRNAs and a non-targeting sgRNA. The right panel of FIG. 30 shows that CRISPR-Cas9 knockout of ADAR1 using ADAR1 sg1 and ADAR1 sg2 resulted in decreased viability after 6 days of shown in FIG. 31, left-side plot, the cell lines NCI-H196, HCC366 and NCI-H1650 were also found to be dependent on ISG15. By contrast, decreased expression of the Type I interferon receptor, IFNAR1 increased the viability of these cell lines (FIG. 31, right-side plot). IFNAR1 binds IFN-α/β to initiate the interferon pathway.

Figure 32:
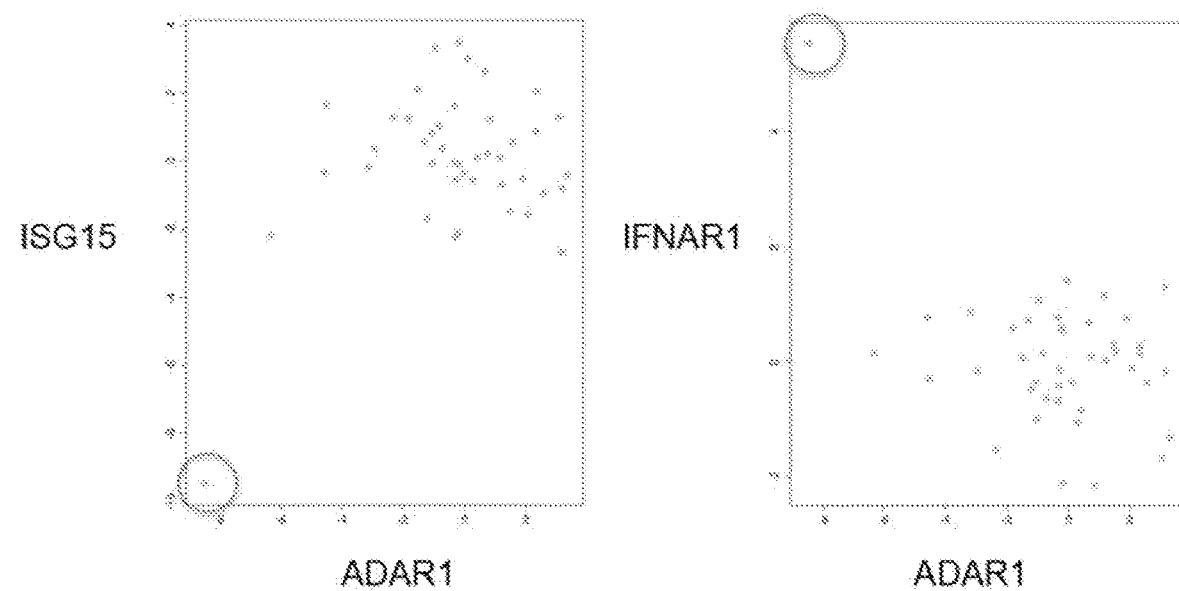
FIG. 32 plots ADAR1 dependence scores against ISG15 dependence scores and IFNAR1 dependence scores of cell lines in the CRISPR-Cas9 Gecko library.
Figure 33:
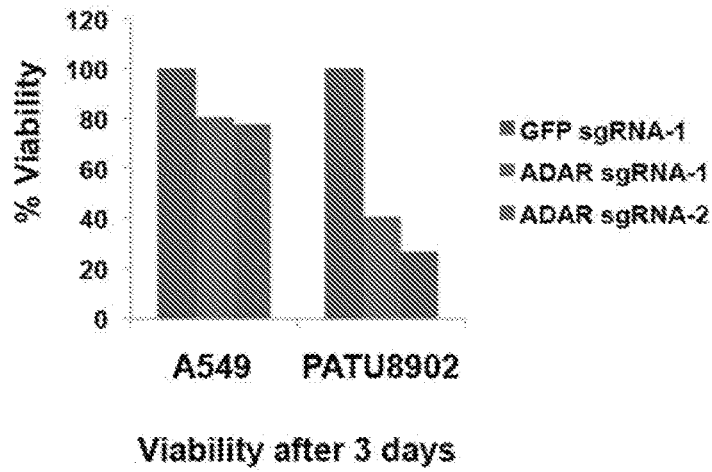
FIG. 33 shows the effects of ADAR1 sg1 and ADAR1 sg2 on the viability of two cell lines.
Figure 34:
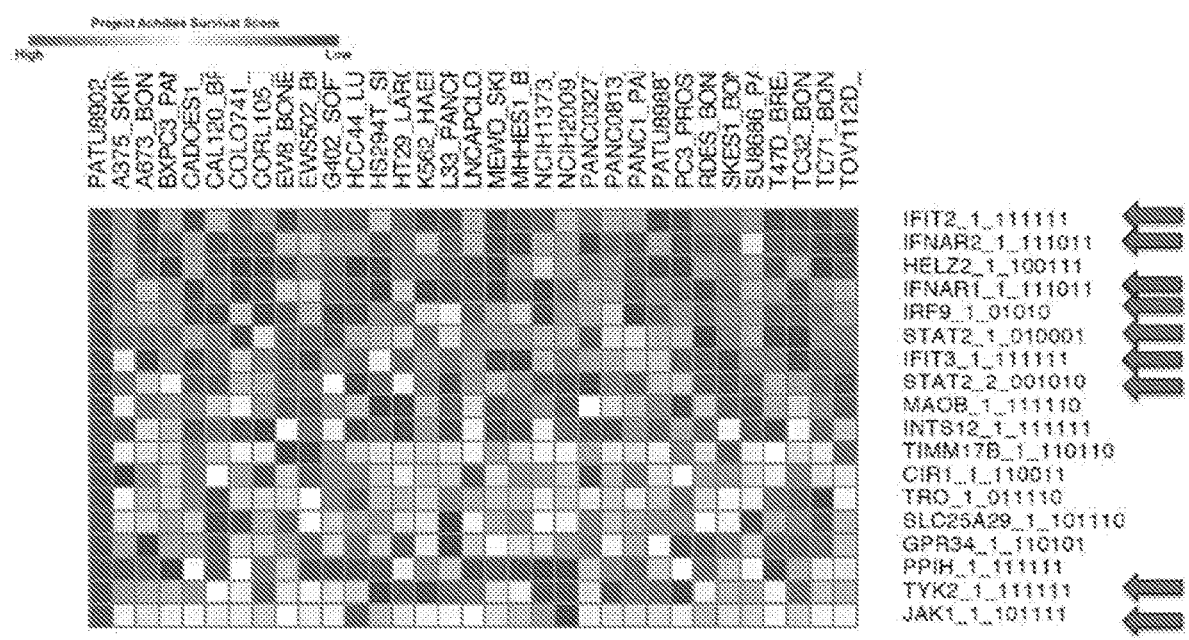
FIG. 34 shows the differential sensitivities of cell lines in response to knockout of various genes.

Data mining of other publicly available databases revealed additional ADAR1 dependent cell lines. For example, a pancreatic cancer cell line, PATU8902, was revealed from the publicly available CRISPR-Cas9 Gecko library (Aguirre et al. (2016) *Cancer Discovery* 6:914-929) (FIG. 32, circled dot). Similar to the three ADAR1 dependent lung cancer cell lines, the viability of PATU8902 was also decreased by ISG15 knockout and increased by IFNAR1 knockout. Independent lentiviral CRISPR-Cas9 knockout of ADAR, using A549 cells as control and sgRNA targeting GFP as a CRISPR-Cas9 control, validated the CRISPR-Cas9 Gecko data (FIG. 33). The CRISPR Gecko library data was further mined to show that knockout of multiple interferon pathway members (as indicated by arrows) enhanced PATU8902 survival (FIG. 34)

Example 9: Cancer Cell Lines Sensitive to ADAR1 or ISG15 Knockdown Display Elevated Interferon Secretion and Downstream Signaling An analysis of gene ontology (GO) categories associated with ADAR1 dependent cells revealed that NCI-H1650 and HCC366 ("HCC-366"), two ADAR1 dependent cell lines, both have elevated basal expression of interferon inducible genes (FIG. 35). The expression levels of interferon-inducible genes were also elevated in NCI-H196 cells (FIG. 36).

Figure 37:
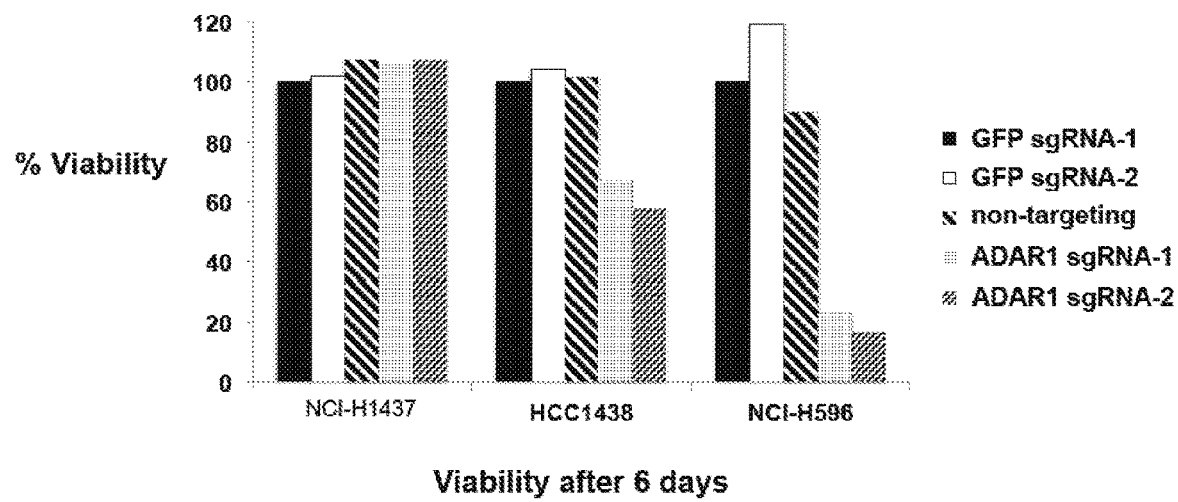
FIG. 37 is a graph showing the effects of ADAR knockout on the viability of various cell lines. The NCI-H1437 cell line without elevated IFN-inducible gene expression was used as a negative control. Two CRISPR sgRNAs, ADAR1 sgRNA-1 and ADAR1 sgRNA-2, were used for ADAR1 knockout. A non-targeting sgRNA and two GFP-targeting sgRNAs were used as negative controls.

In light of the correlation between ADAR1 dependency and the expression of interferon-inducible genes, additional cancer cell lines from the Molecular Signatures Database (MSigDB) (Liberzon et al. (2015) *Cell Systems* 1:417-425)

was examined. Cancer Cell Line Encyclopedia (CCLE) clustering was performed based on the Type I/Interferon-a gene set, which contained 97 genes including PKR. The resulting cluster included HCC366, NCI-H1650 and 9 additional lung cell lines. Among these cell lines, HCC1438 and NCI-H596 were sensitive to knockout of ADAR1 by lentiviral CRISPR-Cas9 (FIG. 37).

Figure 38:
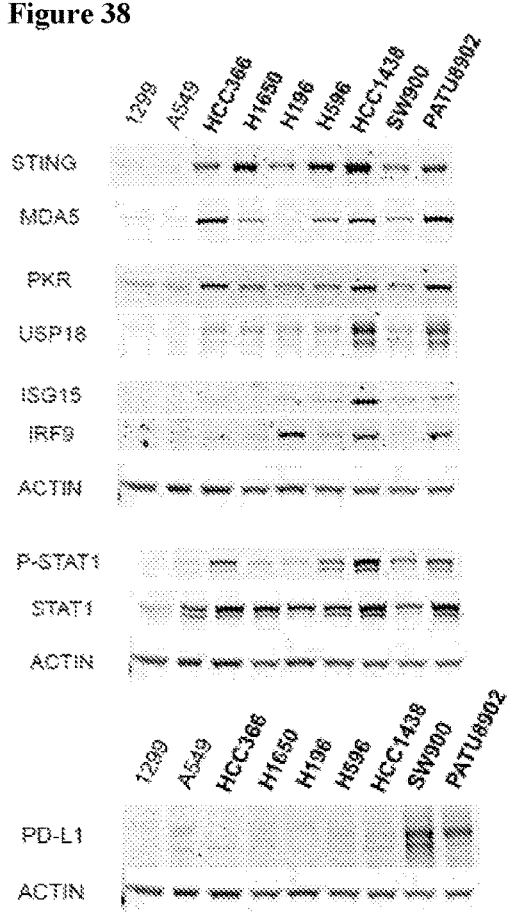
FIG. 38 is an immunoblot image showing the expression levels of interferon stimulated genes in ADAR1 dependent cell lines.
Figure 41:
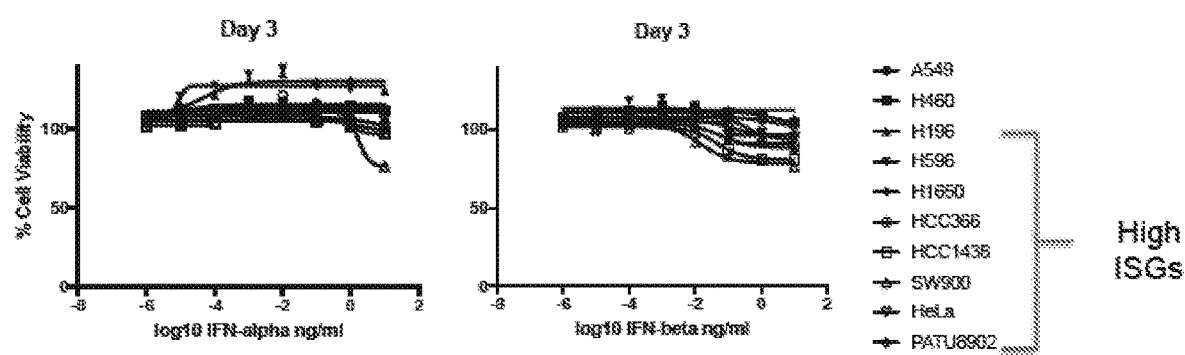
FIG. 41 is a graph showing the effect of adding IFN-α and IFN-β on the viability of a number of cell lines as indicated.

All the above-identified ADAR1 dependent cancer cell lines showed elevated interferon signaling markers, e.g., phosphorylation of STAT1 and expression of interferon-stimulated gene (ISGs) (FIG. 38). Elevated interferon signaling in the ADAR1 dependent cancer cell lines did not necessarily lead to PD-L1 overexpression (FIG. 38). Cell lines in the high interferon signaling cluster (LN215_CENTRAL_NERVOUS_SYSTEM, NCIH596_LUNG, HCC1438_LUNG, T3M10_LUNG, NCIH1869_LUNG, SW900_LUNG, HCC366_LUNG, SKLU1_LUNG, NCIH1650_LUNG, HCC4006_LUNG, and NCIH1648_LUNG) displayed high IFN-β, but not IFN-α (FIG. 39). As such, cancer cell lines sensitive to ADAR1 or ISG15 knockdown displayed elevated interferon secretion and downstream signaling. To further investigate the relationship between ADAR1 and IFN-β secretion, it was found that ADAR1 knockout led to amplified IFN-β secretion in cell lines primed with high basal interferon activation (FIG. 40). It was also found that ADAR1 dependent cell lines do not show enhanced sensitivity to IFN-α or IFN-β alone (FIG. 41).

Figure 42:
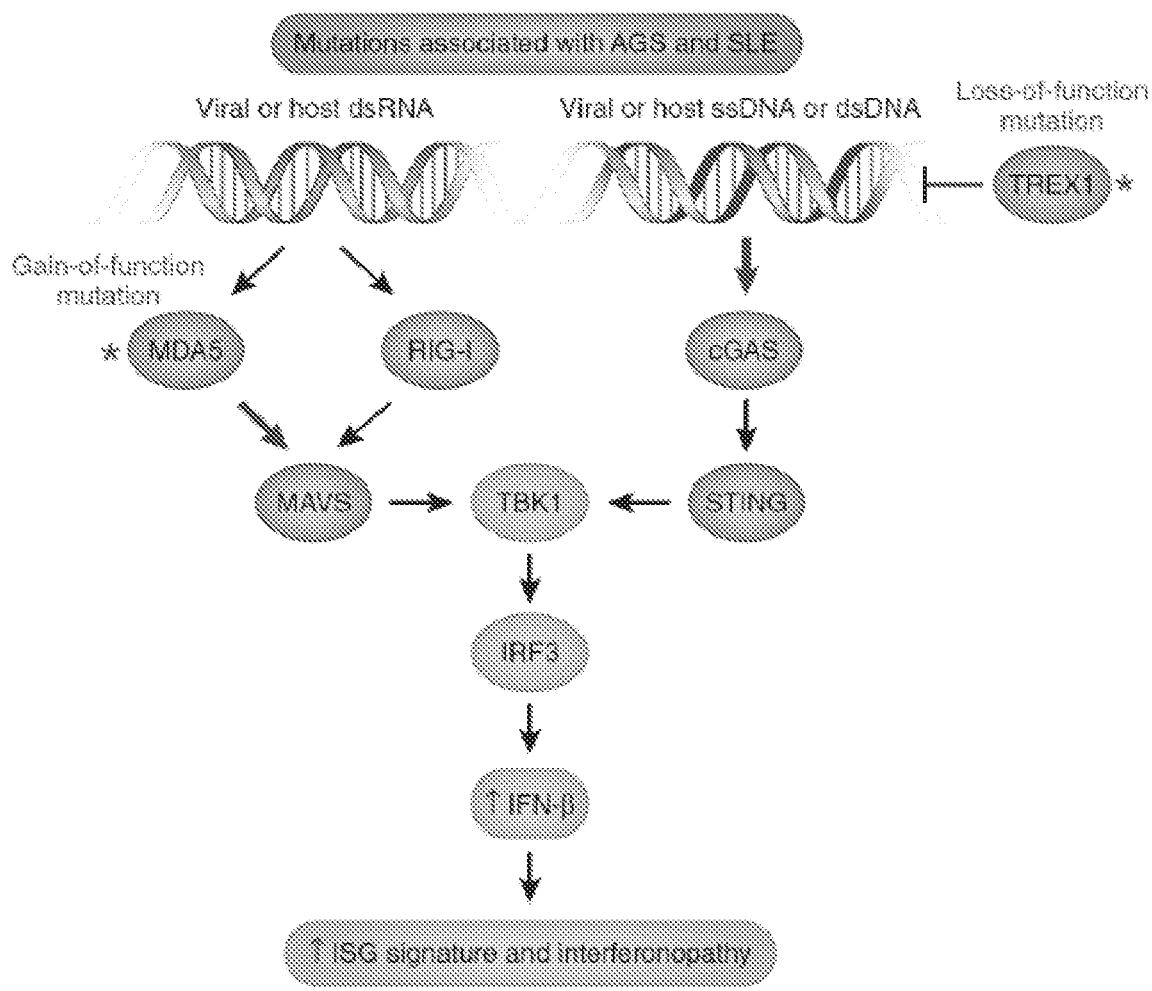
FIG. 42 shows a schematic of a cytosolic nucleic acid signaling pathway.

Example 10: Elevated ISGs in Cancer Cell Line Subset is Dependent on Cytosolic DNA Sensing Pathway, but not RNA Sensing Pathway Mutations in ADAR1 are known to cause Aicardi-Goutières syndrome (AGS), an early onset childhood inflammatory disorder. The clinical features of AGS can mimic those of in utero acquired infection, and some characteristics of the condition also overlap with the autoimmune disease systemic lupus erythematosus (SLE). Mutations associated with AGS and SLE can lead to increased ISG signature and interferonopathy via a nucleic acid sensing pathway, as shown in the schematic depicted in FIG. 42.

Figure 43:
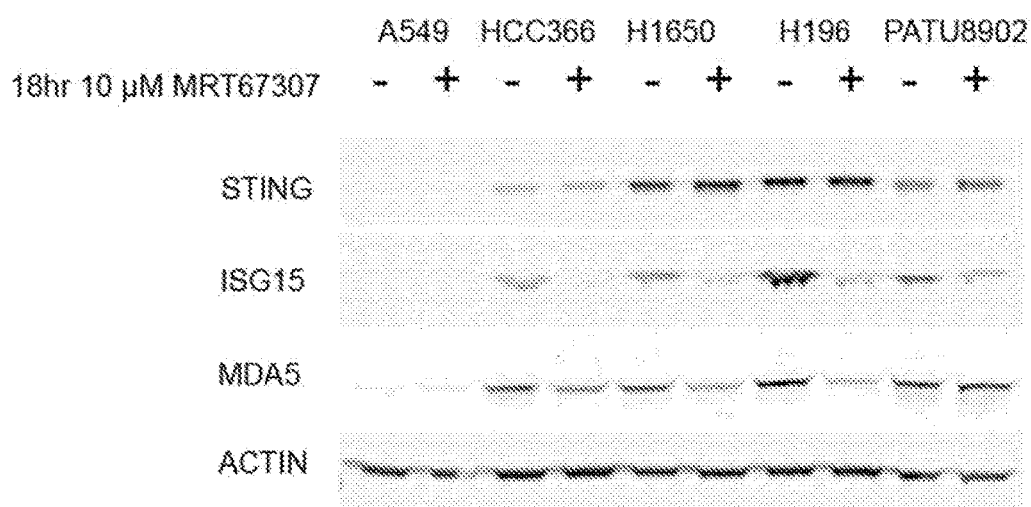
FIG. 43 is an immunoblot image showing the effects of the TBK1 inhibitor MRT67307 on the expression of interferon stimulated genes.
Figure 44:
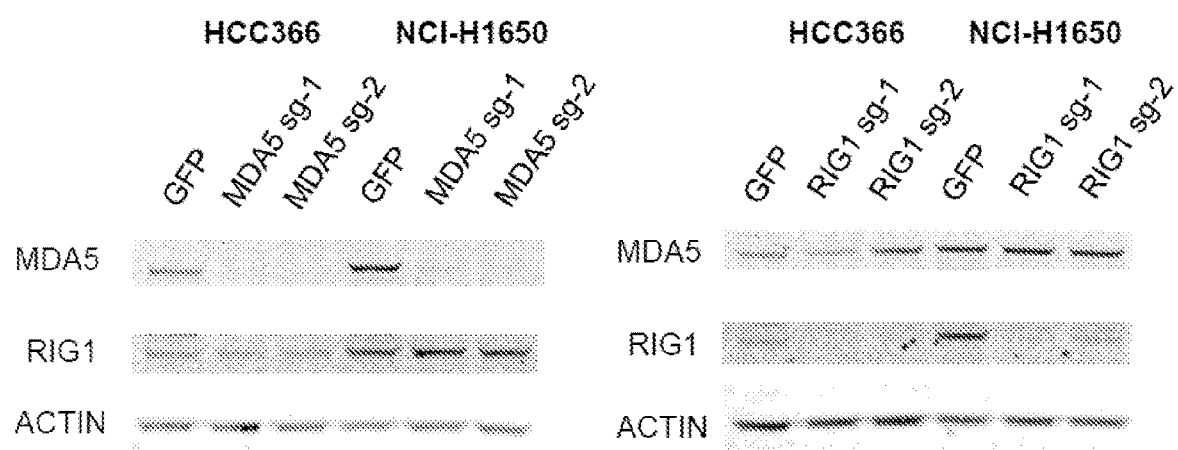
FIG. 44 provides a set of immunoblot images showing the effects of MDA5 and RIG1 knockdown on the expression of interferon stimulated genes.
Figure 45:
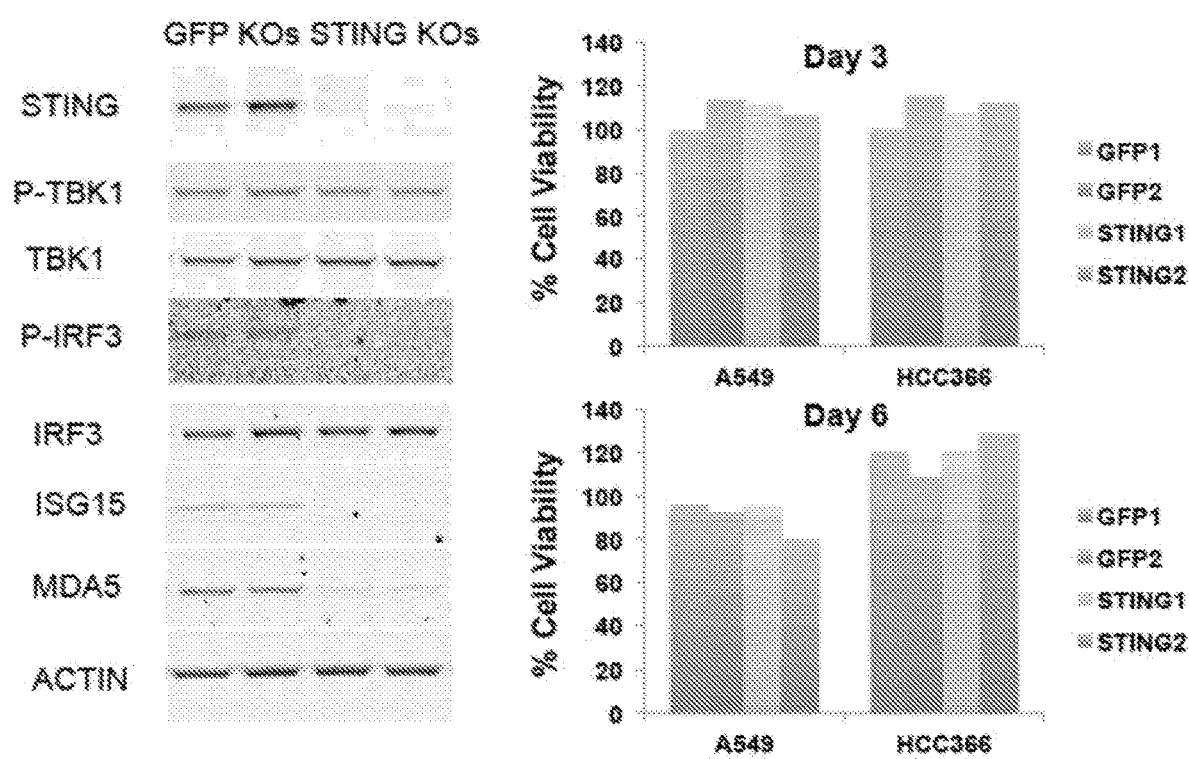
FIG. 45 shows the effects of STING1 knockout on the expression of interferon stimulated genes and on the viability of two cell lines. The left panel is an immunoblot image showing the levels of IFN inducible markers in HCC366 cells 7 days after infection with lentivirus expressing Cas9 and a STING sgRNA. Cells infected with lentivirus expressing Cas9 and a sgRNA targeting GFP were used as negative control. The right panels are graphs showing the viability of these cells 3 days (upper right) and 6 days (lower right) after infection.
Figure 46:
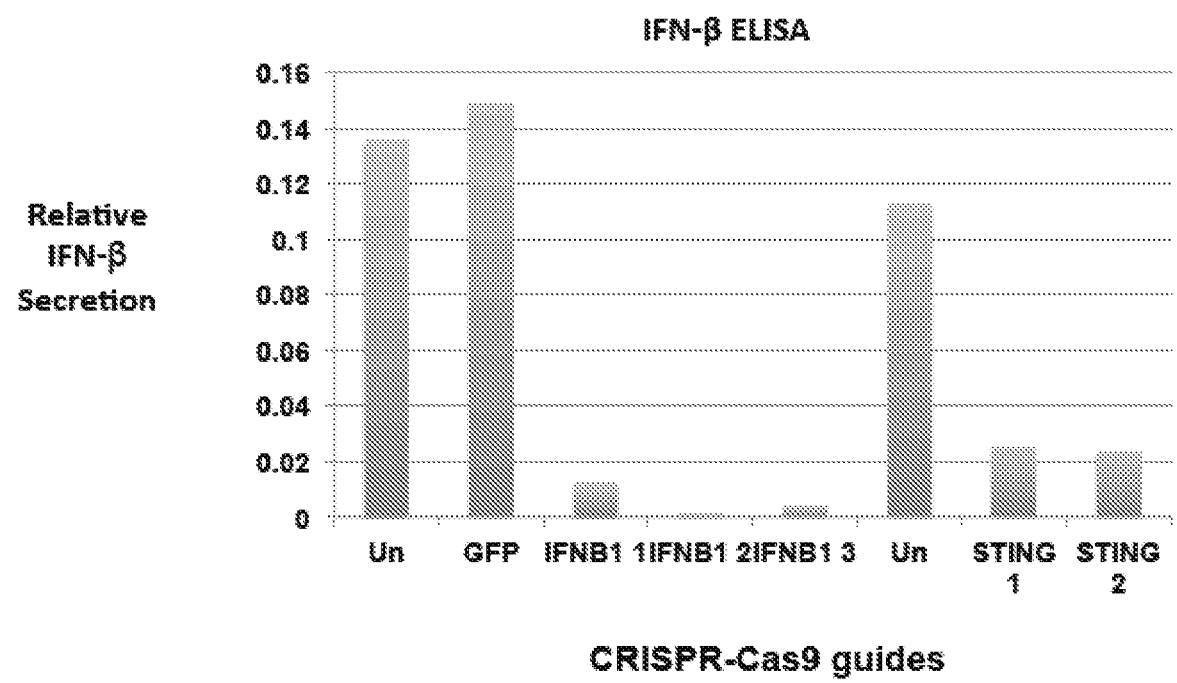
FIG. 46 shows the effects of STING knockout on IFN-β secretion in HCC366 cells. HCC366 cells were infected with lentivirus expressing Cas9 and a non-targeting sgRNA or an sgRNA targeting GFP (negative control), IFN-01 (positive control), or STING. The levels of IFN-β secretion were measured by ELISA, and the relative strength of signal (proportional to the amount of IFN-β) is shown.
Figure 49:
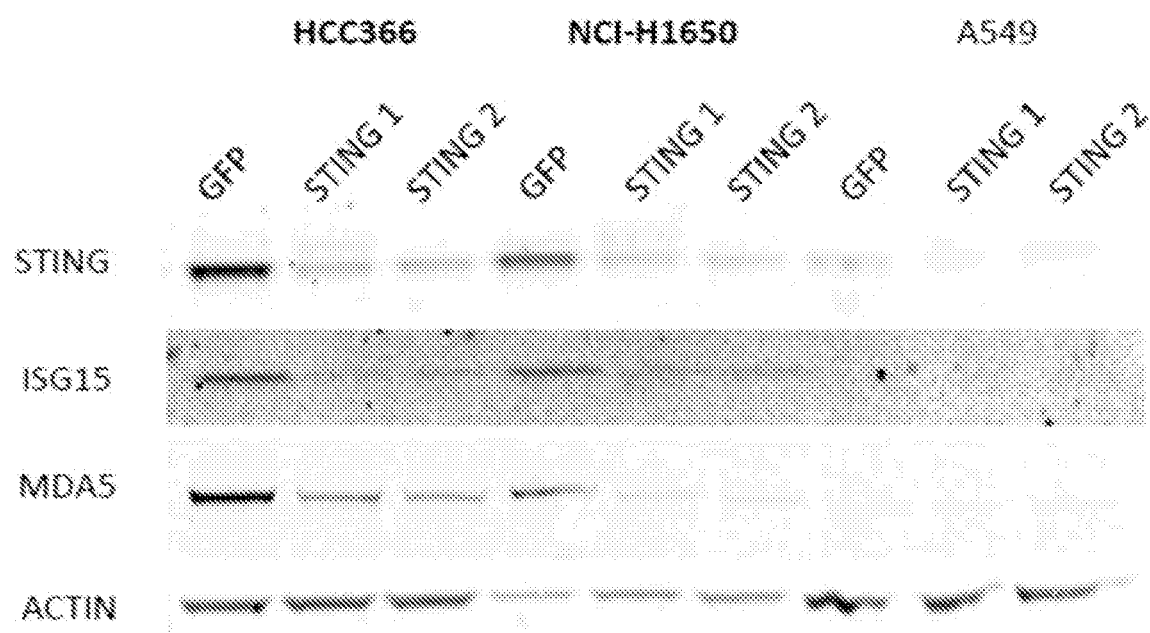
FIG. 49 shows a set of immunoblot images showing the effects of STING knockout on the expression of interferon stimulated genes in various cell lines.
Figure 49:
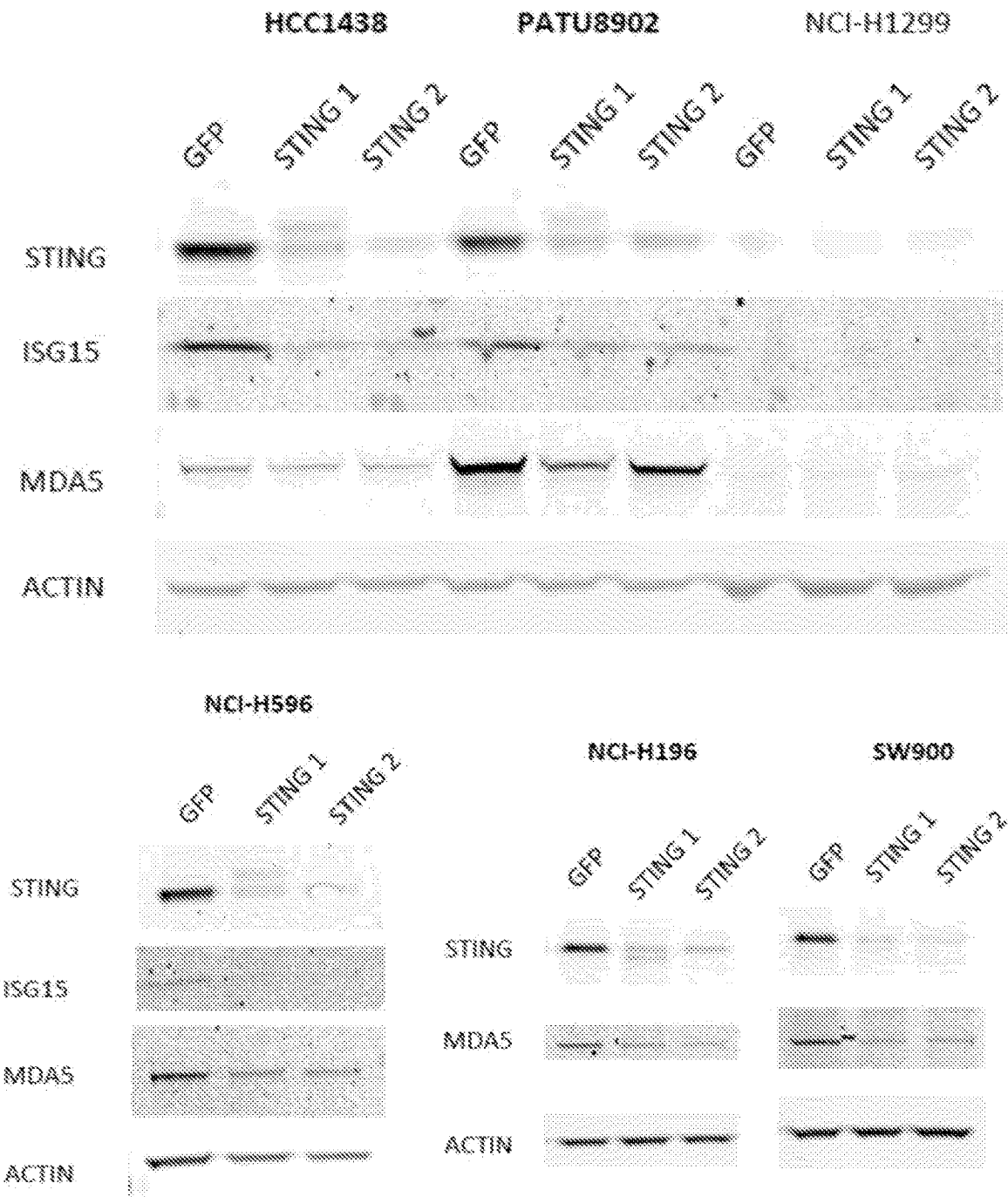

To investigate the relationship between ADAR1 dependence and nucleic acid sensing, ISG expression was examined in cells treated with the TBK1 inhibitor MRT67307. ISG expression was reduced (FIG. 43). TBK1 is a critical downstream factor of both the MDA5 and RIG1 mediated dsRNA sensing pathway and the cGAS and STING mediated ssDNA or dsDNA sensing pathway. To determine whether pathway is attributable to the elevated ISGs, ISG expression was examined in cells with the respective knockouts. It was found that knockout of MDA5 or RIG1 did not affect the expression of ISGs RIG and MDA5, respectively (FIG. 44), whereas knockout of STING led to decreased ISG expression and decreased IFN-β secretion in HCC366 cells (FIGS. 45 and 46). Similar results were obtained in the other ADAR1 dependent cell lines, including NCI-H1650, HCC1438, PATU8902, NCI-H596, NCI-H196, and SW900 (FIG. 49). Notably, Crispr-Cas9 knockout of STING did not decrease the viability of HCC366 cells as compared to A549 cells (FIG. 45).

Figure 47:
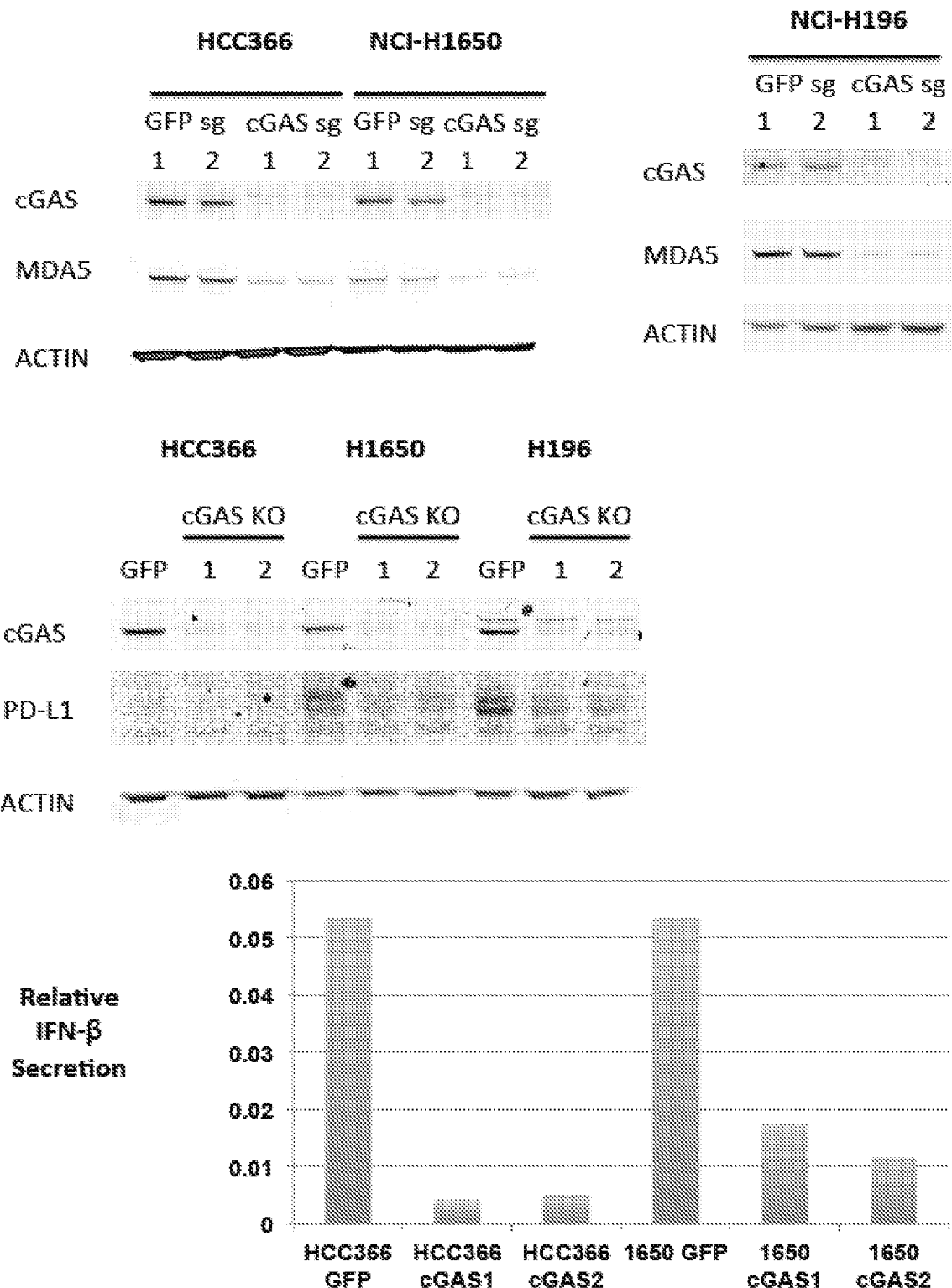
FIG. 47 shows a set of immunoblot image showing the effects of cGAS knockdown on the expression of interferon stimulated genes in HCC366, NCI-H1650 and NCI-H196 cells, and a graph showing the effects of cGAS knockdown on IFN-β secretion.

Similarly, cGAS knockout led to decreased ISG expression in HCC366, NCI-H1650 and NCI-H196 cells (FIG. 47). cGAS knockout also led to decreased IFN-β secretion in HCC366 and NCI-H1650 cells.

Figure 48:
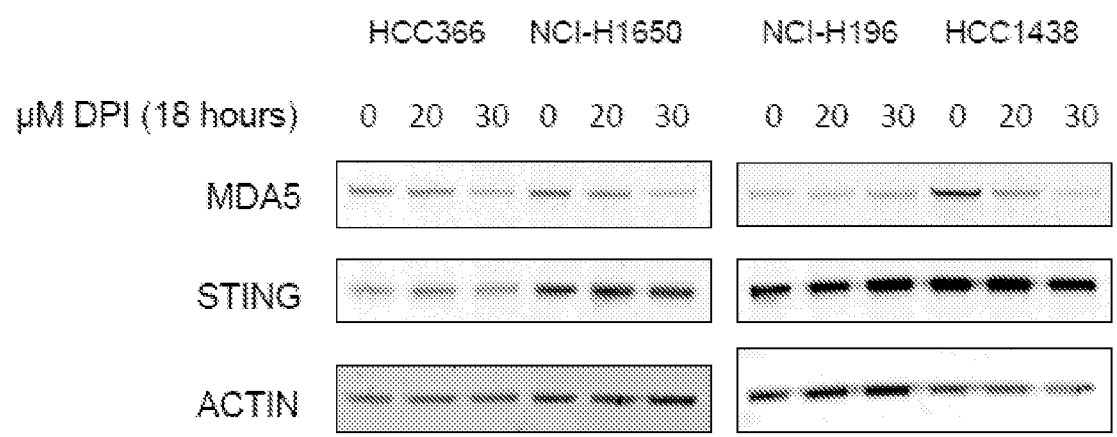
FIG. 48 shows antioxidant treatment using diphenylene iodonium (DPI) partially alleviates interferon signaling in ADAR-knockout sensitive cell lines suggesting that reactive oxygen species might trigger constitutive interferon signaling and lead to dependence on ADAR in these cells.

Increased levels of reactive oxygen species (ROS) have been shown to increase DNA damage, which could lead to increased cytosolic DNA sensor activation (Cadet and Wagner 2013 *Cold Spring Harbor Perspectives in Biology*). To test if ROS has a role in elevating interferon in ADAR-dependent cell lines, ADAR-dependent cell lines were treated with the antioxidant molecule diphenylene iodonium (DPI) (FIG. 48). DPI treatment partially decreased ISG expression, suggesting ROS levels have a role in cGAS-STING-IFN activation.

Figure 50:
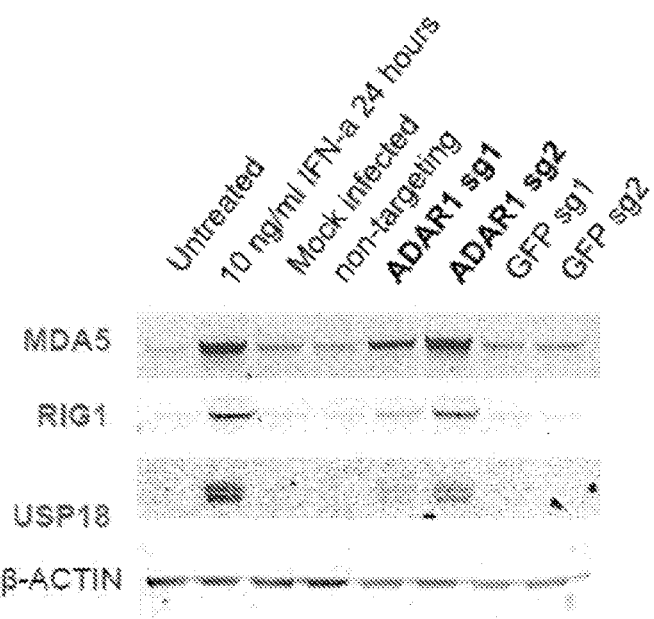
FIG. 50 shows the effects of ADAR1 knockout on the expression of interferon stimulated genes in A549 cells.
Figure 51:
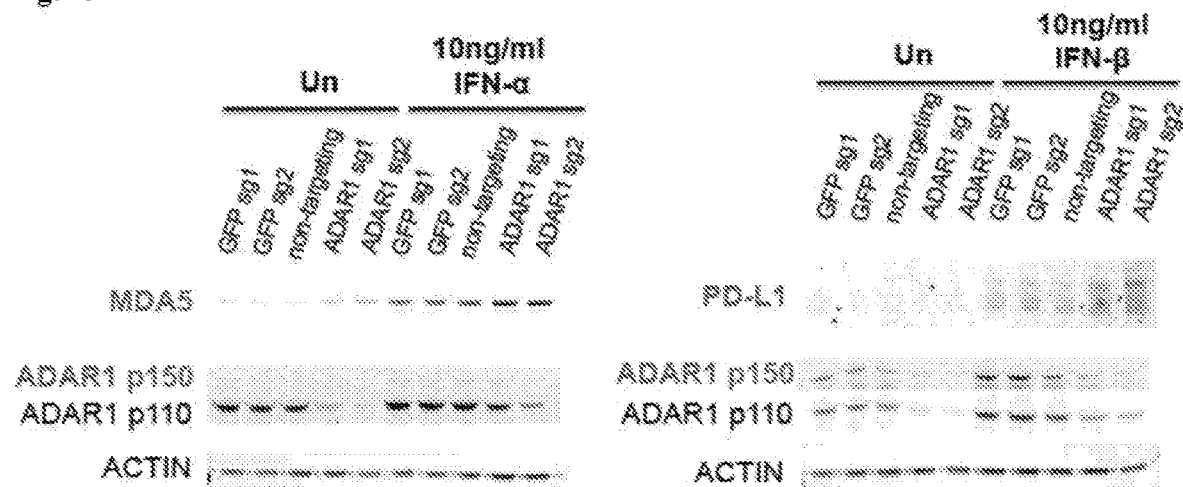
FIG. 51 shows the effects of ADAR1 knockout on the expression of interferon stimulated genes with and without IFN treatment in A549 cells.
Figure 52:
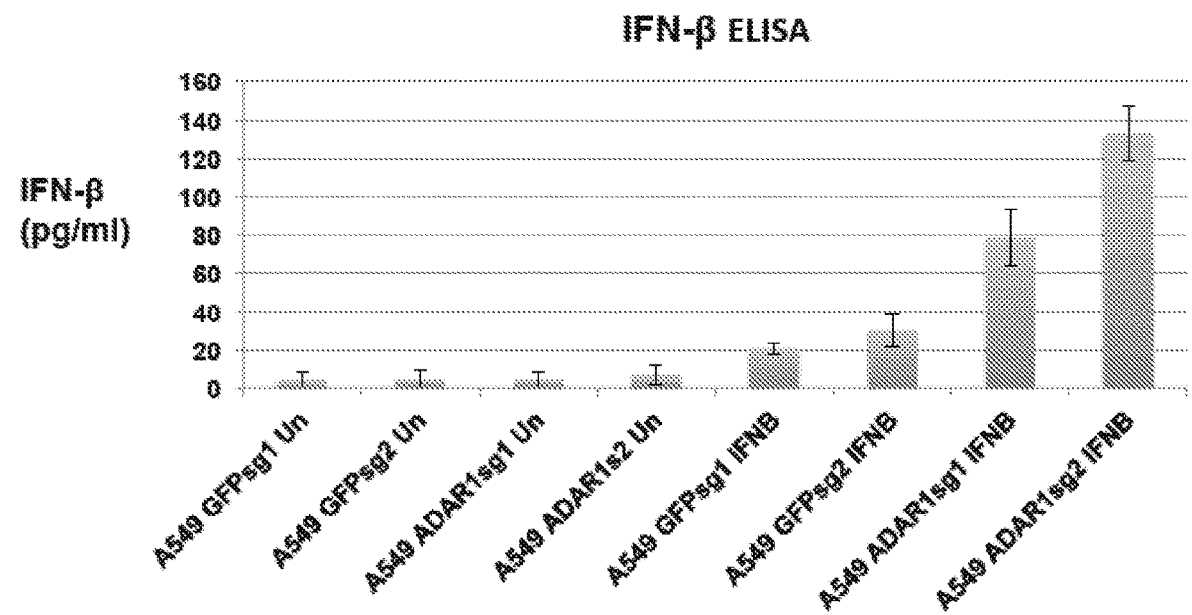
FIG. 52 shows the effects of IFN-β secretion from ADAR1 knockout A549 cells with and without IFN-β overnight treatment.
Figure 53:
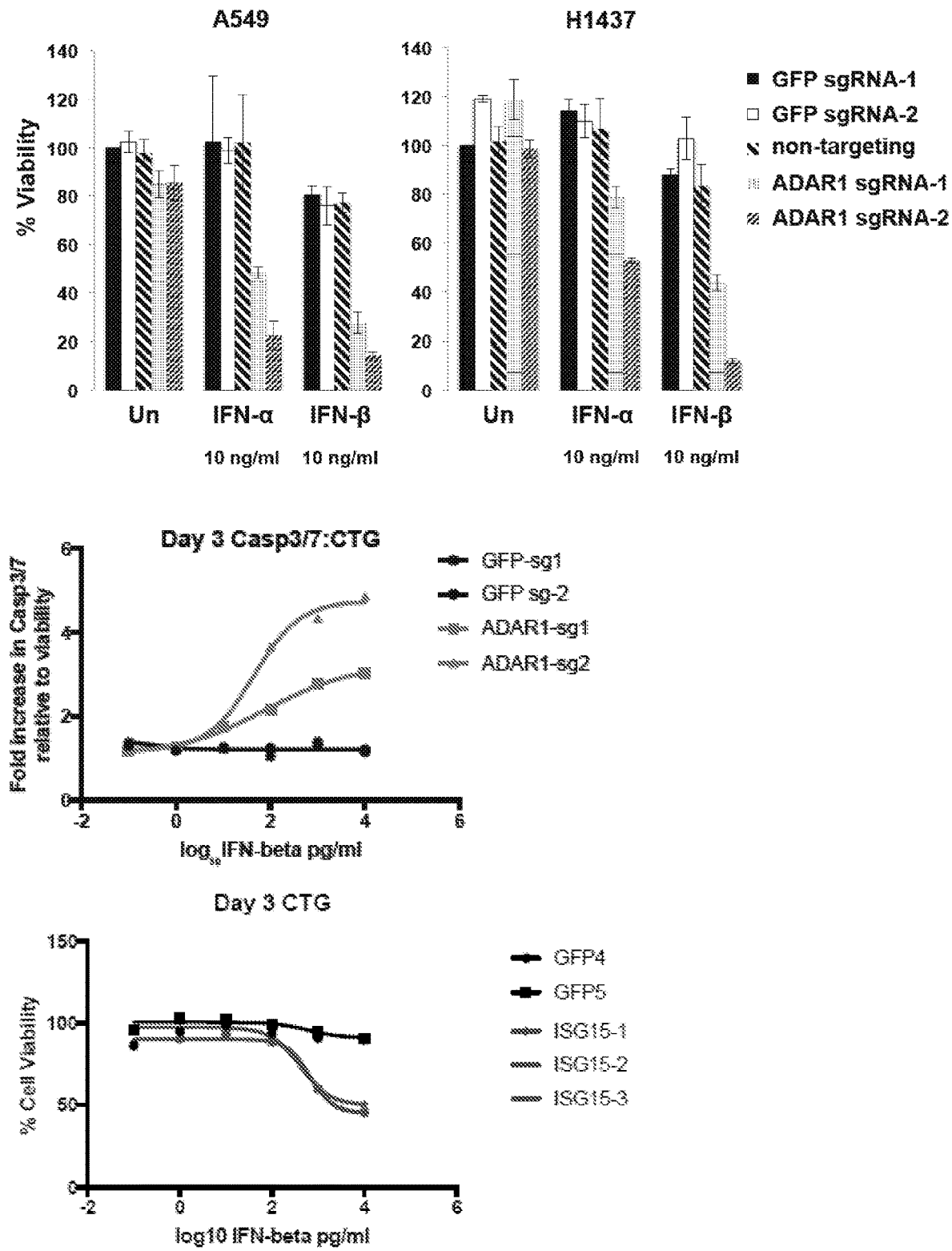
FIG. 53 shows the effects of Type I interferon treatment on two different ADAR1 knockout cell lines, the effects of Type I interferon treatment on Casp3/7 relative to viability on ADAR1 knockout cell lines, and the effects of Type I interferon treatment on A549 ISG15 knockout cells.
Figure 54:
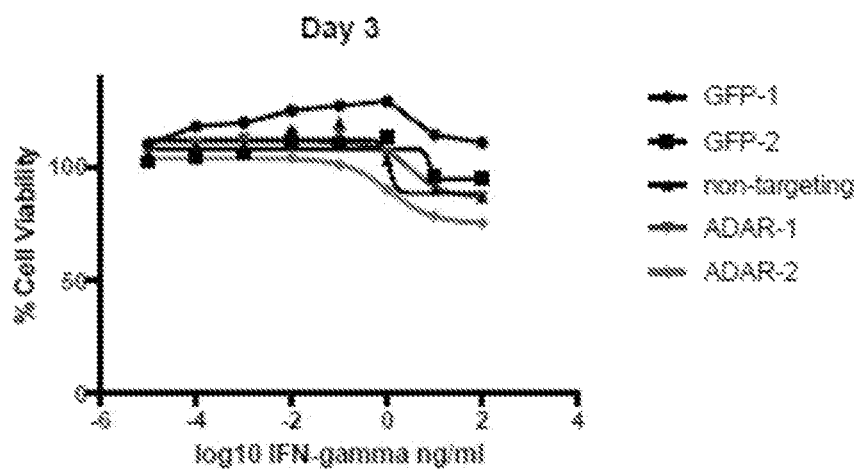
FIG. 54 shows the effects of Type II interferon treatment on ADAR1 knockout A549 cells. CRISPR-Cas9 controls were sgRNA targeting GFP and non-targeting sgRNA.
Figure 55:
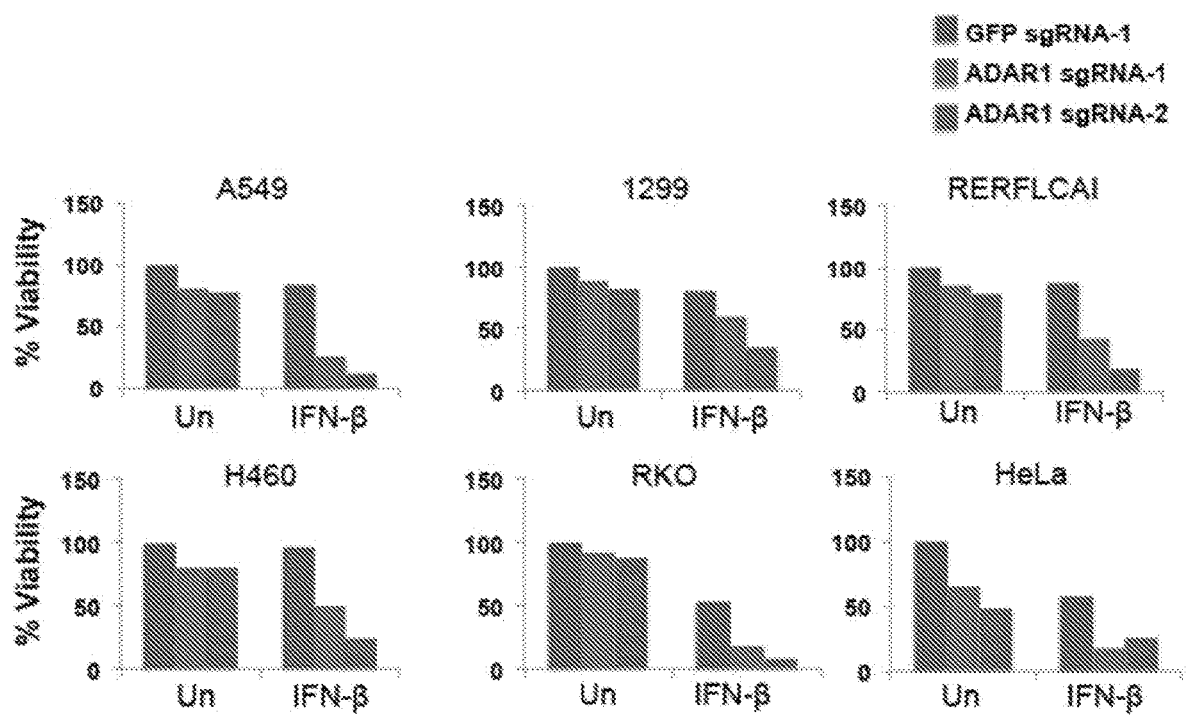
FIG. 55 shows the effects of ADAR1 knockout on the viability of different cell lines with and without 10 ng/ml IFN-β treatment. CRISPR-Cas9 control was sgRNA targeting GFP.

Example 11: Cancer Cell Lines are Sensitized to ADAR1 Knockout after Treatment with Exogenous Interferon The relationship between ADAR1 knockout and interferon signaling was investigated, and it was found that interferon signaling was induced in A549 cells after ADAR1 knockout (FIG. 50). Type I interferon treatment led to amplification of interferon regulated gene expression in A549 ADAR1 knockout cells, as soon as 3 days after interferon treatment (FIG. 50). A549 ADAR1 knockout cells treated with 10 ng/ml IFN-β overnight followed by media alone overnight increased IFN-β secretion (FIG. 52). Furthermore, Type I interferon treatment sensitizes A549 and H1437 cells to ADAR1 knockout (FIG. 53). Type I interferon treatment was found to increase Caspase 3/7 (Casp3/7) relative to viability in ADAR1 knockout cell lines using a luminescent cell viability assay (FIG. 53). Similar results were obtained in additional cell lines, including NCI-H1299 ("1299"), RERFLCAI, H460, RKO, and Hela (FIG. 54). Type I interferon treatment was also found to sensitize A549 cells to ISG15 knockout (FIG. 53).

Figure 56:
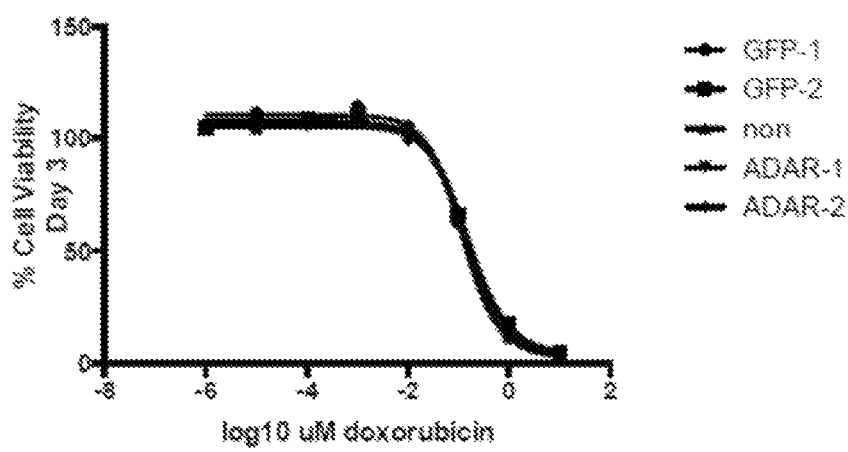
FIG. 56 shows a dose response curve for doxorubicin in A549 cells.
Figure 57:
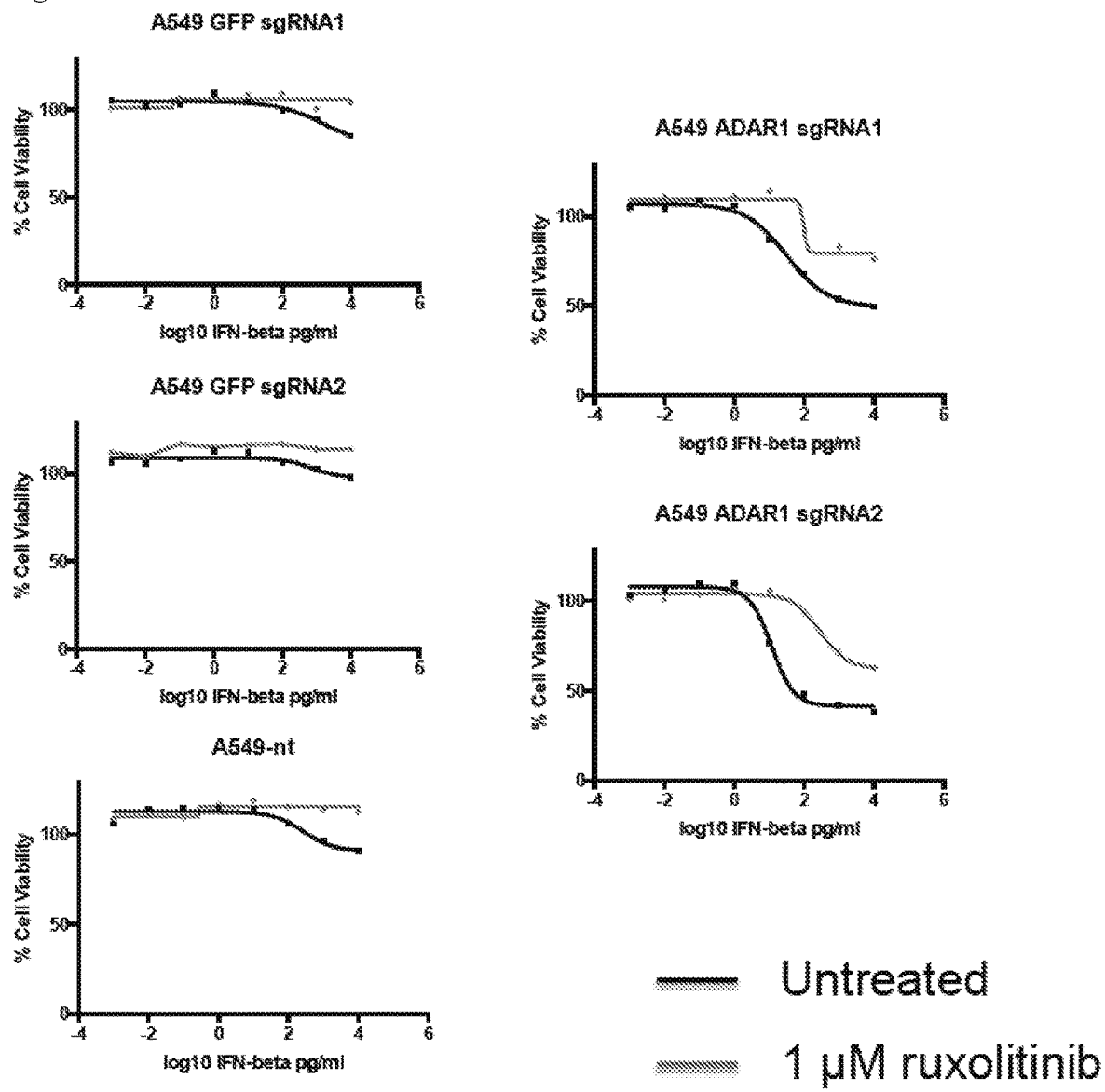
FIG. 57 shows the effect of ruxolitinib on different cell lines treated with IFN-0.
Figure 58:
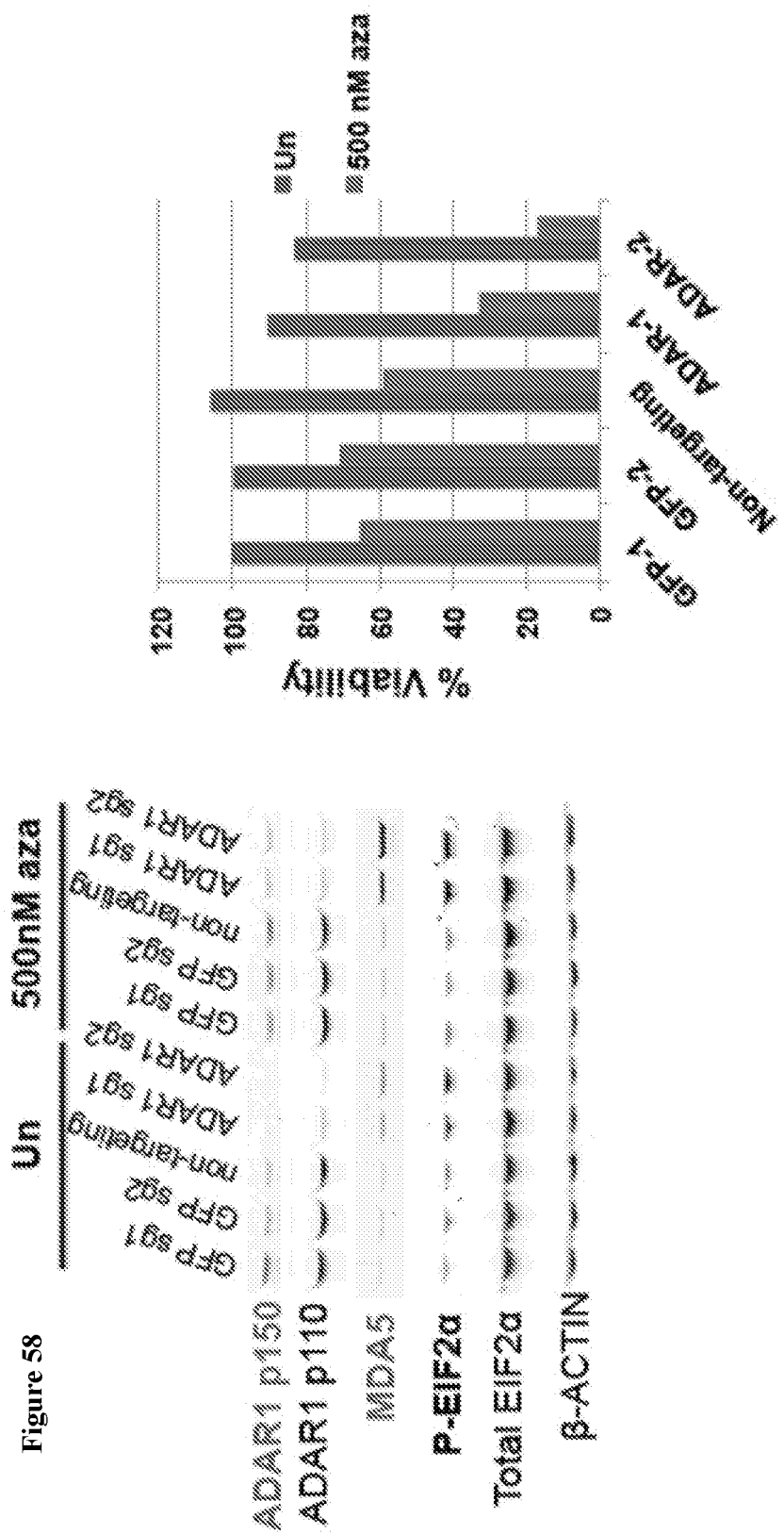
FIG. 58 shows the effects of 500 nM azacitidine ("aza") on expression of interferon regulated gene MDA5 and phosphorylation of EIF2a in ADAR1 knockout cell lines (left panel), and the effects of azacitidine on the viability of ADAR1 knockout cell lines (right panel). CRISPR-Cas9 controls were sgRNA targeting GFP and non-targeting sgRNA; Un means untreated.

Ruxolitinib, a known Jak1/Jak2 inhibitor, partially rescued lethality to IFN-β treatment in ADAR1 knockout A549 cells (FIG. 57), confirming that the sensitization of ADAR knockout cells was dependent on the interferon pathway. The synthetic lethality of interferon and ADAR deficiency was specific to Type I interferon, as Type II interferon treatment did not sensitize A549 cells to ADAR1 knockout (FIG. 54). Consistently, doxorubicin, which is known to induce IFN-γ-JAK-STAT1 signaling, failed to sensitize A549 cells to ADAR1 knockout (FIG. 56). DNA methylation inhibitors such as azacitidine, which could trigger dsRNA antiviral response, induced expression of interferon regulated gene MDA5, increased phosphorylation of EIF2α, and sensitized A549 cells to ADAR1 knockout (FIG. 58).

Example 12: HPV Infected HeLa Cells are Sensitive to ADAR1 Disruption

Figure 59:
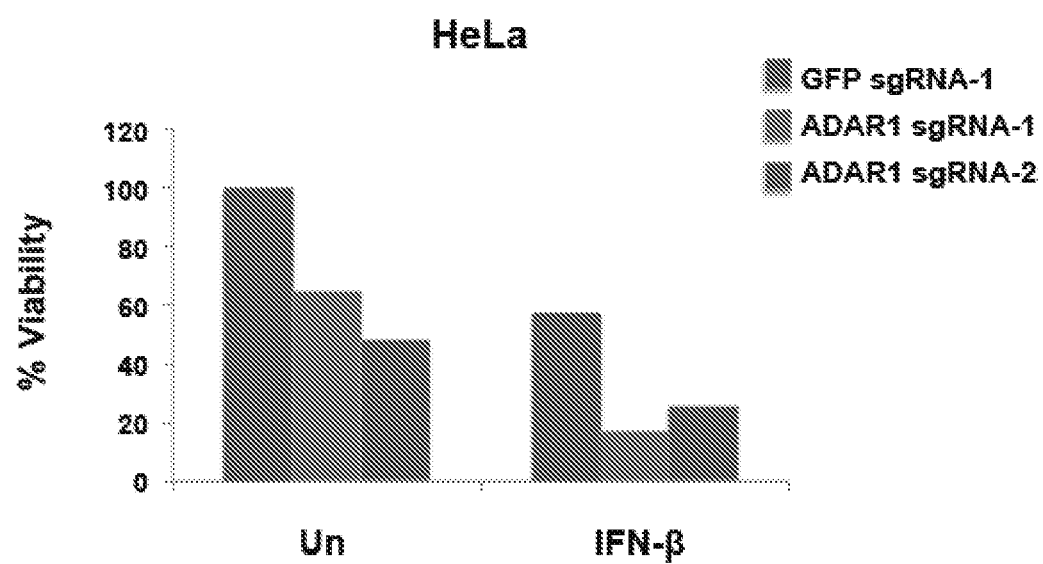
FIG. 59 shows the effect of ADAR1 knockout and ADAR1 knockout with exogenous IFN-β treatment on HeLa cells.

HeLa cells were obtained from a cervical cancer cell line infected with HPV, and were found to be sensitive to ADAR1 knockout. This differential sensitivity was enhanced after exogenous treatment with 10 ng/ml IFN-β (FIG. 59).

Example 13: Experimental Procedures for Examples 8-12 Described Herein

Knockdown (shRNA), Knockout (CRISPR-Cas9), and RNA Sequencing Data Sets:
public shRNA (Achilles v2.20.2 Expanded-GeneZSolsCleaned.csv) and CRISPR data (Achilles v3.3.8 Achilles_v3.3.8.Gs.gct) were obtained from the Project Achilles data portal (available on the World Wide Web atportals.broadinstitute.org/achilles/) (Tsherniak et al. (2017) *Cell* 170:564-576; Aguirre et al. (2016) *Cancer Discovery* 6:914-929). Additional, public ADAR knockdown data were obtained from the Project DRIVE data portal as of August, 31st, 2017 (available on the World Wide Web at oncologynibr.shinyapps.io/drive/) (McDonald III et al. (2017) *Cell* 170:577-592). Data are presented as z-scores, which are the number of standard deviations away from the mean for each data point. RNA sequencing gene expression data (CCLE_RNAseq_081117.rpkm.gct) were acquired from the public Cancer Cell Line Encyclopedia (CCLE) data portal (available on the World Wide Web at broadinstitute.org/ccle). Differential expression differences between groups of ADAR knockdown sensitive and insensitive cell lines were generated by Mann-Whitney U tests.

Data Mining and Analyses:

Cancer cell line sequencing and gene expression data were acquired from the public Cancer Cell Line Encyclopedia (CCLE) data portal (available on the World Wide Web at broadinstitute.org/ccle). GOrilla (available on the World Wide Web at cbl-gorilla.cs.technion.ac.il) was used for gene ontology analysis for genes enriched in individual cell lines compared to all other lines in CCLE. For gene knockdown data, the shRNA-level data for Project Achilles shRNA level dependency values are expressed as the log 2 fold change in shRNA abundance after 16 population doublings or 40 days in culture compared to the initial DNA plasmid pool. For gene-level scores, the ATARiS module on GenePattern (available on the World Wide Web at broadinstitute.org/cancer/ataris") was used. The gene-level score is a normalized value indicating the magnitude of dependence (negative score) or relative enhancement (positive score) of survival after shRNA knockdown. These same analyses were performed using in a published genome-wide CRISPR-Cas9 knockout screen (available on the World Wide Web at portals.broadinstitute.org/achilles/datasets/7/download).

Inhibitor Treatment Analysis:

For drug treatment assays, cells were plated at a density of 3000 cells per well in a 96-well assay plate. The following day, cells were treated with ruxolitinib (INCB018424) from Selleck Chemicals; MRT67307 hydrocloride (SML0702) from Sigma-Aldrich; human interferon-alpha1 (#8927) from Cell Signaling; recombinant human IFN-beta 1a (mammalian) protein (114151) and recombinant human IFN-gamma protein (285-IF-100) from R&D Systems. For preincubation drug treatment experiments, cells were plated in the presence of ruxolitinib and were treated with interferon-0 and ruxolitinib the following day. Control wells were treated with dimethylsulfoxide (DMSO). Cell viability was assayed 3 or 6 days after drug treatment with CellTiter-Glo® Luminescent Cell Viability Assay kit (Promega). Viability was normalized to DMSO controls.

Immunoblots:

Cells were lysed in RIPA lysis buffer (Thermo Scientific) supplemented with 1× protease and phosphatase inhibitor cocktails (Roche). Protein extracts were analyzed by standard immunoblotting with the following antibodies: ADAR1 (D7E2M), MDA5 (D74E4), RIG-I (D14G6), ISG15 (22D2), USP18 (D4E7), PKR (#3072), STING (D2P2F), cGAS (D1D3G), IRF9 (D2T8M), PD-L1 (E1L3N), P-IRF3 Ser396 (4D4G), IRF3 (D6I4C), P-TBK1 Ser172 (D52C2), TBK1 (D1B4), P-EIF2α Ser51 (#9721), and EIF2α (D7D3) from Cell Signaling; P-PKR Thr446 (ab32036) from Abcam; R-actin C4 (sc-47778) from Santa Cruz. All antibodies were used at a dilution of 1:1000 except R-actin which was used at 1:4000). The following secondary antibodies were used at 1:5000 dilution: Goat anti-Rabbit IRDye 800CW (LI-COR, 926-32211) and Goat anti-Mouse IRDye 608LT (LI-COR, 926-68020). All immunoblots were imaged using the LI-COR digital imaging system and ImageJ.

Interferon-β and Interferon-α ELISAs:

all interferon-β detection experiments utilized the VeriKine-HS Human IFN Beta Serum ELISA Kit and all interferon-α detection experiments utilized the VeriKine-HS Interferon Alpha All Subtype ELISA Kit (PBL Assay Science). For basal cancer cell line interferon detection, $4 \times 10^5$ cells were seeded in 6-well culture plates on day 1. On day 2, the media was replaced with 1.5 ml fresh media for each well. On day 3, 200 µl of conditioned media from each well was collected and spun at 10,000 rpm for 5 minutes to pellet cells. For each replicate experiment, samples were assayed in duplicate, with 50 µl of the supernatant media added per well of the 96-well assay plate. Fresh media was used as the diluent for all standards and blanks. Each kit's protocol was carried out and all concentrations of interferon were calculated according to the standard curve of each replicate. For exogenous interferon treatment experiments, $2 \times 10^5$ cells were seeded in 6-well culture plates on day 1. On day 2, the media was replaced with media supplemented with recombinant 10 ng/ml interferon- or interferon-a. On day 3, the media was replaced with 1.5 ml fresh media for each well. On day 4, the ELISA was performed as described above.

CRISPR-Cas9 Gene Knockout:

guide RNA sequences were designed using the sgRNA designer tool on The RNAi Consortium (TRC) portal (available on the World Wide Web at portals.broadinstitute.org/gpp/public/analysis-tools/sgrnadesign). Guide sequences are displayed in Table 3. Guide sequences were cloned into the Cas9 expressing lentiviral vector CRISPRv2 (available on the World Wide Web at genomeengineering.org/crispr). For virus production, each CRISPRv2 vector and packaging vectors were introduced into 293T cells via calcium phosphate transfection (Clontech). Lentivirus was harvested in RPMI media supplemented with 10% FBS and filtered before addition to each cancer cell line. Infected cells were selected in 2 µg/ml puromycin or 10 µg/ml blasticidin for 7 days. Following this, protein lysates were harvested or cells were plated for proliferation assays in 96 well plates and grown in the presence of RPMI containing 10% FBS and 1 µg/ml puromycin or 5 µg/ml blasticidin. Immunoblotting confirmed decreased protein levels of each gene across the pool of infected cells. For cell viability experiments, cells were plated at a density of 3000 cells per well in a 96-well assay plate. Cell viability was assayed 3 and 6 days later with the CellTiter-Glo® Luminescent Cell Viability Assay kit (Promega). For double knockout cells, stable knockout cell lines under 2 µg/ml puromycin selection were infected with Cas9 and second gene guides with a blasticidin resistance marker. After 7 days under selection of both 2 g/ml puromycin and 10 µg/ml blasticidin, cells were plated for proliferation or stained using crystal violet in 6- or 12-well plates. For crystal violet staining, cells were washed with cold PBS, fixed with cold methanol, stained with 0.5% crystal violet solution made in 25% methanol for 10 minutes, and rinsed with water.

TABLE 3

| Protein | Guide | Target sequence |
|---|---|---|
| GFP | GFP sg1 | GGAGCGCACCATCTTCTTCA |
| GFP | GFP sg2 | GAAGTTCGAGGGCGACACCC |
| NA | Nontargeting | GCTTGAGTGTATGCACAAAT |
| ADAR1 | ADAR sg1 | GTGCATACACTCAAGCAGTG |

TABLE 3-continued

| Protein | Guide | Target sequence |
|---|---|---|
| ADAR1 | ADAR sg2 | AGATAGCCATGCTGAGCCAC |
| RIG-I | DDX58 sg1 | CTAGGGCATCCAAAAAGCCA |
| RIG-I | DDX58 sg2 | GTTCCTGTTGGAGCTCCAGG |
| MDA5 | IFIH1 sg1 | GTGCATATGCGCTTTCCCAG |
| MDA5 | IFIH1 sg2 | AGGACTGAGGAATCAGCACG |
| MAVS | MAVS sg1 | CCTCTCCTGGAACTTCCGGT |
| MAVS | MAVS sg2 | GGTATTGAAGAGATGCCAGA |
| STING | TMEM173 sg1 | GGTCTCAAGAGAAATCCGTG |
| STING | TMEM173 sg2 | TTCACAGGTTGAAGACACCG |
| cGAS | MB21D1 sg1 | CCGCCGTGGAGATATCATCG |
| cGAS | MB21D1 sg2 | TGGGGCCTCGAAGCTCCGGG |
| PKR | EIF2AK2 sg1 | GCAAGACTATGGAAAGGAAG |
| PKR | EIF2AK2 sg2 | AAAGGCAATACGTACCACTG |

Cancer Cell Lines:

cancer cell lines were grown and maintained in RPMI media supplemented with 10% FBS, penicillin, streptomycin, and L-glutamine. The following cancer cell lines were provided by the CCLE: A549, NCI-1H460, NCI-1H1299, NCI-H1437, NC-H1650, HCC366, NCI-1H196, HCC1438, SW900, NCI-1H596, and RERFLCAI (lung); PATU-8902 (pancreas); RKO (colorectal); AGS (stomach); BT20 (breast); RKN (soft tissue). Cell line authentication and *mycoplasma* testing were provided by the CCLE before receipt.

Interferon Treatment:

for interferon treatment assays, cells were plated at a low density of 3000 cells per well in a 96-well assay plate. The following day, cells were treated with human interferon-alpha 1 (Cell Signaling, #8927) or recombinant human IFN-beta 1a (mammalian) protein (PBL Assay Science, 114151). Control wells were treated with water. Cell viability was assayed 3 or 6 days after drug treatment with CellTiter-Glo© Luminescent Cell Viability Assay kit (Promega). Viability was normalized to controls. Apoptosis was assayed 3 days after interferon treatment with Caspase-Glo®3/7 Assay kit (Promega). Dose curves were obtained using least-squares nonlinear regression on a standard four-parameter logistic model using GraphPad Prism.

RNA Sequencing:

for A549 cells with stably infected with ADAR or GFP guides, cells were treated with 10 ng/ml IFN-β or water for 24 hours before RNA isolation. For HCC366, NCI-H1650, and NCI-H196 cells, RNA was isolated 5 days after infection with Cas9 and corresponding ADAR or GFP guides. RNA was isolated using the RNeasy® Kit (Qiagen) with on-column DNase I treatment, followed by ribosomal RNA depletion using the NEBNext® rRNA Depletion Kit (E6310). RNA sequencing libraries were prepared using the NEBNext® Ultra™ Directional RNA library prep kit (NEB, E7420S) and sequenced on the Illumina® HiSeq™ instrument (150-bp paired end reads). Alignment against the human genome (hg19) was performed using the STAR aligner (Dobin et al. (2013) *Bioinformatics* 29:15-21). Reads were quantified using HTSeq (Anders et al. (2015) *Bioinformatics* 31:166-169), and each gene was then fit with a generalized linear model using DESeq2 (Love et al. (2014) *Genome Biol.* 15: 550). Gene set enrichment analysis was performed with normalized gene expression values using GenePattern (Reich et al. (2006) *Nat. Genet.* 38:500-501). Heat maps showed standardized t-statistics (Tij) of normalized expression values for each sample per gene calculated using $Tij=(xij-xj)/(sj/\sqrt{n})$, where xij=normalized expression value for sample i and gene j, xj=sample mean for normalized expression of gene j, sj=sample standard deviation for normalized expression of gene j, and n=number of samples.

RNA Editing Analyses:

the quality of the sequence reads was checked by FastQC with default parameters. Sequence reads were aligned using STAR (Dobin et al. (2013) *Bioinformatics* 29:15-21) to hg19 reference genome with parameters that accept only uniquely aligned reads and limit the number of mismatches to 0.05 of the mapped length. Adapters were clipped using clip3pAdapterSeq parameter. To calculate Alu editing index (AEI), a previously published algorithm was followed (Paz-Yaacov et al. (2015) *Cell Rep.* 13:267-276). This AEI measures the averaged editing level across all Alu adenosines, weighted by their expression. This index is the ratio of the number of A-to-G mismatches (presumably due to inosines) to the total number of reads—nucleotides aligned to a genomic adenosine within an Alu repeat (representing edited and non-edited transcript adenosines). AEI averages over millions of adenosines and is, therefore, rather robust to statistical noise. Hyper-editing analysis is an additional global estimate of RNA editing levels. This pipeline quantifies heavily edited reads, which differ so widely from the corresponding DNA to the extent that standard schemes fail to align them properly (Porath et al. (2014) *Nat. Commun.* 5:1-10). In this approach, all As to Gs in both the unmapped reads and the reference genome were transformed and re-aligned. For each sample, the number of hyper-edited reads per million mapped reads is used to quantify the level of hyper-editing.

TCGA Analysis:

the interferon gene expression signature score for each Achilles cell line was computed by taking the sum of log 2(x+1) transformed RPKM expression values across all 27 genes in the signature. These raw sums and report the z-scores are standardized as the final IFN-GES scores. An optimal interferon gene expression signature threshold for ADAR dependency was computed by maximizing the geometric mean of the precision (PPV) and the sensitivity of the cutoff in predicting ADAR dependency for the Achilles cell lines. This cell line interferon signature threshold was then applied to the set of TCGA tumors' standardized IFN-GES scores to identify primary human tumors with high interferon activation. Data generated by TCGA were obtained from (available on the World Wide Web at cancergenome.nih.gov). Enrichment of copy number alterations in high-IFN tumors was assessed using Fisher's exact tests on gene-level amplification and deletion calls generated by GISTIC2.0 (Mermel et al. (2011) *Genome Biol.* 12:R41). Multiple hypothesis testing correction was performed using the Benjamini-Hochberg procedure. For the genes most frequently subject to homozygous deletion, the sample set is composed of ABSOLUTE® (Carter et al. (2012) *Nat. Biotechnol.* 30:413-421) data for 9853 tumors across the 33 TCGA tumor types. The 23,030 genes with coverage by ABSOLUTE® segments were ranked by the number of samples with homozygous deletions.

Immunofluorescence Microscopy:

cells were seeded at 30,000 cells per well in 24-well plates (ibidi #82406) and fixed 1-2 days later with 4% paraformaldehyde for 15 minutes, washed twice with PBS, and stored at 4° C. for up to one day. Cells were then permeablized with PBS with 0.5% Triton-X100 for 5 minutes and washed three times with PBS. Blocking and subsequent antibody incubations were performed in PBS with 3% BSA at room temperature for 1 hour for each step. Anti-LAP2 primary antibody (BD Biosciences #611000) was added at 1:750 dilution; anti-mouse, Alexa 488-conjugated secondary antibody (Thermo Fisher #A-11029) was diluted 1:1000. Following each antibody incubation, three washes were performed with PBS with 0.05% Triton X-100 at room temperature for 5 minutes for each wash. DNA staining was performed with Hoechst 33342 (Thermo Fisher #H3570), diluted 1:2500 in PBS, for 20 minutes at room temperature. Cells were washed twice with PBS and exchanged into SlowFade™ Diamond Antifade (Thermo Fisher #S36963) just before imaging. Microscopy was performed using a Nikon Ti-E inverted microscope with a 60× Plan Apo 1.4 NA objective. Images were recorded with a CoolSnap HQ2 CCD camera (Photometrics) through a Yokogawa CSU-22 spinning disk confocal head. Cells were scored visually for the presence of nuclear abnormalities based on LAP2 and Hoechst staining.

Example 14: Further Confirmation that ADAR1-Dependency in Interferon-Activated Cancer Cells The following examples provide additional data and results that further confirm those of the examples presented above.

The identification of genomic alterations in human cancer has informed the development of therapeutic strategies that target the altered state of the cancer cell (Paez et al. (2004) Science 304:1497-1500; Druker et al. (2001) N. Eng. J. Med. 344:1031-1037; Olaussen et al. (2006) N. Eng. J. Med. 355:983-991). By analyzing genome-scale loss-of-function datasets (Tsherniak et al. (2017) Cell 170:564-576; McDonald III et al. (2017) Cell 170:577-592; Aguirre et al. (2016) Cancer Discovery 6:914-929), the RNA adenosine deaminase enzyme, ADAR1, was identified as essential for survival of a subset of cancer cell lines. ADAR-dependent cell lines were characterized by constitutive interferon production and activated interferon gene expression signatures. ADAR1 inactivation in dependent lines led to decreased global RNA editing, activation of the dsRNA binding protein PKR, and apoptosis. Accordingly, inactivation of PKR, or of the dsDNA sensors, cyclic GMP-AMP synthase (cGAS) and stimulator of interferon genes (STING), could rescue cell lethality caused by ADAR1 depletion. Analysis of human tumors from The Cancer Genome Atlas (TCGA) showed evidence of endogenous interferon activation, representing a potential therapeutic opportunity for use of ADAR1 inhibitors in this subset of cancers. Frequent homozygous deletion of the type I interferon locus on chromosome 9p was also observed, consistent with negative selection against interferon activation in some cancers. Taken together, these observations indicate ADAR1 inhibition as a new avenue for therapeutic intervention in human cancer.

The treatment of human lung cancer, the leading cause of cancer death, has advanced in recent years with targeted therapies that inhibit activity of the receptor tyrosine kinase/Ras/Raf signaling pathway (Bollag et al. (2010) Nature 467:596-599) and immunomodulatory therapies that can treat smoking-associated lung cancers with high tumor mutational burdens (Carbone et al. (2017) N. Eng. J. Med. 376:2415-2426). However, as many patients with lung cancer lack known, targetable genomic alterations (Campbell et al. (2016) Nat. Genet. 48:607-616), the need for new therapeutic modalities remains critical.

Figure 60:
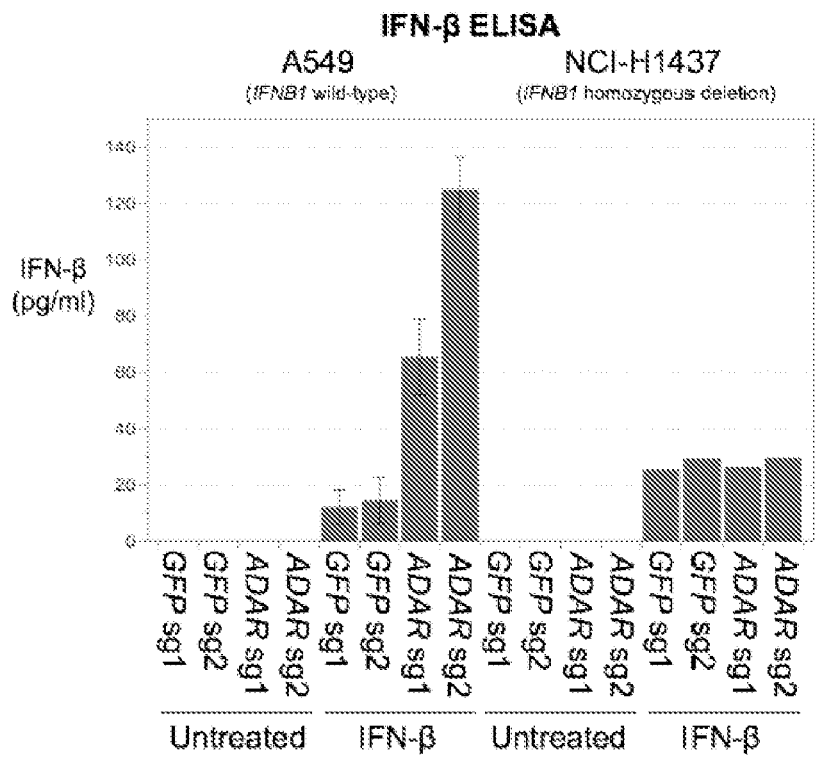
FIG. 60 includes nine panels, identified as panels A, B, C, D, E, F, G, H, and I, which show that cancer cell lines with endogenous or exogenous type I interferon activation are sensitive to ADAR suppression and deletion. Panel A shows z-scores for lethality of ADAR suppression for lung cancer cell lines from Tsherniak et al. (2017) *Cell* 170:564-576. Red dots: outlier cell lines with highest sensitivity to ADAR knockdown. Panel B shows cell viability 6 days after ADAR knockout by CRISPR-Cas9. All values relative to GFP sg1, n=3, error bars=standard deviation. Panel C shows HCC366 is sensitive to knockout of ADAR1 p150 isoform alone (sg1-6) in addition to knockout of both p110 and p150 (sg1-4). Panel D shows ADAR lethality z-scores compared to ISG15 (top panel) or IFNAR1 (bottom panel) lethality z-scores in lung cancer cell lines from Tsherniak et al. (2017) *Cell* 170:564-576. Panel E shows immunoblots for ISG protein levels in control cell lines (NCI-H1299 and A549) and high interferon signature cell lines. Actin: loading control. Panel F shows ELISA of IFN-β secretion 24 hours after media replacement. Panel G shows cell viability assessed 6 days after ADAR deletion by CRISPR-Cas9. All values relative to GFP sg1. Panel H shows cell viability assessed 3 days after 10 ng/ml IFN-β treatment in ADAR deletion cell lines. All values relative to GFP sg1. n=3, error bars=standard deviation. Panel I shows ELISA of IFN-β levels secreted after interferon stimulation in culture. Cells were stimulated with 10 ng/ml IFN-β for 24 hours followed by wash and replacement of fresh media. IFN-β levels were measured 24 hours after media replacement. For A549, n=3; error bars=standard deviation.
Figure 61:
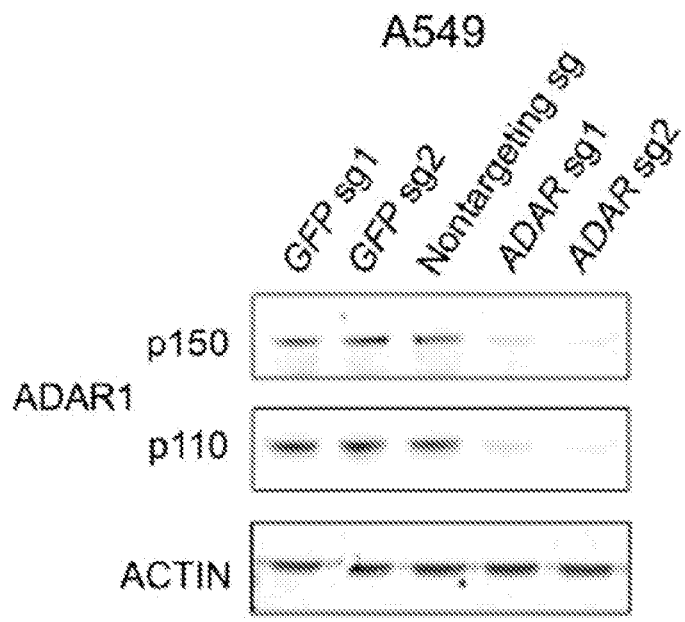
FIG. 61 includes five panels, identified as panels A, B, C, D, and E, which show that inactivation of ADAR1 leads to decreased viability in PATU-8902 cells and a panel of cells treated with IFN-β. Panel A shows ADAR1 protein levels assessed by western blot in control (GFP and non-targeting guides), and ADAR1 knockout (ADAR guides) in A549 cells 10 days after infection with CRISPRCas9/guide. Actin was used as a loading control. Panel B shows plots of ADAR dependence z-scores compared to ISG15 dependence z-scores and IFNAR1 dependence z-scores of cancer cell lines from published CRISPR-Cas9 knockout data (Aguirre et al. (2016) *Cancer Discovery* 6:914-929). Red dot: outlier cell line with highest sensitivity to ADAR knockout. ADAR knockdown outlier cell line. Panel C shows cell viability assessed 6 days after ADAR knockout by CRISPR-Cas9. All values relative to GFP sg1. Panel D shows cell viability assessed 3 days after 10 ng/ml IFN-β treatment in ADAR knockout cell lines. All values relative to GFP sg1. Panel E shows caspase 3/7 activity assayed by Caspase-Glo 3/7 3 days after 10 ng/ml IFN-β treatment in ADAR knockout A549 cells. Values are fold increase in luminescence compared to untreated.
Figure 61D:
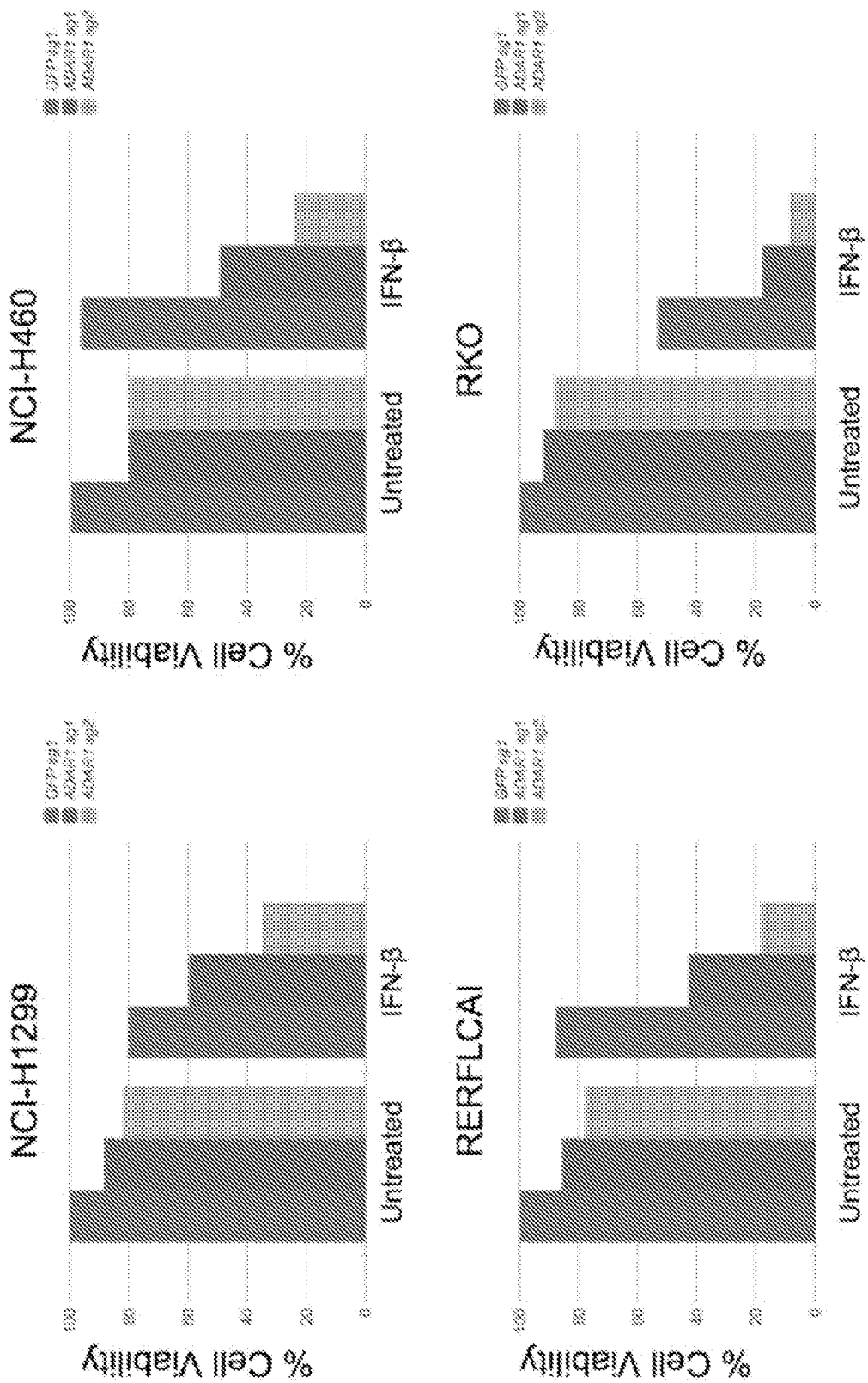

To identify novel cellular vulnerabilities in lung cancer, genetic dependencies were searched for using publicly available data on the effects of genome-scale shRNA treatment (Tsherniak et al. (2017) Cell 170:564-576). Eleven genes were identified that were required for the survival of lung cancer cell lines but not of cell lines of other lineages (Table 4), using the previously described criterion of lethality induced by gene-specific shRNAs in a given cell line to a degree of at least 6 standard deviations from the mean for all cell lines (Tsherniak et al. (2017) Cell 170:564-576). These genes include SMARCA2 and PRKDC, which were previously discovered as synthetic lethal targets in subsets of lung cancers (Oike et al. (2013) Cancer Res. 73:5508-5518; Zhou et al. (2014) BMC Cancer 14:1-13), as well as the putative lung adenocarcinoma oncogene, ADAR (adenosine deaminase acting on RNA) (Anadon et al. (2015) Oncogene 35:4407-4413). Suppression of ADAR gene expression showed outlier lethality in HCC366, NCI-H196, and NCI-H1650 lung cancer cells compared to other tested lung cancer cell lines (FIG. 60). CRISPR-Cas9 mediated gene deletion provided orthogonal evidence for the dependency of these cells on ADAR expression (FIG. 60, panel B and FIG. 61, panel A).

TABLE 4

| Gene | Number of 6 Standard Deviation Cell Lines | Minimum Dependency z-score | 98 k Library Lines | 55 k Library Lines | Non Lung Six SD Count | Lung Six SD Count | Non Lung Rest Count | Lung Rest Count | ChiSq Test p value | Fisher Exact Test p value |
|---|---|---|---|---|---|---|---|---|---|---|
| SMARCA2 | 9 | −9.961 | 285 | 216 | 0 | 9 | 385 | 107 | 0.0000 | 0.0000 |
| ATP5H | 3 | −8.123 | 285 | 216 | 0 | 3 | 385 | 113 | 0.0016 | 0.0122 |
| PRKDC | 3 | −7.137 | 285 | 216 | 0 | 3 | 385 | 113 | 0.0016 | 0.0122 |
| ADAR | 2 | −6.099 | 285 | 216 | 0 | 2 | 385 | 114 | 0.0098 | 0.0533 |
| CSDE1 | 2 | −8.606 | 285 | 216 | 0 | 2 | 385 | 114 | 0.0098 | 0.0533 |
| CSNK2B | 2 | −7.489 | 285 | 216 | 0 | 2 | 385 | 114 | 0.0098 | 0.0533 |
| CXCR4 | 2 | −7.339 | 285 | 216 | 0 | 2 | 385 | 114 | 0.0098 | 0.0533 |
| FBXL5 | 2 | −7.315 | 285 | 216 | 0 | 2 | 385 | 114 | 0.0098 | 0.0533 |
| RACGAP1 | 2 | −7.632 | 285 | 216 | 0 | 2 | 385 | 114 | 0.0098 | 0.0533 |
| SARS | 2 | −6.867 | 285 | 216 | 0 | 2 | 385 | 114 | 0.0098 | 0.0533 |
| USPL1 | 2 | −7.022 | 285 | 216 | 0 | 2 | 385 | 114 | 0.0098 | 0.0533 |

ADAR encodes two isoforms (constitutively expressed p110 and interferon-inducible p150) (Patterson & Samuel (1995) *Mol. Cell. Bio.* 15:5376-5388) of the double-stranded RNA (dsRNA) adenosine deaminase enzyme, ADAR1, which converts adenosine (A) to inosine (I) (Patterson & Samuel (1995) *Mol. Cell. Bio.* 15:5376-5388; Mannion et al. (2014) *Cell Reports* 9:1482-1494; Liddicoat et al. (2015) *Science* 349:1115-1121; Pfaller et al. (2011) *Curr. Opin. Immunol.* 23:573-582). A-to-I editing masks endogenous dsRNAs from cytosolic RNA binding proteins such as PKR (EIF2AK2), RIG-I (DDX58), and MDA5 (IFIH1) (Mannion et al. (2014) *Cell Reports* 9:1482-1494; Liddicoat et al. (2015) *Science* 349:1115-1121; Pfaller et al. (2011) *Curr. Opin. Immunol.* 23:573-582). GermlineADAR editase domain mutations in humans cause Aicardi-Goutières syndrome, an interferonopathy characterized by constitutively active interferon pathway signaling (Rice et al. (2012) *Nat. Genet.* 44:1243-1248), highlighting the importance of ADAR1 in curbing aberrant interferon responses and activation. Of note, deletion of the p150 isoform alone (sg1-6) showed the same phenotypic effect as knockdown of both isoforms (sg1-4) in HCC366 cells (FIG. 60, panel C).

Given the role of ADAR1 in the interferon pathway, the response of lung cancer cell lines to knockdown of other regulators of the interferon response was evaluated. The cell lines sensitive to ADAR knockdown were also sensitive to knockdown of ISG15 (FIG. 60, panel D), an interferon stimulated gene that mediates a negative feedback loop to decrease interferon signaling (Tsherniak et al. (2017) *Cell* 170:564-576; Zhang et al. (2015) *Nature* 517: 89-93). Consistent with these data, knockdown of the gene encoding the interferon-alpha/beta receptor, IFNAR1, increased survival in HCC366 and NCI-H196 cells (Tsherniak et al. (2017) *Cell* 170:564-576) (FIG. 60, panel D). Analysis of CRISPR-Cas9 gene knockout data from a recently published set of 33 cell lines (Aguirre et al. (2016) *Cancer Discovery* 6:914-929) identified a similar dependency pattern of ADAR and ISG15 knockout lethality and IFNAR1 knockout growth advantage in the pancreatic cancer cell line, PATU-8902 (FIG. 61, panel B, and FIG. 61, panel C). These data indicate a central role for interferon signaling in the survival of ADAR-dependent cell lines.

To address pathway activation in the ADAR-dependent lung cancer cell lines, Gene Set Enrichment Analysis (GSEA) of public RNA sequencing data from cancer cell lines of the Cancer Cell Line Encyclopedia (CCLE) (Barretina et al. (2012) *Nature* 483:603-607) was performed and elevated expression of type I interferon-stimulated genes (ISGs) was found in the ADAR-dependent cells. This finding allowed the identification of additional cell lines with increased interferon gene expression signatures (IFN-GESs) that had not been analyzed in the CRISPR or shRNA screens. These cell lines expressed high levels of known interferon-inducible proteins, particularly PKR, MDA5, and STING (FIG. 60, panel E), and spontaneously secreted interferon-beta (IFN-β) (FIG. 60, panel F). Cell lines with a high interferon gene expression signature (McDonald III et al. (2017) *Cell* 170:577-592) that were not part of the initial knockdown screens (NCI-H596, HCC1438, and SW900) were also sensitive to ADAR knockout, indicating that high IFN-GES is a predictor of ADAR dependence (FIG. 60, panel G).

To investigate whether enhanced interferon signaling confers sensitivity to ADAR inhibition, A549 and NCI-H1437 cells, which normally tolerate ADAR1 deficiency, were treated with type I interferon. Treatment with either interferon-alpha (IFN-α) or IFN-β sensitized both cell lines to ADAR knockout (FIG. 60, panel H); similar results were seen for an extended panel of cell lines treated with IFN-β (FIG. 61, panel D). A549 ADAR-knockout cells treated with IFN-β showed increased caspase 3/caspase 7 activity, indicative of increased apoptosis (FIG. 61, panel E). Consistent with the known role of ADAR1 in suppressing IFN-β expression (Mannion et al. (2014) *Cell Reports* 9:1482-1494; Rice et al. (2012) *Nat. Genet.* 44:1243-1248), ADAR knockout A549 cells showed persistently higher IFN-β secretion 24 hours after IFN-β stimulation (FIG. 60, panel F); this was not observed in NCI-H1437 cells that harbor homozygous loss of IFNβI and thus cannot express endogenous IFN-β.

Example 15: cGAS/STING DNA Sensing Pathway Activity Involved in ADAR1 Dependency and Enhanced Interferon Signaling The mechanism by which spontaneous type I interferon signaling could induce ADAR dependence in cultured cancer cells was next determined. Deficiency of STING, a key cellular dsDNA sensor, reduced expression of ISGs, such as ISG15 and MDA5, in ADAR-dependent cell lines (Kato et al. (2013) *Annual Rev. Biochem.* 339:541-566; Chen et al. (2016) *Nat. Immunol.* 17:1142-1149) (FIG. 62, panel A, and FIG. 63, panel B), indicating that DNA sensing mechanisms contribute to interferon activation and ADAR1-dependency. Upstream of STING, knockout of MB21D1, encoding the dsDNA sensor, cGAS (Kato et al. (2013) *Annual Rev. Biochem.* 339:541-566; Chen et al. (2016) *Nat. Immunol.* 17:1142-1149), also led to reduction of ISG expression (FIG. 62, panels B and C) and diminished IFN-β secretion (FIG. 62, panel D) in ADAR1-dependent cell lines.

Figure 62:
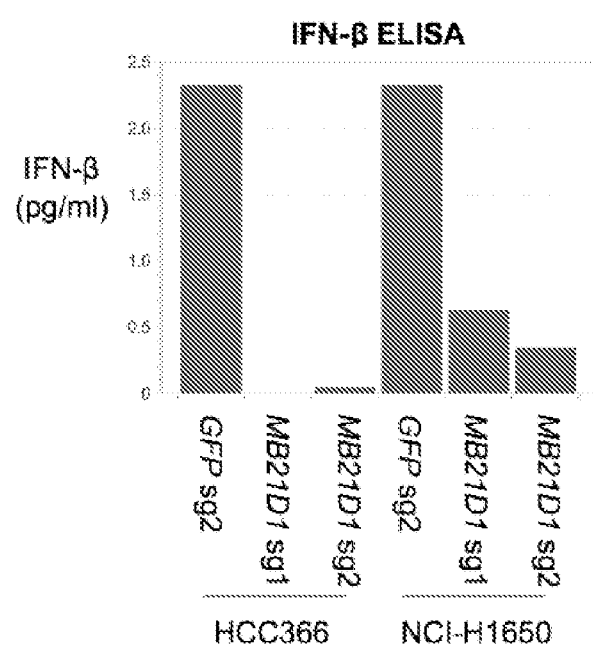
FIG. 62 includes five panels, identified as panels A, B, C, D, and E, which show that interferon production and ADAR deletion lethality are dependent on the cytosolic DNA sensing pathway. Panel A shows the protein levels in control (GFP guides) and STING knockout (TMEM173 guides) HCC366 cells, assessed by immunoblotting. Panel B and Panel C show immunoblotting results of ISG protein levels in control (GFP guides) and cGAS knockout (MB21D1 guides) cells. Panel D shows secreted IFN-β levels in stable cGAS knockout (MB21D1 guides) cells, measured by ELISA 24 hours after media replacement in culture. Panel E shows the crystal violet staining of GFP, IFIH1, TMEM173 or MB21D1 knockout cells, following infection with ADAR or GFP targeting guides. Panel E also shows NCI-H1650 ADAR knockout lethality is not rescued by concurrent knockout of MAVS or MDA5, while NCI-H1650 ADAR knockout lethality is rescued by concurrent knockout of cGAS. Additionally, HCC366 ADAR knockout lethality is not rescued by concurrent knockout of MAVS.
Figure 62:
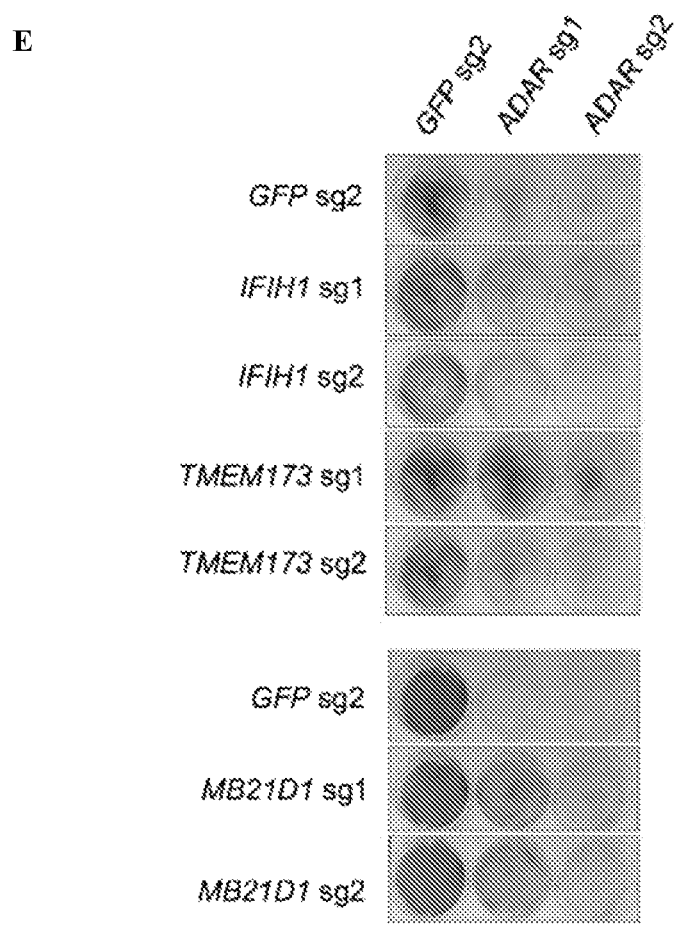
Figure 62:
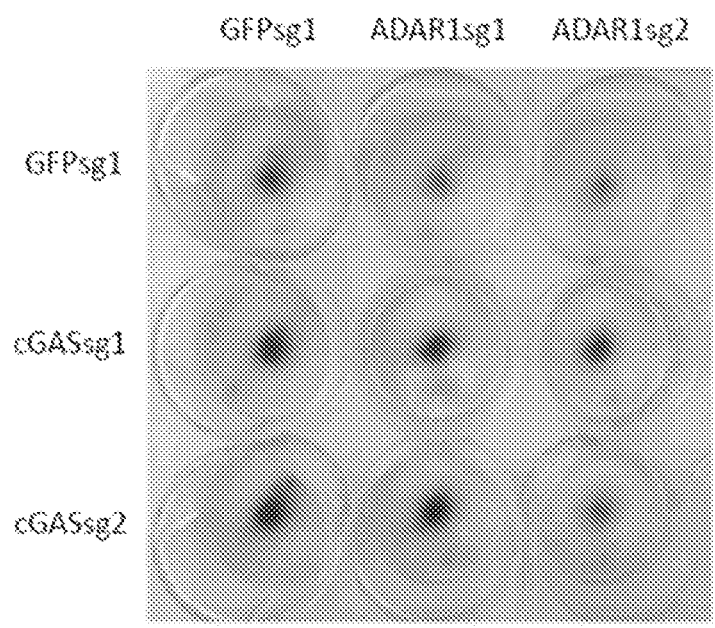
Figure 63:
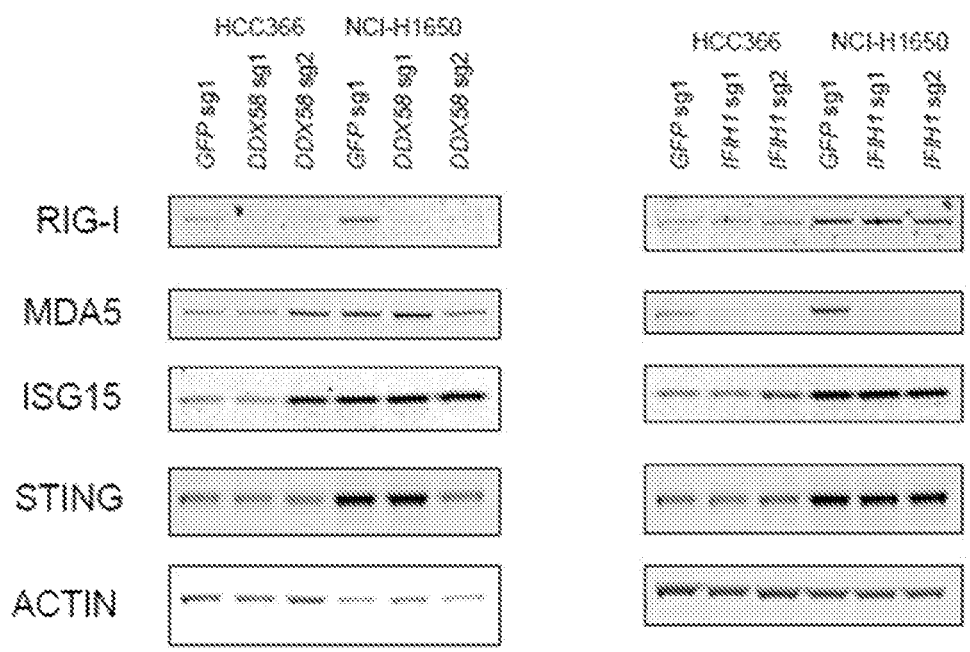
FIG. 63 includes three panels, identified as panels A, B, and C, which show that STING inactivation, but not deletion of the RNA sensors MDA5 or RIG-I, leads to reduction of ISG expression in ADAR1-dependent cell lines. Panel A shows ISG15 and MDA5 protein levels in control (GFP guides) and STING knockout (TMEfM173 guides) assessed by western blot. Panel B shows knockout of MDA5 or RIG1 does not affect ISG expression. Panel C shows frequencies of cells with detectable micronuclei or chromosome bridges by LAP2 immunofluorescence staining, error bars=counting statistics for frequency measurements.
Figure 63:
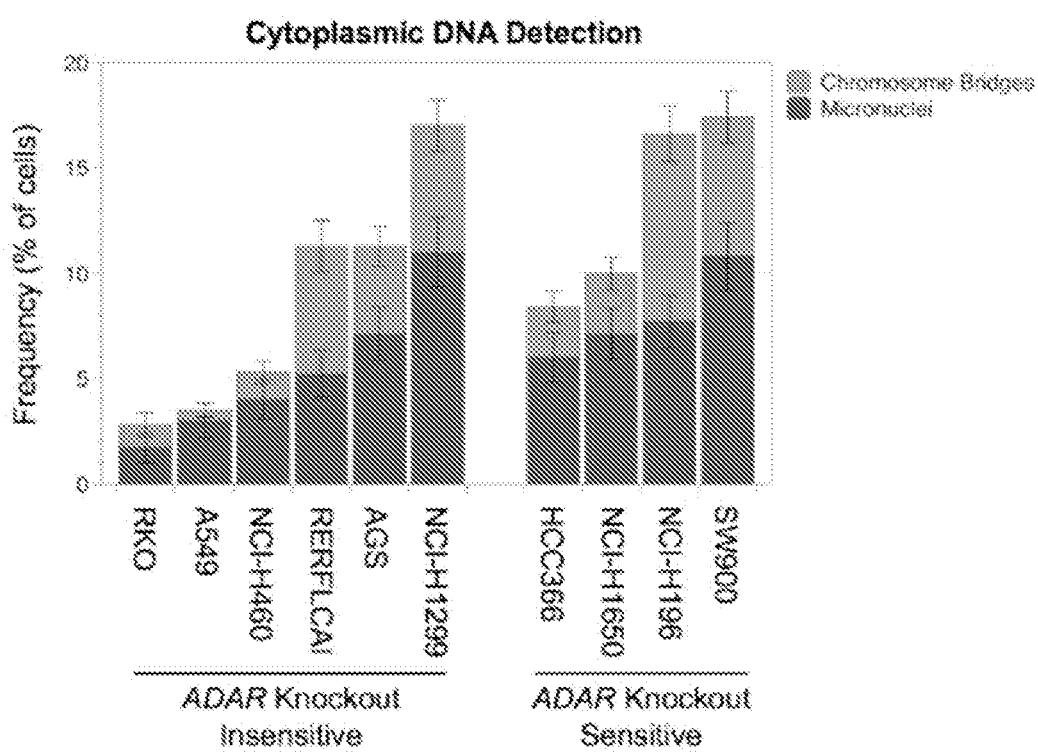

Inactivation of the DNA sensing pathway member cGAS or STING not only abrogated interferon signaling but also partially rescued lethality after decreased ADAR expression in HCC366 and NCI-H1650 cells (FIG. 62, panel E). Reduction of the dsRNA sensors, MDA5, RIG-1, or MAVS, did not have major detectable phenotypic effects in HCC366 or NCI-H1650 cells (FIG. 62, panel E, and FIG. 63, panel B). Genomic analyses did not reveal evidence for pathogen genomes, gene-specific mutations, or recurrent copy number alterations that differentiated ADAR1-dependent from ADAR1-independent cell lines. Likewise, no correlation was observed between vulnerability to ADAR1 deficiency and the frequency of micronuclei or chromosome bridges, which are known activators of cGAS and STING (Mackenzie et al. (2017) *Nature* 548:461-465; Harding et al. (2017) *Nature* 548:466-470) (FIG. 63, panel C). These results indicate that a subgroup of cancer cell lines exhibit enhanced interferon signaling and ADAR dependency via activation of the cGAS/STING DNA sensing pathway.

Example 16: ADAR1 Modulation Modulates PKR Activation

Figure 64:
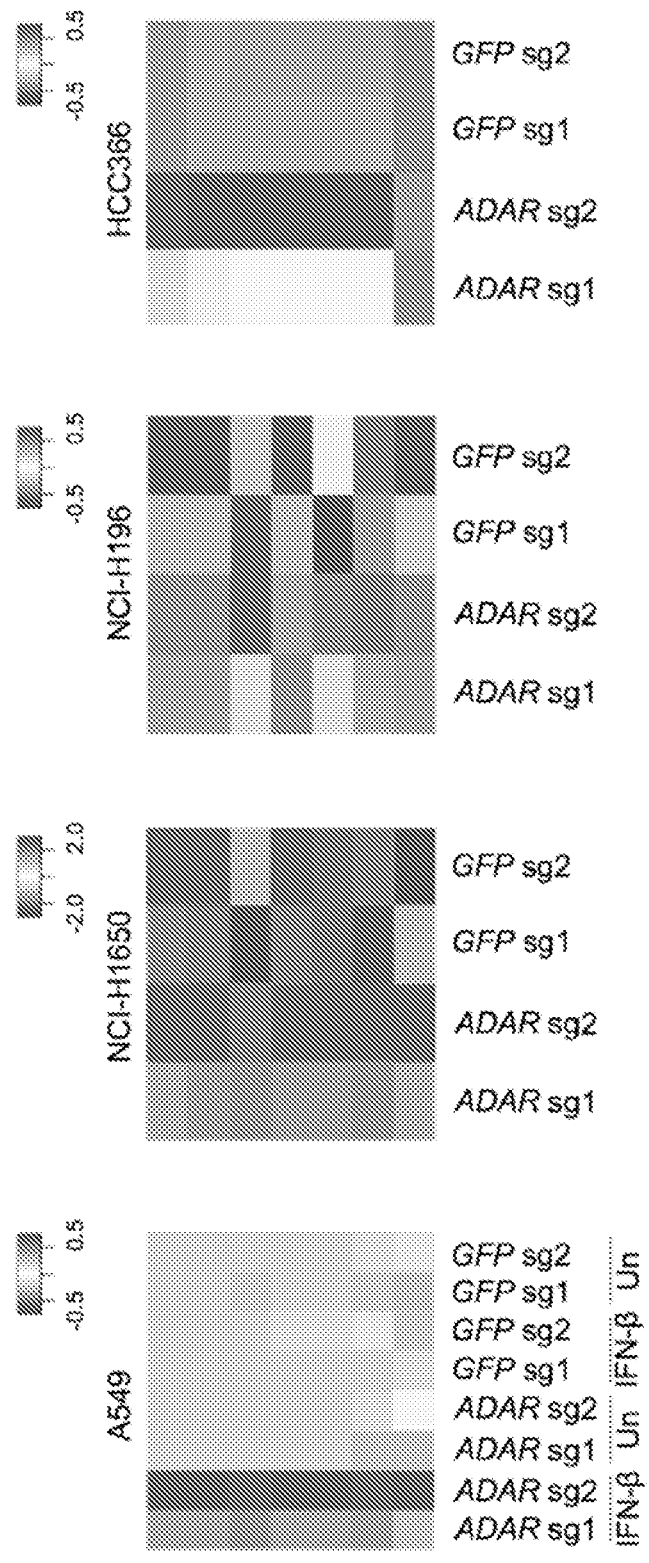
FIG. 64 includes ten panels, identified as panels A, B, C, D, E, F, G, H, I and J, which show that PKR levels and activation determine sensitivity to ADAR inactivation. Panel A shows correlation plot of RNA editing Alu index and hyper-editing index in A549 cells treated with the indicated sgRNAs. Cells were treated with 10 ng/ml IFN-β or vehicle for 24 hours before RNA harvest. 95% confidence interval shaded in gray. Panel B shows RNA-seq data of Alu editing and hyper-editing. Panel C shows differentially expressed genes between ADAR suppression sensitive and insensitive cells using gene expression data from Tsherniak et al. (2017) *Cell* 170:564-576, McDonald III et al. (2017) *Cell* 170:577-592, and Aguirre et al. (2016) *Cancer Discovery* 6:914-929 are plotted by −log (q value) compared to log 2 (mean fold change). Panel D and Panel E show immunoblots of phosphorylated PKR (Thr-446) and total PKR (Panel C, NCI-H1650, NCI-H196, and HCC366 lysates 5 days after infection with CRISPRCas9/guides; Panel E shows A549 and NCI-H1437 lysates 24 hours after 10 ng/ml IFN-β treatment). Panel F shows the crystal violet staining of HCC366 cells following infection with the indicated targeting guides. Panel G shows PATU8902 ADAR knockout lethality is rescued by concurrent knockout of PKR. Panel H shows cell viability assessed 3 days after 10 ng/ml IFN-β treatment in A549 cells. Panel I shows immunoblots of ADAR1, phosphorylated EIF2α (residue Ser-51), and total EIF2α. A549 cells were treated with the indicated sgRNAs and 10 ng/ml IFN-β for 24 hours. Panel J shows heat maps of standardized t-statistics of normalized expression values for each sample per gene. A549 cells were untreated or treated with 10 ng/ml IFN-β for 24 hours. RNA from NCI-H1650, NCI-H196, and HCC366 cells was harvested 5 days after infection with CRISPR-Cas9/guides.

The impact of ADAR-knockout on RNA editing was next investigated by applying previously described analytic approaches (Paz-Yaacov et al. (2015) *Cell Rep.* 13:267-276; Porath et al. (2014) *Nat. Commun.* 5:1-10) to RNA sequencing data from ADAR knockout and control A549 cells. ADAR knockout A549 cells, regardless of interferon treatment, showed decreased editing of repetitive Alu elements, the primary target for editing by ADAR1 in the transcriptome, and a reduction in noncoding RNA regions containing clusters of A-to-I editing, known as hyper-edited regions (Porath et al. (2014) *Nat. Commun.* 5:1-10) (FIG. 64). This was also shown in the ADAR-dependent cell line NCI-H1650 5 days after ADAR knockout (FIG. 64, panel B). In contrast, interferon treatment of control A549 cells (with 9 intact ADAR) increased RNA editing compared to untreated cells, corresponding to ADAR1 protein induction (FIG. 64, panel A).

Differential gene expression analysis between an expanded set of ADAR1-dependent and non-ADAR1-dependent cell lines, drawn from recently published studies (Tsherniak et al. (2017) Cell 170:564-576; McDonald III et al. (2017) Cell 170:577-592; Aguirre et al. (2016) Cancer Discovery 6:914-929), confirmed that the top genes enriched in ADAR-dependent solid tumor cell lines are ISGs. The most statistically significant differentially expressed gene in ADAR1-dependent cell lines is EIF2AK2, which encodes the dsRNA-activated kinase, PKR (FIG. 64, panel C). PKR (Protein Kinase regulated by RNA) is an antiviral, cytosolic protein kinase that undergoes dimerization and autophosphorylation at threonine residue 446 after binding unedited dsRNAs (Pfaller et al. (2011) Curr. Opin. Immunol. 23:573-582; Dey et al. (2014) J. Bio. Chem. 289:5747-5757).

It was hypothesized that ADAR1 deficiency and subsequent decreased RNA editing would correspond to increased activation of PKR. Cell lines that produce high levels of interferon have constitutively elevated total PKR levels, but show autophosphorylation of PKR only after ADAR knockout (FIG. 64, panel D). Similarly, PKR activation after ADAR knockout in A549 and NCIH1437 cell lines, which normally do not exhibit ADAR dependency, was detectable only after IFN-β treatment (FIG. 64, panel E).

It was hypothesized that that cells stimulated with endogenous or exogenous IFN-β are sensitive to ADAR1 knockdown because they are primed with high levels of PKR protein following interferon exposure. To test this, PKR (encoded by EIF2AK2) was inactivated in ADAR knockout HCC366 and PATU-8902 cells and it was found that EIF2AK2 deletion could rescue cell lethality induced by ADAR1-deficiency (FIG. 64, panel F and panel G). Correspondingly, A549 ADAR-knockout lethality triggered by IFN-β treatment was rescued by concurrent deletion of EIF2AK2 (FIG. 64, panel H), but not by co-deletion of other RNA or DNA sensing pathway genes (FIG. 65, panels A and B). These results indicate that the lethality induced by deletion of ADAR is mediated through activated PKR. PKR activation after dsRNA binding is known to phosphorylate EIF2α which leads to activation of the ATF4 transcription factor, inhibition of protein translation, and apoptosis (Claudio et al. (2013) EMBO J. 32:1214-1224).

Phosphorylation of the PKR kinase target EIF2α was maximal after IFN-β stimulation in A549 ADAR knockout cells (FIG. 64, panel I). Likewise, expression of canonical ATF4-regulated genes, such as PPP1R5A, ATF3, DDIT3, GADD45A, GADD45B, TRIB3, and ASNS was enriched across ADAR-knockout cells in the presence of endogenous or exogenous IFN-β (FIG. 64, panel J), providing further evidence for activation of PKR and, in turn, increased ATF4 transcription factor function upon ADAR1 loss.

Example 17: Primary Human Tumors Exhibit Interferon Activation

Figure 67:
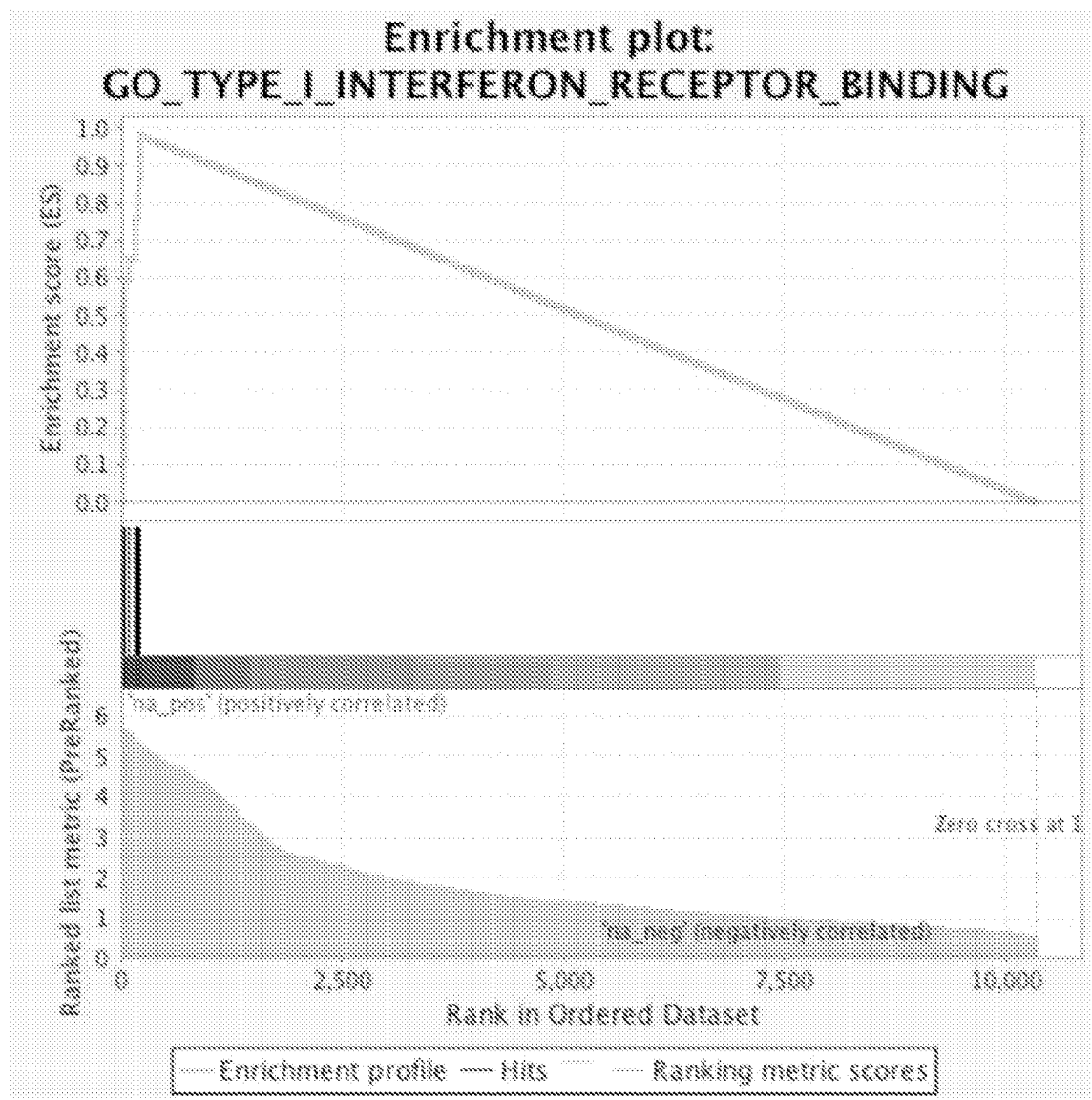
FIG. 67 shows Gene Set Enrichment Analysis results showing amplification of the interferon gene cluster on chromosome 9p is enriched in high interferon tumors. GSEA enrichment plots of genes ranked by significance of amplification between high and low interferon tumors with high tumor purity are shown. Gene-level amplification and deletion calls were generated using relative copy number data by GISTIC2.0.

Since interferon signaling is spontaneously activated in a subset of cancer cells and exposes potential therapeutic vulnerabilities, it was tested whether there is evidence for similar endogenous interferon activation in primary human tumors. An IFN-GES threshold was computed to predict ADAR dependency across the CCLE cell lines and was determined to be a z-score above 2.26 (FIG. 66, panel A). This threshold was applied to The Cancer Genome Atlas (TCGA) tumors, to identify primary cancers with similarly high interferon activation. Restricting the analysis to the 4,072 samples analyzed by TCGA with at least 70% tumor purity as estimated by the ABSOLUTE algorithm (Carter et al. (2012) Nat. Biotechnol. 30:413-421), 2.7% of TCGA tumors displayed IFN-GESs above this threshold (FIG. 66, panel B and. GSEA of amplified genes in these high purity, high interferon tumors revealed the top pathway as "Type I Interferon Receptor Binding", comprising 17 genes that all encode type I interferons and are clustered on chromosome 9p21.3 (FIG. 67).

Furthermore, analysis of TCGA copy number data showed that the interferon gene cluster including IFN-β (IFNβI), IFN-ε (IFNE), IFN-ω (IFNWI), and all 13 subtypes of IFN-α on chromosome 9p21.3, proximal to the CDKN2A/CDKN2B tumor suppressor locus, is one of the most frequently homozygously deleted regions in the cancer genome. The interferon genes comprise 16 of the 26 most frequently deleted coding genes across 9,853 TCGA cancer specimens for which ABSOLUTE copy number data are available (FIG. 66, panels C and D). Interferon signaling and activation, both in tumors with high IFN-GESs or deletions in chromosome 9p, therefore represent a biomarker to stratify patients who benefit from interferon modulating therapies.

In summary, specific cancer cell lines have been identified with elevated IFN-β signaling triggered by an activated cytosolic DNA sensing pathway, conferring dependence on the RNA editing enzyme, ADAR1. In cells with low, basal interferon signaling, the cGAS-STING pathway is inactive and PKR levels are reduced (FIG. 68, panel A). Upon cGAS-STING activation, interferon signaling and PKR protein levels are elevated but ADAR1 is still able to suppress PKR activation (FIG. 68, panel B). However, once ADAR1 is deleted, the abundant PKR becomes activated and leads to downstream signaling and cell death (FIG. 68, panel C). This is also shown in normal cells lines (e.g. A549 and NCI-H1437) once exogenous interferon is introduced (FIG. 68, panel D). ADAR1 deficiency in cell lines with high interferon levels, whether from endogenous or exogenous sources, led to phosphorylation and activation of PKR, ATF4-mediated gene expression, and apoptosis. Recent studies have shown that cGAS activation and innate interferon signaling, induced by cytosolic DNA released from the nucleus by DNA damage and genome instability (Mackenzie et al. (2017) Nature 548:461-465; Harding et al. (2017) Nature 548:466-470), led to elevated interferon-related gene expression signatures, which have been linked to resistance to DNA damage, chemotherapy, and radiation in cancer cells (Weichselbaum et al. (2008) Proc. Natl. Acad. Sci. USA 105:18490-18495). In high-interferon tumors, blocking ADAR1 might be effective to induce PKR-mediated apoptotic pathways while upregulating type I interferon signaling, which could contribute to anti-tumor immune responses (Parker et al. (2016) Nature 16:131-144). Alternatively, in tumors without activated interferon signaling, ADAR1 inhibition can be combined with localized interferon inducers, such as STING agonists, chemotherapy, or radiation. Generation of specific small molecule inhibitors targeting ADAR1 exploits this novel vulnerability in lung and other cancers and serves to enhance innate immunity in combination with immune checkpoint inhibitors.

Example 18: In Vivo Studies of ADAR1 and ISG1S Dependence

To study ADAR1 and ISG15 dependence in vivo xenograft mouse models are generated using the cell lines that have been studied in vitro. To ensure that tumors are established, inducible Cas9 and guide RNA expression vectors are used to infect the cell lines before implantation. Once the tumors for each cell line are formed, Cas9 expression is induced, which deletes each gene of interest. As ADAR1 knockout in these cell lines greatly reduces viability in vitro, similar effects to occur in the xenograft tumors are expected, with ADAR1 knockout reducing tumor progression in cell lines with interferon gene expression signatures after Cas9 induction. Alternatively, nanoparticles containing siRNAs targeting each gene can be used after these cell lines form tumors in the mice. These experiments further the understanding of the dependence on interferon-regulating genes in specific cell lines in vivo.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web at tigr.org and/or the National Center for Biotechnology Information (NCBI) on the World Wide Web at ncbi.nlm.nih.gov.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating a subject afflicted with a cancer having spontaneous interferon beta (IFNβ) secretion and constitutive expression of Protein Kinase regulated by RNA (PKR) comprising administering to the subject a therapeutically effective amount of a small molecule inhibitor of ADAR1 selected from the group consisting of selected pentostatin, erythro-9-(2-hydroxy-3-nonyl)adenine (EHNC), 1-deazaadenosine and naringin.

2. The method of claim 1, wherein the small molecule inhibitor of ADAR1 selectively decreases the catalytic activity and/or the substrate binding activity of ADAR.

3. The method of claim 1, wherein the small molecule inhibitor of ADAR1 increases inflammation within the tumor microenvironment.

4. The method of claim 1, wherein the small molecule inhibitor of ADAR1 increases the sensitivity of the cancer cells to an immunotherapy.

5. The method of claim 1, wherein the small molecule inhibitor of ADAR1 increases the sensitivity of the cancer cells to a modulator of intratumoral interferon.

6. The method of claim 1, wherein the small molecule inhibitor of ADAR1 increases the sensitivity of the cancer cells to IFNβ and/or IFNγ.

7. The method of claim 6, wherein the increased sensitivity of the cancer cells to IFN IFNβ and/or IFNγ is EIF2AK2-dependent.

8. The method of claim 1, wherein the small molecule inhibitor of ADAR1 increases secretion of IFNβ of the cancer cells.

9. The method of claim 1, wherein the small molecule inhibitor of ADAR1 promotes anti-viral dsRNA editing, sensing, and/or metabolism in the subject.

10. The method of claim 1, wherein the small molecule inhibitor reduces the number of proliferating cells in the cancer and/or reduces the volume or size of a tumor comprising the cancer cells.

11. The method of claim 1, further comprising administering to the subject an additional therapy, wherein the additional therapy is immunotherapy.

12. The method of claim 11, wherein the immunotherapy (i) comprises an anti-cancer vaccine and/or virus, (ii) is cell-based, and/or (iii) inhibits an immune checkpoint.

13. The method of claim 12, wherein the immune checkpoint is selected from the group consisting of CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRP, CD47, CD48, 2B4 (CD244), B7.1, B7.2, ILT-2, ILT-4, TIGIT, HHLA2, butyrophilins, IDO, CD39, CD73 and A2aR.

14. The method of claim 1, further comprising administering to the subject an additional therapy, wherein the additional therapy is a modulator of intratumoral interferon selected from the group consisting of radiation, a radiosensitizer, an immunogenic chemotherapy that induces interferon production by the cancer cells or at the site of a tumor, interferon, an interferon-inducing agent, a topical inflammatory agent, and a topical TLR agonist.

15. The method of claim 1, further comprising administering to the subject an additional therapy, wherein the additional therapy is interferon.

16. The method of claim 1, further comprising administering to the subject an additional therapy, wherein the additional therapy increases interferon levels in the microenvironment of the cancer cells.

17. The method of claim 1, wherein the subject is selected from the group consisting of an animal model of the cancer, a mouse model of the cancer, a mammal, and a human.

18. The method of any one of claims 1-10, wherein the cancer is selected from the group consisting of melanoma, colorectal cancer, Aicardi Goutieres Syndrome (AGS), gliomas, neuroblastoma, prostate cancer, breast cancer, pancreatic ductal carcinoma, epithelial ovarian cancer, B-CLL, leukemia, B cell lymphoma, and renal cell carcinoma.

\* \* \* \* \*

SEQUENCE LISTING

```
<160> NUMBER OF SEQ ID NOS: 111

<210> SEQ ID NO 1
<211> LENGTH: 6692
<212> TYPE: DNA
<213> ORGANISM: Homo sapiens

<400> SEQUENCE: 1
gcccctcctc ttggccaaac tttccggagg ggaaggcttt ccgaggaaac gaaagcgaaa      60
ttgaaccgga gccatcttgg gcccggcgcg cagacccgcg gagtttcccg tgccgacgcc     120
ccggggccac ttccagtgcg gagtagcgga ggcgtggggg cctcgagggg ctggcgcggc     180
ccagcggtcg ggccagggtc gtgccgccgg cgggtcgggc cgggcaatgc ctcgcgggcg     240
caatgaatcc gcggcagggg tattccctca gcggatacta cacccatcca tttcaaggct     300
atgagcacag acagctcagg taccagcagc ctgggccagg atcttccccc agtagtttcc     360
tgcttaagca aatagaattt ctcaaggggc agctcccaga agcaccggtg attggaaagc     420
agacaccgtc actgccacct tccctcccag gactccggcc aaggtttcca gtactacttg     480
cctccagtac cagaggcagg caagtggaca tcagggtgt ccccaggggc gtgcatctcg      540
gaagtcaggg gctccagaga gggttccagc atccttcacc acgtggcagg agtctgccac     600
agagaggtgt tgattgcctt tcctcacatt tccaggaact gagtatctac caagatcagg     660
aacaaaggat cttaaagttc ctggaagagc ttggggaagg gaaggccacc acagcacatg     720
atctgtctgg gaaacttggg actccgaaga aagaaatcaa tcgagtttta tactccctgg     780
caaagaaggg caagctacag aaagaggcag gaacaccccc tttgtggaaa atcgcggtct     840
ccactcaggc ttggaaccag cacagcggag tggtaagacc agacggtcat agccaaggag     900
ccccaaactc agacccgagt ttggaaccgg aagacagaaa ctccacatct gtctcagaag     960
atcttcttga gccttttatt gcagtctcag ctcaggcttg gaaccagcac agcggagtgg    1020
taagaccaga cagtcatagc caaggatccc caaactcaga cccaggtttg gaacctgaag    1080
acagcaactc cacatctgcc ttggaagatc ctcttgagtt tttagacatg gccgagatca    1140
aggagaaaat ctgcgactat ctcttcaatg tgtctgactc ctctgccctg aatttggcta    1200
aaaatattgg ccttaccaag gcccgagata taaatgctgt gctaattgac atggaaaggc    1260 aggggatgt ctatagacaa gggacaaccc ctcccatatg gcatttgaca gacaagaagc     1320
```

```
gagagaggat gcaaatcaag agaaatacga acagtgttcc tgaaaccgct ccagctgcaa      1380
tccctgagac caaagaaac gcagagttcc tcacctgtaa tatacccaca tcaaatgcct       1440
caaataacat ggtaaccaca gaaaaagtgg agaatgggca ggaacctgtc ataaagttag      1500
aaaacaggca agaggccaga ccagaaccag caagactgaa accacctgtt cattacaatg      1560 gccccctcaaa agcagggtat gttgactttg aaaatggcca gtgggccaca gatgacatcc    1620
cagatgactt gaatagtatc cgcgcagcac caggtgagtt tcgagccatc atggagatgc     1680
cctccttcta cagtcatggc ttgccacggt gttcacccta caagaaactg acagagtgcc    1740
agctgaagaa ccccatcagc gggctgttag aatatgccca gttcgctagt caaacctgtg     1800
agttcaacat gatagagcag agtggaccac cccatgaacc tcgatttaaa ttccaggttg     1860
tcatcaatgg ccgagagttt ccccagctg aagctggaag caagaaagtg gccaagcagg     1920
atgcagctat gaaagccatg acaattctgc tagaggaagc caaagccaag gacagtggaa     1980
aatcagaaga atcatcccac tattccacag agaaagaatc agagaagact gcagagtccc     2040
agacccccac cccttcagcc acatccttct tttctgggaa gagccccgtc accacactgc      2100
ttgagtgtat gcacaaattg gggaactcct gcgaattccg tctcctgtcc aaagaaggcc     2160
ctgcccatga acccaagttc caatactgtg ttgcagtggg agcccaaact ttccccagtg     2220
tgagtgctcc cagcaagaaa gtggcaaagc agatggccgc agaggaagcc atgaaggccc    2280
tgcatgggga ggcgaccaac tccatggctt ctgataacca gcctgaaggt atgatctcag     2340
agtcacttga taacttggaa tccatgatgc caacaaggt caggaagatt ggcgagctcg      2400
tgagatacct gaacaccaac cctgtgggtg gccttttgga gtacgcccgc tcccatggct     2460
ttgctgctga attcaagttg gtcgaccagt ccggacctcc tcacgagccc aagttcgttt     2520
accaagcaaa agttgggggt cgctggttcc cagccgtctg cgcacacagc aagaagcaag     2580
gcaagcagga agcagcagat gcggctctcc gtgtcttgat tggggagaac gagaaggcag    2640
aacgcatggg tttcacagag gtaaccccag tgacaggggc cagtctcaga agaactatgc     2700
tcctcctctc aaggtcccca gaagcacagc caaagacact ccctctcact ggcagcacct     2760
tccatgacca gatagccatg ctgagccacc ggtgcttcaa cactctgact aacagcttcc     2820
agccctcctt gctcggccgc aagattctgg ccgccatcat tatgaaaaaa gactctgagg     2880
acatgggtgt cgtcgtcagc ttgggaacag ggaatcgctg tgtgaaagga gattctctca     2940
gcctaaaagg agaaactgtc aatgactgcc atgcagaaat aatctcccgg agaggcttca     3000 tcaggttct ctacagtgag ttaatgaaat acaactccca gactgcgaag gatagtatat       3060
ttgaacctgc taagggagga gaaaagctcc aaataaaaaa gactgtgtca ttccatctgt      3120
atatcagcac tgctccgtgt ggagatggcg ccctctttga caagtcctgc agcgaccgtg     3180
ctatggaaag cacagaatcc cgccactacc ctgtcttcga gaatcccaaa caaggaaagc     3240
tccgcaccaa ggtggagaac ggagaaggca caatccctgt ggaatccagt gacattgtgc     3300
ctacgtggga tggcattcgg ctcggggaga gactccgtac catgtcctgt agtgacaaaa     3360
tcctacgctg gaacgtgctg ggcctgcaag gggcactgtt gacccacttc ctgcagccca    3420
tttatctcaa atctgtcaca ttgggttacc ttttcagcca agggcatctg acccgtgcta     3480
tttgctgtcg tgtgacaaga gatgggagtg catttgagga tggactacga catcccttta     3540
ttgtcaacca ccccaaggtt ggcagagtca gcatatatga ttccaaaagg caatccggga     3600
agactaagga gacaagcgtc aactggtgtc tggctgatgg ctatgacctg agatcctgg     3660 acggtaccag aggcactgtg gatgggccac ggaatgaatt gtcccgggtc tccaaaaaga    3720
```

```
acatttttct tctatttaag aagctctgct ccttccgtta ccgcagggat ctactgagac   3780
tctcctatgg tgaggccaag aaagctgccc gtgactacga gacggccaag aactacttca   3840
aaaaaggcct gaaggatatg ggctatggga actggattag caaacccag gaggaaaaga    3900 acttttatct ctgcccagta tagtatgctc cagtgacaga tggattaggg tgtgtcatac   3960
tagggtgtga gagaggtagg tcgtagcatt cctcatcaca tggtcagggg attttttttt   4020 ctccttttt tttcttttta agccataatt ggtgatactg aaaactttgg gttcccattt    4080
atcctgcttt ctttgggatt gctaggcaag gtctggccag gcccccttt tttcccccaa    4140 gtgaagaggc agaaacctaa gaagttatct tttctttcta cccaaagcat acatagtcac   4200
tgagcacctg cggtccattt cctcttaaaa gttttgtttt gatttgtttc catttccttt   4260 cccttttgtgt ttgctacact gacctcttgc ggtcttgatt aggtttcagt caactctgga   4320
tcatgtcagg gactgataat ttcatttgtg gattacgcag accctctac ttcccctctt    4380 tcccttctga gattctttcc ttgtgatctg aatgtctcct tttcccctc agagggcaaa    4440 gaggtgaaca taaaggattt ggtgaaacat ttgtaagggt aggagttgaa aactgcagtt   4500
cccagtgcca cggaagtgtg attggagcct gcagataatg cccagccatc ctcccatcct   4560
gcactttagc cagctgcagg gcgggcaagg caaggaaagc tgcttccctg gaagtgtatc   4620
actttctccg gcagctggga agtctagaac cagccagact gggttaaggg agctgctcaa   4680
gcaatagcag aggtttcacc cggcaggatg acacagacca cttcccaggg agcacgggca   4740
tgccttggaa tattgccaag cttccagctg cctcttctcc taaagcattc ctaggaatat   4800
tttccccgcc aatgctgggc gtacacccta gccaacggga caaatcctag agggtataaa   4860
atcatctctg ctcagataat catgacttag caagaataag ggcaaaaaat cctgttggct   4920
taacgtcact gttccacccg gtgtaatatc tctcatgaca gtgacaccaa gggaagttga   4980
ctaagtcaca tgtaaattag gagtgttta aagaatgcca tagatgttga ttcttaactg    5040
ctacagataa cctgtaattg agcagattta aaattcaggc atacttttcc attatccaa    5100 gtgctttcat ttttccagat ggcttcagaa gtaggctcgt gggcagggcg cagacctgat   5160
ctttataggg ttgacataga aagcagtagt tgtgggtgaa agggcaggtt gtcttcaaac   5220
tctgtgaggt agaatccttt gtctataccct ccatgaacat tgactcgtgt gttcagagcc   5280
tttggcctct ctgtggagtc tggctctctg gctcctgtgc attctttgaa tagtcactcg   5340
taaaaactgt cagtgcttga aactgttttcc tttactcatg ttgaagggac tttgttggct   5400
tttagagtgt tggtcatgac tccaagagca gagcagggaa gagcccaagc atagacttgg   5460
tgccgtggtg atggctgcag tccagttttg tgatgctgct tttacgtgtc cctcgataac   5520
agtcagctag acacactcag gaggactact gaggctctgc gaccttcagg agctgagcct   5580
gcctctctcc tttagatgac agaccttcat ctgggaacgt gctgagccag cacctcaga    5640 tgatttccct ccaaactgct gactaggtca tcctctgtct ggtagagaca ttcacatctt   5700
tgcttttatt ctatgctctc tgtacttttg accaaaaatt gaccaaagta agaaaatgca   5760
agttctaaaa atagactaag gatgcctttg cagaacacca aagcatccca aggaactggt   5820
agggaagtgg cgcctgtctc ctggagtgga agaggcctgc tccctggctc tgggtctgct   5880 ggggcacag taaatcagtc ttggcaccca catccagggc agagaggtct gtggttctca   5940
gcatcagaag gcagcgcagc ccctctcctc ttcaggctac aggggtgtca cctgctgagt   6000
cctcaggttg tttggcctct ctggtccatc ttgggcatta ggttctccag cagagctctg   6060
```

-continued

```
gccagctgcc tcttctttaa ctgggaacac aggctctcac aagatcagaa ccccccactca    6120 cccccaagat cttatctagc aagcctgtag tattcagttt ctgttgtagg aagagagcga    6180
ggcatccctg aattccacgc atctgctgga aacgagccgt gtcagatcgc acatccctgc    6240
gcccccatgc ccctctgagt cacacaggac agaggaggca gagcttctgc ccactgttat    6300
cttcactttc tttgtccagt cttttgtttt taataagcag tgaccctccc tactcttctt    6360
tttaatgatt tttgtagttg atttgtctga actgtggcta ctgtgcattc cttgaataat    6420
cacttgtaaa aattgtcagt gcttgaagct gtttccttta ctcacattga agggacttcg    6480
ttggtttttt ggagtcttgg ttgtgactcc aagagcagag tgaggaagac ccccaagcat    6540
agactcgggt actgtgatga tggctgcagt ccagttttat gattctgctt ttatgtgtcc    6600
cttgataaca gtgacttaac aatatacatt cctcataaat aaaaaaaaaa caagaatctg    6660
aattcttaga aaaaaaaaaa aaaaaaaaaa aa                                   6692
```

<210> SEQ ID NO 2
<211> LENGTH: 1226
<212> TYPE: PRT
<213> ORGANISM: Homo sapiens

<400> SEQUENCE: 2

```
Met Asn Pro Arg Gln Gly Tyr Ser Leu Ser Gly Tyr Tyr Thr His Pro
1               5                   10                  15

Phe Gln Gly Tyr Glu His Arg Gln Leu Arg Tyr Gln Gln Pro Gly Pro
                20                  25                  30

Gly Ser Ser Pro Ser Ser Phe Leu Leu Lys Gln Ile Glu Phe Leu Lys
            35                  40                  45

Gly Gln Leu Pro Glu Ala Pro Val Ile Gly Lys Gln Thr Pro Ser Leu
        50                  55                  60

Pro Pro Ser Leu Pro Gly Leu Arg Pro Arg Phe Pro Val Leu Leu Ala
65                  70                  75                  80

Ser Ser Thr Arg Gly Arg Gln Val Asp Ile Arg Gly Val Pro Arg Gly
                85                  90                  95

Val His Leu Gly Ser Gln Gly Leu Gln Arg Gly Phe Gln His Pro Ser
            100                 105                 110

Pro Arg Gly Arg Ser Leu Pro Gln Arg Gly Val Asp Cys Leu Ser Ser
        115                 120                 125

His Phe Gln Glu Leu Ser Ile Tyr Gln Asp Gln Gln Arg Ile Leu
        130                 135                 140

Lys Phe Leu Glu Glu Leu Gly Glu Gly Lys Ala Thr Thr Ala His Asp
145                 150                 155                 160

Leu Ser Gly Lys Leu Gly Thr Pro Lys Lys Glu Ile Asn Arg Val Leu
                165                 170                 175

Tyr Ser Leu Ala Lys Lys Gly Lys Leu Gln Lys Glu Ala Gly Thr Pro
            180                 185                 190

Pro Leu Trp Lys Ile Ala Val Ser Thr Gln Ala Trp Asn Gln His Ser
        195                 200                 205

Gly Val Val Arg Pro Asp Gly His Ser Gln Gly Ala Pro Asn Ser Asp
    210                 215                 220

Pro Ser Leu Glu Pro Glu Asp Arg Asn Ser Thr Ser Val Ser Glu Asp
225                 230                 235                 240

Leu Leu Glu Pro Phe Ile Ala Val Ser Ala Gln Ala Trp Asn Gln His
                245                 250                 255

Ser Gly Val Val Arg Pro Asp Ser His Ser Gln Gly Ser Pro Asn Ser
```

```
                260             265              270
Asp Pro Gly Leu Glu Pro Glu Asp Ser Asn Ser Thr Ser Ala Leu Glu
            275                 280             285
Asp Pro Leu Glu Phe Leu Asp Met Ala Glu Ile Lys Glu Lys Ile Cys
            290                 295             300
Asp Tyr Leu Phe Asn Val Ser Asp Ser Ser Ala Leu Asn Leu Ala Lys
305                 310                 315                 320
Asn Ile Gly Leu Thr Lys Ala Arg Asp Ile Asn Ala Val Leu Ile Asp
                325                 330                 335
Met Glu Arg Gln Gly Asp Val Tyr Arg Gln Gly Thr Thr Pro Pro Ile
            340                 345             350
Trp His Leu Thr Asp Lys Lys Arg Glu Arg Met Gln Ile Lys Arg Asn
            355                 360             365
Thr Asn Ser Val Pro Glu Thr Ala Pro Ala Ile Pro Glu Thr Lys
            370                 375             380
Arg Asn Ala Glu Phe Leu Thr Cys Asn Ile Pro Thr Ser Asn Ala Ser
385                 390                 395                 400
Asn Asn Met Val Thr Thr Glu Lys Val Glu Asn Gly Gln Glu Pro Val
                405                 410                 415
Ile Lys Leu Glu Asn Arg Gln Glu Ala Arg Pro Glu Pro Ala Arg Leu
            420                 425             430
Lys Pro Pro Val His Tyr Asn Gly Pro Ser Lys Ala Gly Tyr Val Asp
            435                 440             445
Phe Glu Asn Gly Gln Trp Ala Thr Asp Asp Ile Pro Asp Asp Leu Asn
            450                 455             460
Ser Ile Arg Ala Ala Pro Gly Glu Phe Arg Ala Ile Met Glu Met Pro
465                 470                 475                 480
Ser Phe Tyr Ser His Gly Leu Pro Arg Cys Ser Pro Tyr Lys Lys Leu
                485                 490                 495
Thr Glu Cys Gln Leu Lys Asn Pro Ile Ser Gly Leu Leu Glu Tyr Ala
            500                 505             510
Gln Phe Ala Ser Gln Thr Cys Glu Phe Asn Met Ile Glu Gln Ser Gly
            515                 520             525
Pro Pro His Glu Pro Arg Phe Lys Phe Gln Val Val Ile Asn Gly Arg
            530                 535             540
Glu Phe Pro Pro Ala Glu Ala Gly Ser Lys Lys Val Ala Lys Gln Asp
545                 550                 555                 560
Ala Ala Met Lys Ala Met Thr Ile Leu Leu Glu Glu Ala Lys Ala Lys
                565                 570                 575
Asp Ser Gly Lys Ser Glu Glu Ser Ser His Tyr Ser Thr Glu Lys Glu
            580                 585             590
Ser Glu Lys Thr Ala Glu Ser Gln Thr Pro Thr Pro Ser Ala Thr Ser
            595                 600             605
Phe Phe Ser Gly Lys Ser Pro Val Thr Thr Leu Leu Glu Cys Met His
            610                 615             620
Lys Leu Gly Asn Ser Cys Glu Phe Arg Leu Leu Ser Lys Glu Gly Pro
625                 630                 635                 640
Ala His Glu Pro Lys Phe Gln Tyr Cys Val Ala Val Gly Ala Gln Thr
                645                 650                 655
Phe Pro Ser Val Ser Ala Pro Ser Lys Lys Val Ala Lys Gln Met Ala
            660                 665             670
Ala Glu Glu Ala Met Lys Ala Leu His Gly Glu Ala Thr Asn Ser Met
            675                 680             685
```

```
Ala Ser Asp Asn Gln Pro Glu Gly Met Ile Ser Glu Ser Leu Asp Asn
690                 695                 700

Leu Glu Ser Met Met Pro Asn Lys Val Arg Lys Ile Gly Glu Leu Val
705                 710                 715                 720

Arg Tyr Leu Asn Thr Asn Pro Val Gly Gly Leu Leu Glu Tyr Ala Arg
            725                 730                 735

Ser His Gly Phe Ala Ala Glu Phe Lys Leu Val Asp Gln Ser Gly Pro
        740                 745                 750

Pro His Glu Pro Lys Phe Val Tyr Gln Ala Lys Val Gly Gly Arg Trp
    755                 760                 765

Phe Pro Ala Val Cys Ala His Ser Lys Lys Gln Gly Lys Gln Glu Ala
770                 775                 780

Ala Asp Ala Ala Leu Arg Val Leu Ile Gly Glu Asn Glu Lys Ala Glu
785                 790                 795                 800

Arg Met Gly Phe Thr Glu Val Thr Pro Val Thr Gly Ala Ser Leu Arg
            805                 810                 815

Arg Thr Met Leu Leu Leu Ser Arg Ser Pro Glu Ala Gln Pro Lys Thr
                820                 825                 830

Leu Pro Leu Thr Gly Ser Thr Phe His Asp Gln Ile Ala Met Leu Ser
            835                 840                 845

His Arg Cys Phe Asn Thr Leu Thr Asn Ser Phe Gln Pro Ser Leu Leu
850                 855                 860

Gly Arg Lys Ile Leu Ala Ala Ile Ile Met Lys Lys Asp Ser Glu Asp
865                 870                 875                 880

Met Gly Val Val Val Ser Leu Gly Thr Gly Asn Arg Cys Val Lys Gly
                885                 890                 895

Asp Ser Leu Ser Leu Lys Gly Glu Thr Val Asn Asp Cys His Ala Glu
            900                 905                 910

Ile Ile Ser Arg Arg Gly Phe Ile Arg Phe Leu Tyr Ser Glu Leu Met
            915                 920                 925

Lys Tyr Asn Ser Gln Thr Ala Lys Asp Ser Ile Phe Glu Pro Ala Lys
            930                 935                 940

Gly Gly Glu Lys Leu Gln Ile Lys Lys Thr Val Ser Phe His Leu Tyr
945                 950                 955                 960

Ile Ser Thr Ala Pro Cys Gly Asp Gly Ala Leu Phe Asp Lys Ser Cys
            965                 970                 975

Ser Asp Arg Ala Met Glu Ser Thr Glu Ser Arg His Tyr Pro Val Phe
            980                 985                 990

Glu Asn Pro Lys Gln Gly Lys Leu Arg Thr Lys Val Glu Asn Gly Glu
        995                 1000                1005

Gly Thr Ile Pro Val Glu Ser Ser Asp Ile Val Pro Thr Trp Asp
    1010                1015                1020

Gly Ile Arg Leu Gly Glu Arg Leu Arg Thr Met Ser Cys Ser Asp
    1025                1030                1035

Lys Ile Leu Arg Trp Asn Val Leu Gly Leu Gln Gly Ala Leu Leu
    1040                1045                1050

Thr His Phe Leu Gln Pro Ile Tyr Leu Lys Ser Val Thr Leu Gly
    1055                1060                1065

Tyr Leu Phe Ser Gln Gly His Leu Thr Arg Ala Ile Cys Cys Arg
    1070                1075                1080

Val Thr Arg Asp Gly Ser Ala Phe Glu Asp Gly Leu Arg His Pro
    1085                1090                1095
```

```
Phe Ile Val Asn His Pro Lys Val Gly Arg Val Ser Ile Tyr Asp
    1100                1105                1110

Ser Lys Arg Gln Ser Gly Lys Thr Lys Glu Thr Ser Val Asn Trp
    1115                1120                1125

Cys Leu Ala Asp Gly Tyr Asp Leu Glu Ile Leu Asp Gly Thr Arg
    1130                1135                1140

Gly Thr Val Asp Gly Pro Arg Asn Glu Leu Ser Arg Val Ser Lys
    1145                1150                1155

Lys Asn Ile Phe Leu Leu Phe Lys Lys Leu Cys Ser Phe Arg Tyr
    1160                1165                1170

Arg Arg Asp Leu Leu Arg Leu Ser Tyr Gly Glu Ala Lys Lys Ala
    1175                1180                1185

Ala Arg Asp Tyr Glu Thr Ala Lys Asn Tyr Phe Lys Lys Gly Leu
    1190                1195                1200

Lys Asp Met Gly Tyr Gly Asn Trp Ile Ser Lys Pro Gln Glu Glu
    1205                1210                1215

Lys Asn Phe Tyr Leu Cys Pro Val
    1220                1225

<210> SEQ ID NO 3
<211> LENGTH: 6614
<212> TYPE: DNA
<213> ORGANISM: Homo sapiens

<400> SEQUENCE: 3
gcccctcctc ttggccaaac tttccggagg ggaaggcttt ccgaggaaac gaaagcgaaa      60
ttgaaccgga gccatcttgg gcccggcgcg cagacccgcg gagtttcccg tgccgacgcc     120
ccggggccac ttccagtgcg gagtagcgga ggcgtggggg cctcgagggg ctggcgcggc     180
ccagcggtcg ggccagggtc gtgccgccgg cgggtcgggc cgggcaatgc ctcgcgggcg     240
caatgaatcc gcggcagggg tattccctca gcggatacta cacccatcca tttcaaggct     300
atgagcacag acagctcagg taccagcagc ctgggccagg atcttccccc agtagtttcc     360
tgcttaagca aatagaattt ctcaaggggc agctcccaga agcaccggtg attggaaagc     420
agacaccgtc actgccacct tccctcccag gactccggcc aaggtttcca gtactacttg     480
cctccagtac cagaggcagg caagtggaca tcagggtgt ccccaggggc gtgcatctcg     540
gaagtcaggg gctccagaga gggttccagc atccttcacc acgtggcagg agtctgccac     600
agagaggtgt tgattgcctt tcctcacatt tccaggaact gagtatctac caagatcagg     660
aacaaaggat cttaaagttc ctggaagagc ttggggaagg gaaggccacc acagcacatg     720
atctgtctgg gaaacttggg actccgaaga agaaatcaa tcgagtttta tactccctgg     780
caaagaaggg caagctacag aaagaggcag gaacaccccc tttgtggaaa atcgcggtct     840
ccactcaggc ttggaaccag cacagcggag tggtaagacc agacggtcat agccaaggag     900
ccccaaactc agacccgagt ttggaaccgg aagacagaaa ctccacatct gtctcagaag     960
atcttcttga gccttttatt gcagtctcag ctcaggcttg gaaccagcac agcggagtgg    1020
taagaccaga cagtcatagc caaggatccc caaactcaga cccaggtttg gaacctgaag    1080
acagcaactc cacatctgcc ttggaagatc ctcttgagtt tttagacatg gccgagatca    1140
aggagaaaat ctgcgactat ctcttcaatg tgtctgactc ctctgccctg aatttggcta    1200
aaaatattgg ccttaccaag gcccgagata taaatgctgt gctaattgac atggaaaggc    1260
agggggatgt ctatagacaa gggacaaccc ctcccatatg gcatttgaca gacaagaagc    1320
```

-continued

```
gagagaggat gcaaatcaag agaaatacga acagtgttcc tgaaaccgct ccagctgcaa    1380
tccctgagac caaagaaac gcagagttcc tcacctgtaa tatacccaca tcaaatgcct     1440
caaataacat ggtaaccaca gaaaaagtgg agaatgggca ggaacctgtc ataaagttag    1500
aaaacaggca agaggccaga ccagaaccag caagactgaa accacctgtt cattacaatg    1560
gccccccaa agcagggtat gttgactttg aaaatggcca gtgggccaca gatgacatcc     1620
cagatgactt gaatagtatc cgcgcagcac caggtgagtt tcgagccatc atggagatgc    1680
cctccttcta cagtcatggc ttgccacggt gttcacccta caagaaactg acagagtgcc    1740
agctgaagaa ccccatcagc gggctgttag aatatgccca gttcgctagt caaacctgtg    1800
agttcaacat gatagagcag agtggaccac cccatgaacc tcgatttaaa ttccaggttg    1860
tcatcaatgg ccgagagttt cccccagctg aagctgaaag caagaaagtg gccaagcagg    1920
atgcagctat gaaagccatg acaattctgc tagaggaagc caaagccaag gacagtggaa    1980
aatcagaaga atcatcccac tattccacag agaaagaatc agagaagact gcagagtccc    2040
agaccccac cccttcagcc acatccttct tttctgggaa gagcccgtc accacactgc       2100
ttgagtgtat gcacaaattg gggaactcct gcgaattccg tctcctgtcc aaagaaggcc    2160
ctgcccatga acccaagttc caatactgtg ttgcagtggg agcccaaact ttccccagtg    2220
tgagtgctcc cagcaagaaa gtggcaaagc agatggccgc agaggaagcc atgaaggccc    2280
tgcatgggga ggcgaccaac tccatggctt ctgataacca gctgaaggt atgatctcag     2340
agtcacttga taacttggaa tccatgatgc ccaacaaggt caggaagatt ggcgagctcg    2400
tgagatacct gaacaccaac cctgtgggtg gccttttgga gtacgcccgc tcccatggct    2460
ttgctgctga attcaagttg gtcgaccagt ccggacctcc tcacgagccc aagttcgttt    2520
accaagcaaa agttgggggt cgctggttcc cagccgtctg cgcacacagc aagaagcaag    2580
gcaagcagga agcagcagat gcggctctcc gtgtcttgat tggggagaac gagaaggcag    2640
aacgcatggg tttcacagag ctcccctctca ctggcagcac cttccatgac cagatagcca    2700
tgctgagcca ccggtgcttc aacactctga ctaacagctt ccagccctcc ttgctcggcc    2760
gcaagattct ggccgccatc attatgaaaa aagactctga ggacatgggt gtcgtcgtca    2820
gcttgggaac agggaatcgc tgtgtgaaag agattctct cagcctaaaa ggagaaactg     2880
tcaatgactg ccatgcagaa ataatctccc ggagaggctt catcaggttt ctctacagtg    2940
agttaatgaa atacaactcc cagactgcga aggatagtat atttgaacct gctaagggag    3000
gagaaaagct ccaaataaaa aagactgtgt cattccatct gtatatcagc actgctccgt    3060
gtggagatgg cgccctcttt gacaagtcct gcagcgaccg tgctatggaa agcacagaat    3120
cccgccacta ccctgtcttc gagaatccca acaaggaaa gctccgcacc aaggtggaga    3180
acggagaagg cacaatccct gtggaatcca gtgacattgt gcctacgtgg gatggcattc    3240
ggctcgggga gagactccgt accatgtcct gtagtgacaa atcctacgc tggaacgtgc     3300
tgggcctgca aggggcactg ttgacccact tcctgcagcc catttatctc aaatctgtca    3360
cattgggtta cctttttcagc caagggcatc tgacccgtgc tatttgctgt cgtgtgacaa    3420
gagatgggag tgcatttgag gatggactac gacatcccct tattgtcaac caccccaagg    3480
ttggcagagt cagcatatat gattccaaaa ggcaatccgg gaagactaag gagacaagcg    3540
tcaactggtg tctggctgat ggctatgacc tggagatcct ggacggtacc agaggcactg    3600
tggatgggcc acggaatgaa ttgtcccggg tctccaaaaa gaacattttt cttctatttta    3660
agaagctctg ctccttccgt taccgcaggg atctactgag actctcctat ggtgaggcca    3720
```

| | |
|---|---|
| agaaagctgc cgtgactac gagacggcca agaactactt caaaaaaggc ctgaaggata | 3780 |
| tgggctatgg gaactggatt agcaaacccc aggaggaaaa gaacttttat ctctgcccag | 3840 |
| tatagtatgc tccagtgaca gatggattag ggtgtgtcat actagggtgt gagagaggta | 3900 |
| ggtcgtagca ttcctcatca catggtcagg ggatttttt ttctccttt tttttctttt | 3960 |
| taagccataa ttggtgatac tgaaaacttt gggttcccat ttatcctgct ttctttggga | 4020 |
| ttgctaggca aggtctggcc aggccccct ttttccccc aagtgaagag cagaaacct | 4080 |
| aagaagttat cttttctttc tacccaaagc atacatagtc actgagcacc tgcggtccat | 4140 |
| ttcctcttaa aagttttgtt ttgatttgtt tccatttcct ttcccttttgt gtttgctaca | 4200 |
| ctgacctctt gcggtcttga ttaggtttca gtcaactctg gatcatgtca gggactgata | 4260 |
| atttcatttg tggattacgc agaccctct acttccctc tttcccttct gagattcttt | 4320 |
| ccttgtgatc tgaatgtctc cttttccccc tcagagggca aagaggtgaa cataaaggat | 4380 |
| ttggtgaaac atttgtaagg gtaggagttg aaaactgcag ttcccagtgc cacggaagtg | 4440 |
| tgattggagc ctgcagataa tgcccagcca tcctcccatc ctgcacttta gccagctgca | 4500 |
| gggcgggcaa ggcaaggaaa gctgcttccc tggaagtgta tcactttctc cggcagctgg | 4560 |
| gaagtctaga accagccaga ctgggttaag ggagctgctc aagcaatagc agaggtttca | 4620 |
| cccggcagga tgacacagac cacttcccag ggagcacggg catgccttgg aatattgcca | 4680 |
| agcttccagc tgcctcttct cctaaagcat tcctaggaat attttccccg ccaatgctgg | 4740 |
| gcgtacaccc tagccaacgg gacaaatcct agagggtata aaatcatctc tgctcagata | 4800 |
| atcatgactt agcaagaata agggcaaaaa atcctgttgg cttaacgtca ctgttccacc | 4860 |
| cggtgtaata tctctcatga cagtgacacc aagggaagtt gactaagtca catgtaaatt | 4920 |
| aggagtgttt taagaatgc catagatgtt gattcttaac tgctacagat aacctgtaat | 4980 |
| tgagcagatt taaaattcag gcatactttt ccatttatcc aagtgctttc atttttccag | 5040 |
| atggcttcag aagtaggctc gtgggcaggg cgcagacctg atctttatag ggttgacata | 5100 |
| gaaagcagta gttgtgggtg aaagggcagg ttgtcttcaa actctgtgag gtagaatcct | 5160 |
| ttgtctatac ctccatgaac attgactcgt gtgttcagag cctttggcct ctctgtggag | 5220 |
| tctggctctc tggctcctgt gcattctttg aatagtcact cgtaaaaact gtcagtgctt | 5280 |
| gaaactgttt cctttactca tgttgaaggg actttgttgg cttttagagt gttggtcatg | 5340 |
| actccaagag cagagcaggg aagagcccaa gcatagactt ggtgccgtgg tgatggctgc | 5400 |
| agtccagttt tgtgatgctg cttttacgtg tccctcgata acagtcagct agacacactc | 5460 |
| aggaggacta ctgaggctct gcgaccttca ggagctgagc ctgcctctct cctttagatg | 5520 |
| acagaccttc atctgggaac gtgctgagcc agcaccctca gatgatttcc ctccaaactg | 5580 |
| ctgactaggt catcctctgt ctggtagaga cattcacatc tttgctttta ttctatgctc | 5640 |
| tctgtacttt tgaccaaaaa ttgaccaaag taagaaaatg caagttctaa aaatagacta | 5700 |
| aggatgcctt tgcagaacac caaagcatcc caaggaactg gtagggaagt ggcgcctgtc | 5760 |
| tcctggagtg gaagaggcct gctccctggc tctgggtctg ctgggggcac agtaaatcag | 5820 |
| tcttggcacc cacatccagg gcagagaggt ctgtggttct cagcatcaga aggcagcgca | 5880 |
| gccctctcc tcttcaggct acagggttgt cacctgctga gtcctcaggt tgtttggcct | 5940 |
| ctctggtcca tcttgggcat taggttctcc agcagagctc tggccagctg cctcttcttt | 6000 |
| aactgggaac acaggctctc acaagatcag aaccccccact caccccccaag atcttatcta | 6060 |

```
gcaagcctgt agtattcagt ttctgttgta ggaagagagc gaggcatccc tgaattccac    6120
gcatctgctg gaaacgagcc gtgtcagatc gcacatccct gcgccccat gccctctga     6180 gtcacacagg acagaggagg cagagcttct gcccactgtt atcttcactt tctttgtcca    6240 gtctttgtt tttaataagc agtgaccctc cctactcttc tttttaatga tttttgtagt    6300
tgatttgtct gaactgtggc tactgtgcat tccttgaata atcacttgta aaaattgtca    6360
gtgcttgaag ctgtttcctt tactcacatt gaagggactt cgttggtttt ttggagtctt    6420
ggttgtgact ccaagagcag agtgaggaag accccaagc atagactcgg gtactgtgat     6480
gatggctgca gtccagtttt atgattctgc ttttatgtgt cccttgataa cagtgactta    6540
acaatataca ttcctcataa ataaaaaaa aacaagaatc tgaattctta gaaaaaaaaa     6600
aaaaaaaaaa aaaa                                                     6614
```

<210> SEQ ID NO 4
<211> LENGTH: 1200
<212> TYPE: PRT
<213> ORGANISM: Homo sapiens

<400> SEQUENCE: 4

```
Met Asn Pro Arg Gln Gly Tyr Ser Leu Ser Gly Tyr Tyr Thr His Pro
1               5                   10                  15

Phe Gln Gly Tyr Glu His Arg Gln Leu Arg Tyr Gln Gln Pro Gly Pro
            20                  25                  30

Gly Ser Ser Pro Ser Ser Phe Leu Leu Lys Gln Ile Glu Phe Leu Lys
        35                  40                  45

Gly Gln Leu Pro Glu Ala Pro Val Ile Gly Lys Gln Thr Pro Ser Leu
    50                  55                  60

Pro Pro Ser Leu Pro Gly Leu Arg Pro Arg Phe Pro Val Leu Leu Ala
65                  70                  75                  80

Ser Ser Thr Arg Gly Arg Gln Val Asp Ile Arg Gly Val Pro Arg Gly
                85                  90                  95

Val His Leu Gly Ser Gln Gly Leu Gln Arg Gly Phe Gln His Pro Ser
            100                 105                 110

Pro Arg Gly Arg Ser Leu Pro Gln Arg Gly Val Asp Cys Leu Ser Ser
        115                 120                 125

His Phe Gln Glu Leu Ser Ile Tyr Gln Asp Gln Glu Gln Arg Ile Leu
    130                 135                 140

Lys Phe Leu Glu Glu Leu Gly Glu Gly Lys Ala Thr Thr Ala His Asp
145                 150                 155                 160

Leu Ser Gly Lys Leu Gly Thr Pro Lys Lys Glu Ile Asn Arg Val Leu
                165                 170                 175

Tyr Ser Leu Ala Lys Lys Gly Lys Leu Gln Lys Glu Ala Gly Thr Pro
            180                 185                 190

Pro Leu Trp Lys Ile Ala Val Ser Thr Gln Ala Trp Asn Gln His Ser
        195                 200                 205

Gly Val Val Arg Pro Asp Gly His Ser Gln Gly Ala Pro Asn Ser Asp
    210                 215                 220

Pro Ser Leu Glu Pro Glu Asp Arg Asn Ser Thr Ser Val Ser Glu Asp
225                 230                 235                 240

Leu Leu Glu Pro Phe Ile Ala Val Ser Ala Gln Ala Trp Asn Gln His
                245                 250                 255

Ser Gly Val Val Arg Pro Asp Ser His Ser Gln Gly Ser Pro Asn Ser
            260                 265                 270
```

```
Asp Pro Gly Leu Glu Pro Glu Asp Ser Asn Ser Thr Ser Ala Leu Glu
        275                 280                 285

Asp Pro Leu Glu Phe Leu Asp Met Ala Glu Ile Lys Glu Lys Ile Cys
290                 295                 300

Asp Tyr Leu Phe Asn Val Ser Asp Ser Ser Ala Leu Asn Leu Ala Lys
305                 310                 315                 320

Asn Ile Gly Leu Thr Lys Ala Arg Asp Ile Asn Ala Val Leu Ile Asp
                325                 330                 335

Met Glu Arg Gln Gly Asp Val Tyr Arg Gln Gly Thr Thr Pro Pro Ile
            340                 345                 350

Trp His Leu Thr Asp Lys Lys Arg Glu Arg Met Gln Ile Lys Arg Asn
        355                 360                 365

Thr Asn Ser Val Pro Glu Thr Ala Pro Ala Ala Ile Pro Glu Thr Lys
    370                 375                 380

Arg Asn Ala Glu Phe Leu Thr Cys Asn Ile Pro Thr Ser Asn Ala Ser
385                 390                 395                 400

Asn Asn Met Val Thr Thr Glu Lys Val Glu Asn Gly Gln Glu Pro Val
                405                 410                 415

Ile Lys Leu Glu Asn Arg Gln Glu Ala Arg Pro Glu Pro Ala Arg Leu
            420                 425                 430

Lys Pro Pro Val His Tyr Asn Gly Pro Ser Lys Ala Gly Tyr Val Asp
        435                 440                 445

Phe Glu Asn Gly Gln Trp Ala Thr Asp Asp Ile Pro Asp Asp Leu Asn
    450                 455                 460

Ser Ile Arg Ala Ala Pro Gly Glu Phe Arg Ala Ile Met Glu Met Pro
465                 470                 475                 480

Ser Phe Tyr Ser His Gly Leu Pro Arg Cys Ser Pro Tyr Lys Lys Leu
                485                 490                 495

Thr Glu Cys Gln Leu Lys Asn Pro Ile Ser Gly Leu Leu Glu Tyr Ala
            500                 505                 510

Gln Phe Ala Ser Gln Thr Cys Glu Phe Asn Met Ile Glu Gln Ser Gly
        515                 520                 525

Pro Pro His Glu Pro Arg Phe Lys Phe Gln Val Val Ile Asn Gly Arg
    530                 535                 540

Glu Phe Pro Pro Ala Glu Ala Gly Ser Lys Lys Val Ala Lys Gln Asp
545                 550                 555                 560

Ala Ala Met Lys Ala Met Thr Ile Leu Leu Glu Glu Ala Lys Ala Lys
                565                 570                 575

Asp Ser Gly Lys Ser Glu Glu Ser Ser His Tyr Ser Thr Glu Lys Glu
            580                 585                 590

Ser Glu Lys Thr Ala Glu Ser Gln Thr Pro Thr Pro Ser Ala Thr Ser
        595                 600                 605

Phe Phe Ser Gly Lys Ser Pro Val Thr Thr Leu Leu Glu Cys Met His
    610                 615                 620

Lys Leu Gly Asn Ser Cys Glu Phe Arg Leu Leu Ser Lys Glu Gly Pro
625                 630                 635                 640

Ala His Glu Pro Lys Phe Gln Tyr Cys Val Ala Val Gly Ala Gln Thr
                645                 650                 655

Phe Pro Ser Val Ser Ala Pro Ser Lys Lys Val Ala Lys Gln Met Ala
            660                 665                 670

Ala Glu Glu Ala Met Lys Ala Leu His Gly Glu Ala Thr Asn Ser Met
        675                 680                 685

Ala Ser Asp Asn Gln Pro Glu Gly Met Ile Ser Glu Ser Leu Asp Asn
```

```
              690                 695                 700
Leu Glu Ser Met Met Pro Asn Lys Val Arg Lys Ile Gly Glu Leu Val
705                 710                 715                 720

Arg Tyr Leu Asn Thr Asn Pro Val Gly Gly Leu Leu Glu Tyr Ala Arg
                725                 730                 735

Ser His Gly Phe Ala Ala Glu Phe Lys Leu Val Asp Gln Ser Gly Pro
                740                 745                 750

Pro His Glu Pro Lys Phe Val Tyr Gln Ala Lys Val Gly Gly Arg Trp
                755                 760                 765

Phe Pro Ala Val Cys Ala His Ser Lys Lys Gln Gly Lys Gln Glu Ala
770                 775                 780

Ala Asp Ala Ala Leu Arg Val Leu Ile Gly Glu Asn Glu Lys Ala Glu
785                 790                 795                 800

Arg Met Gly Phe Thr Glu Leu Pro Leu Thr Gly Ser Thr Phe His Asp
                805                 810                 815

Gln Ile Ala Met Leu Ser His Arg Cys Phe Asn Thr Leu Thr Asn Ser
                820                 825                 830

Phe Gln Pro Ser Leu Leu Gly Arg Lys Ile Leu Ala Ala Ile Ile Met
                835                 840                 845

Lys Lys Asp Ser Glu Asp Met Gly Val Val Ser Leu Gly Thr Gly
850                 855                 860

Asn Arg Cys Val Lys Gly Asp Ser Leu Ser Leu Lys Gly Glu Thr Val
865                 870                 875                 880

Asn Asp Cys His Ala Glu Ile Ile Ser Arg Arg Gly Phe Ile Arg Phe
                885                 890                 895

Leu Tyr Ser Glu Leu Met Lys Tyr Asn Ser Gln Thr Ala Lys Asp Ser
                900                 905                 910

Ile Phe Glu Pro Ala Lys Gly Gly Glu Lys Leu Gln Ile Lys Lys Thr
                915                 920                 925

Val Ser Phe His Leu Tyr Ile Ser Thr Ala Pro Cys Gly Asp Gly Ala
                930                 935                 940

Leu Phe Asp Lys Ser Cys Ser Asp Arg Ala Met Glu Ser Thr Glu Ser
945                 950                 955                 960

Arg His Tyr Pro Val Phe Glu Asn Pro Lys Gln Gly Lys Leu Arg Thr
                965                 970                 975

Lys Val Glu Asn Gly Glu Gly Thr Ile Pro Val Glu Ser Ser Asp Ile
                980                 985                 990

Val Pro Thr Trp Asp Gly Ile Arg  Leu Gly Glu Arg Leu Arg Thr Met
                995                1000                1005

Ser Cys  Ser Asp Lys Ile Leu  Arg Trp Asn Val Leu  Gly Leu Gln
                1010                1015                1020

Gly Ala  Leu Leu Thr His Phe  Leu Gln Pro Ile Tyr  Leu Lys Ser
                1025                1030                1035

Val Thr  Leu Gly Tyr Leu Phe  Ser Gln Gly His Leu  Thr Arg Ala
                1040                1045                1050

Ile Cys  Cys Arg Val Thr Arg  Asp Gly Ser Ala Phe  Glu Asp Gly
                1055                1060                1065

Leu Arg  His Pro Phe Ile Val  Asn His Pro Lys Val  Gly Arg Val
                1070                1075                1080

Ser Ile  Tyr Asp Ser Lys Arg  Gln Ser Gly Lys Thr  Lys Glu Thr
                1085                1090                1095

Ser Val  Asn Trp Cys Leu Ala  Asp Gly Tyr Asp Leu  Glu Ile Leu
                1100                1105                1110
```

Asp Gly Thr Arg Gly Thr Val Asp Gly Pro Arg Asn Glu Leu Ser
    1115                1120                1125

Arg Val Ser Lys Lys Asn Ile Phe Leu Leu Phe Lys Lys Leu Cys
    1130                1135                1140

Ser Phe Arg Tyr Arg Arg Asp Leu Leu Arg Leu Ser Tyr Gly Glu
    1145                1150                1155

Ala Lys Lys Ala Ala Arg Asp Tyr Glu Thr Ala Lys Asn Tyr Phe
    1160                1165                1170

Lys Lys Gly Leu Lys Asp Met Gly Tyr Gly Asn Trp Ile Ser Lys
    1175                1180                1185

Pro Gln Glu Glu Lys Asn Phe Tyr Leu Cys Pro Val
    1190                1195                1200

<210> SEQ ID NO 5
<211> LENGTH: 6557
<212> TYPE: DNA
<213> ORGANISM: Homo sapiens

<400> SEQUENCE: 5

| | | | | | |
|---|---|---|---|---|---|
| gcccctcctc | ttggccaaac | tttccggagg | ggaaggcttt | ccgaggaaac | gaaagcgaaa | 60 |
| ttgaaccgga | gccatcttgg | gcccggcgcg | cagacccgcg | gagtttcccg | tgccgacgcc | 120 |
| ccggggccac | ttccagtgcg | gagtagcgga | ggcgtggggg | cctcgagggg | ctggcgcggc | 180 |
| ccagcggtcg | ggccagggtc | gtgccgccgg | cgggtcgggc | cgggcaatgc | ctcgcgggcg | 240 |
| caatgaatcc | gcggcagggg | tattccctca | gcggatacta | cacccatcca | tttcaaggct | 300 |
| atgagcacag | acagctcagg | taccagcagc | ctgggccagg | atcttccccc | agtagtttcc | 360 |
| tgcttaagca | aatagaattt | ctcaagggggc | agctcccaga | agcaccggtg | attggaaagc | 420 |
| agacaccgtc | actgccacct | tccctcccag | gactccggcc | aaggtttcca | gtactacttg | 480 |
| cctccagtac | cagaggcagg | caagtggaca | tcagggggtgt | ccccagggggc | gtgcatctcg | 540 |
| gaagtcaggg | gctccagaga | gggttccagc | atccttcacc | acgtggcagg | agtctgccac | 600 |
| agagaggtgt | tgattgcctt | tcctcacatt | tccaggaact | gagtatctac | caagatcagg | 660 |
| aacaaaggat | cttaaagttc | ctggaagagc | ttggggaagg | gaaggccacc | acagcacatg | 720 |
| atctgtctgg | gaaacttggg | actccgaaga | aagaaatcaa | tcgagttttta | tactccctgg | 780 |
| caaagaaggg | caagctacag | aaagaggcag | gaacaccccc | tttgtggaaa | atcgcggtct | 840 |
| ccactcaggc | ttggaaccag | cacagcggag | tggtaagacc | agacggtcat | agccaaggag | 900 |
| ccccaaactc | agacccgagt | ttggaaccgg | aagacagaaa | ctccacatct | gtctcagaag | 960 |
| atcttcttga | gccttttatt | gcagtctcag | ctcaggcttg | gaaccagcac | agcggagtgg | 1020 |
| taagaccaga | cagtccatagc | caaggatccc | caaactcaga | cccaggtttg | gaacctgaag | 1080 |
| acagcaactc | cacatctgcc | ttggaagatc | ctcttgagtt | tttagacatg | gccgagatca | 1140 |
| aggagaaaat | ctgcgactat | ctcttcaatg | tgtctgactc | ctctgccctg | aatttggcta | 1200 |
| aaaatattgg | ccttaccaag | gcccgagata | taaatgctgt | gctaattgac | atggaaaggc | 1260 |
| agggggatgt | ctatagacaa | ggacaacccc | ctcccatatg | gcatttgaca | gacaagaagc | 1320 |
| gagagaggat | gcaaatcaag | agaaatacga | acagtgttcc | tgaaaccgct | ccagctgcaa | 1380 |
| tccctgagac | caaaagaaac | gcagagttcc | tcacctgtaa | tatacccaca | tcaaatgcct | 1440 |
| caaataacat | ggtaaccaca | gaaaaagtgg | agaatgggca | ggaacctgtc | ataaagttag | 1500 |
| aaaacaggca | agaggccaga | ccagaaccag | caagactgaa | accacctgtt | cattacaatg | 1560 |

```
gcccctcaaa agcagggtat gttgactttg aaaatggcca gtgggccaca gatgacatcc    1620
cagatgactt gaatagtatc cgcgcagcac caggtgagtt tcgagccatc atggagatgc    1680
cctccttcta cagtcatggc ttgccacggt gttcacccta caagaaactg acagagtgcc    1740
agctgaagaa ccccatcagc gggctgttag aatatgccca gttcgctagt caaacctgtg    1800
agttcaacat gatagagcag agtggaccac cccatgaacc tcgatttaaa ttccaggttg    1860
tcatcaatgg ccgagagttt cccccagctg aagctggaag caagaaagtg gccaagcagg    1920
atgcagctat gaaagccatg acaattctgc tagaggaagc caaagccaag gacagtggaa    1980
aatcagaaga atcatcccac tattccacag agaaagaatc agagaagact gcagagtccc    2040 agaccccac cccttcagcc acatccttct tttctgggaa gagccccgtc accacactgc     2100
ttgagtgtat gcacaaattg gggaactcct gcgaattccg tctcctgtcc aagaaggcc     2160 ctgcccatga acccaagttc caatactgtg ttgcagtggg agcccaaact ttccccagtg    2220
tgagtgctcc cagcaagaaa gtggcaaagc agatggccgc agaggaagcc atgaaggccc    2280
tgcatgggga ggcgaccaac tccatggctt ctgataacca ggtcaggaag attggcgagc    2340
tcgtgagata cctgaacacc aaccctgtgg gtggcctttt ggagtacgcc cgctcccatg    2400
gctttgctgc tgaattcaag ttggtcgacc agtccggacc tcctcacgag cccaagttcg    2460
tttaccaagc aaaagttggg ggtcgctggt tcccagccgt ctgcgcacac agcaagaagc    2520
aaggcaagca ggaagcagca gatgcggctc tccgtgtctt gattggggag aacgagaagg    2580
cagaacgcat gggtttcaca gagctccctc tcactggcag caccttccat gaccagatag    2640
ccatgctgag ccaccggtgc ttcaacactc tgactaacag cttccagccc tccttgctcg    2700
gccgcaagat tctggccgcc atcattatga aaaagactc tgaggacatg ggtgtcgtcg     2760
tcagcttggg aacagggaat cgctgtgtga aggagattc tctcagccta aaggagaaa     2820 ctgtcaatga ctgccatgca gaaataatct cccggagagg cttcatcagg tttctctaca    2880
gtgagttaat gaaatacaac tcccagactg cgaaggatag tatatttgaa cctgctaagg    2940
gaggagaaaa gctccaaata aaaaagactg tgtcattcca tctgtatatc agcactgctc    3000
cgtgtgagga tggcgccctc tttgacaagt cctgcagcga ccgtgctatg gaaagcacag    3060
aatcccgcca ctaccctgtc ttcgagaatc ccaaacaagg aaagctccgc accaaggtgg    3120
agaacggaga aggcacaatc cctgtggaat ccagtgacat tgtgcctacg tgggatggca    3180
ttcggctcgg ggagagactc cgtaccatgt cctgtagtga caaaatccta cgctggaacg    3240
tgctgggcct gcaaggggca ctgttgaccc acttcctgca gcccatttat ctcaaatctg    3300
tcacattggg ttaccttttc agccaagggc atctgacccg tgctatttgc tgtcgtgtga    3360
caagagatgg gagtgcattt gaggatggac tacgacatcc ctttattgtc aaccaccca    3420 aggttggcag agtcagcata tatgattcca aaaggcaatc cggaagact aaggagacaa     3480 gcgtcaactg gtgtctggct gatggctatg acctggagat cctggacggt accagaggca    3540
ctgtggatgg gccacggaat gaattgtccc gggtctccaa aaagaacatt tttcttctat    3600
ttaagaagct ctgctccttc cgttaccgca gggatctact gagactctcc tatggtgagg    3660
ccaagaaagc tgcccgtgac tacgagacgg ccaagaacta cttcaaaaaa ggcctgaagg    3720
atatgggcta tgggaactgg attagcaaac cccaggagga aaagaacttt tatctctgcc    3780
cagtatagta tgctccagtg acagatggat tagggtgtgt catactaggg tgtgagagag    3840
gtaggtcgta gcattcctca tcacatggtc aggggatttt ttttctcct tttttttct     3900 ttttaagcca taattggtga tactgaaaac tttgggttcc catttatcct gctttctttg    3960
```

-continued

```
ggattgctag gcaaggtctg gccaggcccc ccttttttcc cccaagtgaa gaggcagaaa     4020
cctaagaagt tatcttttct ttctacccaa agcatacata gtcactgagc acctgcggtc     4080
catttcctct taaaagtttt gttttgattt gtttccattt cctttcccctt tgtgtttgct    4140 acactgacct cttgcggtct tgattaggtt tcagtcaact ctggatcatg tcagggactg     4200
ataatttcat ttgtggatta cgcagacccc tctacttccc ctctttccct tctgagattc     4260
tttccttgtg atctgaatgt ctccttttcc ccctcagagg gcaaagaggt gaacataaag     4320
gatttggtga acatttgta agggtaggag ttgaaaactg cagttcccag tgccacggaa      4380
gtgtgattgg agcctgcaga taatgcccag ccatcctccc atcctgcact ttagccagct     4440
gcagggcggg caaggcaagg aaagctgctt ccctggaagt gtatcacttt ctccggcagc     4500
tgggaagtct agaaccagcc agactgggtt aagggagctg ctcaagcaat agcagaggtt    4560
tcacccggca ggatgacaca gaccacttcc cagggagcac gggcatgcct tggaatattg     4620
ccaagcttcc agctgcctct tctcctaaag cattcctagg aatattttcc ccgccaatgc     4680
tgggcgtaca ccctagccaa cgggacaaat cctagagggt ataaaatcat ctctgctcag     4740
ataatcatga cttagcaaga ataagggcaa aaaatcctgt tggcttaacg tcactgttcc     4800
acccggtgta atatctctca tgacagtgac accaagggaa gttgactaag tcacatgtaa     4860
attaggagtg ttttaaagaa tgccatagat gttgattctt aactgctaca gataacctgt     4920
aattgagcag atttaaaatt caggcatact tttccattta tccaagtgct ttcattttc      4980 cagatggctt cagaagtagg ctcgtgggca gggcgcagac ctgatcttta tagggttgac     5040
atagaaagca gtagttgtgg gtgaaagggc aggttgtctt caaactctgt gaggtagaat     5100
cctttgtcta tacctccatg aacattgact cgtgtgttca gagcctttgg cctctctgtg     5160
gagtctggct ctctggctcc tgtgcattct ttgaatagtc actcgtaaaa actgtcagtg     5220
cttgaaactg tttcctttac tcatgttgaa gggactttgt tggcttttag agtgttggtc     5280
atgactccaa gagcagagca gggaagagcc caagcataga cttggtgccg tggtgatggc    5340
tgcagtccag ttttgtgatg ctgcttttac gtgtccctcg ataacagtca gctagacaca    5400
ctcaggagga ctactgaggc tctgcgacct tcaggagctg agcctgcctc tctcctttag    5460
atgacagacc ttcatctggg aacgtgctga gccagcaccc tcagatgatt tccctccaaa    5520
ctgctgacta ggtcatcctc tgtctggtag agacattcac atctttgctt ttattctatg    5580
ctctctgtac ttttgaccaa aaattgacca aagtaagaaa atgcaagttc taaaaataga    5640
ctaaggatgc ctttgcagaa caccaaagca tcccaaggaa ctggtaggga agtggcgcct    5700
gtctcctgga gtggaagagg cctgctccct ggctctgggt ctgctggggg cacagtaaat    5760
cagtcttggc acccacatcc agggcagaga ggtctgtggt tctcagcatc agaaggcagc    5820
gcagcccctc tcctcttcag gctacagggt tgtcacctgc tgagtcctca ggttgtttgg    5880
cctctctggt ccatcttggg cattaggttc tccagcagag ctctggccag ctgcctcttc    5940
tttaactggg aacacaggct ctcacaagat cagaaccccc actcaccccc aagatcttat    6000
ctagcaagcc tgtagtattc agtttctgtt gtaggaagag agcgaggcat ccctgaattc    6060
cacgcatctg ctggaaacga gccgtgtcag atcgcacatc cctgcgcccc catgcccctc    6120
tgagtcacac aggacagagg aggcagagct tctgcccact gttatcttca ctttctttgt    6180
ccagtctttt gttttaata agcagtgacc ctccctactc ttcttttaa tgattttgt       6240 agttgatttg tctgaactgt ggctactgtg cattccttga ataatcactt gtaaaaattg    6300
```

```
tcagtgcttg aagctgtttc ctttactcac attgaaggga cttcgttggt tttttggagt    6360
cttggttgtg actccaagag cagagtgagg aagaccccca agcatagact cgggtactgt    6420
gatgatggct gcagtccagt tttatgattc tgcttttatg tgtcccttga taacagtgac    6480
ttaacaatat acattcctca taaataaaaa aaaacaaga atctgaattc ttagaaaaaa    6540
aaaaaaaaaa aaaaaa                                                    6557
```

<210> SEQ ID NO 6
<211> LENGTH: 1181
<212> TYPE: PRT
<213> ORGANISM: Homo sapiens

<400> SEQUENCE: 6

```
Met Asn Pro Arg Gln Gly Tyr Ser Leu Ser Gly Tyr Tyr Thr His Pro
1               5                   10                  15

Phe Gln Gly Tyr Glu His Arg Gln Leu Arg Tyr Gln Pro Gly Pro
                20                  25                  30

Gly Ser Ser Pro Ser Ser Phe Leu Leu Lys Gln Ile Glu Phe Leu Lys
        35                  40                  45

Gly Gln Leu Pro Glu Ala Pro Val Ile Gly Lys Gln Thr Pro Ser Leu
    50                  55                  60

Pro Pro Ser Leu Pro Gly Leu Arg Pro Arg Phe Pro Val Leu Leu Ala
65                  70                  75                  80

Ser Ser Thr Arg Gly Arg Gln Val Asp Ile Arg Gly Val Pro Arg Gly
                85                  90                  95

Val His Leu Gly Ser Gln Gly Leu Gln Arg Gly Phe Gln His Pro Ser
            100                 105                 110

Pro Arg Gly Arg Ser Leu Pro Gln Arg Gly Val Asp Cys Leu Ser Ser
        115                 120                 125

His Phe Gln Glu Leu Ser Ile Tyr Gln Asp Gln Gln Arg Ile Leu
    130                 135                 140

Lys Phe Leu Glu Glu Leu Gly Glu Gly Lys Ala Thr Thr Ala His Asp
145                 150                 155                 160

Leu Ser Gly Lys Leu Gly Thr Pro Lys Lys Glu Ile Asn Arg Val Leu
                165                 170                 175

Tyr Ser Leu Ala Lys Lys Gly Lys Leu Gln Lys Glu Ala Gly Thr Pro
            180                 185                 190

Pro Leu Trp Lys Ile Ala Val Ser Thr Gln Ala Trp Asn Gln His Ser
        195                 200                 205

Gly Val Val Arg Pro Asp Gly His Ser Gln Gly Ala Pro Asn Ser Asp
    210                 215                 220

Pro Ser Leu Glu Pro Glu Asp Arg Asn Ser Thr Ser Val Ser Glu Asp
225                 230                 235                 240

Leu Leu Glu Pro Phe Ile Ala Val Ser Ala Gln Ala Trp Asn Gln His
                245                 250                 255

Ser Gly Val Val Arg Pro Asp Ser His Ser Gln Gly Ser Pro Asn Ser
            260                 265                 270

Asp Pro Gly Leu Glu Pro Glu Asp Ser Asn Ser Thr Ser Ala Leu Glu
        275                 280                 285

Asp Pro Leu Glu Phe Leu Asp Met Ala Glu Ile Lys Glu Lys Ile Cys
    290                 295                 300

Asp Tyr Leu Phe Asn Val Ser Asp Ser Ser Ala Leu Asn Leu Ala Lys
305                 310                 315                 320

Asn Ile Gly Leu Thr Lys Ala Arg Asp Ile Asn Ala Val Leu Ile Asp
```

```
              325                 330                 335
Met Glu Arg Gln Gly Asp Val Tyr Arg Gln Gly Thr Thr Pro Pro Ile
            340                 345                 350
Trp His Leu Thr Asp Lys Lys Arg Glu Arg Met Gln Ile Lys Arg Asn
            355                 360                 365
Thr Asn Ser Val Pro Glu Thr Ala Pro Ala Ala Ile Pro Glu Thr Lys
            370                 375                 380
Arg Asn Ala Glu Phe Leu Thr Cys Asn Ile Pro Thr Ser Asn Ala Ser
385                 390                 395                 400
Asn Asn Met Val Thr Thr Glu Lys Val Glu Asn Gly Gln Glu Pro Val
            405                 410                 415
Ile Lys Leu Glu Asn Arg Gln Glu Ala Arg Pro Glu Pro Ala Arg Leu
            420                 425                 430
Lys Pro Pro Val His Tyr Asn Gly Pro Ser Lys Ala Gly Tyr Val Asp
            435                 440                 445
Phe Glu Asn Gly Gln Trp Ala Thr Asp Asp Ile Pro Asp Asp Leu Asn
            450                 455                 460
Ser Ile Arg Ala Ala Pro Gly Glu Phe Arg Ala Ile Met Glu Met Pro
465                 470                 475                 480
Ser Phe Tyr Ser His Gly Leu Pro Arg Cys Ser Pro Tyr Lys Lys Leu
                485                 490                 495
Thr Glu Cys Gln Leu Lys Asn Pro Ile Ser Gly Leu Leu Glu Tyr Ala
                500                 505                 510
Gln Phe Ala Ser Gln Thr Cys Glu Phe Asn Met Ile Glu Gln Ser Gly
            515                 520                 525
Pro Pro His Glu Pro Arg Phe Lys Phe Gln Val Val Ile Asn Gly Arg
            530                 535                 540
Glu Phe Pro Pro Ala Glu Ala Gly Ser Lys Lys Val Ala Lys Gln Asp
545                 550                 555                 560
Ala Ala Met Lys Ala Met Thr Ile Leu Leu Glu Glu Ala Lys Ala Lys
                565                 570                 575
Asp Ser Gly Lys Ser Glu Glu Ser Ser His Tyr Ser Thr Glu Lys Glu
            580                 585                 590
Ser Glu Lys Thr Ala Glu Ser Gln Thr Pro Thr Pro Ser Ala Thr Ser
            595                 600                 605
Phe Phe Ser Gly Lys Ser Pro Val Thr Thr Leu Leu Glu Cys Met His
            610                 615                 620
Lys Leu Gly Asn Ser Cys Glu Phe Arg Leu Leu Ser Lys Glu Gly Pro
625                 630                 635                 640
Ala His Glu Pro Lys Phe Gln Tyr Cys Val Ala Val Gly Ala Gln Thr
                645                 650                 655
Phe Pro Ser Val Ser Ala Pro Ser Lys Lys Val Ala Lys Gln Met Ala
                660                 665                 670
Ala Glu Glu Ala Met Lys Ala Leu His Gly Glu Ala Thr Asn Ser Met
            675                 680                 685
Ala Ser Asp Asn Gln Val Arg Lys Ile Gly Glu Leu Val Arg Tyr Leu
            690                 695                 700
Asn Thr Asn Pro Val Gly Gly Leu Leu Glu Tyr Ala Arg Ser His Gly
705                 710                 715                 720
Phe Ala Ala Glu Phe Lys Leu Val Asp Gln Ser Gly Pro Pro His Glu
                725                 730                 735
Pro Lys Phe Val Tyr Gln Ala Lys Val Gly Gly Arg Trp Phe Pro Ala
                740                 745                 750
```

```
Val Cys Ala His Ser Lys Lys Gln Gly Lys Gln Glu Ala Ala Asp Ala
        755                 760                 765
Ala Leu Arg Val Leu Ile Gly Glu Asn Glu Lys Ala Glu Arg Met Gly
        770                 775                 780
Phe Thr Glu Leu Pro Leu Thr Gly Ser Thr Phe His Asp Gln Ile Ala
785                 790                 795                 800
Met Leu Ser His Arg Cys Phe Asn Thr Leu Thr Asn Ser Phe Gln Pro
            805                 810                 815
Ser Leu Leu Gly Arg Lys Ile Leu Ala Ala Ile Ile Met Lys Lys Asp
                820                 825                 830
Ser Glu Asp Met Gly Val Val Ser Leu Gly Thr Gly Asn Arg Cys
        835                 840                 845
Val Lys Gly Asp Ser Leu Ser Leu Lys Gly Glu Thr Val Asn Asp Cys
    850                 855                 860
His Ala Glu Ile Ile Ser Arg Arg Gly Phe Ile Arg Phe Leu Tyr Ser
865                 870                 875                 880
Glu Leu Met Lys Tyr Asn Ser Gln Thr Ala Lys Asp Ser Ile Phe Glu
                885                 890                 895
Pro Ala Lys Gly Gly Glu Lys Leu Gln Ile Lys Lys Thr Val Ser Phe
            900                 905                 910
His Leu Tyr Ile Ser Thr Ala Pro Cys Gly Asp Gly Ala Leu Phe Asp
        915                 920                 925
Lys Ser Cys Ser Asp Arg Ala Met Glu Ser Thr Glu Ser Arg His Tyr
        930                 935                 940
Pro Val Phe Glu Asn Pro Lys Gln Gly Lys Leu Arg Thr Lys Val Glu
945                 950                 955                 960
Asn Gly Glu Gly Thr Ile Pro Val Glu Ser Ser Asp Ile Val Pro Thr
                965                 970                 975
Trp Asp Gly Ile Arg Leu Gly Glu Arg Leu Arg Thr Met Ser Cys Ser
            980                 985                 990
Asp Lys Ile Leu Arg Trp Asn Val Leu Gly Leu Gln Gly Ala Leu Leu
        995                 1000                1005
Thr His Phe Leu Gln Pro Ile Tyr Leu Lys Ser Val Thr Leu Gly
    1010                1015                1020
Tyr Leu Phe Ser Gln Gly His Leu Thr Arg Ala Ile Cys Cys Arg
    1025                1030                1035
Val Thr Arg Asp Gly Ser Ala Phe Glu Asp Gly Leu Arg His Pro
    1040                1045                1050
Phe Ile Val Asn His Pro Lys Val Gly Arg Val Ser Ile Tyr Asp
    1055                1060                1065
Ser Lys Arg Gln Ser Gly Lys Thr Lys Glu Thr Ser Val Asn Trp
    1070                1075                1080
Cys Leu Ala Asp Gly Tyr Asp Leu Glu Ile Leu Asp Gly Thr Arg
    1085                1090                1095
Gly Thr Val Asp Gly Pro Arg Asn Glu Leu Ser Arg Val Ser Lys
    1100                1105                1110
Lys Asn Ile Phe Leu Leu Phe Lys Lys Leu Cys Ser Phe Arg Tyr
    1115                1120                1125
Arg Arg Asp Leu Leu Arg Leu Ser Tyr Gly Glu Ala Lys Lys Ala
    1130                1135                1140
Ala Arg Asp Tyr Glu Thr Ala Lys Asn Tyr Phe Lys Lys Gly Leu
    1145                1150                1155
```

| Lys | Asp | Met | Gly | Tyr | Gly | Asn | Trp | Ile | Ser | Lys | Pro | Gln | Glu | Glu |
|-----|-----|-----|-----|-----|-----|-----|-----|-----|-----|-----|-----|-----|-----|-----|
| 1160 | | | | | 1165 | | | | | 1170 | | | | |

| Lys | Asn | Phe | Tyr | Leu | Cys | Pro | Val |
|-----|-----|-----|-----|-----|-----|-----|-----|
| 1175 | | | | | 1180 | | |

<210> SEQ ID NO 7
<211> LENGTH: 6561
<212> TYPE: DNA
<213> ORGANISM: Homo sapiens

<400> SEQUENCE: 7

```
gaccagacca ttgattcccg actgaaggta gagaaggcta cgtggtgggg gagggtgggg      60
ggagggtcgc ggccgcactg gcagcctccg ggtgtccggc cgtgtcccga ggaagtgcaa     120
gacccggggt attccctcag cggatactac acccatccat ttcaaggcta tgagcacaga     180
cagctcaggt accagcagcc tgggccagga tcttccccca gtagtttcct gcttaagcaa     240
atagaatttc tcaaggggca gctcccagaa gcaccggtga ttggaaagca gacaccgtca     300
ctgccacctt ccctcccagg actccggcca aggtttccag tactacttgc ctccagtacc     360
agaggcaggc aagtggacat caggggtgtc cccaggggcg tgcatctcgg aagtcagggg     420
ctccagagag ggttccagca tccttcacca cgtggcagga gtctgccaca gagaggtgtt     480
gattgccttt cctcacattt ccaggaactg agtatctacc aagatcagga acaaaggatc     540
ttaaagttcc tggaagagct tggggaaggg aaggccacca cagcacatga tctgtctggg     600
aaacttggga ctccgaagaa agaaatcaat cgagttttat actccctggc aaagaagggc     660
aagctacaga aagaggcagg aacacccct ttgtggaaaa tcgcggtctc cactcaggct     720
tggaaccagc acagcggagt ggtaagacca gacggtcata gccaaggagc cccaaactca     780
gacccgagtt tggaaccgga agacagaaac tccacatctg tctcagaaga tcttcttgag     840
ccttttattg cagtctcagc tcaggcttgg aaccagcaca gcggagtggt aagaccagac     900
agtcatagcc aaggatcccc aaactcagac ccaggtttgg aacctgaaga cagcaactcc     960
acatctgcct tggaagatcc tcttgagttt ttagacatgg ccgagatcaa ggagaaaatc    1020
tgcgactatc tcttcaatgt gtctgactcc tctgccctga atttggctaa aaatattggc    1080
cttaccaagg cccgagatat aaatgctgtg ctaattgaca tggaaaggca ggggatgtc    1140
tatagacaag gacaacccc tcccatatgg catttgacag acaagaagcg agagaggatg    1200
caaatcaaga gaaatacgaa cagtgttcct gaaaccgctc agctgcaat ccctgagacc    1260
aaaagaaacg cagagttcct cacctgtaat atacccacat caaatgcctc aaataacatg    1320
gtaaccacag aaaaagtgga gaatgggcag gaacctgtca taagttaga aacaggcaa    1380
gaggccagac cagaaccagc aagactgaaa ccacctgttc attacaatgg cccctcaaaa    1440
gcagggtatg ttgactttga aaatggccag tgggccacag atgacatccc agatgacttg    1500
aatagtatcc gcgcagcacc aggtgagttt cgagccatca tggagatgcc ctccttctac    1560
agtcatggct tgccacggtg ttcaccctac aagaaactga cagagtgcca gctgaagaac    1620
cccatcagcg ggctgttaga atatgcccag ttcgctagtc aaacctgtga gttcaacatg    1680
atagagcaga gtgaccacc ccatgaacct cgatttaaat tccaggttgt catcaatggc    1740
cgagagtttc ccccagctga agctggaagc aagaaagtgg ccaagcagga tgcagctatg    1800
aaagccatga caattctgct agaggaagcc aaagccaagg acagtggaaa atcagaagaa    1860
tcatcccact attccacaga gaagaatca gagaagactg cagagtccca gaccccaccc    1920
ccttcagcca catccttctt ttctgggaag agccccgtca ccacactgct tgagtgtatg    1980
```

```
cacaaattgg ggaactcctg cgaattccgt ctcctgtcca agaaggccc tgcccatgaa    2040 cccaagttcc aatactgtgt tgcagtggga gcccaaactt tccccagtgt gagtgctccc    2100
agcaagaaag tggcaaagca gatggccgca gaggaagcca tgaaggccct gcatggggag    2160
gcgaccaact ccatggcttc tgataaccag cctgaaggta tgatctcaga gtcacttgat    2220
aacttggaat ccatgatgcc caacaaggtc aggaagattg gcgagctcgt gagatacctg    2280
aacaccaacc ctgtgggtgg cctttttggag tacgcccgct cccatggctt tgctgctgaa    2340
ttcaagttgg tcgaccagtc cggacctcct cacgagccca gttcgtttta ccaagcaaaa    2400
gttgggggtc gctggttccc agccgtctgc gcacacagca agaagcaagg caagcaggaa    2460
gcagcagatg cggctctccg tgtcttgatt ggggagaacg agaaggcaga acgcatgggt    2520
ttcacagagg taaccccagt gacagggggcc agtctcagaa gaactatgct cctcctctca    2580
aggtccccag aagcacagcc aaagacactc cctctcactg gcagcacctt ccatgaccag    2640
atagccatgc tgagccaccg gtgcttcaac actctgacta acagcttcca gccctccttg    2700
ctcggccgca agattctggc cgccatcatt atgaaaaaag actctgagga catgggtgtc    2760
gtcgtcagct tgggaacagg gaatcgctgt gtgaaaggag attctctcag cctaaaagga    2820
gaaactgtca atgactgcca tgcagaaata atctcccgga gaggcttcat caggtttctc    2880
tacagtgagt taatgaaata caactcccag actgcgaagg atagtatatt tgaacctgct    2940
aagggaggag aaaagctcca aataaaaaag actgtgtcat tccatctgta tatcagcact    3000
gctccgtgtg gagatggcgc cctctttgac aagtcctgca gcgaccgtgc tatggaaagc    3060
acagaatccc gccactaccc tgtcttcgag aatcccaaac aaggaaagct ccgcaccaag    3120
gtggagaacg gagaaggcac aatccctgtg gaatccagtg acattgtgcc tacgtgggat    3180
ggcattcggc tcggggagag actccgtacc atgtcctgta gtgacaaaat cctacgctgg    3240
aacgtgctgg gcctgcaagg ggcactgttg acccacttcc tgcagcccat ttatctcaaa    3300
tctgtcacat tgggttacct tttcagccaa gggcatctga cccgtgctat ttgctgtcgt    3360
gtgacaagag atgggagtgc atttgaggat ggactacgac atcccttttat tgtcaaccac    3420 cccaaggttg gcagagtcag catatatgat tccaaaaggc aatccgggaa gactaaggag    3480
acaagcgtca actggtgtct ggctgatggc tatgacctgg agatcctgga cggtaccaga    3540
ggcactgtgg atgggccacg gaatgaattg tcccgggtct ccaaaaagaa cattttttctt    3600 ctatttaaga agctctgctc cttccgttac cgcagggatc tactgagact ctcctatggt    3660
gaggccaaga agctgcccg tgactacgag acggccaaga actacttcaa aaaaggcctg    3720
aaggatatgg gctatgggaa ctggattagc aaaccccagg aggaaaagaa cttttatctc    3780
tgcccagtat agtatgctcc agtgacagat ggattagggt gtgtcatact agggtgtgag    3840
agaggtaggt cgtagcattc ctcatcacat ggtcagggga tttttttttc tccttttttt    3900 ttcttttttaa gccataattg gtgatactga aaactttggg ttcccattta tcctgctttc    3960
tttgggattg ctaggcaagg tctggccagg cccccctttt ttcccccaag tgaagaggca    4020
gaaacctaag aagttatctt ttcttttctac ccaaagcata catagtcact gagcacctgc    4080
ggtccatttc ctcttaaaag ttttgtttttg atttgtttcc atttcctttc cttttgtgtt    4140
tgctacactg acctcttgcg gtcttgatta ggtttcagtc aactctggat catgtcaggg    4200
actgataatt tcatttgtgg attacgcaga ccctctact tccctctctt cccttctgag    4260
attctttcct tgtgatctga atgtctcctt ttcccccctca gagggcaaag aggtgaacat    4320
```

| | |
|---|---|
| aaaggatttg gtgaaacatt tgtaagggta ggagttgaaa actgcagttc ccagtgccac | 4380 |
| ggaagtgtga ttggagcctg cagataatgc ccagccatcc tcccatcctg cactttagcc | 4440 |
| agctgcaggg cgggcaaggc aaggaaagct gcttccctgg aagtgtatca ctttctccgg | 4500 |
| cagctgggaa gtctagaacc agccagactg ggttaaggga gctgctcaag caatagcaga | 4560 |
| ggtttcaccc ggcaggatga cacagaccac ttcccaggga gcacgggcat gccttggaat | 4620 |
| attgccaagc ttccagctgc ctcttctcct aaagcattcc taggaatatt ttccccgcca | 4680 |
| atgctgggcg tacaccctag ccaacgggac aaatcctaga gggtataaaa tcatctctgc | 4740 |
| tcagataatc atgacttagc aagaataagg gcaaaaaatc ctgttggctt aacgtcactg | 4800 |
| ttccacccgg tgtaatatct ctcatgacag tgacaccaag ggaagttgac taagtcacat | 4860 |
| gtaaattagg agtgttttaa agaatgccat agatgttgat tcttaactgc tacagataac | 4920 |
| ctgtaattga gcagatttaa aattcaggca tactttttcca tttatccaag tgctttcatt | 4980 |
| tttccagatg gcttcagaag taggctcgtg ggcagggcgc agacctgatc tttatagggt | 5040 |
| tgacatagaa agcagtagtt gtgggtgaaa gggcaggttg tcttcaaact ctgtgaggta | 5100 |
| gaatcctttg tctataccct ccatgaacatt gactcgtgtg ttcagagcct ttggcctctc | 5160 |
| tgtggagtct ggctctctgg ctcctgtgca ttctttgaat agtcactcgt aaaaactgtc | 5220 |
| agtgcttgaa actgttttcct ttactcatgt tgaagggact ttgttggctt ttagagtgtt | 5280 |
| ggtcatgact ccaagagcag agcagggaag agcccaagca tagacttggt gccgtggtga | 5340 |
| tggctgcagt ccagttttgt gatgctgctt ttacgtgtcc ctcgataaca gtcagctaga | 5400 |
| cacactcagg aggactactg aggctctgcg accttcagga gctgagcctg cctctctcct | 5460 |
| ttagatgaca gaccttcatc tgggaacgtg ctgagccagc accctcagat gatttccctc | 5520 |
| caaactgctg actaggtcat cctctgtctg gtagagacat tcacatcttt gcttttattc | 5580 |
| tatgctctct gtacttttga ccaaaaattg accaaagtaa gaaaatgcaa gttctaaaaa | 5640 |
| tagactaagg atgcctttgc agaacaccaa agcatcccaa ggaactggta gggaagtggc | 5700 |
| gcctgtctcc tggagtggaa gaggcctgct ccctggctct gggtctgctg ggggcacagt | 5760 |
| aaatcagtct tggcacccac atccagggca gagaggtctg tggttctcag catcagaagg | 5820 |
| cagcgcagcc cctctcctct tcaggctaca gggttgtcac ctgctgagtc ctcaggttgt | 5880 |
| ttggcctctc tggtccatct tgggcattag gttctccagc agagctctgg ccagctgcct | 5940 |
| cttctttaac tgggaacaca ggctctcaca agatcagaac ccccactcac ccccaagatc | 6000 |
| ttatctagca agcctgtagt attcagtttc tgttgtagga agagagcgag gcatccctga | 6060 |
| attccacgca tctgctggaa acgagccgtg tcagatcgca catccctgcg ccccatgcc | 6120 |
| cctctgagtc acacaggaca gaggaggcag agcttctgcc cactgttatc ttcactttct | 6180 |
| ttgtccagtc ttttgttttt aataagcagt gaccctccct actcttcttt ttaatgattt | 6240 |
| ttgtagttga tttgtctgaa ctgtggctac tgtgcattcc ttgaataatc acttgtaaaa | 6300 |
| attgtcagtg cttgaagctg tttcctttac tcacattgaa gggacttcgt tggttttttg | 6360 |
| gagtcttggt tgtgactcca agagcagagt gaggaagacc cccaagcata gactcgggta | 6420 |
| ctgtgatgat ggctgcagtc cagttttatg attctgcttt tatgtgtccc ttgataacag | 6480 |
| tgacttaaca atatacattc ctcataaata aaaaaaaac aagaatctga attcttagaa | 6540 |
| aaaaaaaaaa aaaaaaaaa a | 6561 |

<210> SEQ ID NO 8
<211> LENGTH: 931

<212> TYPE: PRT
<213> ORGANISM: Homo sapiens

<400> SEQUENCE: 8

```
Met Ala Glu Ile Lys Glu Lys Ile Cys Asp Tyr Leu Phe Asn Val Ser
1               5                   10                  15

Asp Ser Ser Ala Leu Asn Leu Ala Lys Asn Ile Gly Leu Thr Lys Ala
            20                  25                  30

Arg Asp Ile Asn Ala Val Leu Ile Asp Met Glu Arg Gln Gly Asp Val
        35                  40                  45

Tyr Arg Gln Gly Thr Thr Pro Pro Ile Trp His Leu Thr Asp Lys Lys
50                  55                  60

Arg Glu Arg Met Gln Ile Lys Arg Asn Thr Asn Ser Val Pro Glu Thr
65                  70                  75                  80

Ala Pro Ala Ala Ile Pro Glu Thr Lys Arg Asn Ala Glu Phe Leu Thr
                85                  90                  95

Cys Asn Ile Pro Thr Ser Asn Ala Ser Asn Asn Met Val Thr Thr Glu
            100                 105                 110

Lys Val Glu Asn Gly Gln Glu Pro Val Ile Lys Leu Glu Asn Arg Gln
        115                 120                 125

Glu Ala Arg Pro Glu Pro Ala Arg Leu Lys Pro Pro Val His Tyr Asn
130                 135                 140

Gly Pro Ser Lys Ala Gly Tyr Val Asp Phe Glu Asn Gly Gln Trp Ala
145                 150                 155                 160

Thr Asp Asp Ile Pro Asp Asp Leu Asn Ser Ile Arg Ala Ala Pro Gly
                165                 170                 175

Glu Phe Arg Ala Ile Met Glu Met Pro Ser Phe Tyr Ser His Gly Leu
            180                 185                 190

Pro Arg Cys Ser Pro Tyr Lys Lys Leu Thr Glu Cys Gln Leu Lys Asn
        195                 200                 205

Pro Ile Ser Gly Leu Leu Glu Tyr Ala Gln Phe Ala Ser Gln Thr Cys
210                 215                 220

Glu Phe Asn Met Ile Glu Gln Ser Gly Pro Pro His Glu Pro Arg Phe
225                 230                 235                 240

Lys Phe Gln Val Val Ile Asn Gly Arg Glu Phe Pro Pro Ala Glu Ala
                245                 250                 255

Gly Ser Lys Lys Val Ala Lys Gln Asp Ala Ala Met Lys Ala Met Thr
            260                 265                 270

Ile Leu Leu Glu Glu Ala Lys Ala Lys Asp Ser Gly Lys Ser Glu Glu
        275                 280                 285

Ser Ser His Tyr Ser Thr Glu Lys Glu Ser Glu Lys Thr Ala Glu Ser
290                 295                 300

Gln Thr Pro Thr Pro Ser Ala Thr Ser Phe Phe Ser Gly Lys Ser Pro
305                 310                 315                 320

Val Thr Thr Leu Leu Glu Cys Met His Lys Leu Gly Asn Ser Cys Glu
                325                 330                 335

Phe Arg Leu Leu Ser Lys Glu Gly Pro Ala His Glu Pro Lys Phe Gln
            340                 345                 350

Tyr Cys Val Ala Val Gly Ala Gln Thr Phe Pro Ser Val Ser Ala Pro
        355                 360                 365

Ser Lys Lys Val Ala Lys Gln Met Ala Ala Glu Glu Ala Met Lys Ala
370                 375                 380

Leu His Gly Glu Ala Thr Asn Ser Met Ala Ser Asp Asn Gln Pro Glu
385                 390                 395                 400
```

```
Gly Met Ile Ser Glu Ser Leu Asp Asn Leu Glu Ser Met Met Pro Asn
                405                 410                 415

Lys Val Arg Lys Ile Gly Glu Leu Val Arg Tyr Leu Asn Thr Asn Pro
            420                 425                 430

Val Gly Gly Leu Leu Glu Tyr Ala Arg Ser His Gly Phe Ala Ala Glu
        435                 440                 445

Phe Lys Leu Val Asp Gln Ser Gly Pro Pro His Glu Pro Lys Phe Val
    450                 455                 460

Tyr Gln Ala Lys Val Gly Gly Arg Trp Phe Pro Ala Val Cys Ala His
465                 470                 475                 480

Ser Lys Lys Gln Gly Lys Gln Glu Ala Ala Asp Ala Ala Leu Arg Val
                485                 490                 495

Leu Ile Gly Glu Asn Glu Lys Ala Glu Arg Met Gly Phe Thr Glu Val
            500                 505                 510

Thr Pro Val Thr Gly Ala Ser Leu Arg Arg Thr Met Leu Leu Leu Ser
        515                 520                 525

Arg Ser Pro Glu Ala Gln Pro Lys Thr Leu Pro Leu Thr Gly Ser Thr
    530                 535                 540

Phe His Asp Gln Ile Ala Met Leu Ser His Arg Cys Phe Asn Thr Leu
545                 550                 555                 560

Thr Asn Ser Phe Gln Pro Ser Leu Leu Gly Arg Lys Ile Leu Ala Ala
                565                 570                 575

Ile Ile Met Lys Lys Asp Ser Glu Asp Met Gly Val Val Ser Leu
            580                 585                 590

Gly Thr Gly Asn Arg Cys Val Lys Gly Asp Ser Leu Ser Leu Lys Gly
        595                 600                 605

Glu Thr Val Asn Asp Cys His Ala Glu Ile Ile Ser Arg Arg Gly Phe
    610                 615                 620

Ile Arg Phe Leu Tyr Ser Glu Leu Met Lys Tyr Asn Ser Gln Thr Ala
625                 630                 635                 640

Lys Asp Ser Ile Phe Glu Pro Ala Lys Gly Gly Glu Lys Leu Gln Ile
                645                 650                 655

Lys Lys Thr Val Ser Phe His Leu Tyr Ile Ser Thr Ala Pro Cys Gly
            660                 665                 670

Asp Gly Ala Leu Phe Asp Lys Ser Cys Ser Asp Arg Ala Met Glu Ser
        675                 680                 685

Thr Glu Ser Arg His Tyr Pro Val Phe Glu Asn Pro Lys Gln Gly Lys
    690                 695                 700

Leu Arg Thr Lys Val Glu Asn Gly Glu Gly Thr Ile Pro Val Glu Ser
705                 710                 715                 720

Ser Asp Ile Val Pro Thr Trp Asp Gly Ile Arg Leu Gly Glu Arg Leu
                725                 730                 735

Arg Thr Met Ser Cys Ser Asp Lys Ile Leu Arg Trp Asn Val Leu Gly
            740                 745                 750

Leu Gln Gly Ala Leu Leu Thr His Phe Leu Gln Pro Ile Tyr Leu Lys
        755                 760                 765

Ser Val Thr Leu Gly Tyr Leu Phe Ser Gln Gly His Leu Thr Arg Ala
    770                 775                 780

Ile Cys Cys Arg Val Thr Arg Asp Gly Ser Ala Phe Glu Asp Gly Leu
785                 790                 795                 800

Arg His Pro Phe Ile Val Asn His Pro Lys Val Gly Arg Val Ser Ile
                805                 810                 815
```

```
Tyr Asp Ser Lys Arg Gln Ser Gly Lys Thr Lys Glu Thr Ser Val Asn
            820                 825                 830

Trp Cys Leu Ala Asp Gly Tyr Asp Leu Glu Ile Leu Asp Gly Thr Arg
            835                 840                 845

Gly Thr Val Asp Gly Pro Arg Asn Glu Leu Ser Arg Val Ser Lys Lys
            850                 855                 860

Asn Ile Phe Leu Leu Phe Lys Lys Leu Cys Ser Phe Arg Tyr Arg Arg
865                 870                 875                 880

Asp Leu Leu Arg Leu Ser Tyr Gly Glu Ala Lys Lys Ala Ala Arg Asp
                885                 890                 895

Tyr Glu Thr Ala Lys Asn Tyr Phe Lys Lys Gly Leu Lys Asp Met Gly
            900                 905                 910

Tyr Gly Asn Trp Ile Ser Lys Pro Gln Glu Glu Lys Asn Phe Tyr Leu
            915                 920                 925

Cys Pro Val
    930

<210> SEQ ID NO 9
<211> LENGTH: 6730
<212> TYPE: DNA
<213> ORGANISM: Homo sapiens

<400> SEQUENCE: 9
```

| | | | | | |
|---|---|---|---|---|---|
| cagcactttg | ggaggccgag | gagggcggat | caggagatcg | acaccatcct | ggccagcatg | 60 |
| gtgaaacccc | atctctacta | aaaatacaaa | aattagctgg | gtgtggtggc | gtgcgcctgt | 120 |
| aatcccagct | actccggagg | ctgaggcagg | agaatcactt | gaacccggga | ggcggagatt | 180 |
| gcagtgagct | gagatcacac | tgcactccag | cctgattgca | gtgagccgag | atcatgccac | 240 |
| tgcactccag | cttggcaaca | gagcgagact | ccgtctcaca | agaaaaaaaa | taaccgggta | 300 |
| ttccctcagc | ggatactaca | cccatccatt | tcaaggctat | gagcacagac | agctcaggta | 360 |
| ccagcagcct | gggccaggat | cttcccccag | tagtttcctg | cttaagcaaa | tagaatttct | 420 |
| caaggggcag | ctcccagaag | caccggtgat | tggaaagcag | acaccgtcac | tgccaccttc | 480 |
| cctcccagga | ctccggccaa | ggtttccagt | actacttgcc | tccagtacca | gaggcaggca | 540 |
| agtggacatc | aggggtgtcc | ccaggggcgt | gcatctcgga | agtcagggc | tccagagagg | 600 |
| gttccagcat | ccttcaccac | gtggcaggag | tctgccacag | agaggtgttg | attgcctttc | 660 |
| ctcacatttc | caggaactga | gtatctacca | agatcaggaa | caaggatct | taaagttcct | 720 |
| ggaagagctt | ggggaaggga | aggccaccac | agcacatgat | ctgtctggga | aacttgggac | 780 |
| tccgaagaaa | gaaatcaatc | gagttttata | ctccctggca | agaagggca | agctacagaa | 840 |
| agaggcagga | acaccccctt | tgtggaaaat | cgcggtctcc | actcaggctt | ggaaccagca | 900 |
| cagcggagtg | gtaagaccag | acggtcatag | ccaaggagcc | ccaaactcag | acccgagttt | 960 |
| ggaaccggaa | gacagaaact | ccacatctgt | ctcagaagat | cttcttgagc | cttttattgc | 1020 |
| agtctcagct | caggcttgga | accagcacag | cggagtggta | agaccagaca | gtcatagcca | 1080 |
| aggatcccca | aactcagacc | caggtttgga | acctgaagac | agcaactcca | catctgcctt | 1140 |
| ggaagatcct | cttgagtttt | tagacatggc | cgagatcaag | gagaaaatct | gcgactatct | 1200 |
| cttcaatgtg | tctgactcct | ctgccctgaa | tttggctaaa | atattggcc | ttaccaaggc | 1260 |
| ccgagatata | aatgctgtgc | taattgacat | ggaaaggcag | ggggatgtct | atagacaagg | 1320 |
| gacaaccccct | cccatatggc | atttgacaga | caagaagcga | gaggatgc | aaatcaagag | 1380 |
| aaatacgaac | agtgttcctg | aaaccgctcc | agctgcaatc | cctgagacca | aagaaacgc | 1440 |

-continued

```
agagttcctc acctgtaata tacccacatc aaatgcctca aataacatgg taaccacaga   1500
aaaagtggag aatgggcagg aacctgtcat aaagttagaa aacaggcaag aggccagacc   1560
agaaccagca agactgaaac cacctgttca ttacaatggc ccctcaaaag cagggtatgt   1620
tgactttgaa aatggccagt gggcacagac tgacatccca gatgacttga atagtatccg   1680
cgcagcacca ggtgagtttc gagccatcat ggagatgccc tccttctaca gtcatggctt   1740
gccacggtgt tcaccctaca agaaactgac agagtgccag ctgaagaacc ccatcagcgg   1800
gctgttagaa tatgcccagt tcgctagtca aacctgtgag ttcaacatga tagagcagag   1860
tggaccaccc catgaacctc gatttaaatt ccaggttgtc atcaatggcc gagagttttc   1920
cccagctgaa gctggaagca agaaagtggc caagcaggat gcagctatga agccatgac    1980 aattctgcta gaggaagcca agccaaggac agtggaaaa tcagaagaat catcccacta    2040
ttccacagag aaagaatcag agaagactgc agagtcccag accccaccc cttcagccac    2100 atccttcttt tctgggaaga gccccgtcac cacactgctt gagtgtatgc acaaattggg   2160
gaactcctgc gaattccgtc tcctgtccaa agaaggccct gcccatgaac ccaagttcca   2220
atactgtgtt gcagtgggag cccaaacttt ccccagtgtg agtgctccca gcaagaaagt   2280
ggcaaagcag atggccgcag aggaagccat gaaggccctg catggggagg cgaccaactc   2340
catggcttct gataaccagc ctgaaggtat gatctcagag tcacttgata acttggaatc   2400
catgatgccc aacaaggtca ggaagattgg cgagctcgtg agatacctga acaccaaccc   2460
tgtgggtggc cttttggagt acgcccgctc ccatggcttt gctgctgaat tcaagttggt   2520
cgaccagtcc ggacctcctc acgagcccaa gttcgtttac caagcaaaag ttgggggtcg   2580
ctggttccca gccgtctgcg cacacagcaa gaagcaaggc aagcaggaag cagcagatgc   2640
ggctctccgt gtcttgattg gggagaacga gaaggcagaa cgcatgggtt tcacagaggt   2700
aaccccagtg acaggggcca gtctcagaag aactatgctc ctcctctcaa ggtccccaga   2760
agcacagcca aagacactcc ctctcactgg cagcaccttc catgaccaga tagccatgct   2820
gagccaccgg tgcttcaaca ctctgactaa cagcttccag ccctccttgc tcggccgcaa   2880
gattctggcc gccatcatta tgaaaaaaga ctctgaggac atgggtgtcg tcgtcagctt   2940
gggaacaggg aatcgctgtg tgaaaggaga ttctctcagc ctaaaaggag aaactgtcaa   3000
tgactgccat gcagaaataa tctcccggag aggcttcatc aggtttctct acagtgagtt   3060
aatgaaatac aactcccaga ctgcgaagga tagtatattt gaacctgcta agggaggaga   3120
aaagctccaa ataaaaaaga ctgtgtcatt ccatctgtat atcagcactg ctccgtgtgg   3180
agatggcgcc ctctttgaca agtcctgcag cgaccgtgct atggaaagca cagaatcccg   3240
ccactaccct gtcttcgaga atcccaaaca aggaaagctc cgcaccaagg tggagaacgg   3300
agaaggcaca atccctgtgg aatccagtga cattgtgcct acgtgggatg gcattcggct   3360
cggggagaga ctccgtacca tgtcctgtag tgacaaaatc ctacgctgga acgtgctggg   3420
cctgcaaggg gcactgttga cccacttcct gcagcccatt tatctcaaat ctgtcacatt   3480
gggttacctt ttcagccaag ggcatctgac ccgtgctatt tgctgtcgtg tgacaagaga   3540
tgggagtgca tttgaggatg gactacgaca tcccttatt gtcaaccacc ccaaggttgg    3600
cagagtcagc atatatgatt ccaaaaggca atccgggaag actaaggaga caagcgtcaa   3660
ctggtgtctg gctgatggct atgacctgga gatcctggac ggtaccagag gcactgtgga   3720
tgggccacgg aatgaattgt cccgggtctc caaaaagaac atttttcttc tatttaagaa   3780
```

```
gctctgctcc ttccgttacc gcagggatct actgagactc tcctatggtg aggccaagaa    3840
agctgcccgt gactacgaga cggccaagaa ctacttcaaa aaaggcctga aggatatggg    3900
ctatgggaac tggattagca aaccccagga ggaaaagaac ttttatctct gcccagtata    3960
gtatgctcca gtgacagatg gattaggttg tgtcatacta gggtgtgaga gaggtaggtc    4020
gtagcattcc tcatcacatg gtcaggggat tttttttct ccttttttt tcttttttaag    4080 ccataattgg tgatactgaa aactttgggt tcccatttat cctgctttct ttgggattgc    4140
taggcaaggt ctggccaggc ccccttttt tcccccaagt gaagaggcag aaacctaaga    4200
agttatcttt tctttctacc caaagcatac atagtcactg agcacctgcg gtccatttcc    4260
tcttaaaagt tttgttttga tttgtttcca tttcctttcc ctttgtgttt gctacactga    4320
cctcttgcgg tcttgattag gtttcagtca actctggatc atgtcaggga ctgataattt    4380
catttgtgga ttacgcagac ccctctactt cccctctttc ccttctgaga ttctttcctt    4440
gtgatctgaa tgtctccttt tccccctcag agggcaaaga ggtgaacata aaggatttgg    4500
tgaaacattt gtaagggtag gagttgaaaa ctgcagttcc cagtgccacg gaagtgtgat    4560
tggagcctgc agataatgcc cagccatcct cccatcctgc actttagcca gctgcagggc    4620
gggcaaggca aggaaagctg cttccctgga agtgtatcac tttctccggc agctgggaag    4680
tctagaacca gccagactgg gttaagggag ctgctcaagc aatagcagag gtttcacccg    4740
gcaggatgac acagaccact tcccagggag cacgggcatg ccttggaata ttgccaagct    4800
tccagctgcc tcttctccta aagcattcct aggaatattt tccccgccaa tgctgggcgt    4860
acaccctagc caacgggaca aatcctagag ggtataaaat catctctgct cagataatca    4920
tgacttagca agaataaggg caaaaaatcc tgttggctta acgtcactgt tccacccggt    4980
gtaatatctc tcatgacagt gacaccaagg gaagttgact aagtcacatg taaattagga    5040
gtgttttaaa gaatgccata gatgttgatt cttaactgct acagataacc tgtaattgag    5100
cagatttaaa attcaggcat acttttccat ttatccaagt gctttcattt ttccagatgg    5160
cttcagaagt aggctcgtgg gcagggcgca gacctgatct ttataggtt gacatagaaa    5220 gcagtagttg tgggtgaaag ggcaggttgt cttcaaactc tgtgaggtag aatcctttgt    5280
ctatacctcc atgaacattg actcgtgtgt tcagagcctt tggcctctct gtggagtctg    5340
gctctctggc tcctgtgcat tctttgaata gtcactcgta aaaactgtca gtgcttgaaa    5400
ctgtttcctt tactcatgtt gaagggactt tgttggcttt tagagtgttg gtcatgactc    5460
caagagcaga gcaggaaga gcccaagcat agacttggtg ccgtggtgat ggctgcagtc    5520
cagttttgtg atgctgcttt tacgtgtccc tcgataacag tcagctagac acactcagga    5580
ggactactga ggctctgcga ccttcaggag ctgagcctgc ctctctcctt tagatgacag    5640
accttcatct gggaacgtgc tgagccagca ccctcagatg atttccctcc aaactgctga    5700
ctaggtcatc ctctgtctgg tagagacatt cacatctttg cttttattct atgctctctg    5760
tacttttgac caaaaattga ccaaagtaag aaaatgcaag ttctaaaaat agactaagga    5820
tgcctttgca gaacaccaaa gcatcccaag gaactggtag ggaagtggcg cctgtctcct    5880
ggagtggaag aggcctgctc cctggctctg ggtctgctgg gggcacagta aatcagtctt    5940
ggcacccaca tccagggcag agaggtctgt ggttctcagc atcagaaggc agcgcagccc    6000
ctctcctctt caggctacag ggttgtcacc tgctgagtcc tcaggttgtt tggcctctct    6060
ggtccatctt gggcattagg ttctccagca gagctctggc cagctgcctc ttctttaact    6120
gggaacacag gctctcacaa gatcagaacc cccactcacc cccaagatct tatctagcaa    6180
```

```
gcctgtagta ttcagtttct gttgtaggaa gagagcgagg catccctgaa ttccacgcat    6240
ctgctggaaa cgagccgtgt cagatcgcac atccctgcgc ccccatgccc ctctgagtca    6300
cacaggacag aggaggcaga gcttctgccc actgttatct tcactttctt tgtccagtct    6360
tttgttttta ataagcagtg accctcccta ctcttctttt taatgatttt tgtagttgat    6420
ttgtctgaac tgtggctact gtgcattcct tgaataatca cttgtaaaaa ttgtcagtgc    6480
ttgaagctgt ttcctttact cacattgaag gacttcgtt ggttttttgg agtcttggtt    6540
gtgactccaa gagcagagtg aggaagaccc ccaagcatag actcgggtac tgtgatgatg    6600
gctgcagtcc agttttatga ttctgctttt atgtgtccct tgataacagt gacttaacaa    6660
tatacattcc tcataaataa aaaaaaaaca agaatctgaa ttcttagaaa aaaaaaaaaa    6720
aaaaaaaaaa                                                           6730

<210> SEQ ID NO 10
<211> LENGTH: 5850
<212> TYPE: DNA
<213> ORGANISM: Mus musculus

<400> SEQUENCE: 10
aacagttggg cggggaagcc ttttcaagga aacgaaagtg aactctgggg agccagccat      60
cttacggcca caggtgcggg ccttgccggc actatgtctc aagggttcag ggacccaca     120 ggggtgttcc ctcaccagac acagtcgtac ttggaccta gtcatgagca tagcaagtgg     180
agatacccgc agccacaggg gccggagtct taccctagga gtttccagct tcagcagata     240
gagtttctca aagggcggct cccagaagca cccttgattg gaatacaaac ccagtcactg     300
ccgccattcc tcccaggaca ctggccaaga ttcccagggc cacctgccca agacaggcaa     360
ctggaaatct gggagttccc caggagtgtg actctcagaa atcaggggtt ccacatagga     420
cccccacttc ctccccccaca cagcagggg acaccatgga gaggtgctga cgggcttttgc    480 tcacacttcc gggagctgag catcagtcag agtccggagc agaaggttct aaaccgcctg     540
gaagagcttg gggagggga ggccaccact gcccatgtgc tagccagaga gctcagaatc      600
cccaaaaggg acatcaatcg tattttgtac tccctgaaa agaagggaaa gctgcacaga     660 ggaagggga acctcctttt gtggagcctt gtgcccttga gtcaggcttg gactcagccc     720
cctggagttg tgaatccaga tagttgtatc caggaattcc ctagaggaga gcctggttttg   780 gacagtgagg acggagaccc tgcctctgac ttagaaggac cttctgagcc tcttgacatg     840
gctgaaatca aggagaagat ctgtgactat ctgttcaatg tgtcaaactc ctctgccctg     900
aacctggcta agaacattgg cctcaccaag gcccgagatg tgacctcagt gctgattgac     960
ttggaaaggc aaggcgatgt ctacaggcaa ggggcaactc ctcccatctg gtacttgacg    1020
gacaagaagc gtgagaggct gcagatgaag agaagtacac acagtgctcc tgcccctacc    1080
ccgacagctg tcccagaggc cactagaagc ccctcattcc ctgcctgcca cccgccccca    1140
gcaggtgcct caagcagtgt ggcagcctcc aagagagtgg agaatgggca ggagcctgcg    1200
ataaagcatg aaagtaggca tgaggccaga ccaggaccaa tgagactgcg gcctcacgct    1260
tatcacaatg gcccctctag agcagggtat gtggcctctg aaaatggcca gtgggccaca    1320
gatgacatcc cagataactt gaatagtatc cacacagcac caggtgagtt tcgagccatc    1380
atggagatgc cctccttcta cagccctacc ttgccacggt gttcacccta caagaagcta    1440
actgagtgcc agctgaagaa ccctgtcagc gggttgttag agtatgctca gttcactagt    1500
```

-continued

| | |
|---|---|
| cagacctgtg atttcaacct gatagagcag agtggaccgt cccatgaacc tcgatttaaa | 1560 |
| ttccaggttg tcatcaatgg gcgggaattt cccccagctg aggctggcag caagaaagta | 1620 |
| gccaagcagg acgcagcagt gaaagccatg gcgattctgc ttcgggaagc caaagccaaa | 1680 |
| gacagtggtc aaccagaaga cttgtcccac tgtcccatgg aagaagactc ggagaaacca | 1740 |
| gcagaggctc aggcccccag ctcctcagca acatccttgt tctctgggaa gagcccagtt | 1800 |
| actacactgc ttgagtgcat gcacaaacta gggaactcct gtgaattccg tctcctgtcc | 1860 |
| aaagaaggcc ctgctcatga ccccaagttc cagtactgtg tagcagtagg agcccagacc | 1920 |
| ttcccccctg tgagcgcccc cagcaagaag gtagcaaagc agatggccgc agaggaagcc | 1980 |
| atgaaggcgc tgcaggagga ggcagccagt tcagcggatg accagtctgg aggtgcgaac | 2040 |
| acagactcac ttgatgaatc tatggctccc aacaagatca ggaggattgg tgagctcgtc | 2100 |
| aggtacctga acaccaaccc cgtaggcggc ttgttggagt acgcccgatc tcatggcttt | 2160 |
| gctgctgagt tcaagctcat tgaccagtct ggacctcctc acgaacccaa gtttgtttac | 2220 |
| caagcaaaag ttgggggccg ctggtttcca gccgtgtgtg cacacagcaa gaaacagggc | 2280 |
| aagcaggatg cagcggatgc agccctccgg gtcttgatcg gggagagcga aaggcagag | 2340 |
| cagttgggtt tcgcagagct tcctctctct ggcagcacct tccacgacca gatagctatg | 2400 |
| ctgagccaca ggtgcttcaa tgctctgacc aacagtttcc agccctccct gctcggccgc | 2460 |
| aagatcctgg ctgccattat tatgaaaaga gatccagagg acatgggtgt tgtcgtgagt | 2520 |
| ttggggacag gcaatcgctg tgtgaaaggg gactctctca gcctgaaggg agagacggtc | 2580 |
| aatgactgcc atgccgaaat catctcccgg aggggcttca tcaggtttct ctacagtgaa | 2640 |
| ctgatgaagt acaaccacca cactgccaag aacagcatat ttgagcttgc caggggagga | 2700 |
| gagaagctgc agataaagaa gacggtttct tttcatctct acatcagcac ggcgccatgt | 2760 |
| ggagatgggg ccctctttga caaatcctgc agtgaccgtg ccgtggaaag cacagagtcc | 2820 |
| cgccattacc ctgtctttga aaatcccaag caaggcaagc ttcgcaccaa ggtggagaat | 2880 |
| ggggaaggca caattcctgt ggagtccagt gatattgtac ccacgtggga tggcatccgc | 2940 |
| cttgggaaa gactccgtac catgtcctgt agtgacaaaa tcctacgctg gaatgtgctg | 3000 |
| ggcctgcaag gggcgttgtt gacgcacttc ctacagcctg tgtacctgaa atctgtaacc | 3060 |
| ttaggttacc ttttcagcca agggcatctg accgtgctga tttgctgccg cgtgaccaga | 3120 |
| gatgggaaag catttgagga tggactacgc tatccctta ttgtcaacca ccccaaggtc | 3180 |
| ggccgagtca gtgtttatga ttccaaaaga cagtccggaa agaccaagga acaagcgtc | 3240 |
| aactggtgca tggctgatgg ctatgaccta gagatcctgg atggcaccag aggcactgtg | 3300 |
| gatggaccag ggaaagagtt gtctcgggtg tccaagaaga atattttcct tcagtttaag | 3360 |
| aagctctgct ccttccgagc ccgcagagat ttactgcagc tctcttatgg tgaagccaag | 3420 |
| aaagctgccc gtgactatga cttagccaag aactacttca agaaaagcct gcgagacatg | 3480 |
| ggctatggga attggatcag caaaccccag gaggaaaaga acttttacct ctgtccagta | 3540 |
| cccaatgact gatagtgggg cgcgtttctc ctggggtcag agggcggtca tggcattcct | 3600 |
| catcacaccg ggccagagga taggagcttt ttttacccac tcccccttt tttaatggta | 3660 |
| gaaccataat agatggtacc aagaactgct ttctttggga tttcaaggtg gggtccagcc | 3720 |
| aagtccccac ctccctttc tcaagggaag aggccaagat taaaggaaat ggaaatgcta | 3780 |
| ccattccata tgtagcacag acagttcttg gtcacatgga gccaggccc ctcgggcttc | 3840 |
| gttttgcgga ggttttttc atctcctttt cctttgctgc actggcctct tgtgggtttg | 3900 |

-continued

```
attccatccc atcagttctc tgtaaatgat gtcaggggcc agtgatgtca cctgcagatg    3960
cgcaggcagg ccgctgctct gtcatccttc cctcctagga tgccttcctg tgatgaggtt    4020
tctccttccc caccccagag gatagaggtg aacataaagg attggtgaaa tgtttacaag    4080
ggcaggagtt gacaaccgtg gtcagggatt gtcgaacaac aggaatgtgg taaactgtgg    4140
ttgggacagg caagccctac ccagtaacag gccgtgctgg cccaccaagg aacttccctt    4200
cctgggcagc agggaagttg agaatcggcc agtgggaccg aggaaggtac ccaaaccaag    4260
cacgtcccag tagggtccca caagcactaa ctagagtgca ccagcattcc atggaatgtc    4320
gctatgcctc catctgcccc tccatgagca ctcccagaag ctggccctgg gcacgtgtgg    4380
tgttggcccc aggccccagc tgtttgtgaa aagcagaggg tgagcatagt gggcagagca    4440
gctttgccca gacggcaaag gtaaaggcag agcatcctgc cggtgcactg ggattcttct    4500
ggtctcagca gaagtgacaa agccctgcat agaattaatg tttctaaaag gccagaggca    4560
ttgattctga actgcatcaa agactggaga tgcaaatatt acttctccat tagtaaatgt    4620
actttcattc tatcagatgg cttcagaagc tgggtcacgg acagggcaca gggccctgga    4680
atctctgccc tgctcctttg aggatcttca tttacataca agtgttgtag gtggcagggc    4740
aggctggcct cccactctgg gatgggcttc tttgactcct ccccctctga cagtgacttg    4800
tgggtatgtg ggagcctctg tagaatctgg ttctagcatc agatcaacca gccagaccct    4860
gctccattct gccccctctag gaccaagccc acctctttcc tctgaatggt gtggctccat    4920
ctggagacag ctggccagtg tgttcaacag tttcctgcac cccttgctt aaccctcaga    4980 gctgctggt tccccaccc tctggcccac tgccaacagc aaacatcaca ttcgtacttc    5040
aagtctaatg gctactgcct cctcaatcta tgaacagatc tggccaacac aagaacctgt    5100
gtcttcacaa tacactgggg atgtctttgc acagccaaat catcctatga aactccagcg    5160
tctgtggaag tgagaaagca gcaccatgct tgtggtgtcg gctggaggcg tgtcaccctc    5220
cggcaactgc atctgaagca gagcccttgt ggtttccagg cctggacagg gagctcttcc    5280
cctggggtct aaaggacaga gatgtctctc cctttgattc ctttggtccc tctggtcctc    5340
cctgggtatt cacacatacc ccaatcctgt ctagacaacg agtggttctg ggtttctgca    5400
gatggaagag agcaaggtgt ccctgagttc tgtggacttg acccccgcat cccaccctga    5460
ccctgcctcc agtcccgctg gccgagggca gagcctcctc ccactgtgct tccttcacgt    5520
ttactttaag aagcagggcc tccctccaca ccgtctctta atactttctg tagttgattt    5580
gtctgaaccg tggctgtctt gcattccttg aataatcatg tgtaagaatt gtcaatgctt    5640
gaaactattt cctgtactca agttgaaggg actttgttgg ccttggggtt ttagcagtga    5700
ctccaagagc agagtgggga agcacccagg catagccttg gcgctgtgat ggatgcagtc    5760
cctccctctg tcccttaca agtgacagta tacattccta aaaataaaaa cactgaagca    5820
tcaggactgt taaaaaaaaa aaaaaaaaa                                      5850
```

<210> SEQ ID NO 11
<211> LENGTH: 1152
<212> TYPE: PRT
<213> ORGANISM: Mus musculus

<400> SEQUENCE: 11

```
Met Ser Gln Gly Phe Arg Gly Pro Thr Gly Val Phe Pro His Gln Thr
1               5                   10                  15

Gln Ser Tyr Leu Asp Pro Ser His Glu His Ser Lys Trp Arg Tyr Pro
```

```
                20                  25                  30
Gln Pro Gln Gly Pro Glu Ser Tyr Pro Arg Ser Phe Gln Leu Gln Gln
                35                  40                  45
Ile Glu Phe Leu Lys Gly Arg Leu Pro Glu Ala Pro Leu Ile Gly Ile
                50                  55                  60
Gln Thr Gln Ser Leu Pro Pro Phe Leu Pro Gly His Trp Pro Arg Phe
65                  70                  75                  80
Pro Gly Pro Pro Ala Gln Asp Arg Gln Leu Glu Ile Trp Glu Phe Pro
                85                  90                  95
Arg Ser Val Thr Leu Arg Asn Gln Gly Phe His Ile Gly Pro Pro Leu
                100                 105                 110
Pro Pro Pro His Ser Arg Gly Thr Pro Trp Arg Gly Ala Asp Gly Leu
                115                 120                 125
Cys Ser His Phe Arg Glu Leu Ser Ile Ser Gln Ser Pro Glu Gln Lys
                130                 135                 140
Val Leu Asn Arg Leu Glu Glu Leu Gly Glu Gly Lys Ala Thr Thr Ala
145                 150                 155                 160
His Val Leu Ala Arg Glu Leu Arg Ile Pro Lys Arg Asp Ile Asn Arg
                165                 170                 175
Ile Leu Tyr Ser Leu Glu Lys Lys Gly Lys Leu His Arg Gly Arg Gly
                180                 185                 190
Lys Pro Pro Leu Trp Ser Leu Val Pro Leu Ser Gln Ala Trp Thr Gln
                195                 200                 205
Pro Pro Gly Val Val Asn Pro Asp Ser Cys Ile Gln Glu Phe Pro Arg
                210                 215                 220
Gly Glu Pro Gly Leu Asp Ser Glu Asp Gly Asp Pro Ala Ser Asp Leu
225                 230                 235                 240
Glu Gly Pro Ser Glu Pro Leu Asp Met Ala Glu Ile Lys Glu Lys Ile
                245                 250                 255
Cys Asp Tyr Leu Phe Asn Val Ser Asn Ser Ser Ala Leu Asn Leu Ala
                260                 265                 270
Lys Asn Ile Gly Leu Thr Lys Ala Arg Asp Val Thr Ser Val Leu Ile
                275                 280                 285
Asp Leu Glu Arg Gln Gly Asp Val Tyr Arg Gln Gly Ala Thr Pro Pro
                290                 295                 300
Ile Trp Tyr Leu Thr Asp Lys Lys Arg Glu Arg Leu Gln Met Lys Arg
305                 310                 315                 320
Ser Thr His Ser Ala Pro Ala Pro Thr Pro Thr Ala Val Pro Glu Ala
                325                 330                 335
Thr Arg Ser Pro Ser Phe Pro Ala Cys His Pro Pro Ala Gly Ala
                340                 345                 350
Ser Ser Ser Val Ala Ala Ser Lys Arg Val Glu Asn Gly Gln Glu Pro
                355                 360                 365
Ala Ile Lys His Glu Ser Arg His Glu Ala Arg Pro Gly Pro Met Arg
                370                 375                 380
Leu Arg Pro His Ala Tyr His Asn Gly Pro Ser Arg Ala Gly Tyr Val
385                 390                 395                 400
Ala Ser Glu Asn Gly Gln Trp Ala Thr Asp Asp Ile Pro Asp Asn Leu
                405                 410                 415
Asn Ser Ile His Thr Ala Pro Gly Glu Phe Arg Ala Ile Met Glu Met
                420                 425                 430
Pro Ser Phe Tyr Ser Pro Thr Leu Pro Arg Cys Ser Pro Tyr Lys Lys
                435                 440                 445
```

```
Leu Thr Glu Cys Gln Leu Lys Asn Pro Val Ser Gly Leu Glu Tyr
    450                 455                 460
Ala Gln Phe Thr Ser Gln Thr Cys Asp Phe Asn Leu Ile Glu Gln Ser
465                 470                 475                 480
Gly Pro Ser His Glu Pro Arg Phe Lys Phe Gln Val Val Ile Asn Gly
                485                 490                 495
Arg Glu Phe Pro Pro Ala Glu Ala Gly Ser Lys Lys Val Ala Lys Gln
                500                 505                 510
Asp Ala Ala Val Lys Ala Met Ala Ile Leu Leu Arg Glu Ala Lys Ala
                515                 520                 525
Lys Asp Ser Gly Gln Pro Glu Asp Leu Ser His Cys Pro Met Glu Glu
    530                 535                 540
Asp Ser Glu Lys Pro Ala Glu Ala Gln Ala Pro Ser Ser Ser Ala Thr
545                 550                 555                 560
Ser Leu Phe Ser Gly Lys Ser Pro Val Thr Thr Leu Leu Glu Cys Met
                565                 570                 575
His Lys Leu Gly Asn Ser Cys Glu Phe Arg Leu Leu Ser Lys Glu Gly
                580                 585                 590
Pro Ala His Asp Pro Lys Phe Gln Tyr Cys Val Ala Val Gly Ala Gln
                595                 600                 605
Thr Phe Pro Pro Val Ser Ala Pro Ser Lys Lys Val Ala Lys Gln Met
    610                 615                 620
Ala Ala Glu Glu Ala Met Lys Ala Leu Gln Glu Glu Ala Ala Ser Ser
625                 630                 635                 640
Ala Asp Asp Gln Ser Gly Gly Ala Asn Thr Asp Ser Leu Asp Glu Ser
                645                 650                 655
Met Ala Pro Asn Lys Ile Arg Arg Ile Gly Glu Leu Val Arg Tyr Leu
                660                 665                 670
Asn Thr Asn Pro Val Gly Gly Leu Leu Glu Tyr Ala Arg Ser His Gly
                675                 680                 685
Phe Ala Ala Glu Phe Lys Leu Ile Asp Gln Ser Gly Pro Pro His Glu
    690                 695                 700
Pro Lys Phe Val Tyr Gln Ala Lys Val Gly Gly Arg Trp Phe Pro Ala
705                 710                 715                 720
Val Cys Ala His Ser Lys Lys Gln Gly Lys Gln Asp Ala Ala Asp Ala
                725                 730                 735
Ala Leu Arg Val Leu Ile Gly Glu Ser Glu Lys Ala Glu Gln Leu Gly
                740                 745                 750
Phe Ala Glu Leu Pro Leu Ser Gly Ser Thr Phe His Asp Gln Ile Ala
    755                 760                 765
Met Leu Ser His Arg Cys Phe Asn Ala Leu Thr Asn Ser Phe Gln Pro
    770                 775                 780
Ser Leu Leu Gly Arg Lys Ile Leu Ala Ala Ile Ile Met Lys Arg Asp
785                 790                 795                 800
Pro Glu Asp Met Gly Val Val Ser Leu Gly Thr Gly Asn Arg Cys
                805                 810                 815
Val Lys Gly Asp Ser Leu Ser Leu Lys Gly Glu Thr Val Asn Asp Cys
                820                 825                 830
His Ala Glu Ile Ile Ser Arg Arg Gly Phe Ile Arg Phe Leu Tyr Ser
                835                 840                 845
Glu Leu Met Lys Tyr Asn His His Thr Ala Lys Asn Ser Ile Phe Glu
    850                 855                 860
```

Leu Ala Arg Gly Gly Glu Lys Leu Gln Ile Lys Lys Thr Val Ser Phe
865                 870                 875                 880

His Leu Tyr Ile Ser Thr Ala Pro Cys Gly Asp Gly Ala Leu Phe Asp
            885                 890                 895

Lys Ser Cys Ser Asp Arg Ala Val Glu Ser Thr Glu Ser Arg His Tyr
        900                 905                 910

Pro Val Phe Glu Asn Pro Lys Gln Gly Lys Leu Arg Thr Lys Val Glu
    915                 920                 925

Asn Gly Glu Gly Thr Ile Pro Val Glu Ser Ser Asp Ile Val Pro Thr
930                 935                 940

Trp Asp Gly Ile Arg Leu Gly Glu Arg Leu Arg Thr Met Ser Cys Ser
945                 950                 955                 960

Asp Lys Ile Leu Arg Trp Asn Val Leu Gly Leu Gln Gly Ala Leu Leu
            965                 970                 975

Thr His Phe Leu Gln Pro Val Tyr Leu Lys Ser Val Thr Leu Gly Tyr
        980                 985                 990

Leu Phe Ser Gln Gly His Leu Thr Arg Ala Ile Cys Cys Arg Val Thr
    995                 1000                1005

Arg Asp Gly Lys Ala Phe Glu Asp Gly Leu Arg Tyr Pro Phe Ile
    1010                1015                1020

Val Asn His Pro Lys Val Gly Arg Val Ser Val Tyr Asp Ser Lys
    1025                1030                1035

Arg Gln Ser Gly Lys Thr Lys Glu Thr Ser Val Asn Trp Cys Met
    1040                1045                1050

Ala Asp Gly Tyr Asp Leu Glu Ile Leu Asp Gly Thr Arg Gly Thr
    1055                1060                1065

Val Asp Gly Pro Gly Lys Glu Leu Ser Arg Val Ser Lys Lys Asn
    1070                1075                1080

Ile Phe Leu Gln Phe Lys Lys Leu Cys Ser Phe Arg Ala Arg Arg
    1085                1090                1095

Asp Leu Leu Gln Leu Ser Tyr Gly Glu Ala Lys Lys Ala Ala Arg
    1100                1105                1110

Asp Tyr Asp Leu Ala Lys Asn Tyr Phe Lys Lys Ser Leu Arg Asp
    1115                1120                1125

Met Gly Tyr Gly Asn Trp Ile Ser Lys Pro Gln Glu Glu Lys Asn
    1130                1135                1140

Phe Tyr Leu Cys Pro Val Pro Asn Asp
    1145                1150

<210> SEQ ID NO 12
<211> LENGTH: 5936
<212> TYPE: DNA
<213> ORGANISM: Mus musculus

<400> SEQUENCE: 12
agtgatgtca ccaatctgcg ccctaaccat tgattcctga ctgaaggtgg aagactacgc     60
gttgggacta gccgggaagg gcgcagcctt gggctcacga gtgggcagcg tccgaggaat    120
cgcgcgcggg ggtgttccct caccagacac agtcgtactt ggaccctagt catgagcata    180
gcaagtggag atacccgcag ccacaggggc cggagtctta ccctaggagt ttccagcttc    240
agcagataga gtttctcaaa gggcggctcc cagaagcacc cttgattgga atacaaaccc    300
agtcactgcc gccattcctc ccaggacact ggccaagatt cccagggcca cctgcccaag    360
acaggcaact ggaaatctgg gagttcccca ggagtgtgac tctcagaaat cagggggttcc   420

-continued

```
acataggacc cccacttcct cccccacaca gcagggtac accatggaga ggtgctgacg    480
ggctttgctc acacttccgg gagctgagca tcagtcagag tccggagcag aaggttctaa   540
accgcctgga agagcttggg gaggggaagg ccaccactgc ccatgtgcta gccagagagc   600
tcagaatccc caaagggac atcaatcgta ttttgtactc cctggaaaag aagggaaagc    660
tgcacagagg aaggggaaa cctcctttgt ggagccttgt gcccttgagt caggcttgga    720
ctcagccccc tggagttgtg aatccagata gttgtatcca ggaattccct agaggagagc   780
ctggtttgga cagtgaggac ggagaccctg cctctgactt agaaggacct tctgagcctc   840
ttgacatggc tgaaatcaag gagaagatct gtgactatct gttcaatgtg tcaaactcct   900
ctgccctgaa cctggctaag aacattggcc tcaccaaggc ccgagatgtg acctcagtgc   960
tgattgactt ggaaaggcaa ggcgatgtct acaggcaagg gcaactcct cccatctggt    1020 acttgacgga caagaagcgt gagaggctgc agatgaagag aagtacacac agtgctcctg   1080
cccctacccc gacagctgtc ccagaggcca ctagaagccc ctcattccct gcctgccacc   1140
cgcccccagc aggtgcctca agcagtgtgg cagcctccaa gagagtggag aatgggcagg   1200
agcctgcgat aaagcatgaa agtaggcatg aggccagacc aggaccaatg agactgcggc   1260
ctcacgctta tcacaatggc ccctctagag cagggtatgt ggcctctgaa aatggccagt   1320
gggccacaga tgcatccca gataacttga atagtatcca cacagcacca ggtgagtttc     1380
gagccatcat ggagatgccc tccttctaca gccctacctt gccacggtgt tcaccctaca   1440
agaagctaac tgagtgccag ctgaagaacc ctgtcagcgg gttgttagag tatgctcagt   1500
tcactagtca gacctgtgat ttcaacctga tagagcagag tggaccgtcc catgaacctc   1560
gatttaaatt ccaggttgtc atcaatgggc gggaatttcc cccagctgag gctggcagca   1620
agaaagtagc caagcaggac gcagcagtga aagccatggc gattctgctt cgggaagcca   1680
aagccaaaga cagtggtcaa ccagaagact tgtcccactg tcccatggaa gaagactcgg   1740
agaaaccagc agaggctcag gccccccagct cctcagcaac atccttgttc tctgggaaga   1800
gcccagttac tacactgctt gagtgcatgc acaaactagg gaactcctgt gaattccgtc   1860
tcctgtccaa agaaggccct gctcatgacc ccaagttcca gtactgtgta gcagtaggag   1920
cccagacctt cccccctgtg agcgccccca gcaagaaggt agcaaagcag atggccgcag   1980
aggaagccat gaaggcgctg caggaggagg cagccagttc agcggatgac cagtctggag   2040
gtgcgaacac agactcactt gatgaatcta tggctcccaa caagatcagg aggattggtg   2100
agctcgtcag gtacctgaac accaaccccg taggcggctt gttggagtac gcccgatctc   2160
atggctttgc tgctgagttc aagctcattg accagtctgg acctcctcac gaacccaagt   2220
ttgtttacca agcaaaagtt gggggccgct ggtttccagc cgtgtgtgca cacagcaaga   2280
aacagggcaa gcaggatgca gcggatgcag ccctccgggt cttgatcggg gagagcgaga   2340
aggcagagca gttgggtttc gcagaggtaa ccccagtaac aggggccagt ctcagaagaa   2400
ctatgctcct cctttccagg tccccagatg cacatccaaa gacacttcct ctctctggca   2460
gcaccttcca cgaccagata gctatgctga ccacaggtg cttcaatgct ctgaccaaca   2520
gtttccagcc ctccctgctc ggccgcaaga tcctggctgc cattattatg aaaagagatc   2580
cagaggacat gggtgttgtc gtgagtttgg ggacaggcaa tcgctgtgtg aaggggact    2640 ctctcagcct gaagggagag acggtcaatg actgccatgc cgaaatcatc tcccggaggg   2700
gcttcatcag gtttctctac agtgaactga tgaagtacaa ccaccacact gccaagaaca   2760
gcatatttga gcttgccagg ggaggagaga agctgcagat aaagaagacg gtttctttc    2820
```

```
atctctacat cagcacggcg ccatgtggag atggggccct ctttgacaaa tcctgcagtg    2880
accgtgccgt ggaaagcaca gagtcccgcc attaccctgt ctttgaaaat cccaagcaag    2940
gcaagcttcg caccaaggtg gagaatgggg aaggcacaat tcctgtggag tccagtgata    3000
ttgtacccac gtgggatggc atccgccttg gggaaagact ccgtaccatg tcctgtagtg    3060
acaaaatcct acgctggaat gtgctgggcc tgcaaggggc gttgttgacg cacttcctac    3120
agcctgtgta cctgaaatct gtaaccttag gttacctttt cagccaaggg catctgaccc    3180
gtgctatttg ctgccgcgtg accagagatg ggaaagcatt tgaggatgga ctacgctatc    3240
cctttattgt caaccacccc aaggtcggcc gagtcagtgt ttatgattcc aaaagacagt    3300
ccggaaagac caaggaaaca agcgtcaact ggtgcatggc tgatggctat gacctagaga    3360
tcctggatgg caccagaggc actgtggatg accagggaa agagttgtct cgggtgtcca    3420
agaagaatat tttccttcag tttaagaagc tctgctcctt ccgagcccgc agagatttac    3480
tgcagctctc ttatggtgaa gccaagaaag ctgcccgtga ctatgactta gccaagaact    3540
acttcaagaa aagcctgcga gacatgggct atgggaattg gatcagcaaa ccccaggagg    3600
aaaagaactt ttacctctgt ccagtaccca atgactgata gtggggcgcg tttctcctgg    3660
ggtcagaggg cggtcatggc attcctcatc acaccgggcc agaggatagg agctttttt    3720 acccactccc ccctttttta atggtagaac cataatagat ggtaccaaga actgctttct    3780
ttgggatttc aaggtggggt ccagccaagt ccccacctcc cttttctcaa gggaagaggc    3840
caagattaaa ggaaatggaa atgctaccat tccatatgta gcacagacag ttcttggtca    3900
catggagccc aggcccctcg ggcttcgttt tgcggaggtt ttttcatct ccttttcctt    3960 tgctgcactg gcctcttgtg ggtttgattc catcccatca gttctctgta aatgatgtca    4020
ggggccagtg atgtcacctg cagatgcgca ggcaggcccc tgctctgtca tccttccctc    4080
ctaggatgcc ttcctgtgat gaggtttctc cttccccacc ccagaggata gaggtgaaca    4140
taaaggattg gtgaaatgtt tacaagggca ggagttgaca accgtggtca gggattgtcg    4200
aacaacagga atgtggtaaa ctgtggttgg gacaggcaag ccctacccag taacaggccg    4260
tgctggccca ccaaggaact tccccttcctg ggcagcaggg aagttgagaa tcggccagtg    4320
ggaccgagga aggtacccaa accaagcacg tcccagtagg ggtccacaag cactaactag    4380
agtgcaccag cattccatgg aatgtcgcta tgcctccatc tgcccctcca tgagcactcc    4440
cagaagctgg ccctgggcac gtgtggtgtt ggccccaggc cccagctgtt tgtgaaaagc    4500
agagggtgag catagtgggc agagcagctt tgcccagacg gcaaaggtaa aggcagagca    4560
tcctgccggt gcactgggat tcttctggtc tcagcagaag tgacaaagcc ctgcatagaa    4620
ttaatgtttc taaaaggcca gaggcattga ttctgaactg catcaaagac tggagatgca    4680
aatattactt ctccattagt aaatgtactt tcattctatc agatggcttc agaagctggg    4740
tcacggacag ggcacagggc cctggaatct ctgcccctgct cctttgagga tcttcattta    4800
catacaagtg ttgtaggtgg cagggcaggc tggcctccca ctctgggatg gcttctttg    4860 actcctcccc ctctgacagt gacttgtggg tatgtgggag cctctgtaga atctggttct    4920
agcatcagat caaccagcca gacctgctc cattctgccc ctctaggacc aagcccacct    4980 cttttcctctg aatggtgtgg ctccatctgg agacagctgg ccagtgtgtt caacagtttc    5040
ctgcaccccc ttgcttaacc ctcagagctg cctggttccc ccaccctctg gcccactgcc    5100
aacagcaaac atcacattcg tacttcaagt ctaatggcta ctgcctcctc aatctatgaa    5160
```

-continued

```
cagatctggc caacacaaga acctgtgtct tcacaataca ctggggatgt ctttgcacag   5220
ccaaatcatc ctatgaaact ccagcgtctg tggaagtgag aaagcagcac catgcttgtg   5280
gtgtcggctg gaggcgtgtc accctccggc aactgcatct gaagcagagc ccttgtggtt   5340
tccaggcctg gacagggagc tcttcccctg gggtctaaag gacagagatg tctctcccct   5400
tgattccttt ggtccctctg gtcctccctg ggtattcaca cataccccaa tcctgtctag   5460
acaacgagtg gttctggggtt tctgcagatg aagagagca aggtgtccct gagttctgtg   5520
gacttgaccc ccgcatccca ccctgaccct gcctccagtc ccgctggccg agggcagagc   5580
ctcctcccac tgtgcttcct tcacgtttac tttaagaagc agggcctccc tccacaccgt   5640
ctcttaatac tttctgtagt tgatttgtct gaaccgtggc tgtcttgcat tccttgaata   5700
atcatgtgta agaattgtca atgcttgaaa ctatttcctg tactcaagtt gaagggactt   5760
tgttggcctt ggggttttag cagtgactcc aagagcagag tggggaagca cccaggcata   5820
gccttggcgc tgtgatggat gcagtccctc cctctgtccc tttacaagtg acagtataca   5880
ttcctaaaaa taaaaacact gaagcatcag gactgttaaa aaaaaaaaaa aaaaaa         5936
```

<210> SEQ ID NO 13
<211> LENGTH: 930
<212> TYPE: PRT
<213> ORGANISM: Mus musculus

<400> SEQUENCE: 13

```
Met Ala Glu Ile Lys Glu Lys Ile Cys Asp Tyr Leu Phe Asn Val Ser
1               5                   10                  15

Asn Ser Ser Ala Leu Asn Leu Ala Lys Asn Ile Gly Leu Thr Lys Ala
            20                  25                  30

Arg Asp Val Thr Ser Val Leu Ile Asp Leu Glu Arg Gln Gly Asp Val
        35                  40                  45

Tyr Arg Gln Gly Ala Thr Pro Pro Ile Trp Tyr Leu Thr Asp Lys Lys
    50                  55                  60

Arg Glu Arg Leu Gln Met Lys Arg Ser Thr His Ser Ala Pro Ala Pro
65                  70                  75                  80

Thr Pro Thr Ala Val Pro Glu Ala Thr Arg Ser Pro Ser Phe Pro Ala
                85                  90                  95

Cys His Pro Pro Ala Gly Ala Ser Ser Val Ala Ala Ser Lys
            100                 105                 110

Arg Val Glu Asn Gly Gln Glu Pro Ala Ile Lys His Glu Ser Arg His
        115                 120                 125

Glu Ala Arg Pro Gly Pro Met Arg Leu Arg Pro His Ala Tyr His Asn
    130                 135                 140

Gly Pro Ser Arg Ala Gly Tyr Val Ala Ser Glu Asn Gly Gln Trp Ala
145                 150                 155                 160

Thr Asp Asp Ile Pro Asp Asn Leu Asn Ser Ile His Thr Ala Pro Gly
                165                 170                 175

Glu Phe Arg Ala Ile Met Glu Met Pro Ser Phe Tyr Ser Pro Thr Leu
            180                 185                 190

Pro Arg Cys Ser Pro Tyr Lys Lys Leu Thr Glu Cys Gln Leu Lys Asn
        195                 200                 205

Pro Val Ser Gly Leu Leu Glu Tyr Ala Gln Phe Thr Ser Gln Thr Cys
    210                 215                 220

Asp Phe Asn Leu Ile Glu Gln Ser Gly Pro Ser His Glu Pro Arg Phe
225                 230                 235                 240
```

```
Lys Phe Gln Val Val Ile Asn Gly Arg Glu Phe Pro Ala Glu Ala
                245                 250                 255

Gly Ser Lys Lys Val Ala Lys Gln Asp Ala Ala Val Lys Ala Met Ala
            260                 265                 270

Ile Leu Leu Arg Glu Ala Lys Ala Lys Asp Ser Gly Gln Pro Glu Asp
            275                 280                 285

Leu Ser His Cys Pro Met Glu Glu Asp Ser Glu Lys Pro Ala Glu Ala
            290                 295                 300

Gln Ala Pro Ser Ser Ser Ala Thr Ser Leu Phe Ser Gly Lys Ser Pro
305                 310                 315                 320

Val Thr Thr Leu Leu Glu Cys Met His Lys Leu Gly Asn Ser Cys Glu
                325                 330                 335

Phe Arg Leu Leu Ser Lys Glu Gly Pro Ala His Asp Pro Lys Phe Gln
                340                 345                 350

Tyr Cys Val Ala Val Gly Ala Gln Thr Phe Pro Pro Val Ser Ala Pro
            355                 360                 365

Ser Lys Lys Val Ala Lys Gln Met Ala Ala Glu Ala Met Lys Ala
            370                 375                 380

Leu Gln Glu Glu Ala Ala Ser Ser Ala Asp Asp Gln Ser Gly Gly Ala
385                 390                 395                 400

Asn Thr Asp Ser Leu Asp Glu Ser Met Ala Pro Asn Lys Ile Arg Arg
                405                 410                 415

Ile Gly Glu Leu Val Arg Tyr Leu Asn Thr Asn Pro Val Gly Gly Leu
            420                 425                 430

Leu Glu Tyr Ala Arg Ser His Gly Phe Ala Ala Glu Phe Lys Leu Ile
            435                 440                 445

Asp Gln Ser Gly Pro Pro His Glu Pro Lys Phe Val Tyr Gln Ala Lys
            450                 455                 460

Val Gly Gly Arg Trp Phe Pro Ala Val Cys Ala His Ser Lys Lys Gln
465                 470                 475                 480

Gly Lys Gln Asp Ala Ala Asp Ala Ala Leu Arg Val Leu Ile Gly Glu
                485                 490                 495

Ser Glu Lys Ala Glu Gln Leu Gly Phe Ala Glu Val Thr Pro Val Thr
            500                 505                 510

Gly Ala Ser Leu Arg Arg Thr Met Leu Leu Leu Ser Arg Ser Pro Asp
            515                 520                 525

Ala His Pro Lys Thr Leu Pro Leu Ser Gly Ser Thr Phe His Asp Gln
            530                 535                 540

Ile Ala Met Leu Ser His Arg Cys Phe Asn Ala Leu Thr Asn Ser Phe
545                 550                 555                 560

Gln Pro Ser Leu Leu Gly Arg Lys Ile Leu Ala Ile Ile Met Lys
                565                 570                 575

Arg Asp Pro Glu Asp Met Gly Val Val Val Ser Leu Gly Thr Gly Asn
                580                 585                 590

Arg Cys Val Lys Gly Asp Ser Leu Ser Leu Lys Gly Glu Thr Val Asn
            595                 600                 605

Asp Cys His Ala Glu Ile Ile Ser Arg Arg Gly Phe Ile Arg Phe Leu
            610                 615                 620

Tyr Ser Glu Leu Met Lys Tyr Asn His His Thr Ala Lys Asn Ser Ile
625                 630                 635                 640

Phe Glu Leu Ala Arg Gly Gly Glu Lys Leu Gln Ile Lys Lys Thr Val
                645                 650                 655

Ser Phe His Leu Tyr Ile Ser Thr Ala Pro Cys Gly Asp Gly Ala Leu
```

| | | | | | | | | | | | |
|---|---|---|---|---|---|---|---|---|---|---|---|
| | | 660 | | | 665 | | | 670 | | | |
| Phe | Asp | Lys | Ser | Cys | Ser | Asp | Arg | Ala | Val | Glu | Ser | Thr | Glu | Ser | Arg |

Phe Asp Lys Ser Cys Ser Asp Arg Ala Val Glu Ser Thr Glu Ser Arg
              660                 665                 670
                    675                     680                     685
His Tyr Pro Val Phe Glu Asn Pro Lys Gln Gly Lys Leu Arg Thr Lys
            690                     695                     700
Val Glu Asn Gly Glu Gly Thr Ile Pro Val Glu Ser Ser Asp Ile Val
705                     710                     715                     720
Pro Thr Trp Asp Gly Ile Arg Leu Gly Glu Arg Leu Arg Thr Met Ser
                    725                     730                     735
Cys Ser Asp Lys Ile Leu Arg Trp Asn Val Leu Gly Leu Gln Gly Ala
                    740                     745                     750
Leu Leu Thr His Phe Leu Gln Pro Val Tyr Leu Lys Ser Val Thr Leu
                755                     760                     765
Gly Tyr Leu Phe Ser Gln Gly His Leu Thr Arg Ala Ile Cys Cys Arg
            770                     775                     780
Val Thr Arg Asp Gly Lys Ala Phe Glu Asp Gly Leu Arg Tyr Pro Phe
785                     790                     795                     800
Ile Val Asn His Pro Lys Val Gly Arg Val Ser Val Tyr Asp Ser Lys
                    805                     810                     815
Arg Gln Ser Gly Lys Thr Lys Glu Thr Ser Val Asn Trp Cys Met Ala
                820                     825                     830
Asp Gly Tyr Asp Leu Glu Ile Leu Asp Gly Thr Arg Gly Thr Val Asp
            835                     840                     845
Gly Pro Gly Lys Glu Leu Ser Arg Val Ser Lys Lys Asn Ile Phe Leu
    850                     855                     860
Gln Phe Lys Lys Leu Cys Ser Phe Arg Ala Arg Arg Asp Leu Leu Gln
865                     870                     875                     880
Leu Ser Tyr Gly Glu Ala Lys Lys Ala Ala Arg Asp Tyr Asp Leu Ala
                    885                     890                     895
Lys Asn Tyr Phe Lys Lys Ser Leu Arg Asp Met Gly Tyr Gly Asn Trp
                900                     905                     910
Ile Ser Lys Pro Gln Glu Glu Lys Asn Phe Tyr Leu Cys Pro Val Pro
            915                     920                     925
Asn Asp
    930

<210> SEQ ID NO 14
<211> LENGTH: 5928
<212> TYPE: DNA
<213> ORGANISM: Mus musculus

<400> SEQUENCE: 14
aacagttggg cggggaagcc ttttcaagga acgaaagtg aactctgggg agccagccat    60
cttacggcca caggtgcggg ccttgccggc actatgtctc aagggttcag gggacccaca   120
ggggtgttcc ctcaccagac acagtcgtac ttggaccta gtcatgagca tagcaagtgg   180
agatacccgc agccacaggg gccggagtct taccctagga gtttccagct tcagcagata   240
gagtttctca aagggcggct cccagaaagca cccttgattg gaatacaaac ccagtcactg   300
ccgccattcc tcccaggaca ctggccaaga ttcccagggc cacctgccca agacaggcaa   360
ctggaaatct gggagttccc caggagtgtg actctcagaa atcaggggtt ccacatagga   420
cccccacttc ctcccccaca cagcaggggt acaccatgga gaggtgctga cgggcttttgc  480
tcacacttcc gggagctgag catcagtcag agtccggagc agaaggttct aaaccgcctg   540

```
gaagagcttg gggaggggaa ggccaccact gcccatgtgc tagccagaga gctcagaatc      600
cccaaaaggg acatcaatcg tattttgtac tccctggaaa agaagggaaa gctgcacaga      660
ggaagggggA aacctccttt gtggagcctt gtgcccttga gtcaggcttg gactcagccc      720
cctggagttg tgaatccaga tagttgtatc caggaattcc ctagaggaga gcctggtttg      780
gacagtgagg acggagaccc tgcctctgac ttagaaggac cttctgagcc tcttgacatg      840
gctgaaatca aggagaagat ctgtgactat ctgttcaatg tgtcaaactc ctctgccctg      900
aacctggcta agaacattgg cctcaccaag gcccgagatg tgacctcagt gctgattgac      960
ttggaaaggc aaggcgatgt ctacaggcaa ggggcaactc ctcccatctg gtacttgacg     1020
gacaagaagc gtgagaggct gcagatgaag agaagtacac acagtgctcc tgcccctacc     1080
ccgacagctg tcccagaggc cactagaagc ccctcattcc ctgcctgcca cccgcccccA     1140
gcaggtgcct caagcagtgt ggcagcctcc aagagagtgg agaatgggca ggagcctgcg     1200
ataaagcatg aaagtaggca tgaggccaga ccaggaccaa tgagactgcg gcctcacgct     1260
tatcacaatg gcccctctag agcagggtat gtggcctctg aaaatggcca gtgggccaca     1320
gatgacatcc cagataactt gaatagtatc cacacagcac caggtgagtt tcgagccatc     1380
atggagatgc cctccttcta cagccctacc ttgccacggt gttcacccta caagaagcta     1440
actgagtgcc agctgaagaa ccctgtcagc gggttgttag agtatgctca gttcactagt     1500
cagacctgtg atttcaacct gatagagcag agtggaccgt cccatgaacc tcgatttaaa     1560
ttccaggttg tcatcaatgg gcgggaattt cccccagctg aggctggcag caagaaagta     1620
gccaagcagg acgcagcagt gaaagccatg gcgattctgc ttcgggaagc caaagccaaa     1680
gacagtggtc aaccagaaga cttgtcccac tgtcccatgg aagaagactc ggagaaacca     1740
gcagaggctc aggcccccag ctcctcagca acatccttgt tctctgggaa gagcccagtt     1800
actacactgc ttgagtgcat gcacaaacta gggaactcct gtgaattccg tctcctgtcc     1860
aaagaaggcc ctgctcatga ccccaagttc cagtactgtg tagcagtagg agcccagacc     1920 ttccccctg tgagcgcccc cagcaagaag gtagcaaagc agatggccgc agaggaagcc     1980
atgaaggcgc tgcaggagga ggcagccagt tcagcggatg accagtctgg aggtgcgaac     2040
acagactcac ttgatgaatc tatggctccc aacaagatca ggaggattgg tgagctcgtc     2100
aggtacctga acaccaaccc cgtaggcggc ttgttggagt acgcccgatc tcatggcttt     2160
gctgctgagt tcaagctcat tgaccagtct ggacctcctc acgaacccaa gtttgtttac     2220
caagcaaaag ttgggggccg ctggtttcca gccgtgtgtg cacacagcaa gaaacagggc     2280
aagcaggatg cagcggatgc agccctccgg gtcttgatcg gggagagcga aaggcagag     2340 cagttgggtt tcgcagaggt aaccccagta acagggcca gtctcagaag aactatgctc     2400
ctcctttcca ggtccccaga tgcacatcca aagacacttc ctctctctgg cagcaccttc     2460
cacgaccaga tagctatgct gagccacagg tgcttcaatg tctgaccaa cagtttccag     2520 ccctccctgc tcggccgcaa gatcctggct gccattatta tgaaaagaga tccagaggac     2580
atgggtgttg tcgtgagttt ggggacaggc aatcgctgtg tgaaagggga ctctctcagc     2640
ctgaagggag agacggtcaa tgactgccat gccgaaatca tctcccggag gggcttcatc     2700
aggtttctct acagtgaact gatgaagtac aaccaccaca ctgccaagaa cagcatattt     2760
gagcttgcca ggggaggaga gaagctgcag ataaagaaga cggtttcttt tcatctctac     2820
atcagcacgg cgccatgtgg agatgggccc tctttgaca aatcctgcag tgaccgtgcc     2880
gtggaaagca cagagtcccg ccattaccct gtctttgaaa atcccaagca aggcaagctt     2940
```

```
cgcaccaagg tggagaatgg ggaaggcaca attcctgtgg agtccagtga tattgtaccc   3000
acgtgggatg gcatccgcct tggggaaaga ctccgtacca tgtcctgtag tgacaaaatc   3060
ctacgctgga atgtgctggg cctgcaaggg gcgttgttga cgcacttcct acagcctgtg   3120
tacctgaaat ctgtaacctt aggttacctt ttcagccaag gcatctgacc ccgtgctatt   3180
tgctgccgcg tgaccagaga tgggaaagca tttgaggatg gactacgcta tcccttt att   3240 gtcaaccacc ccaaggtcgg ccgagtcagt gtttatgatt ccaaaagaca gtccggaaag   3300
accaaggaaa caagcgtcaa ctggtgcatg gctgatggct atgacctaga gatcctggat   3360
ggcaccagag gcactgtgga tggaccaggg aaagagttgt ctcgggtgtc caagaagaat   3420 atttccttc agtttaagaa gctctgctcc ttccgagccc gcagagattt actgcagctc   3480
tcttatggtg aagccaagaa agctgcccgt gactatgact tagccaagaa ctacttcaag   3540
aaaagcctgc gagacatggg ctatgggaat tggatcagca accccagga ggaaaagaac   3600 ttttacctct gtccagtacc caatgactga tagtggggcg cgtttctcct ggggtcagag   3660
ggcggtcatg gcattcctca tcacaccggg ccagaggata ggagcttttt ttacccactc   3720 ccccctttt taatggtaga accataatag atggtaccaa gaactgcttt ctttgggatt   3780
tcaaggtggg gtccagccaa gtccccacct cccttttctc aagggaagag gccaagatta   3840
aaggaaatgg aaatgctacc attccatatg tagcacagac agttcttggt cacatggagc   3900
ccaggcccct cgggcttcgt tttgcggagg ttttttttcat ctccttttcc tttgctgcac   3960
tggcctcttg tgggtttgat tccatcccat cagttctctg taaatgatgt cagggccag   4020 tgatgtcacc tgcagatgcg caggcaggcc cctgctctgt catccttccc tcctaggatg   4080
ccttcctgtg atgaggtttc tccttcccca ccccagagga tagaggtgaa cataaaggat   4140
tggtgaaatg tttacaaggg caggagttga caaccgtggt cagggattgt cgaacaacag   4200
gaatgtggta aactgtggtt gggacaggca agccctaccc agtaacaggc cgtgctggcc   4260
caccaaggaa cttcccttcc tgggcagcag ggaagttgag aatcggccag tgggaccgag   4320
gaaggtaccc aaaccaagca cgtcccagta ggggtccaca agcactaact agagtgcacc   4380
agcattccat ggaatgtcgc tatgcctcca tctgcccctc catgagcact cccagaagct   4440
ggccctgggc acgtgtggtg ttggccccag gccccagctg tttgtgaaaa gcagagggtg   4500
agcatagtgg gcagagcagc tttgcccaga cggcaaaggt aaaggcagag catcctgccg   4560
gtgcactggg attcttctgg tctcagcaga agtgacaaag ccctgcatag aattaatgtt   4620 tctaaaggc cagaggcatt gattctgaac tgcatcaaag actggagatg caaatattac   4680
ttctccatta gtaaatgtac tttcattcta tcagatggct tcagaagctg ggtcacggac   4740
agggcacagg gccctggaat ctctgccctg ctcctttgag gatcttcatt tacatacaag   4800
tgttgtaggt ggcagggcag gctggcctcc cactctggga tgggcttctt tgactcctcc   4860
ccctctgaca gtgacttgtg ggtatgtggg agcctctgta gaatctggtt ctagcatcag   4920
atcaaccagc cagaccctgc tccattctgc ccctctagga ccaagcccac ctctttcctc   4980
tgaatggtgt ggctccatct ggagacagct ggccagtgtg ttcaacagtt tcctgcaccc   5040
ccttgcttaa ccctcagagc tgcctggttc ccccacccctc tggcccactg ccaacagcaa   5100
acatcacatt cgtacttcaa gtctaatggc tactgcctcc tcaatctatg aacagatctg   5160
gccaacacaa gaacctgtgt cttcacaata cactggggat gtctttgcac agccaaatca   5220
tcctatgaaa ctccagcgtc tgtggaagtg agaaagcagc accatgcttg tggtgtcggc   5280
```

```
tggaggcgtg tcaccctccg gcaactgcat ctgaagcaga gcccttgtgg tttccaggcc    5340
tggacaggga gctcttcccc tggggtctaa aggacagaga tgtctctccc tttgattcct    5400
ttggtccctc tggtcctccc tgggtattca cacataccc aatcctgtct agacaacgag     5460
tggttctggg tttctgcaga tggaagagag caaggtgtcc ctgagttctg tggacttgac    5520
ccccgcatcc caccctgacc ctgcctccag tcccgctggc cgagggcaga gcctcctccc    5580
actgtgcttc cttcacgttt actttaagaa gcagggcctc cctccacacc gtctcttaat    5640
actttctgta gttgatttgt ctgaaccgtg gctgtcttgc attccttgaa taatcatgtg    5700
taagaattgt caatgcttga aactatttcc tgtactcaag ttgaagggac tttgttggcc    5760
ttggggtttt agcagtgact ccaagagcag agtggggaag cacccaggca tagccttggc    5820
gctgtgatgg atgcagtccc tccctctgtc cctttacaag tgacagtata cattcctaaa    5880
aataaaaaca ctgaagcatc aggactgtta aaaaaaaaaa aaaaaaa                  5928
```

<210> SEQ ID NO 15
<211> LENGTH: 1178
<212> TYPE: PRT
<213> ORGANISM: Mus musculus

<400> SEQUENCE: 15

```
Met Ser Gln Gly Phe Arg Gly Pro Thr Gly Val Phe Pro His Gln Thr
1               5                   10                  15

Gln Ser Tyr Leu Asp Pro Ser His Glu His Ser Lys Trp Arg Tyr Pro
            20                  25                  30

Gln Pro Gln Gly Pro Glu Ser Tyr Pro Arg Ser Phe Gln Leu Gln Gln
        35                  40                  45

Ile Glu Phe Leu Lys Gly Arg Leu Pro Glu Ala Pro Leu Ile Gly Ile
    50                  55                  60

Gln Thr Gln Ser Leu Pro Pro Phe Leu Pro Gly His Trp Pro Arg Phe
65                  70                  75                  80

Pro Gly Pro Pro Ala Gln Asp Arg Gln Leu Glu Ile Trp Glu Phe Pro
                85                  90                  95

Arg Ser Val Thr Leu Arg Asn Gln Gly Phe His Ile Gly Pro Pro Leu
            100                 105                 110

Pro Pro Pro His Ser Arg Gly Thr Pro Trp Arg Gly Ala Asp Gly Leu
        115                 120                 125

Cys Ser His Phe Arg Glu Leu Ser Ile Ser Gln Ser Pro Glu Gln Lys
    130                 135                 140

Val Leu Asn Arg Leu Glu Glu Leu Gly Glu Gly Lys Ala Thr Thr Ala
145                 150                 155                 160

His Val Leu Ala Arg Glu Leu Arg Ile Pro Lys Arg Asp Ile Asn Arg
                165                 170                 175

Ile Leu Tyr Ser Leu Glu Lys Lys Gly Lys Leu His Arg Gly Arg Gly
            180                 185                 190

Lys Pro Pro Leu Trp Ser Leu Val Pro Leu Ser Gln Ala Trp Thr Gln
        195                 200                 205

Pro Pro Gly Val Val Asn Pro Asp Ser Cys Ile Gln Glu Phe Pro Arg
    210                 215                 220

Gly Glu Pro Gly Leu Asp Ser Glu Asp Gly Asp Pro Ala Ser Asp Leu
225                 230                 235                 240

Glu Gly Pro Ser Glu Pro Leu Asp Met Ala Glu Ile Lys Glu Lys Ile
                245                 250                 255

Cys Asp Tyr Leu Phe Asn Val Ser Asn Ser Ser Ala Leu Asn Leu Ala
```

```
                260             265              270
Lys Asn Ile Gly Leu Thr Lys Ala Arg Asp Val Thr Ser Val Leu Ile
            275                 280             285

Asp Leu Glu Arg Gln Gly Asp Val Tyr Arg Gln Ala Thr Pro Pro
290                 295                 300

Ile Trp Tyr Leu Thr Asp Lys Lys Arg Glu Arg Leu Gln Met Lys Arg
305                 310                 315                 320

Ser Thr His Ser Ala Pro Ala Pro Thr Pro Thr Ala Val Pro Glu Ala
            325                 330                 335

Thr Arg Ser Pro Ser Phe Pro Ala Cys His Pro Pro Ala Gly Ala
            340                 345                 350

Ser Ser Ser Val Ala Ala Ser Lys Arg Val Glu Asn Gly Gln Glu Pro
            355                 360                 365

Ala Ile Lys His Glu Ser Arg His Glu Ala Arg Pro Gly Pro Met Arg
            370                 375                 380

Leu Arg Pro His Ala Tyr His Asn Gly Pro Ser Arg Ala Gly Tyr Val
385                 390                 395                 400

Ala Ser Glu Asn Gly Gln Trp Ala Thr Asp Asp Ile Pro Asp Asn Leu
                405                 410                 415

Asn Ser Ile His Thr Ala Pro Gly Glu Phe Arg Ala Ile Met Glu Met
                420                 425                 430

Pro Ser Phe Tyr Ser Pro Thr Leu Pro Arg Cys Ser Pro Tyr Lys Lys
            435                 440                 445

Leu Thr Glu Cys Gln Leu Lys Asn Pro Val Ser Gly Leu Leu Glu Tyr
            450                 455                 460

Ala Gln Phe Thr Ser Gln Thr Cys Asp Phe Asn Leu Ile Glu Gln Ser
465                 470                 475                 480

Gly Pro Ser His Glu Pro Arg Phe Lys Phe Gln Val Val Ile Asn Gly
                485                 490                 495

Arg Glu Phe Pro Pro Ala Glu Ala Gly Ser Lys Lys Val Ala Lys Gln
                500                 505                 510

Asp Ala Ala Val Lys Ala Met Ala Ile Leu Leu Arg Glu Ala Lys Ala
            515                 520                 525

Lys Asp Ser Gly Gln Pro Glu Asp Leu Ser His Cys Pro Met Glu Glu
            530                 535                 540

Asp Ser Glu Lys Pro Ala Glu Ala Gln Ala Pro Ser Ser Ser Ala Thr
545                 550                 555                 560

Ser Leu Phe Ser Gly Lys Ser Pro Val Thr Thr Leu Leu Glu Cys Met
                565                 570                 575

His Lys Leu Gly Asn Ser Cys Glu Phe Arg Leu Leu Ser Lys Glu Gly
            580                 585                 590

Pro Ala His Asp Pro Lys Phe Gln Tyr Cys Val Ala Val Gly Ala Gln
            595                 600                 605

Thr Phe Pro Pro Val Ser Ala Pro Ser Lys Lys Val Ala Lys Gln Met
610                 615                 620

Ala Ala Glu Glu Ala Met Lys Ala Leu Gln Glu Ala Ala Ser Ser
625                 630                 635                 640

Ala Asp Asp Gln Ser Gly Gly Ala Asn Thr Asp Ser Leu Asp Glu Ser
                645                 650                 655

Met Ala Pro Asn Lys Ile Arg Arg Ile Gly Glu Leu Val Arg Tyr Leu
                660                 665                 670

Asn Thr Asn Pro Val Gly Gly Leu Leu Glu Tyr Ala Arg Ser His Gly
            675                 680                 685
```

```
Phe Ala Ala Glu Phe Lys Leu Ile Asp Gln Ser Gly Pro Pro His Glu
    690                 695                 700
Pro Lys Phe Val Tyr Gln Ala Lys Val Gly Gly Arg Trp Phe Pro Ala
705                 710                 715                 720
Val Cys Ala His Ser Lys Lys Gln Gly Lys Gln Asp Ala Ala Asp Ala
                    725                 730                 735
Ala Leu Arg Val Leu Ile Gly Glu Ser Glu Lys Ala Glu Gln Leu Gly
                740                 745                 750
Phe Ala Glu Val Thr Pro Val Thr Gly Ala Ser Leu Arg Arg Thr Met
            755                 760                 765
Leu Leu Leu Ser Arg Ser Pro Asp Ala His Pro Lys Thr Leu Pro Leu
770                 775                 780
Ser Gly Ser Thr Phe His Asp Gln Ile Ala Met Leu Ser His Arg Cys
785                 790                 795                 800
Phe Asn Ala Leu Thr Asn Ser Phe Gln Pro Ser Leu Leu Gly Arg Lys
                805                 810                 815
Ile Leu Ala Ala Ile Ile Met Lys Arg Asp Pro Glu Asp Met Gly Val
                820                 825                 830
Val Val Ser Leu Gly Thr Gly Asn Arg Cys Val Lys Gly Asp Ser Leu
            835                 840                 845
Ser Leu Lys Gly Glu Thr Val Asn Asp Cys His Ala Glu Ile Ile Ser
850                 855                 860
Arg Arg Gly Phe Ile Arg Phe Leu Tyr Ser Glu Leu Met Lys Tyr Asn
865                 870                 875                 880
His His Thr Ala Lys Asn Ser Ile Phe Glu Leu Ala Arg Gly Gly Glu
                885                 890                 895
Lys Leu Gln Ile Lys Lys Thr Val Ser Phe His Leu Tyr Ile Ser Thr
                900                 905                 910
Ala Pro Cys Gly Asp Gly Ala Leu Phe Asp Lys Ser Cys Ser Asp Arg
            915                 920                 925
Ala Val Glu Ser Thr Glu Ser Arg His Tyr Pro Val Phe Glu Asn Pro
930                 935                 940
Lys Gln Gly Lys Leu Arg Thr Lys Val Glu Asn Gly Glu Gly Thr Ile
945                 950                 955                 960
Pro Val Glu Ser Ser Asp Ile Val Pro Thr Trp Asp Gly Ile Arg Leu
                965                 970                 975
Gly Glu Arg Leu Arg Thr Met Ser Cys Ser Asp Lys Ile Leu Arg Trp
                980                 985                 990
Asn Val Leu Gly Leu Gln Gly Ala Leu Leu Thr His Phe Leu Gln Pro
            995                 1000                1005
Val Tyr Leu Lys Ser Val Thr Leu Gly Tyr Leu Phe Ser Gln Gly
    1010                1015                1020
His Leu Thr Arg Ala Ile Cys Cys Arg Val Thr Arg Asp Gly Lys
    1025                1030                1035
Ala Phe Glu Asp Gly Leu Arg Tyr Pro Phe Ile Val Asn His Pro
    1040                1045                1050
Lys Val Gly Arg Val Ser Val Tyr Asp Ser Lys Arg Gln Ser Gly
    1055                1060                1065
Lys Thr Lys Glu Thr Ser Val Asn Trp Cys Met Ala Asp Gly Tyr
    1070                1075                1080
Asp Leu Glu Ile Leu Asp Gly Thr Arg Gly Thr Val Asp Gly Pro
    1085                1090                1095
```

```
Gly Lys Glu Leu Ser Arg Val Ser Lys Lys Asn Ile Phe Leu Gln
    1100            1105            1110

Phe Lys Lys Leu Cys Ser Phe Arg Ala Arg Arg Asp Leu Leu Gln
    1115            1120            1125

Leu Ser Tyr Gly Glu Ala Lys Lys Ala Ala Arg Asp Tyr Asp Leu
    1130            1135            1140

Ala Lys Asn Tyr Phe Lys Lys Ser Leu Arg Asp Met Gly Tyr Gly
    1145            1150            1155

Asn Trp Ile Ser Lys Pro Gln Glu Glu Lys Asn Phe Tyr Leu Cys
    1160            1165            1170

Pro Val Pro Asn Asp
    1175

<210> SEQ ID NO 16
<211> LENGTH: 7190
<212> TYPE: DNA
<213> ORGANISM: Homo sapiens

<400> SEQUENCE: 16
cttttagttt ctcttctttc taaagaaggc tcgcggagcc cggctggaga acctcaccct      60
cgccgagcct agaaccgaga gggggccacc ccaggcggtc accagcagat ttgcccgcgc     120
gttctctttc tttccaccca gttgcccttg cggccggctg taaacctgcc actaggaccc     180
ggtcggtgag atctagcctc ttgacctgag agccgagagt ggatcgctgg gctgggctaa     240
cggcgacgga gagcgcgccc tcgctgactc cgggcgcgcc cagcagtagc accgcccgcg     300
cccgcccctg gacacttgta agtttcgatt tccgatttcc gcggaaccga gtcccgcgcc     360
gcggcagagc cagcacagcc agcgcgccat ggcggacccg gaggtgtgct gcttcatcac     420
caaaatcctg tgcgcccacg ggggccgcat ggccctggac gcgctgctcc aggagatcgc     480
gctgtctgag ccgcagctct gtgaggtgct gcaggtggcc gggcccgacc gctttgtggt     540
gttggagacc ggcggcgagg ccgggatcac ccgatcggtg gtggccacca ctcgagcccg     600
ggtctgccgt cgcaagtact gccagagacc ctgcgataac ctgcatctct gcaaactcaa     660
cttgctgggc cggtgcaact attcgcagtc cgagcggaat ttatgcaaat attctcatga     720
ggttctctca aagagaact tcaaagtcct gaaaaatcac gaactctctg gactgaacaa     780
agaggaatta gcagtgctcc tcctccaaag tgatcctttt tttatgcccg agatatgcaa     840
aagttataag ggagagggtc ggcagcagat ttgtaaccag cagccaccgt gttcaagact     900
ccacatctgt gaccacttca cccgagggaa ctgtcgtttt cccaactgcc tccggtccca     960
taacctgatg gacagaaagg tgctggccat catgagggag cacgggctga accccgacgt    1020
ggtccagaac atccaggaca tctgcaacag caagcacatg cagaagaatc ccccagggcc    1080
cagagctcct tcttcacatc gtagaaacat ggcatatagg gctagaagca agagtagaga    1140
tcggttcttt cagggcagcc aagaatttct tgcgtctgct tcagcgtctg ctgagaggtc    1200
ctgcacacct agtccagatc agatcagcca cagggcttcc ctggaggacg cgcctgtgga    1260
cgatctcacc cgcaagttca cgtatctggg gagtcaggat cgcgctcggc ctccctcagg    1320
ctcgtccaag gctactgatc ttggaggaac aagtcaggcc gggacaagcc agaggttttt    1380
agagaacggc agtcaagagg acctcttgca tggaaatcca ggcagcactt accttgcttc    1440
caattcaaca tcagccccca actggaagag cctcacatcc tggacgaatg accaaggcgc    1500
caggagaaag actgtgtttt ctcccacgct acctgccgcc cgtcttctc ttggctctct    1560
gcaaacacct gaagctgtga ccaccagaaa gggcacaggc ttgctttcct cagactacag    1620
```

-continued

```
gatcatcaat ggcaaaagtg gaactcagga catccagcct ggccctcttt ttaataataa   1680
tgctgatgga gtggccacag atataacttc taccagatcc ttaaattaca aaagcactag   1740
cagcggtcac agagaaatat catcacctag gattcaggat gctggacctg cttcccgaga   1800
tgtccaggcc actggcagaa tcgcagatga tgctgaccca agagtagcac ttgttaacga   1860
ttctttatct gatgtcacaa gtaccacatc ttctagggtg gatgatcatg actcagagga   1920
aatttgtctt gaccatctgt gtaagggttg tccgcttaat ggtagctgca gcaaagtcca   1980
cttccatctg ccttaccggt ggcagatgct tattggtaaa acctggacgg actttgagca   2040
catggagacg atcgagaaag gctactgtaa ccccggaatc cacctctgtt ctgtaggaag   2100
ttatacaatc aattttcggg taatgagttg tgattccttt cccatccgac gcctctccac   2160
tccttcttct gtcaccaagc cagccaattc tgtcttcacc accaaatgga tttggtattg   2220
gaagaatgaa tctggcacat ggattcagta tggagaagag aaagacaaac ggaaaaattc   2280
aaacgtcgac tcttcatacc tggagtctct ctatcaatcc tgtccgaggg gagttgtgcc   2340
atttcaggcg ggctcacgga actatgagct gagtttccaa gggatgattc agacaaacat   2400
agcttccaaa actcaaaagg atgtcatcag aagaccaaca tttgtgcctc agtggtatgt   2460
gcagcagatg aagagagggc cagaccatca gccagcaaag acctcgtcag tgtctttaac   2520
tgcgaccttt cgtcctcagg aggactttg cttcctatcc tcaaagaaat ataagttgtc   2580
agagatccat cacctacatc cagaatatgt cagagtaagt gagcatttta aagcttccat   2640
gaaaaatttc aagattgaaa agataaagaa gatcgagaac tcagagctcc tggataaatt   2700
tacatggaag aaatcgcaga tgaaggaaga aggaaaactc ctattttatg cgacaagccg   2760
tgcctatgtg gaatctatct gttcgaataa ttttgacagt ttcctacatg aaactcatga   2820
aaacaaatac ggaaaaggaa tttactttgc aaaagatgcc atctattccc acaaaaattg   2880
cccgtatgat gccaaaaacg tcgttatgtt tgtagcccaa gttctggttg aaagtttac   2940
tgaaggaaat ataacgtaca cgagccctcc tccacagttc gacagctgtg tggataccag   3000
atcgaatccc tccgtttttg tcatctttca gaaagatcag gtttaccac aatatgtgat   3060
tgaatatact gaagacaaag cctgcgtgat tagttagaac cgatgaatac agcgtcagaa   3120
ggatgccata accattctgt tcctttacag aactaaattg ccgcagacag gagttaaagt   3180
tttatatttt cctgctcagt tatctaatgt cttagatcag tggtccccaa attttgctac   3240
atattagaat catctgggag gttttaaaca aattctgatg cccaggttgc accccatgcc   3300
aatgaaatca tttctgggcg tcagcgccag gcagttgtat tttttttttt tttttttttt   3360
ttgagactga atctcactcc atcgtccagg ctggagtgca gtggcgcgat ctcggctcac   3420
tgcaacctct gcctcccggg ttcaagcaat tctcctgcct cagcctcccg agtagctgga   3480
actacaggca cacactgccg cgcccagcta attttttgta tttttttagta gagacagggt   3540
ttcactgtgt tgcccaggct ggtctcaaac tcctgagctc aggcaatctg cccgccttgg   3600
cctcccaaag tgctaggatt acaggtatga gccaccatgc ccggctggca gttgtatttt   3660
ttaaagccct tctgatgatt ccaatgtgtt ggaaagttta ccttgtctca gatgtaactg   3720
gtaaaggcta atttctaaat tttctgtaat tgcagcaacc tttctctcct gtctaccctt   3780
ttagtttact gtatgccatg gttttgtttt ggttacattg aaagaaagtt aatttggaaa   3840
atttgggaga aatctaatca tgcctattaa ggatgtaaga cattcagcc ttagaagaaa   3900
gattgtgaaa agctggggag aaaatgctta aggacatgct aggggaaaaa aaagtaaaat   3960
```

```
tgaagtgcta ttgcagacat ggctgcagta ctgtacctta tcattctgat gaaactgatt      4020
tggagcaccc ttttctttat cgctacattt atttagggga caaactccat ccaggttgac      4080
tctctctgga atgcggtaat aagagctggc aagtaaggct cagagagaag caaccaactg      4140
gagttaattg cccatttggg ctctttgtat aattatggca aagtagacat ttatgttcta      4200
attaatatga ttacagagaa ggcttttttct caggtcaggc ttttcatgaa agtattttga     4260
gaacaatgaa ttgcaataac cagcttcaca caagcataac tgataaacgc gagtgctatt      4320
gtagtcttgg caagtgagcc aagaacctag gagcagggcc attcctactg aaggacgggc      4380
cccctacgga gatgaaattt gtttcctggt gagcacagaa tcagaacaaa gaacaatatc      4440
ccaaagaggc cctgtgtcta ccaggagctt cttttccaa atgtaatgga ttatgtggaa       4500
ttgtagtgcc atcggttttt acttagagcc cttgacgtgc ttggaccaat atttccttcc     4560
ttcttatgaa ccaggttttt ccttctgatt ttcccttttc aacattcctt accagtcacc     4620
aaagtttcct gttataattt cttttagcag acaagttata agtcagattt aattagcatc     4680
agagttgatt ttatattagt cagattttgg atcatcacag atctccac aactccttgg       4740 cttaaacagc tccaccggta aaaaaaaaaa aaaaaaaaa aaaaaaaat agttttttta       4800 gagtagagtt attttctggg agagttacta caaatgctta ttctcattga cttatttctt     4860
tcatggtaac tttcgttttg gagtgttcat tttctgaact tgaccctcac attgtagggg     4920
tgcagtttgt ccaactcttt ccaacagccc attagacacc actagctgga tatttcacag     4980
gcatctttga ttcaatatgt ccaaagtgga actctccatc tacctccctc acatgaacct     5040
gttcctctct caggatctgt atgtaagtga aaagcatcac catctaccca ttggctcaag    5100
cagaaatctg gaagtcatct ttgactcctt cctctccctc ctgataaaca tctaagcagt     5160
ttctaagtct agttttacct cttaaatatc tctgttccct tctaagttgt ttgctgtgtt    5220
ttcttcagag caagaaggtt atatttttta aaatttactt agtaatgcac attcaaaaca    5280
cacatcaagt cttcaggata aagttcaaaa ccgctgtcat ggcccccatgt gatctctccc    5340 tcccctaccc ctctatcatt tagtttcttc tgcgcaagcc actctggctt cctttcagtt    5400
ttgtggttcc cattttttagc tagttcagtg gttttcaatg ggcatttctg ccttttttt    5460 tctaaacgac aaatagaaat acatcttctt tattatcctc caaatccaat tcagaggtaa    5520
tatgctccac ctacacacaa ttttagaaat aaattaaaaa ttaaataaaa ctaatatgaa     5580
cataaagagg aaataaaagg tacctaactt gggcacagct gtaactgaag acctaatgaa     5640
gtagtcagat gcttacaact atttataatg catcaatttg aacttagaag gtaggagatc    5700
agatcatatg tgggaaaatg taaaagcagg gatatcagtg ggcattagaa taaaaactag    5760
ggatacaata acttctttgc atatgacaat acttatttgt atataagaga aagaacgaaa    5820
taacctttat tgaaataaag atactatgca agaaaatgta cagttgtcga agtggagaaa    5880
atgaggatat attcttgcag acgagctata ggtcatacat gaatgtctag tgagacattc    5940
aaaattcgta tagggtgcag agtaatttct tattgtgagg aactgtccaa tgtattgcaa    6000
gatgttctgc atacttggct ctcacatact aaatgctagt agcgcccccca ccccacgcc     6060 cagtcacggt gacaaccaca aaccctatca gatctattca ccttttttcag agcagatatt    6120 ttgtaacatt ctctttgctg acctgaaatg actcatagat aatacaatct acttacacac    6180
atgaatttct taaaaaaatc aatttaatgc cctaactctc ttattaagga gaaatagaaa    6240
agaagaaatt tataatgaaa agaagatgaa tttcattatg taaacgctca ggcatgacta    6300
cgctgtttga aacagacaga tgtttactct tccttgtaat gagtaggttt ggatttaaga    6360
```

```
gccgattaga ggctacttcc tgtaaacaag tacaggaaaa tgaaactaga cgggtgggg    6420 acactagaat gaaaaccagt gttagggtaa agacaaaaca gactatgtac ataatctgta   6480
tatgggaaaa gaaagagcga aattacctta cttaaggata ataggacaag acaaattaca   6540
gattgtctca gagaaaacaa atgagttact ctctcggaca agctgtaggt cctacctaaa   6600
tgtccagcag gacattagac agtcgtacag ggtacagaat aattcttcgt tgtgtggcac   6660
taacccacac actgcaggac atcgttctcc ctggctgcat ccactcagtg ctgggagtag   6720
tccccagtta ttatgaaacc accaataacc cactgaccac agtgagaacc actgatttt    6780 tccactgacc tactgaatat ctagcatcct tagattggct caactgttac tttcctaagg   6840
agtccttcta cagaataggt cagatcttgg cctcccaaac cccttatttt taaaatactt   6900
tgcgccttgc tttgataatt tgtattatgt atccaaactg aaattatctg ctttctgcat   6960
tagaatgtaa gcccctgag ggttgagtca gtctgtcttg tttgctgtgc cacgcctgat    7020
gcccagccca gcagcatgct ttgtacactg atatattggg taaattttgt tgaataaatt   7080
aagctcaact atttgtattt caatagttga gttgtattgc ttcctgttct tcaagcttaa   7140
tttgaactgt ctaataaaaa gaagtaatta aaaaaaaaaa aaaaaaaaaa              7190
```

<210> SEQ ID NO 17
<211> LENGTH: 902
<212> TYPE: PRT
<213> ORGANISM: Homo sapiens

<400> SEQUENCE: 17

```
Met Ala Asp Pro Glu Val Cys Cys Phe Ile Thr Lys Ile Leu Cys Ala
1               5                   10                  15

His Gly Gly Arg Met Ala Leu Asp Ala Leu Leu Gln Glu Ile Ala Leu
            20                  25                  30

Ser Glu Pro Gln Leu Cys Glu Val Leu Gln Val Ala Gly Pro Asp Arg
        35                  40                  45

Phe Val Val Leu Glu Thr Gly Gly Glu Ala Gly Ile Thr Arg Ser Val
    50                  55                  60

Val Ala Thr Thr Arg Ala Arg Val Cys Arg Arg Lys Tyr Cys Gln Arg
65                  70                  75                  80

Pro Cys Asp Asn Leu His Leu Cys Lys Leu Asn Leu Leu Gly Arg Cys
                85                  90                  95

Asn Tyr Ser Gln Ser Glu Arg Asn Leu Cys Lys Tyr Ser His Glu Val
            100                 105                 110

Leu Ser Glu Glu Asn Phe Lys Val Leu Lys Asn His Glu Leu Ser Gly
        115                 120                 125

Leu Asn Lys Glu Glu Leu Ala Val Leu Leu Leu Gln Ser Asp Pro Phe
    130                 135                 140

Phe Met Pro Glu Ile Cys Lys Ser Tyr Lys Gly Glu Gly Arg Gln Gln
145                 150                 155                 160

Ile Cys Asn Gln Gln Pro Pro Cys Ser Arg Leu His Ile Cys Asp His
                165                 170                 175

Phe Thr Arg Gly Asn Cys Arg Phe Pro Asn Cys Leu Arg Ser His Asn
            180                 185                 190

Leu Met Asp Arg Lys Val Leu Ala Ile Met Arg Glu His Gly Leu Asn
        195                 200                 205

Pro Asp Val Val Gln Asn Ile Gln Asp Ile Cys Asn Ser Lys His Met
    210                 215                 220
```

```
Gln Lys Asn Pro Pro Gly Pro Arg Ala Pro Ser Ser His Arg Arg Asn
225                 230                 235                 240

Met Ala Tyr Arg Ala Arg Ser Lys Ser Arg Asp Arg Phe Phe Gln Gly
            245                 250                 255

Ser Gln Glu Phe Leu Ala Ser Ala Ser Ala Ser Ala Glu Arg Ser Cys
        260                 265                 270

Thr Pro Ser Pro Asp Gln Ile Ser His Arg Ala Ser Leu Glu Asp Ala
    275                 280                 285

Pro Val Asp Asp Leu Thr Arg Lys Phe Thr Tyr Leu Gly Ser Gln Asp
290                 295                 300

Arg Ala Arg Pro Pro Ser Gly Ser Ser Lys Ala Thr Asp Leu Gly Gly
305                 310                 315                 320

Thr Ser Gln Ala Gly Thr Ser Gln Arg Phe Leu Glu Asn Gly Ser Gln
            325                 330                 335

Glu Asp Leu Leu His Gly Asn Pro Gly Ser Thr Tyr Leu Ala Ser Asn
        340                 345                 350

Ser Thr Ser Ala Pro Asn Trp Lys Ser Leu Thr Ser Trp Thr Asn Asp
    355                 360                 365

Gln Gly Ala Arg Arg Lys Thr Val Phe Ser Pro Thr Leu Pro Ala Ala
370                 375                 380

Arg Ser Ser Leu Gly Ser Leu Gln Thr Pro Glu Ala Val Thr Thr Arg
385                 390                 395                 400

Lys Gly Thr Gly Leu Leu Ser Ser Asp Tyr Arg Ile Ile Asn Gly Lys
            405                 410                 415

Ser Gly Thr Gln Asp Ile Gln Pro Gly Pro Leu Phe Asn Asn Asn Ala
        420                 425                 430

Asp Gly Val Ala Thr Asp Ile Thr Ser Thr Arg Ser Leu Asn Tyr Lys
    435                 440                 445

Ser Thr Ser Ser Gly His Arg Glu Ile Ser Ser Pro Arg Ile Gln Asp
450                 455                 460

Ala Gly Pro Ala Ser Arg Asp Val Gln Ala Thr Gly Arg Ile Ala Asp
465                 470                 475                 480

Asp Ala Asp Pro Arg Val Ala Leu Val Asn Asp Ser Leu Ser Asp Val
            485                 490                 495

Thr Ser Thr Thr Ser Ser Arg Val Asp Asp His Asp Ser Glu Glu Ile
        500                 505                 510

Cys Leu Asp His Leu Cys Lys Gly Cys Pro Leu Asn Gly Ser Cys Ser
    515                 520                 525

Lys Val His Phe His Leu Pro Tyr Arg Trp Gln Met Leu Ile Gly Lys
530                 535                 540

Thr Trp Thr Asp Phe Glu His Met Glu Thr Ile Glu Lys Gly Tyr Cys
545                 550                 555                 560

Asn Pro Gly Ile His Leu Cys Ser Val Gly Ser Tyr Thr Ile Asn Phe
            565                 570                 575

Arg Val Met Ser Cys Asp Ser Phe Pro Ile Arg Arg Leu Ser Thr Pro
        580                 585                 590

Ser Ser Val Thr Lys Pro Ala Asn Ser Val Phe Thr Thr Lys Trp Ile
    595                 600                 605

Trp Tyr Trp Lys Asn Glu Ser Gly Thr Trp Ile Gln Tyr Gly Glu Glu
610                 615                 620

Lys Asp Lys Arg Lys Asn Ser Asn Val Asp Ser Ser Tyr Leu Glu Ser
625                 630                 635                 640

Leu Tyr Gln Ser Cys Pro Arg Gly Val Val Pro Phe Gln Ala Gly Ser
```

|   |   | 645 |   |   |   | 650 |   |   |   | 655 |   |
|---|---|---|---|---|---|---|---|---|---|---|---|

Arg Asn Tyr Glu Leu Ser Phe Gln Gly Met Ile Gln Thr Asn Ile Ala
            660                 665                 670

Ser Lys Thr Gln Lys Asp Val Ile Arg Arg Pro Thr Phe Val Pro Gln
        675                 680                 685

Trp Tyr Val Gln Gln Met Lys Arg Gly Pro Asp His Gln Pro Ala Lys
    690                 695                 700

Thr Ser Ser Val Ser Leu Thr Ala Thr Phe Arg Pro Gln Glu Asp Phe
705                 710                 715                 720

Cys Phe Leu Ser Ser Lys Lys Tyr Lys Leu Ser Glu Ile His His Leu
                725                 730                 735

His Pro Glu Tyr Val Arg Val Ser Glu His Phe Lys Ala Ser Met Lys
            740                 745                 750

Asn Phe Lys Ile Glu Lys Ile Lys Lys Ile Glu Asn Ser Glu Leu Leu
        755                 760                 765

Asp Lys Phe Thr Trp Lys Lys Ser Gln Met Lys Glu Glu Gly Lys Leu
    770                 775                 780

Leu Phe Tyr Ala Thr Ser Arg Ala Tyr Val Glu Ser Ile Cys Ser Asn
785                 790                 795                 800

Asn Phe Asp Ser Phe Leu His Glu Thr His Glu Asn Lys Tyr Gly Lys
                805                 810                 815

Gly Ile Tyr Phe Ala Lys Asp Ala Ile Tyr Ser His Lys Asn Cys Pro
            820                 825                 830

Tyr Asp Ala Lys Asn Val Val Met Phe Val Ala Gln Val Leu Val Gly
        835                 840                 845

Lys Phe Thr Glu Gly Asn Ile Thr Tyr Thr Ser Pro Pro Gln Phe
    850                 855                 860

Asp Ser Cys Val Asp Thr Arg Ser Asn Pro Ser Val Phe Val Ile Phe
865                 870                 875                 880

Gln Lys Asp Gln Val Tyr Pro Gln Tyr Val Ile Glu Tyr Thr Glu Asp
                885                 890                 895

Lys Ala Cys Val Ile Ser
            900

<210> SEQ ID NO 18
<211> LENGTH: 3218
<212> TYPE: DNA
<213> ORGANISM: Homo sapiens

<400> SEQUENCE: 18
cttttagttt ctcttctttc taaagaaggc tcgcggagcc cggctggaga acctcaccct      60
cgccgagcct agaaccgaga gggggccacc ccaggcggtc accagcagat ttgcccgcgc     120
gttctctttc tttccaccca gttgcccttg cggccggctg taaacctgcc actaggaccc     180
ggtcggtgag atctagcctc ttgacctgag agccgagagt ggatcgctgg gctgggctaa     240
cggcgacgga gagcgcgccc tcgctgactc cgggcgcgcc cagcagtagc accgcccgcg     300
cccgcccctg acacttgtaa gtttcgatt tccgatttcc gcggaaccga gtcccgcgcc     360
gcggcagagc cagcacagcc agcgcgccat ggcggacccg gaggtgtgct gcttcatcac     420
caaaatcctg tgcgcccacg ggggccgcat ggccctggac gcgctgctcc aggagatcgc     480
gctgtctgag ccgcagctct gtgaggtgct gcaggtggcc gggcccgacc gctttgtggt     540
gttggagacc ggcggcgagg ccgggatcac ccgatcggtg gtggccacca ctcgagcccg     600
ggtctgccgt cgcaagtact gccagagacc ctgcgataac ctgcatctct gcaaactcaa     660

| | |
|---|---|
| cttgctgggc cggtgcaact attcgcagtc cgagcggaat ttatgcaaat attctcatga | 720 |
| ggttctctca agagagaact tcaaagtcct gaaaaatcac gaactctctg gactgaacaa | 780 |
| agaggaatta gcagtgctcc tcctccaaag tgatcctttt tttatgcccg agatatgcaa | 840 |
| aagttataag ggagagggtc ggcagcagat ttgtaaccag cagccaccgt gttcaagact | 900 |
| ccacatctgt gaccacttca cccgagggaa ctgtcgtttt cccaactgcc tccggtccca | 960 |
| taacctgatg gacagaaagg tgctggccat catgagggag cacgggctga accccgacgt | 1020 |
| ggtccagaac atccaggaca tctgcaacag caagcacatg cagaagaatc ccccagggcc | 1080 |
| cagagctcct tcttcacatc gtagaaacat ggcatatagg gctagaagca agagtagaga | 1140 |
| tcggttcttt cagggcagcc aagaatttct tgcgtctgct tcagcgtctg ctgagaggtc | 1200 |
| ctgcacacct agtccagatc agatcagcca cagggcttcc ctggaggacg cgcctgtgga | 1260 |
| cgatctcacc cgcaagttca cgtatctggg gagtcaggat cgcgctcggc ctccctcagg | 1320 |
| ctcgtccaag gctactgatc ttggaggaac aagtcaggcc gggacaagcc agaggttttt | 1380 |
| agagaacggc agtcaagagg acctcttgca tggaaatcca ggcagcactt accttgcttc | 1440 |
| caattcaaca tcagccccca actggaagag cctcacatcc tggacgaatg accaaggcgc | 1500 |
| caggagaaag actgtgtttt ctcccacgct acctgccgcc cgctcttctc ttggctctct | 1560 |
| gcaaacacct gaagctgtga ccaccagaaa gggcacaggc ttgctttcct cagactacag | 1620 |
| gatcatcaat ggcaaaagtg gaactcagga catccagcct ggccctcttt ttaataataa | 1680 |
| tgctgatgga gtggccacag atataacttc taccagatcc ttaaattaca aaagcactag | 1740 |
| cagcggtcac agagaaatat catcacctag gattcaggat gctggacctg cttcccgaga | 1800 |
| tgtccaggcc actggcagaa tcgcagatga tgctgaccca agagtagcac ttgttaacga | 1860 |
| ttctttatct gatgtcacaa gtaccacatc ttctagggtg gatgatcatg actcagagga | 1920 |
| aatttgtctt gaccatctgt gtaagggttg tccgcttaat ggtagctgca gcaaagtcca | 1980 |
| cttccatctg ccttaccggt ggcagatgct tattggtaaa acctggacgg actttgagca | 2040 |
| catggagacg atcgagaaag gctactgtaa ccccggaatc cacctctgtt ctgtaggaag | 2100 |
| ttatacaatc aattttcggg taatgagttg tgattccttt cccatccgac gcctctccac | 2160 |
| tccttcttct gtcaccaagc cagccaattc tgtcttcacc accaaatgga tttggtattg | 2220 |
| gaagaatgaa tctggcacat ggattcagta tggagaagag aaagacaaac ggaaaaattc | 2280 |
| aaacgtcgac tcttcatacc tggagtctct ctatcaatcc tgtccgaggg gagttgtgcc | 2340 |
| atttcaggcg ggctcacgga actatgagct gagtttccaa gggatgattc agacaaacat | 2400 |
| agcttccaaa actcaaaagg atgtcatcag aagaccaaca tttgtgcctc agtggtatgt | 2460 |
| gcagcagatg aagagagggc cagagtaagt gttctgaagc agctgtttgc tgacagatgc | 2520 |
| ttgagatgtt catgccctgg gctcatcaag tcactcgtga atctggagcc tgttttcctg | 2580 |
| aaaagttcct gtttgcatta ctctgcagtt tccatttgca ttatcgatga gtaagatgct | 2640 |
| tgttaagcag catggtgtga ctgaaaggat actagatcgg aaaatgaatt tctttctga | 2700 |
| aagggaagtc tgagcgagtc tcctaaatac tctgggcttt agcttctcca gctgtgaaga | 2760 |
| gctggattga tgcagtacac ctaaggaata atcatatata ctgggttttt gttttgctgt | 2820 |
| ggattctttt ttttttttt tttttagag ggggtctcac tttgttgccc aggctggtct | 2880 |
| tgaactcctg agctcaagtg atcctcctac ctcagtctcc caaagtgctg ggattacagg | 2940 |
| catgagccac cgtgcctggc tttgctgtgg attcttttgg gtgtcttttg ttttcctaca | 3000 |

```
cgatttatag aggatgaggg gcggagaaag agatagaaaa aagggatgag ctagctgtta    3060
gagcaagggt tttggtgaga gataatattg attgaaggga ttttaaagga aatgttgctg    3120
tgggggattc attgtaactc tccttgtgaa ctgctcagta aactctacat tgttcatgaa    3180
caaaaaaaaa aaaaaaaaaa aaaaaaaaaa aaaaaaaa                            3218
```

<210> SEQ ID NO 19
<211> LENGTH: 699
<212> TYPE: PRT
<213> ORGANISM: Homo sapiens

<400> SEQUENCE: 19

```
Met Ala Asp Pro Glu Val Cys Cys Phe Ile Thr Lys Ile Leu Cys Ala
1               5                   10                  15

His Gly Gly Arg Met Ala Leu Asp Ala Leu Leu Gln Glu Ile Ala Leu
            20                  25                  30

Ser Glu Pro Gln Leu Cys Glu Val Leu Gln Val Ala Gly Pro Asp Arg
        35                  40                  45

Phe Val Val Leu Glu Thr Gly Gly Glu Ala Gly Ile Thr Arg Ser Val
    50                  55                  60

Val Ala Thr Thr Arg Ala Arg Val Cys Arg Arg Lys Tyr Cys Gln Arg
65                  70                  75                  80

Pro Cys Asp Asn Leu His Leu Cys Lys Leu Asn Leu Leu Gly Arg Cys
                85                  90                  95

Asn Tyr Ser Gln Ser Glu Arg Asn Leu Cys Lys Tyr Ser His Glu Val
            100                 105                 110

Leu Ser Glu Glu Asn Phe Lys Val Leu Lys Asn His Glu Leu Ser Gly
        115                 120                 125

Leu Asn Lys Glu Glu Leu Ala Val Leu Leu Gln Ser Asp Pro Phe
    130                 135                 140

Phe Met Pro Glu Ile Cys Lys Ser Tyr Lys Gly Glu Gly Arg Gln Gln
145                 150                 155                 160

Ile Cys Asn Gln Gln Pro Pro Cys Ser Arg Leu His Ile Cys Asp His
                165                 170                 175

Phe Thr Arg Gly Asn Cys Arg Phe Pro Asn Cys Leu Arg Ser His Asn
            180                 185                 190

Leu Met Asp Arg Lys Val Leu Ala Ile Met Arg Glu His Gly Leu Asn
        195                 200                 205

Pro Asp Val Val Gln Asn Ile Gln Asp Ile Cys Asn Ser Lys His Met
    210                 215                 220

Gln Lys Asn Pro Pro Gly Pro Arg Ala Pro Ser Ser His Arg Arg Asn
225                 230                 235                 240

Met Ala Tyr Arg Ala Arg Ser Lys Ser Arg Asp Arg Phe Phe Gln Gly
                245                 250                 255

Ser Gln Glu Phe Leu Ala Ser Ala Ser Ala Ser Ala Glu Arg Ser Cys
            260                 265                 270

Thr Pro Ser Pro Asp Gln Ile Ser His Arg Ala Ser Leu Glu Asp Ala
        275                 280                 285

Pro Val Asp Asp Leu Thr Arg Lys Phe Thr Tyr Leu Gly Ser Gln Asp
    290                 295                 300

Arg Ala Arg Pro Pro Ser Gly Ser Ser Lys Ala Thr Asp Leu Gly Gly
305                 310                 315                 320

Thr Ser Gln Ala Gly Thr Ser Gln Arg Phe Leu Glu Asn Gly Ser Gln
                325                 330                 335
```

Glu Asp Leu Leu His Gly Asn Pro Gly Ser Thr Tyr Leu Ala Ser Asn
        340                 345                 350

Ser Thr Ser Ala Pro Asn Trp Lys Ser Leu Thr Ser Trp Thr Asn Asp
    355                 360                 365

Gln Gly Ala Arg Arg Lys Thr Val Phe Ser Pro Thr Leu Pro Ala Ala
370                 375                 380

Arg Ser Ser Leu Gly Ser Leu Gln Thr Pro Glu Ala Val Thr Thr Arg
385                 390                 395                 400

Lys Gly Thr Gly Leu Leu Ser Ser Asp Tyr Arg Ile Ile Asn Gly Lys
                405                 410                 415

Ser Gly Thr Gln Asp Ile Gln Pro Gly Pro Leu Phe Asn Asn Asn Ala
            420                 425                 430

Asp Gly Val Ala Thr Asp Ile Thr Ser Thr Arg Ser Leu Asn Tyr Lys
        435                 440                 445

Ser Thr Ser Ser Gly His Arg Glu Ile Ser Ser Pro Arg Ile Gln Asp
    450                 455                 460

Ala Gly Pro Ala Ser Arg Asp Val Gln Ala Thr Gly Arg Ile Ala Asp
465                 470                 475                 480

Asp Ala Asp Pro Arg Val Ala Leu Val Asn Asp Ser Leu Ser Asp Val
                485                 490                 495

Thr Ser Thr Thr Ser Ser Arg Val Asp Asp His Asp Ser Glu Glu Ile
            500                 505                 510

Cys Leu Asp His Leu Cys Lys Gly Cys Pro Leu Asn Gly Ser Cys Ser
        515                 520                 525

Lys Val His Phe His Leu Pro Tyr Arg Trp Gln Met Leu Ile Gly Lys
    530                 535                 540

Thr Trp Thr Asp Phe Glu His Met Glu Thr Ile Glu Lys Gly Tyr Cys
545                 550                 555                 560

Asn Pro Gly Ile His Leu Cys Ser Val Gly Ser Tyr Thr Ile Asn Phe
                565                 570                 575

Arg Val Met Ser Cys Asp Ser Phe Pro Ile Arg Arg Leu Ser Thr Pro
            580                 585                 590

Ser Ser Val Thr Lys Pro Ala Asn Ser Val Phe Thr Thr Lys Trp Ile
        595                 600                 605

Trp Tyr Trp Lys Asn Glu Ser Gly Thr Trp Ile Gln Tyr Gly Glu Glu
    610                 615                 620

Lys Asp Lys Arg Lys Asn Ser Asn Val Asp Ser Ser Tyr Leu Glu Ser
625                 630                 635                 640

Leu Tyr Gln Ser Cys Pro Arg Gly Val Val Pro Phe Gln Ala Gly Ser
                645                 650                 655

Arg Asn Tyr Glu Leu Ser Phe Gln Gly Met Ile Gln Thr Asn Ile Ala
            660                 665                 670

Ser Lys Thr Gln Lys Asp Val Ile Arg Arg Pro Thr Phe Val Pro Gln
        675                 680                 685

Trp Tyr Val Gln Gln Met Lys Arg Gly Pro Glu
    690                 695

<210> SEQ ID NO 20
<211> LENGTH: 3784
<212> TYPE: DNA
<213> ORGANISM: Mus musculus

<400> SEQUENCE: 20
actctcctca ggctcatcaa aactccaccc gagcctcacg aacgtccttc cttcctctct    60

```
tcctggtagc agccttgcag tcccgagctc gggggacctc acgtctagcc tggaaccgag    120
ggtaccgcgc cgcggcggac ctgcccgcct aacgtcgctc gcttcccatt cgctctcccg    180
cgcggctgac tttaaatctg accccaggac ctcgtcgtcg aggtcgggcc tcgcgacacc    240
accgccggag ttggaaagcg aaaccgctct gctctgcgag cggcaccgcc cgcgtccgcc    300
cctgggaccg cgcgtaagtt tcgattctcc gtgaagccga gtcccgcgca gcggccggag    360
cagcggcagc catagcgcgc catgacggat cccgaggtat tctgtttcat caccaagatc    420
ctgtgcgctc acggggccg catgaccctg aggaactgc tgggtgagat cagcctcccc    480
gaagcgcaac tctacgagct gctgaaggca gcagggcccg atcgctttgt gctattggag    540
actggagacc aggccgggat cactcggtcg gtggtggcta ctactcgagc ccgcgtctgc    600
cgtcgcaagt actgccagag accctgcgac agcctgcacc tttgcaagct taatctgctc    660
ggccggtgcc actatgcaca gtcccagcgg aacctctgca atatattctca cgatgttctc    720 tcggaacaga acttccaggt cctgaagaat catgagctct ccgggcttaa ccaagaggag    780
ctggcggtcc tcctggtcca aagcgaccct ttcttcatgc ctgagatatg caagagttac    840
aaaggagagg ccgcaaaca gatctgcggg cagccgcagc cctgcgagag actccacatc    900
tgtgagcact caccccgggg caactgcagt tacctcaact gtctcaggtc tcataacctg    960
atggacagga aggtgttggc catcatgagg gagcatgggc tgagttctga tgtggtccag   1020
aacatccagg atatctgcaa caacaaacac actcggagga accccctag catgagagct   1080 ccccacccac atcgcagagg cggggcacac agggacagaa gcaaaagcag agaccgcttc   1140
catcacaaca gtctagaggt tctctcaacg gtctcacctc tgggatctgg tcccctagc    1200 ccagatgtca ccggctgtaa ggatccctg gaggatgtgt ctgcagatgt cacccagaag   1260
ttcaagtacc tggggactca ggaccgtgca cagctttcct ccgtctcatc taaggccgct   1320
ggtgtccgag acccagtca atgagagca agccaggagt ttttggagga tggggatcca   1380
gatggcttgt tttctaggaa tcgttctgat tcgtccacaa gtcgaacctc tgctgctggc   1440
tttcctctcg ttgcggcaca agaaatgaa gctggggcca tgaaaatggg catgccttca   1500
ggacaccacg tcgaggtcaa gggcaagaac gaggacattg atcgcgtccc gttttaaat   1560 agttatattg atggggtaac aatggaagaa gcaacagtct caggaattct aggtaaaagg   1620
gccacagaca acgtctgga agaaatgata ctatctagca accatcagaa gagtgtggct   1680
aagacccagg atccccagac cgctggcaga atcactgaca gtggccaaga cacggcattc   1740
ctgcatagta aatatgaaga aaacccagcg tggccaggta catctaccca taacggccca   1800 aatggctta gtcaaattat ggatgaaacg cctaatgtct ctaaaagtag tcccactggt   1860
tttggcataa aatcagcagt cactggagga aagaagcag tctattctgg agttcagagt   1920
ctgagaagcc atgtcctggc tatgcctggg gagaccacta ctcctgtaca gggcagcaat   1980
aggctgcctc cgtcacctct gtcttcttcc acaagccaca gagttgcagc ctctgggagc   2040
cctggcaaga gctccaccca tgcctctgtg agccagcca gtgagccctc gaggatgatg   2100
atgatgatgt cagaccctgc tgagtattcc ctatgctaca tcgtaaatcc tgtatctcct   2160
aggatggatg atcatggcct gaaggaaatc tgtctggatc atctgtacag gggctgtcag   2220
caggtcaact gcaacaagaa ccacttccat ctgccctacc ggtggcagct gttcatattg   2280
cccacttgga tggactttca ggacatggag tatatcgagc gggcctattg tgatccccaa   2340
attgaaatca ttgtgataga aaaacatcgg atcaatttca agaaaatgac ttgtgattcc   2400
taccccatcc gtcgcctctc cactccttca tttgtcgaaa aaacacttaa ttctgtcttc   2460
```

```
accaccaagt ggctttggta ttggaggaat gaattgaatg aatatactca gtatgggcat    2520
gagagcccaa gccataccag ctccgaaatt aattctgcat acctggagtc tttcttccac    2580
tcctgtccca ggggagtttt gcagttccac gctggttcac agaattacga gttaagcttt    2640
caagggatga ttcagacgaa atatagcttcc aagactcaaa ggcatgttgt gagaaggcca    2700 gttttttgttt cttcgaagga tgtggagcag aagagaagag gtccagacca tcagccagtg    2760
atgccccagg cagatgctct gaccctgttt tcttctcccc agaggaatgc tagcactgtt    2820
tcttctaacg aatatgagtt tatagagctc aataaccagg atgaggagta tgccaaaata    2880
agtgaacagt ttaaagcatc catgaaacaa ttcaagattg tgacgataaa gaggatatgg    2940
aaccagaagc tctgggacac ttttgagaga aagaagcaaa agatgaaaaa caagactgag    3000
atgttcctat ttcacgcggt gggccggatt catatggatt acatctgtaa gaataatttc    3060
gagtggatcc tacatggaaa ccgggagatc agatatggaa aaggtttgtg ctggaggaga    3120
gagaactgtg actccagcca tgcgcatggt ttccttgaga tgcccttggc atcacttggt    3180
agaactgcat ctctggactc cagtggcctt cagagaaaat aagctgagtt accttgttag    3240
gacagctcca ttgtcttgag ggtgctttgc cttggcccta gggctccttg tctgtttgtc    3300
tttttctctg ggaacaactc aagatcttcc tatttgtaaa ctgttccgtc tgctggctat    3360
gttctctgcc attgctgttt actagagatg gcttttcctg atcgctgtct gtggctgcag    3420
agctattcaa agtagctttc taattaatgc cactgatggt tccaggggag agtggggaga    3480
agcccgttct catctcaggg ctctgccctc acacagaatg cttttttttt tatgaaccct    3540
tcattctttg tgggtgttta aggaataaga tatggtcaga cctgacagtg caggcttagg    3600
aggccgaggc aggaagattt atttagtcca aggctagtgt gtactacaaa gctagctcaa    3660
agctagccac aacaacttag taagaccaag tcttaaaata gaaagaaaaa aggttggggc    3720
tatttcttaa tggtagaggc ctggtctagc ctgagagagg ccccacaggt ttagctacag    3780
tacc                                                                3784
```

<210> SEQ ID NO 21
<211> LENGTH: 946
<212> TYPE: PRT
<213> ORGANISM: Mus musculus

<400> SEQUENCE: 21

```
Met Thr Asp Pro Glu Val Phe Cys Phe Ile Thr Lys Ile Leu Cys Ala
1               5                   10                  15

His Gly Gly Arg Met Thr Leu Glu Glu Leu Leu Gly Glu Ile Ser Leu
            20                  25                  30

Pro Glu Ala Gln Leu Tyr Glu Leu Leu Lys Ala Ala Gly Pro Asp Arg
        35                  40                  45

Phe Val Leu Leu Glu Thr Gly Asp Gln Ala Gly Ile Thr Arg Ser Val
    50                  55                  60

Val Ala Thr Thr Arg Ala Arg Val Cys Arg Arg Lys Tyr Cys Gln Arg
65                  70                  75                  80

Pro Cys Asp Ser Leu His Leu Cys Lys Leu Asn Leu Leu Gly Arg Cys
                85                  90                  95

His Tyr Ala Gln Ser Gln Arg Asn Leu Cys Lys Tyr Ser His Asp Val
            100                 105                 110

Leu Ser Glu Gln Asn Phe Gln Val Leu Lys Asn His Glu Leu Ser Gly
        115                 120                 125
```

Leu Asn Gln Glu Glu Leu Ala Val Leu Leu Val Gln Ser Asp Pro Phe
130                 135                 140

Phe Met Pro Glu Ile Cys Lys Ser Tyr Lys Gly Glu Gly Arg Lys Gln
145                 150                 155                 160

Ile Cys Gly Gln Pro Gln Pro Cys Glu Arg Leu His Ile Cys Glu His
                165                 170                 175

Phe Thr Arg Gly Asn Cys Ser Tyr Leu Asn Cys Leu Arg Ser His Asn
                180                 185                 190

Leu Met Asp Arg Lys Val Leu Ala Ile Met Arg Glu His Gly Leu Ser
            195                 200                 205

Ser Asp Val Val Gln Asn Ile Gln Asp Ile Cys Asn Asn Lys His Thr
210                 215                 220

Arg Arg Asn Pro Pro Ser Met Arg Ala Pro His Pro His Arg Arg Gly
225                 230                 235                 240

Gly Ala His Arg Asp Arg Ser Lys Ser Arg Asp Arg Phe His His Asn
                245                 250                 255

Ser Leu Glu Val Leu Ser Thr Val Ser Pro Leu Gly Ser Gly Pro Pro
                260                 265                 270

Ser Pro Asp Val Thr Gly Cys Lys Asp Pro Leu Glu Asp Val Ser Ala
                275                 280                 285

Asp Val Thr Gln Lys Phe Lys Tyr Leu Gly Thr Gln Asp Arg Ala Gln
                290                 295                 300

Leu Ser Ser Val Ser Ser Lys Ala Ala Gly Val Arg Gly Pro Ser Gln
305                 310                 315                 320

Met Arg Ala Ser Gln Glu Phe Leu Glu Asp Gly Asp Pro Asp Gly Leu
                325                 330                 335

Phe Ser Arg Asn Arg Ser Asp Ser Ser Thr Ser Arg Thr Ser Ala Ala
                340                 345                 350

Gly Phe Pro Leu Val Ala Ala Gln Arg Asn Glu Ala Gly Ala Met Lys
                355                 360                 365

Met Gly Met Pro Ser Gly His His Val Glu Val Lys Gly Lys Asn Glu
                370                 375                 380

Asp Ile Asp Arg Val Pro Phe Leu Asn Ser Tyr Ile Asp Gly Val Thr
385                 390                 395                 400

Met Glu Glu Ala Thr Val Ser Gly Ile Leu Gly Lys Arg Ala Thr Asp
                405                 410                 415

Asn Gly Leu Glu Glu Met Ile Leu Ser Ser Asn His Gln Lys Ser Val
                420                 425                 430

Ala Lys Thr Gln Asp Pro Gln Thr Ala Gly Arg Ile Thr Asp Ser Gly
                435                 440                 445

Gln Asp Thr Ala Phe Leu His Ser Lys Tyr Glu Glu Asn Pro Ala Trp
                450                 455                 460

Pro Gly Thr Ser Thr His Asn Gly Pro Asn Gly Phe Ser Gln Ile Met
465                 470                 475                 480

Asp Glu Thr Pro Asn Val Ser Lys Ser Ser Pro Thr Gly Phe Gly Ile
                485                 490                 495

Lys Ser Ala Val Thr Gly Gly Lys Glu Ala Val Tyr Ser Gly Val Gln
                500                 505                 510

Ser Leu Arg Ser His Val Leu Ala Met Pro Gly Glu Thr Thr Thr Pro
                515                 520                 525

Val Gln Gly Ser Asn Arg Leu Pro Pro Ser Pro Leu Ser Ser Ser Thr
530                 535                 540

Ser His Arg Val Ala Ala Ser Gly Ser Pro Gly Lys Ser Ser Thr His

-continued

```
            545                 550                 555                 560
        Ala Ser Val Ser Pro Ala Ser Glu Pro Ser Arg Met Met Met Met
                        565                 570                 575

Ser Asp Pro Ala Glu Tyr Ser Leu Cys Tyr Ile Val Asn Pro Val Ser
                        580                 585                 590

Pro Arg Met Asp Asp His Gly Leu Lys Glu Ile Cys Leu Asp His Leu
                        595                 600                 605

Tyr Arg Gly Cys Gln Gln Val Asn Cys Asn Lys Asn His Phe His Leu
                        610                 615                 620

Pro Tyr Arg Trp Gln Leu Phe Ile Leu Pro Thr Trp Met Asp Phe Gln
        625                 630                 635                 640

Asp Met Glu Tyr Ile Glu Arg Ala Tyr Cys Asp Pro Gln Ile Glu Ile
                            645                 650                 655

Ile Val Ile Glu Lys His Arg Ile Asn Phe Lys Lys Met Thr Cys Asp
                        660                 665                 670

Ser Tyr Pro Ile Arg Arg Leu Ser Thr Pro Ser Phe Val Glu Lys Thr
                        675                 680                 685

Leu Asn Ser Val Phe Thr Thr Lys Trp Leu Trp Tyr Trp Arg Asn Glu
                        690                 695                 700

Leu Asn Glu Tyr Thr Gln Tyr Gly His Glu Ser Pro Ser His Thr Ser
        705                 710                 715                 720

Ser Glu Ile Asn Ser Ala Tyr Leu Glu Ser Phe Phe His Ser Cys Pro
                        725                 730                 735

Arg Gly Val Leu Gln Phe His Ala Gly Ser Gln Asn Tyr Glu Leu Ser
                        740                 745                 750

Phe Gln Gly Met Ile Gln Thr Asn Ile Ala Ser Lys Thr Gln Arg His
                        755                 760                 765

Val Val Arg Arg Pro Val Phe Val Ser Ser Lys Asp Val Glu Gln Lys
                        770                 775                 780

Arg Arg Gly Pro Asp His Gln Pro Val Met Pro Gln Ala Asp Ala Leu
        785                 790                 795                 800

Thr Leu Phe Ser Ser Pro Gln Arg Asn Ala Ser Thr Val Ser Ser Asn
                        805                 810                 815

Glu Tyr Glu Phe Ile Glu Leu Asn Asn Gln Asp Glu Glu Tyr Ala Lys
                        820                 825                 830

Ile Ser Glu Gln Phe Lys Ala Ser Met Lys Gln Phe Lys Ile Val Thr
                        835                 840                 845

Ile Lys Arg Ile Trp Asn Gln Lys Leu Trp Asp Thr Phe Glu Arg Lys
                        850                 855                 860

Lys Gln Lys Met Lys Asn Lys Thr Glu Met Phe Leu Phe His Ala Val
        865                 870                 875                 880

Gly Arg Ile His Met Asp Tyr Ile Cys Lys Asn Asn Phe Glu Trp Ile
                        885                 890                 895

Leu His Gly Asn Arg Glu Ile Arg Tyr Gly Lys Gly Leu Cys Trp Arg
                        900                 905                 910

Arg Glu Asn Cys Asp Ser Ser His Ala His Gly Phe Leu Glu Met Pro
                        915                 920                 925

Leu Ala Ser Leu Gly Arg Thr Ala Ser Leu Asp Ser Ser Gly Leu Gln
                        930                 935                 940

Arg Lys
        945

<210> SEQ ID NO 22
```

```
<211> LENGTH: 3396
<212> TYPE: DNA
<213> ORGANISM: Mus musculus

<400> SEQUENCE: 22
actctcctca ggctcatcaa aactccaccc gagcctcacg aacgtcctta cttcctctct    60
tcctggtagc agccttgcag tcccgagctc gggggacctc acgtctagcc tggaaccgag   120
ggtaccgcgc cgcggcggac ctgcccgcct aacgtcgctc gcttcccatt cgctctcccg   180
cgcggctgac tttaaatctg accccaggac ctcgtcgtcg aggtcgggcc tcgcgacacc   240
accgccggag ttggaaagcg aaaccgctct gctctgcgag cggcaccgcc cgcgtccgcc   300
cctgggaccg cgcgtaagtt tcgattctcc gtgaagccga gtcccgcgca gcggccggag   360
cagcggcagc catagcgcgc catgacggat cccgaggtat tctgtttcat caccaagatc   420
ctgtgcgctc acggggccg catgaccctg aggaactgc tgggtgagat cagcctcccc    480
gaagcgcaac tctacgagct gctgaaggca gcagggcccg atcgctttgt gctattggag   540
actggagacc aggccgggat cactcggtcg gtggtggcta ctactcgagc ccgcgtctgc   600
cgtcgcaagt actgccagag accctgcgac agcctgcacc tttgcaagct taatctgctc   660
ggccggtgcc actatgcaca gtcccagcgg aacctctgca aatattctca cgatgttctc   720
tcggaacaga acttccaggt cctgaagaat catgagctct ccgggcttaa ccaagaggag   780
ctggcggtcc tcctggtcca aagcgaccct ttcttcatgc ctgagatatg caagagttac   840
aaaggagagg gccgcaaaca gatctgcggg cagccgcagc cctgcgagag actccacatc   900
tgtgagcact tcaccggggg caactgcagt tacctcaact gtctcaggtc tcataacctg   960
atggacagga aggtgttggc catcatgagg gagcatgggc tgagttctga tgtggtccag  1020
aacatccagg atatctgcaa caacaaacac actcggagga accccctag catgagagct   1080 cccccacccac atcgcagagg cggggcacac agggacagaa gcaaaagcag agaccgcttc  1140
catcacaaca gtctagaggt tctctcaacg gtctcacctc tgggatctgg tccccctagc   1200
ccagatgtca ccggctgtaa ggatcccctg gaggatgtgt ctgcagatgt cacccagaag  1260
ttcaagtacc tggggactca ggaccgtgca cagctttcct ccgtctcatc taaggccgct  1320
ggtgtccgag acccagtca atgagagca agccaggagt ttttggagga tggggatcca    1380
gatggcttgt tttctaggaa tcgttctgat tcgtccacaa gtcgaacctc tgctgctggc  1440
tttcctctcg ttgcggcaca agaaatgaa gctggggcca tgaaaatggg catgccttca   1500
ggacaccacg tcgaggtcaa gggcaagaac gaggacattg atcgcgtccc gttttaaat   1560 agttatattg atggggtaac aatggaagaa gcaacagtct caggaattct aggtaaaagg  1620
gccacagaca acggtctgga agaaatgata ctatctagca accatcagaa gagtgtggct  1680
aagacccagg atccccagac cgctggcaga atcactgaca gtggccaaga cacggcattc  1740
ctgcatagta aatatgaaga aaacccagcg tggccaggta catctaccca taacggccca  1800 aatggctta gtcaaattat ggatgaaacg cctaatgtct ctaaaagtag tcccactggt   1860
tttggcataa aatcagcagt cactggagga aaagaagcag tctattctgg agttcagagt  1920
ctgagaagcc atgtcctggc tatgcctggg agaccacta ctcctgtaca gggcagcaat    1980
aggctgcctc cgtcacctct gtcttcttcc acaagccaca gagttgcagc ctctgggagc  2040
cctggcaaga gctccacccca tgcctctgtg agcccagcca gtgagccctc gaggatgatg  2100
atgatgatgt cagaccctgc tgagtattcc ctatgctaca tcgtaaatcc tgtatctcct  2160
aggatggatg atcatggcct gaaggaaatc tgtctggatc atctgtacag gggctgtcag  2220
```

```
caggtcaact gcaacaagaa ccacttccat ctgccctacc ggtggcagct gttcatattg    2280
cccacttgga tggactttca ggacatggag tatatcgagc gggcctattg tgatccccaa    2340
attgaaatca ttgtgataga aaaacatcgg atcaatttca agaaaatgac ttgtgattcc    2400
taccccatcc gtcgcctctc cactccttca tttgtcgaaa aaacacttaa ttctgtcttc    2460
accaccaagt ggctttggta ttggaggaat gaattgaatg aatatactca gtatgggcat    2520
gagagcccaa gccataccag ctccgaaatt aattctgcat acctggagtc tttcttccac    2580
tcctgtccca ggggagtttt gcagttccac gctggttcac agaattacga gttaagcttt    2640
caagggatga ttcagacgaa tatagcttcc aagactcaaa ggcatgttgt gagaaggcca    2700
gtttttgttt cttcgaagga tgtggagcag aagagaagag gtccagagta agtgttcagc    2760
agctgttagc tcaggccatg atcttgctgc gtcatgctgc gtcatgctgt gtcatgcatc    2820
tggaggtctg tgttcttggg aagttcctgc ctctgtctta ctgtagtttc tgtttgattt    2880
atctatgagt aaggaaattg ttaagcagtg tgacataact gaaagtttcc tggccagggg    2940
actagggagt gcaagcactt ggttaagctt tgtgtaacag atacaaggcc ttgggtttag    3000
agtgtaggag gaagggatgc tataccatga aaccagcatc cgcctttagc ttacaggcta    3060
tttagctgct cgctctcatc tgcactctgg gccttacttg ctccagctgc gactggctgg    3120
atcaaggagt gtacaagtgt atacactgga tttttgtttt gttggggtc ctctctgtgt    3180 ctttggttgt gctgagagga caggaggctg agaaagaggc ttaagttagt agcctgggga    3240
aagagctgga gagatgaagt tcactaaagg cattggtgtt agatttaatc gacttgtaat    3300
cattgtaccc atggggcatt tcaaggtggg ttttgctgtg gggaattcat tgtaacttgc    3360
ctgtctctat gaaactcagt aaaatctcat tgttcg                              3396
```

<210> SEQ ID NO 23
<211> LENGTH: 789
<212> TYPE: PRT
<213> ORGANISM: Mus musculus

<400> SEQUENCE: 23

```
Met Thr Asp Pro Glu Val Phe Cys Phe Ile Thr Lys Ile Leu Cys Ala
1               5                   10                  15

His Gly Gly Arg Met Thr Leu Glu Glu Leu Leu Gly Glu Ile Ser Leu
            20                  25                  30

Pro Glu Ala Gln Leu Tyr Glu Leu Leu Lys Ala Ala Gly Pro Asp Arg
        35                  40                  45

Phe Val Leu Leu Glu Thr Gly Asp Gln Ala Gly Ile Thr Arg Ser Val
    50                  55                  60

Val Ala Thr Thr Arg Ala Arg Val Cys Arg Arg Lys Tyr Cys Gln Arg
65                  70                  75                  80

Pro Cys Asp Ser Leu His Leu Cys Lys Leu Asn Leu Leu Gly Arg Cys
                85                  90                  95

His Tyr Ala Gln Ser Gln Arg Asn Leu Cys Lys Tyr Ser His Asp Val
            100                 105                 110

Leu Ser Glu Gln Asn Phe Gln Val Leu Lys Asn His Glu Leu Ser Gly
        115                 120                 125

Leu Asn Gln Glu Glu Leu Ala Val Leu Leu Val Gln Ser Asp Pro Phe
    130                 135                 140

Phe Met Pro Glu Ile Cys Lys Ser Tyr Lys Gly Glu Gly Arg Lys Gln
145                 150                 155                 160
```

```
Ile Cys Gly Gln Pro Gln Pro Cys Glu Arg Leu His Ile Cys Glu His
            165                 170                 175

Phe Thr Arg Gly Asn Cys Ser Tyr Leu Asn Cys Leu Arg Ser His Asn
            180                 185                 190

Leu Met Asp Arg Lys Val Leu Ala Ile Met Arg Glu His Gly Leu Ser
            195                 200                 205

Ser Asp Val Val Gln Asn Ile Gln Asp Ile Cys Asn Asn Lys His Thr
            210                 215                 220

Arg Arg Asn Pro Pro Ser Met Arg Ala Pro His Pro His Arg Arg Gly
225                 230                 235                 240

Gly Ala His Arg Asp Arg Ser Lys Ser Arg Asp Arg Phe His His Asn
            245                 250                 255

Ser Leu Glu Val Leu Ser Thr Val Ser Pro Leu Gly Ser Gly Pro Pro
            260                 265                 270

Ser Pro Asp Val Thr Gly Cys Lys Asp Pro Leu Glu Asp Val Ser Ala
            275                 280                 285

Asp Val Thr Gln Lys Phe Lys Tyr Leu Gly Thr Gln Asp Arg Ala Gln
            290                 295                 300

Leu Ser Ser Val Ser Ser Lys Ala Ala Gly Val Arg Gly Pro Ser Gln
305                 310                 315                 320

Met Arg Ala Ser Gln Glu Phe Leu Glu Asp Gly Asp Pro Asp Gly Leu
            325                 330                 335

Phe Ser Arg Asn Arg Ser Asp Ser Ser Thr Ser Arg Thr Ser Ala Ala
            340                 345                 350

Gly Phe Pro Leu Val Ala Ala Gln Arg Asn Glu Ala Gly Ala Met Lys
            355                 360                 365

Met Gly Met Pro Ser Gly His His Val Glu Val Lys Gly Lys Asn Glu
            370                 375                 380

Asp Ile Asp Arg Val Pro Phe Leu Asn Ser Tyr Ile Asp Gly Val Thr
385                 390                 395                 400

Met Glu Glu Ala Thr Val Ser Gly Ile Leu Gly Lys Arg Ala Thr Asp
            405                 410                 415

Asn Gly Leu Glu Glu Met Ile Leu Ser Ser Asn His Gln Lys Ser Val
            420                 425                 430

Ala Lys Thr Gln Asp Pro Gln Thr Ala Gly Arg Ile Thr Asp Ser Gly
            435                 440                 445

Gln Asp Thr Ala Phe Leu His Ser Lys Tyr Glu Glu Asn Pro Ala Trp
            450                 455                 460

Pro Gly Thr Ser Thr His Asn Gly Pro Asn Gly Phe Ser Gln Ile Met
465                 470                 475                 480

Asp Glu Thr Pro Asn Val Ser Lys Ser Ser Pro Thr Gly Phe Gly Ile
            485                 490                 495

Lys Ser Ala Val Thr Gly Gly Lys Glu Ala Val Tyr Ser Gly Val Gln
            500                 505                 510

Ser Leu Arg Ser His Val Leu Ala Met Pro Gly Glu Thr Thr Thr Pro
            515                 520                 525

Val Gln Gly Ser Asn Arg Leu Pro Pro Ser Pro Leu Ser Ser Ser Thr
            530                 535                 540

Ser His Arg Val Ala Ala Ser Gly Ser Pro Gly Lys Ser Ser Thr His
545                 550                 555                 560

Ala Ser Val Ser Pro Ala Ser Glu Pro Ser Arg Met Met Met Met Met
            565                 570                 575

Ser Asp Pro Ala Glu Tyr Ser Leu Cys Tyr Ile Val Asn Pro Val Ser
```

```
                     580             585              590
Pro Arg Met Asp Asp His Gly Leu Lys Glu Ile Cys Leu Asp His Leu
            595                 600                 605

Tyr Arg Gly Cys Gln Gln Val Asn Cys Asn Lys Asn His Phe His Leu
        610                 615                 620

Pro Tyr Arg Trp Gln Leu Phe Ile Leu Pro Thr Trp Met Asp Phe Gln
625                 630                 635                 640

Asp Met Glu Tyr Ile Glu Arg Ala Tyr Cys Asp Pro Gln Ile Glu Ile
                645                 650                 655

Ile Val Ile Glu Lys His Arg Ile Asn Phe Lys Lys Met Thr Cys Asp
            660                 665                 670

Ser Tyr Pro Ile Arg Arg Leu Ser Thr Pro Ser Phe Val Glu Lys Thr
        675                 680                 685

Leu Asn Ser Val Phe Thr Thr Lys Trp Leu Trp Tyr Trp Arg Asn Glu
            690                 695                 700

Leu Asn Glu Tyr Thr Gln Tyr Gly His Glu Ser Pro Ser His Thr Ser
705                 710                 715                 720

Ser Glu Ile Asn Ser Ala Tyr Leu Glu Ser Phe His Ser Cys Pro
                725                 730                 735

Arg Gly Val Leu Gln Phe His Ala Gly Ser Gln Asn Tyr Glu Leu Ser
            740                 745                 750

Phe Gln Gly Met Ile Gln Thr Asn Ile Ala Ser Lys Thr Gln Arg His
            755                 760                 765

Val Val Arg Arg Pro Val Phe Val Ser Ser Lys Asp Val Glu Gln Lys
770                 775                 780

Arg Arg Gly Pro Glu
785

<210> SEQ ID NO 24
<211> LENGTH: 5274
<212> TYPE: DNA
<213> ORGANISM: Mus musculus

<400> SEQUENCE: 24
actctcctca ggctcatcaa aactccaccc gagcctcacg aacgtcctta cttcctctct      60
tcctggtagc agccttgcag tcccgagctc gggggacctc acgtctagcc tggaaccgag     120
ggtaccgcgc cgcggcggac ctgcccgcct aacgtcgctc gcttcccatt cgctctcccg     180
cgcggctgac tttaaatctg accccaggac ctcgtcgtcg aggtcgggcc tcgcgacacc     240
accgccggag ttggaaagcg aaaccgctct gctctgcgag cggcaccgcc cgcgtccgcc     300
cctgggaccg cgcgtaagtt tcgattctcc gtgaagccga gtcccgcgca gcggccggag     360
cagcggcagc catagcgcgc catgacggat cccgaggtat tctgtttcat caccaagatc     420
ctgtgcgctc acggggccg  catgaccctg aggaactgc  tgggtgagat cagcctcccc     480
gaagcgcaac tctacgagct gctgaaggca gcagggcccg atcgctttgt gctattggag     540
actggagacc aggccgggat cactcggtcg gtggtggcta ctactcgagc ccgcgtctgc     600
cgtcgcaagt actgccagag accctgcgac agcctgcacc tttgcaagct taatctgctc     660
ggccggtgcc actatgcaca gtcccagcgg aactctgcaa atattctca  cgatgttctc     720 tcggaacaga acttccaggt cctgaagaat catgagctct ccgggcttaa ccaagaggag     780
ctggcggtcc tcctggtcca aagcgaccct tcttcatgc  ctgagatatg caagagttac     840
aaaggagagg gccgcaaaca gatctgcggg cagccgcagc cctgcgagag actccacatc     900
```

```
tgtgagcact tcacccgggg caactgcagt tacctcaact gtctcaggtc tcataacctg    960
atggacagga aggtgttggc catcatgagg gagcatgggc tgagttctga tgtggtccag   1020
aacatccagg atatctgcaa caacaaacac actcggagga accccctag catgagagct    1080
ccccacccac atcgcagagg cggggcacac agggacagaa gcaaaagcag agaccgcttc   1140
catcacaaca gtctagaggt tctctcaacg gtctcacctc tgggatctgg tccccctagc   1200
ccagatgtca ccggctgtaa ggatcccctg gaggatgtgt ctgcagatgt cacccagaag   1260
ttcaagtacc tggggactca ggaccgtgca cagctttcct ccgtctcatc taaggccgct   1320
ggtgtccgag acccagtcaa atgagagcaa gccaggagt ttttggagga tggggatcca    1380
gatggcttgt tttctaggaa tcgttctgat tcgtccacaa gtcgaacctc tgctgctggc   1440
tttcctctcg ttgcggcaca agaaatgaa gctggggcca tgaaaatggg catgccttca    1500
ggacaccacg tcgaggtcaa gggcaagaac gaggacattg atcgcgtccc gttttaaat    1560
agttatattg atggggtaac aatgaagaa gcaacagtct caggaattct aggtaaaagg    1620
gccacagaca acggtctgga agaaatgata ctatctagca accatcagaa gagtgtggct   1680
aagacccagg atccccagac cgctggcaga atcactgaca gtggccaaga cacggcattc   1740
ctgcatagta aatatgaaga aaacccagcg tggccaggta catctaccca taacggccca   1800
aatggcttta gtcaaattat ggatgaaacg cctaatgtct ctaaaagtag tcccactggt   1860
tttggcataa aatcagcagt cactggagga aagaagcag tctattctgg agttcagagt    1920
ctgagaagcc atgtcctggc tatgcctggg gagaccacta ctcctgtaca gggcagcaat   1980
aggctgcctc cgtcacctct gtcttcttcc acaagccaca gagttgcagc ctctgggagc   2040
cctggcaaga gctccaccca tgcctctgtg agcccagcca gtgagccctc gaggatgatg   2100
atgatgatgt cagaccctgc tgagtattcc ctatgctaca tcgtaaatcc tgtatctcct   2160
aggatggatg atcatggcct gaaggaaatc tgtctggatc atctgtacag gggctgtcag   2220
caggtcaact gcaacaagaa ccacttccat ctgccctacc ggtggcagct gttcatattg   2280
cccacttgga tggactttca ggacatggag tatatcgagc gggcctattg tgatccccaa   2340
attgaaatca ttgtgataga aaacatcgg atcaatttca agaaaatgac ttgtgattcc    2400
taccccatcc gtcgcctctc cactccttca tttgtcgaaa aaacacttaa ttctgtcttc   2460
accaccaagt ggctttggta ttggaggaat gaattgaatg aatatactca gtatgggcat   2520
gagagcccaa gccataccag ctccgaaatt aattctgcat acctggagtc tttcttccac   2580
tcctgtccca ggggagtttt gcagttccac gctggttcac agaattacga gttaagcttt   2640
caagggatga ttcagacgaa tatagcttcc aagactcaaa ggcatgttgt gagaaggcca   2700
gttttttgttt cttcgaagga tgtggagcag aagagaagag gtccagacca tcagccagtg   2760
atgccccagg cagatgctct gaccctgttt tcttctcccc agaggaatgc tagcactgtt   2820
tcttctaacg aatatgagtt tatagagctc aataaccagg atgaggagta tgccaaaata   2880
agtgaacagt ttaaagcatc catgaaacaa ttcaagattg tgacgataaa gaggatatgg   2940
aaccagaagc tctgggacac ttttgagaga agaagcaaa agatgaaaaa caagactgag    3000
atgttcctat ttcacgcgt gggccggatt catatggatt acatctgtaa gaataatttc   3060
gagtggatcc tacatggaaa ccgggagatc agatatggaa aaggaaatta ttttacaaaa   3120
gaagccatgt attcacacaa gagttgttca tatgattcca gaggcactgt catgttcgta   3180
gcccgagtcc tggttggaag tgtcattgaa ggaaatatga cattaagtag ccctcccgcg   3240
ctctatgaca gctgtgtgga caccaggctg aatccgtccg tctttgtcat tttccggaaa   3300
```

| | |
|---|---|
| gaacagattt acccagagta tgtgattgag tatatggagt tagagaaaga gaaaggatgc | 3360 |
| ataattagtt agaaaggatg tataccatgc tgaaaccatt ctgttgctat ttaggaccaa | 3420 |
| aacattttca gacagtaggt aggctttttac attcccttgc tccgttacct aacgacttaa | 3480 |
| accagttcct tgcttccccc atccctacac attgttccta agtctgattt tacctcccca | 3540 |
| ataccagcca gtatcaggtg ttcttatagt ccttggcgcc tttgcatcta attcattggt | 3600 |
| tctagacgaa ctattctgtc agttttacc acctagtagg caatacctgt tttgtctaat | 3660 |
| attcaaagtg caattcgcgt ctagattatc cacacaattt cactaattga aaaatatcaa | 3720 |
| atttactatt ataatgtaag agagaaatat aggtcataac ttcggcacga ctttaagtac | 3780 |
| taagcaataa tggagtcgtc agacgcctcc gcttaccgtg aaccagtatg agcttgggag | 3840 |
| aaaggaactg gaagaacatg aaaaagcagg ggcatgtgta gacattagtg aaaattaaca | 3900 |
| atgcacgtta tttgcaaatg tcagcaatta tctgtacatg gtaagaacga aaaatacctt | 3960 |
| cattgaaata aagctacagc acaagacaac ttacagattg tgaaacagcg agaatgaaga | 4020 |
| gctacattct tgcagacgag ctgtaggtcg tacacgaatg tctaaagaga cattcaaaac | 4080 |
| tcgaataggg tgcagagtaa tttcttactg tgaggaattg cccaatgtat ggaaagatgc | 4140 |
| atagttggct ctcacatgct aaatgccagt agcgccctcc ttcgcttgaa gtcatgacaa | 4200 |
| ccacagtccc tactagacct gttcatcttt ttttttttt ttttttttt ttttggtgtt | 4260 |
| tttgagacag ggtttctctg cgtagtccta gctgtcctgg aactcacttt gtagaccagg | 4320 |
| ctggcctcga actcagaaat ccgcctgcct ctgcctcccg agtgctggga ttaaaggcgt | 4380 |
| gcgccaccac gcccggctct gttcatcctt ttaaaggtag atcttttata acatcctttg | 4440 |
| ccaccttgag atgatttata ggtaatataa tctacatttg agtttattca gacttaatttt | 4500 |
| agtgccctac ttgtgttata atggaaactt agaaggtcag aactctgtaa tggacataaa | 4560 |
| ctgttaagta ctcaggcatg actacgctat cagctacgaa acatgttaac tctcactagg | 4620 |
| aatagctttg gcttaagagt ccagcagggg caacttcctg agatgaatga agtacaggaa | 4680 |
| aatgaaagat tagagggatg tgtgacggaa tacagtatta gggttcacca tagcagactc | 4740 |
| tgcgctttat ctgtctatgg tgaaggatag ggcgcaatca ctttaattgt aatgatagat | 4800 |
| aaataagaca ggacaaacta cagtttgtct cagaggaatc caaggattct ttttcagaca | 4860 |
| agttgtaggt cccgcataca tgtccaccag gacattagac agtcgtaaag atgcagaacg | 4920 |
| aacagtttgt gtgtgggact gacccaccca cacacagcag ggcacttgtt ctgcctcagg | 4980 |
| ctgcatctac tcagtgccgt taataaactt tagatacaaa ccaacaacca ccattctcca | 5040 |
| gtatactaca gtgggaatca ctgatctagt taacggcagc actcttggat taattcaatt | 5100 |
| gttatttcta ctctttaaca acagaataag ccagatcctt gactctcaag cccccagttt | 5160 |
| ttaaaaacaa ggtgttcctt gatttataat ccttcttgtt tatgctgtgt tctttgattt | 5220 |
| ataatccttg tttgctcaat aaaagaaaa ataatttga ttcatttgcc ctca | 5274 |

<210> SEQ ID NO 25
<211> LENGTH: 996
<212> TYPE: PRT
<213> ORGANISM: Mus musculus

<400> SEQUENCE: 25

Met Thr Asp Pro Glu Val Phe Cys Phe Ile Thr Lys Ile Leu Cys Ala
1               5                   10                  15

His Gly Gly Arg Met Thr Leu Glu Glu Leu Leu Gly Glu Ile Ser Leu

```
            20                  25                  30
Pro Glu Ala Gln Leu Tyr Glu Leu Leu Lys Ala Ala Gly Pro Asp Arg
        35                  40                  45
Phe Val Leu Leu Glu Thr Gly Asp Gln Ala Gly Ile Thr Arg Ser Val
        50                  55                  60
Val Ala Thr Thr Arg Ala Arg Val Cys Arg Lys Tyr Cys Gln Arg
 65                  70                  75                  80
Pro Cys Asp Ser Leu His Leu Cys Lys Leu Asn Leu Leu Gly Arg Cys
                85                  90                  95
His Tyr Ala Gln Ser Gln Arg Asn Leu Cys Lys Tyr Ser His Asp Val
            100                 105                 110
Leu Ser Glu Gln Asn Phe Gln Val Leu Lys Asn His Glu Leu Ser Gly
            115                 120                 125
Leu Asn Gln Glu Glu Leu Ala Val Leu Val Gln Ser Asp Pro Phe
            130                 135                 140
Phe Met Pro Glu Ile Cys Lys Ser Tyr Lys Gly Glu Gly Arg Lys Gln
145                 150                 155                 160
Ile Cys Gly Gln Pro Gln Pro Cys Glu Arg Leu His Ile Cys Glu His
                165                 170                 175
Phe Thr Arg Gly Asn Cys Ser Tyr Leu Asn Cys Leu Arg Ser His Asn
                180                 185                 190
Leu Met Asp Arg Lys Val Leu Ala Ile Met Arg Glu His Gly Leu Ser
            195                 200                 205
Ser Asp Val Val Gln Asn Ile Gln Asp Ile Cys Asn Asn Lys His Thr
            210                 215                 220
Arg Arg Asn Pro Pro Ser Met Arg Ala Pro His Pro His Arg Arg Gly
225                 230                 235                 240
Gly Ala His Arg Asp Arg Ser Lys Ser Arg Asp Arg Phe His His Asn
                245                 250                 255
Ser Leu Glu Val Leu Ser Thr Val Ser Pro Leu Gly Ser Gly Pro Pro
            260                 265                 270
Ser Pro Asp Val Thr Gly Cys Lys Asp Pro Leu Glu Asp Val Ser Ala
            275                 280                 285
Asp Val Thr Gln Lys Phe Lys Tyr Leu Gly Thr Gln Asp Arg Ala Gln
            290                 295                 300
Leu Ser Ser Val Ser Ser Lys Ala Ala Gly Val Arg Gly Pro Ser Gln
305                 310                 315                 320
Met Arg Ala Ser Gln Glu Phe Leu Glu Asp Gly Asp Pro Asp Gly Leu
                325                 330                 335
Phe Ser Arg Asn Arg Ser Asp Ser Ser Thr Ser Arg Thr Ser Ala Ala
                340                 345                 350
Gly Phe Pro Leu Val Ala Ala Gln Arg Asn Glu Ala Gly Ala Met Lys
                355                 360                 365
Met Gly Met Pro Ser Gly His His Val Glu Val Lys Gly Lys Asn Glu
            370                 375                 380
Asp Ile Asp Arg Val Pro Phe Leu Asn Ser Tyr Ile Asp Gly Val Thr
385                 390                 395                 400
Met Glu Glu Ala Thr Val Ser Gly Ile Leu Gly Lys Arg Ala Thr Asp
                405                 410                 415
Asn Gly Leu Glu Glu Met Ile Leu Ser Ser Asn His Gln Lys Ser Val
            420                 425                 430
Ala Lys Thr Gln Asp Pro Gln Thr Ala Gly Arg Ile Thr Asp Ser Gly
            435                 440                 445
```

```
Gln Asp Thr Ala Phe Leu His Ser Lys Tyr Glu Asn Pro Ala Trp
    450                 455                 460
Pro Gly Thr Ser Thr His Asn Gly Pro Asn Gly Phe Ser Gln Ile Met
465                 470                 475                 480
Asp Glu Thr Pro Asn Val Ser Lys Ser Ser Pro Thr Gly Phe Gly Ile
                485                 490                 495
Lys Ser Ala Val Thr Gly Gly Lys Glu Ala Val Tyr Ser Gly Val Gln
                500                 505                 510
Ser Leu Arg Ser His Val Leu Ala Met Pro Gly Glu Thr Thr Thr Pro
            515                 520                 525
Val Gln Gly Ser Asn Arg Leu Pro Pro Ser Pro Leu Ser Ser Ser Thr
    530                 535                 540
Ser His Arg Val Ala Ala Ser Gly Ser Pro Gly Lys Ser Ser Thr His
545                 550                 555                 560
Ala Ser Val Ser Pro Ala Ser Glu Pro Ser Arg Met Met Met Met Met
                565                 570                 575
Ser Asp Pro Ala Glu Tyr Ser Leu Cys Tyr Ile Val Asn Pro Val Ser
                580                 585                 590
Pro Arg Met Asp Asp His Gly Leu Lys Glu Ile Cys Leu Asp His Leu
            595                 600                 605
Tyr Arg Gly Cys Gln Gln Val Asn Cys Asn Lys Asn His Phe His Leu
    610                 615                 620
Pro Tyr Arg Trp Gln Leu Phe Ile Leu Pro Thr Trp Met Asp Phe Gln
625                 630                 635                 640
Asp Met Glu Tyr Ile Glu Arg Ala Tyr Cys Asp Pro Gln Ile Glu Ile
                645                 650                 655
Ile Val Ile Glu Lys His Arg Ile Asn Phe Lys Lys Met Thr Cys Asp
            660                 665                 670
Ser Tyr Pro Ile Arg Arg Leu Ser Thr Pro Ser Phe Val Glu Lys Thr
    675                 680                 685
Leu Asn Ser Val Phe Thr Thr Lys Trp Leu Trp Tyr Trp Arg Asn Glu
690                 695                 700
Leu Asn Glu Tyr Thr Gln Tyr Gly His Glu Ser Pro Ser His Thr Ser
705                 710                 715                 720
Ser Glu Ile Asn Ser Ala Tyr Leu Glu Ser Phe Phe His Ser Cys Pro
                725                 730                 735
Arg Gly Val Leu Gln Phe His Ala Gly Ser Gln Asn Tyr Glu Leu Ser
            740                 745                 750
Phe Gln Gly Met Ile Gln Thr Asn Ile Ala Ser Lys Thr Gln Arg His
    755                 760                 765
Val Val Arg Arg Pro Val Phe Val Ser Ser Lys Asp Val Glu Gln Lys
770                 775                 780
Arg Arg Gly Pro Asp His Gln Pro Val Met Pro Gln Ala Asp Ala Leu
785                 790                 795                 800
Thr Leu Phe Ser Ser Pro Gln Arg Asn Ala Ser Thr Val Ser Ser Asn
                805                 810                 815
Glu Tyr Glu Phe Ile Glu Leu Asn Asn Gln Asp Glu Glu Tyr Ala Lys
            820                 825                 830
Ile Ser Glu Gln Phe Lys Ala Ser Met Lys Gln Phe Lys Ile Val Thr
    835                 840                 845
Ile Lys Arg Ile Trp Asn Gln Lys Leu Trp Asp Thr Phe Glu Arg Lys
850                 855                 860
```

| | | | | | | | | | | | |
|---|---|---|---|---|---|---|---|---|---|---|---|
| Lys | Gln | Lys | Met | Lys | Asn | Lys | Thr | Glu | Met | Phe | Leu | Phe | His | Ala | Val |
| 865 | | | | 870 | | | | | 875 | | | | | 880 | |

Lys Gln Lys Met Lys Asn Lys Thr Glu Met Phe Leu Phe His Ala Val
865                 870                 875                 880

Gly Arg Ile His Met Asp Tyr Ile Cys Lys Asn Asn Phe Glu Trp Ile
                885                 890                 895

Leu His Gly Asn Arg Glu Ile Arg Tyr Gly Lys Gly Asn Tyr Phe Thr
            900                 905                 910

Lys Glu Ala Met Tyr Ser His Lys Ser Cys Ser Tyr Asp Ser Arg Gly
        915                 920                 925

Thr Val Met Phe Val Ala Arg Val Leu Val Gly Ser Val Ile Glu Gly
    930                 935                 940

Asn Met Thr Leu Ser Ser Pro Pro Ala Leu Tyr Asp Ser Cys Val Asp
945                 950                 955                 960

Thr Arg Leu Asn Pro Ser Val Phe Val Ile Phe Arg Lys Glu Gln Ile
                965                 970                 975

Tyr Pro Glu Tyr Val Ile Glu Tyr Met Glu Leu Glu Lys Glu Lys Gly
            980                 985                 990

Cys Ile Ile Ser
        995

<210> SEQ ID NO 26
<211> LENGTH: 2399
<212> TYPE: DNA
<213> ORGANISM: Homo sapiens

<400> SEQUENCE: 26

```
ataaaagcct agtggccatt gtgttcgttg ctcttatcgg ttcccatccc agttgttgat      60
cttatgcaag acgctgcacg accccgcgcc cgcttgtcgc cacggcactt gaggcagccg     120
gagatactct gagttactcg gagcccgacg cctgagggtg agatgaacgc gctggcctcc     180
ctaaccgtcc ggacctgtga tcgcttctgg cagaccgaac cggcgctcct gccccgggg      240
tgacgcgcag ctcccagccg cccagacaca tggccccagg ccaagcaccc catcaggcta     300
ccccgtggag ggatgcccac cctttcttcc tcctgtcccc agtgatgggc ctcctcagcc     360
gcgcctggag ccgcctgagg ggcctgggac tctagagcc ctggctggtg aagcagtaa      420
aaggagcagc tctggtagaa gctggcctgg agggagaagc taggactcct ctggcaatcc     480
cccatacccc ttggggcaga cgccctgaag aggaggctga agacagtgga ggccctggag     540
aggacagaga aacactgggg ctgaaaacca gcagttccct tcctgaagcc tggggacttt     600
tggatgatga tgatggcatg tatggtgagc gagaggcaac cagtgtccct agagggcagg     660
gaagtcaatt tgcagatggc cagcgtgctc ccctgtctcc cagccttctg ataaggacac     720
tgcaaggttc tgataagaac ccaggggagg agaaagccga ggaagaggga gttgctgaag     780
aggagggagt taacaagttc tcttatccac catcacaccg ggagtgttgt ccagccgtgg     840
aggaggagga cgatgaagaa gctgtaaaga aagaagctca cagaacctct acttctgcct     900
tgtctccagg atccaagccc agcacttggg tgtcttgccc aggggaggaa agaatcaag      960
ccacggagga taaaagaaca gaaagaagta aaggagccag gaagacctcc gtgtccccc     1020
gatcttcagg ctccgacccc aggtcctggg agtatcgttc aggagaggcg tccgaggaga    1080
aggaggaaaa ggcacacaaa gaaactggga aggagaagc tgcccaggg ccgcaatcct     1140
cagccccagc ccagaggccc cagctcaagt cctggtggtg ccaacccagt gatgaagagg    1200
agggtgaggt caaggctttg ggggcagctg agaaggatgg agaagctgag tgtcctccct    1260
gcatccccc accaagtgcc ttcctgaagg cctgggtgta ttggccagga gaggacacag    1320
```

```
aggaagagga agatgaggaa gaagatgagg acagtgactc tggatcagat gaggaagagg    1380
gagaagctga ggcttcctct tccactcctg ctacaggtgt cttcttgaag tcctgggtct    1440
atcagccagg agaggacaca gaggaggagg aagatgagga cagtgataca ggatcagccg    1500
aggatgaaag agaagctgag acttctgctt ccacaccccc tgcaagtgct ttcttgaagg    1560
cctgggtgta tcggccagga gaggacacgg aggaggagga agatgaggat gtggatagtg    1620
aggataagga agatgattca gaagcagcct gggagaagc tgagtcagac ccacatccct    1680
cccacccgga ccagagggcc cacttcaggg gctggggata tcgacctgga aaagagacag    1740
aggaagagga agctgctgag gactggggag aagctgagcc ctgccccttc cgagtggcca    1800
tctatgtacc tggagagaag ccaccgcctc cctgggctcc tcctaggctg ccctccgac    1860 tgcaaaggcg gctcaagcgc ccagaaaccc ctactcatga tccggacccct gagactcccc    1920 taaaggccag aaaggtgcgc ttctccgaga aggtcactgt ccatttcctg gctgtctggg    1980
cagggccggc ccaggccgcc cgccagggcc cctgggagca gcttgctcgg gatcgcagcc    2040
gcttcgcacg ccgcatcacc caggcccagg aggagctgag cccctgcctc accccctgctg    2100 cccgggccag agcctgggca cgcctcagga acccaccttt agcccccatc cctgccctca    2160 cccagaccctt gccttcctcc tctgtcccctt cgtccccagt ccagaccacg cccttgagcc    2220
aagctgtggc cacaccttcc cgctcgtctg ctgctgcagc ggctgccctg gacctcagtg    2280
ggaggcgtgg ctgagaccaa ctggtttgcc tataatttat taactattta ttttttctaa    2340
gtgtgggttt atataaggaa taaagccttt tgatttgtag cgaaaaaaaa aaaaaaaaa    2399
```

<210> SEQ ID NO 27
<211> LENGTH: 674
<212> TYPE: PRT
<213> ORGANISM: Homo sapiens

<400> SEQUENCE: 27

```
Met Ala Pro Gly Gln Ala Pro His Gln Ala Thr Pro Trp Arg Asp Ala
1               5                   10                  15

His Pro Phe Phe Leu Leu Ser Pro Val Met Gly Leu Leu Ser Arg Ala
            20                  25                  30

Trp Ser Arg Leu Arg Gly Leu Gly Pro Leu Glu Pro Trp Leu Val Glu
        35                  40                  45

Ala Val Lys Gly Ala Ala Leu Val Glu Ala Gly Leu Glu Gly Glu Ala
    50                  55                  60

Arg Thr Pro Leu Ala Ile Pro His Thr Pro Trp Gly Arg Arg Pro Glu
65                  70                  75                  80

Glu Glu Ala Glu Asp Ser Gly Gly Pro Gly Glu Asp Arg Glu Thr Leu
                85                  90                  95

Gly Leu Lys Thr Ser Ser Ser Leu Pro Glu Ala Trp Gly Leu Leu Asp
            100                 105                 110

Asp Asp Asp Gly Met Tyr Gly Glu Arg Glu Ala Thr Ser Val Pro Arg
        115                 120                 125

Gly Gln Gly Ser Gln Phe Ala Asp Gly Gln Arg Ala Pro Leu Ser Pro
    130                 135                 140

Ser Leu Leu Ile Arg Thr Leu Gln Gly Ser Asp Lys Asn Pro Gly Glu
145                 150                 155                 160

Glu Lys Ala Glu Glu Glu Gly Val Ala Glu Glu Gly Val Asn Lys
                165                 170                 175

Phe Ser Tyr Pro Pro Ser His Arg Glu Cys Cys Pro Ala Val Glu Glu
            180                 185                 190
```

```
Glu Asp Asp Glu Glu Ala Val Lys Lys Glu Ala His Arg Thr Ser Thr
            195                 200                 205
Ser Ala Leu Ser Pro Gly Ser Lys Pro Ser Thr Trp Val Ser Cys Pro
            210                 215                 220
Gly Glu Glu Asn Gln Ala Thr Glu Asp Lys Arg Thr Glu Arg Ser
225                 230                 235                 240
Lys Gly Ala Arg Lys Thr Ser Val Ser Pro Arg Ser Ser Gly Ser Asp
                245                 250                 255
Pro Arg Ser Trp Glu Tyr Arg Ser Gly Glu Ala Ser Glu Glu Lys Glu
            260                 265                 270
Glu Lys Ala His Lys Glu Thr Gly Lys Gly Glu Ala Ala Pro Gly Pro
            275                 280                 285
Gln Ser Ser Ala Pro Ala Gln Arg Pro Gln Leu Lys Ser Trp Trp Cys
            290                 295                 300
Gln Pro Ser Asp Glu Glu Gly Glu Val Lys Ala Leu Gly Ala Ala
305                 310                 315                 320
Glu Lys Asp Gly Glu Ala Glu Cys Pro Pro Cys Ile Pro Pro Ser
                325                 330                 335
Ala Phe Leu Lys Ala Trp Val Tyr Trp Pro Gly Glu Asp Thr Glu Glu
            340                 345                 350
Glu Glu Asp Glu Glu Glu Asp Glu Asp Ser Asp Ser Gly Ser Asp Glu
            355                 360                 365
Glu Glu Gly Glu Ala Glu Ala Ser Ser Ser Thr Pro Ala Thr Gly Val
            370                 375                 380
Phe Leu Lys Ser Trp Val Tyr Gln Pro Gly Glu Asp Thr Glu Glu Glu
385                 390                 395                 400
Glu Asp Glu Asp Ser Asp Thr Gly Ser Ala Glu Asp Glu Arg Glu Ala
                405                 410                 415
Glu Thr Ser Ala Ser Thr Pro Ala Ser Ala Phe Leu Lys Ala Trp
            420                 425                 430
Val Tyr Arg Pro Gly Glu Asp Thr Glu Glu Glu Asp Glu Asp Val
            435                 440                 445
Asp Ser Glu Asp Lys Glu Asp Ser Glu Ala Ala Leu Gly Glu Ala
            450                 455                 460
Glu Ser Asp Pro His Pro Ser His Pro Asp Gln Arg Ala His Phe Arg
465                 470                 475                 480
Gly Trp Gly Tyr Arg Pro Gly Lys Glu Thr Glu Glu Glu Ala Ala
                485                 490                 495
Glu Asp Trp Gly Glu Ala Glu Pro Cys Pro Phe Arg Val Ala Ile Tyr
            500                 505                 510
Val Pro Gly Glu Lys Pro Pro Pro Trp Ala Pro Pro Arg Leu Pro
            515                 520                 525
Leu Arg Leu Gln Arg Arg Leu Lys Arg Pro Glu Thr Pro Thr His Asp
            530                 535                 540
Pro Asp Pro Glu Thr Pro Leu Lys Ala Arg Lys Val Arg Phe Ser Glu
545                 550                 555                 560
Lys Val Thr Val His Phe Leu Ala Val Trp Ala Gly Pro Ala Gln Ala
                565                 570                 575
Ala Arg Gln Gly Pro Trp Glu Gln Leu Ala Arg Asp Arg Ser Arg Phe
            580                 585                 590
Ala Arg Arg Ile Thr Gln Ala Gln Glu Glu Leu Ser Pro Cys Leu Thr
            595                 600                 605
```

```
Pro Ala Ala Arg Ala Arg Ala Trp Ala Arg Leu Arg Asn Pro Pro Leu
    610                 615                 620
Ala Pro Ile Pro Ala Leu Thr Gln Thr Leu Pro Ser Ser Ser Val Pro
625                 630                 635                 640
Ser Ser Pro Val Gln Thr Thr Pro Leu Ser Gln Ala Val Ala Thr Pro
                645                 650                 655
Ser Arg Ser Ser Ala Ala Ala Ala Ala Leu Asp Leu Ser Gly Arg
                660                 665                 670
Arg Gly
```

<210> SEQ ID NO 28
<211> LENGTH: 2345
<212> TYPE: DNA
<213> ORGANISM: Mus musculus

<400> SEQUENCE: 28

```
agcgccgcgt cagggtataa aagccgcgtg gacgatgttg gcgcagattg agtcagctct      60
gagtttgtgg aagattacat gcgatatccc gcgcgacccc gcatcccttt gccggccggg     120
acagcctttg ctacagcctg tgaaacattg cgtccccgag ccccacgcct gagggcgaca     180
tgaacccgct ggcttcgcga gcagtccgga cccacgatcg cttttggcaa ccagaaccgg     240
cgcttcagcc cccggggtga cgtgcagccc gccgcccaga cacatggccc cgagcccaag     300
accccagcat gtcctgcact ggaggacgc ccacaacttc tatctcctgt ccccactgat      360
gggcttgctc agtcgggcct ggagccgcct gaggggccca aagtcccag aggcatggct      420
ggcaaaaaca gtaacaggag cagatcagat agaagctgcg gctctgctga cacctacccc     480
tgtctctggt aacctcctcc ctcatgggga gactgaagaa agtggatctc ctgaacagag     540
tcaagcagcc cagaggctct gccttgtgga agctgaaagt tcccctcctg aaacttgggg     600
actttcaaat gttgatgagt acaatgcaaa gccaggacaa gatgacctta gagagaagga     660
aatggaacgc acagctggca aggccacact acagcccgct ggcctgcaag gggctgataa     720
gaggcttggg gaggtggtgg ctagagaaga gggagtggct gagcccgctt atcccacatc     780
acagctggag ggtggtccag ctgagaatga agaggatgga gaaacagtga agacttacca     840
agcttctgct gcttccatag ctccgggata caaacccagc accctgtgc ctttcttggg      900
ggaggcagaa catcaagcca cggaagaaaa aggaacagaa acaaggctg acccctccaa      960
ctctccttct tcaggctccc actccagagc ctgggagtac tactctagag agaagcctaa    1020
gcaggaggga gaagccaagg tagaggcaca cagggcaggg cagggtcacc cttgtcggaa    1080
tgctgaggct gaggaaggag gacctgagac aacttttgtc tgtactggaa atgccttcct    1140
gaaggcctgg gtgtatcgcc caggagagga cacagaggaa gaagacaaca gcgattcgga    1200
ttcagctgag gaagacacag ctcagaccgg tgccacccc catacaagtg ccttcctgaa     1260
ggcctgggtg tatcgcccag gagaggacac agaggaagaa gacagcgatt cggattcagc    1320
tgaggaagac acagctcaga ccggtgccac ccccataca agtgccttcc tgaaggcctg     1380
ggtgtatcgc ccaggagagg acacagagga agaaacagc gatttggatt cagctgagga    1440
agacacagct cagaccggtg ccaccccca tacaagtgcc ttcctgaagg cctgggtgta     1500
tcgcccagga gaggacacag aggaagaaaa cagcgatttg gattcagctg aggaagacac    1560
agctcagacc ggtgccaccc cacatacaag tccttcctg aaggcctggg tgtatcgccc     1620
aggagaggac acagaagatg acacagaaga ggaagaggac agtgagaatg tggccccagg    1680
tgactcagaa acagctgact caagccagag tccctgcctt cagccccagc gttgtctacc    1740
```

-continued

```
aggagagaag accaagggac gtggggaaga gcccctctc ttccaggtgg ccttctattt   1800
acccggagag aagccagaat caccttgggc tgcacctaag ctgcccttc gactgcagag   1860
gcggctcaga ttgttcaaag cccccacccg ggatcaggac cccgagattc ctctaaaagc   1920
tcggaaggta cacttcgctg agaaagtcac agtccatttc cttgctgtct gggcaggacc   1980
agcccaagct gcccgtcgag gtccctggga gcagtttgca cgagatcgaa gccgctttgc   2040
tcgacgcatt gcccaggcag aggagaagct gggtccctac cttacccctg attccagggc   2100
cagagcatgg gcacgcctta gaaacccatc tcttccacag tccgagcctc gctcttcctc   2160
tgaggccact cccttgaccc aagatgtgac cacaccctct cccttccca gtgaaacccc    2220
ttcgcccagc ctgtacttgg gagggaggcg gggctaagcc tgagtagttt cctattattt   2280
atttatttat ttatttgaat aagaaataaa gccttttaat ttgtagtgat aaaaaaaaaa   2340
aaaaa                                                              2345
```

<210> SEQ ID NO 29
<211> LENGTH: 657
<212> TYPE: PRT
<213> ORGANISM: Mus musculus

<400> SEQUENCE: 29

```
Met Ala Pro Ser Pro Arg Pro Gln His Val Leu His Trp Arg Asp Ala
1               5                   10                  15

His Asn Phe Tyr Leu Leu Ser Pro Leu Met Gly Leu Leu Ser Arg Ala
            20                  25                  30

Trp Ser Arg Leu Arg Gly Pro Glu Val Pro Glu Ala Trp Leu Ala Lys
        35                  40                  45

Thr Val Thr Gly Ala Asp Gln Ile Glu Ala Ala Leu Leu Thr Pro
    50                  55                  60

Thr Pro Val Ser Gly Asn Leu Leu Pro His Gly Glu Thr Glu Ser
65                  70                  75                  80

Gly Ser Pro Glu Gln Ser Gln Ala Ala Gln Arg Leu Cys Leu Val Glu
                85                  90                  95

Ala Glu Ser Ser Pro Pro Glu Thr Trp Gly Leu Ser Asn Val Asp Glu
            100                 105                 110

Tyr Asn Ala Lys Pro Gly Gln Asp Asp Leu Arg Glu Lys Glu Met Glu
        115                 120                 125

Arg Thr Ala Gly Lys Ala Thr Leu Gln Pro Ala Gly Leu Gln Gly Ala
    130                 135                 140

Asp Lys Arg Leu Gly Glu Val Val Ala Arg Glu Gly Val Ala Glu
145                 150                 155                 160

Pro Ala Tyr Pro Thr Ser Gln Leu Glu Gly Gly Pro Ala Glu Asn Glu
                165                 170                 175

Glu Asp Gly Glu Thr Val Lys Thr Tyr Gln Ala Ser Ala Ala Ser Ile
            180                 185                 190

Ala Pro Gly Tyr Lys Pro Ser Thr Pro Val Pro Phe Leu Gly Glu Ala
        195                 200                 205

Glu His Gln Ala Thr Glu Glu Lys Gly Thr Glu Asn Lys Ala Asp Pro
    210                 215                 220

Ser Asn Ser Pro Ser Ser Gly Ser His Ser Arg Ala Trp Glu Tyr Tyr
225                 230                 235                 240

Ser Arg Glu Lys Pro Lys Gln Glu Gly Glu Ala Lys Val Glu Ala His
                245                 250                 255
```

-continued

```
Arg Ala Gly Gln Gly His Pro Cys Arg Asn Ala Glu Ala Glu Glu Gly
                260                 265                 270

Gly Pro Glu Thr Thr Phe Val Cys Thr Gly Asn Ala Phe Leu Lys Ala
            275                 280                 285

Trp Val Tyr Arg Pro Gly Glu Asp Thr Glu Glu Asp Asn Ser Asp
        290                 295                 300

Ser Asp Ser Ala Glu Glu Asp Thr Ala Gln Thr Gly Ala Thr Pro His
305                 310                 315                 320

Thr Ser Ala Phe Leu Lys Ala Trp Val Tyr Arg Pro Gly Glu Asp Thr
                325                 330                 335

Glu Glu Glu Asp Ser Asp Ser Asp Ser Ala Glu Glu Asp Thr Ala Gln
            340                 345                 350

Thr Gly Ala Thr Pro His Thr Ser Ala Phe Leu Lys Ala Trp Val Tyr
        355                 360                 365

Arg Pro Gly Glu Asp Thr Glu Glu Glu Asn Ser Asp Leu Asp Ser Ala
    370                 375                 380

Glu Glu Asp Thr Ala Gln Thr Gly Ala Thr Pro His Thr Ser Ala Phe
385                 390                 395                 400

Leu Lys Ala Trp Val Tyr Arg Pro Gly Glu Asp Thr Glu Glu Glu Asn
                405                 410                 415

Ser Asp Leu Asp Ser Ala Glu Glu Asp Thr Ala Gln Thr Gly Ala Thr
            420                 425                 430

Pro His Thr Ser Pro Phe Leu Lys Ala Trp Val Tyr Arg Pro Gly Glu
        435                 440                 445

Asp Thr Glu Asp Thr Glu Glu Glu Asp Ser Glu Asn Val Ala
    450                 455                 460

Pro Gly Asp Ser Glu Thr Ala Asp Ser Ser Gln Ser Pro Cys Leu Gln
465                 470                 475                 480

Pro Gln Arg Cys Leu Pro Gly Glu Lys Thr Lys Gly Arg Gly Glu Glu
                485                 490                 495

Pro Pro Leu Phe Gln Val Ala Phe Tyr Leu Pro Gly Glu Lys Pro Glu
            500                 505                 510

Ser Pro Trp Ala Ala Pro Lys Leu Pro Leu Arg Leu Gln Arg Arg Leu
        515                 520                 525

Arg Leu Phe Lys Ala Pro Thr Arg Asp Gln Asp Pro Glu Ile Pro Leu
    530                 535                 540

Lys Ala Arg Lys Val His Phe Ala Glu Lys Val Thr Val His Phe Leu
545                 550                 555                 560

Ala Val Trp Ala Gly Pro Ala Gln Ala Arg Arg Gly Pro Trp Glu
                565                 570                 575

Gln Phe Ala Arg Asp Arg Ser Arg Phe Ala Arg Arg Ile Ala Gln Ala
            580                 585                 590

Glu Glu Lys Leu Gly Pro Tyr Leu Thr Pro Asp Ser Arg Ala Arg Ala
        595                 600                 605

Trp Ala Arg Leu Arg Asn Pro Ser Leu Pro Gln Ser Glu Pro Arg Ser
    610                 615                 620

Ser Ser Glu Ala Thr Pro Leu Thr Gln Asp Val Thr Pro Ser Pro
625                 630                 635                 640

Leu Pro Ser Glu Thr Pro Ser Pro Ser Leu Tyr Leu Gly Gly Arg Arg
                645                 650                 655

Gly
```

<210> SEQ ID NO 30

<211> LENGTH: 4361
<212> TYPE: DNA
<213> ORGANISM: Homo sapiens

<400> SEQUENCE: 30

```
agcagacgag ggcttgtgcg agaggggggcc gggcggctgc agggaaggcg gagtccaagg      60
ggaaaacgaa actgagaacc agctctcccg aagccgcggg tctccggccg gcggcggcgg     120
cggcggcggc ggcggcgcag tttgctcata ctttgtgact tgcggtcaca gtggcattca     180
gctccacact tggtagaacc acaggcacga caagcataga aacatcctaa acaatcttca     240
tcgaggcatc gaggtccatc ccaataaaaa tcaggagacc ctggctatca tagaccttag     300
tcttcgctgg tatcactcgt ctgtctgaac cagcggttgc atttttttaa gccttctttt     360
ttctctttta ccagtttctg gagcaaattc agtttgcctt cctggatttg taaattgtaa     420
tgacctcaaa actttagcag ttcttccatc tgactcaggt ttgcttctct ggcggtcttc     480
agaatcaaca tccacacttc cgtgattatc tgcgtgcatt ttggacaaag cttccaacca     540
ggatacggga agaagaaatg gctggtgatc tttcagcagg tttcttcatg gagaactta      600
atacataccg tcagaagcag ggagtagtac ttaaatatca agaactgcct aattcaggac     660
ctccacatga taggaggttt acatttcaag ttataataga tggaagagaa tttccagaag     720
gtgaaggtag atcaaagaag gaagcaaaaa atgccgcagc caaattagct gttgagatac     780
ttaataagga aaagaaggca gttagtcctt tattattgac aacaacgaat tcttcagaag     840
gattatccat ggggaattac ataggcctta tcaatagaat tgcccagaag aaaagactaa     900
ctgtaaatta tgaacagtgt gcatcggggg tgcatgggcc agaaggattt cattataaat     960
gcaaaatggg acagaaagaa tatagtattg gtacaggttc tactaaacag aagcaaaac    1020
aattggccgc taaacttgca tatcttcaga tattatcaga agaaacctca gtgaaatctg    1080
actacctgtc ctctggttct tttgctacta cgtgtgagtc ccaaagcaac tctttagtga    1140
ccagcacact cgcttctgaa tcatcatctg aaggtgactt ctcagcagat acatcagaga    1200
taaattctaa cagtgacagt ttaaacagtt cttcgttgct tatgaatggt ctcagaaata    1260
atcaaaggaa ggcaaaaaga tctttggcac ccagatttga ccttcctgac atgaaagaaa    1320
caaagtatac tgtggacaag aggtttggca tggattttaa agaaatagaa ttaattggct    1380
caggtggatt tggccaagtt ttcaaagcaa acacagaat tgacggaaag acttacgtta    1440
ttaaacgtgt taaatataat aacgagaagg cggagcgtga agtaaaagca ttggcaaaac    1500
ttgatcatgt aaatattgtt cactacaatg gctgttggga tggatttgat tatgatcctg    1560
agaccagtga tgattctctt gagagcagtg attatgatcc tgagaacagc aaaaatagtt    1620
caaggtcaaa gactaagtgc ctttcatcc aaatggaatt ctgtgataaa gggaccttgg    1680
aacaatggat tgaaaaaaga agaggcgaga actagacaa agttttggct ttggaactct    1740
ttgaacaaat aacaaagggg gtggattata cattcaaa aaaattaatt catagagatc    1800
ttaagccaag taatatattc ttagtagata caaaacaagt aaagattgga gactttggac    1860
ttgtaacatc tctgaaaaat gatggaaagc gaacaaggag taagggaact ttgcgataca    1920
tgagcccaga acagatttct tcgcaagact atggaaggga agtggacctc tacgctttgg    1980
ggctaattct tgctgaactt cttcatgtat gtgacactgc ttttgaaaca tcaaagtttt    2040
tcacagacct acgggatggc atcatctcag atatatttga taaaaagaa aaaactcttc    2100
tacagaaatt actctcaaag aaacctgagg atcgacctaa cacatctgaa atactaagga    2160
ccttgactgt gtggaagaaa agcccagaga aaatgaacg acacacatgt tagagccctt    2220
```

```
ctgaaaaagt atcctgcttc tgatatgcag ttttccttaa attatctaaa atctgctagg    2280
gaatatcaat agatatttac cttttatttt aatgtttcct ttaattttttt actatttta    2340 ctaatctttc tgcagaaaca gaaaggtttt cttcttttg cttcaaaaac attcttacat     2400 tttactttt cctggctcat ctctttattc tttttttttt tttaaagaca gagtctcgct     2460
ctgttgccca ggctggagtg caatgacaca gtcttggctc actgcaactt ctgcctcttg    2520
ggttcaagtg attctcctgc ctcagcctcc tgagtagctg gattacaggc atgtgccacc    2580
cacccaacta attttgtgt ttttaataaa gacagggttt caccatgttg gccaggctgg     2640
tctcaaactc ctgacctcaa gtaatccacc tgcctcggcc tcccaaagtg ctgggattac    2700
agggatgagc caccgcgccc agcctcatct ctttgttcta aagatggaaa aaccacccc    2760 aaatttctt tttatactat taatgaatca atcaattcat atctatttat taaatttcta     2820
ccgcttttag gccaaaaaaa tgtaagatcg ttctctgcct cacatagctt acaagccagc    2880
tggagaaata tggtactcat taaaaaaaaa aaaaaagtg atgtacaacc acttcggaaa     2940
acaatttggc attatctagt aaagttgaat ccatgtatac ccacatagct atcaattcta    3000
ttcctacata cgtgcttaca agaatgtcca taaaaccctg tttataatag ccaaaagaac    3060
agggaacaac cataatgcac atcaaaagaa gaatggatta aaaaaattat attcacacac    3120
aggagtacta tatagtattg aaaacaattg aagtacagct aaatgtaata acgtaacaca    3180
atacaactct cagaaacata atgttaagcg aacaaagcag gttttcagaa aatatatgca    3240
gaataattcc atttatataa agttccagag catgcaaaac taaatcattt tgtataaaaa    3300
acccaacaaa tgtgatgaga caataatggg aaggaaggga atgagaaata ttaaattctg    3360
gatggtggtt atctttgagg gaggggaatg atgtgattgg ggaaatggac tttcaaaggt    3420
aatggtaact tccttaagct ggatggtagg tccactagtg tttgctgcat agttataccta   3480 tttatcttaa atacattttg tatctattgt aacaaccact ttaaagacaa ccgtgctgta    3540
aggcagtagc taaaaacaga aaatagtcca tcgggaaggg taagatggct ttctgctgag    3600
cacagggcta gaagtgacag cccagtgggc cttccaacta tatgccaggg tgttagatga    3660
gtagagagga gaccacccag gaagtctgga caaggggtct ggcatgagct ctggagaaga    3720
tatatttgag gaacatgggg tatgctagtt tgttgtcctg aattgctgta gagaagataa    3780
tttaaattgc atcttagaag acgaccctga gggtgaattt caacttaggg caattgtttt    3840
agtttgtttc ttattggttt aaatggatac ttgaagctgg ataatttata aggaaaagag    3900
atttatatga cttacagttc tgcaggctgt acaagaaaca tggcaccagc atctgcttct    3960
tccccggctg cttccactca tggtggaagg tgaaggggag ccggatgtgc agagatcata    4020
tggcaagaga ggaagcaaga gagcgaggga gaaggtgcca ggctctttt aaataaccgg     4080 ctcttgaggg aactaataga ttgagaactc cttgcttctc ctccccagca cacccaccc    4140 ccagggacgg cattaatgta ttcatgaggg gtcttccccc atgacccaaa cacctcccat    4200
caggccccac ctccaacact gggatcaaat ttcaacatga gatttttgggg gacaaacatg    4260 caaactatag cagcaaccag ctaccattct aaaactgcca tatgatttta ggattttaa     4320 aaagggccaa atttaggtta agcaaaaaaa aaaaaaaaa a                         4361
```

<210> SEQ ID NO 31
<211> LENGTH: 551
<212> TYPE: PRT
<213> ORGANISM: Homo sapiens

<400> SEQUENCE: 31

```
Met Ala Gly Asp Leu Ser Ala Gly Phe Phe Met Glu Glu Leu Asn Thr
1               5                   10                  15

Tyr Arg Gln Lys Gln Gly Val Val Leu Lys Tyr Gln Glu Leu Pro Asn
            20                  25                  30

Ser Gly Pro Pro His Asp Arg Arg Phe Thr Phe Gln Val Ile Ile Asp
        35                  40                  45

Gly Arg Glu Phe Pro Glu Gly Glu Gly Arg Ser Lys Lys Glu Ala Lys
50                  55                  60

Asn Ala Ala Ala Lys Leu Ala Val Glu Ile Leu Asn Lys Glu Lys Lys
65                  70                  75                  80

Ala Val Ser Pro Leu Leu Leu Thr Thr Thr Asn Ser Ser Glu Gly Leu
            85                  90                  95

Ser Met Gly Asn Tyr Ile Gly Leu Ile Asn Arg Ile Ala Gln Lys Lys
        100                 105                 110

Arg Leu Thr Val Asn Tyr Glu Gln Cys Ala Ser Gly Val His Gly Pro
    115                 120                 125

Glu Gly Phe His Tyr Lys Cys Lys Met Gly Gln Lys Glu Tyr Ser Ile
130                 135                 140

Gly Thr Gly Ser Thr Lys Gln Glu Ala Lys Gln Leu Ala Ala Lys Leu
145                 150                 155                 160

Ala Tyr Leu Gln Ile Leu Ser Glu Glu Thr Ser Val Lys Ser Asp Tyr
            165                 170                 175

Leu Ser Ser Gly Ser Phe Ala Thr Thr Cys Glu Ser Gln Ser Asn Ser
        180                 185                 190

Leu Val Thr Ser Thr Leu Ala Ser Glu Ser Ser Glu Gly Asp Phe
    195                 200                 205

Ser Ala Asp Thr Ser Glu Ile Asn Ser Asn Ser Asp Ser Leu Asn Ser
210                 215                 220

Ser Ser Leu Leu Met Asn Gly Leu Arg Asn Asn Gln Arg Lys Ala Lys
225                 230                 235                 240

Arg Ser Leu Ala Pro Arg Phe Asp Leu Pro Asp Met Lys Glu Thr Lys
            245                 250                 255

Tyr Thr Val Asp Lys Arg Phe Gly Met Asp Phe Lys Glu Ile Glu Leu
        260                 265                 270

Ile Gly Ser Gly Gly Phe Gly Gln Val Phe Lys Ala Lys His Arg Ile
    275                 280                 285

Asp Gly Lys Thr Tyr Val Ile Lys Arg Val Lys Tyr Asn Asn Glu Lys
290                 295                 300

Ala Glu Arg Glu Val Lys Ala Leu Ala Lys Leu Asp His Val Asn Ile
305                 310                 315                 320

Val His Tyr Asn Gly Cys Trp Asp Gly Phe Asp Tyr Asp Pro Glu Thr
            325                 330                 335

Ser Asp Asp Ser Leu Glu Ser Ser Asp Tyr Asp Pro Glu Asn Ser Lys
        340                 345                 350

Asn Ser Ser Arg Ser Lys Thr Lys Cys Leu Phe Ile Gln Met Glu Phe
    355                 360                 365

Cys Asp Lys Gly Thr Leu Glu Gln Trp Ile Glu Lys Arg Arg Gly Glu
370                 375                 380

Lys Leu Asp Lys Val Leu Ala Leu Glu Leu Phe Glu Gln Ile Thr Lys
385                 390                 395                 400

Gly Val Asp Tyr Ile His Ser Lys Lys Leu Ile His Arg Asp Leu Lys
            405                 410                 415
```

```
Pro Ser Asn Ile Phe Leu Val Asp Thr Lys Gln Val Lys Ile Gly Asp
            420                 425                 430

Phe Gly Leu Val Thr Ser Leu Lys Asn Asp Gly Lys Arg Thr Arg Ser
            435                 440                 445

Lys Gly Thr Leu Arg Tyr Met Ser Pro Glu Gln Ile Ser Ser Gln Asp
450                 455                 460

Tyr Gly Lys Glu Val Asp Leu Tyr Ala Leu Gly Leu Ile Leu Ala Glu
465                 470                 475                 480

Leu Leu His Val Cys Asp Thr Ala Phe Glu Thr Ser Lys Phe Phe Thr
                485                 490                 495

Asp Leu Arg Asp Gly Ile Ile Ser Asp Ile Phe Asp Lys Lys Glu Lys
            500                 505                 510

Thr Leu Leu Gln Lys Leu Leu Ser Lys Lys Pro Glu Asp Arg Pro Asn
            515                 520                 525

Thr Ser Glu Ile Leu Arg Thr Leu Thr Val Trp Lys Lys Ser Pro Glu
530                 535                 540

Lys Asn Glu Arg His Thr Cys
545                 550

<210> SEQ ID NO 32
<211> LENGTH: 4127
<212> TYPE: DNA
<213> ORGANISM: Homo sapiens

<400> SEQUENCE: 32
agcagacgag ggcttgtgcg agaggggggcc gggcggctgc agggaaggcg gagtccaagg    60
ggaaaacgaa actgagaacc agctctcccg aagccgcggg tctccggccg gcggcggcgg   120
cggcggcggc ggcggcgcag tttctggagc aaattcagtt tgccttcctg gatttgtaaa   180
ttgtaatgac ctcaaaactt tagcagttct tccatctgac tcaggtttgc ttctctggcg   240
gtcttcagaa tcaacatcca cacttccgtg attatctgcg tgcattttgg acaaagcttc   300
caaccaggat acgggaagaa gaaatggctg gtgatctttc agcaggtttc ttcatggagg   360
aacttaatac ataccgtcag aagcagggag tagtacttaa atatcaagaa ctgcctaatt   420
caggacctcc acatgatagg aggtttacat ttcaagttat aatagatgga agagaatttc   480
cagaaggtga aggtagatca aagaaggaag caaaaaatgc cgcagccaaa ttagctgttg   540
agatacttaa taaggaaaag aaggcagtta gtcctttatt attgacaaca acgaattctt   600
cagaaggatt atccatgggg aattacatag gccttatcaa tagaattgcc cagaagaaaa   660
gactaactgt aaattatgaa cagtgtgcat cgggggtgca tgggccagaa ggatttcatt   720
ataaatgcaa aatgggacag aaagaatata gtattggtac aggttctact aaacaggaag   780
caaaacaatt ggccgctaaa cttgcatatc ttcagatatt atcagaagaa acctcagtga   840
aatctgacta cctgtcctct ggttcttttg ctactacgtg tgagtcccaa agcaactctt   900
tagtgaccag cacactcgct tctgaatcat catctgaagg tgacttctca gcagatacat   960
cagagataaa ttctaacagt gacagtttaa acagttcttc gttgcttatg aatggtctca  1020
gaaataatca aggaaggca aaaagatctt tggcacccag atttgacctt cctgacatga  1080
aagaaacaaa gtatactgtg acaagaggt ttggcatgga ttttaaagaa atagaattaa  1140
ttggctcagg tggatttggc caagtttttca aagcaaaaca cagaattgac ggaaagactt  1200
acgttattaa acgtgttaaa tataataacg agaaggcgga gcgtgaagta aaagcattgg  1260
caaaacttga tcatgtaaat attgttcact acaatggctg ttgggatgga tttgattatg  1320
```

```
atcctgagac cagtgatgat tctcttgaga gcagtgatta tgatcctgag aacagcaaaa   1380
atagttcaag gtcaaagact aagtgccttt tcatccaaat ggaattctgt gataaaggga   1440
ccttggaaca atggattgaa aaagaagag gcgagaaact agacaaagtt ttggctttgg    1500
aactctttga acaaataaca aaggggtgg attatataca ttcaaaaaaa ttaattcata    1560
gagatcttaa gccaagtaat atattcttag tagatacaaa acaagtaaag attggagact   1620
ttggacttgt aacatctctg aaaaatgatg gaaagcgaac aaggagtaag ggaactttgc   1680
gatacatgag cccagaacag atttcttcgc aagactatgg aaaggaagtg gacctctacg   1740
ctttggggct aattcttgct gaacttcttc atgtatgtga cactgctttt gaaacatcaa   1800 agttttcac agacctacgg gatggcatca tctcagatat atttgataaa aagaaaaaa     1860 ctcttctaca gaaattactc tcaaagaaac ctgaggatcg acctaacaca tctgaaatac   1920
taaggacctt gactgtgtgg aagaaaagcc cagagaaaaa tgaacgacac acatgttaga   1980
gcccttctga aaagtatcc tgcttctgat atgcagtttt ccttaaatta tctaaaatct     2040
gctagggaat atcaatagat atttaccttt tattttaatg tttcctttaa ttttttacta   2100
tttttactaa tctttctgca gaaacagaaa ggttttcttc tttttgcttc aaaaacattc   2160
ttacatttta cttttcctg gctcatctct ttattctttt ttttttttta aagacagagt    2220
ctcgctctgt tgcccaggct ggagtgcaat gacacagtct ggctcactg caacttctgc     2280 ctcttgggtt caagtgattc tcctgcctca gcctcctgag tagctggatt acaggcatgt   2340
gccacccacc caactaattt ttgtgttttt aataaagaca gggtttcacc atgttggcca   2400
ggctggtctc aaactcctga cctcaagtaa tccacctgcc tcggcctccc aaagtgctgg   2460
gattacaggg atgagccacc gcgcccagcc tcatctcttt gttctaaaga tggaaaaacc   2520
acccccaaat tttcttttta tactattaat gaatcaatca attcatatct atttattaaa   2580
tttctaccgc ttttaggcca aaaaaatgta agatcgttct ctgcctcaca tagcttacaa   2640
gccagctgga gaaatatggt actcattaaa aaaaaaaaa aaagtgatgt acaaccactt    2700
cggaaaacaa tttggcatta tctagtaaag ttgaatccat gtatacccac atagctatca   2760
attctattcc tacatacgtg cttacaagaa tgtccataaa accctgttta taatagccaa   2820
aagaacaggg aacaaccata atgcacatca aaagaagaat ggattaaaaa aattatattc   2880
acacacagga gtactatata gtattgaaaa caattgaagt acagctaaat gtaataacgt   2940
aacacaatac aactctcaga aacataatgt taagcgaaca aagcaggttt tcagaaaata   3000
tatgcagaat aattccattt atataaagtt ccagagcatg caaaactaaa tcattttgta   3060 taaaaaccc aacaaatgtg atgagacaat aatgggaagg aagggaatga gaaatattaa    3120
attctggatg tggttatct ttgagggagg ggaatgatgt gattgggaa atggactttc      3180 aaaggtaatg gtaacttcct taagctggat ggtaggtcca ctagtgtttg ctgcatagtt   3240 ataccttta tcttaaatac attttgtatc tattgtaaca accactttaa agacaaccgt    3300
gctgtaaggc agtagctaaa aacagaaaat agtccatcgg gaagggtaag atggctttct   3360
gctgagcaca gggctagaag tgacagccca gtgggccttc caactatatg ccagggtgtt   3420
agatgagtag agaggagacc acccaggaag tctggacaag gggtctggca tgagctctgg   3480
agaagatata tttgaggaac atggggtatg ctagtttgtt gtcctgaatt gctgtagaga   3540
agataattta aattgcatct tagaagacga ccctgagggt gaatttcaac ttagggcaat   3600
tgttttagtt tgtttcttat tggtttaaat ggatacttga agctggataa tttataagga   3660
```

| | |
|---|---|
| aaagagattt atatgactta cagttctgca ggctgtacaa gaaacatggc accagcatct | 3720 |
| gcttcttccc cggctgcttc cactcatggt ggaaggtgaa ggggagccgg atgtgcagag | 3780 |
| atcatatggc aagagaggaa gcaagagagc gagggagaag gtgccaggct cttttttaaat | 3840 |
| aaccggctct tgagggaact aatagattga gaactccttg cttctcctcc ccagcacacc | 3900 |
| ccaccccag ggacggcatt aatgtattca tgaggggtct tcccccatga cccaaacacc | 3960 |
| tcccatcagg ccccacctcc aacactggga tcaaatttca acatgagatt ttggggggaca | 4020 |
| aacatgcaaa ctatagcagc aaccagctac cattctaaaa ctgccatatg attttaggat | 4080 |
| ttttaaaaag ggccaaattt aggttaagca aaaaaaaaa aaaaaaa | 4127 |

<210> SEQ ID NO 33
<211> LENGTH: 3697
<212> TYPE: DNA
<213> ORGANISM: Homo sapiens

<400> SEQUENCE: 33

| | |
|---|---|
| gatacgggaa gaagaaatgg ctggtgatct ttcagcaggt ttcttcatgg aggaacttaa | 60 |
| tacataccgt cagaagcagg gagtagtact taaatatcaa gaactgccta attcaggacc | 120 |
| tccacatgat aggaggttta catttcaagt tataatagat ggaagagaat ttccagaagg | 180 |
| tgaaggtaga tcaagaaagg aagcaaaaaa tgccgcagcc aaattagctg ttgagatact | 240 |
| taataaggaa aagaaggcag ttagtccttt attattgaca caacgaatt cttcagaagg | 300 |
| attatccatg gggaattaca taggccttat caatagaatt gcccagaaga aaagactaac | 360 |
| tgtaaattat gaacagtgtg catcggggt gcatgggcca gaaggatttc attataaatg | 420 |
| caaaatggga cagaaagaat atagtattgg tacaggttct actaaacagg aagcaaaaca | 480 |
| attggccgct aaacttgcat atcttcgat attatcagaa gaaacctcag tgaaatctga | 540 |
| ctacctgtcc tctggttctt tgctactac gtgtgagtcc caaagcaact ctttagtgac | 600 |
| cagcacactc gcttctgaat catcatctga aggtgacttc tcagcagata catcagagat | 660 |
| aaattctaac agtgacagtt taaacagttc ttcgttgctt atgaatggtc tcagaaataa | 720 |
| tcaaaggaag gcaaaaagat cttttggcacc cagatttgac cttcctgaca tgaaagaaac | 780 |
| aaagtatact gtggacaaga ggaaggcgga gcgtgaagta aaagcattgg caaaacttga | 840 |
| tcatgtaaat attgttcact acaatggctg ttgggatgga tttgattatg atcctgagac | 900 |
| cagtgatgat tctcttgaga gcagtgatta tgatcctgag aacagcaaaa atagttcaag | 960 |
| gtcaaagact aagtgccttt tcatccaaat ggaattctgt gataaaggga ccttggaaca | 1020 |
| atggattgaa aaagaagag gcgagaaact agacaaagtt ttggctttgg aactctttga | 1080 |
| acaaataaca aaggggtgg attatataca ttcaaaaaaa ttaattcata gagatcttaa | 1140 |
| gccaagtaat atattcttag tagatacaaa acaagtaaag attggagact ttggacttgt | 1200 |
| aacatctctg aaaatgatg gaaagcgaac aaggagtaag ggaacttttgc gatacatgag | 1260 |
| cccagaacag atttcttcgc aagactatgg aaaggaagtg gacctctacg ctttgggct | 1320 |
| aattcttgct gaacttcttc atgtatgtga cactgctttt gaaacatcaa gttttttcac | 1380 |
| agacctacgg gatggcatca tctcagatat atttgataaa aagaaaaaa ctcttctaca | 1440 |
| gaaattactc tcaaagaaac ctgaggatcg acctaacaca tctgaaatac taaggaccttt | 1500 |
| gactgtgtgg aagaaaagcc cagagaaaaa tgaacgacac acatgttaga gcccttctga | 1560 |
| aaagtatcc tgcttctgat atgcagtttt ccttaaatta tctaaaatct gctagggaat | 1620 |
| atcaatagat atttacctttt tattttaatg tttcctttaa ttttttacta tttttactaa | 1680 |

```
tctttctgca gaaacagaaa ggttttcttc tttttgcttc aaaaacattc ttacattttta     1740
cttttttcctg gctcatctct ttattctttt tttttttttta aagacagagt ctcgctctgt    1800
tgcccaggct ggagtgcaat gacacagtct tggctcactg caacttctgc ctcttgggtt      1860
caagtgattc tcctgcctca gcctcctgag tagctggatt acaggcatgt gccacccacc      1920
caactaattt ttgtgttttt aataaagaca gggtttcacc atgttggcca ggctggtctc      1980
aaactcctga cctcaagtaa tccacctgcc tcggcctccc aaagtgctgg gattacaggg      2040
atgagccacc gcgcccagcc tcatctcttt gttctaaaga tggaaaaacc accccccaaat    2100
tttcttttta tactattaat gaatcaatca attcatatct atttattaaa tttctaccgc     2160
ttttaggcca aaaaaatgta agatcgttct ctgcctcaca tagcttacaa gccagctgga     2220
gaaatatggt actcattaaa aaaaaaaaaa aaagtgatgt acaaccactt cggaaaacaa      2280
tttggcatta tctagtaaag ttgaatccat gtatacccac atagctatca attctattcc     2340
tacatacgtg cttacaagaa tgtccataaa accctgttta taatagccaa agaacaggg       2400
aacaaccata atgcacatca aagaagaat ggattaaaaa aattatattc acacacagga      2460
gtactatata gtattgaaaa caattgaagt acagctaaat gtaataacgt aacacaatac     2520
aactctcaga aacataatgt taagcgaaca aagcaggttt tcagaaaata tatgcagaat     2580
aattccattt atataaagtt ccagagcatg caaaactaaa tcattttgta taaaaaaccc    2640
aacaaatgtg atgagacaat aatgggaagg aagggaatga gaaatattaa attctggatg    2700
gtggttatct ttgagggagg ggaatgatgt gattggggaa atggactttc aaaggtaatg    2760
gtaacttcct taagctggat ggtaggtcca ctagtgtttg ctgcatagtt ataccttta     2820
tcttaaatac attttgtatc tattgtaaca accactttaa agacaaccgt gctgtaaggc    2880
agtagctaaa aacagaaaat agtccatcgg gaagggtaag atggctttct gctgagcaca    2940
gggctagaag tgacagccca gtgggccttc caactatatg ccagggtgtt agatgagtag    3000
agaggagacc acccaggaag tctggacaag gggtctggca tgagctctgg agaagatata    3060
tttgaggaac atggggtatg ctagtttgtt gtcctgaatt gctgtagaga agataattta    3120
aattgcatct tagaagacga ccctgagggt gaatttcaac ttagggcaat tgttttagtt    3180
tgtttcttat tggtttaaat ggatacttga agctggataa tttataagga aaagagattt    3240
atatgactta cagttctgca ggctgtacaa gaaacatggc accagcatct gcttcttccc    3300
cggctgcttc cactcatggt ggaaggtgaa ggggagccgg atgtgcagag atcatatggc    3360
aagagaggaa gcaagagagc gagggagaag gtgccaggct cttttaaat aaccggctct     3420
tgagggaact aatagattga gaactccttg cttctcctcc ccagcacacc ccaccccag     3480
ggacggcatt aatgtattca tgaggggtct tcccccatga cccaaacacc tcccatcagg    3540
ccccacctcc aacactggga tcaaatttca acatgagatt ttggggggaca aacatgcaaa    3600
ctatagcagc aaccagctac cattctaaaa ctgccatatg attttaggat ttttaaaaag   3660
ggccaaattt aggttaagca aaaaaaaaaa aaaaaaa                               3697
```

<210> SEQ ID NO 34
<211> LENGTH: 510
<212> TYPE: PRT
<213> ORGANISM: Homo sapiens

<400> SEQUENCE: 34

```
Met Ala Gly Asp Leu Ser Ala Gly Phe Phe Met Glu Glu Leu Asn Thr
1               5                   10                  15
```

Tyr Arg Gln Lys Gln Gly Val Val Leu Lys Tyr Gln Glu Leu Pro Asn
         20                  25                  30

Ser Gly Pro Pro His Asp Arg Arg Phe Thr Phe Gln Val Ile Ile Asp
             35                  40                  45

Gly Arg Glu Phe Pro Glu Gly Glu Gly Arg Ser Lys Lys Glu Ala Lys
 50                  55                  60

Asn Ala Ala Ala Lys Leu Ala Val Glu Ile Leu Asn Lys Glu Lys Lys
 65                  70                  75                  80

Ala Val Ser Pro Leu Leu Leu Thr Thr Thr Asn Ser Ser Glu Gly Leu
                 85                  90                  95

Ser Met Gly Asn Tyr Ile Gly Leu Ile Asn Arg Ile Ala Gln Lys Lys
                100                 105                 110

Arg Leu Thr Val Asn Tyr Glu Gln Cys Ala Ser Gly Val His Gly Pro
             115                 120                 125

Glu Gly Phe His Tyr Lys Cys Lys Met Gly Gln Lys Glu Tyr Ser Ile
 130                 135                 140

Gly Thr Gly Ser Thr Lys Gln Glu Ala Lys Gln Leu Ala Ala Lys Leu
145                 150                 155                 160

Ala Tyr Leu Gln Ile Leu Ser Glu Glu Thr Ser Val Lys Ser Asp Tyr
                165                 170                 175

Leu Ser Ser Gly Ser Phe Ala Thr Thr Cys Glu Ser Gln Ser Asn Ser
                180                 185                 190

Leu Val Thr Ser Thr Leu Ala Ser Glu Ser Ser Glu Gly Asp Phe
                195                 200                 205

Ser Ala Asp Thr Ser Glu Ile Asn Ser Asn Ser Asp Ser Leu Asn Ser
 210                 215                 220

Ser Ser Leu Leu Met Asn Gly Leu Arg Asn Asn Gln Arg Lys Ala Lys
225                 230                 235                 240

Arg Ser Leu Ala Pro Arg Phe Asp Leu Pro Asp Met Lys Glu Thr Lys
                245                 250                 255

Tyr Thr Val Asp Lys Arg Lys Ala Glu Arg Glu Val Lys Ala Leu Ala
                260                 265                 270

Lys Leu Asp His Val Asn Ile Val His Tyr Asn Gly Cys Trp Asp Gly
                275                 280                 285

Phe Asp Tyr Asp Pro Glu Thr Ser Asp Asp Ser Leu Glu Ser Ser Asp
 290                 295                 300

Tyr Asp Pro Glu Asn Ser Lys Asn Ser Ser Arg Ser Lys Thr Lys Cys
305                 310                 315                 320

Leu Phe Ile Gln Met Glu Phe Cys Asp Lys Gly Thr Leu Glu Gln Trp
                325                 330                 335

Ile Glu Lys Arg Arg Gly Glu Lys Leu Asp Lys Val Leu Ala Leu Glu
                340                 345                 350

Leu Phe Glu Gln Ile Thr Lys Gly Val Asp Tyr Ile His Ser Lys Lys
                355                 360                 365

Leu Ile His Arg Asp Leu Lys Pro Ser Asn Ile Phe Leu Val Asp Thr
                370                 375                 380

Lys Gln Val Lys Ile Gly Asp Phe Gly Leu Val Thr Ser Leu Lys Asn
385                 390                 395                 400

Asp Gly Lys Arg Thr Arg Ser Lys Gly Thr Leu Arg Tyr Met Ser Pro
                405                 410                 415

Glu Gln Ile Ser Ser Gln Asp Tyr Gly Lys Glu Val Asp Leu Tyr Ala
                420                 425                 430

```
Leu Gly Leu Ile Leu Ala Glu Leu His Val Cys Asp Thr Ala Phe
        435                 440                 445

Glu Thr Ser Lys Phe Phe Thr Asp Leu Arg Asp Gly Ile Ile Ser Asp
    450                 455                 460

Ile Phe Asp Lys Glu Lys Thr Leu Leu Gln Lys Leu Leu Ser Lys
465                 470                 475                 480

Lys Pro Glu Asp Arg Pro Asn Thr Ser Glu Ile Leu Arg Thr Leu Thr
                485                 490                 495

Val Trp Lys Lys Ser Pro Glu Lys Asn Glu Arg His Thr Cys
            500                 505                 510

<210> SEQ ID NO 35
<211> LENGTH: 4343
<212> TYPE: DNA
<213> ORGANISM: Mus musculus

<400> SEQUENCE: 35
```

| | | | | |
|---|---|---|---|---|
| gaaggcggag tccgccggga aaacgaaaca gaagagaacc ggccaggccc ggacttccat | 60 |
| gggcagcagc agcggcaggg aacggagggc gaatagattt cagagcctgc acctgaagta | 120 |
| caattcgaat cctgctccag ggagcgagcc actgtccgga tccagaaact ttggccactg | 180 |
| ggaggaaaaa tggccagtga tacccccagt ttctacatgg acaaacttaa taaataccgc | 240 |
| cagatgcacg gagtagccat tacgtataaa gaacttagta cttcgggacc tccacatgac | 300 |
| agaaggttta catttcaagt tttaatagat gagaaggaat ttccagaagc caaaggtaga | 360 |
| tcaaagcagg aggcaagaaa cgctgcagcc aaattagctg ttgatatact tgataacgaa | 420 |
| aacaaggtgg attgtcacac gagtgcatct gagcaaggct tgttcgttgg taactacata | 480 |
| ggccttgtca atagctttgc ccagaagaaa aagctgtctg taaattatga acagtgtgag | 540 |
| cccaactctg agttgcctca agatttatt tgtaaatgca aaattgggca gacaatgtat | 600 |
| ggtactggtt caggtgtcac caaacaggag gcaaagcagt tggctgcgaa agaagcctat | 660 |
| cagaagctgt taaagagccc gccgaaaact gccggaacat cctctagcgt tgtcacatct | 720 |
| acattcagtg ctttttccag cagctcgtct atgacaagta atggtgtttc ccagtcagca | 780 |
| cctggaagtt tttcctcaga aacgtgtttt acgaacggtc tcggagaaaa taaaggaaa | 840 |
| tcaggagtaa aagtatcccc tgatgatgtg caaagaaata atatacctt ggacgccagg | 900 |
| tttaacagcg attttgaaga catagaagaa attggcttag gtggatttgg tcaagttttc | 960 |
| aaagcgaaac acagaattga tggaaagaga tacgctatta gcgcgttaa atataacacg | 1020 |
| gagaaggcgg agcacgaagt acaagcgctg gcagaactca atcacgtcaa cattgtccaa | 1080 |
| taccatagtt gttgggaggg agttgactat gatcctgagc acagcatgag tgatacaagt | 1140 |
| cgatacaaaa cccggtgcct ctttattcaa atggaattct gtgataaagg aactttggag | 1200 |
| caatggatga aaacagaaa tcagagtaaa gtggacaaag ctttgatttt ggacttatat | 1260 |
| gaacaaatcg tgaccggagt ggagtatata cactcgaaag ggttaattca cagagatctt | 1320 |
| aagccaggta atatattttt agtagatgaa agacacatta gatcggaga ctttggcctt | 1380 |
| gcaacagccc tggaaaatga tggaaaatcc cgaacaagga gaacaggaac tcttcaatac | 1440 |
| atgagtccag aacagttatt tttaaagcac tatgaaaag aagtggacat ctttgctttg | 1500 |
| ggccttattc tagctgaact tcttcacacg tgcttcacgg agtcagagaa aataaagttt | 1560 |
| ttcgaaagtc taagaaaagg cgacttctct aatgatatat cgacaacaa agaaaaaagc | 1620 |
| cttctaaaaa aactactctc agagaaaccc aaggaccgac ctgagacatc tgaaatcctg | 1680 |

-continued

```
aagaccttgg ctgaatggag gaacatctca gagaaaaaga aaagaaacac atgttagggc   1740
ctttctgaga aaacattcct ctgccgtggt tttccttaa cgatctgcag tctgagggga   1800
gtatcagtga atattatcct tcttttctta ataccactct cccagacagg ttttggttag   1860
ggtgacccac agacattgta tttattaggc tatgaaaaag tatgcccatt tcctcaattg   1920
ttaattgctg ggcctgtggc tggctagcta gccaaatatg taaatgcttg tttctcgtct   1980
gcccaaagag aaaggcaggc tcctgtgtgg gaagtcacag agcccccaaa gccaactgga   2040
tgaggaagga ctctggcttt tggcataaaa aagagctggt agtcagagct ggggcagaag   2100
gtcctgcaga cagacagaca gacagacaga cagacagaca gacagacaga gacacaaaga   2160
catggactag aatggaggag ggagggagga agggagggag ggagagagag agagagaaag   2220
aaagagagag agaccacatg gagagacaaa atggcttaag ttagctgggc tacctgagag   2280
actgtcccag aaaacaggcc aacaaccttc cttatgctat atagatgtct cagtgtcttt   2340
atcattaaac accaagcagg actgctaaaa actctgcaat agggttttt ttttcctgtt   2400 acttcaaaag caatcttaca aagttatttt tttgacaatt ccatacatgc attgtgttct   2460
gatcccactc tgaaccctct gccattcatg ccttgtctgt catgtgaact gttgcctctg   2520 aatgtgggg tccaaattaa ccctctgccc ttgagtggct tctctcaggt agtgattgtg   2580
atgagaaaag taatgagatg ctggcaaaga tgtgcagaaa aagaacact tctccactgc   2640 tggtaggatt gcaagctggt acaaccaccc tggaaatcag actggaggtt cctcagaaac   2700
acagtactac ctgaggaccc aacaatacca ctactggtca tatacccaga agatggtcca   2760
acatgtaata tggacacatg cgccactatg ttcatagtag ccttatttat aatagccagg   2820
agctggaaag aacccagatg tccctcagca gaggaatgga tacagaaaat gtggcacatt   2880
tacacaatgg agtactactc agctattaaa atgaattca tgaaattctt agacaaatgg   2940
atggatctgg aggatatcat cttgagtgag gtaacccaat cgcaaaagaa cacacatgat   3000
atgcactcac tgataagtgg atattagccc aaaagctcca aataaccaag atacaattca   3060
cagactacat gaagctcaag aagaaggaag accaaagtgt gggtgctttg gtccctctta   3120 gaagggaac aaagtactca caggagcaaa tatggagata gagtgtagag cagagactga   3180
aggaaaggcc atccagagac tgtcccatat acagagactg ggaattcatc ccatacacag   3240
ttaccaaacc cagacactat tgtggatgcc aagacattca tgctgacagg agcctgatat   3300
ggctgtctcc tgagaggtcc tgccagagcc ttacaataca gagactgatg ctcacagcca   3360
accactggac tgagtgtggg gtccccaata gaggagttag agaaaggact gaaggagttg   3420
aaggggtttg caaccccata agaacaacaa tatcaaccaa gcagacccc cagagctccc   3480 agtgactaag ccatcaacca aggagtacac atggctccag ctgcatatgt agcagaggat   3540
ggccttgtca tgtatcaaaa ggaggagagg tccttggtcc tatgaaggtg cgatagatgc   3600
cccagtatag gggaatcaag ggcagatagg tgggttggag gaacaccctc atagaagcag   3660
ggggagtaag gaaggatatg gggatttctg ggagggtgg aaactaggaa aggggtaac   3720 atttgaaatg taaataaaga aaatatccaa ttaaaaaaaa aagaaaaaga aaaagaaaa   3780 gaatagtaat aaaaatggtac aggaagtaga gttatattgc aataaaccta ctgttgggct   3840
ttcaggactg gtttgtggga ggaatgtgaa aaagtttgaa gccccaggtt agagaagtcc   3900
tcaaatggta tacgtcaaac ttactgtggt agctcaaaag tctcctgaga ggccctgctt   3960
ggagttagcc ttgtagaggt ccagtctttc cttgttgttc tttcagactt gctttgtaga   4020
atattggtag ttactttgtg cctttgtatg ctgtaatagt tgttttatag ggcctcacag   4080
```

```
ctaagagttt ctcgctgctt ctcaaagcac tttggacctt tgcatggagt tgagtattaa    4140
gattatggga atttctgagg tgggactgaa agcattttgc attatgagat ggccatgagc    4200
caacagagac ttggacacac tcctccactg tcaaccgagg cttctgccaa atcttccctg    4260
tcatgaagga ttgtatcatc tgaaattgag tctaaataga taaataaata agtaaataaa    4320
tctctcaaaa aaaaaaaaaa aaa                                           4343
```

```
<210> SEQ ID NO 36
<211> LENGTH: 515
<212> TYPE: PRT
<213> ORGANISM: Mus musculus

<400> SEQUENCE: 36
```

Met Ala Ser Asp Thr Pro Gly Phe Tyr Met Asp Lys Leu Asn Lys Tyr
1               5                   10                  15

Arg Gln Met His Gly Val Ala Ile Thr Tyr Lys Glu Leu Ser Thr Ser
                20                  25                  30

Gly Pro Pro His Asp Arg Arg Phe Thr Phe Gln Val Leu Ile Asp Glu
            35                  40                  45

Lys Glu Phe Pro Glu Ala Lys Gly Arg Ser Lys Gln Glu Ala Arg Asn
        50                  55                  60

Ala Ala Ala Lys Leu Ala Val Asp Ile Leu Asp Asn Glu Asn Lys Val
65                  70                  75                  80

Asp Cys His Thr Ser Ala Ser Glu Gln Gly Leu Phe Val Gly Asn Tyr
                85                  90                  95

Ile Gly Leu Val Asn Ser Phe Ala Gln Lys Lys Lys Leu Ser Val Asn
                100                 105                 110

Tyr Glu Gln Cys Glu Pro Asn Ser Glu Leu Pro Gln Arg Phe Ile Cys
            115                 120                 125

Lys Cys Lys Ile Gly Gln Thr Met Tyr Gly Thr Gly Ser Gly Val Thr
        130                 135                 140

Lys Gln Glu Ala Lys Gln Leu Ala Ala Lys Glu Ala Tyr Gln Lys Leu
145                 150                 155                 160

Leu Lys Ser Pro Pro Lys Thr Ala Gly Thr Ser Ser Ser Val Val Thr
                165                 170                 175

Ser Thr Phe Ser Gly Phe Ser Ser Ser Ser Met Thr Ser Asn Gly
                180                 185                 190

Val Ser Gln Ser Ala Pro Gly Ser Phe Ser Ser Glu Asn Val Phe Thr
            195                 200                 205

Asn Gly Leu Gly Glu Asn Lys Arg Lys Ser Gly Val Lys Val Ser Pro
        210                 215                 220

Asp Asp Val Gln Arg Asn Lys Tyr Thr Leu Asp Ala Arg Phe Asn Ser
225                 230                 235                 240

Asp Phe Glu Asp Ile Glu Glu Ile Gly Leu Gly Gly Phe Gly Gln Val
                245                 250                 255

Phe Lys Ala Lys His Arg Ile Asp Gly Lys Arg Tyr Ala Ile Lys Arg
            260                 265                 270

Val Lys Tyr Asn Thr Glu Lys Ala Glu His Glu Val Gln Ala Leu Ala
        275                 280                 285

Glu Leu Asn His Val Asn Ile Val Gln Tyr His Ser Cys Trp Glu Gly
    290                 295                 300

Val Asp Tyr Asp Pro Glu His Ser Met Ser Asp Thr Ser Arg Tyr Lys
305                 310                 315                 320

```
Thr Arg Cys Leu Phe Ile Gln Met Glu Phe Cys Asp Lys Gly Thr Leu
            325                 330                 335

Glu Gln Trp Met Arg Asn Arg Asn Gln Ser Lys Val Asp Lys Ala Leu
            340                 345                 350

Ile Leu Asp Leu Tyr Glu Gln Ile Val Thr Gly Val Glu Tyr Ile His
            355                 360                 365

Ser Lys Gly Leu Ile His Arg Asp Leu Lys Pro Gly Asn Ile Phe Leu
            370                 375                 380

Val Asp Glu Arg His Ile Lys Ile Gly Asp Phe Gly Leu Ala Thr Ala
385                 390                 395                 400

Leu Glu Asn Asp Gly Lys Ser Arg Thr Arg Arg Thr Gly Thr Leu Gln
            405                 410                 415

Tyr Met Ser Pro Glu Gln Leu Phe Leu Lys His Tyr Gly Lys Glu Val
            420                 425                 430

Asp Ile Phe Ala Leu Gly Leu Ile Leu Ala Glu Leu Leu His Thr Cys
            435                 440                 445

Phe Thr Glu Ser Glu Lys Ile Lys Phe Phe Glu Ser Leu Arg Lys Gly
            450                 455                 460

Asp Phe Ser Asn Asp Ile Phe Asp Asn Lys Glu Lys Ser Leu Leu Lys
465                 470                 475                 480

Lys Leu Leu Ser Glu Lys Pro Lys Asp Arg Pro Glu Thr Ser Glu Ile
            485                 490                 495

Leu Lys Thr Leu Ala Glu Trp Arg Asn Ile Ser Glu Lys Lys Lys Arg
            500                 505                 510

Asn Thr Cys
        515

<210> SEQ ID NO 37
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 37
gcctgctgtc acttgctacg                                              20

<210> SEQ ID NO 38
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 38
aatcaaccag agaatttccg                                              20

<210> SEQ ID NO 39
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 39
ggtccagctc ccgttctaca                                              20
```

```
<210> SEQ ID NO 40
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 40
gtatggcagc aacgtcacga                                                    20

<210> SEQ ID NO 41
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 41
tatagagctg aaaaaccgca                                                    20

<210> SEQ ID NO 42
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 42
ccacattacg gacgatgcaa                                                    20

<210> SEQ ID NO 43
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 43
tcttacgagg aggagaaagg                                                    20

<210> SEQ ID NO 44
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 44
gcaagtgtag tttcccacca                                                    20

<210> SEQ ID NO 45
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 45
gcgaggtatt cggctccgcg                                                    20

<210> SEQ ID NO 46
```

```
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 46
gctttcacgg aggttcgacg                                               20

<210> SEQ ID NO 47
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 47
atgttgcagt tcggctcgat                                               20

<210> SEQ ID NO 48
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 48
acgtgtaagg cgaacgcctt                                               20

<210> SEQ ID NO 49
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 49
attgttcgac cgtctacggg                                               20

<210> SEQ ID NO 50
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 50
caccgtctgg attcacaact ccagg                                         25

<210> SEQ ID NO 51
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 51
aaaccctgga gttgtgaatc cagac                                         25

<210> SEQ ID NO 52
<211> LENGTH: 25
```

```
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 52
caccgtctac agccctacct tgcca                                           25

<210> SEQ ID NO 53
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 53
aaactggcaa ggtagggctg tagac                                           25

<210> SEQ ID NO 54
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 54
caccgtgtga ctctcagaaa tcag                                            24

<210> SEQ ID NO 55
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 55
aaacctgatt tctgagagtc acac                                            24

<210> SEQ ID NO 56
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 56
caccgttcca agtcaatcag cactg                                           25

<210> SEQ ID NO 57
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 57
aaaccagtgc tgattgactt ggaac                                           25

<210> SEQ ID NO 58
<211> LENGTH: 25
<212> TYPE: DNA
```

```
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 58
caccgcacac agcaggggta cacca                                          25

<210> SEQ ID NO 59
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 59
aaactggtgt accctgctg tgtgc                                           25

<210> SEQ ID NO 60
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 60
caccgtccgt caagtaccag atggg                                          25

<210> SEQ ID NO 61
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 61 aaacccatc tggtacttga cggac                                           25

<210> SEQ ID NO 62
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 62
caccgatggg tgtagtatcc gctga                                          25

<210> SEQ ID NO 63
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 63
aaactcagcg gatactacac ccatc                                          25

<210> SEQ ID NO 64
<211> LENGTH: 25
<212> TYPE: DNA
<213> ORGANISM: Artificial Sequence
```

```
<220> FEATURE:
<223> OTHER INFORMATION: /note="Description of Artificial Sequence:
      Synthetic sgRNA targeting sequence"

<400> SEQUENCE: 64
caccgtgtgg cagactcctg ccacg                                              25

<210> SEQ ID NO 65
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 65
aaaccgtggc aggagtctgc cacac                                              25

<210> SEQ ID NO 66
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 66
caccgagggg gatgtctata gacaa                                              25

<210> SEQ ID NO 67
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 67
aaacttgtct atagacatcc ccctc                                              25

<210> SEQ ID NO 68
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 68
caccgttctt gtagggtgaa caccg                                              25

<210> SEQ ID NO 69
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 69
aaaccggtgt tcaccctaca agaac                                              25

<210> SEQ ID NO 70
<211> LENGTH: 25
<212> TYPE: DNA
<213> ORGANISM: Artificial Sequence
<220> FEATURE:
```

```
<223> OTHER INFORMATION: /note="Description of Artificial Sequence:
      Synthetic sgRNA targeting sequence"

<400> SEQUENCE: 70
caccgtctgg attcacaact ccagg                                          25

<210> SEQ ID NO 71
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 71
caccgtcaca gccctacctt gcca                                           24

<210> SEQ ID NO 72
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 72
caccgtgtga ctctcagaaa tcag                                           24

<210> SEQ ID NO 73
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 73
accgttccaa gtcaatcagc actg                                           24

<210> SEQ ID NO 74
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 74
caccgcacac agcaggggta cacca                                          25

<210> SEQ ID NO 75
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 75
caccgtccgt caagtaccag atggg                                          25

<210> SEQ ID NO 76
<211> LENGTH: 25
<212> TYPE: DNA
<213> ORGANISM: Artificial Sequence
<220> FEATURE:
<223> OTHER INFORMATION: /note="Description of Artificial Sequence:
```

Synthetic sgRNA targeting sequence"

<400> SEQUENCE: 76
caccgcgttg gagatgctaa gaccg                                              25

<210> SEQ ID NO 77
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 77
caccgtccgc cagagatgaa cgaag                                              25

<210> SEQ ID NO 78
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 78
caccgtggct actccgtgca tctgg                                              25

<210> SEQ ID NO 79
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 79
caccgctcgt ctatgacaag taat                                               24

<210> SEQ ID NO 80
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 80
caccgtgtgg gtttgacata gcgcg                                              25

<210> SEQ ID NO 81
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 81
caccgcctga gggtgaacgt cccag                                              25

<210> SEQ ID NO 82
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

```
<400> SEQUENCE: 82
caccgtacca gagggtgtag ttag                                          24

<210> SEQ ID NO 83
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 83
caccacacaa gctgaggaga ccga                                          24

<210> SEQ ID NO 84
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 84
cacccgactt cagggtgaaa tacg                                          24

<210> SEQ ID NO 85
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 85
caccggtatt cccagcatac gaca                                          24

<210> SEQ ID NO 86
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 86
caccgccggt tcccgatctg cctgt                                         25

<210> SEQ ID NO 87
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 87
caccgggaac cgggacacac tctg                                          24

<210> SEQ ID NO 88
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"
```

-continued

<400> SEQUENCE: 88
caccgatcat ctacaactgt ctga                                          24

<210> SEQ ID NO 89
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 89
caccgtacga tgacagtttc ccca                                          24

<210> SEQ ID NO 90
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 90
caccgcgagg tattcggctc cgcg                                          24

<210> SEQ ID NO 91
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 91
caccgctttc acggaggttc gacg                                          24

<210> SEQ ID NO 92
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 92
caccatgttg cagttcggct cgat                                          24

<210> SEQ ID NO 93
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 93
caccacgtgt aaggcgaacg cctt                                          24

<210> SEQ ID NO 94
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 94
caccattgtt cgaccgtcta cggg    24

<210> SEQ ID NO 95
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 95
ggagcgcacc atcttcttca    20

<210> SEQ ID NO 96
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 96
gaagttcgag ggcgacaccc    20

<210> SEQ ID NO 97
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 97
gcttgagtgt atgcacaaat    20

<210> SEQ ID NO 98
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 98
gtgcatacac tcaagcagtg    20

<210> SEQ ID NO 99
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 99
agatagccat gctgagccac    20

<210> SEQ ID NO 100
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 100
ctagggcatc caaaaagcca                                              20

<210> SEQ ID NO 101
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 101
gttcctgttg gagctccagg                                              20

<210> SEQ ID NO 102
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 102
gtgcatatgc gctttcccag                                              20

<210> SEQ ID NO 103
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 103
aggactgagg aatcagcacg                                              20

<210> SEQ ID NO 104
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 104
cctctcctgg aacttccggt                                              20

<210> SEQ ID NO 105
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 105
ggtattgaag agatgccaga                                              20

<210> SEQ ID NO 106
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 106
ggtctcaaga gaaatccgtg                                              20

<210> SEQ ID NO 107
<211> LENGTH: 20
<212> TYPE: DNA
<213> ORGANISM: Artificial Sequence
<220> FEATURE:
<223> OTHER INFORMATION: /note="Description of Artificial Sequence:
    Synthetic sgRNA targeting sequence"

<400> SEQUENCE: 107
ttcacaggtt gaagacaccg                                           20

<210> SEQ ID NO 108
<211> LENGTH: 20
<212> TYPE: DNA
<213> ORGANISM: Artificial Sequence
<220> FEATURE:
<223> OTHER INFORMATION: /note="Description of Artificial Sequence:
    Synthetic sgRNA targeting sequence"

<400> SEQUENCE: 108
ccgccgtgga gatatcatcg                                           20

<210> SEQ ID NO 109
<211> LENGTH: 20
<212> TYPE: DNA
<213> ORGANISM: Artificial Sequence
<220> FEATURE:
<223> OTHER INFORMATION: /note="Description of Artificial Sequence:
    Synthetic sgRNA targeting sequence"

<400> SEQUENCE: 109
tggggcctcg aagctccggg                                           20

<210> SEQ ID NO 110
<211> LENGTH: 20
<212> TYPE: DNA
<213> ORGANISM: Artificial Sequence
<220> FEATURE:
<223> OTHER INFORMATION: /note="Description of Artificial Sequence:
    Synthetic sgRNA targeting sequence"

<400> SEQUENCE: 110
gcaagactat ggaaaggaag                                           20

<210> SEQ ID NO 111
<211> LENGTH: 20
<212> TYPE: DNA
<213> ORGANISM: Artificial Sequence
<220> FEATURE:
<223> OTHER INFORMATION: /note="Description of Artificial Sequence:
    Synthetic sgRNA targeting sequence"

<400> SEQUENCE: 111
aaaggcaata cgtaccactg                                           20